United States Patent
Shen et al.

(10) Patent No.: US 9,815,796 B2
(45) Date of Patent: Nov. 14, 2017

(54) PYRIMIDONE CARBOXAMIDE COMPOUNDS AS PDE2 INHIBITORS

(71) Applicants: Merck Sharp & Dohme Corp., Rahway, NJ (US); MSD R & D (China) Co. Ltd., Shanghai (CN)

(72) Inventors: Dong Ming Shen, Edison, NJ (US); Melissa Egbertson, Ambler, PA (US); Richard Berger, Harleysville, PA (US); XiaoXia Qian, New York, NY (US); Yimin Qian, Plainsboro, NJ (US); Bart Harper, New York, NY (US); Meng Yang, Westfield, NJ (US); Zack Zhiqiang Guo, Morganville, NJ (US); Vanessa L. Rada, Hatfield, PA (US); Deping Wang, Furlong, PA (US); Timothy A. Cernak, Boston, MA (US); Christopher Sinz, Middletown, NJ (US); Ming Wang, Belle Mead, NJ (US); Jonathan E. Wilson, South Orange, NJ (US); Shimin Xu, Beijing (CN)

(73) Assignees: Merck Sharp & Dohme Corp., Rahway, NJ (US); MSD R & D (China) Co. LTD., Shanghai (CN)

( * ) Notice: Subject to any disclaimer, the term of this patent is extended or adjusted under 35 U.S.C. 154(b) by 0 days.

(21) Appl. No.: 15/107,233

(22) PCT Filed: Dec. 17, 2014

(86) PCT No.: PCT/CN2014/094092
§ 371 (c)(1),
(2) Date: Jun. 22, 2016

(87) PCT Pub. No.: WO2015/096651
PCT Pub. Date: Jul. 2, 2015

(65) Prior Publication Data
US 2017/0015633 A1    Jan. 19, 2017

Related U.S. Application Data

(60) Provisional application No. 61/920,270, filed on Dec. 23, 2013.

(51) Int. Cl.
| | |
|---|---|
| *C07D 239/36* | (2006.01) |
| *C07D 401/12* | (2006.01) |
| *C07D 401/06* | (2006.01) |
| *C07D 403/04* | (2006.01) |
| *C07D 403/14* | (2006.01) |
| *C07D 487/04* | (2006.01) |
| *C07D 405/12* | (2006.01) |
| *C07D 405/14* | (2006.01) |

(Continued)

(52) U.S. Cl.
CPC ......... *C07D 239/36* (2013.01); *C07D 401/06* (2013.01); *C07D 401/12* (2013.01); *C07D 403/04* (2013.01); *C07D 403/06* (2013.01); *C07D 403/12* (2013.01); *C07D 403/14* (2013.01); *C07D 405/12* (2013.01); *C07D 405/14* (2013.01); *C07D 413/04* (2013.01); *C07D 417/04* (2013.01); *C07D 487/04* (2013.01)

(58) Field of Classification Search
CPC .. C07D 239/36; C07D 401/12; C07D 401/06; C07D 403/04; C07D 403/06; C07D 403/12; C07D 403/14; C07D 487/04; C07D 405/12; C07D 405/14; C07D 413/04; C07D 417/04
See application file for complete search history.

(56) References Cited

U.S. PATENT DOCUMENTS

| 6,573,263 B2 | 6/2003 | Niewohner et al. |
| 7,419,969 B2 | 9/2008 | Naidu et al. |

(Continued)

FOREIGN PATENT DOCUMENTS

| EP | 3061754 | 8/2016 |
| WO | WO03035076 | 5/2003 |

(Continued)

OTHER PUBLICATIONS

Ahlstrom et al., Inactivation of Atrial Natriuretic Factor-Stimulated, Biochemical Pharmacology, 2000, 1133-1139, 59.
Arulomozhi et al., Migraine: Current Therapeutic Targets and Future Avenues, Current Vascular Pharmacology, 2006, 117-128, 4.
Beavo et al., Cyclic GMP as Substrate and Regulator of Cyclic Nucleotide Phosphodiesterases (PDEs), Rev. Physio Biochem Pharm, 1999, 67-104, 135.
Bernard et al., PDE2 Is a Novel Target for Attenuating Tumor Formation in a Mouse Model of UVB-Induced Skin Carcinogenesis, Plos One, 2014, 1-8, 9.

(Continued)

*Primary Examiner* — Alexander R Pagano
*Assistant Examiner* — Ebenezer O Sackey
(74) *Attorney, Agent, or Firm* — Sylvia A. Ayler; John C. Todaro

(57) ABSTRACT

Disclosed are pyrimidine carboxamide compounds of formula (I) which are useful as therapeutic agents for the treatment of central nervous system disorders associated with phosphodiesterase 2 (PDE2), pharmaceutical compositions and uses thereof.

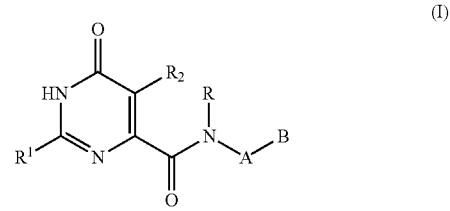

21 Claims, No Drawings

(51) Int. Cl.
 C07D 413/04 (2006.01)
 C07D 417/04 (2006.01)
 C07D 403/12 (2006.01)
 C07D 403/06 (2006.01)

(56) References Cited

U.S. PATENT DOCUMENTS

| | | |
|---|---|---|
| 2007/0135457 A1 | 6/2007 | Beyer et al. |
| 2007/0281917 A1 | 12/2007 | Naidu et al. |
| 2009/0253677 A1 | 10/2009 | Beaulieu et al. |
| 2012/0214791 A1 | 8/2012 | Helal et al. |

FOREIGN PATENT DOCUMENTS

| | | | |
|---|---|---|---|
| WO | WO03035077 A1 | | 5/2003 |
| WO | WO2004096128 | | 11/2004 |
| WO | WO2005041957 | | 5/2005 |
| WO | WO2005061497 | | 7/2005 |
| WO | WO2006024640 | | 3/2006 |
| WO | WO2007058646 | | 5/2007 |
| WO | WO2008002671 | | 1/2008 |
| WO | WO2008043461 | | 4/2008 |
| WO | 2009016498 | * | 2/2009 |
| WO | WO2009016498 | | 2/2009 |
| WO | WO2009117540 | | 9/2009 |
| WO | WO2010136493 | | 12/2010 |
| WO | WO2012151567 | | 11/2012 |
| WO | WO2012168817 | | 12/2012 |
| WO | WO2013410382 | | 1/2013 |
| WO | WO2013034755 | | 3/2013 |
| WO | WO2013034758 | | 3/2013 |
| WO | WO2013034761 | | 3/2013 |
| WO | WO2013098373 | | 7/2013 |
| WO | WO2013161913 | | 10/2013 |

OTHER PUBLICATIONS

Boess et al., Inhibition of phosphodiesterase 2 increases neuronal cGMP, synaptic plasticity and memory, Neuropharmacology, 2004, 1081-92, 47.
Boyd et al., 2-Substituted -4,5-Dihydroxypyrimidine-6-Carboxamide Antiviral Targeted Libraries, J. Comb. Chem, 2009, 1100-1104, 11.
Brandon et al., Potential CNS Applications for, Annual Reports in Medicinal Chemistry, 1997, 3-11, 42.
Cote et al., Comparative Involvement of Cyclic Nucleotide, Endocrinology, 1999, 3594-3601, 140.
Dickinson et al., Activation of cGMP-stimulated phosphodiesterase by nitroprusside limits, Biochem J., 1997, 371-377, 323.
Domek-Lopacinska et al., The Effect of Selective Inhibition of Cyclic GMP Hydrolyzing Phosphodiesterases 2 and 5 on Learning Memory Processes and Nitric Oxide Synthase Activity, Brain Research, 2008, 68-77, 1216.
Ducrot et al., CoMFA and CoMSIA 3D-Quantitative Structure-Activity Relationship Model on Benzodiaepine Derivatives, Inhibitors of Phosphodiesterase IV, J. of Computer Aided Molecular Designs, 2001, 767-785, 15.
Duran et al., The NO cascade, eNOS Location, and Microvascular Permeability, Cardiovascular Research, 2010, 254-261, 87.
Favot et al., VEGF-Induced HUVEC Migration and Proliferation, Schattauer GmbH Stuttgart, 2003, 3443-343, 90.
Haynes et al., Erythro-9-(2-Hydroxy-3-Nonyl) Adenine Inhibits Cyclic-3',5' Guanosine Monophosphate -Stimulated Phosphodiesterase to Reverse Hypoxic Pulmonary Vasoconstriction in the Perfused Rat Lung, The J. of Pharmacology, 1996, 752-757, 276.
Herring et al., NO-cGMP Pathway Increases the Hyperpolarisation-Activated Current ,I, and Heart Rate During Adrenergic Stimulation, Cardiovascular Research, 2001, 446-453, 52.
Hiramoto et al., Role of Phosphodiesterase 2 in Growth and Invasion of HUman Maligant Melanoma, Cellular Signanling, 2014, 1807-1817, 26.
Huang et al., A Fluroescence Polarization Assay for Cyclic Nucleotide Phosphodiesterases, J. of Biomolecular Screening, 2002, pp. 215-222, 7.

Jorgensen et al., Selective Inhibitors of PDE2, PDE9, and PDE10: Modulators of Activity of the Central Nervous System, Annual Reports in Medicinal Chemistry, 2013, pp. 37-55, 48.
Kawano et al., Lithium Acetate-Catalyzed Crossed Aldol Reaction between Aldehydes and Trimethylsilyl Enolates Generated from Other Aldehydes, Chemistry Letters, 2005, 614-615, 34.
Keravis et al., Cyclic Nucleotide Hydrolysis in Bovine Aortic Endothelial Cells in Culture: Differential Regulation in Cobblestone and Spindle Phenotypes, J. Vasc. Res, 2000, 235-249, 37.
Kirsch et al., Liquid Crystals Based on Hypervalent Sulfur Fluorides: Exploring the Steric, Eur. J. Org. Chem., 2005, 3095-3100, 14.
Lieberman et al., Effectiveness of Antipsychotic Drugs in Patients with Chronic Schizophrenia, New England J. of Medicine, Sep. 22, 2005, pp. 1209-1223, 353, US.
Masood et al., Anxiolytic Effects of Phosphodiesterase-2 Inhibitors Associated with Increased cGMP Signaling, J. of Pharmacology, 2009, 690-699, 331.
Masood et al., Reversal of Oxidative Stress-Induced Anxiety by Inhibition of Phosphodiesterase-2 in Mice, J. of Pharmacology and Experimental Therapeutics, 2008, 369-379, 326.
Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.
Morita et al., Characterization of Phosphodiesterase 2A in Human Malignant Melanoma PMP Cells, Oncology Reports, 2013, 1275-1284, 29.
Netherton et al., Vascular Endothelial Cell Cyclic Nucleotide phosphodiesterases and Regulated Cell Migration: IMplications in Angiogenesis, Molecular Pharmacology, 2005, 263-272, 67.
Pace et al., Dihydroxypyrimidine-4-Carboxamides as Novel Poten and Selective HIV Integrase Inhibitors, J. Med Chem., 2007, 2225-2239, 50.
Petrocchi et al., From dihydroxypyrimidine carboxylic acids to carboxamide, Bioorganic & Medicinal Chemistry Letters, 2007, 350-353, 17.
Plummer et al., Discovery of Poten, Selective, Bioavailable Phosphodiesterase 2 (PDE2) Inhibitors Active in an Osteoarthritis Pain Model, Part I: Transformation of Selective Pyrazolodiazepinone Phosphodiesterase 4 (PDE4) Inhibitors into Selective PDE2 Inhibitors, Biorganic & Medicinal Chemistry Letters, 2013, 3438-3442, 23.
Plummer et al., Discovery of potent selective bioavailable phosphodiesterase, Bioorganic & Medicinal Chemistry Letters, 2013, 3443-3447, 23.
Rivet-Bastide et al., cGMP-stimulated Cyclic Nucleotide Phosphodiesterase Regulates the Basal, J. Clin. Invest, 1997, 2710-2718, 99.
Sadhu et al., Differential Expression of the Cyclic GMP-Stimulated Phosphodiesterase PDE2A in HUman Venous and Capillary Endothelial Cells, J. of Histochemistry & Cytochemistry, 1999, 895-905, 47.
Savai et al., Targeting Cancer with Phosphodiesterase Inhibitors, Expert Opinion, 2010, 117-131, 19.
Surapisitchat et al., Differential Regulation of Endothelial Cell Permeability by cGMP via Phosphodiesterases 2 and 3, Circulation Research, 2007, 811-818, 101.
Suvrana et al., Hydrolysis of N-Methyl-D-aspartate Receptor-Stimulated cAMP, J. of Pharmacology, 2002, 249-256, 302.
Van Staveren et al., The effects of phosphodiesterase inhibition on cyclic GMP and cyclic, Brain Research, 2001, 275-286, 888.
Vandecasteele, Cyclic GMP regulation of the L-type Ca2+ channel current, J. of Physiology, 2001, 329-340, 533.
Velardez et al., Role of Phosphodiesterase and Protein Kinase G on Nitric Oxide-Induced Inhibition of Prolactin Relase from the Rat Anterior Pituitary, Europe J. of Endocrinology, 2000, 279-284, 143.
Wakabayashi et al., Involvement of Phosphodiesterase Isozymes in Osteoblastic, J. of Bone and Mineral Research, 2002, 249-253, 17.
Weil et al., 1, 3-Diethynlallenes: Stabel Monomers, Length-Defined Oligomers, Asymmetric Synthesis and Optical Resolution, Eur J. Org Chem., 2007, 3449-3462, 21.

* cited by examiner

PYRIMIDONE CARBOXAMIDE COMPOUNDS AS PDE2 INHIBITORS

CROSS REFERENCE TO RELATED APPLICATIONS

This application is the National Stage of International Application No. PCT/CN2014/094092 filed on Dec. 17, 2014, which claims the benefit under 35 U.S.C. 119(e) of U.S. Provisional Application No. 61/920,270, filed Dec. 23, 2013.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication.

Dissatisfaction with therapy is attributed to lack of efficacy or intolerable and unacceptable side effects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic D2 receptor associated with cyclic adenosine monophosphate (cAMP). These ubiquitous second messengers are responsible for altering the function of many intracellular proteins. Cyclic AMP is thought to regulate the activity of cAMP-dependent protein kinase (PKA), which in turn phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these enzymes, known as 3',5'-cyclic nucleotide specific phosphodiesterases (PDEs). The PDE superfamily includes twenty-one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45%, suggests that it may be possible to develop selective inhibitors for each of these families.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et. al., Brain Res., 888, 275 (2001) and J. O'Donnell, et. al., J. Pharm. Exp. Ther., 302, 249 (2002)); prolactin and aldosterone secretion (M. O. Velardez, et. al., Eur. J. Endo., 143, 279 (2000) and N. Gallo-Payet, et. al., Endo., 140, 3594 (1999)); bone cell differentiation, growth, and bone resorption (C. Allardt-Lamberg, et. al., Biochem. Pharm., 59, 1133 (2000) and S. Wakabayashi, et. al., J. Bone, Miner. Res., 17, 249 (2002); immunological response (M. D. Houslay, et. al., Cell. Signal., 8, 97 (1996); vascular angiogenesis (T. Keravis, et. al., J. Vasc. Res., 37, 235 (2000); inflammatory cell transit (S. L. Wolda, et. al., J. Histochem. Cytochem., 47, 895 (1999); cardiac contraction (R. Fischmeister, et. al., J. Clin. Invest., 99, 2710 (1997), P. Donzeau-Gouge, et al., J. Physiol., 533, 329 (2001), and D. J. Paterson, et. Al., Card. Res., 52, 446 (2001); platelet aggregation (R. J. Haslam, et. Al., Biochem. J., 323, 371 (1997); female sexual arousal disorder (C. P. Wayman, et. al., EP Patent Publications EP10977707 and EP1097706; osteoarthritis pain (M. Plummer et, al., Bioorganic & Medicinal Chemistry Letters, 23(11), 3438-3442 and 3443-3447 (2013)); malignant melanoma (H. Morita, et al., Oncology Reports, 29, 1275-1284, 2013; and hypoxic pulmonary vasoconstriction (J. Haynes, et. al., J. Pharm. Exp. Ther., 276, 752 (1996). See also 2-Substituted-4,5-dihydroxypyrimidine-6-carboxamide Antiviral Targeted Libraries, Vincent Boyd et al., Journal of Combinatorial Chemistry (2009), 11(6), 1100-1104; From Dihydroxypyrimidine Carboxylic Acids to Carboxamide HIV-1 Integrase Inhibitors: SAR Around the Amide Moiety, Alessia Petrocchi et al., Bioorganic & Medicinal Chemistry Letters (2007), 17(2), 350-353; Dihydroxypyrimidine-4-carboxamides as Novel Potent and Selective HIV Integrase Inhibitors, Paola Pare et al., Journal of Medicinal Chemistry (2007), 50(9), 2225-2239; US2007135457, WO2012151567, US20090253677, US20070281917, WO2004096128, WO2003035077, WO2003035076, WO2007058646, WO2009117540, and U.S. Pat. No. 7,419, 969.

Inhibition of PDE2 (e.g., PDE2A) has been shown to enhance cognitive function across multiple preclinical models of cognitive performance that reflect improvements in recognition memory, social interactions and working memory, which are all deficient in schizophrenia (Boess et al., *Inhibition of Phosphodiesterase 2 Increases Neuronal cGMP, Synaptic Plasticity and Memory Performance*, Neuropharmacology, 47(7):1081-92, 2004). PDE2A inhibition was also shown to improve cognitive deficits that develop in aging and Alzheimer's disease (Domek-Lopacinska and Strosznajder, *The Effect of Selective Inhibition of Cyclic GMP Hydrolyzing Phosphodiesterases 2 and 5 on Learning and Memory Processes and Nitric Oxide Synthetase Activity in Brain During Aging*, Brain Research, 1216:68-77, 2008). The role of PDE2 inhibition in cognitive disorders was also shown in Brandon et al., *Potential CNS Applications for Phosphodiesterase Enzyme Inhibitors, Annual Reports in Medicinal Chemistry* 42: 4-5, 2007 (compound BAY 60-7550 was reported to have significant potency at other PDE isoforms, had high clearance and limited brain penetration). See also Jorgenson, et al, Annual Reports in Medicinal Chemistry 48: 37-55, 2013. "Selective Inhibitors of PDE2, PDE9, and PDE10: Modulators of Activity of the Central Nervous System".

PDE2 inhibitors have also been shown to have efficacy in preclinical models of anxiety and depression (Masood et al., Anxiolytic Effects of Phosphodiesterase-2 Inhibitors Associated with Increased cGMP Signaling, JPET 331(2):690-699, 2009; Masood et al., Reversal of Oxidative Stress-Induced Anxiety by Inhibition of Phosphodiesterase-2 in Mice, JPET 326(2):369-379, 2008; Reierson et al., Repeated Antidepressant Therapy Increases Cyclic GMP Signaling in Rat Hippocampus, Neurosci. Lett., 466(3):149-53, 2009). See also Ducrot et al., CoMFA and CoMSIA 3D-quantitative structure-activity relationship model on benzodiazepine derivatives, inhibitors of phosphodieserase IV, J Computer-Aided Molecular Design, 15: 767785, 2001; US20120214791; WO2012168817; WO2013034755; WO2013034758; WO2013034761; WO2005041957; WO2005061497; WO2006024640; WO2013161913; WO2010136493; WO 2013098373; WO 2009016498; U.S. Pat. No. 6,573,263; M. Plummer et al., Bioorg Med Chem Lett 23(11), 3438, 2013; and M. Plummer et al., Bioorg Med Chem Lett 23(11), 3443, 2013.

An increase in vascular permeability has been shown to be attributable to an increase activity of PDE2. PDE2 and PDE3 in the endothelium can act as a sensor or switch to detect normal versus pathological concentrations of cGMP and thus regulate endothelial permeability accordingly with potential relevance to migraine. See Surapisitchat et al, *Differential Regulation of Endothelial Cell Permeability by cGMP via Phosphodieserase 2 and 3*, Circulation Research, 2007; 101, pgs.: 811-818 and Duran et al., *The NO Cascade, eNOS Location and Microvascular Permeability*, Cardiovascular Res. (2010) 87, 254-261. Cerebral vasodilation is considered a major cause of migraine. See P. C. Tfelt-Hansen and P. J. Koehler, *One hundred years of migraine research: major clinical and scientific observations from 1910 to 2010*, Headache, 2011. 51(5), 752-578 and D. K. Arulmozhi et al., *Migraine: current therapeutic targets and future avenues*, Current Vascular Pharmacology, 2006, 4(2), 117-128. Therefore, PDE2 inhibition may have utility as a treatment or prophylactic for migraine.

The need for new and improved PDE2 modulators believed to be useful for treating PDE2 conditions, diseases or disorders such as Alzheimer's disease, cognitive impairment associated with schizophrenia, depression, migraines, and the like continues to exist. Inhibitors of PDE2 are not only believed to be useful in treating schizophrenia but also a wide variety of conditions or disorders that would benefit from increasing levels of cAMP and/or cGMP within neurons, including a variety neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to pyrimidone carboxamide compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Hunington's disease, and those associated with striatal hypofunction or basal ganglia dysfunction.

DETAILED DESCRIPTION OF THE INVENTION

The present invention is directed to pyrimidine carboxamide compounds of formula (I):

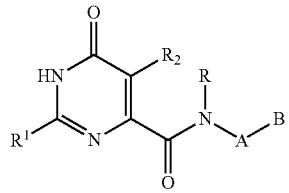

or a pharmaceutically acceptable salt or hydrate thereof, wherein:
A is $CR^4R^5$, $C_{3-6}$cycloalkyl, or $C_{4-6}$heterocyclyl, said cycloalkyl and heterocyclyl unsubstituted or substituted with 1 to 3 groups of $R^a$;
B is selected from the group consisting of phenyl, naphthyl, indolyl, $C_{3-6}$cycloalkyl, pyridyl, pyrimidinyl, piperonyl, benzodioxinyl, benzodioxolyl, benzofuranyl, or phthalanyl, said phenyl, naphthyl, indolyl, $C_{3-6}$cycloalkyl, pyridyl, pyrimidinyl, piperonyl, and phthalanyl unsubstituted or substituted with 1 to 3 groups of $R^a$;
R is hydrogen or $C_{1-6}$alkyl;
or R can combine with A and the nitrogen atom to which A is attached to form a five to six membered heterocycle, said heterocycle optionally substituted with one to three groups of $R^a$;
or R and B can combine with A and the nitrogen atom to which A is attached to form a five to ten membered heterocycle, said heterocycle optionally substituted with one to three groups of $R^a$;
$R^1$ is selected from the group consisting of H, $C_{1-6}$alkyl, $C_{1-6}$alkylSR, $C_{3-10}$cycloalkyl, $(CRR)_nC_{4-10}$heterocyclyl, and $(CRR)_nC_{6-10}$aryl, said alkyl, cycloalkyl, heterocyclyl and aryl optionally substituted with one to three groups of $R^a$;
$R^2$ is selected from the group consisting of hydrogen, $C_{1-6}$alkyl, $C_{3-10}$cycloallkyl, and $C_{1-4}$haloalkyl;
$R^4$ and $R^5$ are independently selected from H, $C_{1-6}$alkyl, $C_{3-10}$cycloalkyl, $C_{1-4}$hydroxyalkyl, and $C_{1-4}$haloalkyl, $(CH_2)_nSC_{1-6}$alkyl, $C(O)OR$, $C(O)N(R)_2$, CN, $(CH_2)_n$ $C_{5-10}$ heterocyclyl, and $(CH_2)_nC_{6-10}$aryl, said alkyl, cycloalkyl, heterocyclyl and aryl optionally substituted with one to three groups of $R^a$,
$R^a$ is selected from the group consisting of H, halo, CN, $C_{1-6}$alkyl, $(CH_2)_nOR$, $(O)_pC_{1-4}$haloalkyl, $C(O)OR$, $-O(CH_2)_nN(R)_2$, $(CHR)_nN(R)_2$, $NO_2$, $SCF_3$, $S(O)_sCF_3$, $S(O)_sR$, $SF_5$, $C_{3-10}$cycloalkyl, $C_{5-10}$heterocyclyl, and $C_{6-10}$aryl, said alkyl, cycloalkyl, heterocyclyl and aryl optionally substituted with one to three groups of $R^b$;
$R^b$ is selected from the group consisting of H, halo, $C_{1-6}$alkyl, $(CH_2)_nOR$, and $(O)_pC_{1-4}$haloalkyl;
n represents 0, 1, 2, 3, or 4;
s represents 0, 1, or 2; and
p represents 0 or 1,
with the proviso that the compound of formula I is not:
N-(1-(4-methoxyphenyl)propyl)-2-methyl-6-oxo-1,6-dihydropyrimidine-4-carboxamide,
N-(4-fluoro-3-methoxybenzyl)-2-methyl-6-oxo-1,6-dihydropyrimidine-4-carboxamide, N-((4-Methoxyphenyl)(phenyl)methyl)-2-methyl-6-oxo-1,6-dihydropyrimidine-4-carboxamide, N-(2,2-dimethylchroman-4-yl)-6-oxo-2-phenyl-1,6-dihydropyrimidine-4-carboxamide, N-(1-(2,3-dihydrobenzo[b][1,4]dioxin-6-yl)-2-phenylethyl)-2-methyl-6-oxo-1,6-dihydropyrimidine-4-carboxamide or 6-Oxo-N-((3-oxo-3,4-dihydro-2H-benzo[b][1,4]oxazin-6-yl)methyl)-1,6-dihydropyrimidine-4-carboxamide.

When n=0 for $(CRR)_n$heteroaryl or $(CRR)_nC_{5-10}$heterocyclyl for $R^1$, it is understood that the heteroaryl or $C_{5-10}$heterocyclylis connected to the pyrimidone core via a carbon atom.

An embodiment of the invention of formula I is realized when A is $CR^4R^5$.

Another embodiment of the invention of formula I is realized when A is $CR^4R^5$ and $R^4$ and $R^5$ are independently selected from the group consisting of hydrogen, $C_{1-6}$ alkyl, $C_{3-10}$cycloalkyl, $C_{1-4}$hydroxyalkyl, and $C_{1-4}$haloalkyl, $(CH_2)_nSC_{1-6}$ alkyl, $C(O)OR$, $C(O)N(R)_2$, CN, $(CH_2)_nC_{5-10}$heterocyclyl, and $(CH_2)_nC_{6-10}$ aryl, said alkyl, cycloalkyl, heterocyclyl and aryl optionally substituted with one to three groups of $R^a$.

Another embodiment of this aspect of the invention is realized when $R^4$ and $R^5$ are independently selected from the group consisting of H, $CH_3$, $CH_2CH_3$, $CH(CH_3)_2$, $C(CH_3)_3$, $CH_2OH$, $CH(CH_3)OH$, $C(CH_3)_2OH$, CN, $C(O)OR$ $C(O)N(R)_2$, cyclopropyl, cyclobutyl, cyclopentyl, tetrazolyl, or phenyl, said tetrazolyl substituted with $R^a$ and phenyl optionally substituted with one to three groups of $R^a$.

Another embodiment of the invention of formula I is realized when $R^4$ and $R^5$ are not both hydrogen at the same time.

Another subembodiment of this aspect of the invention is realized when $R^4$ and $R^5$ are both hydrogen at the same time when $R^1$ is optionally substituted phenyl, $CH_3$, $CH_2CH_3$, or cyclopropyl Another embodiment of this aspect of the invention when A is $CR^4R^5$ is realized when one of $R^4$ and $R^5$ is hydrogen and the other is selected from $C_{1-6}$alkyl, $C_{3-10}$cycloalkyl, $C_{1-4}$hydroxyalkyl, and $C_{1-4}$ haloalkyl, $(CH_2)_nSC_{1-6}$alkyl, $C(O)OR$, $C(O)N(R)_2$, CN, $(CH_2)_nC_{5-10}$heterocyclyl, and $(CH_2)_nC_{6-10}$aryl, said alkyl, cycloalkyl, heterocyclyl and aryl optionally substituted with one to three groups of $R^a$. A subembodiment of this aspect of the invention is realized when one of $R^4$ and $R^5$ is hydrogen and the other is $CH_3$, $CH_2CH_3$, $CH(CH_3)_2$, $C(CH_3)_3$, $CH_2OH$, $CH(CH_3)OH$, $C(CH_3)_2OH$, CN, $C(O)OR$ $C(O)N(R)_2$, cyclopropyl, cyclobutyl, cyclopentyl, tetrazolyl, or phenyl, said tetrazolyl substituted with $R^a$ and phenyl optionally substituted with one to three groups of $R^a$. Still another subembodiment of this aspect of the invention is realized when one of $R^4$ and $R^5$ is hydrogen and the other is $CH_3$, $CH_2CH_3$, $CH(CH_3)_2$, $C(CH_3)_3$, $CH_2OH$, $CH(CH_3)OH$, $C(CH_3)_2OH$, CN, $C(O)OR$ $C(O)N(R)_2$. Still another subembodiment of this aspect of the invention is realized when one of $R^4$ and $R^5$ is hydrogen and the other is $CH_3$. Another subembodiment of this aspect of the invention is realized when one of $R^4$ and $R^5$ is hydrogen and the other is cyclopropyl, cyclobutyl, or cyclopentyl. Another subembodiment of this aspect of the invention is realized when one of $R^4$ and $R^5$ is hydrogen and the other is tetrazolyl, or phenyl, said tetrazolyl substituted with $R_a$ and phenyl optionally substituted with one to three groups of $R^a$. Still another subembodiment of this aspect of the invention is realized when one of $R^4$ and $R^5$ is hydrogen and the other is $CH_3$.

Another embodiment of the invention when A is $CR^4R^5$ is realized when both $R^4$ and $R^5$ are $CH_3$.

Another embodiment of the invention of formula I is realized when A is $C_{3-6}$cycloalkyl. A subembodiment of this aspect of the invention is realized when the cycloalkyl is cyclopropyl, cyclobutyl, or cyclopentyl. Another subembodiment of this aspect of the invention is realized when A is cyclopropyl. Another subembodiment of this aspect of the invention is realized when A is cyclobutyl. Another subembodiment of this aspect of the invention is realized when A is cyclopentyl.

Another embodiment of the invention of formula I is realized when A is $C_{4-6}$ heterocyclyl, said heterocyclyl optionally substituted with one to three groups of $R^a$. A subembodiment of this aspect of the invention is realized when the heterocyclyl is oxetane.

Another embodiment of the invention of formula I is realized when $R^a$ is selected from H, OH, halo, $CH_3$, $CH_2CH_3$, $CH(CH_3)_2$, $C(CH_3)_3$, $C(O)OCH_3$, $OCH_3$, $OC(CH_3)_2$, $CH_2F$, $CF_3$, $OCHF_2$, $OCF_3$, $CH_2CF_3$, $SCH_3$, $SCF_3$, $SF_5$, $SOCF_3$, $SO_2CF_3$, $SO_2CH_3$, $CH_2NH_2$, $(CH_2)_nN(CH_3)_2$, $NO_2$, CN, cyclopropyl, phenyl, naphthyl, pyrimidinyl, pyridyl, said cyclopropyl, phenyl, naphthyl, pyrimidinyl, and pyridyl optionally substituted with one to three groups of Rb.

Still another embodiment of the invention of formula I is realized when B is selected from the group consisting of phenyl, naphthyl, indolyl, pyridyl, pyrimidinyl, piperonyl, benzodioxolyl, benzfuranyl, benzodioxinyl or phthalanyl, said phenyl, naphthyl, indolyl, pyridyl, pyrimidinyl, piperonyl, benzodioxolyl, benzfuranyl, benzodioxinyl and phthalanyl, said groups optionally substituted with one, two, or three groups of $R^a$. A subembodiment of this aspect of the invention is realized when there is one $R^a$ substituent on B. Another subembodiment of this aspect of the invention is realized when there are two $R^a$ substituents on B. Still another subembodiment of this aspect of the invention is realized when there are three $R^a$ substituents on B.

Another embodiment of the invention of formula I is realized when B is unsubstituted or substituted phenyl.

Another embodiment of the invention of formula I is realized when B is unsubstituted or substituted naphthyl.

Another embodiment of the invention of formula I is realized when B is unsubstituted or substituted indolyl.

Another embodiment of the invention of formula I is realized when B is unsubstituted or substituted pyridyl. A sub-embodiment of this aspect of the invention of formula I is realized when B is substituted pyridyl.

Another embodiment of the invention of formula I is realized when B is unsubstituted or substituted pyrimidinyl. A sub-embodiment of this aspect of the invention of formula I is realized when B is substituted pyrimidinyl.

Another embodiment of the invention of formula I is realized when B is unsubstituted or substituted piperonyl.

Another embodiment of the invention of formula I is realized when B is unsubstituted or substituted phthalanyl.

Another embodiment of the invention of formula I is realized when B is unsubstituted or substituted benzodioxinyl.

Another embodiment of the invention of formula I is realized when B is unsubstituted or substituted benzodioxolyl.

Another embodiment of the invention of formula I is realized when B is unsubstituted or substituted benzofuranyl.

Still another embodiment of the invention of formula I is realized when R is hydrogen.

Yet another embodiment of the invention of formula I is realized when R and B together with A and the nitrogen atom to which A is attached combine to form a five to 10 membered heterocycle, said heterocycle optionally substituted with one to three groups of $R^a$. A subembodiment of this aspect of the invention is realized when R and B together with A and the nitrogen atom to which it is attached combine to form isochromenyl, tetrahydronaphthalenyl, piperidinyl, or pyrrolopyrimidinyl.

Another embodiment of the invention of formula I is realized when $R^1$ is hydrogen.

Another embodiment of the invention of formula I is realized when $R^1$ is optionally substituted $C_{1-6}$alkyl. A subembodiment of this aspect of the invention is realized when the optionally substituted alkyl is $CH_3$, $CH_2CH_3$, or $CH_2OCH_3$.

Another embodiment of the invention of formula I is realized when $R^1$ is optionally substituted $C_{3-10}$cycloalkyl. A subembodiment of this aspect of the invention is realized when the cycloalkyl is cyclopropyl, or cyclobutyl.

Another embodiment of the invention of formula I is realized when $R^1$ is optionally substituted $(CRR)_nC_{5-10}$heteroaryl wherein n is 0 or 1. A subembodiment of $(CRR)_nC_{5-10}$heteroaryl is realized when n is 0. Another subembodiment of $(CRR)_nC_{5-10}$heteroaryl is realized when n is 1. A subembodiment of this aspect of the invention is realized when the heteroaryl is pyrimidinyl, thiazolyl, oxazolyl, or pyrazolyl. Another subembodiment of this aspect of the invention is realized when the heteroaryl is optionally substituted pyrimidinyl. Another subembodiment of this aspect of the invention is realized when the heteroaryl is optionally substituted pyrazolyl. Another subembodiment of this aspect of the invention is realized when the heteroaryl is optionally substituted thiazolyl. Another subembodiment of this aspect of the invention is realized when the heteroaryl is optionally substituted oxazolyl.

An embodiment of the invention of formula I is realized when $R^1$ is optionally substituted $(CRR)_nC_{6-10}$aryl, wherein n is 0 or 1. A subembodiment of $(CRR)_nC_{6-10}$aryl is realized when n is 0. Another subembodiment of $(CRR)_nC_{6-10}$aryl is realized when n is 1. Another subembodiment of this aspect of the invention is realized when the aryl is unsubstituted or substituted phenyl.

Another embodiment of this aspect of the invention is realized when $(CRR)_nC_{6-10}$aryl is unsubstituted or substituted phenyl, or benzyl and the n is 0 or 1.

An embodiment of the invention of formula I is realized when $R^2$ is selected from the group consisting of hydrogen, $CH_3$, $CH_2CH_3$, or cyclobutyl. A subembodiment of this aspect of the invention is realized when $R^2$ is hydrogen.

Still another embodiment of the invention of formula I is represented by structural formula II:

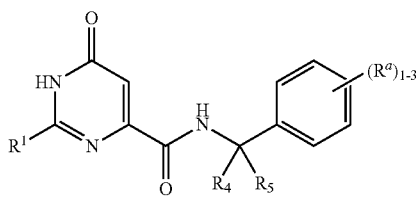

II and pharmaceutically acceptable salts and hydrates thereof, wherein: $R^1$, $R^4$, $R^5$ and $R^a$ are as previously described.

The compound of formula II which includes the hydroxypryimidine compounds.

Another embodiment of the invention of formula II is realized when $R^1$ is optionally substituted $C_{1-6}$alkyl. Another embodiment of the invention of formula II is realized when $R^1$ is optionally substituted $C_{3-10}$cycloalkyl. Another embodiment of the invention of formula II is realized when $R^1$ is optionally substituted $(CRR)_nC_{5-10}$heteroaryl, wherein n is 0 or 1. An embodiment of the invention of formula II is realized when $R^1$ is optionally substituted $(CRR)_nC_{6-10}$aryl wherein n is 0 or 1. Another subembodiment of this aspect of the invention is realized when the aryl is optionally substituted phenyl.

Another embodiment of the invention of formula II is realized when $R^1$ is selected from the group consisting of optionally substituted $CH_3$, $CH_2CH_3$, or $CH_2OCH_3$, cyclopropyl, cyclobutyl, phenyl, pyrimidinyl, benzyl, or pyrazolyl. A subembodiment of this aspect of the invention of formula II is realized when $R^1$ is $CH_3$. Another subembodiment of this aspect of the invention of formula II is realized when $R^1$ is $CH_2OCH_3$. A subembodiment of this aspect of the invention of formula II is realized when $R^1$ is optionally substituted $(CRR)_n$phenyl. A subembodiment of this aspect of the invention of formula II is realized when $R^1$ is optionally substituted pyrimidinyl. A subembodiment of this aspect of the invention of formula II is realized when $R^1$ is optionally substituted benzyl. A subembodiment of this aspect of the invention of formula II is realized when $R^1$ is cyclopropyl. A subembodiment of this aspect of the invention of formula II is realized when $R^1$ is cyclobutyl.

Another embodiment of the invention of formula II is realized when one of $R^4$ and $R^5$ is hydrogen and the other is $CH_3$, $CH_2CH_3$, $CH(CH_3)_2$, $C(CH_3)_3$, $CH_2OH$, $CH(CH_3)OH$, $C(CH_3)_2OH$, CN, $C(O)OR$ $C(O)N(R)_2$, cyclopropyl, cyclobutyl, cyclopentyl, tetrazolyl, or phenyl, said tetrazolyl substituted with $R^a$ and phenyl optionally substituted with one to three groups of $R^a$. A subembodiment of this aspect of the invention of formula II is realized when one of $R^4$ and $R^5$ is hydrogen and the other is $CH_3$, $CH_2CH_3$, $CH(CH_3)_2$, $C(CH_3)_3$, $CH_2OH$, $CH(CH_3)OH$, $C(CH_3)_2OH$. A subembodiment of this aspect of the invention of formula II is realized when one of $R^4$ and $R^5$ is hydrogen and the other is cyclopropyl, cyclobutyl, or cyclopentyl. Still a subembodiment of this aspect of the invention of formula II is realized when one of $R^4$ and $R^5$ is hydrogen and the other is optionally substituted tetrazolyl or phenyl.

Another embodiment of the invention of formula II is realized when both $R^4$ and $R^5$ are $CH_3$.

Another embodiment of the invention of formula II is realized when $R^1$ is selected from the group consisting of $CH_3$, $CH_2CH_3$, or $CH_2OCH_3$, cyclopropyl, cyclobutyl, or optionally substituted $(CRR)_n$phenyl, pyrimidinyl, benzyl, or pyrazolyl and one of $R^4$ and $R^5$ is hydrogen and the other is $CH_3$, $CH_2CH_3$, $CH(CH_3)_2$, $C(CH_3)_3$, $CH_2OH$, $CH(CH_3)OH$, $C(CH_3)_2OH$, CN, $C(O)OR$ $C(O)N(R)_2$, cyclopropyl, cyclobutyl, cyclopentyl, tetrazolyl, or phenyl, said tetrazolyl and phenyl optionally substituted with one to three groups of $R^a$. Another subembodiment of the invention of formula II is realized when $R^1$ is $CH_3$, and one of $R^4$ and $R^5$ is hydrogen and the other is $CH_3$, $CH_2CH_3$, $CH(CH_3)_2$, $C(CH_3)_3$, $CH_2OH$, $CH(CH_3)OH$, $C(CH_3)_2OH$, CN, $C(O)OR$ $C(O)N(R)_2$, cyclopropyl, cyclobutyl, cyclopentyl, tetrazolyl, or phenyl, said tetrazolyl substituted with $R^a$ and phenyl optionally substituted with one to three groups of $R^a$. Another subembodiment of the invention of formula II is realized when $R^1$ is optionally substituted $(CH_2)_n$ phenyl, and one of $R^4$ and $R^5$ is hydrogen and the other is $CH_3$, CH$_2$CH$_3$, CH(CH$_3$)$_2$, C(CH$_3$)$_3$, CH$_2$OH, CH(CH$_3$)OH, C(CH$_3$)$_2$OH, CN, C(O)OR C(O)N(R)$_2$, cyclopropyl, cyclobutyl, cyclopentyl, tetrazolyl, or phenyl, said tetrazolyl substituted with R$^a$ and phenyl optionally substituted with one to three groups of R$^a$. Another subembodiment of the invention of formula II is realized when R$^1$ is optionally substituted pyrimidinyl, and one of R$^4$ and R$^5$ is hydrogen and the other is CH$_3$, CH$_2$CH$_3$, CH(CH$_3$)$_2$, C(CH$_3$)$_3$, CH$_2$OH, CH(CH$_3$)OH, C(CH$_3$)$_2$OH, CN, C(O)OR C(O)N(R)$_2$, cyclopropyl, cyclobutyl, cyclopentyl, tetrazolyl, or phenyl, said tetrazolyl substituted with R$^a$ and phenyl optionally substituted with one to three groups of R$^a$. Another subembodiment of the invention of formula II is realized when R$^1$ is cyclopropyl, and one of R$^4$ and R$^5$ is hydrogen and the other is CH$_3$, CH$_2$CH$_3$, CH(CH$_3$)$_2$, C(CH$_3$)$_3$, CH$_2$OH, CH(CH$_3$)OH, C(CH$_3$)$_2$OH, CN, C(O)OR C(O)N(R)$_2$, cyclopropyl, cyclobutyl, cyclopentyl, tetrazolyl, or phenyl, said tetrazolyl substituted with R$^a$ and phenyl optionally substituted with one to three groups of R$^a$.

Still another embodiment of the invention of formula I is represented by structural formula III:

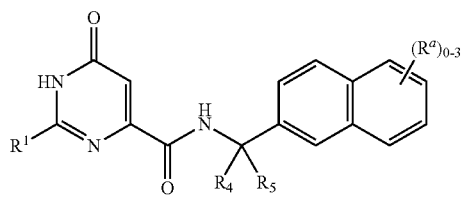

III and pharmaceutically acceptable salts and hydrates thereof, wherein: R$^1$, R$^4$, R$^5$ and R$^a$ are as previously described. A subembodiment of the invention of formula III is realized when R$^1$ is selected from the group consisting of optionally substituted CH$_3$, CH$_2$CH$_3$, or CH$_2$OCH$_3$, cyclopropyl, cyclobutyl, or (CRR)$_n$phenyl, pyrimidinyl, or pyrazolyl and one of R$^4$ and R$^5$ is hydrogen and the other is CH$_3$, CH$_2$CH$_3$, CH(CH$_3$)$_2$, C(CH$_3$)$_3$, CH$_2$OH, CH(CH$_3$)OH, C(CH$_3$)$_2$OH, CN, C(O)OR C(O)N(R)$_2$, cyclopropyl, cyclobutyl, cyclopentyl, tetrazolyl, or phenyl, said tetrazolyl substituted with R$^a$ and phenyl optionally substituted with one to three groups of R$^a$. The compound of formula III which includes the hydroxypryimidine compounds.

Yet another embodiment of the invention of formula I is realized when both R and R$^2$ are hydrogen, A is cyclopropyl, cyclobutyl, or cyclopentyl, B is optionally substituted phenyl, naphthyl, pyridyl, pyrimidinyl, piperonyl, or phthalanyl, R is selected from the group consisting of CH$_3$, CH$_2$CH$_3$, CH$_2$OCH$_3$, cyclopropyl, cyclobutyl, or optionally substituted phenyl, pyrimidinyl, or pyrazolyl and one of R$^4$ and R$^5$ is hydrogen and the other is CH$_3$, CH$_2$CH$_3$, CH(CH$_3$)$_2$, C(CH$_3$)$_3$, CH$_2$OH, CH(CH$_3$)OH, C(CH$_3$)$_2$OH, CN, C(O) OR C(O)N(R)$_2$, cyclopropyl, cyclobutyl, cyclopentyl, tetrazolyl, or phenyl, said tetrazolyl substituted with R$^a$ and phenyl optionally substituted with one to three groups of R$^a$.

Another embodiment of the invention of formula I is realized when both R and R$^2$ are hydrogen, A is a bond, B is optionally substituted phenyl, naphthyl, pyridyl, pyrimidinyl, piperonyl, or phthalanyl, R$^1$ is selected from the group consisting of optionally substituted CH$_3$, CH$_2$CH$_3$, CH$_2$OCH$_3$, cyclopropyl, cyclobutyl, or phenyl, pyrimidinyl, or pyrazolyl and one of R$^4$ and R$^5$ is hydrogen and the other is CH$_3$, CH$_2$CH$_3$, CH(CH$_3$)$_2$, C(CH$_3$)$_3$, CH$_2$OH, CH(CH$_3$) OH, C(CH$_3$)$_2$OH, CN, C(O)OR C(O)N(R)$_2$, cyclopropyl, cyclobutyl, cyclopentyl, tetrazolyl, or phenyl, said tetrazolyl substituted with R$^a$ and phenyl optionally substituted with one to three groups of R$^a$.

The invention is also directed to a method for the treatment of central nervous system disorders associated with phosphodiesterase 2 (PDE2) using the compounds of Formula I. More specifically, the present invention relates to the use of such compounds for treating neurological and psychiatric disorders, such as schizophrenia, psychosis, Alzheimer's, cognitive impairment, anxiety, depression, migraines, or Huntington's disease, and those associated with striatal hypofunction or basal ganglia dysfunction using the compounds of formula I.

Examples of compounds of the invention can be found throughout the specification.

The invention also encompasses pharmaceutical compositions containing a compound of formula I, II and/or III, and methods for treatment or prevention of phosphodiesterase mediated diseases using compounds of formula I, II and/or III.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds.

As used herein, the term "alkyl," by itself or as part of another substituent, means a saturated straight or branched chain hydrocarbon radical having the number of carbon atoms designated (e.g., C$_{1-10}$ alkyl means an alkyl group having from one to ten carbon atoms). Preferred alkyl groups for use in the invention are C$_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. C$_0$ alkyl means a bond.

As used herein, the term "cycloalkyl," by itself or as part of another substituent, means a saturated cyclic hydrocarbon radical having the number of carbon atoms designated (e.g., C$_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic C$_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure.

The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

It should be appreciated by any one skilled in the art that the compounds of this invention can exist in several tautomeric forms as shown below:

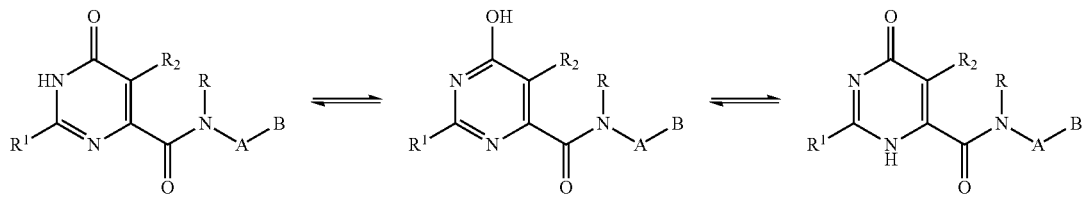

Previous researchers have studied similar compounds and found that one of these tautomers can exist as the predominant form depending on structures and conditions. See B. M. Giuliano, et al. J. Phys. Chem. A, 114, 12725-12730, 2010; B. M. Giuliano, et al. J. Phys. Chem. A, 115, 8178-8179, 2011; A. Gerega, et al. J. Phys. Chem. A, 111, 4934-4943, 2007; R. Sanchez, et al., J. Amer. Chem. Soc., 129(19), 6287-6290, 2007; C. Lopez, et al., Spectroscopy 14, 121-126, 2000; and G. M. Kheifets, et al., Russ. J. Org. Chem., 36(9), 1373-1387, 2000. For brevity and simplicity, we have represented the compounds of the present invention using Formula I and it is intended to represent all possible tautomeric forms for these compounds without regard to what actually is the predominant tautomeric form in existence for a particular compound.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula I, II and III. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically enriched compounds within generic formula I, II and III can be prepared without undue experimentation by conventional techniques well known to those skilled in the art or by processes analogous to those described in the Schemes and Examples herein using appropriate isotopically enriched reagents and/or intermediates.

The term "substantially pure" means that the isolated material is at least 90% pure, and preferably 95% pure, and even more preferably 99% pure as assayed by analytical techniques known in the art.

For purposes of this specification, the following abbreviations have the indicated meanings:

Ac=acetyl
ACN=acetonitrile
AcO=acetate
BOC=t-butyloxycarbonyl
CBZ=carbobenzoxy
CDI=carbonyldiimidazole
DCC=1,3-dicyclohexylcarbodiimide
DCE=1,2-dichloroethane
(dF(CF3)ppy)=2-(2,4-difluorophenyl)-5-trifluoromethylpyridine
DI=de-ionized
DIBAL=diisobutyl aluminum hydride
DIPEA or DIEA=N,N-diisoproylethylamine, also known as Hunig's base
DMA=dimethylacetamide
DMAP=4-(dimethylamino)pyridine
DMF=dimethylformamide
DMP=Dess-Martin periodinane
DPPA=Diphenylphosphoryl azide
DPPP=1,3-bis(diphenylphosphino)propane
Dtbbpy=4,4'-di-tert-butyl-2,2'-dipyridyl
EDC or EDCI=1-(3-dimethylaminopropyl)-3-ethylcarbodiimide hydrochloride
EDTA=ethylenediaminetetraacetic acid, tetrasodium salt Hydrate
EtOAc=ethyl acetate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluroniumhexafluorophosphate
HOAt=1-Hydroxy-7-azabenzotriazole
HOBt=1-hydroxybenzotriazole
HRMS=high resolution mass spectrometry
ICBF=isobutyl chloroformate
KHMDS=potassium hexamethyldisilazane
LC-MS=Liquid chromatography-mass spectrometry
LDA=lithium diisopropylamide
LiHMDS=lithium hexamethyldisilazane
MCPBA=metachloroperbenzoic acid
MMPP=magnesium monoperoxyphthlate hexahydrate
Ms=methanesulfonyl=mesyl
MsO=methanefulfonate=mesylate
MTBE=Methyl t-butyl ether
NBS=N-bromosuccinimide
NMM=4-methylmorpholine
NMP=N-methylpyrrolidinone
NMR=Nuclear magnetic resonance
PCC=pyridinium chlorochromate
PDC=pyridinium dichromate
Ph=phenyl
PPTS=pyridinium p-toluene sulfonate
pTSA=p-toluene sulfonic acid
PyH·Br3=pyridine hydrobromide perbromide
r.t./RT=room temperature
rac.=racemic
T3P=2,4,6-Tripropyl-1,3,5,2,4,6-trioxatriphosphinane 2,4,6-trioxide
TFA=trifluoroacetic acid
TfO=trifluoromethanesulfonate=triflate
THF=tetrahydrofuran
TLC=thin layer chromatography
TMSCI=trimethylsilyl chloride The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE2 dysfunction in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE2 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 function in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

Treating" or "treatment of" a disease state includes: 1 prevention 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to enhance cellular signaling. Without wishing to be bound by any theory, applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment the compounds of this invention there is provided a method for treating or ameliorating diseases or conditions in neuronal development, learning, and memory, prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "'selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. Preferably, a selective PDE2 inhibitor is an organic molecule, having a Ki for inhibition of PDE2 that is less than or about five-hundredth that for a substance that is an inhibitor for another PDE enzyme. In other words, the organic molecule inhibits PDE2 activity to the same degree at a concentration of about five-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE 10 and/or PDE11A.

Phosphodiesterase enzymes including PDE2 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, *cannabis*, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temperal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, *cannabis*, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder, an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Angiogenesis is the physiological process through which new blood vessels form, and agents that inhibit this process have been shown to be effective treatments for some cancers. As initiation of angiogenesis involves migration and proliferation of vascular endothelial cells, and agents that elevate cAMP inhibit these processes, PDE2 inhibition may have utility as a treatment for cancer. See Savai, et al, *Targeting cancer with phosphodiesterase inhibitors*, Expert Opin. Investig. Drugs (2010) 19(1):117-131. PDE2 has been shown to be expressed in human vascular endothelial cells (VECs) and inhibition of PDE2 by treatment with selective inhibitors inhibited VEGF promoted migration of VECs. See Netherton and Maurice, *Vascular Endothelial Cell Cyclic Nucleotide Phosphodiesterases and Regulated Cell Migration: Implications in Angiogenesis*, Mol Pharmacol (2005) 67:263-272 and Favot, et al, *VEGF-induced HUVEC migration and proliferation are decreased by PDE2 and PDE4 inhibitors*. Thromb Haemost (2003) 90:334-343. Reduction of PDE2 activity with either small molecule inhibitors or PDE2A siRNA suppressed cell growth and invasion in a human malignant melanoma PMP cell line. See Hiramoto, et al, *Role of phosphodiesterase 2 in growth and invasion of human malignant melanoma cells*, Cellular Signalling (2014), 26:1807-1817. Reduction of PDE2 activity with a small molecule inhibitor attenuated tumor formation in a mouse model of ultraviolet light B-induced tumorigenesis. See Bernard, et al, *PDE2 is a Novel Target for Attenuating Tumor Formation in a Mouse Model of UVB-Induced Skin Carcinogenesis*, PLoS ONE (2014), 9(10):e109862. Thus, in another specific embodiment, compounds of the invention provide methods for treating, preventing, controlling, and/or reducing, attenuating cancers, such as malignant melanomas, skin cancer, and the like.

The subject compounds may be further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, AChEis (Aricept (donepezil)) and NMDA blocker Namenda (memantine), beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with thesubject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an antidepressant or antianxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, $5-HT_{1A}$ agonists or antagonists, especially $5-HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods, schemes, and examples for preparing representative compounds of this invention are illustrated below and can be found in further detail in U.S. Pat. No. 7,144,913, which is incorporated by reference herein in its entirety. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

The representative examples of the compounds of the invention are illustrated in the following non-limiting schemes and Examples.

General

Starting materials used were obtained from commercial sources or prepared in other examples, unless otherwisely noted.

The progress of reactions was often monitored by TLC or LC-MS. The LC-MS was recorded using one of the following methods.

Method A

Column: BEH C-18 column (1×50 mm, 1.7 μm)

Mobile Phase A: 0.05% TFA in Water

Mobile Phase B: 0.05% TFA in Acetonitrile

Detection: 215 nm

TABLE A

| Method A Gradient | | | | |
|---|---|---|---|---|
| Time(min) | Flow(mL/min) | Temperature (C.) | % A | % B |
| 0 | 0.3 | 50 | 90 | 10 |
| 1.6 | 0.3 | 50 | 5 | 99 |
| 2.0 | 0.3 | 50 | 5 | 99 |

Method B: Supelco Ascentis Express C18, 3×50 mm, 2.7 um column. 2.0 uL injection, 1.25 ml/min flow rate, 170-900 amu scan range, 200-400 nm UV range, 10-99% (over 2.0 min) gradient with MeCN (0.05% TFA) and water (0.05%); 3 minute total run time.

Method C: Supelco Ascentis Express C18, 3×100 mm, 2.7 um column. 2.0 uL injection, 1.00 ml/min flow rate, 170-900 amu scan range, 200-400 nm UV range, 10-99% (over 4.0 min) gradient with MeCN (0.05% TFA) and water (0.05%); 5 minute total run time.

Method D: Waters Acquity UPLC, HSS C18 1.8 um, 2.1×50 mm, MeCN and water with 0.1% trifluoroacetic acid, 1 mL/min flow rate, gradient 5%-100% MeCN over 1.4 min.

Method E: Waters Acquity UPLC, HSS C18 1.8 um, 2.1×50 mm, MeCN and water with 0.1% formic acid, 1 mL/min flow rate, gradient 5%-100% MeCN over 1.4 min.

NMR was recorded at room temperature unless noted otherwise on Varian Inova 400 or 500 MHz spectrometers with the solvent peak used as the reference.

The methods used for the preparation of the compounds of this invention are illustrated by the following schemes. Often it involves an amide coupling of a carboxylic acid and enantiomerically pure or enriched amine or its HCl salt to yield the desired product. When a racemic amine was used, the resulting enantiomers were separated by chiral SFC. Unless specified otherwise, the acids and amines or amines salts used are commercially available. Schemes A-C, E, H, and I illustrated several conditions used for coupling of acids and amines. People with ordinary skills in the art will be able to find many more different coupling reagents to prepare amides from acids or their derivatives plus amines.

Scheme A
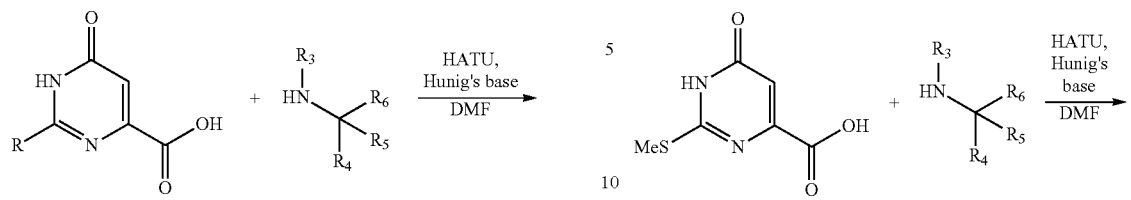
Scheme B
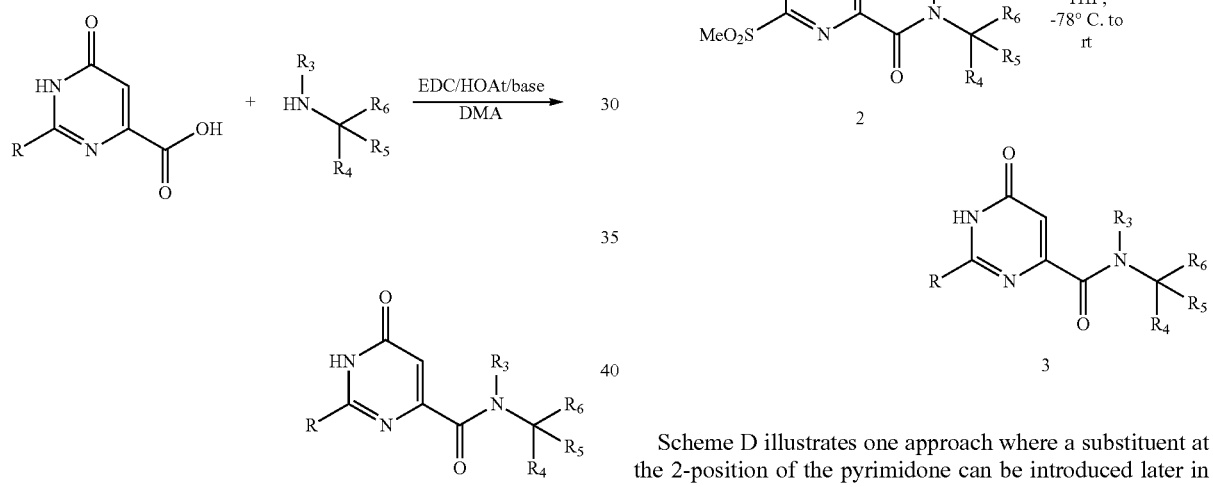
Scheme C
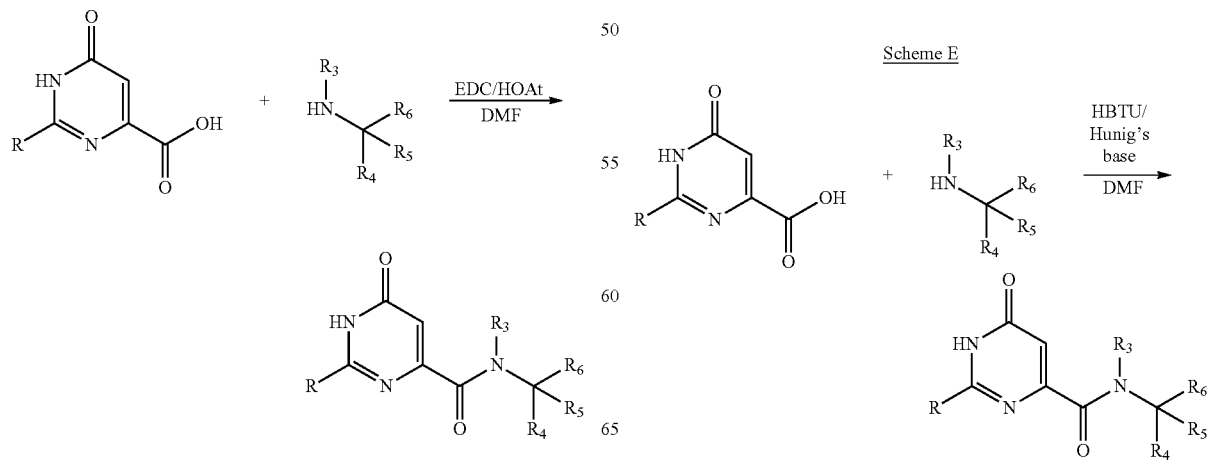
Scheme D
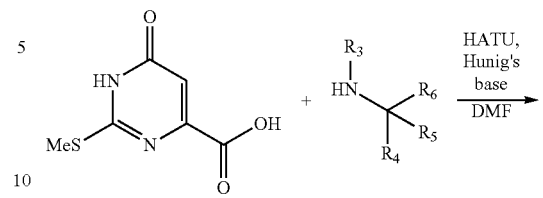
Scheme D illustrates one approach where a substituent at the 2-position of the pyrimidone can be introduced later in the sequence. If the amine used is racemic, the intermediate compound 1 can be resolved by chiral separation to give individual enantiomers before they are converted to compounds 2 and 3.
Scheme E

Scheme F

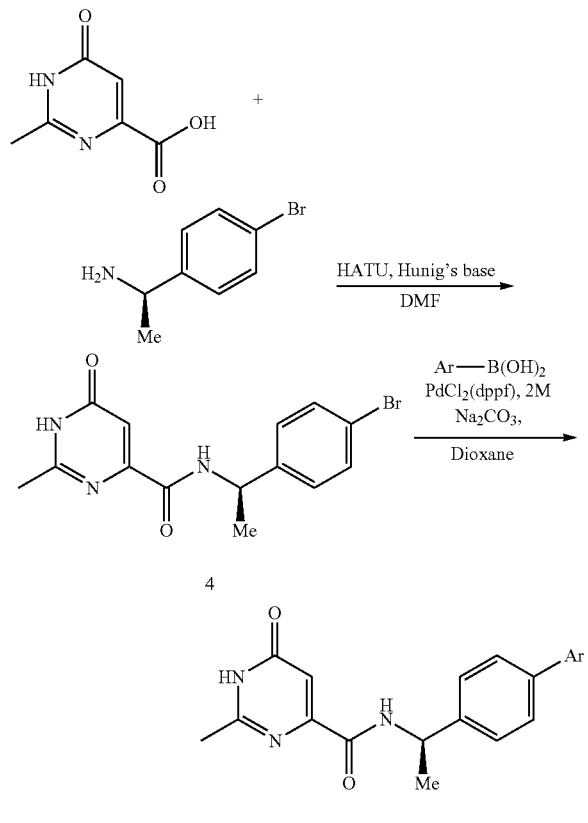

In Scheme F, intermediate 4 was prepared using the procedure in Scheme A and used in a Suzuki coupling to prepare various derivatives 5.

Scheme G

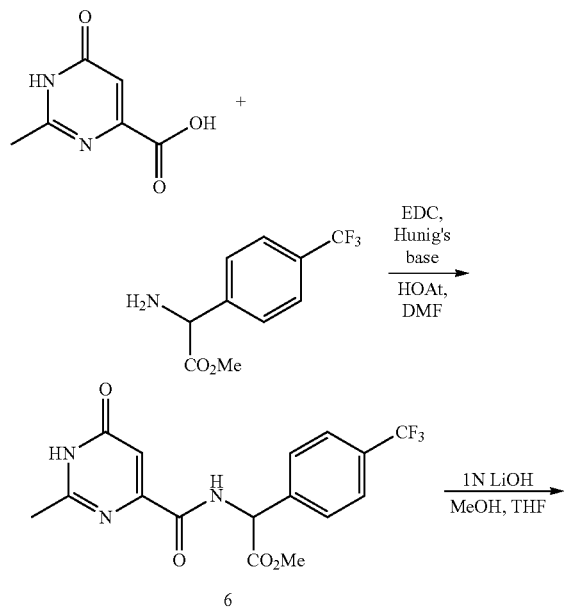

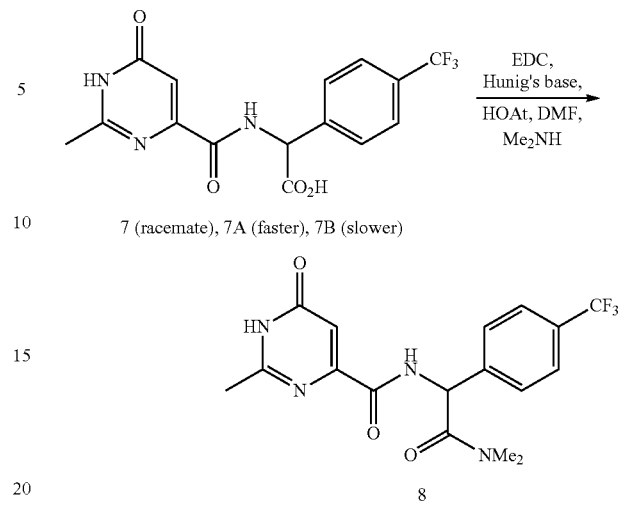

In Scheme G, compound 6 was prepared using procedure described in Example 15 and Scheme B using commercially available carboxylic acid and racemic amine HCl salt. Subsequent hydrolysis of 6 afforded racemate 7. 7A and 7B were isolated from 7 after chiral chromatography. Compound 8 was prepared by amide coupling of 7 with dimethylamine.

Scheme H

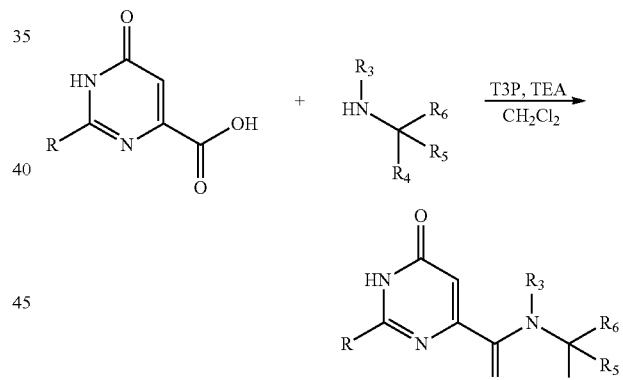

In Scheme H, amide coupling was conducted using yet another reagent 2,4,6-tripropyl-1,3,5,2,4,6-trioxatriphosphinane 2,4,6-trioxide (T3P) in the presence of triethylamine (TEA) in dichloromethane.

Scheme I

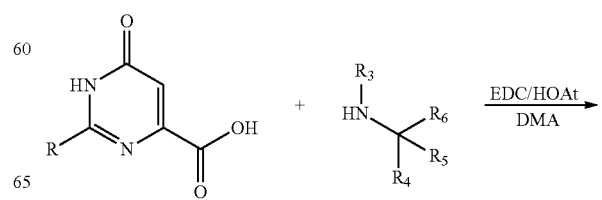

31
-continued

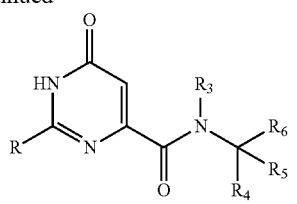

Scheme I shows yet another method for the preparation of the compounds of this invention. This method is the same as that described for Scheme C except a slightly different solvent was used in Scheme I. Other experimental details are the same as in Scheme C.

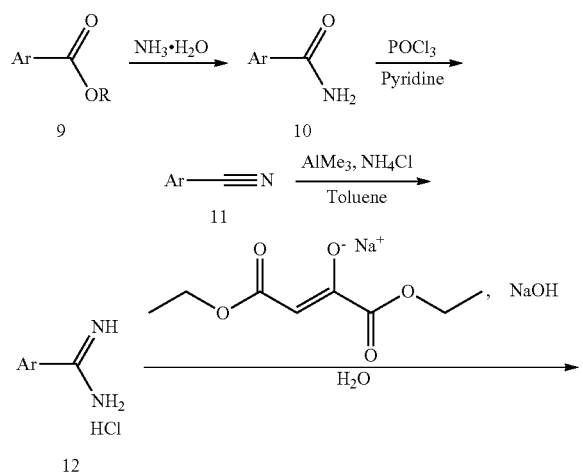

Scheme J illustrates the procedures for the syntheses of pyrimidone carboxylic acids such as 13. Aryl ester 9 is converted to amide 10 using ammonia. The latter is dehydrated to nitrile 11 using a dehydrating agent such as phosphorus oxychloride in pyridine. The nitrile 11 is converted to amidine 12, which is condensed with an enolate salt shown to afford intermediate 13 after in situ hydrolysis of an ester intermediate using sodium hydroxide.

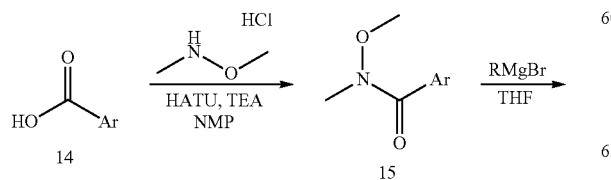

32
-continued

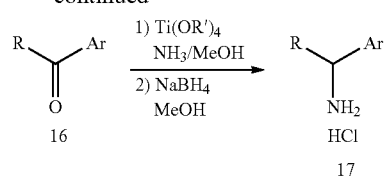

Scheme K illustrates one procedure for the syntheses of amines such as 17. The coupling of aryl carboxylic acid 14 and N,O-dimethylhydroxylamine hydrochloride gives Weinreb amide 15. The ketone 16 is obtained by addition of a Grignard reagent RMgBr to the Weinreb amide 15. The ketone 16 is converted to amine 17 via a reductive amination using Ti(OR')$_4$, NH$_3$ and NaBH$_4$.

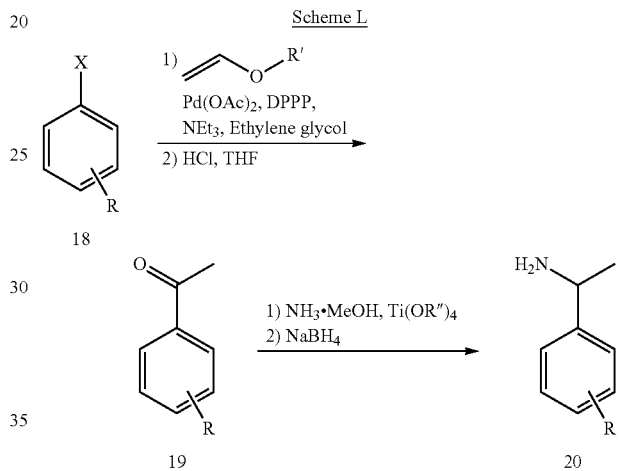

Scheme L illustrates another procedure for the syntheses of amines such as 20. Aryl halide 18 is converted to ketone 19 using a Heck reaction followed by hydrolysis. The ketone 19 is converted to amine 20 via a reductive amination reaction using Ti(OR")$_4$, NH$_3$ and NaBH$_4$.

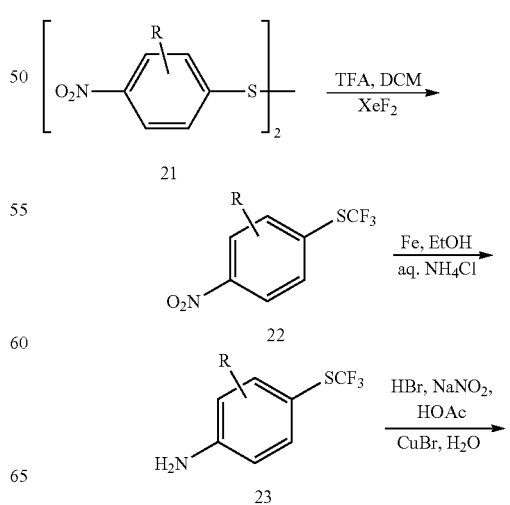

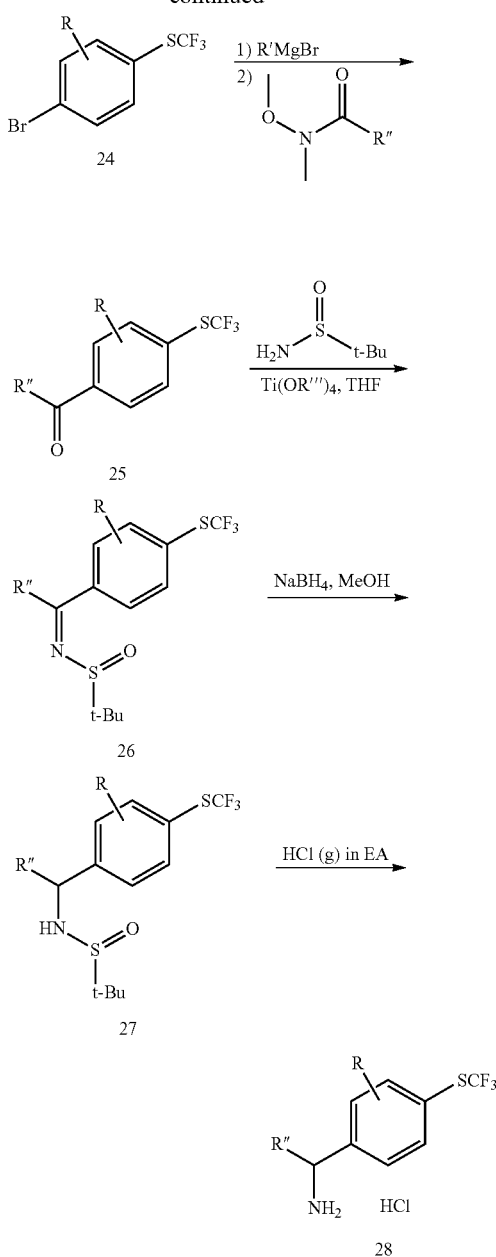

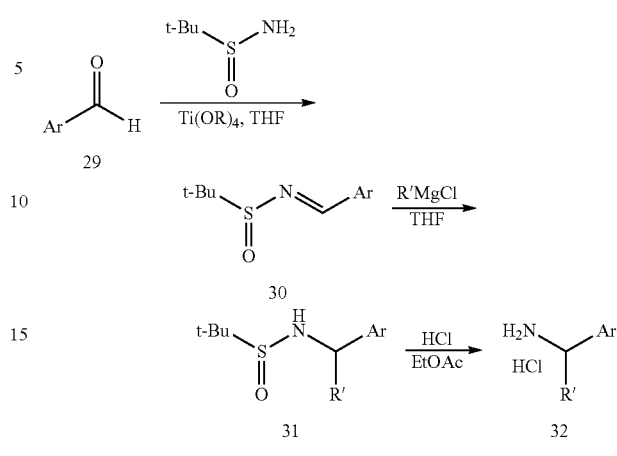

Scheme N illustrates another sequence for the syntheses of amines such as 32. The condensation of aldehyde 29 and tert-butanesulfinamide in the presence of Ti(OR)$_4$ in THF gives sulfinimine 30. Addition of a Grignard reagent R'MgCl to sulfinimine 30 in THF leads to sulfinamide 31. The sulfinyl group is readily removed under acidic conditions to give amine 32.

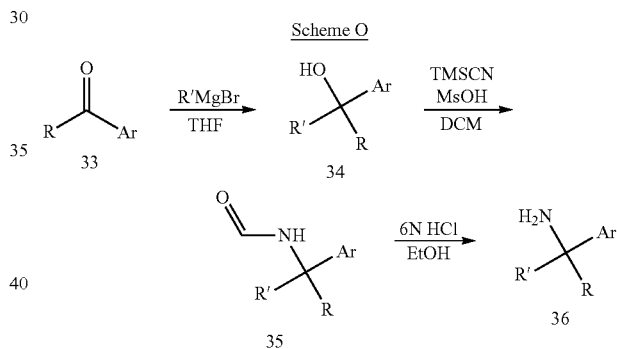

Scheme O illustrates one sequence for the syntheses of amines such as 36. Arylalkylketone 33 is converted to tertiary alcohol 34 via a nucleophilic addition using a Grignard reagent R'MgBr. The alcohol 34 is converted to formamide 35 via a Ritter reaction using TMSCN under acidic conditions. The formamide 35 is hydrolyzed under acidic conditions to afford the amine 36.

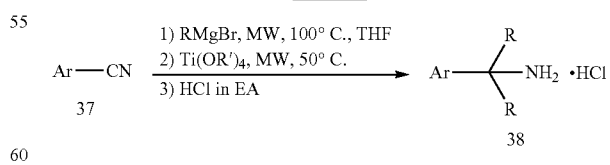

Scheme P illustrates another sequence for the syntheses of α,α-disubstituted amines 38. Addition of a Grignard reagent RMgBr to aromatic nitrile 37 gives a magnesium-imine complex, to which a second equivalent of a Grignard reagent RMgBr is added mediated by Ti(OR')$_4$ to form α,α-disubstituted amine 38.

Scheme M illustrates a procedure for the syntheses of amines such as 28. Disulfane compound 21 is prepared according to the methods described by Kirsch et al. in *European Journal of Organic Chemistry*, 2005, 14, 3095-3100. Nitrobenzene compound 22 is prepared from disulfane compound 21 by treatment with TFA and XeF$_2$. Reduction of nitrobenzene compound 22 using iron and ammonium chloride forms aniline 23. Aniline 23 is converted to aryl bromide through a Sandmeyer reaction. Transmetalation of aryl halide 24 using a Grignard reagent followed by the addition of a Weinreb amide leads to ketone 25. The condensation of ketone 25 and tert-butanesulfinamide in the presence of Ti(OR''')$_4$ in THF gives sulfinimine 26. The sulfinimine 26 was reduced by NaBH$_4$ in MeOH to give sulfinamide 27. The sulfinyl group is readily removed under acidic conditions to give amine 28.

Scheme Q

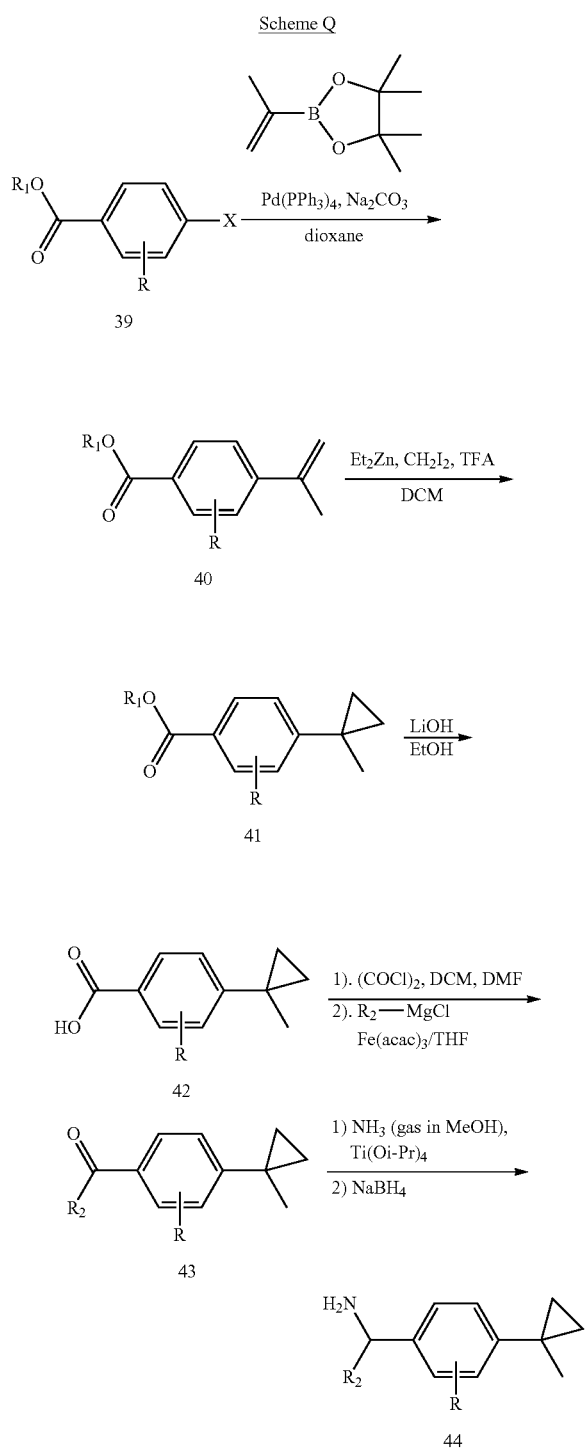

Scheme R

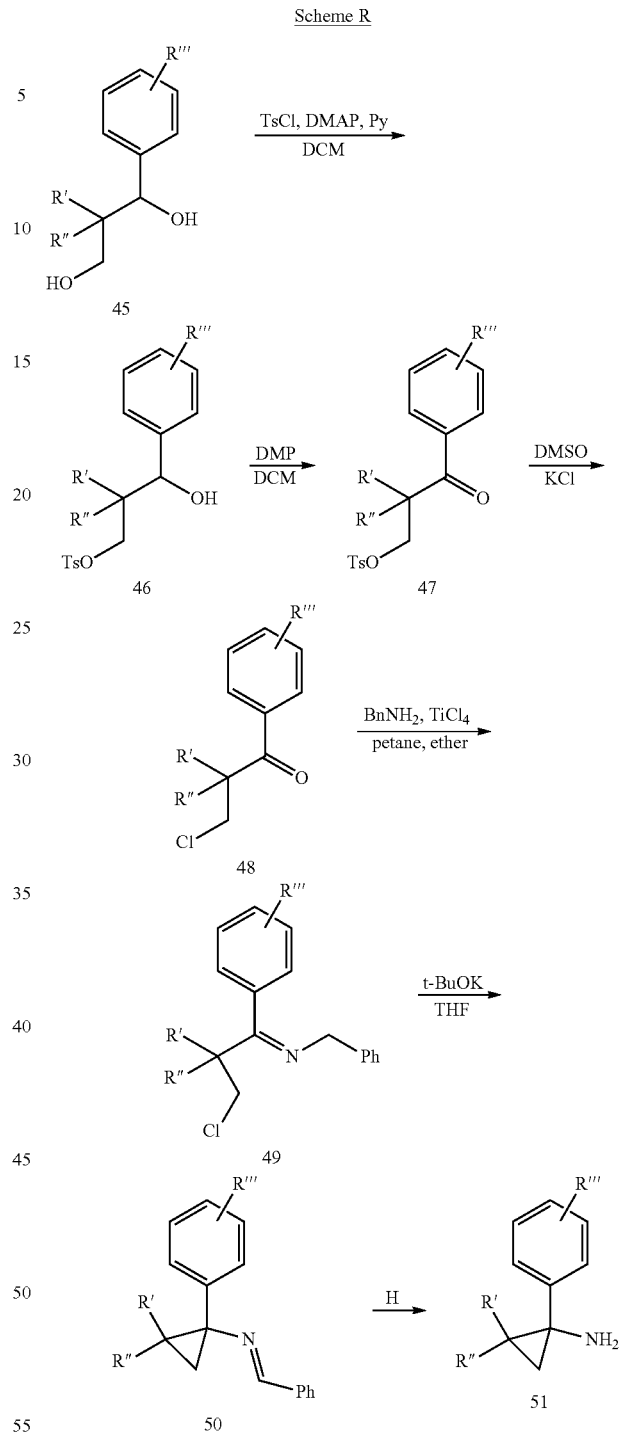

Scheme Q illustrates one sequence for the syntheses of amines such as 44. Aryl halide 39 is converted to olefin 40 by a Suzuki coupling. Cyclopropanation of olefin 40 using $Et_2Zn$ and $CH_2I_2$ affords ester 41. Then ester 41 is hydrolyzed to acid 42. The acid 42 is converted to acyl chloride, which is converted to ketone 43 by a Grignard addition in the presence of tris(acetylacetonate)iron(III). The ketone 43 is converted to amine 44 via a reductive amination using $Ti(OR')_4$, $NH_3$ and $NaBH_4$.

Scheme R illustrates one sequence for the syntheses of amines such as 51. The primary alcohol in diol 45 is protected using TsCl, pyridine and DMAP in DCM. The secondary alcohol 46 is oxidized to aryl ketone 47 using a reagent such as DMP in DCM. The tosyl group of 47 is replaced by chloride to afford chloroketone 48, which is condensed with $BnNH_2$ to give imine 49. Under basic conditions, imine 50 is obtained through cyclopropanation. Hydrolysis of imine 50 affords amine 51 under acidic conditions.

Scheme S

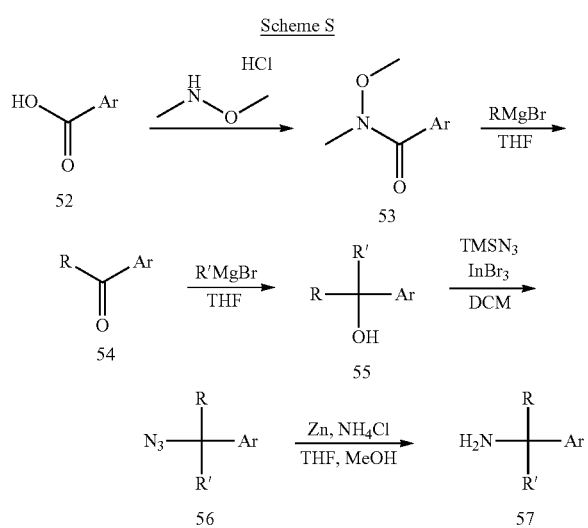

Scheme S illustrates yet another sequence for the syntheses of amines such as 57. The coupling of aryl carboxylic acid 52 and N,O-dimethylhydroxylamine hydrochloride gives Weinreb amide 53. The arylaklylketone 54 is obtained by addition of a Grignard reagent RMgBr to the Weinreb amide 53. Ketone 54 is converted to tertiary alcohol 55 via a nucleophilic addition using a Grignard reagent R'MgBr. The alcohol 55 is converted to azide 56 using TMSN$_3$ catalyzed by Lewis acid. The azide 56 is reduced to afford the amine 57.

PREPARATORY EXAMPLES

Preparatory Example 1

1-(4-(Trifluoromethyl)phenyl)cyclobutanamine hydrobromide

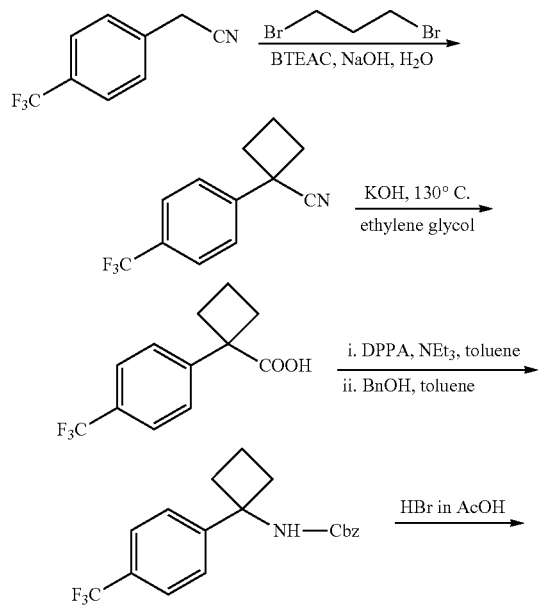

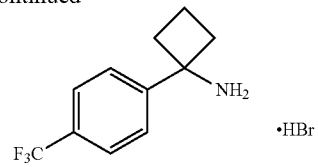

Step 1. 1-(4-(Trifluoromethyl)phenyl)cyclobutanecarbonitrile

A solution of 2-[4-(trifluoromethyl)phenyl]acetonitrile (200 g, 1.08 mol), 1,3-dibromopropane (164 mL, 1.62 mol), and benzyl triethyl ammonium chloride (5.00 g, 0.02 mol) was heated to 50° C. Sodium hydroxide (260 g, 6.48 mol) in DI water (400 mL) was added at 50° C. slowly over 30 min (exotherm observed 10° C.), and the mixture stirred for 16 h at 60° C. After TLC analysis, the reaction mixture was diluted with water (1.0 L) and 2 M HCl (1.6 L), and extracted with CH$_2$Cl$_2$ (2.0 L). The separated aqueous layer was washed with CH$_2$Cl$_2$ (1.0 L). The combined organic layers were dried over Na$_2$SO$_4$ and concentrated under reduced pressure. The crude residue was purified by column chromatography (petroleum ether/EtOAc, 9:1) to afford the title compound as an oil. $^1$H NMR (400 MHz, CDCl$_3$)) δ 7.67 (d, J=8.4 Hz, 2H), 7.56 (d, J=8.4 Hz, 2H), 2.91-2.86 (m, 2H), 2.85-2.60 (m, 2H), 2.54-2.17 (m, 1H), 2.16-2.12 (m, 1H).

Step 2. 1-(4-(Trifluoromethyl)phenyl)cyclobutanecarboxylic acid

A solution of 1-(4-(trifluoromethyl)phenyl)cyclobutanecarbonitrile (115 g, 0.51) in 518 mL of ethylene glycol was charged with potassium hydroxide (114.5 g, 2.04 mol), and the mixture stirred for 3 h at 130° C. After TLC analysis, the reaction mixture was cooled to room temperature, diluted with DI water (800 mL), and extracted with toluene (800 mL). The separated aqueous layer was acidified with 2 M HCl (820 mL), adjusted to pH=2, and extracted with CH$_2$Cl$_2$ (1.0 L). The separated aqueous layer was extracted with CH$_2$Cl$_2$ (1.0 L). The combined organic layers were dried over Na$_2$SO$_4$ and concentrated under reduced pressure to afford the title compound as a solid. $^1$H NMR (400 MHz, CDCl$_3$)) δ 7.60 (d, J=8 Hz, 2H), 7.43 (d, J=8 Hz, 2H), 2.93-2.58 (m, 2H), 2.55-2.49 (m, 2H), 2.17-2.10 (m, 1H), 1.94-1.90 (m, 1H).

Step 3. Benzyl (1-(4-(trifluoromethyl)phenyl)cyclobutyl)carbamate

A solution of 1-(4-(trifluoromethyl)phenyl)cyclobutanecarboxylic acid (88 g, 0.35 mol) in 350 mL of toluene was charged with triethylamine (75.6 mL, 0.53 mol) and DPPA (85.5 mL, 0.39 mol) at room temperature. The reaction mixture was stirred for 1 h at the same temperature. After TLC analysis, the reaction mixture was diluted with DI water (200 mL) and extracted with MTBE (200 mL). The separated aqueous layer was extracted with MTBE (100 mL). The combined organic layers were dried over Na$_2$SO$_4$ and concentrated under reduced pressure. Crude benzyl (1-(4-(trifluoromethyl)phenyl)cyclobutyl)carbamate in toluene (500 mL) was charged with benzyl alcohol (74.4 mL, 0.71 mol) at room temperature and the mixture stirred for 16 h at 80° C. After TLC analysis, the reaction mixture was cooled to room temperature. The reaction mixture was diluted with DI water (300 mL) and extracted with MTBE (200 mL). The separated aqueous layer was extracted with MTBE (200 mL). The combined organic layers were dried over Na$_2$SO$_4$ and concentrated under reduced pressure. The crude residue was purified by column chromatography (petroleum ether/EtOAc 9.5:0.5) to afford the title compound as a solid. $^1$H NMR (400 MHz, CDCl$_3$) δ 7.60-7.55 (m, 4H), 7.39-7.27 (m, 5H), 5.47 (bs, 1H), 5.02 (s, 2H), 2.57-2.55 (m, 4H), 2.19-2.15 (m, 1H), 1.93-1.89 (m, 1H).

Step 4.
1-(4-(Trifluoromethyl)phenyl)cyclobutanamine hydrobromide

A solution of benzyl (1-(4-(trifluoromethyl)phenyl)cyclobutyl)-carbamate (88 g, 0.25 mol) in HBr and AcOH (880 mL) stirred for 1 h at room temperature. After TLC analysis, the reaction mixture was concentrated under reduced pressure. Petroleum ether (200 mL×2) was added and the mixture was concentrated to remove residual amounts of acetic acid. The obtained solids were slurried with petroleum ether (200 mL) and the mixture stirred for 30 min. The solids were filtered and dried under vacuum to afford the title compound as a solid. $^1$H NMR (400 MHz, MeOD) δ 7.82 (d, J=8.4 Hz, 2H), 7.74 (d, J=8 Hz, 2H), 2.86-2.79 (m, 2H), 2.72-2.65 (m, 2H), 2.35-2.24 (m, 1H), 2.05-2.02 (m, 1H). $^1$H NMR (400 MHz, DMSO-d$_6$) δ 8.75 (bs, 1H), 7.83 (d, J=8 Hz, 2H), 7.75 (d, J=8.4 Hz, 2H), 2.60 (t, J=15.6 Hz, 4H), 2.22-2.16 (m, 1H), 1.82-1.76 (m, 1H). $^{13}$C NMR (100 MHz, D$_2$O) δ 145.33, 129.69, 127.93, 125.78, 123.08, 58.50, 35.43, 14.19. MS: Multimode m/z: 216

Preparatory Example 2

1-(4-(Trifluoromethyl)phenyl)cyclopropanamine

Using the same procedure as on Preparatory Example 1 and starting from 2-[4-(trifluoromethyl) phenyl]acetonitrile and 1,2-dibromoethane, the title compound was prepared. $^1$H NMR (400 MHz, CDCl$_3$) δ 7.57 (d, J=8.4 Hz, 2H), 7.39 (d, J=8.4 Hz, 2H), 1.74 (s, 2H), 1.17 (q, J=4.8 Hz, 2H), 1.04 (q, J=4.8 Hz, 2H).

Preparatory Example 3

1-Methylcyclopropanamine Oxalate

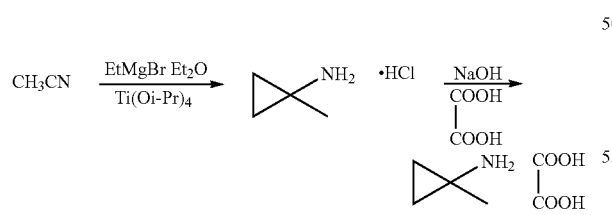

Step 1. 1-Methylcyclopropanamine Hydrochloride

Into a 10 4-necked round-bottom flask purged and maintained with an inert atmosphere of nitrogen, was placed a suspension of Mg (351.2 g, 14.63 mol, 2.50 equiv.) in Et$_2$O (4000 ml). To the above was added ethyl bromide (1595 g, 14.63 mol, 2.50 equiv.) dropwise with stirring, while warming to a temperature of 30-35° C. over a time period of 3 hours. The reaction mixture was stirred at reflux temperature for 30 minutes to give mixture A. Into a 10 4-necked round-bottom flask purged and maintained with an inert atmosphere of nitrogen, was placed acetonitrile (240 g, 5.85 mol, 1.00 equiv.) in Et$_2$O (4 L). To the mixture was added Ti(Oi-Pr)$_4$ (1828.6 g, 5.15 mol, 1.10 equiv., 80%). Addition of mixture A above was followed, which was added dropwise while maintained at a temperature of 30-35° C. The reaction mixture was stirred at 30° C. for 1.5 hours. To the above was added BF$_3$.Et$_2$O (1680 g, 11.61 mol, 47%) dropwise with stirring, while warming to a temperature of 30-35° C. over a time period of 60 minutes. The resulting solution was allowed to react, with stirring, overnight while the temperature was maintained at room temperature. The reaction mixture was cooled to −10° C. Adjustment of the pH to 9.0 was accomplished by the addition of NaOH. The mixture was dried over Na$_2$CO$_3$. The final product was purified by distillation under reduced pressure (760 mm Hg) and the fraction was collected at 50-60° C., which was then reacted with HCl gas. This resulted in the title compound as a solid.

Step 2. 1-Methylcyclopropanamine Oxalate

Into a 2 4-necked round-bottom flask, was placed a suspension of 1-methylcyclopropanamine hydrochloride (110 g, 925.23 mmol, 1.00 equiv., 90%) in Et$_2$O (1000 ml). This was followed by the addition of a solution of NaOH (49 g, 1.23 mol, 1.20 equiv.) in H$_2$O (200 ml). This was followed by the addition of a solution of oxalic acid (92.5 g, 1.03 mol, 1.00 equiv.) in Et$_2$O/EtOH (400 ml), which was added dropwise with stirring, while maintaining the contents at room temperature over a time period of 20 minutes. The resulting solution was allowed to react, with stirring, for 30 minutes while the temperature was maintained at room temperature. A filtration was performed. The solid was washed 2 times with 200 ml of Et$_2$O. This resulted in the title compound as a solid. LC-MS (+ESI) m/z=72. $^1$H NMR (400 MHz, D$_2$O) δ 0.64 (2H, d), 0.85 (2H, d), 1.34 (3H, s).

Preparatory Example 4

2-Methyl-2-(1H-pyrazol-1-yl)propanimidamide acetate

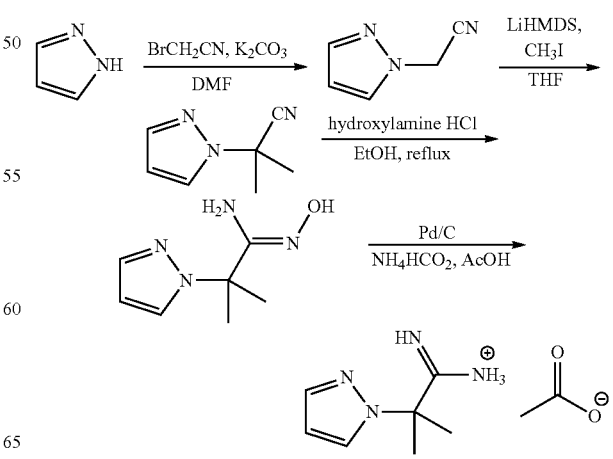

Step 1. 2-(1H-pyrazol-1-yl)acetonitrile

To a solution of pyrazole (10 g, 0.147 mol) in dry dimethylformamide (150 ml) was added anhydrous potassium carbonate and stirred at room temperature for 10 minutes. Bromoacetonitrile (40 ml, 0.588 mol) was then added and stirred at room temperature overnight. Potassium carbonate was filtered off and the filtrate concentrated at reduced pressure. The resulting mass was then diluted with ethyl acetate (500 ml) and the ethyl acetate layer was washed with brine solution and dried over sodium sulphate. Volatiles were evaporated and residue obtained was purified by column chromatography over silica gel using ethyl acetate and petroleum ether (1:4) as eluent. The title compound was obtained as a liquid.

Step 2. 2-Methyl-2-(1H-pyrazol-1-yl)propanenitrile

A solution of 2-(1H-pyrazol-1-yl)acetonitrile (1.07 g, 0.01 mol) was dissolved in 20 ml of THF and the solution was chilled to 0° C. Iodomethane (3.1 ml, 0.05 mol) was added followed by the slow addition of 30 ml (0.03 mol) of 1 M LiHMDS in THF. The mixture was stirred overnight. The mixture was partitioned between ethyl acetate and saturated $NH_4Cl$ and then the ethyl acetate was washed with water and brine, and dried with $Na_2SO_4$, filtered, and concentrated. The title compound was obtained as a liquid.

Step 3. (Z)—N'-hydroxy-2-methyl-2-(1H-pyrazol-1-yl)propanimidamide

Sodium carbonate (1.35 g, 7.5 mmol) and hydroxylamine hydrochloride (1.05 g, 15 mmol) were added to a stirred suspension of 2-methyl-2-(1H-pyrazol-1-yl)propanenitrile (1.35 g, 10 mmol) in 50 percent aqueous ethanol (20 ml) and the mixture heated under reflux for 18 hours, then allowed to cool. The resulting precipitate was collected, and extracted with ethyl acetate, concentrated to afford the title compound as a solid.

Step 4. 2-Methyl-2-(1H-pyrazol-1-yl)propanimidamide acetate

A solution of (Z)—N'-hydroxy-2-methyl-2-(1H-pyrazol-1-yl)propanimidamide (0.504 g, 3.0 mmol) was stirred in acetic acid (10 ml) and to it added Pd/C (0.05 g, 10%) and ammonium formate (0.567 g, 9.0 mmol). After the reaction was complete, the solids were filtered and the filtrate concentrated down. The title compound was obtained as acetic acid salt. $^1$H NMR (300 MHz, DMSO-$d_6$) δ: 7.92-7.90 (m, H), 7.57 (m, 1 H), 7.34-7.33 (m, H), 1.81 (s, 6 H), 1.70 (s, 3 H).

Step 5. 2-(2-(1H-pyrazol-1-yl)propan-2-yl)-6-oxo-1,6-dihydropyrimidine-4-carboxylic acid Diethyl oxalacetate sodium salt (50 mg, 0.238 mmol) and 2-methyl-2-(1H-pyrazol-1-yl)propanimidamide acetate (55.5 mg, 0.262 mmol) were combined together in a vial. To this, water (476 µl) and 6.25 M sodium hydroxide (76 µl, 0.476 mmol) were added and the reaction mixture was agitated via a thermomixer at room temperature for 18 h. The reaction contents were concentrated under vacuum to give crude title compound as a solid. This was used as is in the next step. MS (+ESI) m/z=249.

Preparatory Example 5

2-Methyl-6-oxo-1,6-dihydropyrimidine-4-carboxylic acid

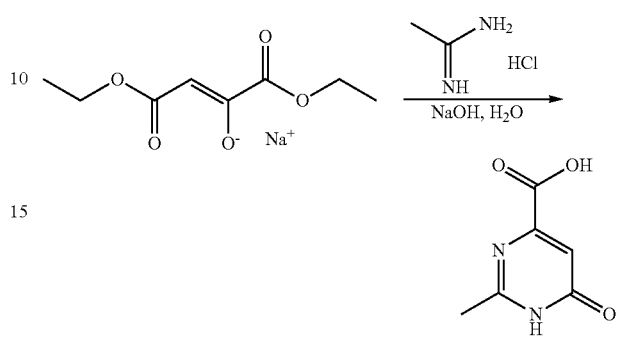

Sodium (Z)-1,4-diethoxy-1,4-dioxobut-2-en-2-olate (2.5 g, 11.90 mmol) was suspended in water (8 mL) and treated with 6.25 M sodium hydroxide (1.903 ml, 11.90 mmol). Separately, the acetimidamide hydrochloride (2.458 g, 26 mmol) was dissolved in water (2 mL). While stirring, the acetimidamide solution was added dropwise to the reaction mixture over the course of 1 minute. The reaction was allowed to stir at room temperature, during which the reaction mixture was checked periodically to ensure pH=11, drops of 6.25 M NaOH were added occasionally to maintain this. After 2 hrs, the reaction mixture was treated with conc. HCl (1 mL) and the resulting precipitate was filtered and washed with 0.1 N HCl (5 mL) to give title compound as a solid. MS (+ESI) m/z=155. $^1$H NMR (500 MHz, DMSO-$d_6$) δ: 12.76 (s, 1H), 6.68 (s, 1H), 2.51 (s, 3H).

Preparatory Example 6

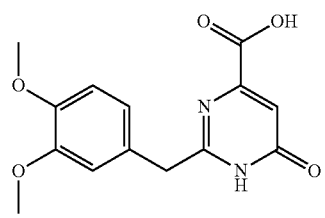 [SMILES: COc1ccc(Cc2nc(C(=O)O)cc(=O)[nH]2)cc1OC]

2-(3,4-Dimethoxybenzyl)-6-oxo-1,6-dihydropyrimidine-4-carboxylic acid

Diethyl oxalacetate sodium salt (50 mg, 0.238 mmol) was suspended in water (200 µl) and treated with 2-(3,4-dimethoxyphenyl)ethanimidamide hydrochloride (60.4 mg, 0.262 mmol) followed by 6.25 M sodium hydroxide (76 µl, 0.476 mmol). The slurry became homogeneous and the reaction contents were agitated at room temperature for 18 h via a thermomixer during which a precipitate formed. The reaction contents were acidified with 1N HCl (3 mL) and diluted with $CH_2Cl_2$ (10 mL). The organic layer was dried ($Na_2SO_4$), filtered and evaporated. The aqueous layer was concentrated under vacuum to give a residue and added to the organic layer. The organic/aqueous residues were purified via reverse phase chromatography C18 column (5-60%

CH₃CN/Water, 0.1% TFA) and lyophilized to afford the title compound. MS (+ESI) m/z=291. ¹H NMR (500 MHz, DMSO-d₆) δ: 12.87-12.95 (m, 2H), 7.00 (s, 1H), 6.92-6.88 (m, 1H), 6.87-6.84 (m, 1H), 6.66-6.71 (m, 1H), 3.82 (s, 2H), 3.73-3.71 (m, 6H).

Preparatory Example 7

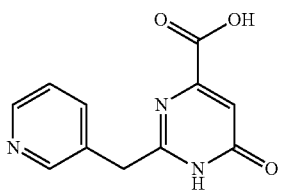 [SMILES: O=C(O)c1cc(=O)[nH]c(Cc2cccnc2)n1]

6-Oxo-2-(pyridin-3-ylmethyl)-1,6-dihydropyrimidine-4-carboxylic acid

A procedure similar to that described in Preparative Example 5 was used to prepare the title compound. MS (+ESI) m/z=232.1.

Preparatory Example 8

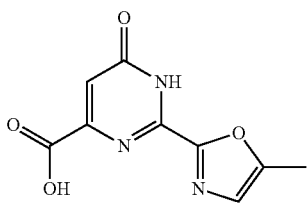 [SMILES: Cc1cnc(-c2nc(C(=O)O)cc(=O)[nH]2)o1]

2-(5-Methyloxazol-2-yl)-6-oxo-1,6-dihydropyrimidine-4-carboxylic acid

Step 1. 5-Methyloxazole-2-carboxamide

Ethyl 5-methyloxazole-2-carboxylate (0.470 g, 3.0 mmol) was added into ammonium hydroxide (4.21 mL, 30.3 mmol). The mixture was stirred at room temperature for 16 h. Then the mixture was concentrated under vacuum. The title compound was obtained as a solid and used in the next step without further purification. MS (+ESI) m/z=127.0.

Step 2. 5-Methyloxazole-2-carbonitrile

To a solution of 5-methyloxazole-2-carboxamide (0.370 g, 2.9 mmol) in pyridine (2.4 mL) was added phosphoryl trichloride (0.675 g, 4.4 mmol). The solution was stirred at room temperature for 16 h. Then the resulting solution was quenched with ice water (10 mL) and the pH value of the resulting mixture was adjusted to 3 with hydrochloric acid (6 M). The mixture was extracted with ether (4×30 mL). The combined organic layer was washed with water (2×20 mL), brine (20 mL), dried with anhydrous Na₂SO₄, and filtered. The filtrate was concentrated under reduced pressure. The title compound was obtained as a liquid and used in the next step without further purification. ¹H NMR (400 MHz, CDCl₃) δ: 6.98 (s, 1H), 2.43 (s, 3H).

Step 3. 5-Methyloxazole-2-carboximidamide hydrochloride

Trimethylaluminum (0.200 g, 2.8 mmol) was added into a mixture of 5-methyloxazole-2-carbonitrile (0.300 g, 2.8 mmol) and ammonium chloride (0.148 g, 2.8 mmol) in toluene (5.0 mL) at 0° C. The reaction mixture was stirred at 0° C. for 1.5 h, and stirred for another 16 h at 85° C. Then the resulting mixture was cooled, diluted with DCM (10 mL) and filtered. The filter cake was washed with methanol (10 mL). The combined filtrate was evaporated under reduced pressure. The title compound was obtained as a solid and used in the next step without further purification. ¹H NMR (400 MHz, DMSO-d₆) δ: 8.20-6.80 (v br, 4H), 7.38 (s, 1H), 2.46 (s, 3H).

Step 4. 2-(5-Methyloxazol-2-yl)-6-oxo-1,6-dihydropyrimidine-4-carboxylic acid

To a solution of sodium 1,4-diethoxy-1,4-dioxobut-2-en-2-olate (0.263 g, 1.2 mmol) in water (3 mL) was added sodium hydroxide (6.25 M in water, 0.50 mL, 3.1 mmol). The resulting mixture was added into the solution of 5-methyloxazole-2-carboximidamide hydrochloride (0.200 g, 1.2 mmol) in water (3 mL). The reaction mixture was stirred at 50° C. for 2 h. Then the resulting mixture was washed with ethyl acetate (2×20 mL). The aqueous layer was evaporated under reduced pressure. The residue was purified by Prep-HPLC with the following conditions: Column: X Bridge C18, 19×250 mm, 5 um; Mobile Phase A: Water/10 mmol ammonium bicarbonate, Mobile Phase B: acetonitrile; Flow rate: 25 mL/min; Gradient: 45% B to 85% B in 8 min; Detector, UV 220 and 254 nm. The title compound was obtained as a solid. MS (+ESI) m/z=221.9.

Table P1

The following compounds in Table P1 were prepared using procedures similar to those described in Preparatory Example 8 using appropriate starting materials.

TABLE P1

| Preparatory Example # | Structure | IUPAC Name | Exact Mass [M + H]⁺ |
|---|---|---|---|
| 9 | ![structure] | 6-oxo-2-(thiazol-2-yl)-1,6-dihydropyrimidine-4-carboxylic acid | Calc'd 224.0, found 223.9 |

TABLE P1-continued

| Preparatory Example # | Structure | IUPAC Name | Exact Mass [M + H]+ |
|---|---|---|---|
| 10 | ![structure] | 2-(oxazol-2-yl)-6-oxo-1,6-dihydropyrimidine-4-carboxylic acid | Calc'd 208.0, found 208.0 |

Preparatory Example 11

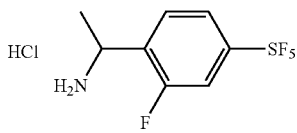

1-(2-Fluoro-4-(pentafluorothio)phenyl)ethanamine hydrochloride

Step 1. 4-(Pentafluorothio)-2-fluoro-N-methoxy-N-methylbenzamide

HATU (0.590 g, 1.6 mmol) was added to a stirred solution of 4-(pentafluorothio)-2-fluorobenzoic acid (0.400 g, 1.3 mmol) in NMP (4 mL) at 0° C. The reaction solution was stirred at 0° C. for 10 min. To the solution were added N,O-dimethylhydroxylamine hydrochloride (0.189 g, 1.9 mmol) and TEA (0.54 mL, 3.9 mmol) at 0° C. The reaction suspension was stirred at room temperature for 16 h. The resulting suspension was diluted with water (100 mL) and extracted with EtOAc (3×20 mL). The combined organic layers was washed with brine (50 mL), dried with anhydrous $Na_2SO_4$ and filtered. The filtrate was concentrated under reduced pressure. The residue was purified by column chromatography over silica gel eluting with 50% ethyl acetate in petroleum ether. The fractions containing desired product were combined and concentrated. The title compound was obtained as a liquid. MS (+ESI) m/z=310.0.

Step 2. 1-(2-Fluoro-4-(pentafluorothio)phenyl)ethanone

Methyl magnesium bromide (1.0 M in THF, 2.56 mL, 2.6 mmol) was added dropwise to a stirred solution of 4-(pentafluorothio)-2-fluoro-N-methoxy-N-methylbenzamide (0.450 g, 1.2 mmol) in THF (5 mL) at 0° C. The reaction solution was stirred at 0° C. for 2 h. The resulting suspension was diluted with sat'd $NH_4Cl$ (40 mL) and extracted with $Et_2O$ (3×20 mL). The combined organic layers was washed with brine (50 mL), dried with anhydrous $Na_2SO_4$ and filtered. The filtrate was concentrated under reduced pressure. The residue was purified by column chromatography over silica gel eluting with 10% ethyl acetate in petroleum ether. The fractions containing desired product were combined and concentrated. The title compound was obtained as a liquid. MS (+EI) m/z=264.0. (GCMS)

Step 3. 1-(2-Fluoro-4-(pentafluorothio)phenyl)ethanamine hydrochloride

To a solution of sat'd $NH_3$ in MeOH (3 mL) were added 1-(2-fluoro-4-(pentafluorothio)phenyl)ethanone (0.165 g, 0.6 mmol) and $Ti(OEt)_4$ (0.37 mL, 1.3 mmol) at room temperature. The reaction mixture was stirred at 60° C. for 2 h. The resulting suspension was cooled. $NaBH_4$ (35.0 mg, 0.9 mmol) was added to the suspension at 0° C. and the reaction mixture was stirred at 0° C. for 30 min. The resulting mixture was concentrated under reduced pressure. The residue was diluted with water (30 mL) and the pH value of the mixture was adjusted to 12 with sat'd NaOH. The mixture was extracted with ethyl acetate (3×15 mL). The combined organic layers was washed with brine (30 mL), dried with anhydrous $Na_2SO_4$ and filtered. The filtrate was concentrated under reduced pressure. The residue was diluted with EtOAc (5 mL) and treated with a sat'd solution of HCl in EtOAc. The resulting precipitate was collected, washed with EtOAc (3×1 mL) and dried. The title compound was obtained as a solid and used in the next step without further purification. MS (+ESI) m/z=266.0.

Preparatory Example 12

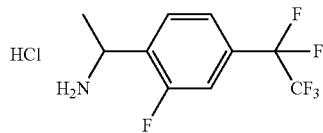 [SMILES: Cl ; CC(N)c1ccc(C(F)(F)C(F)(F)F)cc1F]

1-(4-(Perfluoroethyl)phenyl)ethanamine hydrochloride

The title compound was prepared using procedures similar to those described in Preparatory Example 11 using appropriate starting materials. MS (+ESI) m/z=258.1.

Preparatory Example 13

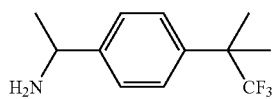

1-(4-(1,1,1-Trifluoro-2-methylpropan-2-yl)phenyl)ethanamine

Step 1. 1-(4-(1,1,1-Trifluoro-2-methylpropan-2-yl)phenyl)ethanone

Palladium(II) acetate (27.7 mg, 0.1 mmol), 1,3-bis(diphenylphosphino)propane (10.2 mg, 0.03 mmol), n-butyl vinyl ether (0.34 g, 3.4 mmol) and triethylamine (0.39 mL, 2.8 mmol) were added to the solution of 1-bromo-4-(1,1,1-trifluoro-2-methylpropan-2-yl)-benzene (0.30 g, 1.1 mmol) in ethylene glycol (2.0 mL). The mixture was purged with nitrogen for 3 times and stirred at 145° C. for 4 h under nitrogen. The mixture was cooled and diluted with ethyl acetate (50 mL). The mixture was washed with water (4×20 mL), brine (20 mL), dried with anhydrous $Na_2SO_4$ and filtered. The filtrate was concentrated under reduced pressure. The residue was diluted with tetrahydrofuran (2 mL). Then hydrochloric acid (6.0 M, 3.0 mL) was added. The reaction mixture was stirred at 25° C. for 2 h. The resulting mixture was extracted with dichloromethane (3×10 mL). The combined organic fractions was washed with water (2×5 mL), dried with anhydrous $Na_2SO_4$, filtered and concentrated. The residue was purified by column chromatography over silica gel eluting with 15% ethyl acetate in petroleum ether. The fractions containing desired product were combined and concentrated. The title compound was obtained as a liquid. $^1$H NMR (300 MHz, $CDCl_3$) δ: 7.95 (d, J=8.4 Hz, 2H), 7.59 (d, J=8.4 Hz, 2H), 2.61 (s, 3H), 1.61 (s, 6H).

Step 2. 1-(4-(1,1,1-Trifluoro-2-methylpropan-2-yl)phenyl)ethanamine

The title compound was prepared as described for Preparatory Example 11 step 3 using 1-(4-(1,1,1-trifluoro-2-methylpropan-2-yl) phenyl)ethanone to give the title compound as a solid, which was used in the next step without further purification. $^1$H NMR (300 MHz, $CDCl_3$) δ: 7.45 (d, J=8.4 Hz, 2H), 7.36 (d, J=8.4 Hz, 2H), 3.98 (q, J=6.9 Hz, 1H), 2.21-2.18 (br, 2H), 1.53 (s, 6H), 1.18 (d, J=7.2 Hz, 3H).

Preparatory Example 14

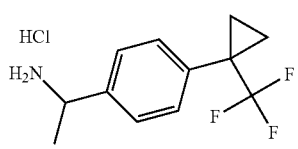

1-(4-(1-(trifluoromethyl)cyclopropyl)phenyl)ethanamine hydrochloride

The title compound was prepared using procedures similar to those described in Preparatory Example 13 using appropriate starting materials. MS (+ESI) m/z=230.1.

Preparatory Example 15

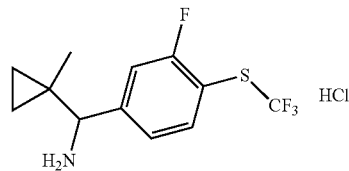 [SMILES: CC1(C(N)c2ccc(SC(F)(F)F)c(F)c2)CC1 ; Cl]

(3-Fluoro-4-((trifluoromethyl)thio)phenyl)(1-methylcyclopropyl)methanamine hydrochloride

Step 1. (2-Fluoro-4-nitrophenyl)(trifluoromethyl)sulfane

To a solution of 2,2,2-trifluoroacetic acid (19.9 g, 0.174 mol) and 1,2-bis(2-fluoro-4-nitrophenyl)disulfane (3.00 g, 8.7 mmol; prepared according to procedures from Kirsch et al. in *European Journal of Organic Chemistry*, 2005, 14, 3095-3100) in DCM (30.0 mL) was added difluoroxenon (3.69 g, 21.8 mmol). The reaction mixture was stirred at 30° C. for 1 h. The resulting mixture was dissolved in 100 mL of DCM and washed with brine (2×50 mL). The organic layer was dried over anhydrous $Na_2SO_4$, filtered and concentrated. The residue was purified by column chromatography over silica gel eluting with 1% ethyl acetate in petroleum ether. The fractions containing desired product were combined and concentrated. The title compound was obtained as a liquid. $^1$H NMR (400 MHz, DMSO-$d_6$) δ: 8.42-8.34 (m, 1H), 8.24-8.16 (m, 1H), 8.16-8.03 (m, 1H).

Step 2. 3-Fluoro-4-((trifluoromethyl)thio)aniline

To a stirred mixture of (2-fluoro-4-nitrophenyl)(trifluoromethyl)sulfane (2.70 g, 11.2 mmol) and sat'd ammonium chloride (15.0 mL) in EtOH (30.0 mL) was added iron powder (3.13 g, 56.0 mmol). The reaction mixture was stirred at 100° C. for 1 h. The resulting mixture was cooled, diluted with ethyl acetate (500 mL) and washed with brine (2×250 mL). The organic layer was dried over anhydrous $Na_2SO_4$ and filtered. Volatiles were evaporated and residue obtained was purified by column chromatography over silica gel eluting with 30% ethyl acetate in petroleum ether. The fractions containing desired product were combined and concentrated. The title compound was obtained as a liquid. MS (+ESI) m/z=212.0.

Step 3. (4-Bromo-2-fluorophenyl)(trifluoromethyl)sulfane

To a solution of 3-fluoro-4-((trifluoromethyl)thio)aniline (1.00 g, 4.7 mmol) in acetic acid (20 mL) was added HBr (20 mL, 0.177 mol). An aqueous solution of sodium nitrite (0.343 g, 5.0 mmol) in water (1 mL) was then added dropwise to the reaction mixture and the resulting mixture was stirred at 0° C. for 10 min. The resulting mixture was added dropwise to a solution of copper(I) bromide (1.36 g, 9.5 mmol) in HBr (20.0 mL, 177 mmol) at 0° C. The reaction solution was stirred at 0° C. for 30 min. The resulting solution was diluted with water (300 mL) and extracted with dichloromethane (3×50 mL). The combined organic layers was washed with brine (200 mL), dried with anhydrous $Na_2SO_4$, filtered and concentrated. The residue was purified by column chromatography over silica gel using hexane as eluent. The fractions containing desired product were combined and concentrated. The title compound was obtained as a liquid. $^1$H NMR (400 MHz, CDCl$_3$) δ: 7.76-7.53 (m, 1H), 7.45-7.39 (m, 2H).

Step 4. (3-Fluoro-4-((trifluoromethyl)thio)phenyl) (1-methylcyclopropyl)methanone Isopropylmagnesium bromide (3.0 M in THF, 0.5 mL, 1.5 mmol) was added dropwise to a solution of (4-bromo-2-fluorophenyl)(trifluoromethyl)sulfane (0.340 g, 1.2 mmol) in THF (3.0 mL) at −78° C. and stirred at room temperature for 1 h. To the reaction solution was added dropwise a solution of N-methoxy-N,1-dimethylcyclopropanecarboxamide (0.168 g, 1.2 mmol) in THF (2.0 mL) at −78° C. and stirred at room temperature for 16 h. The resulting solution was diluted with sat'd NH$_4$Cl (10.0 mL) and extracted with Et$_2$O (3×5.0 mL). The combined organic layers was washed with brine (10 mL), dried with anhydrous Na$_2$SO$_4$, filtered and concentrated. The residue was purified by column chromatography over silica gel using hexane as eluent. The fractions containing desired product were combined and concentrated. The title compound was obtained as a liquid. $^1$H NMR (400 MHz, DMSO-d$_6$) δ: 7.78-7.74 (m, 1H), 7.61-7.54 (m, 2H), 1.46 (s, 3H), 1.38-1.34 (m, 2H), 0.90-0.83 (m, 2H).

Step 5. (Z)—N-((3-fluoro-4-((trifluoromethyl)thio) phenyl)(1-methylcyclopropyl)methylene)-2-methylpropane-2-sulfinamide To a solution of (3-fluoro-4-((trifluoromethyl)thio)phenyl)(1-methylcyclopropyl)methanone (40.0 mg, 0.1 mmol) in THF (0.5 mL) was added 2-methylpropane-2-sulfinamide (34.8 mg, 0.3 mmol) and titanium(IV) ethoxide (0.131 g, 0.6 mmol). The reaction mixture was stirred at 70° C. for 16 h. The resulting solution was cooled, diluted with ethyl acetate (8.0 mL) and quenched with water (0.5 mL). The mixture was filtered. The filter cake was washed with ethyl acetate (3×0.5 mL). The combined filtrates was washed with brine (5 mL), dried with anhydrous Na$_2$SO$_4$ and filtered. Volatiles were evaporated and residue obtained was purified by Prep-TLC over silica gel eluting with 5% ethyl acetate in petroleum ether. The fractions containing desired product were combined and concentrated. The title compound was obtained as a liquid. MS (+ESI) m/z=382.2.

Step 6. N-((3-fluoro-4-((trifluoromethyl)thio)phenyl)(1-methylcyclopropyl)methyl)-2-methylpropane-2-sulfinamide NaBH$_4$ (45.0 mg, 1.2 mmol) was added to a solution of (Z)—N-((3-fluoro-4-((trifluoromethyl)thio)phenyl)(1-methylcyclopropyl)methylene)-2-methylpropane-2-sulfinamide (0.45 g, 1.2 mmol) in MeOH (5.0 mL). The reaction solution was stirred at 0° C. for 30 min. The resulting solution was concentrated under reduced pressure. The residue was purified by column chromatography over silica gel using 35-50% gradient of ethyl acetate in petroleum ether as eluent. The fractions containing desired product were combined and concentrated. The title compound was obtained as a liquid. MS (+ESI) m/z=384.2.

Step 7. (3-Fluoro-4-((trifluoromethyl)thio)phenyl) (1-methylcyclopropyl)methanamine hydrochloride Hydrochloric acid in ethyl acetate (0.5 mL, 0.8 mmol) was added dropwise to a stirred solution of N-((3-fluoro-4-((trifluoromethyl)thio)phenyl)(1-methylcyclopropyl) methyl)-2-methylpropane-2-sulfinamide (0.320 g, 0.8 mmol) in ethyl acetate (8.0 mL). The resulting suspension was stirred at room temperature for 2 h and was filtered. The filter cake was washed with diethyl ether (3×2.0 mL) and dried to give the title compound as a solid which was used in the next step without further purification. $^1$H NMR (400 MHz, DMSO-d$_6$) δ: 8.80-8.68 (br, 3H), 7.93 (t, J=7.8 Hz, 1H), 7.65 (d, J=10.4 Hz, 1H), 7.48 (d, J=8.0 Hz, 1H), 3.96-3.87 (m, 1H), 0.92 (s, 3H), 0.92-0.91 (m, 1H), 0.83-0.78 (m, 1H), 0.58-0.55 (m, 1H), 0.38-0.32 (m, 1H).

Preparatory Example 16

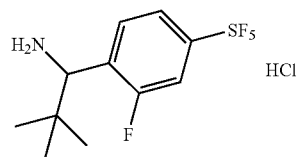

1-(2-Fluoro-4-(pentafluorosulfanyl)phenyl)-2,2-dimethylpropan-1-amine hydrochloride Step 1. N-(2-fluoro-4-(pentafluorosulfanyl)benzylidene)-2-methylpropane-2-sulfinamide The title compound was prepared using procedures similar to those described in step 5 of Preparatory Example 15 using 2-fluoro-4-(pentafluorosulfanyl)benzaldehyde to afford the title compound as a liquid. MS (+ESI) m/z=354.1.

Step 2. N-(1-(2-fluoro-4-(pentafluorosulfanyl)phenyl)-2,2-dimethylpropyl)-2-methylpropane-2-sulfinamide To a stirred solution of N-(2-fluoro-4-(pentafluorosulfanyl)benzylidene)-2-methylpropane-2-sulfinamide (0.220 g, 0.6 mmol) in THF (3 mL) was added dropwise tert-butylmagnesium chloride (1.0 M in THF, 1.30 mL, 1.3 mmol) at 0° C. The reaction solution was stirred at 0° C. for 2 h. The resulting solution was quenched with sat'd NH$_4$Cl (5 mL) and extracted with EtOAc (3×2 mL). The combined organic layers was washed with brine (5 mL), dried with anhydrous Na$_2$SO$_4$ and filtered. The filtrate was concentrated under reduced pressure. The residue was purified by column chromatography over silica gel using 0-40% gradient of ethyl acetate in petroleum ether as eluent. The combined organic fractions containing desired product were combined and concentrated under reduced pressure to give the crude product which was further purified by column chromatography over C18silica gel using 70-95% gradient of methanol in water as eluent. The title compound was obtained as a solid. MS (+ESI) m/z=412.2.

Step 3. 1-(2-Fluoro-4-(pentafluorosulfanyl)phenyl)-2,2-dimethylpropan-1-amine hydrochloride The title compound was prepared using procedures similar to those described in step 7 of Preparatory Example 15 using N-(1-(2-fluoro-4-(pentafluorosulfanyl)phenyl)-2,2-dimethylpropyl)-2-methylpropane-2-sulfinamide to afford the title compound as a solid, which was used to next step without further purification. MS (+ESI) m/z=308.1.

Preparatory Example 17

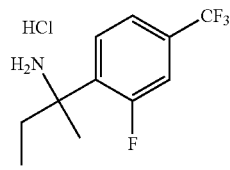 [SMILES: CCC(C)(N)c1ccc(C(F)(F)F)cc1F ; Cl]

2-(2-Fluoro-4-(trifluoromethyl)phenyl)butan-2-amine hydrochloride

Step 1.
2-(2-Fluoro-4-(trifluoromethyl)phenyl)butan-2-ol

To a solution of 1-(2-fluoro-4-(trifluoromethyl)phenyl) ethanone (0.650 g, 3.2 mmol) in THF (6 mL) was added dropwise ethyl magnesium bromide (1.0 M in THF, 9.46 mL, 9.5 mmol) with stirring under nitrogen atmosphere at 0° C. The reaction mixture was stirred under nitrogen atmosphere for 2 h at 0° C. and stirred for another 2 h at room temperature. The resulting mixture was quenched with brine (30 mL) at 0° C. and extracted with ethyl acetate (3×30 mL). The combined organic layers was dried over anhydrous Na$_2$SO$_4$ and filtered. The filtrate was concentrated under vacuum. The residue was purified by column chromatography over silica gel eluting with 10% ethyl acetate in petroleum ether. The fractions containing desired product were combined and concentrated. The title compound was obtained as a liquid. MS (−ESI) m/z=234.9.

Step 2. N-(2-(2-fluoro-4-(trifluoromethyl)phenyl)butan-2-yl)formamide

To a stirred solution of 2-(2-fluoro-4-(trifluoromethyl) phenyl)butan-2-ol (0.300 g, 0.64 mmol) and trimethylsilyl cyanide (0.17 mL, 1.3 mmol) in dichloromethane (5 mL) was added dropwise methanesulfonic acid (0.8 mL, 12.3 mmol) at 0° C. The reaction solution was stirred at room temperature for 16 h. The resulting solution was cooled, diluted with aqueous Na$_2$CO$_3$ (2 M, 50 mL) and extracted with DCM (3×20 mL). The combined organic layers was washed with brine (50 mL), dried with anhydrous Na$_2$SO$_4$ and filtered. The filtrate was concentrated under reduced pressure. The residue was purified by column chromatography over silica gel using 0-100% gradient of ethyl acetate in petroleum ether as eluent. The fractions containing desired product were combined and concentrated. The title compound was obtained as a solid. MS (+ESI) m/z=264.1.

Step 3. 2-(2-Fluoro-4-(trifluoromethyl)phenyl)butan-2-amine hydrochloride

To a stirred suspension of N-(2-(2-fluoro-4-(trifluoromethyl)phenyl)butan-2-yl)formamide (0.100 g, 0.4 mmol) in EtOH (3 mL) was added portions of HCl (6 M, 1 mL, 6.0 mmol) at room temperature. The reaction suspension was stirred at 60° C. for 3 h. The resulting solution was cooled and concentrated under reduced pressure. The crude title compound was obtained as a solid and used for next step directly without further purification. MS (+ESI) m/z=235.7.

Preparatory Example 18

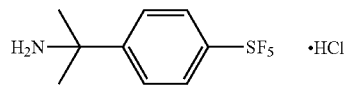

2-(4-(Pentafluorosulfanyl)phenyl)propan-2-amine hydrochloride 2-(4-(Pentafluorosulfanyl)phenyl)propan-2-amine hydrochloride A 20 mL Biotage microwave tube with stir bar was charged with 4-(pentafluorosulfanyl)benzonitrile (0.100 g, 0.4 mmol) and THF (5 ml) followed by methylmagnesium bromide (1.0 M in THF, 1.53 mL, 1.5 mmol). The resulting mixture was heated at 100° C. under microwave irradiation for 10 min. The resulting reaction mixture was cooled to 25° C., then titanium(IV) isopropoxide (0.124 g, 0.4 mmol) was added. After heating at 50° C. under microwave irradiation for 1 h, brine (10 mL) was added. The resulting mixture was extracted with ethyl acetate (3×15 mL). The combined organic fractions was dried over anhydrous Na$_2$SO$_4$ and filtered. HCl (1.0 N) in EtOAc was added to the filtrate and the filtrate was concentrated under reduced pressure. The crude product was triturated with EtOAc to afford the title compound as a solid and used for next step directly without further purification. MS (+ESI) m/z=262.1.

Preparatory Example 19

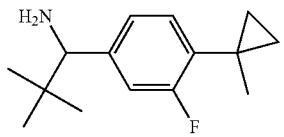 [SMILES: CC1(c2ccc(C(N)C(C)(C)C)cc2F)CC1]

1-(3-Fluoro-4-(1-methylcyclopropyl)phenyl)-2,2-dimethylpropan-1-amine

Step 1. Methyl 3-fluoro-4-(prop-1-en-2-yl)benzoate

Aqueous sodium carbonate (2.0 M, 32.2 mL, 64.4 mmol) was added to a solution of methyl 4-bromo-3-fluorobenzoate (5.0 g, 21.5 mmol) and 4,4,5,5-tetramethyl-2-(prop-1-en-2-yl)-1,3,2-dioxaborolane (4.69 g, 27.9 mmol) in 1,4-dioxane (150 mL) at room temperature. The reaction mixture was purged with nitrogen for 3 times, then to the mixture was added tetrakis(triphenylphosphine) palladium(0) (1.24 g, 1.1 mmol). The resulting mixture was purged with nitrogen for 3 times again and stirred under nitrogen atmosphere at 110° C. for 3 h. The reaction mixture was cooled and concentrated under reduced pressure. The residue was diluted with water (300 mL) and extracted with DCM (3×100 mL). The combined organic layers was washed with brine (3×200 mL), dried with anhydrous Na$_2$SO$_4$ and filtered. The filtrate was concentrated under reduced pressure. The residue was purified by column chromatography over silica gel using hexane as eluent. The fractions containing desired product were combined and concentrated. The title compound was obtained as a liquid. MS (+ESI): m/z=195.1.

Step 2. Methyl 3-fluoro-4-(1-methylcyclopropyl)benzoate

A solution of 2,2,2-trifluoroacetic acid (2.98 mL, 38.6 mmol) in DCM (10.0 mL) was added dropwise to a solution of diethylzine (1.0 M in hexane, 38.6 mL, 38.6 mmol) in DCM (150 mL) at 0° C. The reaction suspension was stirred at 0° C. for 15 min. Then to the reaction suspension was added a solution of diiodomethane (3.12 mL, 38.6 mmol) in DCM (10 mL) at 0° C. The reaction suspension was stirred at 0° C. for 15 min. To the reaction suspension was added dropwise a solution of methyl 3-fluoro-4-(prop-1-en-2-yl)benzoate (3.00 g, 15.5 mmol) in DCM (10 mL) at 0° C. The reaction mixture was stirred at 0° C. for 30 min and warmed to room temperature, stirred for additional 16 h. The resulting suspension was quenched with sat'd $NH_4Cl$ (200 mL) and extracted with DCM (3×100 mL). The combined organic layers was washed with brine (1×300 mL), dried with anhydrous $Na_2SO_4$ and filtered. The filtrate was concentrated under reduced pressure. The residue was purified by column chromatography over silica gel using hexane as eluent. The fractions containing desired product were combined and concentrated. The title compound was obtained as a liquid: MS (+ESI): m/z=209.1.

Step 3. 3-Fluoro-4-(1-methylcyclopropyl)benzoic acid

Lithium hydroxide (2.0 M in water, 30.0 mL, 60.0 mmol) was added to a solution of methyl 3-fluoro-4-(1-methylcyclopropyl)benzoate (3.10 g, 14.9 mmol) in ethanol (60.0 mL). The reaction mixture was stirred at 20° C. for 16 h. The pH value of the resulting mixture was adjusted to 5 with aqueous hydrochloric acid solution (1.0 M). The resulting mixture was washed with brine (200 mL). The separated aqueous phase was extracted with ethyl acetate (3×200 mL). The combined organic layers was dried with anhydrous $Na_2SO_4$ and filtered. The filtrate was concentrated. The title compound was obtained as a solid and used for next step directly without further purification. MS (−ESI): m/z=192.9.

Step 4. 1-(3-Fluoro-4-(1-methylcyclopropyl)phenyl)-2,2-dimethylpropan-1-one

Oxalyl dichloride (0.216 g, 1.7 mmol) was added to a solution of 3-fluoro-4-(1-methylcyclopropyl)benzoic acid (0.150 g, 0.8 mmol) and DMF (0.6 µl, 7.7 mol) in DCM (4.0 mL) dropwise with stirring at 0° C. The reaction mixture was stirred under nitrogen atmosphere at 0° C. for 2 h. Then the reaction mixture was concentrated to give 3-fluoro-4-(1-methylcyclopropyl)benzoyl chloride as a liquid. The residue was dissolved in THF (4.0 mL) and was added iron(III) acetylacetonate (8.2 mg, 0.02 mmol). This was followed by dropwise addition of tert-butylmagnesium chloride (1.0 M in THF, 0.77 mL, 0.77 mmol) with stirring at 0° C. in 5 min. The reaction mixture was stirred under nitrogen atmosphere at room temperature for 1 h. The resulting mixture was quenched with brine (20 mL) and extracted with ethyl acetate (3×20 mL). The combined organic layers was washed with brine (3×50 mL), dried with anhydrous $Na_2SO_4$, filtered and concentrated. The title compound was obtained as a liquid and used for next step directly without further purification. MS (+ESI) m/z=235.1.

Step 5. 1-(3-Fluoro-4-(1-methylcyclopropyl)phenyl)-2,2-dimethylpropan-1-amine The title compound was prepared using procedures similar to those described in Preparatory Example 11 step 3 using 1-(3-fluoro-4-(1-methylcyclopropyl)phenyl)-2,2-dimethylpropan-1-one to afford the tile compound as a liquid. MS (+ESI) m/z=236.2.

Preparatory Example 20

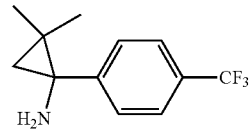 [SMILES: CC1(C)CC1(N)c1ccc(C(F)(F)F)cc1]

2,2-Dimethyl-1-(4-(trifluoromethyl)phenyl)cyclopropanamine

Step 1. 3-Hydroxy-2,2-dimethyl-3-(4-(trifluoromethyl)phenyl)propyl 4-methylbenzenesulfonate To a solution of 2,2-dimethyl-1-(4-(trifluoromethyl)phenyl)propane-1,3-diol (0.650 g, 2.6 mmol, prepared according to procedures from Kawano et al. in *Chemistry Letters*, 2005, 34, 614-615.) and TsCl (0.599 g, 3.1 mmol) in DCM (10 mL) were added pyridine (0.4 mL, 5.2 mmol) and DMAP (32.0 mg, 0.3 mmol) at 0° C. The reaction solution was stirred at 0° C. for 1 h, warmed to room temperature, and stirred for additional 16 h. The resulting solution was quenched with aqueous HCl (10 M, 20 mL) and extracted with DCM (3×10 mL). The combined organic layers was dried with anhydrous $Na_2SO_4$ and filtered. The filtrate was concentrated under reduced pressure to give the crude title compound as a solid and used for next step directly without further purification. $^1$H NMR (400 MHz, DMSO-$d_6$) δ: 7.79 (d, J=8.0 Hz, 2H), 7.62 (d, J=8.0 Hz, 2H), 7.48 (d, J=8.0 Hz, 2H), 7.43 (d, J=8.0 Hz, 2H), 4.48 (s, 1H), 3.94 (d, J=9.2 Hz, 1H), 3.71 (d, J=9.2 Hz, 1H), 2.42 (s, 3H), 0.74 (s, 3H), 0.69 (s, 3H).

Step 2. 2,2-Dimethyl-3-oxo-3-(4-(trifluoromethyl)phenyl)propyl 4-methylbenzenesulfonate To a solution of 3-hydroxy-2,2-dimethyl-3-(4-(trifluoromethyl)phenyl)propyl 4-methylbenzenesulfonate (0.860 g, 1.3 mmol) in DCM (15 mL) was added DMP (0.816 g, 1.9 mmol) at 0° C. The reaction suspension was stirred at 0° C. for 30 min and warmed to room temperature, stirred for additional 16 h. The resulting mixture was filtered. The filter cake was washed with DCM (3×1 mL). The combined organic fractions were concentrated under reduced pressure. The residue was purified by column chromatography over silica gel using 0-30% gradient of ethyl acetate in petroleum ether as eluent. The fractions containing desired product were combined and concentrated. The title compound was obtained as a solid. MS (+ESI) m/z: 401.2.

Step 3. 3-Chloro-2,2-dimethyl-1-(4-(trifluoromethyl)phenyl)propan-1-one

To a solution of 2,2-dimethyl-3-oxo-3-(4-(trifluoromethyl)phenyl)propyl 4-methylbenzenesulfonate (0.200 g, 0.5 mmol) in dry DMSO (2.5 mL) was added KCl (74.0 mg, 1.0 mmol) at room temperature. The reaction solution was stirred at 120° C. for 6 h. The resulting solution was cooled, diluted with water (100 mL) and extracted with EtOAc (3×20 mL). The combined organic layers was washed with brine (50 mL), dried with anhydrous $Na_2SO_4$ and filtered. The filtrate was concentrated under reduced pressure. The crude title compound was obtained as a liquid. $^1H$ NMR (300 MHz, DMSO-$d_6$) δ: 7.89-7.84 (m, 4H), 3.90 (s, 2H), 1.36 (s, 6H).

Step 4. N-(3-chloro-2,2-dimethyl-1-(4-(trifluoromethyl)phenyl)propylidene)-1-phenylmethanamine To a solution of benzyl amine (60.7 mg, 0.6 mmol) and 3-chloro-2,2-dimethyl-1-(4-(trifluoromethyl)phenyl)propan-1-one (50.0 mg, 0.2 mmol) in ethyl ether (1.0 mL) was added dropwise a solution of $TiCl_4$ (12.0 μL, 0.1 mmol) in pentane (0.1 mL) at 0° C. The reaction suspension was refluxed for 48 h. The resulting suspension was cooled, diluted with diethyl ether (2 mL) and filtered. The filtrate was concentrated under reduced pressure to give the crude title compound as a liquid and was used for next step directly without further purification. MS (+ESI) m/z: 354.0/356.0.

Step 5. N-benzylidene-2,2-dimethyl-1-(4-(trifluoromethyl)phenyl)cyclopropanamine To a solution of N-(3-chloro-2,2-dimethyl-1-(4-(trifluoromethyl)phenyl)propylidene)-1-phenylmethanamine (28.0 mg, 0.08 mmol) in THF (0.5 mL) was added t-BuOK (26.6 mg, 0.2 mmol) at room temperature. The reaction suspension was refluxed for 3 h. The resulting mixture was cooled, diluted with brine (4 mL) and extracted with EtOAc (3×1 mL). The combined organic layers was dried with anhydrous $Na_2SO_4$ and filtered. The filtrate was concentrated under reduced pressure. The residue was purified by column chromatography over reverse phase C18 silica gel using 70-100% gradient of methanol in water as eluent. The fractions containing desired product were combined and concentrated. The title compound was obtained as a solid. MS (+ESI) m/z: 318.1.

Step 6. 2,2-Dimethyl-1-(4-(trifluoromethyl)phenyl)cyclopropanamine

Oxalic acid (70.9 mg, 0.8 mmol) and water (0.2 mL) were added to a stirred mixture of N-benzylidene-2,2-dimethyl-1-(4-(trifluoromethyl)phenyl)cyclopropanamine (25.0 mg, 0.08 mmol) in MeOH (0.4 mL) and THF (0.4 mL). The reaction mixture was stirred at room temperature for 16 h. The resulting mixture was washed with EtOAc (3×5 mL). Then the pH value of the separated aqueous phase was adjusted to 9 with NaOH (3 M) and extracted with DCM (3×5 mL). The combined organic fractions was dried with anhydrous $Na_2SO_4$ and filtered. The filtrate was concentrated under reduced pressure to give the title compound as a liquid. MS (+ESI) m/z: 230.0.

Preparatory Example 21

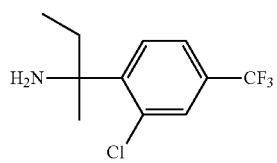

2-(2-Chloro-4-(trifluoromethyl)phenyl)butan-2-amine

Step 1. 2-Chloro-N-methoxy-N-methyl-4-(trifluoromethyl)benzamide

To a solution of 2-chloro-4-(trifluoromethyl)benzoic acid (6.00 g, 26.7 mmol) and DMF (cat.) in DCM (100 mL) was added oxalyl chloride (5.09 g, 40.1 mmol) at 0° C. under nitrogen atmosphere. The reaction solution was stirred for 16 h at room temperature. The resulting solution was concentrated under reduced pressure to give the crude 2-chloro-4-(trifluoromethyl)benzoyl chloride as a liquid.

To a mixture of $Na_2CO_3$ (19.8 g, 187 mmol) in DCM (150 mL) and water (150 mL) were added N,O-dimethylhydroxylamine hydrochloride (13.0 g, 133 mmol) and then dropped slowly a solution of the crude 2-chloro-4-(trifluoromethyl)benzoyl chloride (6.46 g, 26.6 mmol) in DCM (50 mL) at 0° C. The reaction mixture was stirred for 1 h at room temperature. The resulting mixture was separated. The aqueous layer was extracted with DCM (3×100 mL). The combined organic layers was dried over anhydrous $Na_2SO_4$ and filtered. The filtrate was concentrated under reduced pressure. The residue was purified by column chromatography over silica gel using 30-50% of gradient of ethyl acetate in petroleum ether as eluent. The fractions containing desired product were combined and concentrated. The title compound was obtained as a liquid. MS (+ESI) m/z=267.9.

Step 2. 1-(2-Chloro-4-(trifluoromethyl)phenyl)propan-1-one

The title compound was prepared using procedures similar to those described in step 2 of Preparatory Example 11 using 2-chloro-N-methoxy-N-methyl-4-(trifluoromethyl)benzamide and ethylmagnesium bromide to give the title compound as a liquid. $^1H$ NMR (400 MHz, $CDCl_3$) δ: 7.69 (s, 1H), 7.59 (d, J=8.0 Hz, 1H), 7.52 (d, J=8.0 Hz, 1H), 2.95 (q, J=7.2 Hz, 2H), 1.23 (t, J=7.2 Hz, 3H).

Step 3. 2-(2-Chloro-4-(trifluoromethyl)phenyl)butan-2-ol

The title compound was prepared using procedures similar to those described in step 1 of Preparatory Example 17 using 1-(2-chloro-4-(trifluoromethyl)phenyl)propan-1-one and methylmagnesium bromide to give the title compound as a liquid. $^1H$ NMR (400 MHz, $CDCl_3$) δ: 7.83 (d, J=8.4 Hz, 1H), 7.52 (s, 1H), 7.43 (d, J=8.4 Hz, 1H), 2.32-2.22 (m, 1H), 1.91-1.81 (m, 1H), 1.63 (s, 3H), 0.69 (t, J=7.4 Hz, 3H).

Step 4. 1-(2-Azidobutan-2-yl)-2-chloro-4-(trifluoromethyl)benzene

To a solution of 2-(2-chloro-4-(trifluoromethyl)phenyl)butan-2-ol (0.350 g, 1.4 mmol) and TMS-$N_3$ (0.4 mL, 2.8 mmol) in DCM (4 mL) was added indium(III) bromide (98.0 mg, 0.3 mmol) at room temperature. The reaction suspension was stirred at room temperature for 24 h. The resulting suspension was diluted with water (80 mL) and extracted with DCM (3×20 mL). The combined organic layers was washed with brine (40 mL), dried with anhydrous Na$_2$SO$_4$ and filtered. The filtrate was concentrated under reduced pressure. The residue was purified by column chromatography over silica gel using hexane as eluent. The fractions containing desired product were combined and concentrated. The title compound was obtained as a liquid. $^1$H NMR (400 MHz, CDCl$_3$) δ: 7.77 (d, J=8.4, 1H), 7.65 (s, 1H), 7.52 (d, J=8.4, 1H), 2.46-2.37 (m, 1H), 2.09-2.00 (m, 1H), 1.84 (s, 3H), 0.76 (t, J=7.4 Hz, 3H).

Step 5. 2-(2-Chloro-4-(trifluoromethyl)phenyl)butan-2-amine

To a solution of 1-(2-azidobutan-2-yl)-2-chloro-4-(trifluoromethyl)benzene (0.100 g, 0.4 mmol) in THF (2 mL) and MeOH (4 mL) were added NH$_4$Cl (0.193 g, 3.6 mmol) and zinc (0.118 g, 1.8 mmol) at room temperature. The reaction mixture was stirred for 3 h at room temperature. The resulting mixture was filtered. The filtrate was concentrated under reduced pressure. The residue was diluted with water (8 mL) and extracted with EtOAc (3×3 mL). The combined organic layers was washed with brine (8 mL), dried with anhydrous Na$_2$SO$_4$ and filtered. The filtrate was concentrated under reduced pressure. The residue was purified by column chromatography over reverse phase C18 silica gel using 70-100% gradient of methanol in water as eluent. The fractions containing desired product were combined and concentrated. The title compound was obtained as a liquid. MS (+ESI) m/z=252.1.

Preparatory Example 22

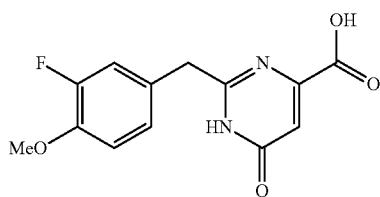

2-(3-fluoro-4-methoxybenzyl)-6-oxo-1,6-dihydropyrimidine-4-carboxylic acid

The title compound was prepared following procedures described in Steps 3 and 4 of Preparatory Example 8. $^1$H NMR (500 MHz, DMSO-d$_6$) δ: 13.00 (s, 1H), 7.21-7.19 (m, 1H), 7.14-7.08 (m, 2H), 6.68 (s, 1H), 3.84 (s, 2H), 3.80 (s, 3H).

Preparatory Example 23

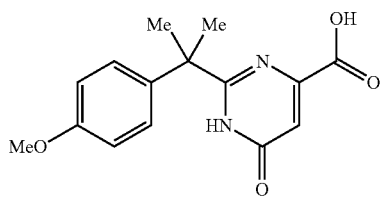 [SMILES: COc1ccc(C(C)(C)c2nc(C(=O)O)cc(=O)[nH]2)cc1]

2-(2-(4-Methoxyphenyl)propan-2-yl)-6-oxo-1,6-dihydropyrimidine-4-carboxylic acid The title compound was prepared from 2-(4-methoxyphenyl)-2-methylpropanenitrile following procedures described in Steps 3 and 4 of Preparatory Example 8. 2-(4-Methoxyphenyl)-2-methylpropanenitrile was in turn synthesized using the procedure outlined in ter Wiel, M. K. J.; Odermatt, S.; Schanen, P.; Seiler, P.; Diederich, F. *Eur. J. Org. Chem.* 2007, 21, 3449-3462. $^1$H NMR (500 MHz, DMSO-d$_6$) δ: 12.19 (br s, 1H), 7.17 (d, J=8.5 Hz, 2H), 6.88 (d, J=8.5 Hz, 2H), 6.72 (s, 1H), 3.73 (s, 3H), 1.63 (s, 6H).

Example 1

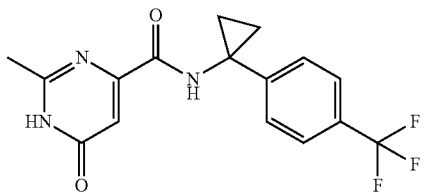 [SMILES: Cc1nc(C(=O)NC2(c3ccc(C(F)(F)F)cc3)CC2)cc(=O)[nH]1]

2-Methyl-6-oxo-N-{1-[4-(trifluoromethyl)phenyl]cyclopropyl}-1,6-dihydropyrimidine-4-carboxamide 2-Methyl-6-oxo-1,6-dihydropyrimidine-4-carboxylic acid from Preparatory Example 5 (50 mg, 0.324 mmol) was dissolved in DMF (811 µl) and treated with 1-(4-(trifluoromethyl)phenyl)cyclopropanamine from Preparatory Example 2 (71.8 mg, 0.357 mmol), DIEA (340 µl, 1.946 mmol) and HATU (136 mg, 0.357 mmol). This was agitated via a thermomixer at room temperature for 1 hr. The reaction contents were diluted with CH$_2$Cl$_2$ (5 mL), washed with sat'd NaHCO$_3$ (3 mL), dried by filtering through a hydrophobic flit and evaporated to afford an orange oil. This was purified via RP-HPLC on a C18 column (15-65% CH$_3$CN/H$_2$O, 0.1% TFA), then lyophilized to give a solid. This was diluted with CH$_2$Cl$_2$ (2 mL) and washed with sat'd NaHCO$_3$ (2 mL), dried by filtering through a hydrophobic frit and evaporating to afford the title compound. MS (+ESI) m/z=338.0. $^1$H NMR (500 MHz, DMSO-d$_6$) δ: 12.45 (s, 1H), 9.35 (s, 1H), 7.62 (d, J=8.1 Hz, 2H), 7.35 (d, J=8.1 Hz, 2H), 6.34 (s, 1H), 5.76 (s, 1H), 2.38 (s, 3H), 1.38-1.35 (m, 4H).

The following compounds in Table 1 were prepared using procedures similar to those described in Example 1 and appropriate starting materials.

TABLE 1

| Example No. | Structure | IUPAC Name | Observed Exact Mass [M + H]+ |
|---|---|---|---|
| 2 | 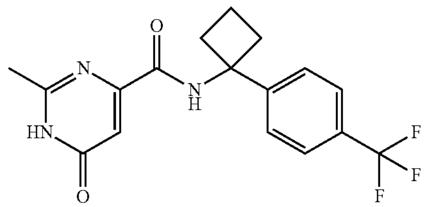 [SMILES: Cc1nc(C(=O)NC2(c3ccc(C(F)(F)F)cc3)CCC2)cc(=O)[nH]1] | 2-methyl-6-oxo-N-{1-[4-(trifluoromethyl)phenyl]cyclobutyl}-1,6-dihydropyrimidine-4-carboxamide | 352.1 |
| 3 | 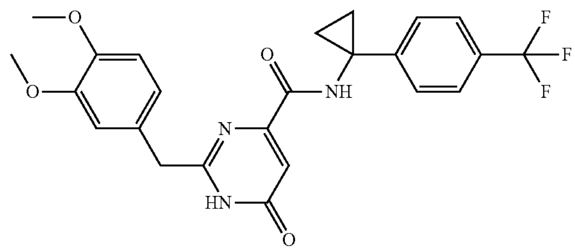 [SMILES: COc1ccc(Cc2nc(C(=O)NC3(c4ccc(C(F)(F)F)cc4)CC3)cc(=O)[nH]2)cc1OC] | 2-(3,4-dimethoxybenzyl)-6-oxo-N-{1-[4-(trifluoromethyl)phenyl]cyclopropyl}-1,6-dihydropyrimidine-4-carboxamide | 474.1 |
| 4 | 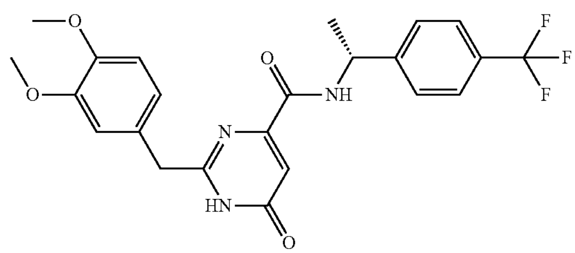 [SMILES: COc1ccc(Cc2nc(C(=O)N[C@H](C)c3ccc(C(F)(F)F)cc3)cc(=O)[nH]2)cc1OC] | 2-(3,4-dimethoxybenzyl)-6-oxo-N-{(1R)-1-[4-(trifluoromethyl)phenyl]ethyl}-1,6-dihydropyrimidine-4-carboxamide | 462.1 |
| 5 | 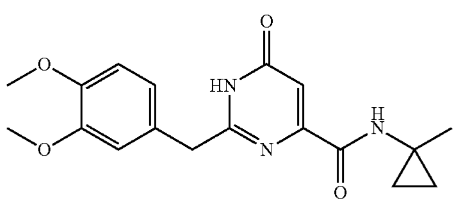 | 2-(3,4-dimethoxybenzyl)-N-(1-methylcyclopropyl)-6-oxo-1,6-dihydropyrimidine-4-carboxamide | 344.1 |
| 6 | 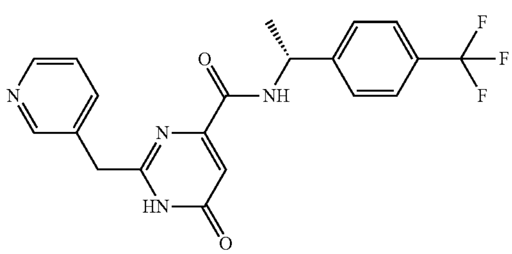 [SMILES: C[C@@H](NC(=O)c1cc(=O)[nH]c(Cc2cccnc2)n1)c1ccc(C(F)(F)F)cc1] | 6-oxo-2-(pyridin-3-ylmethyl)-N-{(1R)-1-[4-(trifluoromethyl)phenyl]ethyl}-1,6-dihydropyrimidine-4-carboxamide | 403.1 |
| 7 | 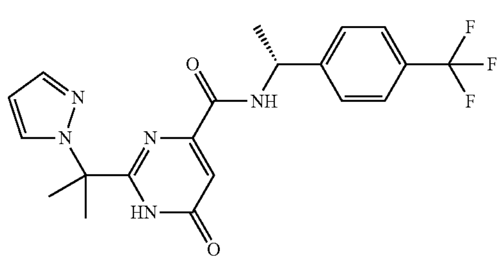 [SMILES: C[C@@H](NC(=O)c1cc(=O)[nH]c(C(C)(C)n2cccn2)n1)c1ccc(C(F)(F)F)cc1] | 2-[1-methyl-1-(1H-pyrazol-1-yl)ethyl]-6-oxo-N-{(1R)-1-[4-(trifluoromethyl)phenyl]ethyl}-1,6-dihydropyrimidine-4-carboxamide | 420.1 |

Example 3: ¹H NMR (500 MHz, DMSO-d₆) δ: 9.43 (s, 1H), 7.62 (d, J=8.3 Hz, 2H), 7.36 (d, J=8.3 Hz, 2H) 7.15 (s, 1H), 6.93-6.84 (m, 2H), 6.65 (s, 1H), 3.85 (s, 2H), 3.75 (s, 3H), 3.72 (s, 3H), 1.40-1.32 (m, 4H).

Example 7: ¹H NMR (500 MHz, CDCl₃) δ: 10.70-10.65 (m, 1H), 7.89-7.87 (m, 1H), 7.15-7.12 (m, 1H), 7.62 (d, J=8.3 Hz, 2H), 7.47 (d, J=8.3 Hz, 2H), 7.13 (s, 1H), 6.38-6.37 (m, 1H), 5.30-5.27 (m, 1H), 2.04 (s, 3H), 2.03 (s, 3H), 1.64-1.62 (m, 1H), 1.25 (s, 3H).

Example 8

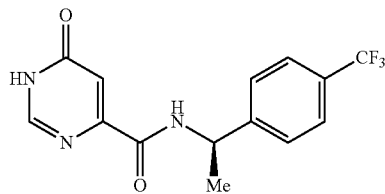 [SMILES: C[C@@H](NC(=O)c1cc(=O)[nH]cn1)c1ccc(C(F)(F)F)cc1]

(R)-6-oxo-N-(1-(4-(trifluoromethyl)phenyl)ethyl)-1,6-dihydropyrimidine-4-carboxamide To a stirred mixture of 6-oxo-1,6-dihydropyrimidine-4-carboxylic acid (0.9 g, 6.42 mmol) in DMF (20 mL) was added (R)-1-(4-(trifluoromethyl)phenyl)ethanamine (1.3 g, 6.87 mmol), HATU (3.66 g, 9.64 mmol) and Hunig's Base (4.49 mL, 25.7 mmol). The resulting mixture was stirred at room temperature overnight. The reaction mixture was diluted with EtOAc and saturated aqueous NH₄Cl. The organic layer was washed with water, brine and dried over anhydrous sodium sulfate and concentrated under reduced pressure. The residue was purified by column chromatography on silica (40 to 95% EtOAc/hexanes) to yield the title compound. MS: 312.0 (M+H). ¹H NMR (500 MHz, CD₃OD) δ 8.27 (s, 1H), 7.65 (d, J=8.3 Hz, 2H), 7.60 (d, J=8.3 Hz, 2H), 7.05 (s, 1H), 5.27 (q, J=7.1 Hz, 1H), 1.62 (d, J=7.1 Hz, 3H).

The following examples in Table 2 were prepared according to scheme A using the procedure outlined in the synthesis of Example 8.

TABLE 2

| Example No. | Structure | IUPAC Name | Observed Exact Mass [M + H]⁺ |
|---|---|---|---|
| 9 | 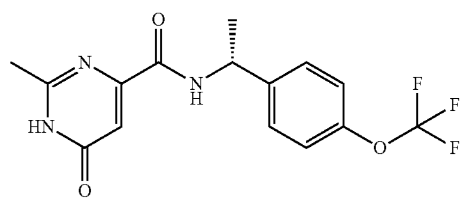 [SMILES: Cc1nc(C(=O)N[C@H](C)c2ccc(OC(F)(F)F)cc2)cc(=O)[nH]1] | 2-methyl-6-oxo-N-{(1R)-1-[4-(trifluoromethoxy)phenyl]ethyl}-1,6-dihydropyrimidine-4-carboxamide | 342.1 |
| 10 | 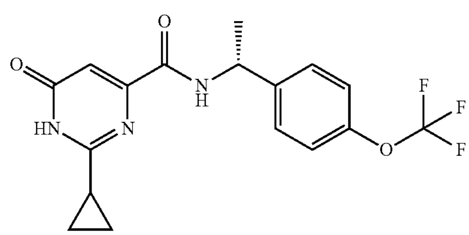 [SMILES: C[C@@H](NC(=O)c1cc(=O)[nH]c(C2CC2)n1)c1ccc(OC(F)(F)F)cc1] | 2-cyclopropyl-6-oxo-N-{(1R)-1-[4-(trifluoromethoxy)phenyl]ethyl}-1,6-dihydropyrimidine-4-carboxamide | 368.0 |
| 11 | 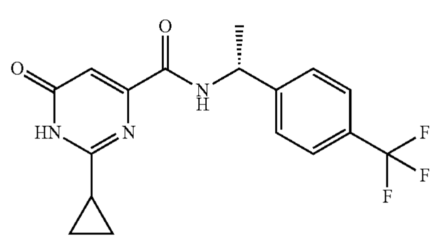 [SMILES: C[C@@H](NC(=O)c1cc(=O)[nH]c(C2CC2)n1)c1ccc(C(F)(F)F)cc1] | 2-cyclopropyl-6-oxo-N-{(1R)-1-[4-(trifluoromethyl)phenyl]ethyl}-1,6-dihydropyrimidine-4-carboxamide | 352.0 |
| 12 | 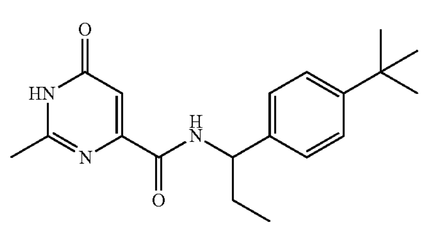 [SMILES: CCC(NC(=O)c1cc(=O)[nH]c(C)n1)c1ccc(C(C)(C)C)cc1] | N-[1-(4-tert-butylphenyl)propyl]-2-methyl-6-oxo-1,6-dihydropyrimidine-4-carboxamide | 328.4 |

TABLE 2-continued

| Example No. | Structure | IUPAC Name | Observed Exact Mass [M + H]+ |
|---|---|---|---|
| 13 | 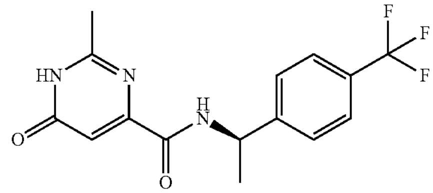 [SMILES: Cc1nc(C(=O)N[C@H](C)c2ccc(C(F)(F)F)cc2)cc(=O)[nH]1] | 2-methyl-6-oxo-N-{(1R)-1-[4-(trifluoromethyl)phenyl]ethyl}-1,6-dihydropyrimidine-4-carboxamide | 326.2 |
| 14 | 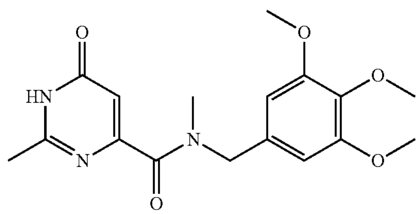 | N,2-dimethyl-6-oxo-N-(3,4,5-trimethoxybenzyl)-1,6-dihydropyrimidine-4-carboxamide | 348.0 |

Example 13: $^1$H NMR (500 MHz, CD$_3$OD) δ 8.96 (bd, J=7.2 Hz, 1H), 7.64 (d, 0.1=8.1 Hz, 2H), 7.58 (d, J=8.1 Hz, 2H), 6.90 (bs, J H), 5.26 (dq, J=7.1 and 7.0 Hz, 1H), 2.47 (s, 3H), 1.61 (d, J=7.1 Hz, 3H).

Example 15

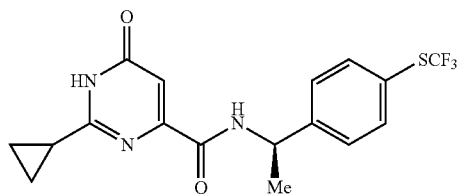

(R)-2-cyclopropyl-6-oxo-N-(1-(4-((trifluoromethyl)thio)phenyl)ethyl)-1,6-dihydro pyrimidine-4-carboxamide To a stirred mixture of 2-cyclopropyl-6-oxo-1,6-dihydropyrimidine-4-carboxylic acid (40 mg, 0.222 mmol) in DMA (1 mL) was added 3H-[1,2,3]triazolo[4,5-b]pyridin-3-ol (36.3 mg, 0.266 mmol), (R)-1-(4-((trifluoromethyl)thio)phenyl)ethanamine HCl salt (60.1 mg, 0.233 mmol) and triethylamine (0.062 mL, 0.444 mmol). After stirring for 10 min, EDC (51.1 mg, 0.266 mmol) was added. The resulting mixture was stirred at room temperature over a weekend. The mixture was filtered and purified by preparative RP-HPLC (C-18), eluting with 10 to 95% Acetonitrile/Water with 0.05% TFA modifier, to yield the title compound. MS: 384.1 (M+H). $^1$H NMR (500 MHz, CD$_3$OD) δ 7.68 (d, J=8.2 Hz, 2H), 7.51 (d, J=8.2 Hz, 2H), 6.82 (s, 1H), 5.215 (q, d, J=6.9 Hz, 1H), 1.95~2.00 (m, 1H), 1.61 (d, J=7.1 Hz 3H), 1.30~1.35 (m, 2H), 1.15-1.19 (m, 2H).

The following examples in Table 3 were prepared according to scheme B using the procedure outlined in the synthesis of Example 15.

TABLE 3

| Example No. | Structure | IUPAC Name | Observed Exact Mass [M + H]+ |
|---|---|---|---|
| 16 | 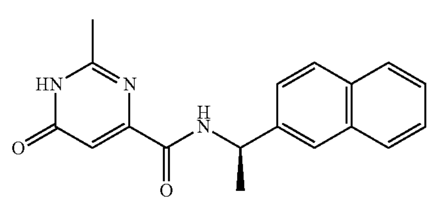 [SMILES: Cc1nc(C(=O)N[C@H](C)c2ccc3ccccc3c2)cc(=O)[nH]1] | 2-methyl-N-[(1R)-1-naphthalen-2-ylethyl]-6-oxo-1,6-dihydropyrimidine-4-carboxamide | 308.1 |

TABLE 3-continued

| Example No. | Structure | IUPAC Name | Observed Exact Mass [M + H]+ |
|---|---|---|---|
| 17 | 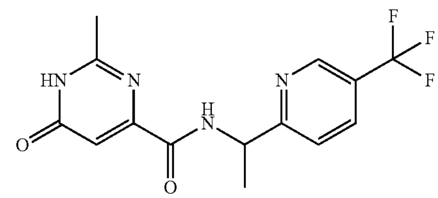 [SMILES: Cc1nc(C(=O)NC(C)c2ccc(C(F)(F)F)cn2)cc(=O)[nH]1] | 2-methyl-6-oxo-N-{1-[5-(trifluoromethyl)pyridin-2-yl]ethyl}-1,6-dihydropyrimidine-4-carboxamide | 327.1 |
| 18 | 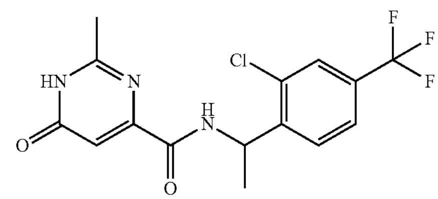 [SMILES: Cc1nc(C(=O)NC(C)c2ccc(C(F)(F)F)cc2Cl)cc(=O)[nH]1] | N-{1-[2-chloro-4-(trifluoromethyl)phenyl]ethyl}-2-methyl-6-oxo-1,6-dihydropyrimidine-4-carboxamide | 360.1/362.0 |
| 19 | 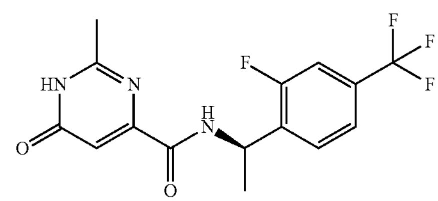 [SMILES: Cc1nc(C(=O)N[C@H](C)c2ccc(C(F)(F)F)cc2F)cc(=O)[nH]1] | N-{(1R)-1-[2-fluoro-4-(trifluoromethyl)phenyl]ethyl}-2-methyl-6-oxo-1,6-dihydropyrimidine-4-carboxamide | 344.1 |
| 20 | 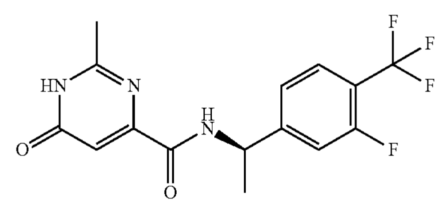 [SMILES: Cc1nc(C(=O)N[C@H](C)c2ccc(C(F)(F)F)c(F)c2)cc(=O)[nH]1] | N-{(1R)-1-[3-fluoro-4-(trifluoromethyl)phenyl]ethyl}-2-methyl-6-oxo-1,6-dihydropyrimidine-4-carboxamide | 344.1 |
| 21 | 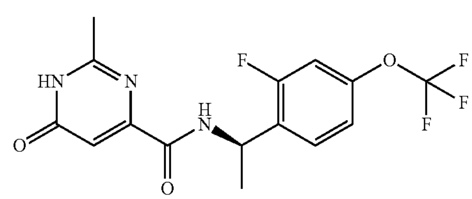 [SMILES: Cc1nc(C(=O)N[C@H](C)c2ccc(OC(F)(F)F)cc2F)cc(=O)[nH]1] | N-{(1R)-1-[2-fluoro-4-(trifluoromethoxy)phenyl]ethyl}-2-methyl-6-oxo-1,6-dihydropyrimidine-4-carboxamide | 360.0 |
| 22 | 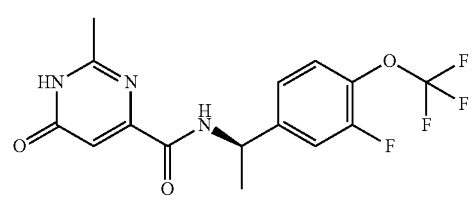 [SMILES: Cc1nc(C(=O)N[C@H](C)c2ccc(OC(F)(F)F)c(F)c2)cc(=O)[nH]1] | N-{(1R)-1-[3-fluoro-4-(trifluoromethoxy)phenyl]ethyl}-2-methyl-6-oxo-1,6-dihydropyrimidine-4-carboxamide | 360.0 |
| 23 | 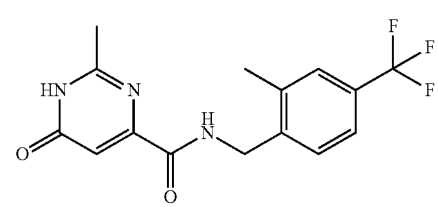 [SMILES: Cc1nc(C(=O)NCc2ccc(C(F)(F)F)cc2C)cc(=O)[nH]1] | 2-methyl-N-[2-methyl-4-(trifluoromethyl)benzyl]-6-oxo-1,6-dihydropyrimidine-4-carboxamide | 326.1 |

TABLE 3-continued

| Example No. | Structure | IUPAC Name | Observed Exact Mass [M + H]+ |
|---|---|---|---|
| 24 | 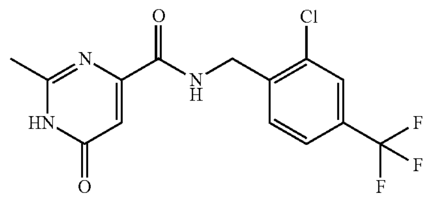 [SMILES: Cc1nc(C(=O)NCc2ccc(C(F)(F)F)cc2Cl)cc(=O)[nH]1] | N-[2-chloro-4-(trifluoromethyl)benzyl]-2-methyl-6-oxo-1,6-dihydropyrimidine-4-carboxamide | 346.1/348.0 |
| 25 | 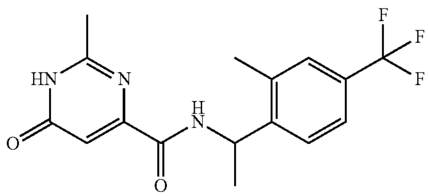 [SMILES: Cc1nc(C(=O)NC(C)c2ccc(C(F)(F)F)cc2C)cc(=O)[nH]1] | 2-methyl-N-{1-[2-methyl-4-(trifluoromethyl)phenyl]ethyl}-6-oxo-1,6-dihydropyrimidine-4-carboxamide | 340.1 |
| 26 | 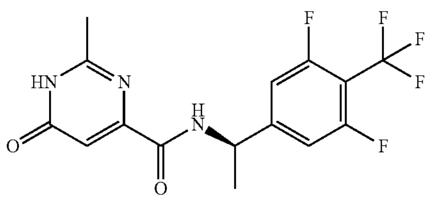 [SMILES: Cc1nc(C(=O)N[C@H](C)c2cc(F)c(C(F)(F)F)c(F)c2)cc(=O)[nH]1] | N-{(1R)-[3,5-difluoro-4-(trifluoromethyl)phenyl]ethyl}-2-methyl-6-oxo-1,6-dihydropyrimidine-4-carboxamide | 362.1 |
| 27 | 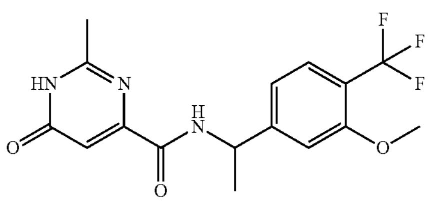 [SMILES: COc1cc(C(C)NC(=O)c2cc(=O)[nH]c(C)n2)ccc1C(F)(F)F] | N-{1-[3-methoxy-4-(trifluoromethyl)phenyl]ethyl}-2-methyl-6-oxo-1,6-dihydropyrimidine-4-carboxamide | 356.1 |
| 28 | 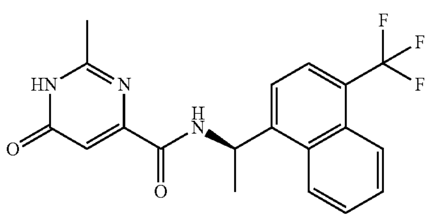 [SMILES: Cc1nc(C(=O)N[C@H](C)c2ccc(C(F)(F)F)c3ccccc23)cc(=O)[nH]1] | 2-methyl-6-oxo-N-{(1R)-1-[4-(trifluoromethyl)naphthalen-1-yl]ethyl}-1,6-dihydropyrimidine-4-carboxamide | 376.1 |
| 29 | 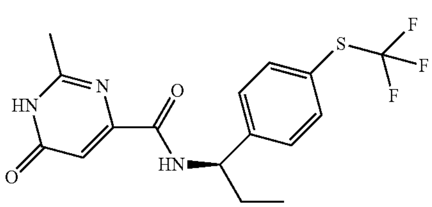 [SMILES: CC[C@@H](NC(=O)c1cc(=O)[nH]c(C)n1)c1ccc(SC(F)(F)F)cc1] | 2-methyl-6-oxo-N-[(1R)-1-{4-[(trifluoromethyl)sulfanyl]phenyl}propyl]-1,6-dihydropyrimidine-4-carboxamide | 372.1 |
| 30 | 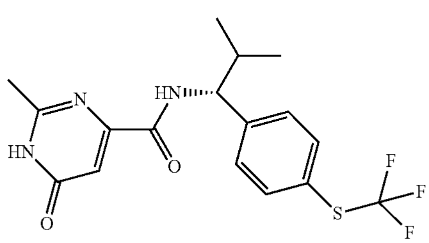 [SMILES: Cc1nc(C(=O)N[C@@H](c2ccc(SC(F)(F)F)cc2)C(C)C)cc(=O)[nH]1] | 2-methyl-N-[(1R)-2-methyl-1-{4-[(trifluoromethyl)sulfanyl]phenyl}propyl]-6-oxo-1,6-dihydropyrimidine-4-carboxamide | 386.1 |

TABLE 3-continued

| Example No. | Structure | IUPAC Name | Observed Exact Mass [M + H]+ |
|---|---|---|---|
| 31 | 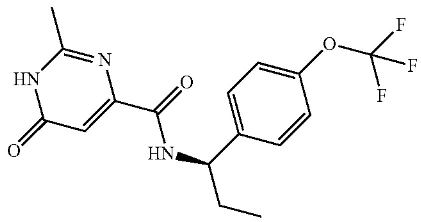 [SMILES: CC[C@@H](NC(=O)c1cc(=O)[nH]c(C)n1)c1ccc(OC(F)(F)F)cc1] | 2-methyl-6-oxo-N-{(1R)-1-[4-(trifluoromethoxy)phenyl]propyl}-1,6-dihydropyrimidine-4-carboxamide | 356.1 |
| 32 | 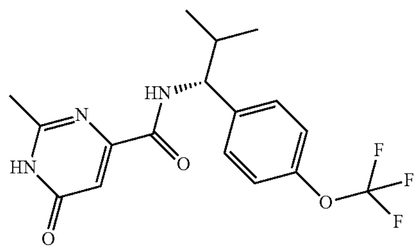 [SMILES: Cc1nc(C(=O)N[C@@H](c2ccc(OC(F)(F)F)cc2)C(C)C)cc(=O)[nH]1] | 2-methyl-N-{(1R)-2-methyl-1-[4-(trifluoromethoxy)phenyl]propyl}-6-oxo-1,6-dihydropyrimidine-4-carboxamide | 370.1 |
| 33 | 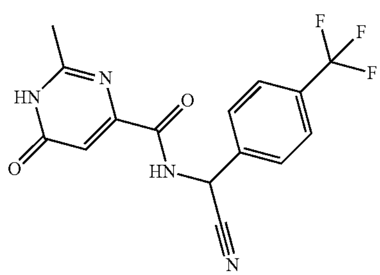 [SMILES: Cc1nc(C(=O)NC(C#N)c2ccc(C(F)(F)F)cc2)cc(=O)[nH]1] | N-{cyano[4-(trifluoromethyl)phenyl]methyl}-2-methyl-6-oxo-1,6-dihydropyrimidine-4-carboxamide | Calc'd 337.1, found 337.0 |
| 34 | 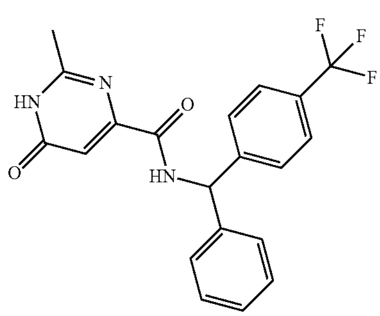 [SMILES: Cc1nc(C(=O)NC(c2ccccc2)c2ccc(C(F)(F)F)cc2)cc(=O)[nH]1] | 2-methyl-6-oxo-N-{phenyl[4-(trifluoromethyl)phenyl]methyl}-1,6-dihydropyrimidine-4-carboxamide | Calc'd 388.1, found 388.0 |

Example 22: ¹H NMR (500 MHz, CD₃OD) δ 7.40-7.37 (m, 2H), 7.30-7.28 (m, 1H), 6.89 (s, 1H), 5.20 (q, J=7.1 Hz, 1H), 2.47 (s, 3H), 1.59 (d, J=7.0 Hz, 3H).

Example 32: ¹H NMR (500 MHz, CD₃OD) δ 8.91 (v bs, 1H), 7.47 (d, J=8.4 Hz, 2H), 7.24 (d, J=8.1 Hz, 2H), 6.90 (v bs, 1H), 4.73-4.75 (m, 1H), 2.45 (bs, 3H), 2.29-2.22 (m, 1H), 1.04 (d, J=6.6 Hz, 3H), 0.84 (d, J=6.6 Hz, 3H).

Example 35

2-Methyl-6-oxo-N-(1-(4-(((trifluoromethyl)thio)phenyl)cyclopropyl)-1,6-dihydroy primidine-4-carboxamide

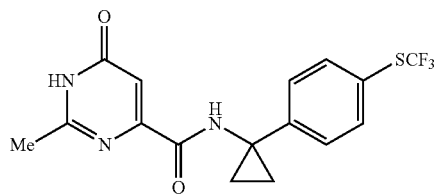

To a stirred mixture of 2-methyl-6-oxo-1,6-dihydropyrimidine-4-carboxylic acid (60 mg, 0.389 mmol) in DMF (1.2 mL) was added 3H-[1,2,3]triazolo[4,5-b]pyridin-3-ol (58.3 mg, 0.428 mmol), 1-(4-((trifluoromethyl)thio)phenyl)cyclopropanamine HCl salt (105 mg, 0.389 mmol). After stirring for 10 min, EDC (82 mg, 0.428 mmol) was added. The resulting mixture was stirred at room temperature overnight. The mixture was filtered and purified by preparative RP-HPLC (C-18), eluting with 10 to 90% Acetonitrile/Water with 0.05% TFA modifier, to give the title compound. MS: 370.1 (M+H). ¹H NMR (500 MHz, CD₃OD) δ 7.62 (d, J=8.3 Hz, 2H), 7.35 (d, J=8.5 Hz, 2H), 6.91 (s, 1H), 2.48 (s, 3H), 1.45 (s, 4H).

The following examples in Table 4 were prepared according to Scheme C using the procedure outlined in the synthesis of Example 35

TABLE 4

| Example No. | Structure | IUPAC Name | Observed Exact Mass [M + H]⁺ |
|---|---|---|---|
| 36 | 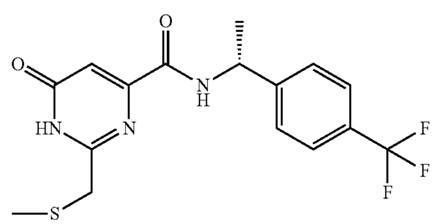 [SMILES: CSCc1nc(C(=O)N[C@H](C)c2ccc(C(F)(F)F)cc2)cc(=O)[nH]1] | 2-[(methylsulfanyl)methyl]-6-oxo-N-{(1R)-1-[4-(trifluoromethyl)phenyl]ethyl}-1,6-dihydropyrimidine-4-carboxamide | 372.1 |
| 37 | 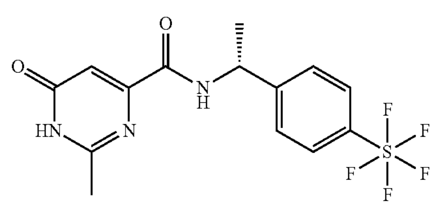 [SMILES: Cc1nc(C(=O)N[C@H](C)c2ccc(S(F)(F)(F)(F)F)cc2)cc(=O)[nH]1] | 2-methyl-6-oxo-N-{(1R)-1-[4-(pentafluoro-λ⁶-sulfanyl)phenyl]ethyl}-1,6-dihydropyrimidine-4-carboxamide | 384.1 |
| 38 | 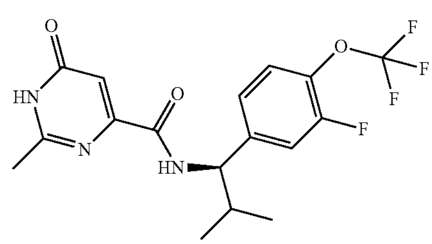 [SMILES: Cc1nc(C(=O)N[C@@H](c2ccc(OC(F)(F)F)c(F)c2)C(C)C)cc(=O)[nH]1] | N-{(1R)-1-[3-fluoro-4-(trifluoromethoxy)phenyl]-2-methylpropyl}-2-methyl-6-oxo-1,6-dihydropyrimidine-4-carboxamide | 388.2 |
| 39 | 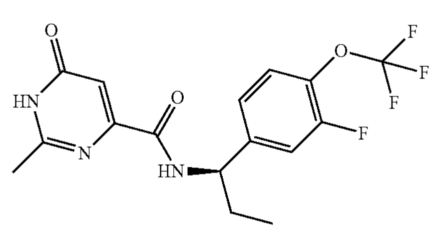 [SMILES: CC[C@@H](NC(=O)c1cc(=O)[nH]c(C)n1)c1ccc(OC(F)(F)F)c(F)c1] | N-{(1R)-1-[3-fluoro-4-(trifluoromethoxy)phenyl]propyl}-2-methyl-6-oxo-1,6-dihydropyrimidine-4-carboxamide | 374.1 |

TABLE 4-continued

| Example No. | Structure | IUPAC Name | Observed Exact Mass [M + H]+ |
|---|---|---|---|
| 40 | 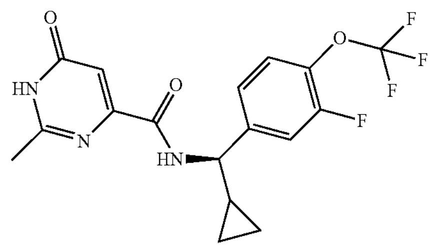 [SMILES: Cc1nc(C(=O)N[C@@H](c2ccc(OC(F)(F)F)c(F)c2)C2CC2)cc(=O)[nH]1] | N-{(R)-cyclopropyl[3-fluoro-4-(trifluoromethoxy)phenyl]methyl}-2-methyl-6-oxo-1,6-dihydropyrimidine-4-carboxamide | 386.2 |
| 41 | 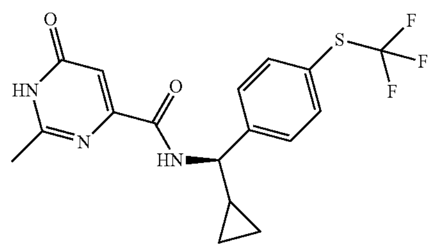 [SMILES: Cc1nc(C(=O)N[C@@H](c2ccc(SC(F)(F)F)cc2)C2CC2)cc(=O)[nH]1] | N-[(R)-cyclopropyl{4-[(trifluoromethyl)sulfanyl]phenyl}methyl]-2-methyl-6-oxo-1,6-dihydropyrimidine-4-carboxamide | 384.1 |
| 42 | 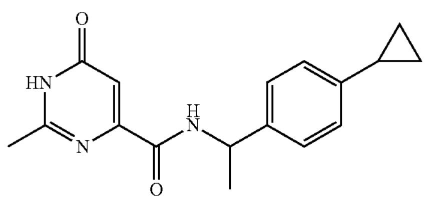 [SMILES: Cc1nc(C(=O)NC(C)c2ccc(C3CC3)cc2)cc(=O)[nH]1] | N-[1-(4-cyclopropylphenyl)ethyl]-2-methyl-6-oxo-1,6-dihydropyrimidine-4-carboxamide | 298.2 |
| 43 | 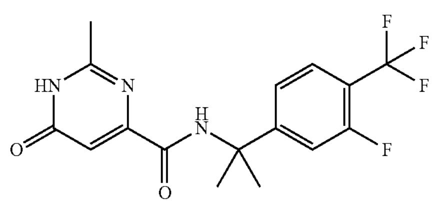 [SMILES: Cc1nc(C(=O)NC(C)(C)c2ccc(C(F)(F)F)c(F)c2)cc(=O)[nH]1] | N-{1-[3-fluoro-4-(trifluoromethyl)phenyl]-1-methylethyl}-2-methyl-6-oxo-1,6-dihydropyrimidine-4-carboxamide | 358.1 |
| 44 | 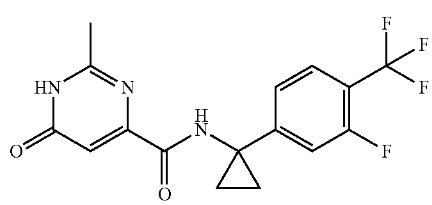 [SMILES: Cc1nc(C(=O)NC2(c3ccc(C(F)(F)F)c(F)c3)CC2)cc(=O)[nH]1] | N-{1-[3-fluoro-4-(trifluoromethyl)phenyl]cyclopropyl}-2-methyl-6-oxo-1,6-dihydropyrimidine-4-carboxamide | 356.1 |
| 45 | 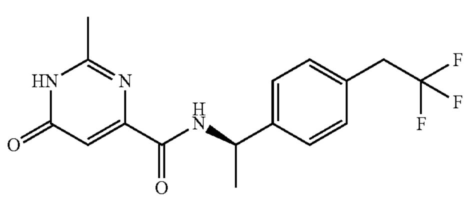 [SMILES: Cc1nc(C(=O)N[C@H](C)c2ccc(CC(F)(F)F)cc2)cc(=O)[nH]1] | 2-methyl-6-oxo-N-{(1R)-1-[4-(2,2,2-trifluoroethyl)phenyl]ethyl}-1,6-dihydropyrimidine-4-carboxamide | 340.1 |
| 46 | 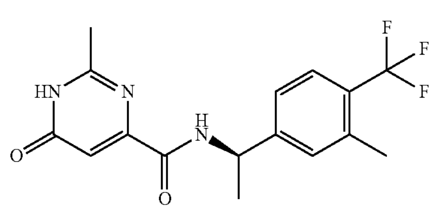 [SMILES: Cc1nc(C(=O)N[C@H](C)c2ccc(C(F)(F)F)c(C)c2)cc(=O)[nH]1] | 2-methyl-N-{(1R)-1-[3-methyl-4-(trifluoromethyl)phenyl]ethyl}-6-oxo-1,6-dihydropyrimidine-4-carboxamide | 340.1 |

TABLE 4-continued

| Example No. | Structure | IUPAC Name | Observed Exact Mass [M + H]+ |
|---|---|---|---|
| 47 | 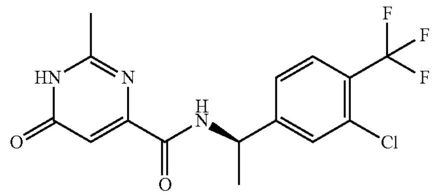 | N-{(1R)-1-[3-chloro-4-(trifluoromethyl)phenyl]ethyl}-2-methyl-6-oxo-1,6-dihydropyrimidine-4-carboxamide | 360.1/361.9 |
| 48 | 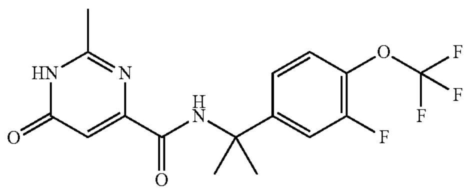 [SMILES: Cc1nc(C(=O)NC(C)(C)c2ccc(OC(F)(F)F)c(F)c2)cc(=O)[nH]1] | N-{1-[3-fluoro-4-(trifluoromethoxy)phenyl]-1-methylethyl}-2-methyl-6-oxo-1,6-dihydropyrimidine-4-carboxamide | 374.1 |
| 49 | 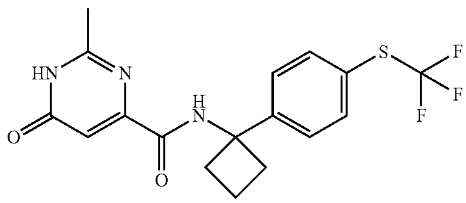 [SMILES: Cc1nc(C(=O)NC2(c3ccc(SC(F)(F)F)cc3)CCC2)cc(=O)[nH]1] | 2-methyl-6-oxo-N-(1-{4-[(trifluoromethyl)sulfanyl]phenyl}cyclobutyl)-1,6-dihydropyrimidine-4-carboxamide | 384.1 |
| 50 | 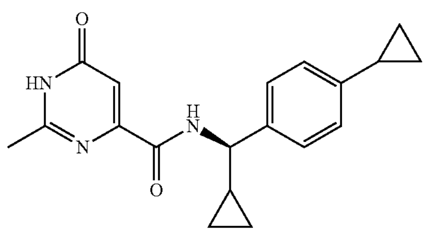 [SMILES: Cc1nc(C(=O)N[C@@H](c2ccc(C3CC3)cc2)C2CC2)cc(=O)[nH]1] | N-[(R)-cyclopropyl(4-cyclopropylphenyl)methyl]-2-methyl-6-oxo-1,6-dihydropyrimidine-4-carboxamide | 324.1, 346.1 (M + Na) |
| 51 | 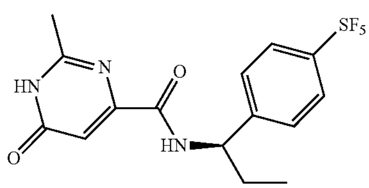 | 2-methyl-6-oxo-N-{(1R)-1-[4-(pentafluoro-λ6-sulfanyl)phenyl]propyl}-1,6-dihydropyrimidine-4-carboxamide | 398.0 |
| 52 | 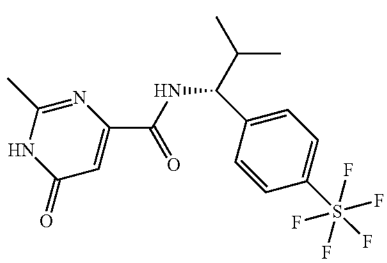 [SMILES: Cc1nc(C(=O)N[C@@H](c2ccc(S(F)(F)(F)(F)F)cc2)C(C)C)cc(=O)[nH]1] | 2-methyl-N-{(1R)-2-methyl-1-[4-(pentafluoro-λ6-sulfanyl)phenyl]propyl}-6-oxo-1,6-dihydropyrimidine-4-carboxamide | 412.0 |
| 53 | 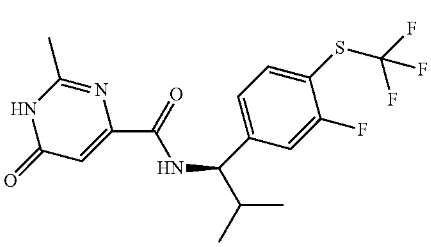 [SMILES: Cc1nc(C(=O)N[C@@H](c2ccc(SC(F)(F)F)c(F)c2)C(C)C)cc(=O)[nH]1] | N-[(1R)-1-{3-fluoro-4-[(trifluoromethyl)sulfanyl]phenyl}-2-methylpropyl]-2-methyl-6-oxo-1,6-dihydropyrimidine-4-carboxamide | 404.0 |

TABLE 4-continued

| Example No. | Structure | IUPAC Name | Observed Exact Mass [M + H]+ |
|---|---|---|---|
| 54 | 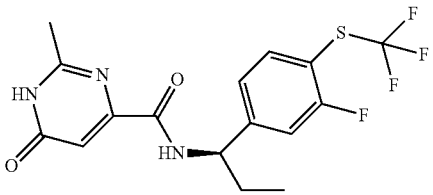 [SMILES: CC[C@@H](NC(=O)c1cc(=O)[nH]c(C)n1)c1ccc(SC(F)(F)F)c(F)c1] | N-[(1R)-1-{3-fluoro-4-[(trifluoromethyl)sulfanyl]phenyl}propyl]-2-methyl-6-oxo-1,6-dihydropyrimidine-4-carboxamide | 390.0 |
| 55 | 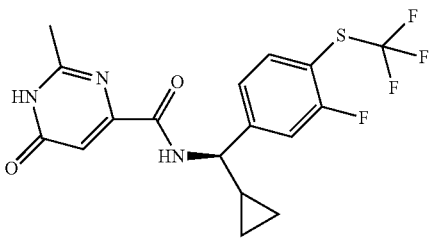 [SMILES: Cc1nc(C(=O)N[C@@H](c2ccc(SC(F)(F)F)c(F)c2)C2CC2)cc(=O)[nH]1] | N-[(R)-cyclopropyl{3-fluoro-4-[(trifluoromethyl)sulfanyl]phenyl}methyl]-2-methyl-6-oxo-1,6-dihydropyrimidine-4-carboxamide | 402.0 |
| 56 | 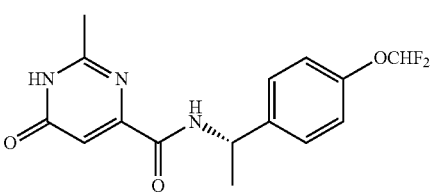 [SMILES: Cc1nc(C(=O)N[C@@H](C)c2ccc(OC(F)F)cc2)cc(=O)[nH]1] | (S)-N-(1-(4-(difluoromethoxy)phenyl)ethyl)-2-methyl-6-oxo-1,6-dihydropyrimidine-4-carboxamide | 324.2 |
| 57 | 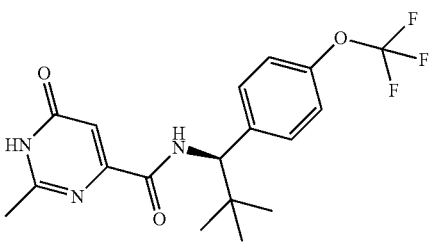 [SMILES: Cc1nc(C(=O)N[C@@H](c2ccc(OC(F)(F)F)cc2)C(C)(C)C)cc(=O)[nH]1] | (R)-N-(2,2-dimethyl-1-(4-(trifluoromethoxy)phenyl)propyl)-2-methyl-6-oxo-1,6-dihydropyrimidine-4-carboxamide | 384.0 |
| 58 | 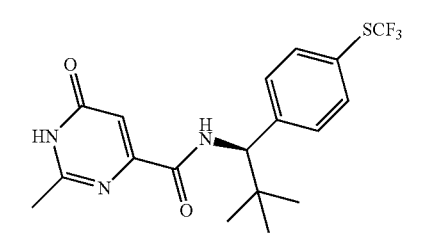 | (R)-N-(2,2-dimethyl-1-(4-((trifluoromethyl)thio)phenyl)propyl)-2-methyl-6-oxo-1,6-dihydropyrimidine-4-carboxamide | 399.9 |
| 59 | 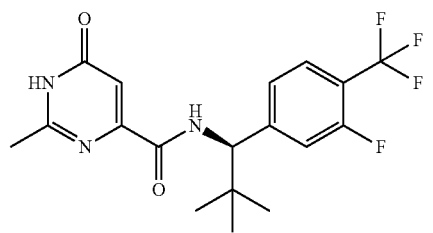 [SMILES: Cc1nc(C(=O)N[C@@H](c2ccc(C(F)(F)F)c(F)c2)C(C)(C)C)cc(=O)[nH]1] | (R)-N-(1-(3-fluoro-4-(trifluoromethoxy)phenyl)-2,2-dimethylpropyl)-2-methyl-6-oxo-1,6-dihydropyrimidine-4-carboxamide | 386.0 |

TABLE 4-continued

| Example No. | Structure | IUPAC Name | Observed Exact Mass [M + H]+ |
|---|---|---|---|
| 60 | 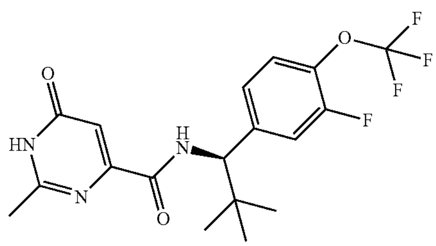 [SMILES: Cc1nc(C(=O)N[C@@H](c2ccc(OC(F)(F)F)c(F)c2)C(C)(C)C)cc(=O)[nH]1] | (R)-N-(1-(3-fluoro-4-(trifluoromethoxy)phenyl)-2,2-dimethylpropyl)-2-methyl-6-oxo-1,6-dihydropyrimidine-4-carboxamide | 402.0 |
| 61 | 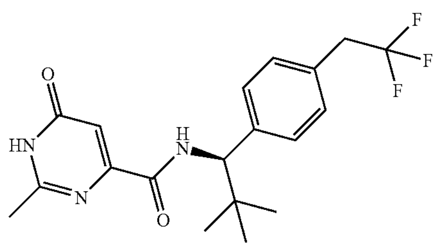 [SMILES: Cc1nc(C(=O)N[C@@H](c2ccc(CC(F)(F)F)cc2)C(C)(C)C)cc(=O)[nH]1] | (R)-N-(2,2-dimethyl-1-(4-(2,2,2-trifluoroethyl)phenyl)propyl)-2-methyl-6-oxo-1,6-dihydropyrimidine-4-carboxamide | 382.1 |
| 62 | 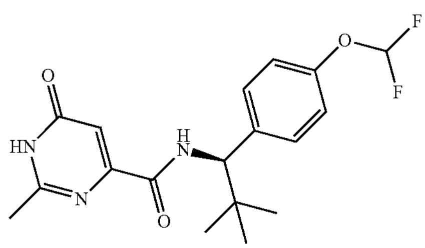 [SMILES: Cc1nc(C(=O)N[C@@H](c2ccc(OC(F)F)cc2)C(C)(C)C)cc(=O)[nH]1] | (R)-N-(1-(4-(difluoromethoxy)phenyl)-2,2-dimethylpropyl)-2-methyl-6-oxo-1,6-dihydropyrimidine-4-carboxamide | 366.1 |
| 63 | 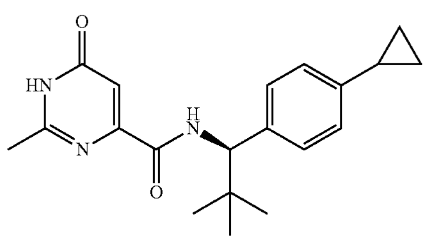 [SMILES: Cc1nc(C(=O)N[C@@H](c2ccc(C3CC3)cc2)C(C)(C)C)cc(=O)[nH]1] | (R)-N-(1-(4-cyclopropylphenyl)-2,2-dimethylpropyl)-2-methyl-6-oxo-1,6-dihydropyrimidine-4-carboxamide | 340.1 |
| 64 | 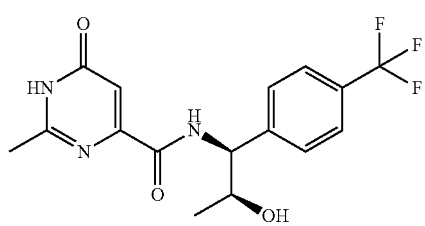 [SMILES: Cc1nc(C(=O)N[C@@H](c2ccc(C(F)(F)F)cc2)[C@H](C)O)cc(=O)[nH]1] | N-((1S,2S)-2-hydroxy-1-(4-(trifluoromethyl)phenyl)propyl)-2-methyl-6-oxo-1,6-dihydropyrimidine-4-carboxamide | 356.1 |
| 65 | 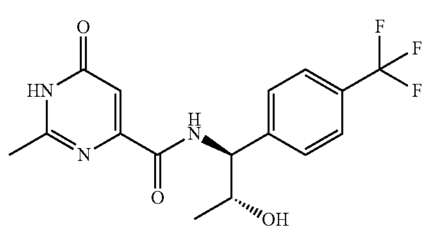 [SMILES: Cc1nc(C(=O)N[C@@H](c2ccc(C(F)(F)F)cc2)[C@@H](C)O)cc(=O)[nH]1] | N-((1S,2R)-2-hydroxy-1-(4-(trifluoromethyl)phenyl)propyl)-2-methyl-6-oxo-1,6-dihydropyrimidine-4-carboxamide | 356.1 |

TABLE 4-continued

| Example No. | Structure | IUPAC Name | Observed Exact Mass [M + H]+ |
|---|---|---|---|
| 66 | 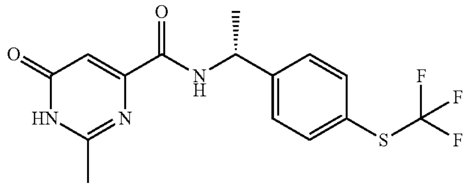 [SMILES: Cc1nc(C(=O)N[C@H](C)c2ccc(SC(F)(F)F)cc2)cc(=O)[nH]1] | 2-methyl-6-oxo-N-[(1R)-1-{4-[(trifluoromethyl)sulfanyl]phenyl}ethyl]-1,6-dihydropyrimidine-4-carboxamide | 358.0 |
| 67 | 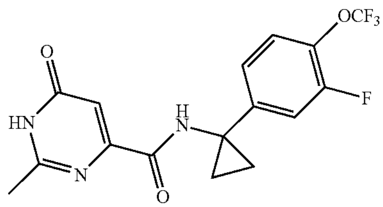 [SMILES: Cc1nc(C(=O)NC2(c3ccc(OC(F)(F)F)c(F)c3)CC2)cc(=O)[nH]1] | N-{1-[3-fluoro-4-(trifluoromethoxy)phenyl]cyclopropyl}-2-methyl-6-oxo-1,6-dihydropyrimidine-4-carboxamide | Calc'd 372.1, found 372.1 |
| 68 | 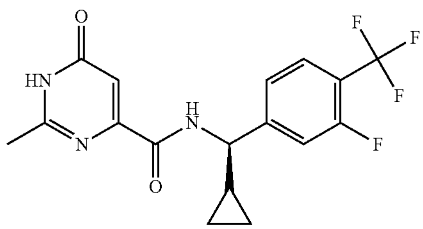 [SMILES: Cc1nc(C(=O)N[C@@H](c2ccc(C(F)(F)F)c(F)c2)C2CC2)cc(=O)[nH]1] | N-{(R)-cyclopropyl[3-fluoro-4-(trifluoromethyl)phenyl]methyl}-2-methyl-6-oxo-1,6-dihydropyrimidine-4-carboxamide | Calc'd 370.1, found 370.2 |
| 69 | 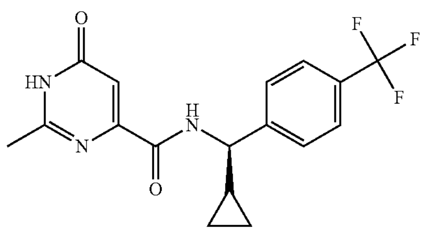 [SMILES: Cc1nc(C(=O)N[C@@H](c2ccc(C(F)(F)F)cc2)C2CC2)cc(=O)[nH]1] | N-{(R)-cyclopropyl[4-(trifluoromethyl)phenyl]methyl}-2-methyl-6-oxo-1,6-dihydropyrimidine-4-carboxamide | Calc'd 352.1, found 352.1 |
| 70 | 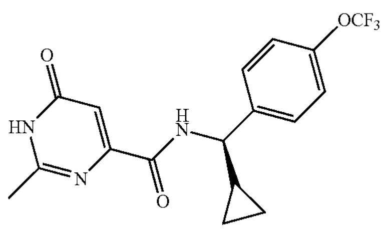 [SMILES: Cc1nc(C(=O)N[C@@H](c2ccc(OC(F)(F)F)cc2)C2CC2)cc(=O)[nH]1] | N-{(R)-cyclopropyl[4-(trifluoromethoxy)phenyl]methyl}-2-methyl-6-oxo-1,6-dihydropyrimidine-4-carboxamide | Calc'd 368.1, found 368.1 |
| 71 | 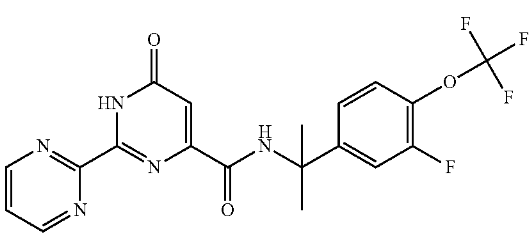 [SMILES: CC(C)(NC(=O)c1cc(=O)[nH]c(-c2ncccn2)n1)c1ccc(OC(F)(F)F)c(F)c1] | N-{1-[3-fluoro-4-(trifluoromethoxy)phenyl]-1-methylethyl}-6-oxo-1,6-dihydro-2,2'-bipyrimidine-4-carboxamide | Calc'd 438.1, found 438.2 |
| 72 | 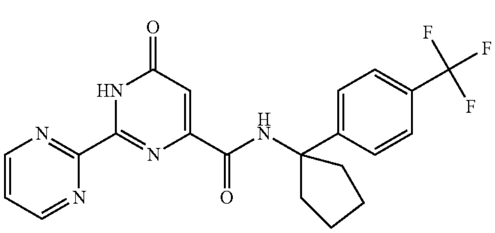 [SMILES: O=C(NC1(c2ccc(C(F)(F)F)cc2)CCCC1)c1cc(=O)[nH]c(-c2ncccn2)n1] | 6-oxo-N-{1-[4-(trifluoromethyl)phenyl]cyclopentyl}-1,6-dihydro-2,2'-bipyrimidine-4-carboxamide | Calc'd 430.1, found 430.2 |

TABLE 4-continued

| Example No. | Structure | IUPAC Name | Observed Exact Mass [M + H]+ |
|---|---|---|---|
| 73 | 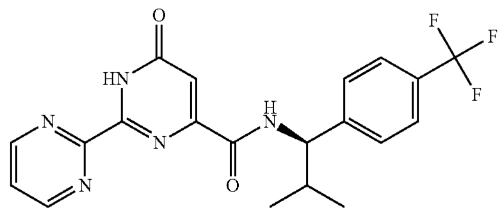 [SMILES: CC(C)[C@@H](NC(=O)c1cc(=O)[nH]c(-c2ncccn2)n1)c1ccc(C(F)(F)F)cc1] | N-{(1R)-2-methyl-1-[4-(trifluoromethyl)phenyl]propyl}-6-oxo-1,6-dihydro-2,2'-bipyrimidine-4-carboxamide | Calc'd 418.1, found 418.3 |
| 74 | 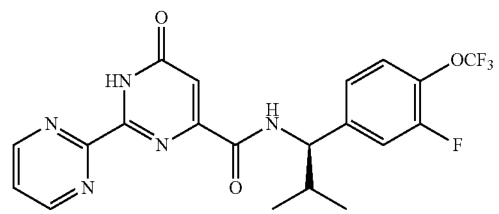 [SMILES: CC(C)[C@@H](NC(=O)c1cc(=O)[nH]c(-c2ncccn2)n1)c1ccc(OC(F)(F)F)c(F)c1] | N-{(1R)-1-[3-fluoro-4-(trifluoromethoxy)phenyl]-2-methylpropyl}-6-oxo-1,6-dihydro-2,2'-bipyrimidine-4-carboxamide | Calc'd 452.1, found 452.3 |
| 75 | 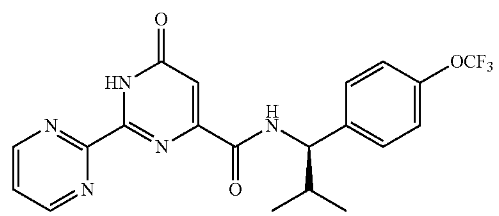 [SMILES: CC(C)[C@@H](NC(=O)c1cc(=O)[nH]c(-c2ncccn2)n1)c1ccc(OC(F)(F)F)cc1] | N-{(1R)-2-methyl-1-[4-(trifluoromethoxy)phenyl]propyl}-6-oxo-1,6-dihydro-2,2'-bipyrimidine-4-carboxamide | Calc'd 434.1, found 434.3 |
| 76 | 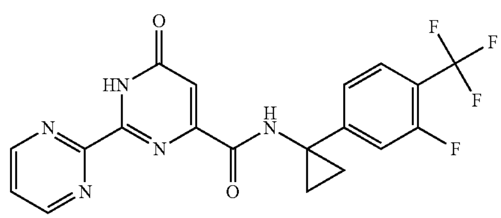 [SMILES: O=C(NC1(c2ccc(C(F)(F)F)c(F)c2)CC1)c1cc(=O)[nH]c(-c2ncccn2)n1] | N-{1-[3-fluoro-4-(trifluoromethyl)phenyl]cyclopropyl}-6-oxo-1,6-dihydro-2,2'-bipyrimidine-4-carboxamide | Calc'd 420.1, found 420.3 |
| 77 | 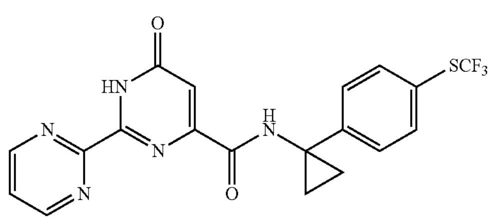 | 6-oxo-N-(1-{4-[(trifluoromethyl)sulfanyl]phenyl}cyclopropyl)-1,6-dihydro-2,2'-bipyrimidine-4-carboxamide | Calc'd 434.1, found 434.2 |
| 78 | 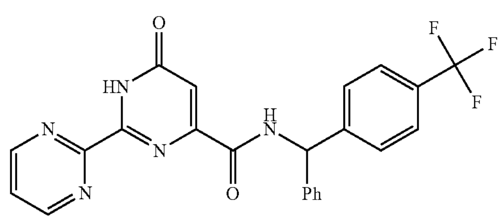 [SMILES: O=C(NC(c1ccccc1)c1ccc(C(F)(F)F)cc1)c1cc(=O)[nH]c(-c2ncccn2)n1] | 6-oxo-N-{phenyl[4-(trifluoromethyl)phenyl]methyl}-1,6-dihydro-2,2'-bipyrimidine-4-carboxamide | Calc'd 452.1, found 452.3 |
| 79 | 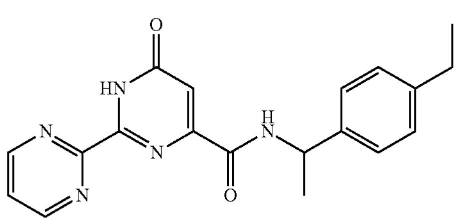 [SMILES: CCc1ccc(C(C)NC(=O)c2cc(=O)[nH]c(-c3ncccn3)n2)cc1] | N-[1-(4-ethylphenyl)ethyl]-6-oxo-1,6-dihydro-2,2'-bipyrimidine-4-carboxamide | Calc'd 350.2, found 350.2 |

TABLE 4-continued

| Example No. | Structure | IUPAC Name | Observed Exact Mass [M + H]+ |
|---|---|---|---|
| 80 | 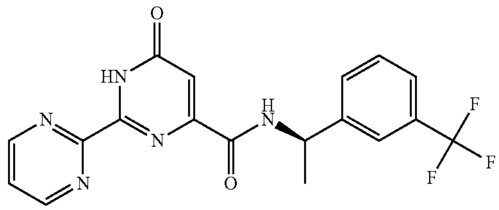 [SMILES: C[C@@H](NC(=O)c1cc(=O)[nH]c(-c2ncccn2)n1)c1cccc(C(F)(F)F)c1] | 6-oxo-N-{(1R)-1-[3-(trifluoromethyl)phenyl]ethyl}-1,6-dihydro-2,2'-bipyrimidine-4-carboxamide | Calc'd 390.1, found 390.2 |
| 81 | 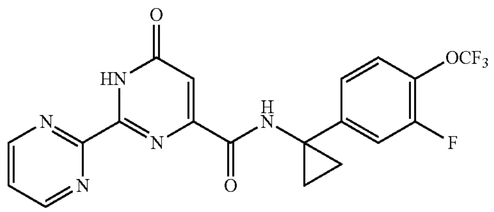 [SMILES: O=C(NC1(c2ccc(OC(F)(F)F)c(F)c2)CC1)c1cc(=O)[nH]c(-c2ncccn2)n1] | N-{1-[3-fluoro-4-(trifluoromethoxy)phenyl]cyclopropyl}-6-oxo-1,6-dihydro-2,2'-bipyrimidine-4-carboxamide | Calc'd 436.1, found 436.2 |
| 82 | 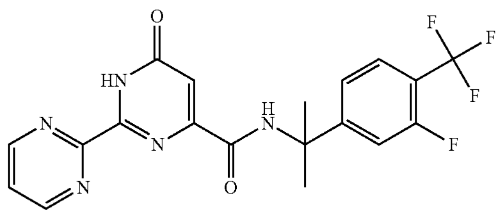 [SMILES: CC(C)(NC(=O)c1cc(=O)[nH]c(-c2ncccn2)n1)c1ccc(C(F)(F)F)c(F)c1] | N-{1-[3-fluoro-4-(trifluoromethyl)phenyl]-1-methylethyl}-6-oxo-1,6-dihydro-2,2'-bipyrimidine-4-carboxamide | Calc'd 422.1, found 422.3 |
| 83 | 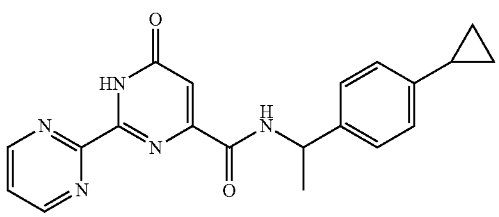 [SMILES: CC(NC(=O)c1cc(=O)[nH]c(-c2ncccn2)n1)c1ccc(C2CC2)cc1] | N-[1-(4-cyclopropylphenyl)ethyl]-6-oxo-1,6-dihydro-2,2'-bipyrimidine-4-carboxamide | Calc'd 362.2, found 362.2 |
| 84 | 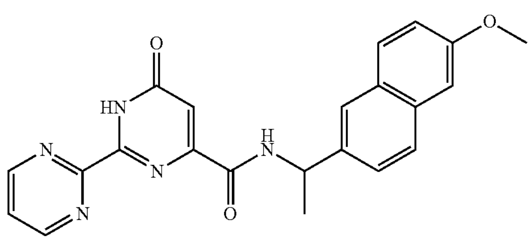 [SMILES: COc1ccc2cc(C(C)NC(=O)c3cc(=O)[nH]c(-c4ncccn4)n3)ccc2c1] | N-[1-(6-methoxynaphthalen-2-yl)ethyl]-6-oxo-1,6-dihydro-2,2'-bipyrimidine-4-carboxamide | Calc'd 402.2, found 402.2 |
| 85 | 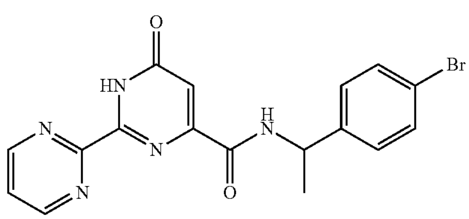 [SMILES: CC(NC(=O)c1cc(=O)[nH]c(-c2ncccn2)n1)c1ccc(Br)cc1] | N-[1-(4-bromophenyl)ethyl]-6-oxo-1,6-dihydro-2,2'-bipyrimidine-4-carboxamide | Calc'd 400.0 Found 400.1 |
| 86 | 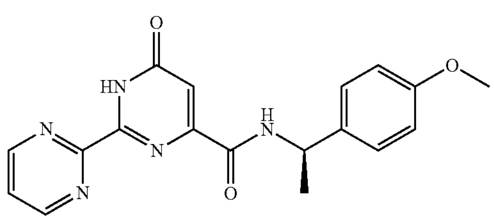 [SMILES: COc1ccc([C@@H](C)NC(=O)c2cc(=O)[nH]c(-c3ncccn3)n2)cc1] | N-[(1R)-1-(4-methoxyphenyl)ethyl]-6-oxo-1,6-dihydro-2,2'-bipyrimidine-4-carboxamide | Calc'd 352.1, found 352.3 |

TABLE 4-continued

| Example No. | Structure | IUPAC Name | Observed Exact Mass [M + H]+ |
|---|---|---|---|
| 87 | 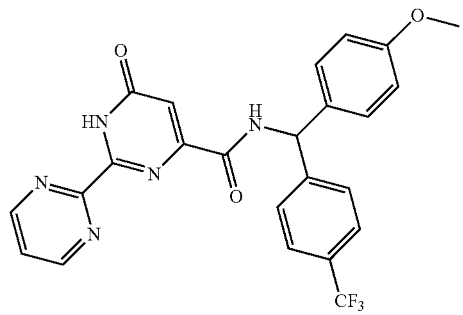 [SMILES: COc1ccc(C(NC(=O)c2cc(=O)[nH]c(-c3ncccn3)n2)c2ccc(C(F)(F)F)cc2)cc1] | N-{(4-methoxyphenyl)[4-(trifluoromethyl)phenyl]methyl}-6-oxo-1,6-dihydro-2,2'-bipyrimidine-4-carboxamide | Calc'd 482.1, found 482.2 |
| 88 | 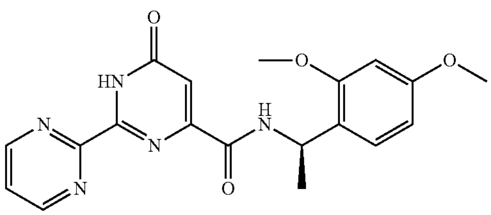 [SMILES: COc1ccc([C@@H](C)NC(=O)c2cc(=O)[nH]c(-c3ncccn3)n2)c(OC)c1] | N-[(1R)-1-(2,4-dimethoxyphenyl)ethyl]-6-oxo-1,6-dihydro-2,2'-bipyrimidine-4-carboxamide | Calc'd 382.2, found 382.0 |
| 89 | 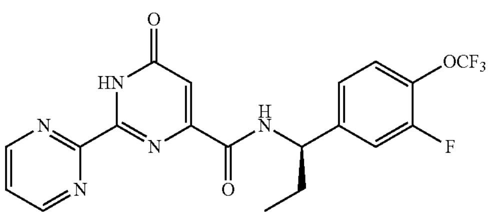 [SMILES: CC[C@@H](NC(=O)c1cc(=O)[nH]c(-c2ncccn2)n1)c1ccc(OC(F)(F)F)c(F)c1] | N-{(1R)-1-[3-fluoro-4-(trifluoromethoxy)phenyl]propyl}-6-oxo-1,6-dihydro-2,2'-bipyrimidine-4-carboxamide | Calc'd 438.1, found 438.2 |
| 90 | 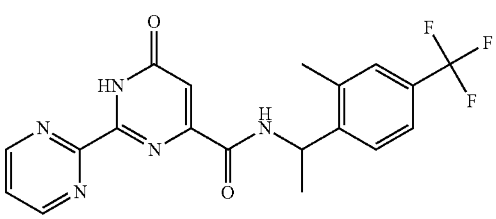 [SMILES: Cc1cc(C(F)(F)F)ccc1C(C)NC(=O)c1cc(=O)[nH]c(-c2ncccn2)n1] | N-{1-[2-methyl-4-(trifluoromethyl)phenyl]ethyl}-6-oxo-1,6-dihydro-2,2'-bipyrimidine-4-carboxamide | Calc'd 404.1, found 404.2 |
| 91 | 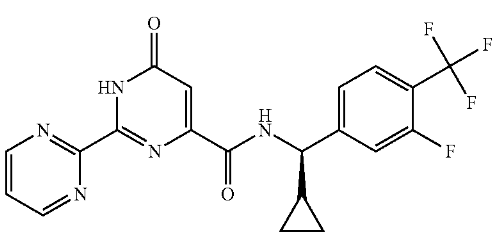 [SMILES: O=C(N[C@@H](c1ccc(C(F)(F)F)c(F)c1)C1CC1)c1cc(=O)[nH]c(-c2ncccn2)n1] | N-{(R)-cyclopropyl[3-fluoro-4-(trifluoromethyl)phenyl]methyl}-6-oxo-1,6-dihydro-2,2'-bipyrimidine-4-carboxamide | Calc'd 434.1, found 434.2 |
| 92 | 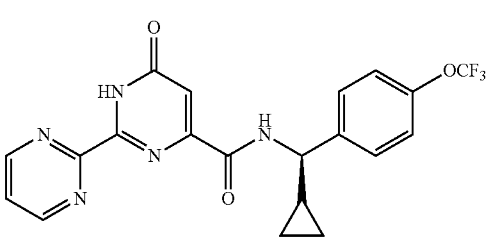 [SMILES: O=C(N[C@@H](c1ccc(OC(F)(F)F)cc1)C1CC1)c1cc(=O)[nH]c(-c2ncccn2)n1] | N-{(R)-cyclopropyl[4-(trifluoromethoxy)phenyl]methyl}-6-oxo-1,6-dihydro-2,2'-bipyrimidine-4-carboxamide | Calc'd 432.1, found 432.2 |

TABLE 4-continued

| Example No. | Structure | IUPAC Name | Observed Exact Mass [M + H]+ |
|---|---|---|---|
| 93 | 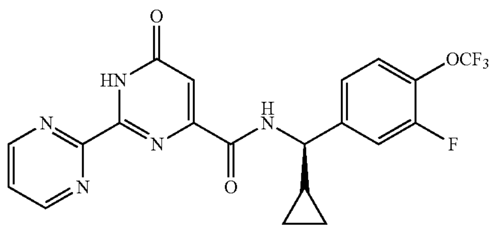 [SMILES: O=C(N[C@@H](c1ccc(OC(F)(F)F)c(F)c1)C1CC1)c1cc(=O)[nH]c(-c2ncccn2)n1] | N-{(R)-cyclopropyl[3-fluoro-4-(trifluoromethoxy)phenyl]methyl}-6-oxo-1,6-dihydro-2,2'-bipyrimidine-4-carboxamide | Calc'd 450.1, found 450.3 |
| 94 | 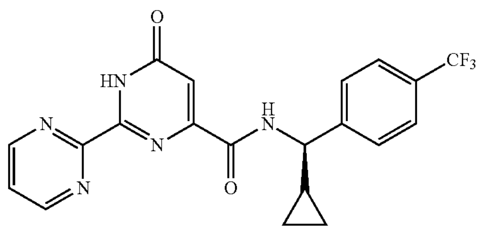 [SMILES: O=C(N[C@@H](c1ccc(C(F)(F)F)cc1)C1CC1)c1cc(=O)[nH]c(-c2ncccn2)n1] | N-{(R)-cyclopropyl[4-(trifluoromethyl)phenyl]methyl}-6-oxo-1,6-dihydro-2,2'-bipyrimidine-4-carboxamide | Calc'd 416.1, found 416.2 |
| 95 | 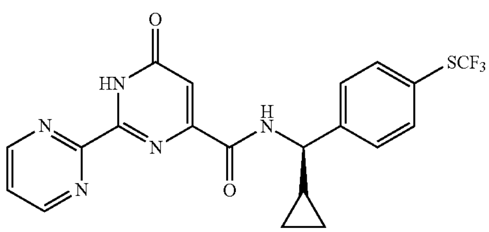 | N-[(R)-cyclopropyl{4-[(trifluoromethyl)sulfanyl]phenyl}methyl]-6-oxo-1,6-dihydro-2,2'-bipyrimidine-4-carboxamide | Calc'd 448.1, found 448.2 |
| 96 | 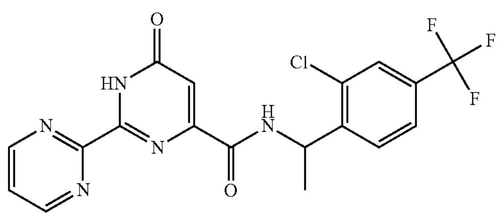 [SMILES: CC(NC(=O)c1cc(=O)[nH]c(-c2ncccn2)n1)c1ccc(C(F)(F)F)cc1Cl] | N-{1-[2-chloro-4-(trifluoromethyl)phenyl]ethyl}-6-oxo-1,6-dihydro-2,2'-bipyrimidine-4-carboxamide | Calc'd 424.1/ 426.1, found 424.2/ 426.1 |
| 97 | 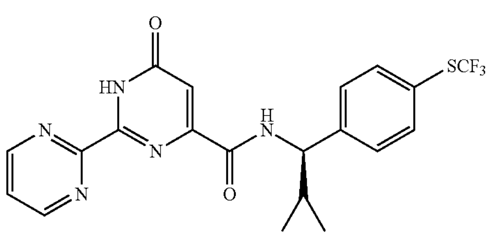 | N-[(1R)-2-methyl-1-{4-[(trifluoromethyl)sulfanyl]phenyl}propyl]-6-oxo-1,6-dihydro-2,2'-bipyrimidine-4-carboxamide | Calc'd 450.1, found 450.3 |
| 98 | 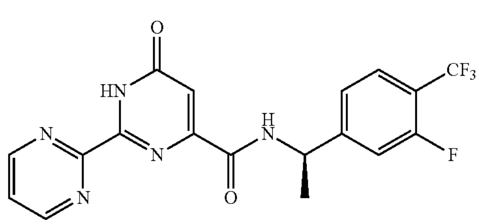 [SMILES: C[C@@H](NC(=O)c1cc(=O)[nH]c(-c2ncccn2)n1)c1ccc(C(F)(F)F)c(F)c1] | N-{(1R)-1-[3-fluoro-4-(trifluoromethyl)phenyl]ethyl}-6-oxo-1,6-dihydro-2,2'-bipyrimidine-4-carboxamide | Calc'd 408.1, found 408.2 |

TABLE 4-continued

| Example No. | Structure | IUPAC Name | Observed Exact Mass [M + H]+ |
|---|---|---|---|
| 99 | 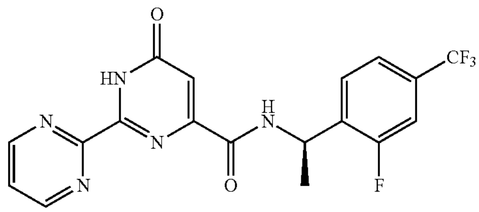 [SMILES: C[C@@H](NC(=O)c1cc(=O)[nH]c(-c2ncccn2)n1)c1ccc(C(F)(F)F)cc1F] | N-[(1R)-1-[2-fluoro-4-(trifluoromethyl)phenyl]ethyl}-6-oxo-1,6-dihydro-2,2'-bipyrimidine-4-carboxamide | Calc'd 408.1, found 408.2 |
| 100 | 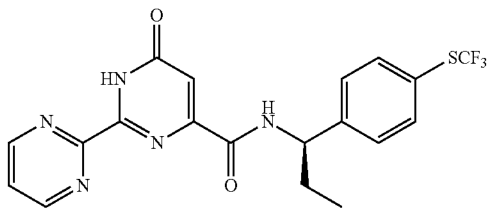 | 6-oxo-N-[(1R)-1-{4-[(trifluoromethyl)sulfanyl]phenyl]propyl]-1,6-dihydro-2,2'-bipyrimidine-4-carboxamide | Calc'd 436.1, found 436.2 |
| 101 | 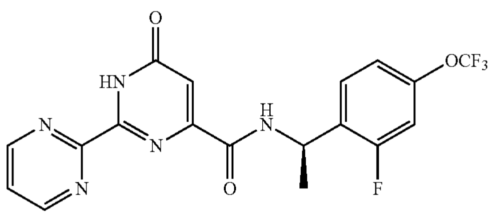 [SMILES: C[C@@H](NC(=O)c1cc(=O)[nH]c(-c2ncccn2)n1)c1ccc(OC(F)(F)F)cc1F] | N-{(1R)-1-[2-fluoro-4-(trifluoromethoxy)phenyl]ethyl}-6-oxo-1,6-dihydro-2,2'-bipyrimidine-4-carboxamide | Calc'd 424.1, found 424.2 |
| 102 | 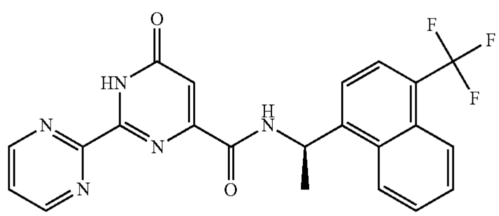 [SMILES: C[C@@H](NC(=O)c1cc(=O)[nH]c(-c2ncccn2)n1)c1ccc(C(F)(F)F)c2ccccc12] | 6-oxo-N-{(1R)-1-[4-(trifluoromethyl)naphthalen-1-yl]ethyl}-1,6-dihydro-2,2'-bipyrimidine-4-carboxamide | Calc'd 440.1, found 440.2 |
| 103 | 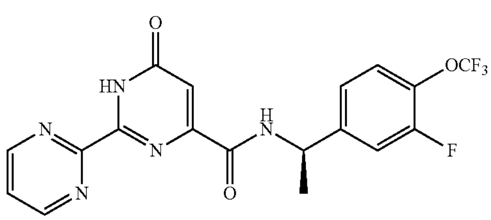 [SMILES: C[C@@H](NC(=O)c1cc(=O)[nH]c(-c2ncccn2)n1)c1ccc(OC(F)(F)F)c(F)c1] | N-{(1R)-1-[3-fluoro-4-(trifluoromethoxy)phenyl]ethyl}-6-oxo-1,6-dihydro-2,2'-bipyrimidine-4-carboxamide | Calc'd 424.1, found 424.2 |
| 104 | 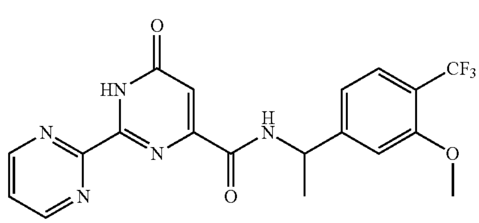 [SMILES: COc1cc(C(C)NC(=O)c2cc(=O)[nH]c(-c3ncccn3)n2)ccc1C(F)(F)F] | N-{1-[3-methoxy-4-(trifluoromethyl)phenyl]ethyl}-6-oxo-1,6-dihydro-2,2'-bipyrimidine-4-carboxamide | Calc'd 420.1, found 420.3 |
| 105 | 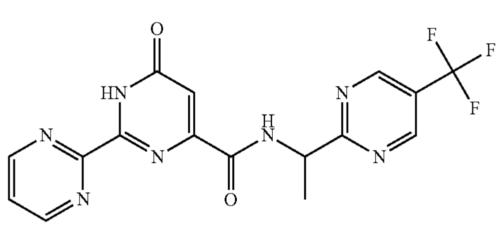 [SMILES: CC(NC(=O)c1cc(=O)[nH]c(-c2ncccn2)n1)c1ncc(C(F)(F)F)cn1] | 6-oxo-N-{1-[5-(trifluoromethyl)pyrimidin-2-yl]ethyl}-1,6-dihydro-2,2'-bipyrimidine-4-carboxamide | Calc'd 392.1, found 392.2 |

TABLE 4-continued

| Example No. | Structure | IUPAC Name | Observed Exact Mass [M + H]+ |
|---|---|---|---|
| 106 | 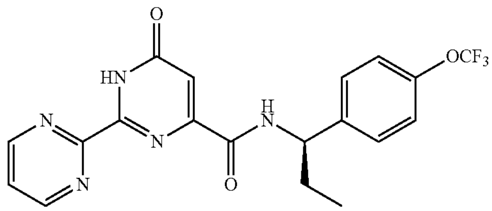 [SMILES: CC[C@@H](NC(=O)c1cc(=O)[nH]c(-c2ncccn2)n1)c1ccc(OC(F)(F)F)cc1] | 6-oxo-N-{(1R)-1-[4-(trifluoromethoxy)phenyl]propyl}-1,6-dihydro-2,2'-bipyrimidine-4-carboxamide | Calc'd 420.1, found 420.3 |
| 107 | 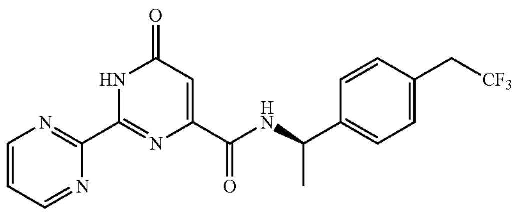 [SMILES: C[C@@H](NC(=O)c1cc(=O)[nH]c(-c2ncccn2)n1)c1ccc(CC(F)(F)F)cc1] | 6-oxo-N-{(1R)-1-[4-(2,2,2-trifluoroethyl)phenyl]ethyl}-1,6-dihydro-2,2'-bipyrimidine-4-carboxamide | Calc'd 404.1, found 404.2 |
| 108 | 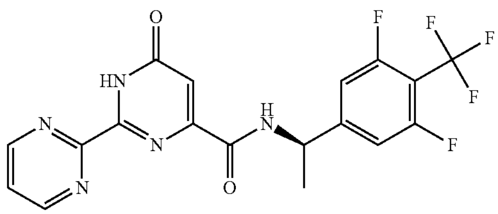 [SMILES: C[C@@H](NC(=O)c1cc(=O)[nH]c(-c2ncccn2)n1)c1cc(F)c(C(F)(F)F)c(F)c1] | N-{(1R)-1-[3,5-difluoro-4-(trifluoromethyl)phenyl]ethyl}-6-oxo-1,6-dihydro-2,2'-bipyrimidine-4-carboxamide | Calc'd 426.1, found 426.2 |
| 109 | 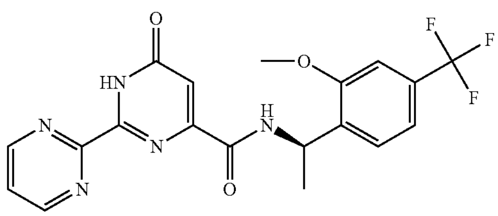 [SMILES: COc1cc(C(F)(F)F)ccc1[C@@H](C)NC(=O)c1cc(=O)[nH]c(-c2ncccn2)n1] | N-{(1R)-1-[2-methoxy-4-(trifluoromethyl)phenyl]ethyl}-6-oxo-1,6-dihydro-2,2'-bipyrimidine-4-carboxamide | Calc'd 420.1, found 420.2 |
| 110 | 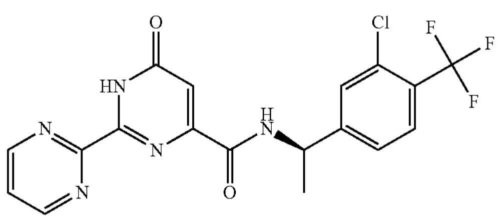 [SMILES: C[C@@H](NC(=O)c1cc(=O)[nH]c(-c2ncccn2)n1)c1ccc(C(F)(F)F)c(Cl)c1] | N-{(1R)-1-[3-chloro-4-(trifluoromethyl)phenyl]ethyl}-6-pxo-1,6-dihydro-2,2'-bipyrimidine-4-carboxamide | Calc'd 424.1/ 426.1, found 424.2/ 426.1 |
| 111 | 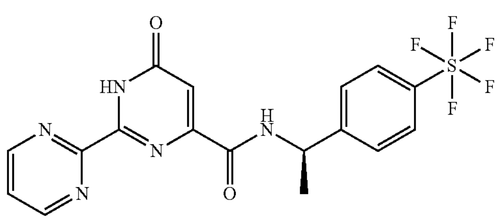 [SMILES: C[C@@H](NC(=O)c1cc(=O)[nH]c(-c2ncccn2)n1)c1ccc(S(F)(F)(F)(F)F)cc1] | 6-oxo-N-{(1R)-1-[4-(pentafluoro-$\lambda^6$-sulfanyl)phenyl]ethyl}-1,6-dihydro-2,2'-bipyrimidine-4-carboxamide | Calc'd 448.1, found 448.4 |
| 112 | 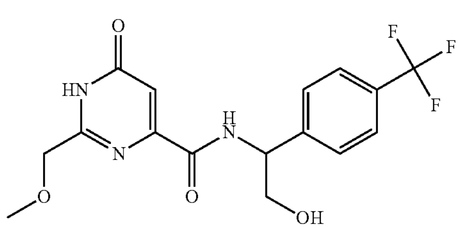 [SMILES: COCc1nc(C(=O)NC(CO)c2ccc(C(F)(F)F)cc2)cc(=O)[nH]1] | N-{2-hydroxy-1-[4-(trifluoromethyl)phenyl]ethyl}-2-(methoxymethyl)-6-oxo-1,6-dihydropyrimidine-4-carboxamide | Calc'd 372.1, found 372.2 |

TABLE 4-continued

| Example No. | Structure | IUPAC Name | Observed Exact Mass [M + H]+ |
|---|---|---|---|
| 113 | 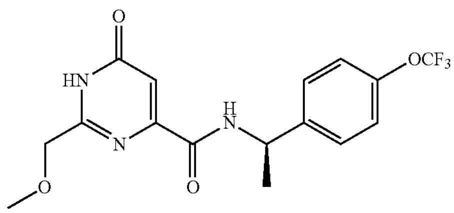 [SMILES: COCc1nc(C(=O)N[C@H](C)c2ccc(OC(F)(F)F)cc2)cc(=O)[nH]1] | 2-(methoxymethyl)-6-oxo-N-{(1R)-1-[4-(trifluoromethoxy)phenyl]ethyl}-1,6-dihydropyrimidine-4-carboxamide | Calc'd 372.1, found 372.2 |
| 114 | 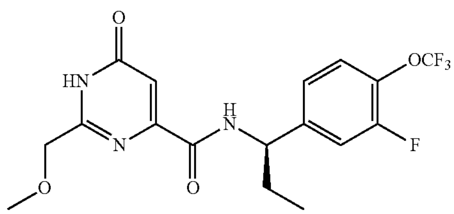 [SMILES: CC[C@@H](NC(=O)c1cc(=O)[nH]c(COC)n1)c1ccc(OC(F)(F)F)c(F)c1] | N-{(1R)-1-[3-fluoro-4-(trifluoromethoxy)phenyl]propyl}-2-(methoxymethyl)-6-oxo-1,6-dihydropyrimidine-4-carboxamide | Calc'd 404.1, found 404.2 |
| 115 | 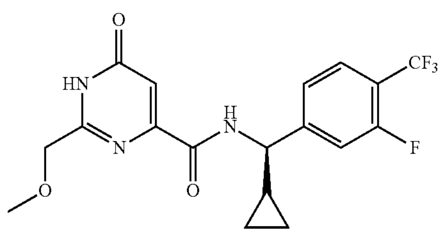 [SMILES: COCc1nc(C(=O)N[C@@H](c2ccc(C(F)(F)F)c(F)c2)C2CC2)cc(=O)[nH]1] | N-{(R)-cyclopropyl[3-fluoro-4-(trifluoromethyl)phenyl]methyl}-2-(methoxymethyl)-6-oxo-1,6-dihydropyrimidine-4-carboxamide | Calc'd 400.1, found 400.2 |
| 116 | 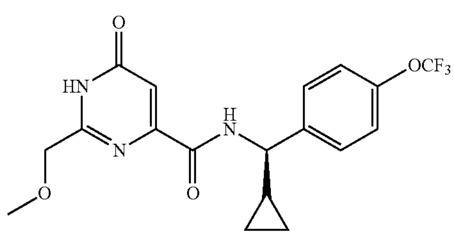 [SMILES: COCc1nc(C(=O)N[C@@H](c2ccc(OC(F)(F)F)cc2)C2CC2)cc(=O)[nH]1] | N-{(R)-cyclopropyl[4-(trifluoromethoxy)phenyl]methyl}-2-(methoxymethyl)-6-oxo-1,6-dihydropyrimidine-4-carboxamide | Calc'd 398.1, found 398.3 |
| 117 | 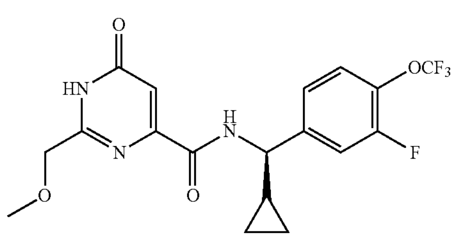 [SMILES: COCc1nc(C(=O)N[C@@H](c2ccc(OC(F)(F)F)c(F)c2)C2CC2)cc(=O)[nH]1] | N-{(R)-cyclopropyl[3-fluoro-4-(trifluoromethoxy)phenyl]methyl}-2-(methoxymethyl)-6-oxo-1,6-dihydropyrimidine-4-carboxamide | Calc'd 416.1, found 416.2 |
| 118 | 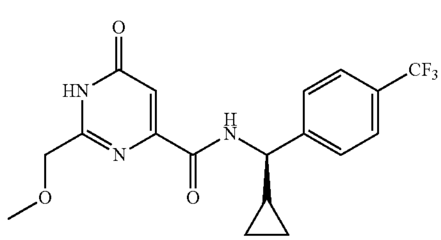 [SMILES: COCc1nc(C(=O)N[C@@H](c2ccc(C(F)(F)F)cc2)C2CC2)cc(=O)[nH]1] | N-{(R)-cyclopropyl[4-(trifluoromethyl)phenyl]methyl}-2-(methoxymethyl)-6-oxo-1,6-dihydropyrimidine-4-carboxamide | Calc'd 382.1. found 382.2 |

TABLE 4-continued

| Example No. | Structure | IUPAC Name | Observed Exact Mass [M + H]+ |
|---|---|---|---|
| 119 | 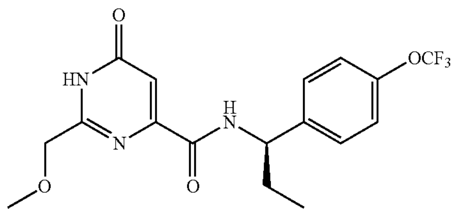 [SMILES: CC[C@@H](NC(=O)c1cc(=O)[nH]c(COC)n1)c1ccc(OC(F)(F)F)cc1] | 2-(methoxymethyl)-6-oxo-N-{(1R)-1-[4-(trifluoromethoxy)phenyl]propyl}-1,6-dihydropyrimidine-4-carboxamide | Calc'd 386.1, found 386.2 |
| 120 | 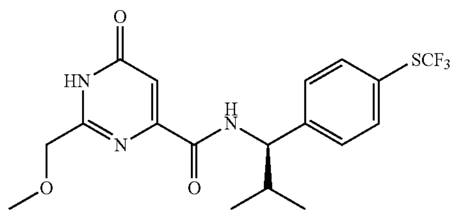 | 2-(methoxymethyl)-N-[(1R)-2-methyl-1-{4-[(trifluoromethyl)sulfanyl]phenyl}propyl]-6-oxo-1,6-dihydropyrimidine-4-carboxamide | Calc'd 416.1, found 416.2 |
| 121 | 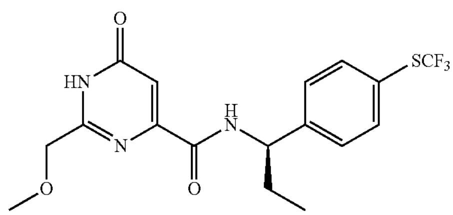 | 2-(methoxymethyl)-6-oxo-N-[(1R)-1-{4-[(trifluoromethyl)sulfanyl]phenyl}propyl]-1,6-dihydropyrimidine-4-carboxamide | Calc'd 402.1, found 402.2 |
| 122 | 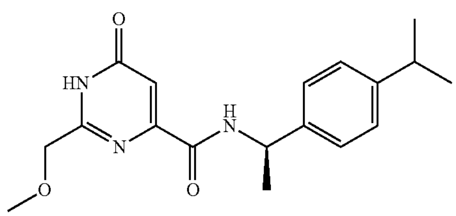 [SMILES: COCc1nc(C(=O)N[C@H](C)c2ccc(C(C)C)cc2)cc(=O)[nH]1] | 2-(methoxymethyl)-N-{(1R)-1-[4-(1-methylethyl)phenyl]ethyl}-6-oxo-1,6-dihydropyrimidine-4-carboxamide | Calc'd 330.2, found 330.2 |
| 123 | 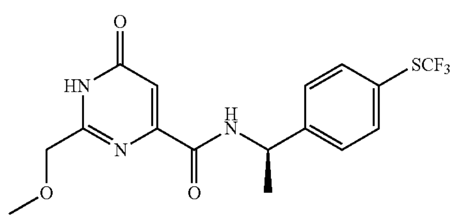 | 2-(methoxymethyl)-6-oxo-N-[(1R)-1-{4-[(trifluoromethyl)sulfanyl]phenyl}ethyl]-1,6-dihydropyrimidine-4-carboxamide | Calc'd 388.1, found 388.2 |
| 124 | 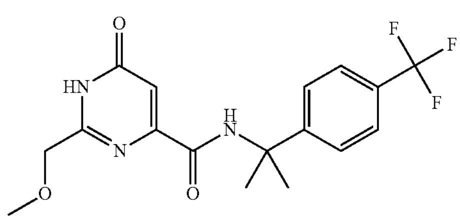 [SMILES: COCc1nc(C(=O)NC(C)(C)c2ccc(C(F)(F)F)cc2)cc(=O)[nH]1] | 2-(methoxymethyl)-N-{1-methyl-1-[4-(trifluoromethyl)phenyl]ethyl}-6-oxo-1,6-dihydropyrimidine-4-carboxamide | Calc'd 370.1, found 370.2 |
| 125 | 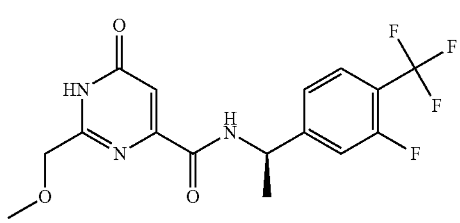 [SMILES: COCc1nc(C(=O)N[C@H](C)c2ccc(C(F)(F)F)c(F)c2)cc(=O)[nH]1] | N-{(1R)-1-[3-fluoro-4-(trifluoromethyl)phenyl]ethyl}-2-(methoxymethyl)-6-oxo-1,6-dihydropyrimidine-4-carboxamide | Calc'd 374.1, found 374.2 |

TABLE 4-continued

| Example No. | Structure | IUPAC Name | Observed Exact Mass [M + H]+ |
|---|---|---|---|
| 126 | 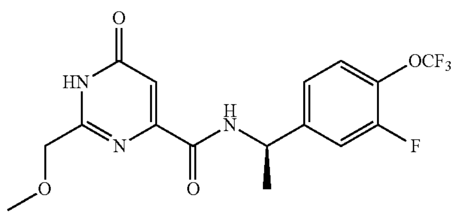 [SMILES: COCc1nc(C(=O)N[C@H](C)c2ccc(OC(F)(F)F)c(F)c2)cc(=O)[nH]1] | N-{(1R)-1-[3-fluoro-4-(trifluoromethoxy)phenyl]-ethyl}-2-(methoxymethyl)-6-oxo-1,6-dihydropyrimidine-4-carboxamide | Calc'd 390.1, found 390.2 |
| 127 | 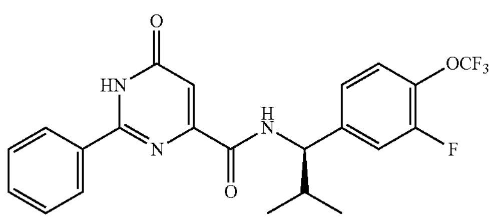 [SMILES: CC(C)[C@@H](NC(=O)c1cc(=O)[nH]c(-c2ccccc2)n1)c1ccc(OC(F)(F)F)c(F)c1] | N-{(1R)-1-[3-fluoro-4-(trifluoromethoxy)phenyl]-2-methylpropyl}-6-oxo-2-phenyl-1,6-dihydropyrimidine-4-carboxamide | Calc'd 450.1, found 450.2 |
| 128 | 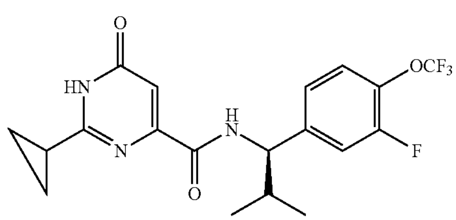 [SMILES: CC(C)[C@@H](NC(=O)c1cc(=O)[nH]c(C2CC2)n1)c1ccc(OC(F)(F)F)c(F)c1] | 2-cyclopropyl-N-{(1R)-1-[3-fluoro-4-(trifluoromethoxy)phenyl]-2-methylpropyl}-6-oxo-1,6-dihydropyrimidine-4-carboxamide | Calc'd 414.1, found 414.2 |
| 129 | 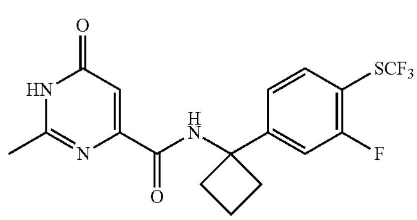 | N-(1-{3-fluoro-4-[(trifluoromethyl)sulfanyl]phenyl}cyclobutyl)-2-methyl-6-oxo-1,6-dihydropyrimidine-4-carboxamide | Calc'd 402.1, found 402.2 |
| 130 | 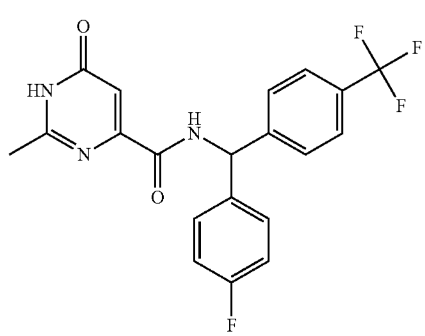 [SMILES: Cc1nc(C(=O)NC(c2ccc(F)cc2)c2ccc(C(F)(F)F)cc2)cc(=O)[nH]1] | N-{(4-fluorophenyl)[4-(trifluoromethyl)phenyl]methyl}-2-methyl-6-oxo-1,6-dihydropyrimidine-4-carboxamide | Calc'd 406.1, found 406.1 |
| 131 | 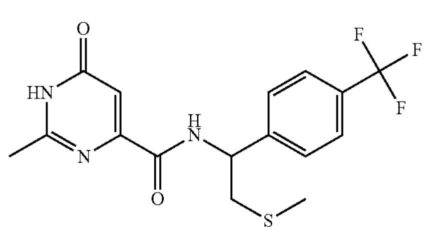 [SMILES: CSCC(NC(=O)c1cc(=O)[nH]c(C)n1)c1ccc(C(F)(F)F)cc1] | 2-methyl-N-{2-(methylsulfanyl)-1-[4-(trifluoromethyl)phenyl]ethyl}-6-oxo-1,6-dihydropyrimidine-4-carboxamide | Calc'd 372.1, found 372.1 |

Example 37: $^1$H NMR (500 MHz, CD$_3$OD) δ 7.79 (d, J=8.8 Hz, 2H), 7.57 (d, J=8.5 Hz, 2H), 6.88 (s, 1H), 5.23 (q, J=7.0 Hz, 1H), 2.46 (s, 3H), 1.61 (d, J=7.1 Hz, 3H).

Example 52: $^1$H NMR (500 MHz, CD$_3$OD) δ 8.96 (bs, 1H), 7.82-7.80 (m, 2H), 7.58 (d, J=7.7 Hz, 2H), 6.89 (bs, 1H), 4.80-4.78 (m, 1H), 2.49 (s, 3H), 2.34-2.27 (m, 1H), 1.07 (d, J=6.5 Hz, 3H), 0.88 (d, J=6.5 Hz, 3H).

Example 57: $^1$H NMR (500 MHz, CD$_3$OD) δ 8.86 (bd, J=8.7 Hz, 1H), 7.43 (d, J=8.7 Hz, 2H), 7.25 (d, J=8.1 Hz, 2H), 6.87 (bs, 1H), 4.88 (s, 1H), 2.50 (s, 3H), 1.00 (s, 9H).

Example 58: $^1$H NMR (500 MHz, CD$_3$OD) δ 8.89 (bs, 1H), 7.66 (d, J=8.1 Hz, 2H), 7.47 (d, J=8.3 Hz, 2H), 6.87 (bs, 1H), 4.92 (s, 1H), 2.50 (s, 3H), 1.00 (s, 9H).

Example 59: $^1$H NMR (500 MHz, CD$_3$OD) δ 8.88 (bs, 1H), 7.67-7.64 (m, 1H), 7.38-7.33 (m, 2H), 6.87 (bs, 1H), 4.91 (s, 1H), 2.51 (s, 3H), 1.02 (s, 9H).

Example 60: $^1$H NMR (500 MHz, CD$_3$OD) δ 8.86 (bs, 1H), 7.40-7.35 (m, 2H), 7.25-7.23 (m, 1H), 6.88 (bs, 1H), 4.87 (s, 1H), 2.50 (s, 3H), 1.01 (s, 9H).

Example 66: $^1$H NMR (500 MHz, CD$_3$OD) δ 7.68 (d, J=8.2 Hz, 2H), 7.54 (d, J=8.2 Hz, 2H), 6.90 (s, 1H), 5.24 (q, J=7.0 Hz, 1H), 2.47 (s, 3H), 1.62 (d, J=7.1 Hz, 3H).

Example 132

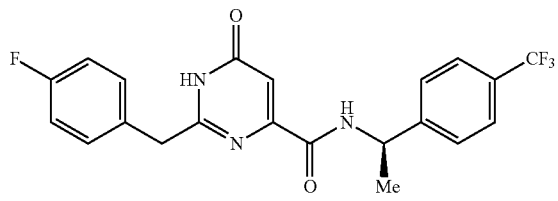 [SMILES: C[C@@H](NC(=O)c1cc(=O)[nH]c(Cc2ccc(F)cc2)n1)c1ccc(C(F)(F)F)cc1]

2-(4-fluorobenzyl)-6-oxo-N-{(1R)-1-[4-(trifluoromethyl)phenyl]ethyl}-1,6-dihydropyrimidine-4-carboxamide Step 1: (R)-2-(methylthio)-6-oxo-N-(1-(4-(trifluoromethyl)phenyl)ethyl)-1,6-dihydropyrimidine-4-carboxamide The racemic mixture of the title compound obtained using procedure described in scheme A and Example 8 was resolved by chiral separation on OJ column with 15% MeOH/CO$_2$ to afford isomer A (faster eluting), (R)-2-(methylthio)-6-oxo-N-(1-(4-(trifluoromethyl)phenyl)ethyl)-1,6-dihydro pyrimidine-4-carboxamide and isomer B (slower eluting), (S)-2-(methylthio)-6-oxo-N-(1-(4-(trifluoromethyl)phenyl)ethyl)-1,6-dihydro pyrimidine-4-carboxamide. MS: 358.1 (M+H).

Step 2: (R)-2-(methylsulfonyl)-6-oxo-N-(1-(4-(trifluoromethyl)phenyl)ethyl)-1,6-dihydro pyrimidine-4-carboxamide To a stirred solution of (R)-2-(methylthio)-6-oxo-N-(1-(4-(trifluoromethyl)phenyl)ethyl)-1,6-dihydropyrimidine-4-carboxamide (3.4 g, 9.51 mmol) in THF (200 mL) was added a solution of Oxone (17.55 g, 28.5 mmol) in water (50 mL). The resulting suspension was stirred at room temperature overnight. Solvent was removed under reduced pressure. The residue was diluted with water (100 mL), extracted with dichloromethane (2×200 mL). The combined organic layers were washed with water, brine, dried over sodium sulfate and concentrated under reduced pressure to yield the title compound, which was used in the next step without further purification. MS: 390.0 (M+H).

Step 3: (R)-2-(4-fluorobenzyl)-6-oxo-N-(1-(4-(trifluoromethyl)phenyl)ethyl)-1,6-dihydropyrimidine-4-carboxamide To a stirred solution of (R)-2-(methylsulfonyl)-6-oxo-N-(1-(4-(trifluoromethyl)phenyl)ethyl)-1,6-dihydropyrimidine-4-carboxamide (90 mg, 0.231 mmol) in THF (2 mL) at −78° C. was added a solution of (4-fluorobenzyl)magnesium chloride (4.16 mL, 1.040 mmol). The resulting mixture was stirred at −78° C. for 1.5 h. The reaction was monitored by LC-MS which indicated only small amount of product. More of the solution of (4-fluorobenzyl)magnesium chloride (4.16 mL, 1.040 mmol) was added. It was slowly warmed up to rt and stirred for 30 min. The mixture was cooled, quenched with 1N HCl, diluted with sat'd ammonium chloride, and extracted with ethyl acetate. The organic layer was washed with brine, dried over sodium sulfate and concentrated. The residue was purified by prep-TLC, eluting with 4% MeOH in CH$_2$Cl$_2$ to collect the residue which was repurified by preparative RP-HPLC (C-18), eluting with 10 to 90% acetonitrile/water with 0.05% TFA modifier, to give the title compound. MS: 420.0 (M+H). $^1$H NMR (500 MHz, CD$_3$OD) δ 8.76 (d, J=7.7 Hz 1H), 7.66 (d, J=8.1 Hz, 2H), 7.54 (d, J=8.3 Hz 2H), 7.38-7.41 (m, 2H), 7.07-7.11 (m, 2H), 6.91 (s, 1H), 5.20-5.26 (m, 1H), 4.04 (s, 2H), 1.59 (d, J=6.9 Hz 3H).

The following examples in Table 5 were prepared according to Scheme D using the procedure outlined in the synthesis of Example 132 with appropriate Grignard reagent and other starting materials.

TABLE 5

| Example No. | Structure | IUPAC Name | Observed Exact Mass [M + H]$^+$ |
| --- | --- | --- | --- |
| 133 | ![structure] | 2-benzyl-6-oxo-N-{(1R)-1-[4-(trifluoromethyl)phenyl]ethyl}-1,6-dihydropyrimidine-4-carboxamide | 402.1 |

TABLE 5-continued

| Example No. | Structure | IUPAC Name | Observed Exact Mass [M + H]+ |
|---|---|---|---|
| 134 | 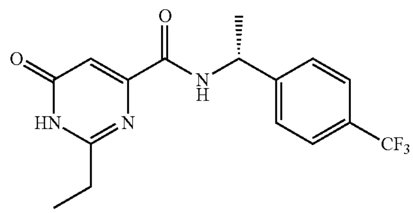 [SMILES: CCc1nc(C(=O)N[C@H](C)c2ccc(C(F)(F)F)cc2)cc(=O)[nH]1] | 2-ethyl-6-oxo-N-{(1R)-1-[4-(trifluoromethyl)phenyl]ethyl}-1,6-dihydropyrimidine-4-carboxamide | 340.0 |
| 135 | 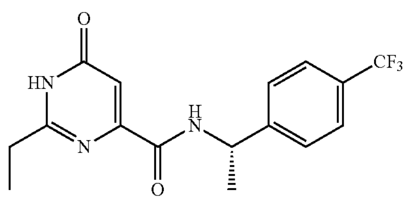 [SMILES: CCc1nc(C(=O)N[C@@H](C)c2ccc(C(F)(F)F)cc2)cc(=O)[nH]1] | 2-ethyl-6-oxo-N-{(1S)-1-[4-(trifluoromethyl)phenyl]ethyl}-1,6-dihydropyrimidine-4-carboxamide | 340.0 |
| 136 | 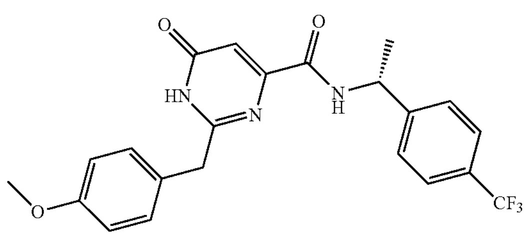 [SMILES: COc1ccc(Cc2nc(C(=O)N[C@H](C)c3ccc(C(F)(F)F)cc3)cc(=O)[nH]2)cc1] | 2-(4-methoxybenzyl)-6-oxo-N-{(1R)-1-[4-(trifluoromethyl)phenyl]ethyl}-1,6-dihydropyrimidine-4-carboxamide | 432.0 |
| 137 | 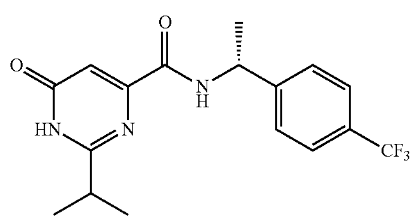 [SMILES: CC(C)c1nc(C(=O)N[C@H](C)c2ccc(C(F)(F)F)cc2)cc(=O)[nH]1] | 2-(1-methylethyl)-6-oxo-N-{(1R)-1-[4-(trifluoromethyl)phenyl]ethyl}-1,6-dihydropyrimidine-4-carboxamide | 354.0 |
| 138 | 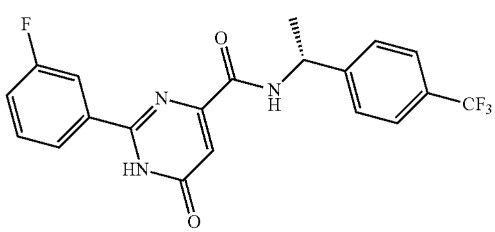 [SMILES: C[C@@H](NC(=O)c1cc(=O)[nH]c(-c2cccc(F)c2)n1)c1ccc(C(F)(F)F)cc1] | 2-(3-fluorophenyl)-6-oxo-N-{(1R)-1-[4-(trifluoromethyl)phenyl]ethyl}-1,6-dihydropyrimidine-4-carboxamide | 406.1 |
| 139 | 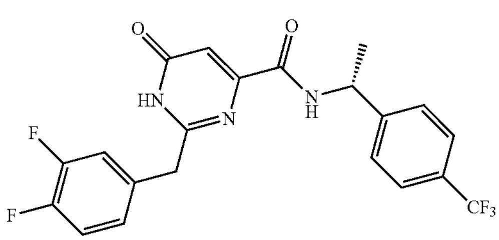 [SMILES: C[C@@H](NC(=O)c1cc(=O)[nH]c(Cc2ccc(F)c(F)c2)n1)c1ccc(C(F)(F)F)cc1] | 2-(3,4-difluorophenyl)-6-oxo-N-{(1R)-1-[4-(trifluoromethyl)phenyl]ethyl}-1,6-dihydropyrimidine-4-carboxamide | 424.1 |

TABLE 5-continued

| Example No. | Structure | IUPAC Name | Observed Exact Mass [M + H]+ |
|---|---|---|---|
| 140 | 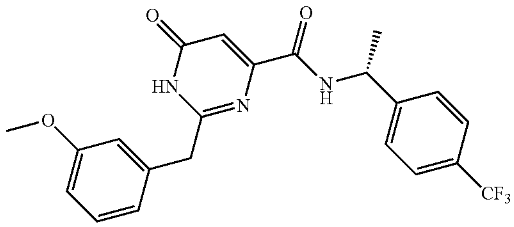 [SMILES: COc1cccc(Cc2nc(C(=O)N[C@H](C)c3ccc(C(F)(F)F)cc3)cc(=O)[nH]2)c1] | 2-(3-methoxybenzyl)-6-oxo-N-{(1R)-1-[4-(trifluoromethyl)phenyl]ethyl}-1,6-dihydropyrimidine-4-carboxamide | 432.2 |
| 141 | 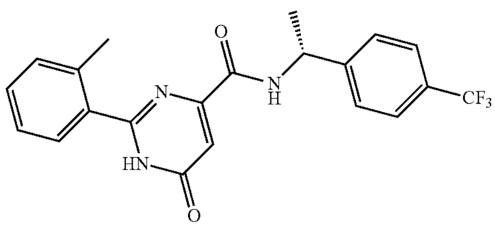 [SMILES: Cc1ccccc1-c1nc(C(=O)N[C@H](C)c2ccc(C(F)(F)F)cc2)cc(=O)[nH]1] | 2-(2-methylphenyl)-6-oxo-N-{(1R)-1-[4-(trifluoromethyl)phenyl]ethyl}-1,6-dihydropyrimidine-4-carboxamide | 402.2 |

Example 142

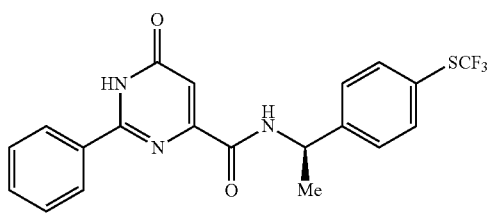

6-Oxo-2-phenyl-N-[(1R)-1-{4-[(trifluoromethyl)sulfanyl]phenyl}ethyl]-1,6-dihydropyrimidine-4-carboxamide To a stirred mixture of 6-oxo-2-phenyl-1,6-dihydropyrimidine-4-carboxylic acid (25 mg, 0.116 mmol) in DMF (1.2 mL) was added (R)-1-(4-((trifluoromethyl)thio)phenyl)ethanamine HCl salt (35.8 mg, 0.139 mmol) and DIPEA (0.061 mL, 0.347 mmol). After stirring for 10 min, HBTU (88 mg, 0.231 mmol) was added. The resulting mixture was stirred at room temperature overnight. The mixture was filtered and purified by preparative RP-HPLC (C-18) to yield the title compound. LC-MS: 420.2 (M+H+).

Compounds in Tables 6 and 7 were prepared using the procedure in Example 142 above using appropriate starting materials (Scheme E).

TABLE 6

| Example No. | Structure | IUPAC Name | Exact Mass [M + H]+ |
|---|---|---|---|
| 143 | 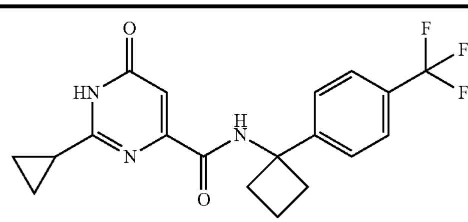 | 2-cyclopropyl-6-oxo-N-{1-[4-(trifluoromethyl)phenyl]cyclobutyl}-1,6-dihydropyrimidine-4-carboxamide | Calc'd 378.1, found 378.2 |
| 144 | 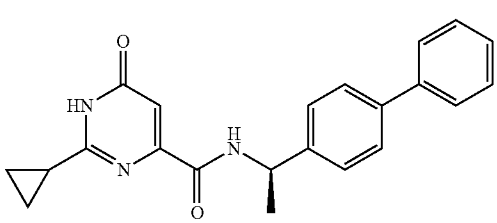 [SMILES: C[C@@H](NC(=O)c1cc(=O)[nH]c(C2CC2)n1)c1ccc(-c2ccccc2)cc1] | N-[(1R)-1-biphenyl-4-ylethyl]-2-cyclopropyl-6-oxo-1,6-dihydropyrimidine-4-carboxamide | Calc'd 360.2, found 360.2 |

TABLE 6-continued

| Example No. | Structure | IUPAC Name | Exact Mass [M + H]+ |
|---|---|---|---|
| 145 | 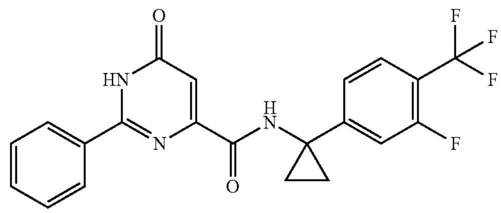 [SMILES: O=C(NC1(c2ccc(C(F)(F)F)c(F)c2)CC1)c1cc(=O)[nH]c(-c2ccccc2)n1] | N-{1-[3-fluoro-4-(trifluoromethyl)phenyl]cyclopropyl}-6-oxo-2-phenyl-1,6-dihydropyrimidine-4-carboxamide | Calc'd 418.1, found 418.2 |
| 146 | 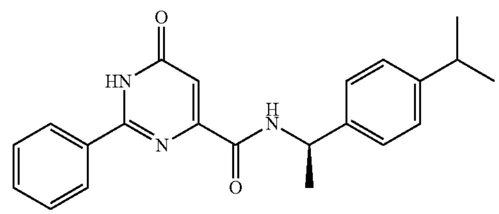 [SMILES: CC(C)c1ccc([C@@H](C)NC(=O)c2cc(=O)[nH]c(-c3ccccc3)n2)cc1] | N-{(1R)-1-[4-(1-methylethyl)phenyl]ethyl}-6-oxo-2-phenyl-1,6-dihydropyrimidine-4-carboxamide | Calc'd 362.2, found 362.2 |
| 147 | 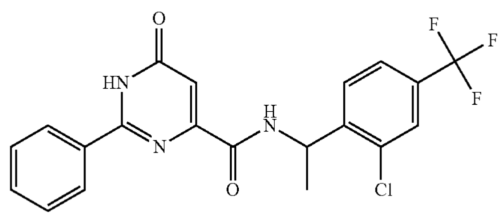 [SMILES: CC(NC(=O)c1cc(=O)[nH]c(-c2ccccc2)n1)c1ccc(C(F)(F)F)cc1Cl] | N-{1-[2-chloro-4-(trifluoromethyl)phenyl]ethyl}-6-oxo-2-phenyl-1,6-dihydropyrimidine-4-carboxamide | Calc'd 422.1/424.1, found 422.2/424.2 |
| 148 | 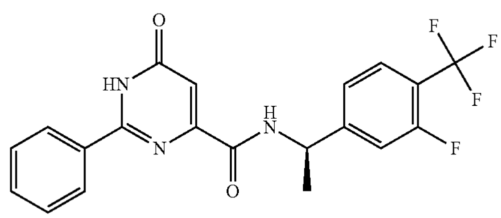 [SMILES: C[C@@H](NC(=O)c1cc(=O)[nH]c(-c2ccccc2)n1)c1ccc(C(F)(F)F)c(F)c1] | N-{(1R)-1-[3-fluoro-4-(trifluoromethyl)phenyl]ethyl}-6-oxo-2-phenyl-1,6-dihydropyrimidine-4-carboxamide | Calc'd 406.1, found 406.2 |
| 149 | 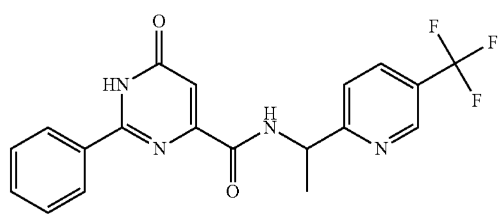 [SMILES: CC(NC(=O)c1cc(=O)[nH]c(-c2ccccc2)n1)c1ccc(C(F)(F)F)cn1] | 6-oxo-2-phenyl-N-{1-[5-(trifluoromethyl)pyridin-2-yl]ethyl}-1,6-dihydropyrimidine-4-carboxamide | Calc'd 389.1, found 389.2 |
| 150 | 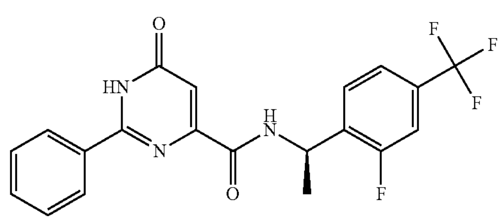 [SMILES: C[C@@H](NC(=O)c1cc(=O)[nH]c(-c2ccccc2)n1)c1ccc(C(F)(F)F)cc1F] | N-{(1R)-1-[2-fluoro-4-(trifluoromethyl)phenyl]ethyl}-6-oxo-2-phenyl-1,6-dihydropyrimidine-4-carboxamide | Calc'd 406.1, found 406.2 |
| 151 | 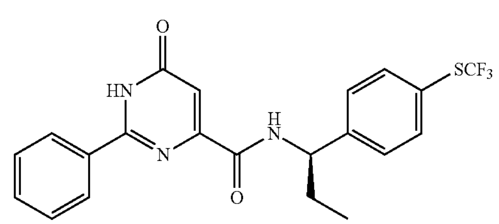 | 6-oxo-2-phenyl-N-[(1R)-1-{4-[(trifluoromethyl)sulfanyl]phenyl}propyl]-1,6-dihydropyrimidine-4-carboxamide | Calc'd 434.1, found 434.2 |

TABLE 6-continued

| Example No. | Structure | IUPAC Name | Exact Mass [M + H]+ |
|---|---|---|---|
| 152 | 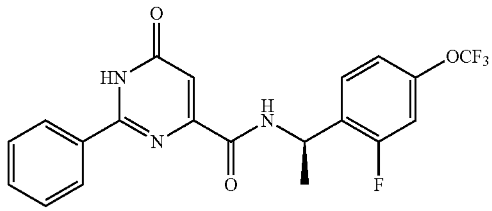 [SMILES: C[C@@H](NC(=O)c1cc(=O)[nH]c(-c2ccccc2)n1)c1ccc(OC(F)(F)F)cc1F] | N-{(1R)-1-[2-fluoro-4-(trifluoromethyl)phenyl]ethyl}-6-oxo-2-phenyl-1,6-dihydropyrimidine-4-carboxamide | Calc'd 422.1, found 422.2 |
| 153 | 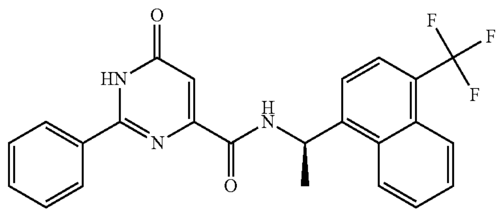 [SMILES: C[C@@H](NC(=O)c1cc(=O)[nH]c(-c2ccccc2)n1)c1ccc(C(F)(F)F)c2ccccc12] | 6-oxo-2-phenyl-N-{(1R)-1-[4-(trifluoromethoxy)naphthalen-1-yl]ethyl}-1,6-dihydropyrimidine-4-carboxamide | Calc'd 438.1, found 438.3 |
| 154 | 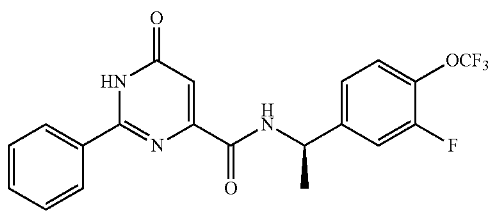 [SMILES: C[C@@H](NC(=O)c1cc(=O)[nH]c(-c2ccccc2)n1)c1ccc(OC(F)(F)F)c(F)c1] | N-{(1R)-1-[3-fluoro-4-(trifluoromethoxy)phenyl]ethyl}-6-oxo-2-phenyl-1,6-dihydropyrimidine-4-carboxamide | Calc'd 422.1, found 422.3 |
| 155 | 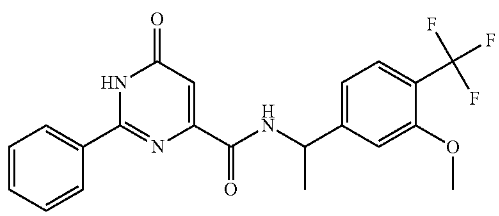 [SMILES: COc1cc(C(C)NC(=O)c2cc(=O)[nH]c(-c3ccccc3)n2)ccc1C(F)(F)F] | N-{1-[3-methoxy-4-(trifluoromethoxy)phenyl]ethyl}-6-oxo-2-phenyl-1,6-dihydropyrimidine-4-carboxamide | Calc'd 418.1, found 418.2 |
| 156 | 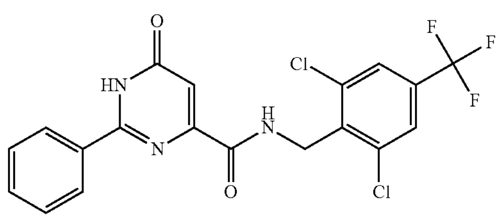 [SMILES: O=C(NCc1c(Cl)cc(C(F)(F)F)cc1Cl)c1cc(=O)[nH]c(-c2ccccc2)n1] | N-[2,6-dichloro-4-(trifluoromethoxy)benzyl]-6-oxo-2-phenyl-1,6-dihydropyrimidine-4-carboxamide | Calc'd 442.0/ 444.0/446.0 Found 442.1/ 444.2/446.1 |
| 157 | 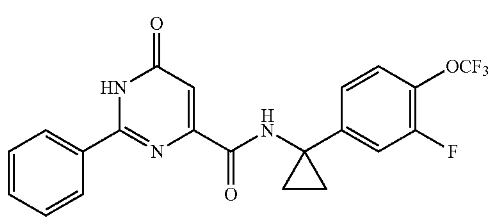 [SMILES: O=C(NC1(c2ccc(OC(F)(F)F)c(F)c2)CC1)c1cc(=O)[nH]c(-c2ccccc2)n1] | N-{1-[3-fluoro-4-(trifluoromethoxy)phenyl]cyclopropyl}-6-oxo-2-phenyl-1,6-dihydropyrimidine-4-carboxamide | Calc'd 434.1, found 434.2 |
| 158 | 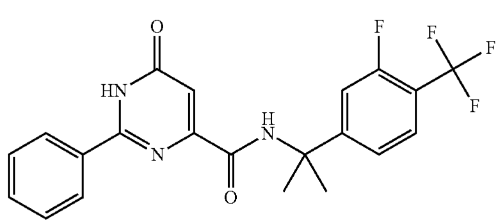 [SMILES: CC(C)(NC(=O)c1cc(=O)[nH]c(-c2ccccc2)n1)c1ccc(C(F)(F)F)c(F)c1] | N-{1-[3-fluoro-4-(trifluoromethyl)phenyl]-1-methylethyl}-6-oxo-2-phenyl-1,6-dihydropyrimidine-4-carboxamide | Calc'd 420.1, found 420.3 |

TABLE 6-continued

| Example No. | Structure | IUPAC Name | Exact Mass [M + H]+ |
|---|---|---|---|
| 159 | 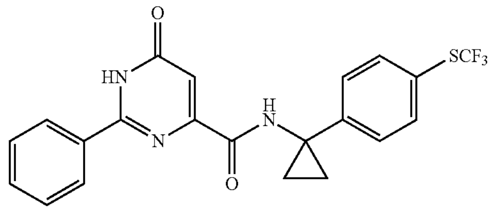 | 6-oxo-2-phenyl-N-(1-{4-[(trifluoromethyl)sulfanyl]phenyl}cyclopropyl)-1,6-dihydropyrimidine-4-carboxamide | Calc'd 432.1, found 432.2 |
| 160 | 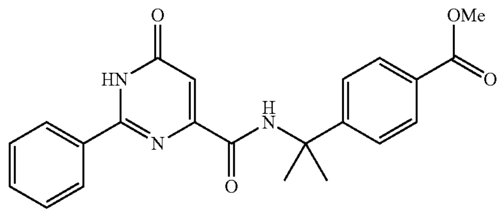 [SMILES: COC(=O)c1ccc(C(C)(C)NC(=O)c2cc(=O)[nH]c(-c3ccccc3)n2)cc1] | methyl 4-(1-methyl-1-{[(6-oxo-2-phenyl-1,6-dihydropyrimidin-4-yl)carbonyl]amino}ethyl)benzoate | Calc'd 392.2, found 392.2 |
| 161 | 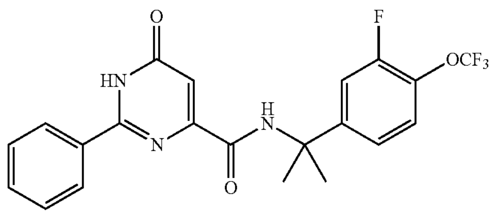 [SMILES: CC(C)(NC(=O)c1cc(=O)[nH]c(-c2ccccc2)n1)c1ccc(OC(F)(F)F)c(F)c1] | N-{1-[3-fluoro-4-(trifluoromethoxy)phenyl]-1-methylethyl}-6-oxo-2-phenyl-1,6-dihydropyrimidine-4-carboxamide | Calc'd 436.1, found 436.3 |
| 162 | 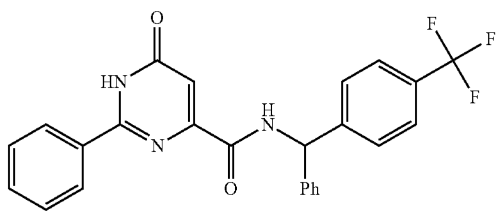 [SMILES: O=C(NC(c1ccccc1)c1ccc(C(F)(F)F)cc1)c1cc(=O)[nH]c(-c2ccccc2)n1] | 6-oxo-2-phenyl-N-{phenyl[4-(trifluoromethyl)phenyl]methyl}-1,6-dihydropyrimidine-4-carboxamide | Calc'd 450.1, found 450.3 |
| 163 | 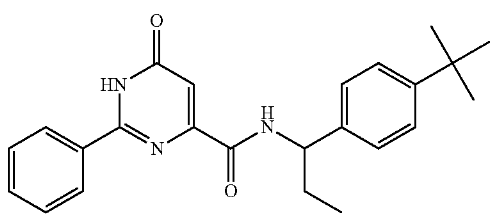 [SMILES: CCC(NC(=O)c1cc(=O)[nH]c(-c2ccccc2)n1)c1ccc(C(C)(C)C)cc1] | N-[1-(4-tert-butylphenyl)propyl]-6-oxo-2-phenyl-1,6-dihydropyrimidine-4-carboxamide | Calc'd 390.2, found 390.3 |
| 164 | 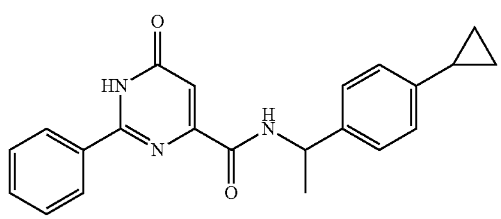 [SMILES: CC(NC(=O)c1cc(=O)[nH]c(-c2ccccc2)n1)c1ccc(C2CC2)cc1] | N-[1-(4-cyclopropylphenyl)ethyl]-6-oxo-2-phenyl-1,6-dihydropyrimidine-4-carboxamide | Calc'd 360.2, found 360.2 |
| 165 | 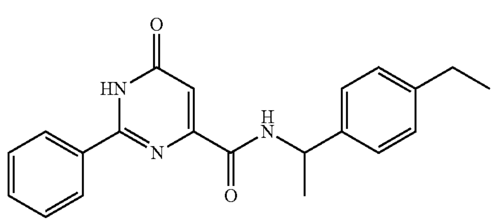 [SMILES: CCc1ccc(C(C)NC(=O)c2cc(=O)[nH]c(-c3ccccc3)n2)cc1] | N-[1-(4-ethylphenyl)ethyl]-6-oxo-2-phenyl-1,6-dihydropyrimidine-4-carboxamide | Calc'd 348.2, found 348.2 |

TABLE 6-continued

| Example No. | IUPAC Name | Exact Mass [M + H]+ |
|---|---|---|
| 166 | N-{(1R)-2-methyl-1-[4-(trifluoromethoxy)phenyl]propyl}-6-oxo-2-phenyl-1,6-dihydropyrimidine-4-carboxamide | Calc'd 432.2, found 432.3 |
| 167 | N-{(1R)-2-methyl-1-[4-(trifluoromethyl)phenyl]propyl}-6-oxo-2-phenyl-1,6-dihydropyrimidine-4-carboxamide | Calc'd 416.2, found 416.3 |
| 168 | 6-oxo-2-phenyl-N-{(1R)-1-[3-(trifluoromethyl)phenyl]ethyl}-1,6-dihydropyrimidine-4-carboxamide | Calc'd 388.1, found 388.2 |
| 169 | 6-oxo-2-phenyl-N-{1-[2-(trifluoromethyl)phenyl]ethyl}-1,6-dihydropyrimidine-4-carboxamide | Calc'd 388.1, found 388.2 |
| 170 | 6-oxo-2-phenyl-N-{1-[5-(trifluoromethyl)pyrimidin-2-yl]ethyl}-1,6-dihydropyrimidine-4-carboxamide | Calc'd 390.1, found 390.2 |
| 171 | 6-oxo-2-phenyl-N-(1-{4-[(trifluoromethyl)sulfanyl]phenyl}cyclobutyl)-1,6-dihydropyrimidine-4-carboxamide | Calc'd 446.1, found 446.2 |
| 172 | N-{(1R)-1-[3-fluoro-4-(trifluoromethyl)phenyl]propyl}-6-oxo-2-phenyl-1,6-dihydropyrimidine-4-carboxamide | Calc'd 436.1, found 436.2 |

TABLE 6-continued

| Example No. | Structure | IUPAC Name | Exact Mass [M + H]+ |
|---|---|---|---|
| 173 | 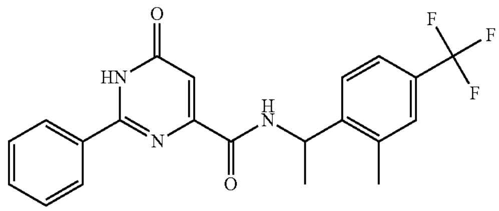 [SMILES: Cc1cc(C(F)(F)F)ccc1C(C)NC(=O)c1cc(=O)[nH]c(-c2ccccc2)n1] | N-{1-[2-methyl-4-(trifluoromethyl)phenyl]ethyl}-6-oxo-2-phenyl-1,6-dihydropyrimidine-4-carboxamide | Calc'd 402.1, found 402.2 |
| 174 | 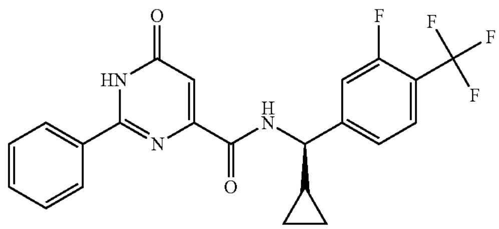 [SMILES: O=C(N[C@@H](c1ccc(C(F)(F)F)c(F)c1)C1CC1)c1cc(=O)[nH]c(-c2ccccc2)n1] | N-{(R)-cyclopropyl[3-fluoro-4-(trifluoromethyl)phenyl]methyl}-6-oxo-2-phenyl-1,6-dihydropyrimidine-4-carboxamide | Calc'd 432.1, found 432.2 |
| 175 | 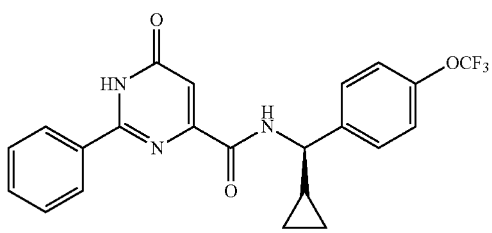 [SMILES: O=C(N[C@@H](c1ccc(OC(F)(F)F)cc1)C1CC1)c1cc(=O)[nH]c(-c2ccccc2)n1] | N-{(R)-cyclopropyl[4-(trifluoromethoxy)phenyl]methyl}-6-oxo-2-phenyl-1,6-dihydropyrimidine-4-carboxamide | Calc'd 430.1, found 430.3 |
| 176 | 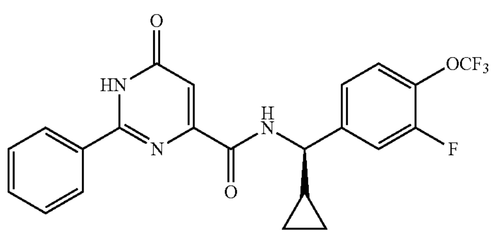 [SMILES: O=C(N[C@@H](c1ccc(OC(F)(F)F)c(F)c1)C1CC1)c1cc(=O)[nH]c(-c2ccccc2)n1] | N-{(R)-cyclopropyl[3-fluoro-4-(trifluoromethyl)phenyl]methyl}-6-oxo-2-phenyl-1,6-dihydropyrimidine-4-carboxaniide | Calc'd 448.1, found 448.2 |
| 177 | 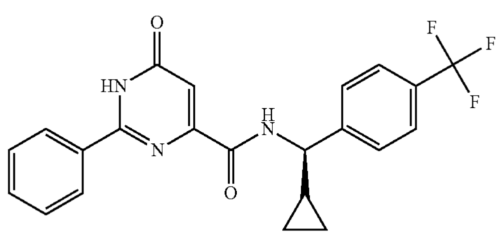 [SMILES: O=C(N[C@@H](c1ccc(C(F)(F)F)cc1)C1CC1)c1cc(=O)[nH]c(-c2ccccc2)n1] | N-{(R)-cyclopropyl[4-(trifluoromethyl)phenyl]methyl}-6-oxo-2-phenyl-1,6-dihydropyrimidine-4-carboxamide | Calc'd 414.1, found 414.2 |
| 178 | 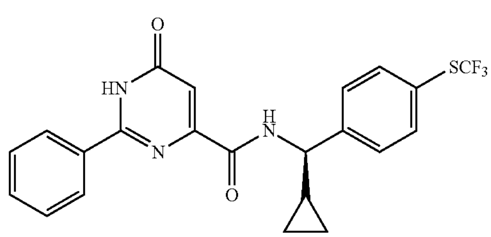 | N-[(R)-cyclopropyl{4-[(trifluoromethyl)sulfanyl]phenyl}methyl]-6-oxo-2-phenyl-1,6-dihydropyrimidine-4-carboxamide | Calc'd 446.1, found 446.3 |

TABLE 6-continued

| Example No. | Structure | IUPAC Name | Exact Mass [M + H]+ |
|---|---|---|---|
| 179 | 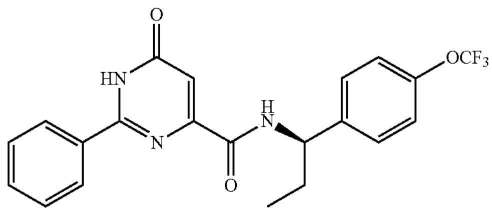 [SMILES: CC[C@@H](NC(=O)c1cc(=O)[nH]c(-c2ccccc2)n1)c1ccc(OC(F)(F)F)cc1] | 6-oxo-2-phenyl-N-{(1R)-1-[4-(trifluoromethoxy)phenyl]propyl}-1,6-dihydropyrimidine-4-carboxamide | Calc'd 418.1, found 418.2 |
| 180 | 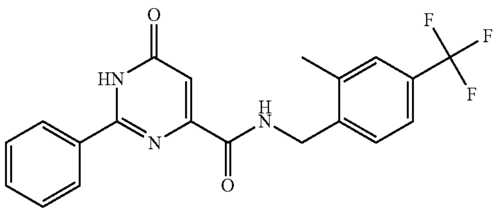 [SMILES: Cc1cc(C(F)(F)F)ccc1CNC(=O)c1cc(=O)[nH]c(-c2ccccc2)n1] | N-[2-methyl-4-(trifluoromethyl)benzyl]-6-oxo-2-phenyl-1,6-dihydropyrimidine-4-carboxamide | Calc'd 388.1, found 388.2 |
| 181 | 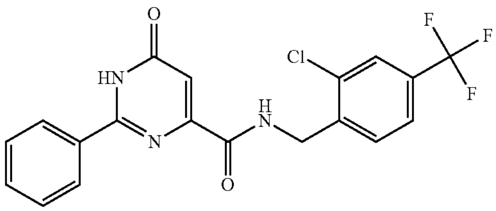 [SMILES: O=C(NCc1ccc(C(F)(F)F)cc1Cl)c1cc(=O)[nH]c(-c2ccccc2)n1] | N-[2-chloro-4-(trifluoromethyl)benzyl]-6-oxo-2-phenyl-1,6-dihydropyrimidine-4-carboxamide | Calc'd 408.1/410.1, found 408.2/410.1 |
| 182 | 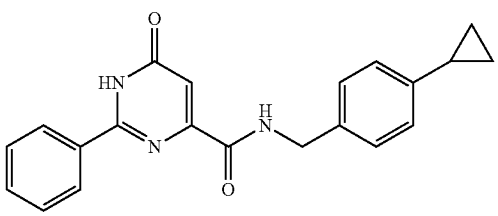 [SMILES: O=C(NCc1ccc(C2CC2)cc1)c1cc(=O)[nH]c(-c2ccccc2)n1] | N-(4-cyclopropylbenzyl)-6-oxo-2-phenyl-1,6-dihydropyrimidine-4-carboxamide | Calc'd 346.2, found 346.2 |
| 183 | 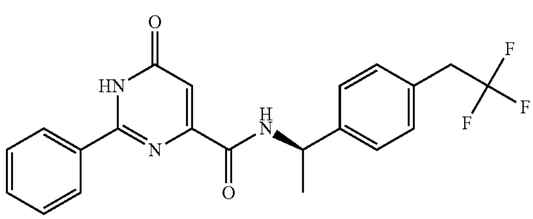 [SMILES: C[C@@H](NC(=O)c1cc(=O)[nH]c(-c2ccccc2)n1)c1ccc(CC(F)(F)F)cc1] | 6-oxo-2-phenyl-N-{(1R)-1-[4-(2,2,2-trifluoromethyl)phenyl]ethyl}-1,6-dihydropyrimidine-4-carboxamide | Calc'd 402.1, found 402.2 |
| 184 | 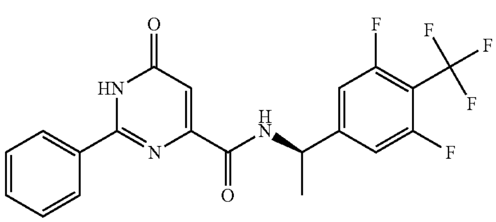 [SMILES: C[C@@H](NC(=O)c1cc(=O)[nH]c(-c2ccccc2)n1)c1cc(F)c(C(F)(F)F)c(F)c1] | N-{(1R)-1-[3,5-difluoro-4-(trifluoromethyl)phenyl]ethyl}-6-oxo-2-phenyl-1,6-dihydropyrimidine-4-carboxamide | Calc'd 424.1, found 424.3 |
| 185 | 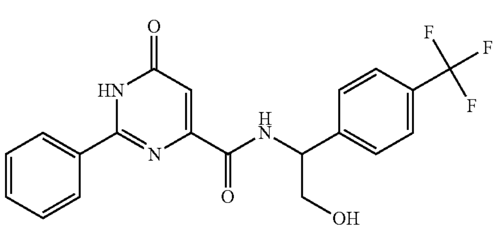 [SMILES: O=C(NC(CO)c1ccc(C(F)(F)F)cc1)c1cc(=O)[nH]c(-c2ccccc2)n1] | N-{2-hydroxy-1-[4-(trifluoromethyl)phenyl]ethyl}-6-oxo-2-phenyl-1,6-dihydropyrimidine-4-carboxamide | Calc'd 404.1, found 404.2 |

TABLE 6-continued

| Example No. | Structure | IUPAC Name | Exact Mass [M + H]+ |
|---|---|---|---|
| 186 | 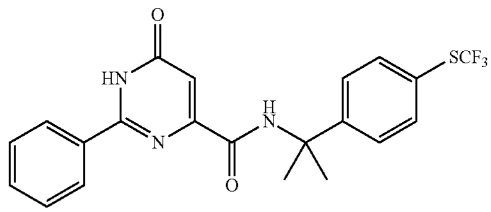 | N-(1-methyl-1-{4-[(trifluoromethyl)sulfanyl]phenyl}ethyl)-6-oxo-2-phenyl-1,6-dihydropyrimidine-4-carboxamide | Calc'd 434.1, found 434.2 |
| 187 | 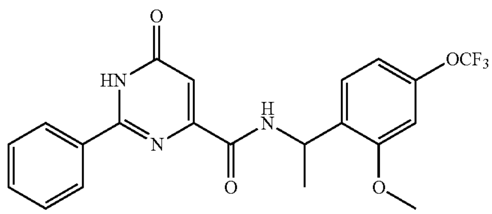 [SMILES: COc1cc(OC(F)(F)F)ccc1C(C)NC(=O)c1cc(=O)[nH]c(-c2ccccc2)n1] | N-{1-[2-methoxy-4-(trifluoromethoxy)phenyl]ethyl}-6-oxo-2-phenyl-1,6-dihydropyrimidine-4-carboxamide | Calc'd 434.1, found 434.3 |
| 188 | 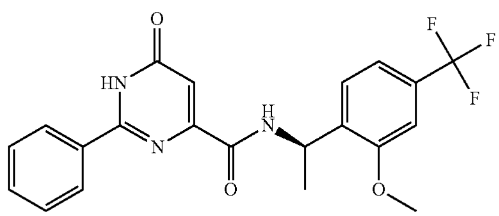 [SMILES: COc1cc(C(F)(F)F)ccc1[C@@H](C)NC(=O)c1cc(=O)[nH]c(-c2ccccc2)n1] | N-{(1R)-1-[2-methoxy-4-(trifluoromethyl)phenyl]ethyl}-6-oxo-2-phenyl-1,6-dihydropyrimidine-4-carboxamide | Calc'd 418.1, found 418.2 |
| 189 | 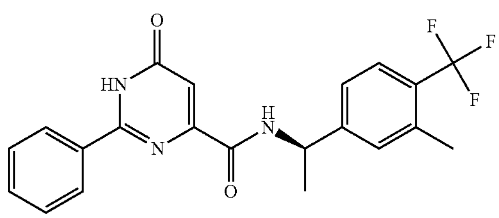 [SMILES: Cc1cc([C@@H](C)NC(=O)c2cc(=O)[nH]c(-c3ccccc3)n2)ccc1C(F)(F)F] | N-{(1R)-1-[3-methyl-4-(trifluoromethoxy)phenyl]ethyl}-6-oxo-2-phenyl-1,6-dihydropyrimidine-4-carboxamide | Calc'd 402.1, found 402.2 |
| 190 | 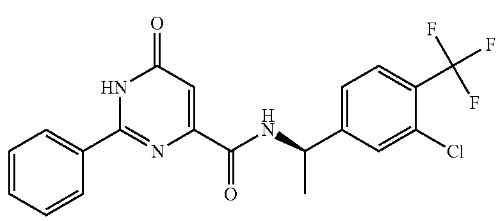 [SMILES: C[C@@H](NC(=O)c1cc(=O)[nH]c(-c2ccccc2)n1)c1ccc(C(F)(F)F)c(Cl)c1] | N-{(1R)-1-[3-chloro-4-(trifluoromethyl)phenyl]ethyl}-6-oxo-2-phenyl-1,6-dihydropyrimidine-4-carboxamide | Calc'd 422.1, found 422.2 |
| 191 | 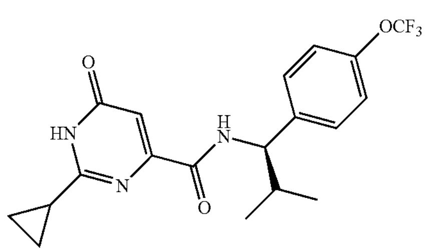 [SMILES: CC(C)[C@@H](NC(=O)c1cc(=O)[nH]c(C2CC2)n1)c1ccc(OC(F)(F)F)cc1] | 2-cyclopropyl-N-{(1R)-2-methyl-1-[4-(trifluoromethoxy)phenyl]propyl}-6-oxo-1,6-dihydropyrimidine-4-carboxamide | Calc'd 396.2, found 396.2 |
| 192 | 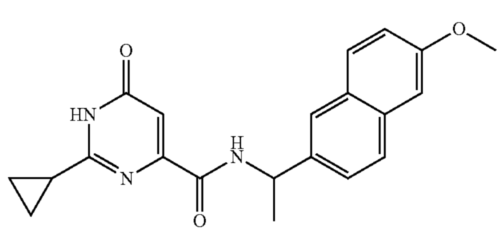 [SMILES: COc1ccc2cc(C(C)NC(=O)c3cc(=O)[nH]c(C4CC4)n3)ccc2c1] | 2-cyclopropyl-N-[1-(6-methoxynaphthalen-2-yl)ethyl]-6-oxo-1,6-dihydropyrimidine-4-carboxamide | Calc'd 364.2, found 364.3 |

TABLE 6-continued

| Example No. | IUPAC Name | Exact Mass [M + H]+ |
|---|---|---|
| 193 | 2-cyclopropyl-N-{(1R)-2-methyl-1-[4-(trifluoromethyl)phenyl]propyl}-6-oxo-1,6-dihydropyrimidine-4-carboxamide | Calc'd 380.2, found 380.2 |
| 194 | 2-cyclopropyl-N-[1-(4-ethylphenyl)ethyl]-6-oxo-1,6-dihydropyrimidine-4-carboxamide | Calc'd 312.2, found 312.2 |
| 195 | 2-cyclopropyl-N-[1-(4-cyclopropylphenyl)ethyl]-6-oxo-1,6-dihydropyrimidine-4-carboxamide | Calc'd 324.2, found 324.2 |
| 196 | 2-cyclopropyl-6-oxo-N-{phenyl[4-(trifluoromethyl)phenyl]methyl}-1,6-dihydropyrimidine-4-carboxamide | Calc'd 414.1, found 414.2 |
| 197 | 2-cyclopropyl-6-oxo-N-{1-[4-(trifluoromethyl)phenyl]cyclopentyl}-1,6-dihydropyrimidine-4-carboxamide | Calc'd 392.2, found 392.3 |
| 198 | 2-cyclopropyl-N-{1-[3-fluoro-4-(trifluoromethyl)phenyl]-1-methylethyl}-6-oxo-1,6-dihydropyrimidine-4-carboxamide | Calc'd 400.1, found 400.2 |
| 199 | 2-cyclopropyl-6-oxo-N-(1-{4-[(trifluoromethyl)sulfanyl]phenyl}cyclopropyl)-1,6-dihydropyrimidine-4-carboxamide | Calc'd 396.1, found 396.2 |

TABLE 6-continued

| Example No. | Structure | IUPAC Name | Exact Mass [M + H]+ |
|---|---|---|---|
| 200 | 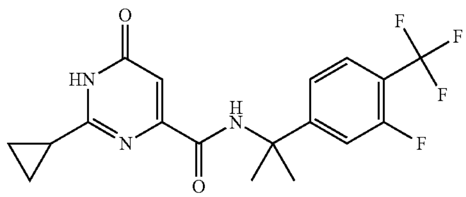 [SMILES: CC(C)(NC(=O)c1cc(=O)[nH]c(C2CC2)n1)c1ccc(C(F)(F)F)c(F)c1] | 2-cyclopropyl-N-{1-[3-fluoro-4-(trifluoromethyl)phenyl]-1-methylethyl}-6-oxo-1,6-dihydropyrimidine-4-carboxamide | Calc'd 384.1, found 384.2 |
| 201 | 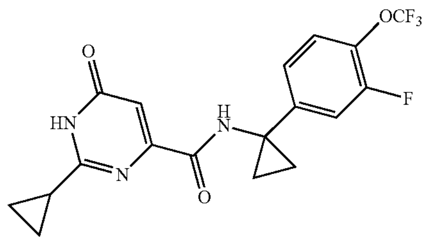 [SMILES: O=C(NC1(c2ccc(OC(F)(F)F)c(F)c2)CC1)c1cc(=O)[nH]c(C2CC2)n1] | 2-cyclopropyl-N-{1-[3-fluoro-4-(trifluoromethyl)phenyl]cyclopropyl}-6-oxo-1,6-dihydropyrimidine-4-carboxamide | Calc'd 398.1, found 398.2 |
| 202 | 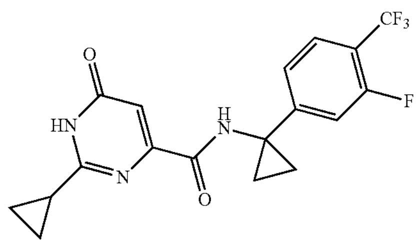 [SMILES: O=C(NC1(c2ccc(C(F)(F)F)c(F)c2)CC1)c1cc(=O)[nH]c(C2CC2)n1] | 2-cyclopropyl-N-{1-[3-fluoro-4-(trifluoromethyl)phenyl]cyclopropyl}-6-oxo-1,6-dihydropyrimidine-4-carboxamide | Calc'd 382.1, found 382.2 |
| 203 | 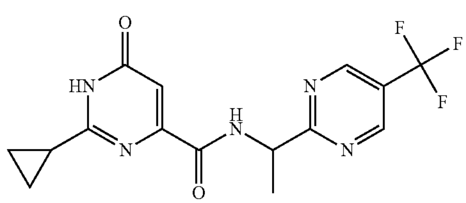 [SMILES: CC(NC(=O)c1cc(=O)[nH]c(C2CC2)n1)c1ncc(C(F)(F)F)cn1] | 2-cyclopropyl-6-oxo-N-{1-[5-(trifluoromethyl)pyrimidin-2-yl]ethyl}-1,6-dihydropyrimidine-4-carboxamide | Calc'd 354.1, found 354.2 |
| 204 | 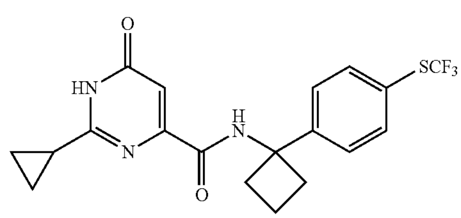 | 2-cyclopropyl-6-oxo-N-(1-{4-[(trifluoromethyl)sulfanyl]phenyl}cyclobutyl)-1,6-dihydropyrimidine-4-carboxamide | Calc'd 410.1, found 410.2 |
| 205 | 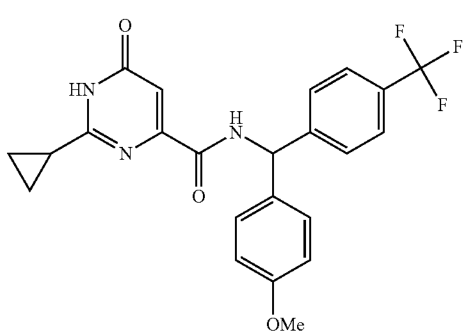 [SMILES: COc1ccc(C(NC(=O)c2cc(=O)[nH]c(C3CC3)n2)c2ccc(C(F)(F)F)cc2)cc1] | 2-cyclopropyl-N-{(4-methoxyphenyl)[4-(trifluoromethyl)phenyl]methyl}-6-oxo-1,6-dihydropyrimidine-4-carboxamide | Calc'd 444.2, found 444.3 |

TABLE 6-continued

| Example No. | Structure | IUPAC Name | Exact Mass [M + H]+ |
|---|---|---|---|
| 206 | 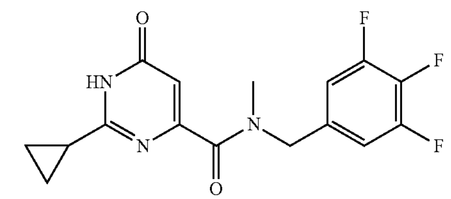 [SMILES: CN(Cc1cc(F)c(F)c(F)c1)C(=O)c1cc(=O)[nH]c(C2CC2)n1] | 2-cyclopropyl-N-methyl-6-oxo-N-(3,4,5-trifluoromethyl)-1,6-dihydropyrimidine-4-carboxamide | Calc'd 338.1, found 338.2 |
| 207 | 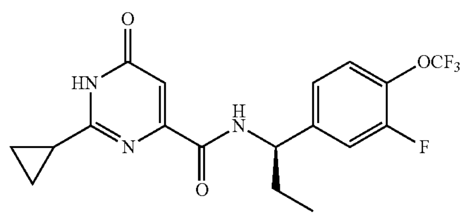 [SMILES: CC[C@@H](NC(=O)c1cc(=O)[nH]c(C2CC2)n1)c1ccc(OC(F)(F)F)c(F)c1] | 2-cyclopropyl-N-{(1R)-1-[3-fluoro-4-(trifluoromethyl)phenyl]propyl}-6-oxo-1,6-dihydropyrimidine-4-carboxamide | Calc'd 400.1, found 400.2 |
| 208 | 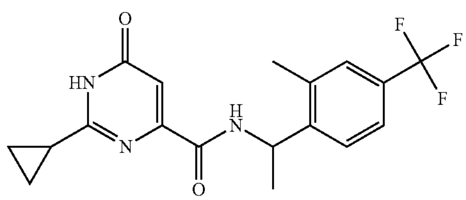 [SMILES: Cc1cc(C(F)(F)F)ccc1C(C)NC(=O)c1cc(=O)[nH]c(C2CC2)n1] | 2-cyclopropyl-N-{1-[2-methyl-4-(trifluoromethyl)phenyl]methyl}-6-oxo-1,6-dihydropyrimidine-4-carboxamide | Calc'd 366.1, found 366.2 |
| 209 | 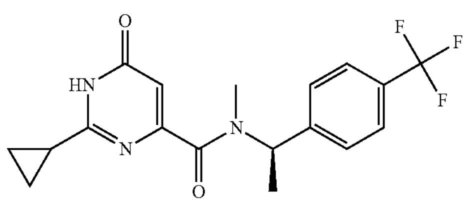 [SMILES: C[C@H](c1ccc(C(F)(F)F)cc1)N(C)C(=O)c1cc(=O)[nH]c(C2CC2)n1] | 2-cyclopropyl-N-methyl-6-oxo-N-{(1R)-1-[4-(trifluoromethyl)phenyl]methyl}-1,6-dihydropyrimidine-4-carboxamide | Calc'd 366.1, found 366.2 |
| 210 | 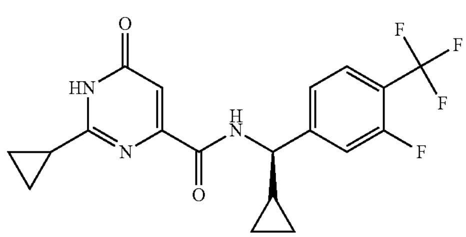 [SMILES: O=C(N[C@@H](c1ccc(C(F)(F)F)c(F)c1)C1CC1)c1cc(=O)[nH]c(C2CC2)n1] | 2-cyclopropyl-N-{(R)-cyclopropyl[3-fluoro-4-(trifluoromethyl)phenyl]methyl}-6-oxo-1,6-dihydropyrimidine-4-carboxamide | Calc'd 396.1, found 396.3 |
| 211 | 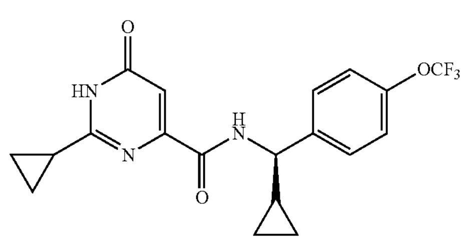 [SMILES: O=C(N[C@@H](c1ccc(OC(F)(F)F)cc1)C1CC1)c1cc(=O)[nH]c(C2CC2)n1] | 2-cyclopropyl-N-{(R)-cyclopropyl[4-(trifluoromethoxy)phenyl]methyl}-6-oxo-1,6-dihydropyrimidine-4-carboxamide | Calc'd 394.1, found 394.3 |
| 212 | 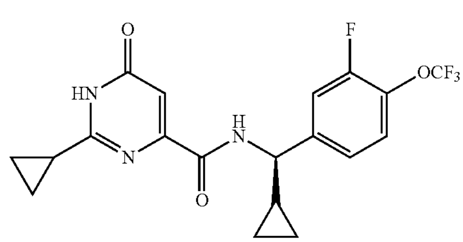 [SMILES: O=C(N[C@@H](c1ccc(OC(F)(F)F)c(F)c1)C1CC1)c1cc(=O)[nH]c(C2CC2)n1] | 2-cyclopropyl-N-{(R)-cyclopropyl[3-fluoro-4-(trifluoromethyl)phenyl]methyl}-6-oxo-1,6-dihydropyrimidine-4-carboxamide | Calc'd 412.1, found 412.3 |

TABLE 6-continued

| Example No. | IUPAC Name | Exact Mass [M + H]+ |
|---|---|---|
| 213 | 2-cyclopropyl-N-{(R)-cyclopropyl[4-(trifluoromethyl)phenyl]methyl}-6-oxo-1,6-dihydropyrimidine-4-carboxamide | Calc'd 378.1, found 378.2 |
| 214 | 2-cyclopropyl-N-[(R)-cyclopropyl{4-[(trifluoromethyl)sulfanyl]phenyl}methyl]-6-oxo-1,6-dihydropyrimidine-4-carboxamide | Calc'd 410.1, found 410.2 |
| 215 | methyl 4-(1-{[(2-cyclopropyl-6-oxo-1,6-dihydropyrimidin-4-yl)carbonyl]amino}-1-methylethyl)benzoate | Calc'd 356.2, found 356.2 |
| 216 | 2-cyclopropyl-N-[(1R)-1-(4-methoxyphenyl)ethyl]-6-oxo-1,6-dihydropyrimidine-4-carboxamide | Calc'd 314.2, found 314.2 |
| 217 | 2-cyclopropyl-6-oxo-N-{(1R)-1-[4-(2,2,2-trifluoroethyl)phenyl]ethyl}-1,6-dihydropyrimidine-4-carboxamide | Calc'd 366.1, found 366.2 |
| 218 | 2-cyclopropyl-N-{(1R)-1-[3,5-difluoro-4-(trifluoromethyl)phenyl]ethyl}-6-oxo-1,6-dihydropyrimidine-4-carboxamide | Calc'd 388.1, found 388.2 |
| 219 | 2-cyclopropyl-N-{(1R)-1-[2-methoxy-4-(trifluoromethyl)phenyl]ethyl}-6-oxo-1,6-dihydropyrimidine-4-carboxamide | Calc'd 382.1, found 382.2 |

TABLE 6-continued

| Example No. | IUPAC Name | Exact Mass [M + H]+ |
|---|---|---|
| 220 | 2-cyclopropyl-6-oxo-N-{1-[2-(trifluoromethyl)phenyl]ethyl}-1,6-dihydropyrimidine-4-carboxamide | Calc'd 352.1, found 352.2 |
| 221 | 2-cyclopropyl-N-(4-cyclopropylbenzyl)-6-oxo-1,6-dihydropyrimidine-4-carboxamide | Calc'd 310.2, found 310.2 |
| 222 | 2-cyclopropyl-N-(1-methyl-1-{4-[(trifluoromethyl)sulfanyl]phenyl}ethyl)-6-oxo-1,6-dihydropyrimidine-4-carboxamide | Calc'd 398.1, found 398.3 |
| 223 | 2-cyclopropyl-N-{(1S)-1-[2-methoxy-4-(trifluoromethyl)phenyl]ethyl}-6-oxo-1,6-dihydropyrimidine-4-carboxamide | Calc'd 382.1, found 382.2 |
| 224 | 2-cyclopropyl-N-[(1R)-1-naphthalen-2-ylethyl]-6-oxo-1,6-dihydropyrimidine-4-carboxamide | Calc'd 334.2, found 334.2 |
| 225 | 2-cyclopropyl-6-oxo-N-{(1R)-1-[4-(trifluoromethoxy)phenyl]propyl}-1,6-dihydropyrimidine-4-carboxamide | Calc'd 382.1, found 382.3 |
| 226 | 2-cyclopropyl-N-{1-[3-methoxy-4-(trifluoromethyl)phenyl]ethyl}-6-oxo-1,6-dihydropyrimidine-4-carboxamide | Calc'd 382.1, found 382.2 |

TABLE 6-continued

| Example No. | IUPAC Name | Exact Mass [M + H]+ |
|---|---|---|
| 227 | 2-cyclopropyl-6-oxo-N-{(1R)-1-[4-(pentafluoro-λ⁶-sulfanyl)phenyl]ethyl}-1,6-dihydropyrimidine-4-carboxamide | Calc'd 410.1, found 410.2 |
| 228 | 2-cyclopropyl-N-[2-methyl-4-(trifluoromethyl)benzyl]-6-oxo-1,6-dihydropyrimidine-4-carboxamide | Calc'd 352.1, found 352.2 |
| 229 | N-[2-chloro-4-(trifluoromethyl)benzyl]-2-cyclopropyl-6-oxo-1,6-dihydropyrimidine-4-carboxamide | Calc'd 372.1/374.1, found 372.2/374.1 |
| 230 | 2-cyclopropyl-N-{1-[2-methoxy-4-(trifluoromethoxy)phenyl]ethyl}-6-oxo-1,6-dihydropyrimidine-4-carboxamide | Calc'd 398.1, found 398.2 |
| 231 | 2-cyclopropyl-N-{(1R)-1-[3-methyl-4-(trifluoromethyl)phenyl]ethyl}-6-oxo-1,6-dihydropyrimidine-4-carboxamide | Calc'd 366.1, found 366.2 |
| 232 | N-{(1R)-1-[3-chloro-4-(trifluoromethyl)phenyl]ethyl}-2-cyclopropyl-6-oxo-1,6-dihydropyrimidine-4-carboxamide | Calc'd 386.1/388.1, found 386.2/388.2 |
| 233 | N-{1-[2-chloro-4-(trifluoromethyl)phenyl]ethyl}-2-cyclopropyl-6-oxo-1,6-dihydropyrimidine-4-carboxamide | Calc'd 386.1/388.2, found 386.2/388.1 |

TABLE 6-continued

| Example No. | Structure | IUPAC Name | Exact Mass [M + H]+ |
|---|---|---|---|
| 234 | 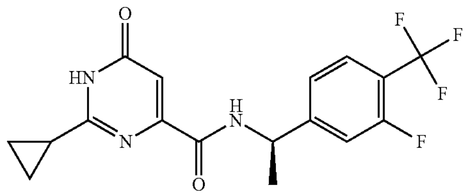 [SMILES: C[C@@H](NC(=O)c1cc(=O)[nH]c(C2CC2)n1)c1ccc(C(F)(F)F)c(F)c1] | 2-cyclopropyl-N-{(1R)-1-[3-fluoro-4-(trifluoromethyl)phenyl]ethyl}-6-oxo-1,6-dihydropyrimidine-4-carboxamide | Calc'd 370.1, found 370.2 |
| 235 | 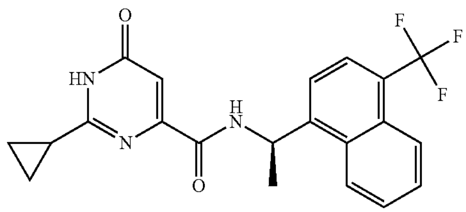 [SMILES: C[C@@H](NC(=O)c1cc(=O)[nH]c(C2CC2)n1)c1ccc(C(F)(F)F)c2ccccc12] | 2-cyclopropyl-6-oxo-N-{(1R)-1-[4-(trifluoromethyl)naphthalen-1-yl]ethyl}-1,6-dihydropyrimidine-4-carboxamide | Calc'd 402.1, found 402.3 |
| 236 | 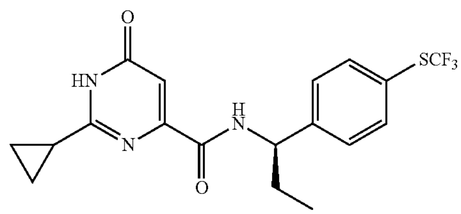 | 2-cyclopropyl-6-oxo-N-[(1R)-1-{4-[(trifluoromethyl)sulfanyl]phenyl}propyl]-1,6-dihydropyrimidine-4-carboxamide | Calc'd 398.1, found 398.2 |
| 237 | 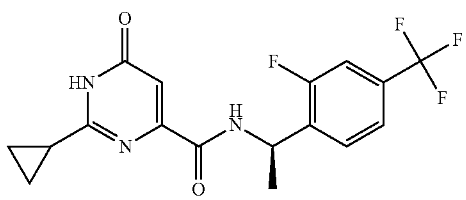 [SMILES: C[C@@H](NC(=O)c1cc(=O)[nH]c(C2CC2)n1)c1ccc(C(F)(F)F)cc1F] | 2-cyclopropyl-N-{(1R)-1-[2-fluoro-4-(trifluoromethyl)phenyl]ethyl}-6-oxo-1,6-dihydropyrimidine-4-carboxamide | Calc'd 370.1, found 370.2 |
| 238 | 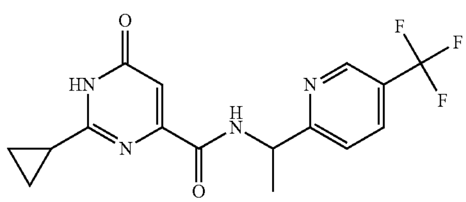 [SMILES: CC(NC(=O)c1cc(=O)[nH]c(C2CC2)n1)c1ccc(C(F)(F)F)cn1] | 2-cyclopropyl-6-oxo-N-{1-[5-(trifluoromethyl)pyridin-2-yl]ethyl}-1,6-dihydropyrimidine-4-carboxamide | Calc'd 353.1, found 353.2 |
| 239 | 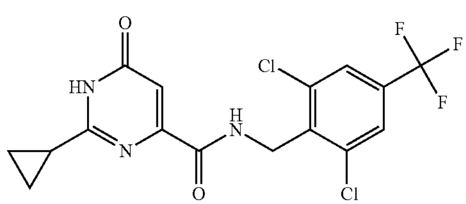 [SMILES: O=C(NCc1c(Cl)cc(C(F)(F)F)cc1Cl)c1cc(=O)[nH]c(C2CC2)n1] | 2-cyclopropyl-N-[2,6-dichloro-4-(trifluoromethyl)benzyl]-6-oxo-1,6-dihydropyrimidine-4-carboxamide | Calc'd 406.0/408.0/410.0, found 406.2/408.1/410.1 |
| 240 | 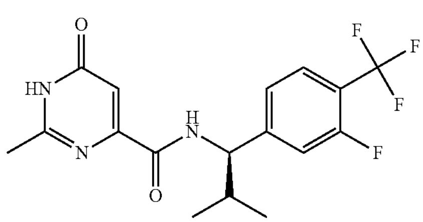 [SMILES: Cc1nc(C(=O)N[C@@H](c2ccc(C(F)(F)F)c(F)c2)C(C)C)cc(=O)[nH]1] | N-{(1R)-1-[3-fluoro-4-(trifluoromethyl)phenyl]-2-methylpropyl}-2-methyl-6-oxo-1,6-dihydropyrimidine-4-carboxamide | Calc'd 372.1, found 372.2 |

TABLE 6-continued

| Example No. | Structure | IUPAC Name | Exact Mass [M + H]+ |
|---|---|---|---|
| 241 | 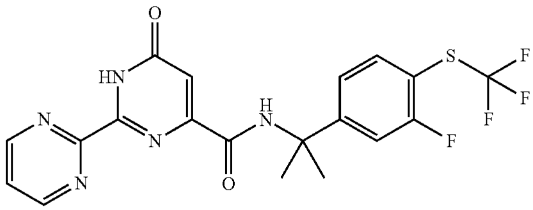 [SMILES: CC(C)(NC(=O)c1cc(=O)[nH]c(-c2ncccn2)n1)c1ccc(SC(F)(F)F)c(F)c1] | N-(1-{3-fluoro-4-[(trifluoromethyl)sulfanyl]phenyl}-1-methylethyl)-6-oxo-1,6-dihydro-2,2'-bipyrimidine-4-carboxamide | Calc'd 454.1, found 454.3 |
| 242 | 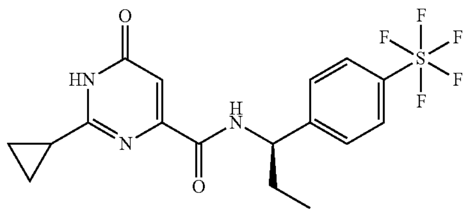 [SMILES: CC[C@@H](NC(=O)c1cc(=O)[nH]c(C2CC2)n1)c1ccc(S(F)(F)(F)(F)F)cc1] | 2-cyclopropyl-6-oxo-N-{(1R)-1-[4-(pentafluoro-$\lambda^6$-sulfanyl)phenyl]propyl}-1,6-dihydropyrimidine-4-carboxamide | Calc'd 424.1, found 424.2 |
| 243 | 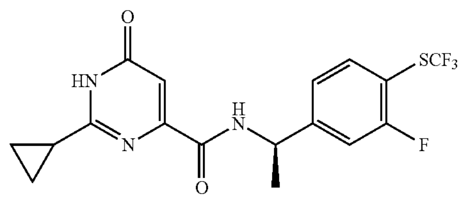 | 2-cyclopropyl-N-[(1R)-1-{3-fluoro-4-[(trifluoromethyl)sulfanyl]phenyl}ethyl]-6-oxo-1,6-dihydropyrimidine-4-carboxamide | Calc'd 402.1, found 402.2 |
| 244 | 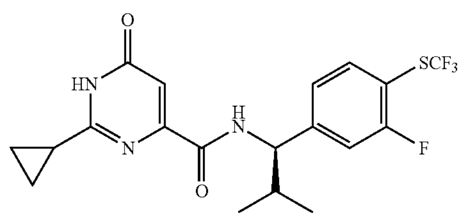 | 2-cyclopropyl-N-[(1R)-1-{3-fluoro-4-[(trifluoromethyl)sulfanyl]phenyl}-2-methylpropyl]-6-oxo-1,6-dihydropyrimidine-4-carboxamide | Calc'd 430.1, found 430.2 |
| 245 | 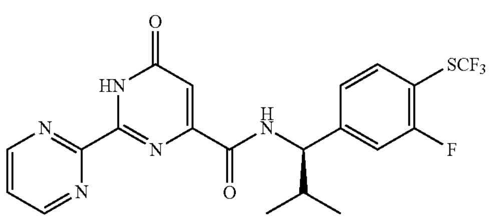 | N-[(1R)-1-{3-fluoro-4-[(trifluoromethyl)sulfanyl]phenyl}-2-methylpropyl]-6-oxo-1,6-dihydro-2,2'-bipyrimidine-4-carboxamide | Calc'd 468.1, found 468.2 |
| 246 | 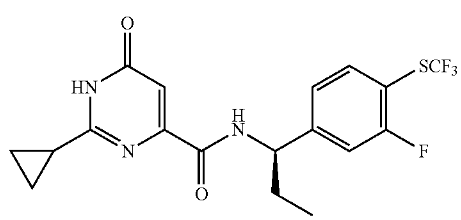 | 2-cyclopropyl-N-[(1R)-1-{3-fluoro-4-[(trifluoromethyl)sulfanyl]phenyl}propyl]-6-oxo-1,6-dihydropyrimidine-4-carboxamide | Calc'd 416.1, found 416.2 |
| 247 | 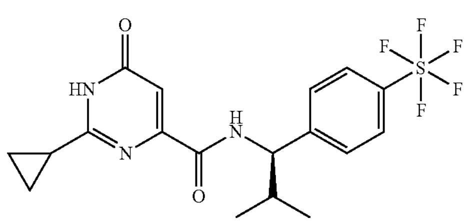 [SMILES: CC(C)[C@@H](NC(=O)c1cc(=O)[nH]c(C2CC2)n1)c1ccc(S(F)(F)(F)(F)F)cc1] | 2-cyclopropyl-N-{(1R)-2-methyl-1-[4-(pentafluoro-$\lambda^6$-sulfanyl)phenyl]propyl}-6-oxo-1,6-dihydropyrimidine-4-carboxamide | Calc'd 438.1, found 438.3 |

TABLE 6-continued

| Example No. | Structure | IUPAC Name | Exact Mass [M + H]+ |
|---|---|---|---|
| 248 | 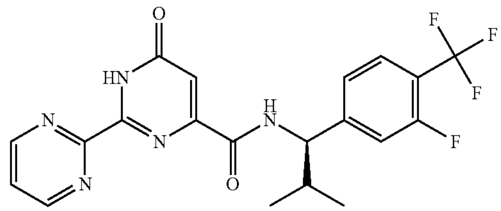 [SMILES: CC(C)[C@@H](NC(=O)c1cc(=O)[nH]c(-c2ncccn2)n1)c1ccc(C(F)(F)F)c(F)c1] | N-{(1R)-1-[3-fluoro-4-(trifluoromethyl)phenyl]-2-methylpropyl}-6-oxo-1,6-dihydro-2,2'-bipyrimidine-4-carboxamide | Calc'd 436.1, found 436.3 |
| 249 | 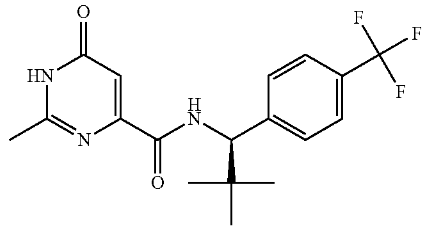 [SMILES: Cc1nc(C(=O)N[C@@H](c2ccc(C(F)(F)F)cc2)C(C)(C)C)cc(=O)[nH]1] | N-{(1R)-2,2-dimethyl-1-[4-(trifluoromethyl)phenyl]propyl}-2-methyl-6-oxo-1,6-dihydropyrimidine-4-carboxamide | Calc'd 368.2, found 368.2 |
| 250 | 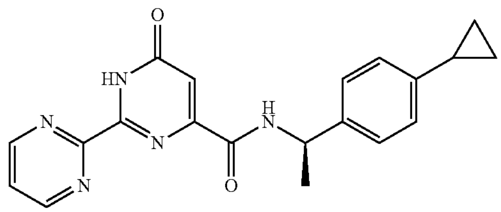 [SMILES: C[C@@H](NC(=O)c1cc(=O)[nH]c(-c2ncccn2)n1)c1ccc(C2CC2)cc1] | N-[(1R)-1-(4-cyclopropylphenyl)ethyl]-6-oxo-1,6-dihydro-2,2'-bipyrimidine-4-carboxamide | Calc'd 362.2, found 362.2 |
| 251 | 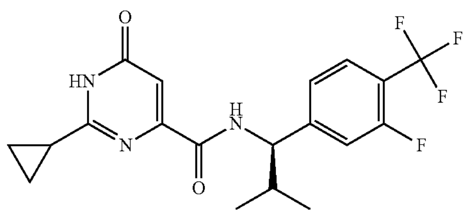 [SMILES: CC(C)[C@@H](NC(=O)c1cc(=O)[nH]c(C2CC2)n1)c1ccc(C(F)(F)F)c(F)c1] | 2-cyclopropyl-N-{(1R)-1-[3-fluoro-4-(trifluoromethyl)phenyl]-2-methylpropyl}-6-oxo-1,6-dihydropyrimidine-4-carboxamide | Calc'd 398.1, found 398.2 |
| 252 | 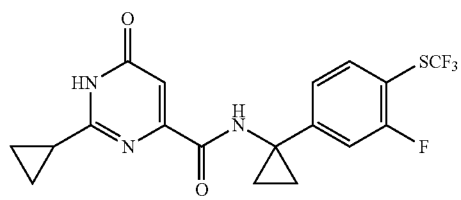 | 2-cyclopropyl-N-(1-{3-fluoro-4-[(trifluoromethyl)sulfanyl]phenyl}cyclopropyl)-6-oxo-1,6-dihydropyrimidine-4-carboxamide | Calc'd 414.1, found 414.2 |
| 253 | 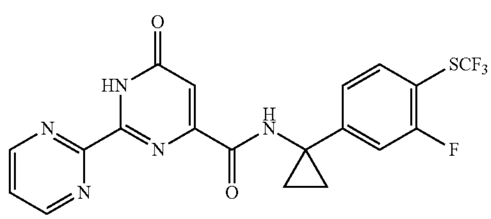 | N-(1-{3-fluoro-4-[(trifluoromethyl)sulfanyl]phenyl}cyclopropyl)-6-oxo-1,6-dihydro-2,2'-bipyrimidine-4-carboxamide | Calc'd 452.1, found 452.2 |
| 254 | 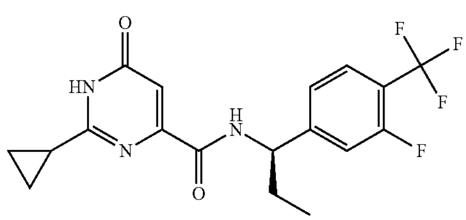 [SMILES: CC[C@@H](NC(=O)c1cc(=O)[nH]c(C2CC2)n1)c1ccc(C(F)(F)F)c(F)c1] | 2-cyclopropyl-N-{(1R)-1-[3-fluoro-4-(trifluoromethyl)phenyl]propyl}-6-oxo-1,6-dihydropyrimidine-4-carboxamide | Calc'd 384.1, found 384.2 |

TABLE 6-continued

| Example No. | Structure | IUPAC Name | Exact Mass [M + H]+ |
|---|---|---|---|
| 255 | 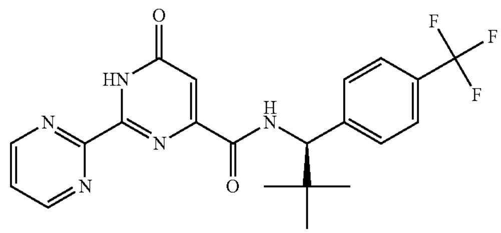 [SMILES: CC(C)(C)[C@@H](NC(=O)c1cc(=O)[nH]c(-c2ncccn2)n1)c1ccc(C(F)(F)F)cc1] | N-{(1R)-2,2-dimethyl-1-[4-(trifluoromethyl)phenyl]propyl}-6-oxo-1,6-dihydro-2,2'-bipyrimidine-4-carboxamide | Calc'd 432.2, found 432.3 |
| 256 | 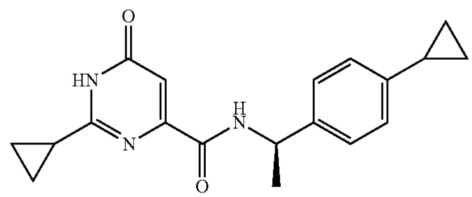 [SMILES: C[C@@H](NC(=O)c1cc(=O)[nH]c(C2CC2)n1)c1ccc(C2CC2)cc1] | 2-cyclopropyl-N-[(1R)-1-(4-cyclopropylphenyl)ethyl]-6-oxo-1,6-dihydropyrimidine-4-carboxamide | Calc'd 324.2, found 324.2 |
| 257 | 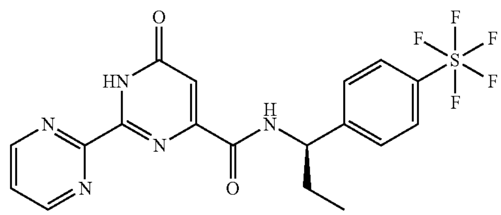 [SMILES: CC[C@@H](NC(=O)c1cc(=O)[nH]c(-c2ncccn2)n1)c1ccc(S(F)(F)(F)(F)F)cc1] | 6-oxo-N-{(1R)-1-[4-(pentafluoro-$\lambda^6$-sulfanyl)phenyl]propyl}-1,6-dihydro-2,2'-bipyrimidine-4-carboxamide | Calc'd 462.1, found 462.2 |
| 258 | 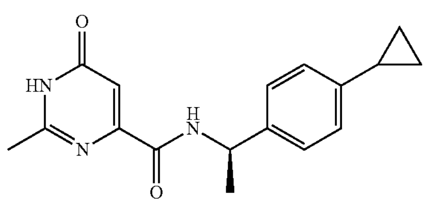 [SMILES: Cc1nc(C(=O)N[C@H](C)c2ccc(C3CC3)cc2)cc(=O)[nH]1] | N-[(1R)-1-(4-cyclopropylphenyl)ethyl]-2-methyl-6-oxo-1,6-dihydropyrimidine-4-carboxamide | Calc'd 298.2, found 298.1 |
| 259 | 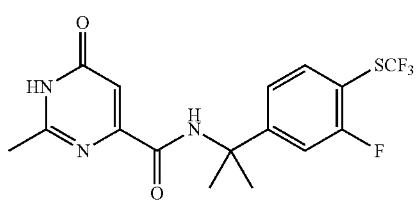 | N-(1-{3-fluoro-4-[(trifluoromethyl)sulfanyl]phenyl}-1-methylethyl)-2-methyl-6-oxo-1,6-dihydropyrimidine-4-carboxamide | Calc'd 390.1, found 390.2 |
| 260 | 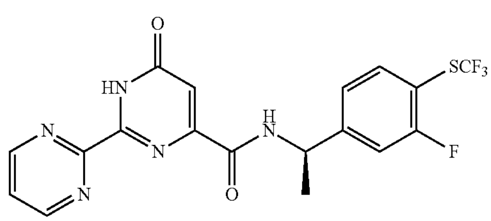 | N-[(1R)-1-{3-fluoro-4-[(trifluoromethyl)sulfanyl]phenyl}ethyl]-6-oxo-1,6-dihydro-2,2'-bipyrimidine-4-carboxamide | Calc'd 440.1, found 440.2 |
| 261 | 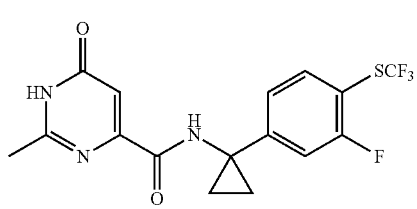 | N-(1-{3-fluoro-4-[(trifluoromethyl)sulfanyl]phenyl}cyclopropyl)-2-methyl-6-oxo-1,6-dihydropyrimidine-4-carboxamide | Calc'd 388.1, found 388.1 |

TABLE 6-continued

| Example No. | Structure | IUPAC Name | Exact Mass [M + H]+ |
|---|---|---|---|
| 262 | 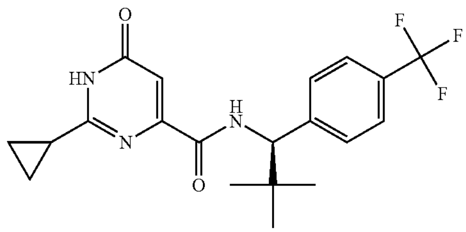 [SMILES: CC(C)(C)[C@@H](NC(=O)c1cc(=O)[nH]c(C2CC2)n1)c1ccc(C(F)(F)F)cc1] | 2-cyclopropyl-N-{(1R)-2,2-dimethyl-1-[4-(trifluoromethyl)phenyl]propyl}-6-oxo-1,6-dihydropyrimidine-4-carboxamide | Calc'd 394.2, found 394.2 |
| 263 | 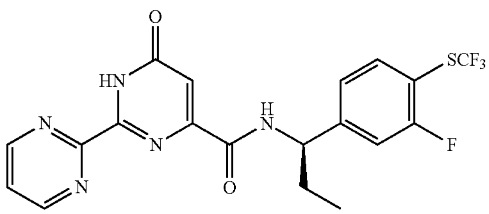 | N-[(1R)-1-{3-fluoro-4-[(trifluoromethyl)sulfanyl]phenyl}propyl]-6-oxo-1,6-dihydro-2,2'-bipyrimidine-4-carboxamide | Calc'd 454.1, found 454.3 |
| 264 | 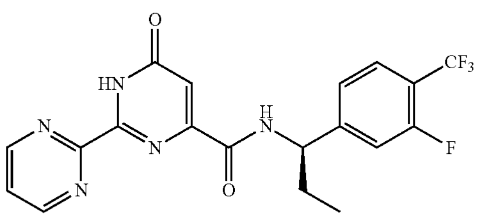 [SMILES: CC[C@@H](NC(=O)c1cc(=O)[nH]c(-c2ncccn2)n1)c1ccc(C(F)(F)F)c(F)c1] | N-{(1R)-1-[3-fluoro-4-(trifluoromethyl)phenyl]propyl}-6-oxo-1,6-dihydro-2,2'-bipyrimidine-4-carboxamide | Calc'd 422.1, found 422.2 |
| 265 | 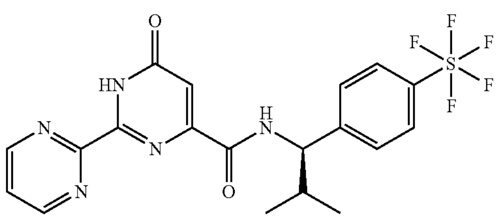 [SMILES: CC(C)[C@@H](NC(=O)c1cc(=O)[nH]c(-c2ncccn2)n1)c1ccc(S(F)(F)(F)(F)F)cc1] | N-{(1R)-2-methyl-1-[4-(pentafluoro-$\lambda^6$-sulfanyl)phenyl]propyl}-6-oxo-1,6-dihydro-2,2'-bipyrimidine-4-carboxamide | Calc'd 476.1, found 476.2 |
| 266 | 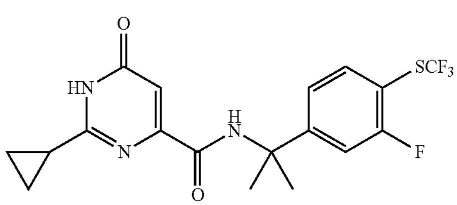 | 2-cyclopropyl-N-(1-{3-fluoro-4-[(trifluoromethyl)sulfanyl]phenyl}-1-methylethyl)-6-oxo-1,6-dihydropyrimidine-4-carboxamide | Calc'd 416.1, found 416.2 |

TABLE 7

| Example No. | Structure | IUPAC Name | Exact Mass [M + H]+ |
|---|---|---|---|
| 267 | 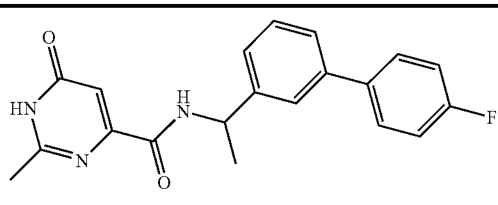 | N-[1-(4'-fluorobiphenyl-3-yl)ethyl]-2-methyl-6-oxo-1,6-dihydropyrimidine-4-carboxamide | Calc'd 352.1, found 352.1 |

TABLE 7-continued

| Example No. | IUPAC Name | Exact Mass [M + H]+ |
|---|---|---|
| 268 | N-[1-(4-ethylphenyl)ethyl]-2-methyl-6-oxo-1,6-dihydropyrimidine-4-carboxamide | Calc'd 286.2, found 286.2 |
| 269 | 2-methyl-6-oxo-N-{1-[4-(trifluoromethyl)phenyl]cyclobutyl}-1,6-dihydropyrimidine-4-carboxamide | Calc'd 368.1, found 368.2 |
| 270 | 2-methyl-6-oxo-N-{1-[4-(trifluoromethyl)phenyl]cyclopentyl}-1,6-dihydropyrimidine-4-carboxamide | Calc'd 366.1, found 366.2 |
| 271 | 2-methyl-6-oxo-N-{(1R)-1-[3-(trifluoromethyl)phenyl]ethyl}-1,6-dihydropyrimidine-4-carboxamide | Calc'd 326.1, found 326.1 |
| 272 | 2-methyl-N-{1-methyl-1-[4-(trifluoromethyl)phenyl]ethyl}-6-oxo-1,6-dihydropyrimidine-4-carboxamide | Calc'd 340.1, found 340.1 |
| 273 | 2-methyl-N-{1-methyl-1-[4-(trifluoromethoxy)phenyl]ethyl}-1,6-oxo-1,6-dihydropyrimidine-4-carboxamide | Calc'd 356.1, found 356.1 |
| 274 | 6-oxo-2-phenyl-N-{(1R)-1-[4-(trifluoromethyl)phenyl]ethyl}-1,6-dihydropyrimidine-4-carboxamide | Calc'd 388.1, found 388.1 |

TABLE 7-continued

| Example No. | Structure | IUPAC Name | Exact Mass [M + H]+ |
|---|---|---|---|
| 275 | 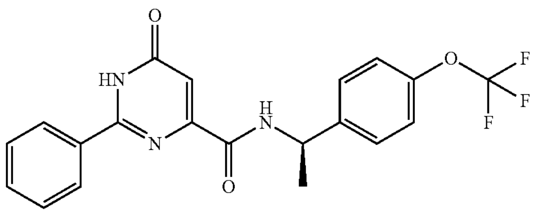 [SMILES: C[C@@H](NC(=O)c1cc(=O)[nH]c(-c2ccccc2)n1)c1ccc(OC(F)(F)F)cc1] | 6-oxo-2-phenyl-N-{(1R)-1-[4-(trifluoromethoxy)phenyl]ethyl}-1,6-dihydropyrimidine-4-carboxamide | Calc'd 404.1, found 404.2 |
| 276 | 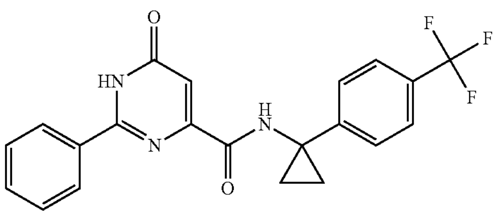 [SMILES: O=C(NC1(c2ccc(C(F)(F)F)cc2)CC1)c1cc(=O)[nH]c(-c2ccccc2)n1] | 6-oxo-2-phenyl-N-{1-[4-(trifluoromethyl)phenyl]cyclopropyl}-1,6-dihydropyrimidine-4-carboxamide | Calc'd 400.1, found 400.2 |
| 277 | 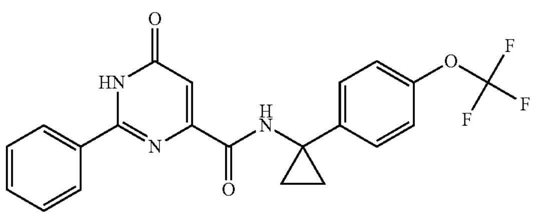 [SMILES: O=C(NC1(c2ccc(OC(F)(F)F)cc2)CC1)c1cc(=O)[nH]c(-c2ccccc2)n1] | 6-oxo-2-phenyl-N-{1-[4-(trifluoromethoxy)phenyl]cyclopropyl}-1,6-dihydropyrimidine-4-carboxamide | Calc'd 416.1, found 416.2 |
| 278 | 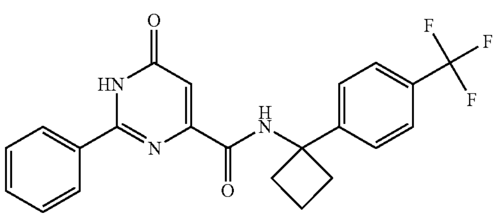 [SMILES: O=C(NC1(c2ccc(C(F)(F)F)cc2)CCC1)c1cc(=O)[nH]c(-c2ccccc2)n1] | 6-oxo-2-phenyl-N-{1-[4-(trifluoromethyl)phenyl]cyclobutyl}-1,6-dihydropyrimidine-4-carboxamide | Calc'd 414.1, found 414.2 |
| 279 | 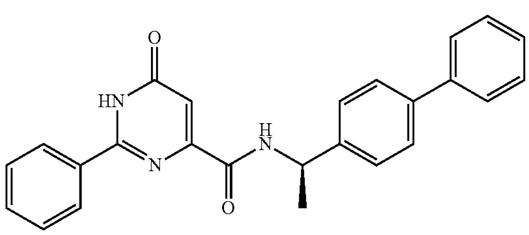 [SMILES: C[C@@H](NC(=O)c1cc(=O)[nH]c(-c2ccccc2)n1)c1ccc(-c2ccccc2)cc1] | N-[(1R)-1-biphenyl-4-ylethyl]-6-oxo-2-phenyl-1,6-dihydropyrimidine-4-carboxamide | Calc'd 396.2, found 396.3 |
| 280 | 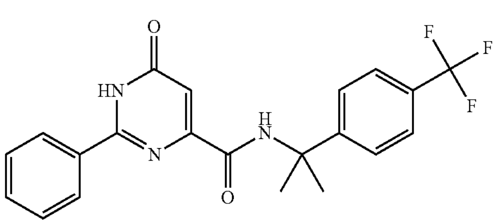 [SMILES: CC(C)(NC(=O)c1cc(=O)[nH]c(-c2ccccc2)n1)c1ccc(C(F)(F)F)cc1] | N-{1-methyl-1-[4-(trifluoromethyl)phenyl]ethyl}-6-oxo-2-phenyl-1,6-dihydropyrimidine-4-carboxamide | Calc'd 402.1, found 402.2 |
| 281 | 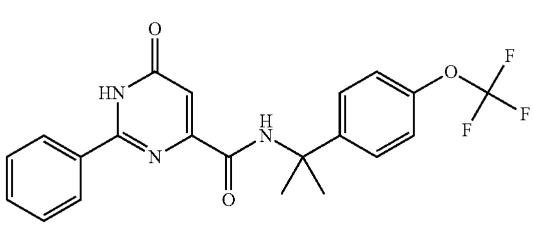 [SMILES: CC(C)(NC(=O)c1cc(=O)[nH]c(-c2ccccc2)n1)c1ccc(OC(F)(F)F)cc1] | N-{1-methyl-1-[4-(trifluoromethoxy)phenyl]ethyl}-6-oxo-2-phenyl-1,6-dihydropyrimidine-4-carboxamide | Calc'd 418.1, found 418.2 |

TABLE 7-continued

| Example No. | Structure | IUPAC Name | Exact Mass [M + H]+ |
|---|---|---|---|
| 282 | 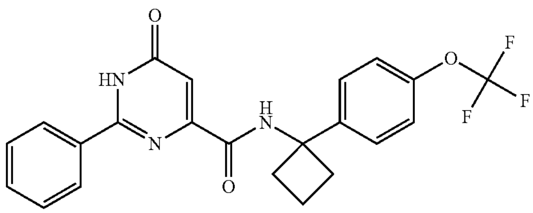 [SMILES: O=C(NC1(c2ccc(OC(F)(F)F)cc2)CCC1)c1cc(=O)[nH]c(-c2ccccc2)n1] | 6-oxo-2-phenyl-N-{1-[4-(trifluoromethyl)phenyl]cyclobutyl}-1,6-dihydropyrimidine-4-carboxamide | Calc'd 430.1, found 430.2 |
| 283 | 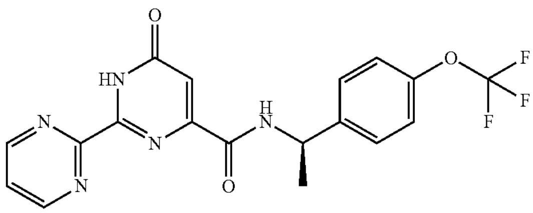 [SMILES: C[C@@H](NC(=O)c1cc(=O)[nH]c(-c2ncccn2)n1)c1ccc(OC(F)(F)F)cc1] | 6-oxo-N-{(1R)-1-[4-(trifluoromethoxy)phenyl]ethyl}-1,6-dihydro-2,2'-bipyrimidine-4-carboxamide | Calc'd 406.1, found 406.2 |
| 284 | 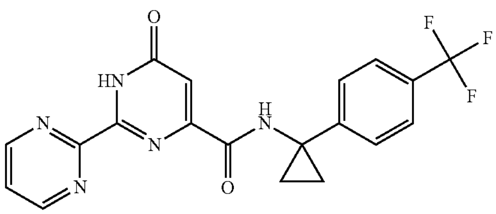 [SMILES: O=C(NC1(c2ccc(C(F)(F)F)cc2)CC1)c1cc(=O)[nH]c(-c2ncccn2)n1] | 6-oxo-N-{1-[4-(trifluoromethyl)phenyl]cyclopropyl}-1,6-dihydro-2,2'-bipyrimidine-4-carboxamide | Calc'd 402.1, found 402.2 |
| 285 | 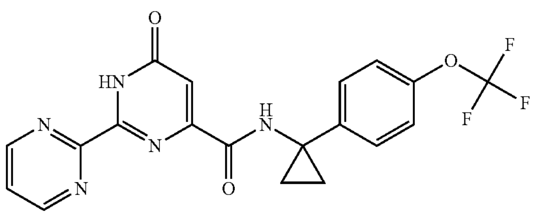 [SMILES: O=C(NC1(c2ccc(OC(F)(F)F)cc2)CC1)c1cc(=O)[nH]c(-c2ncccn2)n1] | 6-oxo-N-{1-[4-(trifluoromethoxy)phenyl]cyclopropyl}-1,6-dihydro-2,2'-bipyrimidine-4-carboxamide | Calc'd 418.1, found 418.3 |
| 286 | 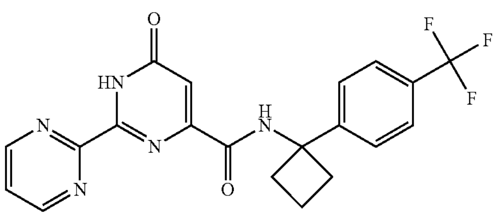 [SMILES: O=C(NC1(c2ccc(C(F)(F)F)cc2)CCC1)c1cc(=O)[nH]c(-c2ncccn2)n1] | 6-oxo-N-{1-[4-(trifluoromethyl)phenyl]cyclobutyl}-1,6-dihydro-2,2'-bipyrimidine-4-carboxamide | Calc'd 416.1, found 416.3 |
| 287 | 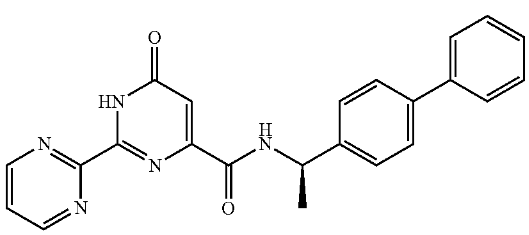 [SMILES: C[C@@H](NC(=O)c1cc(=O)[nH]c(-c2ncccn2)n1)c1ccc(-c2ccccc2)cc1] | N-[(1R)-1-biphenyl-4-ylethyl]-6-oxo-1,6-dihydro-2,2'-bipyrimidine-4-carboxamide | Calc'd 398.2, found 398.3 |
| 288 | 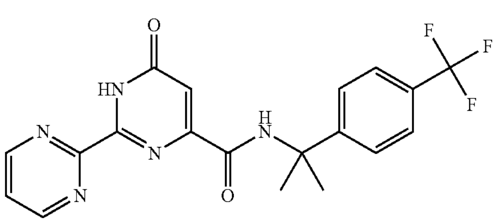 [SMILES: CC(C)(NC(=O)c1cc(=O)[nH]c(-c2ncccn2)n1)c1ccc(C(F)(F)F)cc1] | N-{1-methyl-1-[4-(trifluoromethyl)phenyl]ethyl}-6-oxo-1,6-dihydro-2,2'-bipyrimidine-4-carboxamide | Calc'd 404.1, found 404.2 |

TABLE 7-continued

| Example No. | Structure | IUPAC Name | Exact Mass [M + H]+ |
|---|---|---|---|
| 289 | 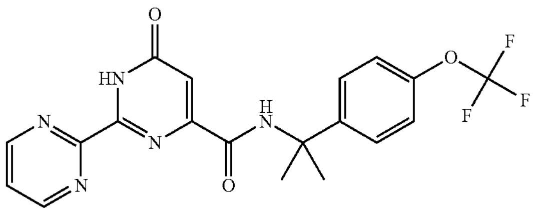 [SMILES: CC(C)(NC(=O)c1cc(=O)[nH]c(-c2ncccn2)n1)c1ccc(OC(F)(F)F)cc1] | N-{1-methyl-1-[4-(trifluoromethoxy)phenyl]ethyl}-6-oxo-1,6-dihydro-2,2'-bipyrimidine-4-carboxamide | Calc'd 420.1, found 420.2 |
| 290 | 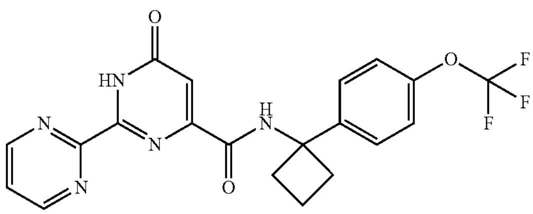 [SMILES: O=C(NC1(c2ccc(OC(F)(F)F)cc2)CCC1)c1cc(=O)[nH]c(-c2ncccn2)n1] | 6-oxo-N-(1-(4-(trifluoromethoxy)phenyl)cyclobutyl)-1,6-dihydro-[2,2'-bipyrimidine]-4-carboxamide | Calc'd 432.1, found 432.2 |
| 291 | 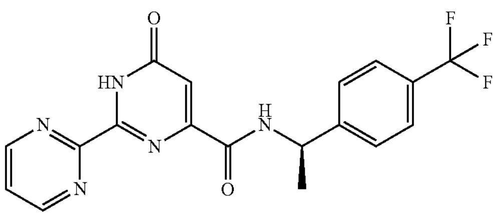 [SMILES: C[C@@H](NC(=O)c1cc(=O)[nH]c(-c2ncccn2)n1)c1ccc(C(F)(F)F)cc1] | 6-oxo-N-{(1R)-1-[4-(trifluoromethyl)phenyl]ethyl}-1,6-dihydro-2,2'-bipyrimidine-4-carboxamide | Calc'd 390.1, found 390.1 |
| 292 | 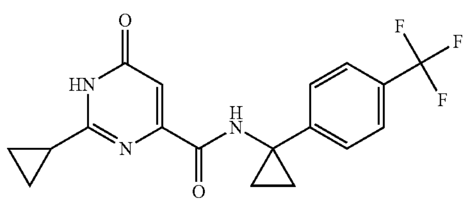 [SMILES: O=C(NC1(c2ccc(C(F)(F)F)cc2)CC1)c1cc(=O)[nH]c(C2CC2)n1] | 2-cyclopropyl-6-oxo-N-{1-[4-(trifluoromethyl)phenyl]cyclopropyl}-1,6-dihydropyrimidine-4-carboxamide | Calc'd 364.1, found 364.2 |
| 293 | 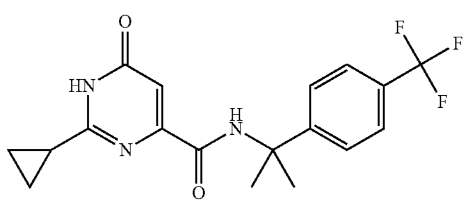 [SMILES: CC(C)(NC(=O)c1cc(=O)[nH]c(C2CC2)n1)c1ccc(C(F)(F)F)cc1] | 2-cyclopropyl-N-{1-methyl-1-[4-(trifluoromethyl)phenyl]ethyl}-6-oxo-1,6-dihydropyrimidine-4-carboxamide | Calc'd 366.1, found 366.2 |
| 294 | 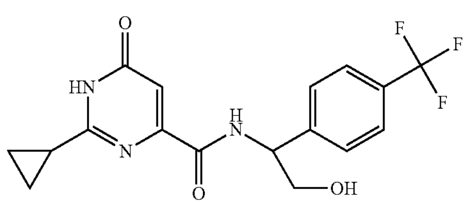 [SMILES: O=C(NC(CO)c1ccc(C(F)(F)F)cc1)c1cc(=O)[nH]c(C2CC2)n1] | 2-cyclopropyl-N-{2-hydroxy-1-[4-(trifluoromethyl)phenyl]ethyl}-6-oxo-1,6-dihydropyrimidine-4-carboxamide | Calc'd 368.1, found 368.2 |
| 295 | 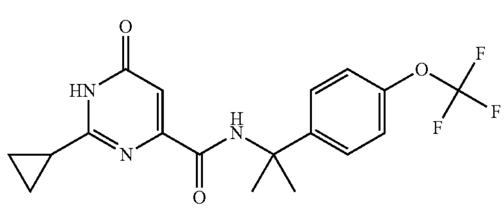 [SMILES: CC(C)(NC(=O)c1cc(=O)[nH]c(C2CC2)n1)c1ccc(OC(F)(F)F)cc1] | 2-cyclopropyl-N-{1-methyl-1-[4-(trifluoromethoxy)phenyl]ethyl}-6-oxo-1,6-dihydropyrimidine-4-carboxamide | Calc'd 382.1, found 382.2 |

TABLE 7-continued

| Example No. | Structure | IUPAC Name | Exact Mass [M + H]+ |
|---|---|---|---|
| 296 | 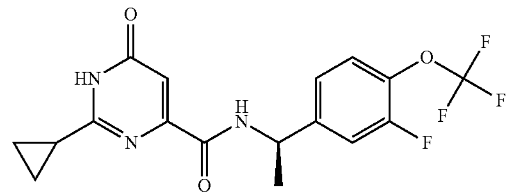 [SMILES: C[C@@H](NC(=O)c1cc(=O)[nH]c(C2CC2)n1)c1ccc(OC(F)(F)F)c(F)c1] | 2-cyclopropyl-N-{(1R)-1-[3-fluoro-4-(trifluoromethoxy)phenyl]ethyl}-6-oxo-1,6-dihydropyrimidine-4-carboxamide | Calc'd 386.1, found 386.2 |
| 297 | 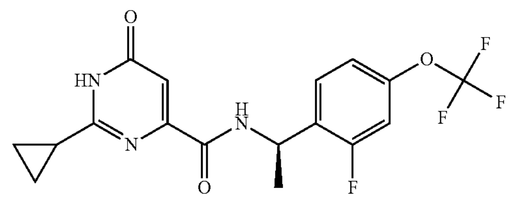 [SMILES: C[C@@H](NC(=O)c1cc(=O)[nH]c(C2CC2)n1)c1ccc(OC(F)(F)F)cc1F] | 2-cyclopropyl-N-{(1R)-1-[2-nuoro-4-(trifluoromethoxy)phenyl]ethyl}-6-oxo-1,6-dihydropyrimidine-4-carboxamide | Calc'd 386.1, found 386.2 |
| 298 | 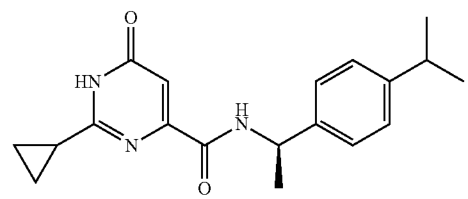 [SMILES: CC(C)c1ccc([C@@H](C)NC(=O)c2cc(=O)[nH]c(C3CC3)n2)cc1] | 2-cyclopropyl-N-{(1R)-1-[4-(1-methylethyl)phenyl]ethyl}-6-oxo-1,6-dihydropyrimidine-4-carboxamide | Calc'd 326.2, found 326.2 |
| 299 | 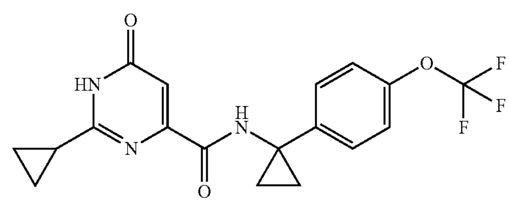 [SMILES: O=C(NC1(c2ccc(OC(F)(F)F)cc2)CC1)c1cc(=O)[nH]c(C2CC2)n1] | 2-cyclopropyl-6-oxo-N-{1-[4-(trifluoromethoxy)phenyl]cyclopropyl}-1,6-dihydropyrimidine-4-carboxamide | Calc'd 380.1, found 380.1 |
| 300 | 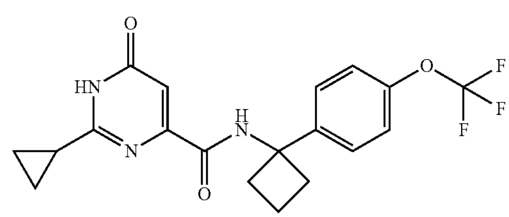 [SMILES: O=C(NC1(c2ccc(OC(F)(F)F)cc2)CCC1)c1cc(=O)[nH]c(C2CC2)n1] | 2-cyclopropyl-6-oxo-N-{1-[4-(trifluoromethoxy)phenyl]cyclobutyl}-1,6-dihydropyrimidine-4-carboxamide | Calc'd 394.1, found 394.3 |
| 301 | 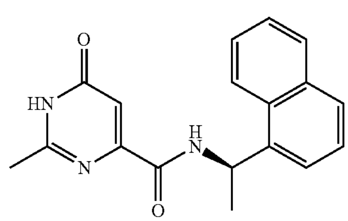 [SMILES: Cc1nc(C(=O)N[C@H](C)c2cccc3ccccc23)cc(=O)[nH]1] | (R)-2-methyl-N-(1-(naphthalen-1-yl)ethyl)-6-oxo-1,6-dihydropyrimidine-4-carboxamide | Calc'd 308.1, found 308.1 |
| 302 | 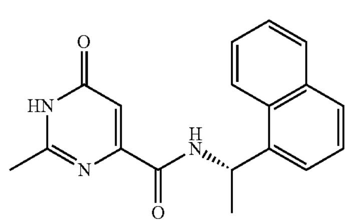 [SMILES: Cc1nc(C(=O)N[C@@H](C)c2cccc3ccccc23)cc(=O)[nH]1] | 2-methyl-N-[(3S)-1-naphthalen-1-ylethyl]-6-oxo-1,6-dihydropyrimidine-4-carboxamide | Calc'd 308.1, found 308.1 |

TABLE 7-continued

| Example No. | Structure | IUPAC Name | Exact Mass [M + H]+ |
|---|---|---|---|
| 303 | 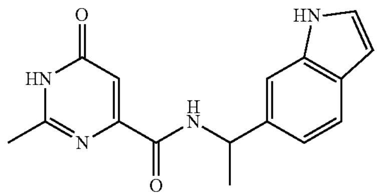 [SMILES: Cc1nc(C(=O)NC(C)c2ccc3cc[nH]c3c2)cc(=O)[nH]1] | N-(1-(1H-indol-6-yl)ethyl)-2-methyl-6-oxo-1,6-dihydropyrimidine-4-carboxamide | Calc'd 297.1, found 297.1 |
| 304 | 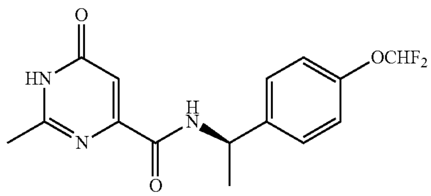 [SMILES: Cc1nc(C(=O)N[C@H](C)c2ccc(OC(F)F)cc2)cc(=O)[nH]1] | (R)-N-(1-(4-(difluoromethoxy)phenyl)ethyl)-2-methyl-6-oxo-1,6-dihydropyrimidine-4-carboxamide | Calc'd 324.1, found 324.1 |

Compounds in Table 8 below were prepared using methods from Scheme specified in the table with racemic starting amines and appropriate acids. The resulting racemic products were separated using chiral columns specified in the table. For the pair of enantiomers, the fast-eluting isomer is always listed first in this table. The stereochemistry of isolated enantiomers was not assigned except for Examples 315 and 316, where Example 316 was correlated to product obtained from commercially available enantiomerically pure amine starting material.

TABLE 8

| Example No. | Structure | IUPAC Name | Exact Mass [M + H]+ or [M + Na]+ | Scheme/ Chiral column |
|---|---|---|---|---|
| 305 | 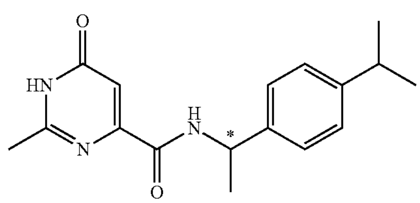 [SMILES: Cc1nc(C(=O)NC(C)c2ccc(C(C)C)cc2)cc(=O)[nH]1] | (R)- or (S)-2-methyl-N-{1-[4-(1-methylethyl)phenyl]ethyl}-6-oxo-1,6-dihydropyrimidine-4-carboxamide | 300.2 | A/OJ |
| 306 | 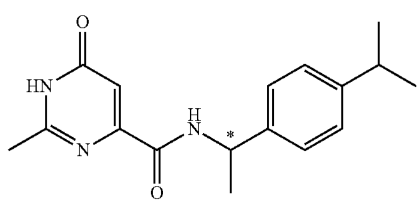 [SMILES: Cc1nc(C(=O)NC(C)c2ccc(C(C)C)cc2)cc(=O)[nH]1] | (S)- or (R)-2-methyl-N-{1-[4-(1-methylethyl)phenyl]ethyl}-6-oxo-1,6-dihydropyrimidine-4-carboxamide | 300.2 | A/OJ |
| 307 | 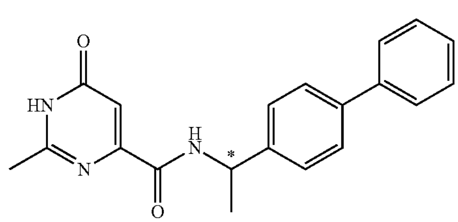 [SMILES: Cc1nc(C(=O)NC(C)c2ccc(-c3ccccc3)cc2)cc(=O)[nH]1] | (R)- or (S)-N-(1-biphenyl-4-ylethyl)-2-methyl-6-oxo-1,6-dihydropyrimidine-4-carboxamide | 334.2 | A/OJ |

TABLE 8-continued

| Example No. | Structure | IUPAC Name | Exact Mass [M + H]+ or [M + Na]+ | Scheme/ Chiral column |
|---|---|---|---|---|
| 308 | 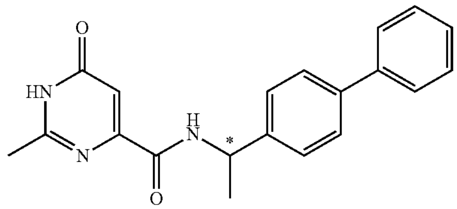 [SMILES: Cc1nc(C(=O)NC(C)c2ccc(-c3ccccc3)cc2)cc(=O)[nH]1] | (S)- or (R)-N-(1-biphenyl-4-ylethyl)-2-methyl-6-oxo-1,6-dihydropyrimidine-4-carboxamide | 334.2 | A/OJ |
| 309 | 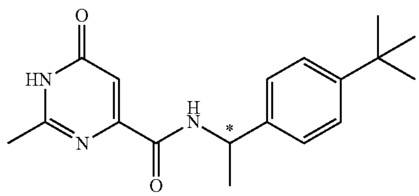 [SMILES: Cc1nc(C(=O)NC(C)c2ccc(C(C)(C)C)cc2)cc(=O)[nH]1] | (R)- or (S)-N-[1-(4-tert-butylphenyl)ethyl]-2-methyl-6-oxo-1,6-dihydropyrimidine-4-carboxamide | 314.3 | A/OJ |
| 310 | 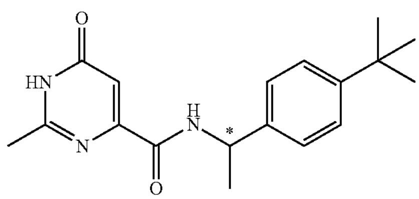 [SMILES: Cc1nc(C(=O)NC(C)c2ccc(C(C)(C)C)cc2)cc(=O)[nH]1] | (S)- or (R)-N-[1-(4-tert-butylphenyl)ethyl]-2-methyl-6-oxo-1,6-dihydropyrimidine-4-carboxamide | 314.3 | A/OJ |
| 311 | 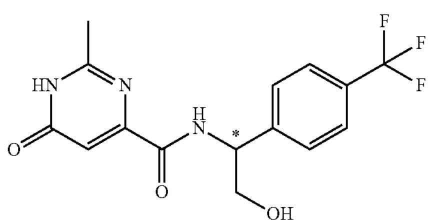 [SMILES: Cc1nc(C(=O)NC(CO)c2ccc(C(F)(F)F)cc2)cc(=O)[nH]1] | (S)- or (R)-N-{2-hydroxy-1-[4-(trifluoromethyl)phenyl]ethyl}-2-methyl-6-oxo-1,6-dihydropyrimidine-4-carboxamide | 342.1 | C/IC |
| 312 | 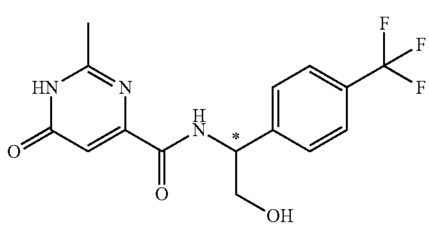 [SMILES: Cc1nc(C(=O)NC(CO)c2ccc(C(F)(F)F)cc2)cc(=O)[nH]1] | (R)- or (S)-N-{2-hydroxy-1-[4-(trifluoromethyl)phenyl]ethyl}-2-methyl-6-oxo-1,6-dihydropyrimidine-4-carboxamide | 342.1 | C/IC |
| 313 | 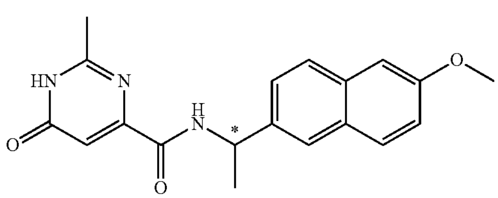 [SMILES: COc1ccc2cc(C(C)NC(=O)c3cc(=O)[nH]c(C)n3)ccc2c1] | (R)- or (S)-N-[1-(6-methoxynaphthalen-2-yl)ethyl]-2-methyl-6-oxo-1,6-dihydropyrimidine-4-carboxamide | 360.1 [M + Na]+ | A/AS |
| 314 | 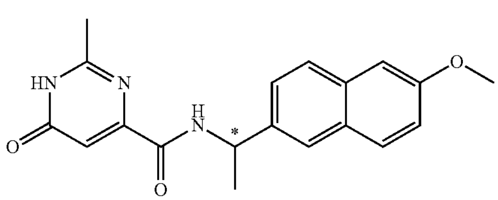 [SMILES: COc1ccc2cc(C(C)NC(=O)c3cc(=O)[nH]c(C)n3)ccc2c1] | (S)- or (R)-N-[1-(6-methoxynaphthalen-2-yl)ethyl]-2-methyl-6-oxo-1,6-dihydropyrimidine-4-carboxamide | 360.1 [M + Na]+ | A/AS |

TABLE 8-continued

| Example No. | Structure | IUPAC Name | Exact Mass [M + H]+ or [M + Na]+ | Scheme/ Chiral column |
|---|---|---|---|---|
| 315 | 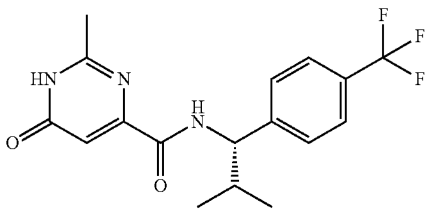 [SMILES: Cc1nc(C(=O)N[C@H](c2ccc(C(F)(F)F)cc2)C(C)C)cc(=O)[nH]1] | 2-methyl-N-{(1S)-2-methyl-1-[4-(trifluoromethyl)phenyl]propyl}-6-oxo-1,6-dihydropyrimidine-4-carboxamide | Calc'd 354.1, found 354.0 | B/OD-H 12% Methanol/ $CO_2$ |
| 316 | 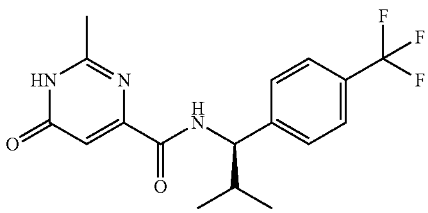 [SMILES: Cc1nc(C(=O)N[C@@H](c2ccc(C(F)(F)F)cc2)C(C)C)cc(=O)[nH]1] | 2-methyl-N-{(1R)-2-methyl-1-[4-(trifluoromethyl)phenyl]propyl}-6-oxo-1,6-dihydropyrimidine-4-carboxamide | Calc'd 354.1, found 354.0 | B/OD-H 12% Methanol/ $CO_2$ |

Example 317

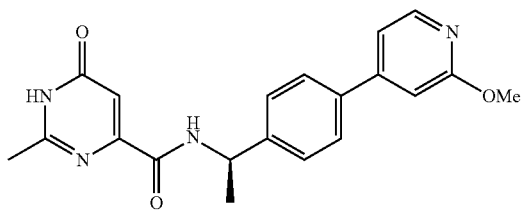 [SMILES: COc1cc(-c2ccc([C@@H](C)NC(=O)c3cc(=O)[nH]c(C)n3)cc2)ccn1]

(R)—N-(1-(4-(2-methoxypyridin-4-yl)phenyl)ethyl)-2-methyl-6-oxo-1,6-dihydropyrimidine-4-carboxamide

Step A. (R)—N-(1-(4-bromophenyl)ethyl)-2-methyl-6-oxo-1,6-dihydropyrimidine-4-carboxamide Preparation of the title compound was carried out via amide coupling of a commercially available carboxylic acid and enantiomerically pure amine HCl salt using conditions described for Example 8. MS: 338.0 (M+H).

Step B. (R)—N-(1-(4-(2-methoxypyridin-4-yl)phenyl)ethyl)-2-methyl-6-oxo-1,6-dihydropyrimidine-4-carboxamide To a stirred solution of (R)—N-(1-(4-bromophenyl)ethyl)-2-methyl-6-oxo-1,6-dihydropyrimidine-4-carboxamide from Step A above (0.035 g, 0.104 mmol) in dioxane (0.521 mL, 0.2M) was added (2-methoxypyridin-4-yl)boronic acid (0.0238 mg, 0.156 mmol), [1,1'-bis(diphenylphosphino)ferrocene]dichloropalladium(II) and followed by 2M $Na_2CO_3$ (0.104 mL, 0.208 mmol). The resulting mixture was degassed, purged with nitrogen and allowed to stir overnight at 90° C. The reaction was filtered over a pad of Celite and washed with 3:1 solution of chloroform/IPA. The filtrate was concentrated under reduced pressure and the resulting residue was purified directly by reverse phase HPLC (Xterra, C18, 19×100 mm, gradient elution, 10-100% acetonitrile/water with 0.1% TFA) to yield the title compound. MS: 365.2 (M+H). $^1$H NMR (500 MHz, $CD_3OD$) δ 7.82-7.44 (m, 8H), 5.25-5.24 (m, 1H), 4.13 (s, 3H), 2.39 (br s, 3H), 1.63 (d, J=6.4 Hz, 3H).

The following examples in Table 9 were prepared according to Scheme F using the procedure outlined in the synthesis of Example 317.

TABLE 9

| Example No. | Structure | IUPAC Name | Observed Exact Mass [M + H]+ or [M + Na]+ |
|---|---|---|---|
| 318 | 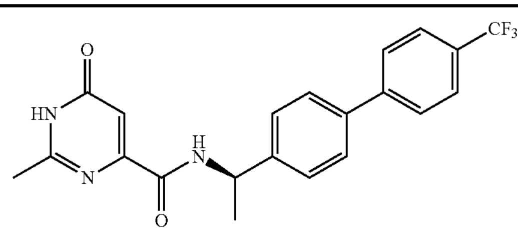 | 2-methyl-6-oxo-N-{(1R)-1-[4'-(trifluoromethyl)biphenyl-4-yl]ethyl}-1,6-dihydropyrimidine-4-carboxamide | 402.1 |

TABLE 9-continued

| Example No. | Structure | IUPAC Name | Observed Exact Mass [M + H]+ or [M + Na]+ |
|---|---|---|---|
| 319 | 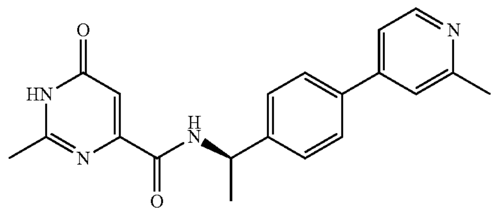 | 2-methyl-N-{(1R)-1-[4-(2-methylpyridin-4-yl)phenyl]ethyl}-6-oxo-1,6-dihydropyrimidine-4-carboxamide | 349.2 |
| 320 | 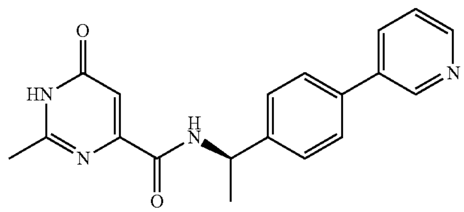 [SMILES: Cc1nc(C(=O)N[C@H](C)c2ccc(-c3cccnc3)cc2)cc(=O)[nH]1] | 2-methyl-6-oxo-N-[(1R)-1-(4-pyridin-3-ylphenyl)ethyl]-1,6-dihydropyrimidine-4-carboxamide | 335.2 |
| 321 | 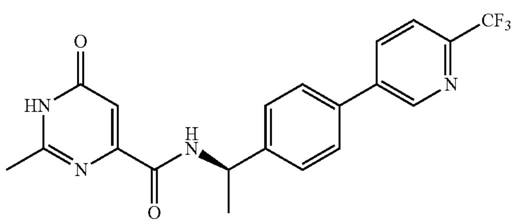 [SMILES: Cc1nc(C(=O)N[C@H](C)c2ccc(-c3ccc(C(F)(F)F)nc3)cc2)cc(=O)[nH]1] | 2-methyl-6-oxo-N-[(1R)-1-{4-[6-(trifluoromethyl)pyridin-3-yl]phenyl}ethyl]-1,6-dihydropyrimidine-4-carboxamide | 403.1 |
| 322 | 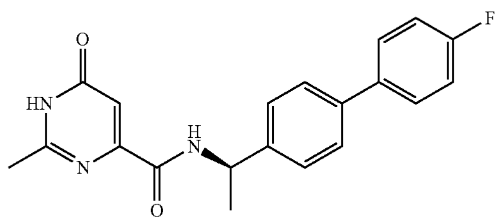 [SMILES: Cc1nc(C(=O)N[C@H](C)c2ccc(-c3ccc(F)cc3)cc2)cc(=O)[nH]1] | N-[(1R)-1-(4'-fluorobiphenyl-4-yl)ethyl]-2-methyl-6-oxo-1,6-dihydropyrimidine-4-carboxamide | 352.2 |
| 323 | 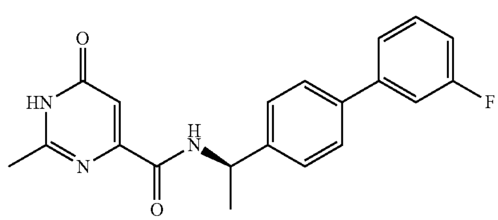 [SMILES: Cc1nc(C(=O)N[C@H](C)c2ccc(-c3cccc(F)c3)cc2)cc(=O)[nH]1] | N-[(1R)-1-(3'-fluorobiphenyl-4-yl)ethyl]-2-methyl-6-oxo-1,6-dihydropyrimidine-4-carboxamide | 352.1 |
| 324 | 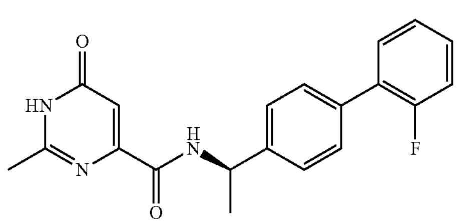 [SMILES: Cc1nc(C(=O)N[C@H](C)c2ccc(-c3ccccc3F)cc2)cc(=O)[nH]1] | N-[(1R)-1-(2'-fluorobiphenyl-4-yl)ethyl]-2-methyl-6-oxo-1,6-dihydropyrimidine-4-carboxamide | 374.1 [M + Na]+ |

Example 325

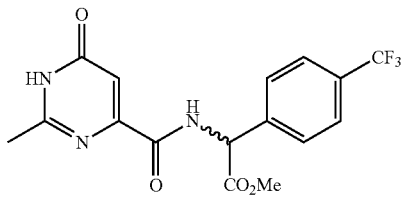 [SMILES: COC(=O)C(NC(=O)c1cc(=O)[nH]c(C)n1)c1ccc(C(F)(F)F)cc1]

Methyl {[(2-methyl-6-oxo-1,6-dihydropyrimidin-4-yl)carbonyl]amino}[4-(trifluoromethyl)phenyl]acetate The title compound was prepared as a racemate using procedures described in Scheme B and Example 15. MS: 370.1 (M+H). $^1$H NMR (500 MHz, CD$_3$OD) δ 7.70 (d, J=7.4 Hz, 2H), 7.64 (d, J=7.6 Hz, 2H), 6.89 (s, 1H), 5.77 (s, 1H), 3.78 (s, 3H), 2.47 (s, 3H).

Examples 326, 327, and 328

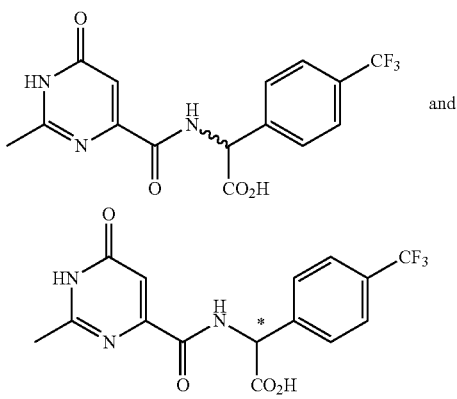

2-(2-Methyl-6-oxo-1,6-dihydropyrimidine-4-carboxamido)-2-(4-(trifluoromethyl)phenyl)acetic acid and (R)- and (S)-2-(2-methyl-6-oxo-1,6-dihydropyrimidine-4-carboxamido)-2-(4-(trifluoromethyl)phenyl)acetic acid To a solution of methyl {[(2-methyl-6-oxo-1,6-dihydropyrimidin-4-yl)carbonyl]amino}[4-(trifluoromethyl)phenyl]acetate (0.1 g, 0.271 mmol) from Example 325 in a 3:1 solution of tetrahydrofuran/methanol (3.248 mL) was added 1N aqueous lithium hydroxide (0.812 mL, 0.812 mmol) and the resulting mixture was stirred at room temperature for 1 h. The solution was concentrated to remove volatiles and then diluted with 1N aqueous HCl (2 mL). The resultant mixture was extracted with 3:1 solution of chloroform/IPA (2 mL×3) dried over magnesium sulfate, filtered and concentrated under reduced pressure. The resulting residue was purified directly by reverse phase HPLC (Xterra, C18, 19×100 mm, gradient elution, 0-90% acetonitrile/water with 0.1% TFA) to yield the title compound as a mixture of two enantiomers (Example 326). MS: 356.1 (M+H). $^1$H NMR (500 MHz, CD$_3$OD) δ 7.69 (d, J=8.3 Hz, 2H), 7.66 (d, J=8.4 Hz, 2H), 6.89 (s, 1H), 5.67 (s, 1H), 2.48 (s, 3H). Chiral resolution of the two enantiomers was achieved by chiral preparative SFC (IC column, 20% MeOH with 0.1% DEA) to afford (Example 327, faster eluting) MS: 356.0 (M+H). $^1$H NMR (500 MHz, CD$_3$OD) δ 7.69 (d, J=8.4 Hz, 2H), 7.66 (d, J=8.3 Hz, 2H), 6.89 (s, 1H), 5.69 (s, 1H), 2.48 (s, 3H) and (Example 328, slower eluting) MS: 356.0 (M+H).
$^1$H NMR (500 MHz, CD$_3$OD) δ 7.69 (d, J=8.2 Hz, 2H), 7.66 (d, J=7.8 Hz, 2H), 6.89 (s, 1H), 5.69 (s, 1H), 2.48 (s, 3H).

Example 329

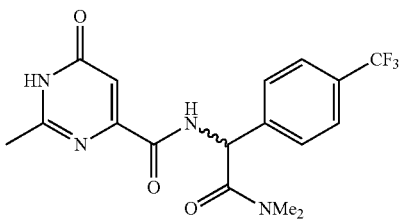 [SMILES: Cc1nc(C(=O)NC(C(=O)N(C)C)c2ccc(C(F)(F)F)cc2)cc(=O)[nH]1]

N-{2-(dimethylamino)-2-oxo-1-[4-(trifluoromethyl)phenyl]ethyl}-2-methyl-6-oxo-1,6-dihydropyrimidine-4-carboxamide The title compound was prepared using procedures described in Scheme B and Example 15 starting from Example 326 and dimethylamine. MS: 383.1 (M+H).

Example 330

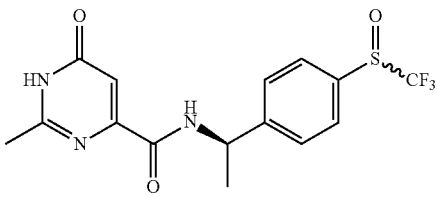 [SMILES: Cc1nc(C(=O)N[C@H](C)c2ccc(S(=O)C(F)(F)F)cc2)cc(=O)[nH]1]

(2-Methyl-6-oxo-N-((1R)-1-(4-((trifluoromethyl)sulfinyl)phenyl)ethyl)-1,6-dihydropyrimidine-4-carboxamide To a solution of (R)-2-methyl-6-oxo-N-(1-(4-((trifluoromethyl)thio)phenyl)ethyl)-1,6-dihydropyrimidine-4-carboxamide (0.020 g, 0.056 mmol) from Example 66 in dichloromethane (0.56 mL, 0.1 M) at 0° C. was added m-chloroperoxybenzoic acid (0.0138 g, 0.062 mmol) and the resulting mixture was stirred and allowed to warm to room temperature. The solution was allowed to continue stirring for 1 h. The mixture was then quenched with saturated aqueous sodium bicarbonate (2 mL) and extracted with dichloromethane (2 mL×3). The organic layers were combined, dried over anhydrous magnesium sulfate, filtered and concentrated under reduced pressure. The resulting residue was purified by reverse phase HPLC (Xterra, C18, 19×100 mm, gradient elution, 10-100% acetonitrile/water with 0.1% TFA) to yield the title compound. MS: 374.1 (M+H). $^1$H NMR (500 MHz, CD$_3$OD) δ 9.03 (br s, 1H), 7.84

(d, J=7.9 Hz, 2H), 7.72 (d, J=8.0 Hz, 2H), 6.91 (br s, 1H), 5.49-5.28 (m, 1H), 2.45 (s, 3H), 1.63 (d, J=6.8, 3H).

Example 331

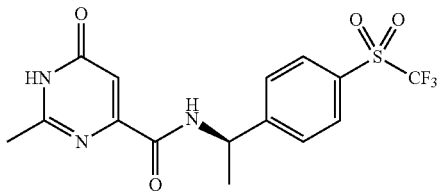 [SMILES: Cc1nc(C(=O)N[C@H](C)c2ccc(S(=O)(=O)C(F)(F)F)cc2)cc(=O)[nH]1]

2-Methyl-6-oxo-N-[(1R)-1-{4-[(trifluoromethyl) sulfonyl]phenyl}ethyl]-1,6-dihydropyrimidine-4-carboxamide To a solution of (R)-2-methyl-6-oxo-N-(1-(4-((trifluoromethyl)thio)phenyl)ethyl)-1,6-dihydropyrimidine-4-carboxamide from Example 66 (0.020 g, 0.056 mmol) in dichloromethane (0.56 mL, 0.1 M) at 0° C. was added m-chloroperoxybenzoic acid (0.0276 g, 0.123 mmol) and the resulting mixture was stirred and allowed to warm to room temperature. The solution was allowed to continue stirring for 1 h. The mixture was then quenched with saturated aqueous sodium bicarbonate (2 mL) and extracted with dichloromethane (2 mL×3). The organic layers were combined, dried over anhydrous magnesium sulfate, filtered and concentrated under reduced pressure. The resulting residue was purified by reverse phase HPLC (Xterra, C18, 19×100 mm, gradient elution, 10-100% acetonitrile/water with 0.1% TFA) to yield the title compound. MS: 390.1 (M+H). $^1$H NMR (500 MHz, CD$_3$OD) δ 8.05 (d, J=8.3 Hz, 2H), 7.80 (d, J=8.3 Hz, 2H), 6.87 (s, 1H), 5.33-5.28 (m, 1H), 2.47 (s, 3H), 1.64 (d, J=7.1, 3H).

Examples 332 and 333

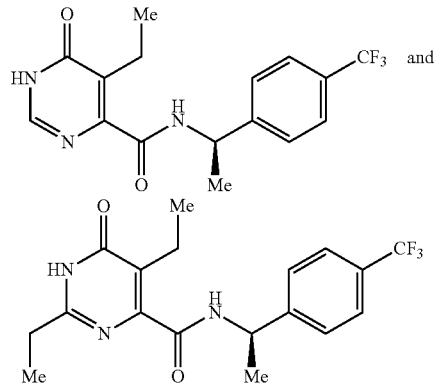

Example 332 (R)-5-ethyl-6-oxo-N-(1-(4-(trifluoromethyl)phenyl)ethyl)-1,6-dihydropyrimidine-4-carboxamide and Example 333 (R)-2,5-diethyl-6-oxo-N-(1-(4-(trifluoromethyl)phenyl)ethyl)-1,6-dihydropyrimidine-4-carboxamide (R)-6-oxo-N-(1-(4-(trifluoromethyl)phenyl)ethyl)-1,6-dihydropyrimidine-4-carboxamide from Example 8 (30 mg, 0.096 mmol), tert-pentyl ethaneperoxoate (35.2 mg, 0.241 mmol) and [Ir(dF(CF$_3$)ppy)$_2$(dtbbpy)](PF$_6$) (5.4 mg, 0.005 mmol) were dissolved in a mixture of acetonitrile (482 uL), acetic acid (482 uL) and trifluoroacetic acid (40 uL) and the mixture was degassed by sparging with nitrogen. The solution was drawn into a syringe and passed into a nitrogen filled perfluoroalkoxy tube (0.02" internal diameter) that was tightly wrapped around a 1" glass tube. The apparatus was then irradiated with blue light emitting diodes for a period of 5 minutes. The yellow solution was passed out of the apparatus under positive pressure and volatiles were removed in vacuo. The residue was purified by preparative reverse-phase HPLC (20-80% acetonitrile in water with 0.05% TFA) to give cleanly separated title compounds. MS of Example 332—[M+H]$^+$ m/z 339.9; MS of Example 333—[M+H]$^+$ m/z 367.6.

Examples 334 and 335

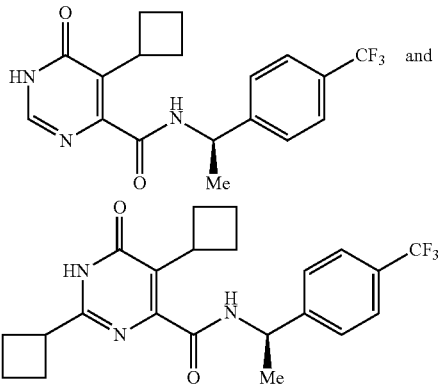

Example 334 (R)-5-cyclobutyl-6-oxo-N-(1-(4-(trifluoromethyl)phenyl)ethyl)-1,6-dihydropyrimidine-4-carboxamide and Example 335 (R)-2,5-dicyclobutyl-6-oxo-N-(1-(4-(trifluoromethyl)phenyl)ethyl)-1,6-dihydropyrimidine-4-carboxamide (R)-6-oxo-N-(1-(4-(trifluoromethyl)phenyl)ethyl)-1,6-dihydropyrimidine-4-carboxamide from Example 8 (30 mg, 0.096 mmol), cyclobutanecarboxylic peroxyanhydride (47.8 mg, 0.241 mmol) and [Ir(dF(CF$_3$)ppy)$_2$(dtbbpy)](PF$_6$) (2.7 mg, 0.0025 mmol) were dissolved in a mixture of acetonitrile (482 uL), acetic acid (482 uL) and trifluoroacetic acid (40 uL) and the mixture was degassed by sparging with nitrogen. The solution was drawn into a syringe and passed into a nitrogen filled perfluoroalkoxy tube (0.02" internal diameter) that was tightly wrapped around a 1" glass tube. The apparatus was then irradiated with blue light emitting diodes for a period of 2.5 minutes. The yellow solution was passed out of the apparatus under positive pressure and volatiles were removed in vacuo. The residue was purified by preparative reverse-phase HPLC (20-80% acetonitrile in water with 0.05% TFA) to give cleanly separated title compounds. MS of Example 334—[M+H]$^+$ m/z 365.8; MS of Example 335—[M+H]$^+$ m/z 419.8.

Example 336

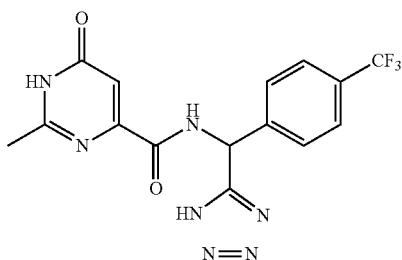

2-Methyl-6-oxo-N-{1H-tetrazol-5-yl[4-(trifluoromethyl)phenyl]methyl}-1,6-dihydropyrimidine-4-carboxamide To a stirred mixture of N-{cyano[4-(trifluoromethyl)phenyl]methyl}-2-methyl-6-oxo-1,6-dihydropyrimidine-4-carboxamide from Example 33 (25 mg, 0.074 mmol) in toluene (1.06 mL) was added azidotrimethyltin (33.7 mg, 0.164 mmol). The resulting mixture was stirred at 115° C. overnight. The reaction was cooled down to room temperature and concentrated under reduced pressure. The residue was purified by reverse phase Prep-HPLC with Sunfire Prep 5 uM 10×100 mm column (10% to 90% ACN/Water with 0.1% TFA) to yield the title compound. MS: 380.0 (M+H). $^1$H NMR (500 MHz, CD$_3$OD) δ7.73 (d, 2H), 7.65 (d, 2H), 6.94 (s, 1H), 6.77 (s, 1H), 2.46 (s, 3H).

Example 337

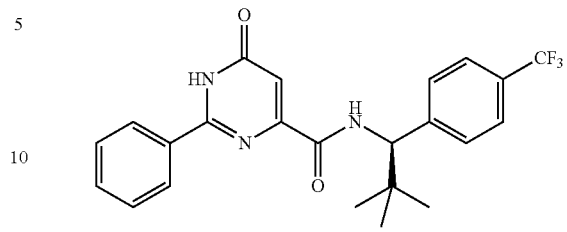

N-{(1R)-2,2-dimethyl-1-[4-(trifluoromethyl)phenyl]propyl}-6-oxo-2-phenyl-1,6-dihydropyrimidine-4-carboxamide To a stirring suspension of commercially available 6-oxo-2-phenyl-1,6-dihydropyrimidine-4-carboxylic acid (20 mg, 0.093 mmol) in CH$_2$Cl$_2$ (925 uL) was added (R)-2,2-dimethyl-1-(4-(trifluoromethyl)phenyl)propan-1-amine (26 mg, 0.102 mmol) from a commercial source and TEA (28.1 mg, 38.7 uL, 0.278 mmol), followed by addition of 2,4,6-tripropyl-1,3,5,2,4,6-trioxatriphosphinane 2,4,6-trioxide (T3P, 50% in DMF, 64.8 mg 0.102 mmol). The reaction mixture was stirred at room temperature for 2 h. Then it was concentrated in a Genevac. The resulting crude reaction mixture was diluted with DMSO and filtered. The filtrate was purified by reverse phase Prep HPLC with Waters Sunfire C18 column, 5 um, 19×100 mm (40% to 70% ACN/Water with 0.1% formic acid) to afford the title compound. MS: 430.3 (M+H). $^1$H NMR (500 MHz, DMSO): δ8.8 (d, 1H); 8.25 (br s, 2 H); 7.70-7.65 (m, 7 H); 6.7 (br s, 1H); 4.94 (d, J=9.1 Hz, 1 H); 0.98 (s, 9 H).

Compounds in Table 10 were prepared using similar conditions as described in Example 337 and illustrated in Scheme H.

TABLE 10

| Example No. | Structure | IUPAC Name | Exact Mass [M + H]+ or [M + Na]+ |
|---|---|---|---|
| 338 | ![structure] | 6-oxo-2-phenyl-N-(3,4,5-trimethoxybenzyl)-1,6-dihydropyrimidine-4-carboxamide | Calc'd 396.2, found 396.2 |
| 339 | ![structure] | N-[(1R)-1-(4-hydroxyphenyl)ethyl]-6-oxo-2-phenyl-1,6-dihydropyrimidine-4-carboxamide | Calc'd 336.1, found 336.2 |
| 340 | ![structure] | N-[1-(4-bromophenyl)-1-methylethyl]-6-oxo-2-phenyl-1,6-dihydropyrimidine-4-carboxamide | Calc'd 412.1/ 414.1, found 412.1/ 414.1 |

TABLE 10-continued

| Example No. | Structure | IUPAC Name | Exact Mass [M + H]+ or [M + Na]+ |
|---|---|---|---|
| 341 | 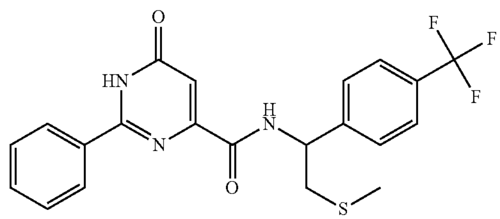 [SMILES: CSCC(NC(=O)c1cc(=O)[nH]c(-c2ccccc2)n1)c1ccc(C(F)(F)F)cc1] | N-{2-(methylsulfanyl)-1-[4-(trifluoromethyl)phenyl]ethyl}-6-oxo-2-phenyl-1,6-dihydropyrimidine-4-carboxamide | Calc'd 434.1, found 434.2 |
| 342 | 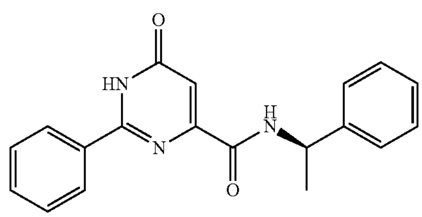 [SMILES: C[C@@H](NC(=O)c1cc(=O)[nH]c(-c2ccccc2)n1)c1ccccc1] | 6-oxo-2-phenyl-N-[(1R)-1-phenylethyl]-1,6-dihydropyrimidine-4-carboxamide | Calc'd 320.1, found 320.1 |
| 343 | 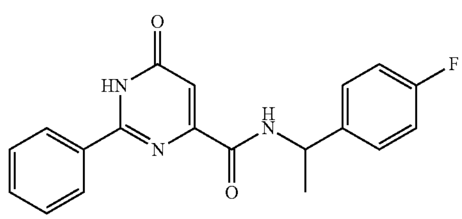 [SMILES: CC(NC(=O)c1cc(=O)[nH]c(-c2ccccc2)n1)c1ccc(F)cc1] | N-[1-(4-fluorophenyl)ethyl]-6-oxo-2-phenyl-1,6-dihydropyrimidine-4-carboxamide | Calc'd 338.1, found 338.1 |
| 344 | 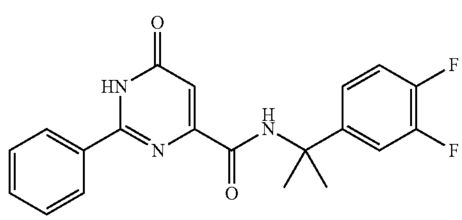 [SMILES: CC(C)(NC(=O)c1cc(=O)[nH]c(-c2ccccc2)n1)c1ccc(F)c(F)c1] | N-[1-(3,4-difluorophenyl)-1-methylethyl]-6-oxo-2-phenyl-1,6-dihydropyrimidine-4-carboxamide | Calc'd 370.1, found 370.2 |
| 345 | 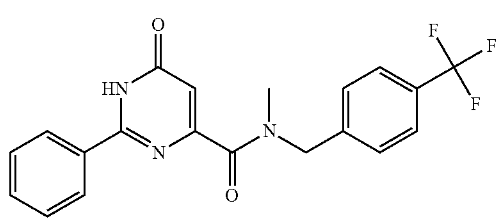 [SMILES: CN(Cc1ccc(C(F)(F)F)cc1)C(=O)c1cc(=O)[nH]c(-c2ccccc2)n1] | N-methyl-6-oxo-2-phenyl-N-[4-(trifluoromethyl)benzyl]-1,6-dihydropyrimidine-4-carboxamide | Calc'd 388.1, found 388.2 |
| 346 | 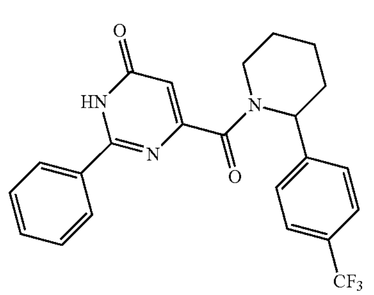 [SMILES: O=C(c1cc(=O)[nH]c(-c2ccccc2)n1)N1CCCCC1c1ccc(C(F)(F)F)cc1] | 2-phenyl-6-({2-[4-(trifluoromethyl)phenyl]piperidin-1-yl}carbonyl)pyrimidin-4(3H)-one | Calc'd 428.2, found 428.3 |

TABLE 10-continued

| Example No. | Structure | IUPAC Name | Exact Mass [M + H]+ or [M + Na]+ |
|---|---|---|---|
| 347 | 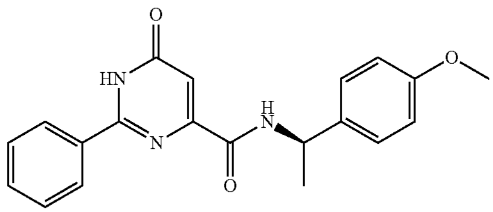 [SMILES: COc1ccc([C@@H](C)NC(=O)c2cc(=O)[nH]c(-c3ccccc3)n2)cc1] | N-[(1R)-1-(4-methoxyphenyl)ethyl]-6-oxo-2-phenyl-1,6-dihydropyrimidine-4-carboxamide | Calc'd 350.2, found 350.2 |
| 348 | 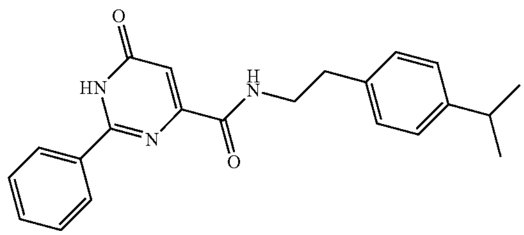 [SMILES: CC(C)c1ccc(CCNC(=O)c2cc(=O)[nH]c(-c3ccccc3)n2)cc1] | N-{2-[4-(1-methylethyl)phenyl]ethyl}-6-oxo-2-phenyl-1,6-dihydropyrimidine-4-carboxamide | Calc'd 362.2, found 362.2 |
| 349 | 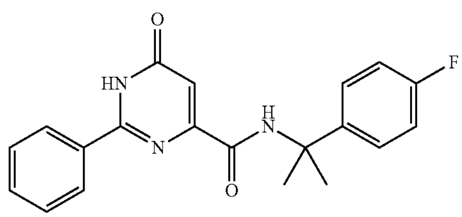 [SMILES: CC(C)(NC(=O)c1cc(=O)[nH]c(-c2ccccc2)n1)c1ccc(F)cc1] | N-[1-(4-fluorophenyl)-1-methylethyl]-6-oxo-2-phenyl-1,6-dihydropyrimidine-4-carboxamide | Calc'd 352.1, found 352.2 |
| 350 | 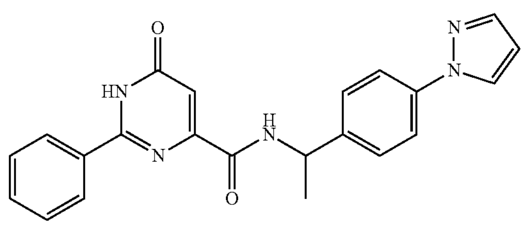 [SMILES: CC(NC(=O)c1cc(=O)[nH]c(-c2ccccc2)n1)c1ccc(-n2cccn2)cc1] | 6-oxo-2-phenyl-N-{1-[4-(1H-pyrazol-1-yl)phenyl]ethyl}-1,6-dihydropyrimidine-4-carboxamide | Calc'd 386.2, found 386.2 |
| 351 | 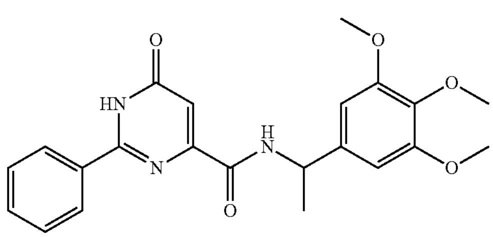 [SMILES: COc1cc(C(C)NC(=O)c2cc(=O)[nH]c(-c3ccccc3)n2)cc(OC)c1OC] | 6-oxo-2-phenyl-N-[1-(3,4,5-trimethoxyphenyl)ethyl]-1,6-dihydropyrimidine-4-carboxamide | Calc'd 410.2, found 410.2 |
| 352 | 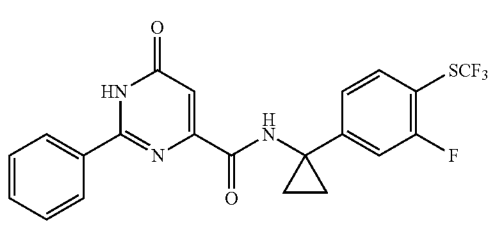 | N-(1-{3-fluoro-4-[(trifluoromethyl)sulfanyl]phenyl}cyclopropyl)-6-oxo-2-phenyl-1,6-dihydropyrimidine-4-carboxamide | Calc'd 450.1, found 450.2 |

TABLE 10-continued

| Example No. | Structure | IUPAC Name | Exact Mass [M + H]+ or [M + Na]+ |
|---|---|---|---|
| 353 | 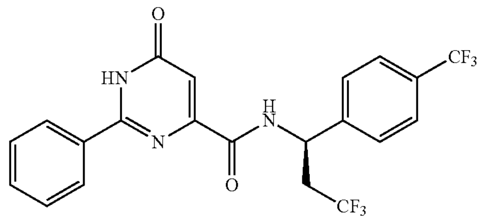 [SMILES: O=C(N[C@H](CC(F)(F)F)c1ccc(C(F)(F)F)cc1)c1cc(=O)[nH]c(-c2ccccc2)n1] | 6-oxo-2-phenyl-N-{(1R)-3,3,3-trifluoro-1-[4-(trifluoromethyl)phenyl]propyl}-1,6-dihydropyrimidine-4-carboxamide | Calc'd 456.1, found 456.2 |
| 354 | 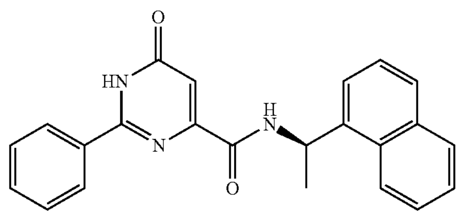 [SMILES: C[C@@H](NC(=O)c1cc(=O)[nH]c(-c2ccccc2)n1)c1cccc2ccccc12] | N-[(1R)-1-naphthalen-1-ylethyl]-6-oxo-2-phenyl-1,6-dihydropyrimidine-4-carboxamide | Calc'd 370.2, found 370.2 |
| 355 | 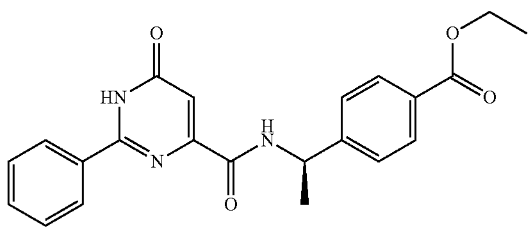 [SMILES: CCOC(=O)c1ccc([C@@H](C)NC(=O)c2cc(=O)[nH]c(-c3ccccc3)n2)cc1] | ethyl 4-[(1R)-1-{[(6-oxo-2-phenyl-1,6-dihydropyrimidin-4-yl)carbonyl]amino}ethyl]benzoate | Calc'd 392.2, found 392.2 |
| 356 | 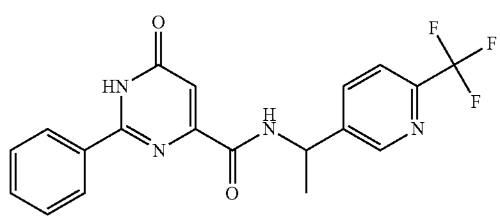 [SMILES: CC(NC(=O)c1cc(=O)[nH]c(-c2ccccc2)n1)c1ccc(C(F)(F)F)nc1] | 6-oxo-2-phenyl-N-{1-[6-(trifluoromethyl)pyridin-3-yl]ethyl}-1,6-dihydropyrimidine-4-carboxamide | Calc'd 389.1, found 389.2 |
| 357 | 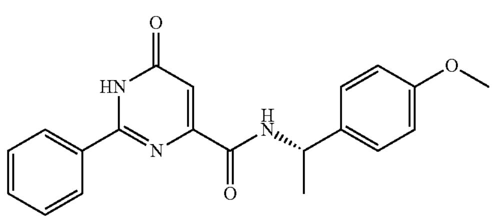 [SMILES: COc1ccc([C@H](C)NC(=O)c2cc(=O)[nH]c(-c3ccccc3)n2)cc1] | N-[(1S)-1-(4-methoxyphenyl)ethyl]-6-oxo-2-phenyl-1,6-dihydropyrimidine-4-carboxamide | Calc'd 350.2, found 350.2 |
| 358 | 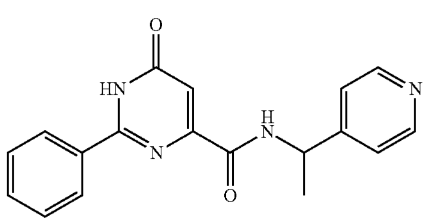 [SMILES: CC(NC(=O)c1cc(=O)[nH]c(-c2ccccc2)n1)c1ccncc1] | 6-oxo-2-phenyl-N-(1-pyridin-4-ylethyl)-1,6-dihydropyrimidine-4-carboxamide | Calc'd 321.1, found 321.1 |
| 359 | 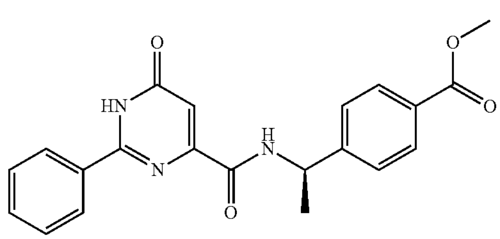 [SMILES: COC(=O)c1ccc([C@@H](C)NC(=O)c2cc(=O)[nH]c(-c3ccccc3)n2)cc1] | methyl 4-[(1R)-1-{[(6-oxo-2-phenyl-1,6-dihydropyrimidin-4-yl)carbonyl]amino}ethyl]benzoate | Calc'd 378.1, found 378.2 |

TABLE 10-continued

| Example No. | Structure | IUPAC Name | Exact Mass [M + H]+ or [M + Na]+ |
|---|---|---|---|
| 360 | 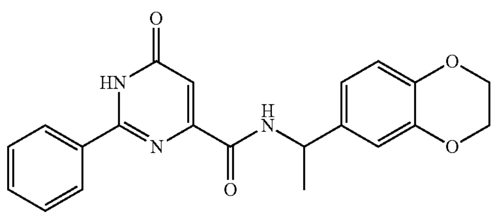 [SMILES: CC(NC(=O)c1cc(=O)[nH]c(-c2ccccc2)n1)c1ccc2c(c1)OCCO2] | N-[1-(2,3-dihydro-1,4-benzodioxin-6-yl)ethyl]-6-oxo-2-phenyl-1,6-dihydropyrimidine-4-carboxamide | Calc'd 378.1, found 378.1 |
| 361 | 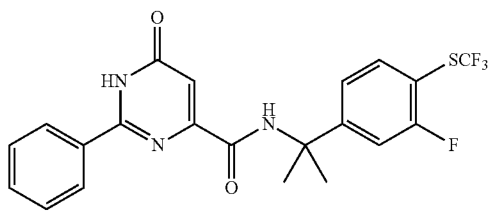 | N-(1-{3-fluoro-4-[(trifluoromethyl)sulfanyl]phenyl}-1-methylethyl)-6-oxo-2-phenyl-1,6-dihydropyrimidine-4-carboxamide | Calc'd 452.1, found 452.2 |
| 362 | 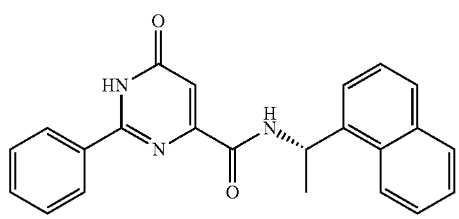 [SMILES: C[C@H](NC(=O)c1cc(=O)[nH]c(-c2ccccc2)n1)c1cccc2ccccc12] | N-[(1S)-1-naphthalen-1-ylethyl]-6-oxo-2-phenyl-1,6-dihydropyrimidine-4-carboxamide | Calc'd 370.2, found 370.1 |
| 363 | 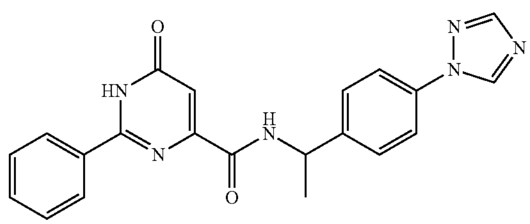 [SMILES: CC(NC(=O)c1cc(=O)[nH]c(-c2ccccc2)n1)c1ccc(-n2cncn2)cc1] | 6-oxo-2-phenyl-N-{1-[4-(1H-1,2,4-triazol-1-yl)phenyl]ethyl}-1,6-dihydropyrimidine-4-carboxamide | Calc'd 387.2, found 387.1 |
| 364 | 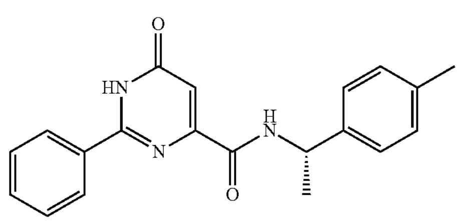 [SMILES: Cc1ccc([C@H](C)NC(=O)c2cc(=O)[nH]c(-c3ccccc3)n2)cc1] | N-[(1S)-1-(4-methylphenyl)ethyl]-6-oxo-2-phenyl-1,6-dihydropyrimidine-4-carboxamide | Calc'd 334.2, found 334.2 |
| 365 | 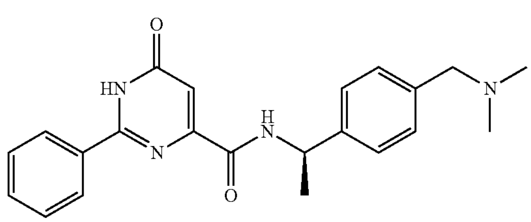 [SMILES: C[C@@H](NC(=O)c1cc(=O)[nH]c(-c2ccccc2)n1)c1ccc(CN(C)C)cc1] | N-[(1R)-1-{4-[(dimethylamino)methyl]phenyl}ethyl]-6-oxo-2-phenyl-1,6-dihydropyrimidine-4-carboxamide | Calc'd 377.2, found 377.3 |
| 366 | 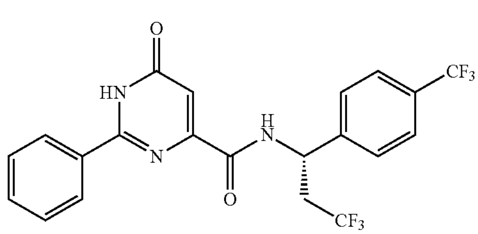 [SMILES: O=C(N[C@@H](CC(F)(F)F)c1ccc(C(F)(F)F)cc1)c1cc(=O)[nH]c(-c2ccccc2)n1] | 6-oxo-2-phenyl-N-{(1S)-3,3,3-trifluoro-1-[4-(trifluoromethyl)phenyl]propyl}-1,6-dihydropyrimidine-4-carboxamide | Calc'd 456.1, found 456.2 |

TABLE 10-continued

| Example No. | Structure | IUPAC Name | Exact Mass [M + H]+ or [M + Na]+ |
|---|---|---|---|
| 367 | 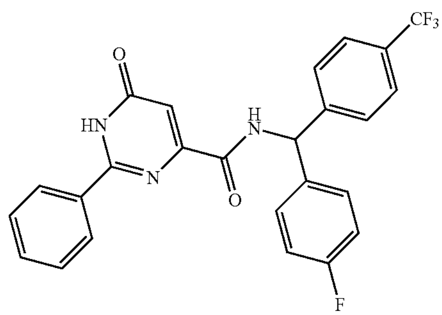 [SMILES: O=C(NC(c1ccc(F)cc1)c1ccc(C(F)(F)F)cc1)c1cc(=O)[nH]c(-c2ccccc2)n1] | N-{(4-fluorophenyl)[4-(trifluoromethyl)phenyl]methyl}-6-oxo-2-phenyl-1,6-dihydropyrimidine-4-carboxamide | Calc'd 468.1, found 468.2 |
| 368 | 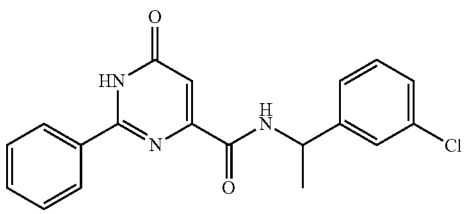 [SMILES: CC(NC(=O)c1cc(=O)[nH]c(-c2ccccc2)n1)c1cccc(Cl)c1] | N-[1-(3-chlorophenyl)ethyl]-6-oxo-2-phenyl-1,6-dihydropyrimidine-4-carboxamide | Calc'd 354.1, found 354.1 |
| 369 | 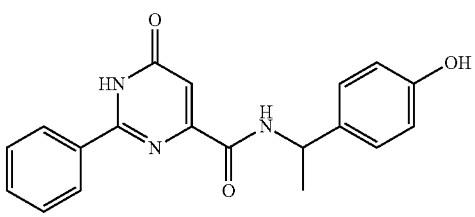 [SMILES: CC(NC(=O)c1cc(=O)[nH]c(-c2ccccc2)n1)c1ccc(O)cc1] | N-[1-(4-hydroxyphenyl)ethyl]-6-oxo-2-phenyl-1,6-dihydropyrimidine-4-carboxamide | Calc'd 336.1, found 336.2 |
| 370 | 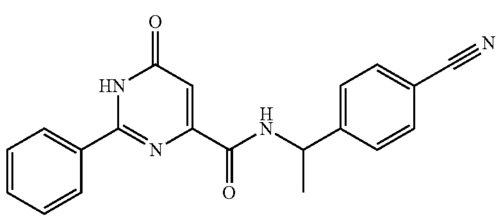 [SMILES: CC(NC(=O)c1cc(=O)[nH]c(-c2ccccc2)n1)c1ccc(C#N)cc1] | N-[1-(4-cyanophenyl)ethyl]-6-oxo-2-phenyl-1,6-dihydropyrimidine-4-carboxamide | Calc'd 345.1, found 345.2 |
| 371 | 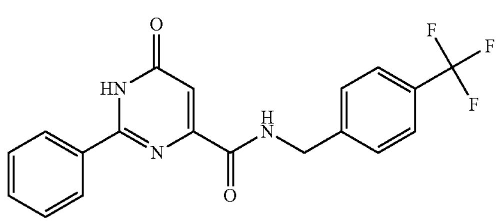 [SMILES: O=C(NCc1ccc(C(F)(F)F)cc1)c1cc(=O)[nH]c(-c2ccccc2)n1] | 6-oxo-2-phenyl-N-[4-(trifluoromethyl)benzyl]-1,6-dihydropyrimidine-4-carboxamide | Calc'd 374.1, found 374.2 |
| 372 | 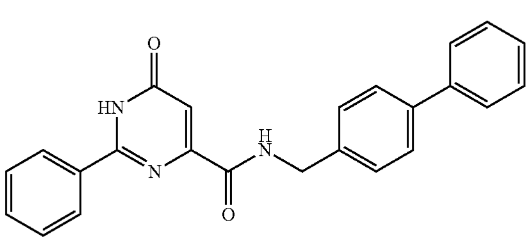 [SMILES: O=C(NCc1ccc(-c2ccccc2)cc1)c1cc(=O)[nH]c(-c2ccccc2)n1] | N-(biphenyl-4-ylmethyl)-6-oxo-2-phenyl-1,6-dihydropyrimidine-4-carboxamide | Calc'd 382.2, found 382.2 |

TABLE 10-continued

| Example No. | Structure | IUPAC Name | Exact Mass [M + H]+ or [M + Na]+ |
|---|---|---|---|
| 373 | 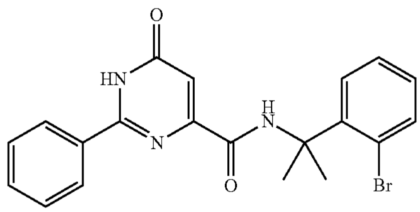 [SMILES: CC(C)(NC(=O)c1cc(=O)[nH]c(-c2ccccc2)n1)c1ccccc1Br] | N-[1-(2-bromophenyl)-1-methylethyl]-6-oxo-2-phenyl-1,6-dihydropyrimidine-4-carboxamide | Calc'd 412.1/ 414.1, found 412.1/ 414.1 |
| 374 | 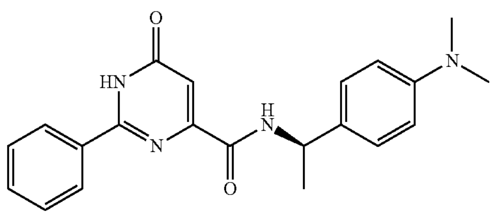 [SMILES: C[C@@H](NC(=O)c1cc(=O)[nH]c(-c2ccccc2)n1)c1ccc(N(C)C)cc1] | N-{(1R)-1-[4-(dimethylamino)phenyl]ethyl}-6-oxo-2-phenyl-1,6-dihydropyrimidine-4-carboxamide | Calc'd 363.2, found 363.2 |
| 375 | 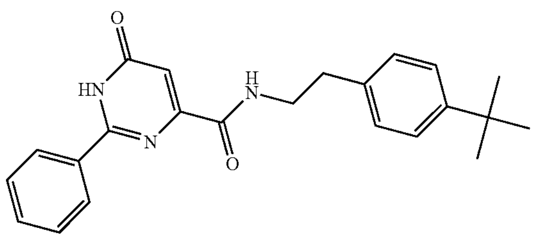 [SMILES: CC(C)(C)c1ccc(CCNC(=O)c2cc(=O)[nH]c(-c3ccccc3)n2)cc1] | N-[2-(4-tert-butylphenyl)ethyl]-6-oxo-2-phenyl-1,6-dihydropyrimidine-4-carboxamide | Calc'd 376.2, found 376.2 |
| 376 | 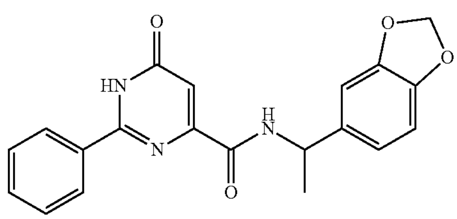 [SMILES: CC(NC(=O)c1cc(=O)[nH]c(-c2ccccc2)n1)c1ccc2c(c1)OCO2] | N-[1-(1,3-benzodioxol-5-yl)ethyl]-6-oxo-2-phenyl-1,6-dihydropyrimidine-4-carboxamide | Calc'd 364.1, found 364.1 |
| 377 | 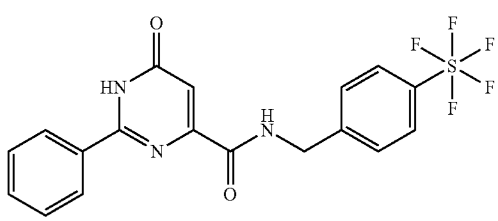 [SMILES: O=C(NCc1ccc(S(F)(F)(F)(F)F)cc1)c1cc(=O)[nH]c(-c2ccccc2)n1] | 6-oxo-N-[4-(pentafluoro-$\lambda^6$-sulfanyl)benzyl]-2-phenyl-1,6-dihydropyrimidine-4-carboxamide | Calc'd 432.1, found 432.1 |
| 378 | 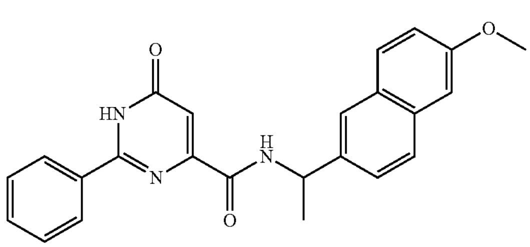 [SMILES: COc1ccc2cc(C(C)NC(=O)c3cc(=O)[nH]c(-c4ccccc4)n3)ccc2c1] | N-[1-(6-methoxynaphthalen-2-yl)ethyl]-6-oxo-2-phenyl-1,6-dihydropyrimidine-4-carboxamide | Calc'd 400.2, found 400.3 |
| 379 | 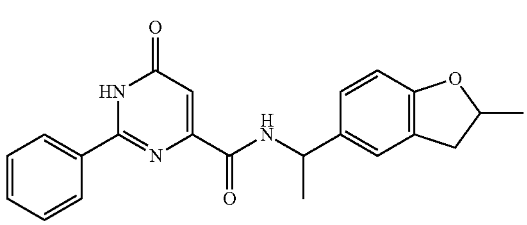 [SMILES: CC1Cc2cc(C(C)NC(=O)c3cc(=O)[nH]c(-c4ccccc4)n3)ccc2O1] | N-[1-(2-methyl-2,3-dihydro-1-benzofuran-5-yl)ethyl]-6-oxo-2-phenyl-1,6-dihydropyrimidine-4-carboxamide | Calc'd 376.2, found 376.2 |

TABLE 10-continued

| Example No. | Structure | IUPAC Name | Exact Mass [M + H]+ or [M + Na]+ |
|---|---|---|---|
| 380 | 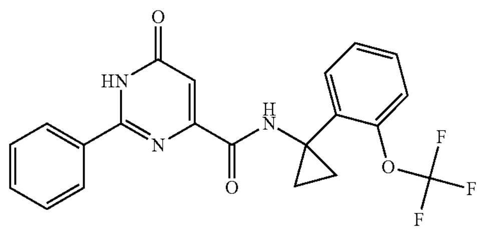 [SMILES: O=C(NC1(c2ccccc2OC(F)(F)F)CC1)c1cc(=O)[nH]c(-c2ccccc2)n1] | 6-oxo-2-phenyl-N-{1-[2-(trifluoromethoxy)phenyl]cyclopropyl}-1,6-dihydropyrimidine-4-carboxamide | Calc'd 416.1, found 416.1 |
| 381 | 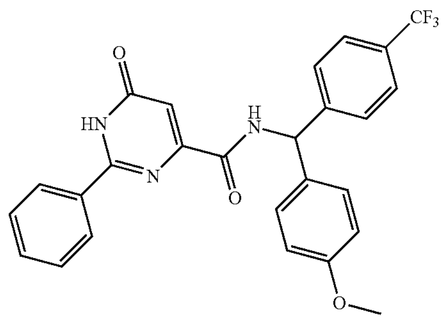 [SMILES: COc1ccc(C(NC(=O)c2cc(=O)[nH]c(-c3ccccc3)n2)c2ccc(C(F)(F)F)cc2)cc1] | N-{(4-methoxyphenyl)[4-(trifluoromethyl)phenyl]methyl}-6-oxo-2-phenyl-1,6-dihydropyrimidine-4-carboxamide | Calc'd 480.2, found 480.1 |
| 382 | 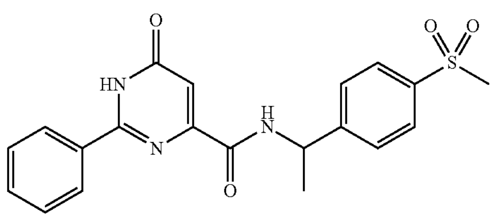 [SMILES: CC(NC(=O)c1cc(=O)[nH]c(-c2ccccc2)n1)c1ccc(S(C)(=O)=O)cc1] | N-{1-[4-(methylsulfonyl)phenyl]ethyl}-6-oxo-2-phenyl-1,6-dihydropyrimidine-4-carboxamide | Calc'd 398.1, found 398.1 |
| 383 | 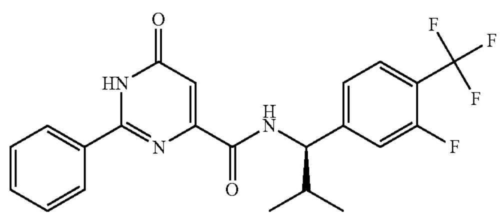 [SMILES: CC(C)[C@@H](NC(=O)c1cc(=O)[nH]c(-c2ccccc2)n1)c1ccc(C(F)(F)F)c(F)c1] | N-{(1R)-1-[3-fluoro-4-(trifluoromethyl)phenyl]-2-methylpropyl}-6-oxo-2-phenyl-1,6-dihydropyrimidine-4-carboxamide | Calc'd 434.1, found 434.2 |
| 384 | 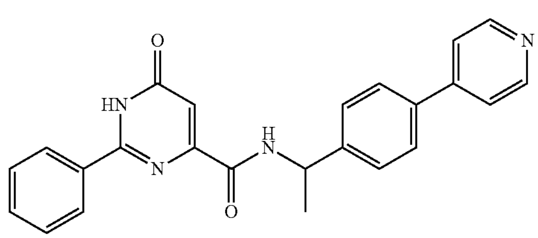 [SMILES: CC(NC(=O)c1cc(=O)[nH]c(-c2ccccc2)n1)c1ccc(-c2ccncc2)cc1] | 6-oxo-2-phenyl-N-[1-(4-pyridin-4-ylphenyl)ethyl]-1,6-dihydropyrimidine-4-carboxamide | Calc'd 397.2, found 397.2 |
| 385 | 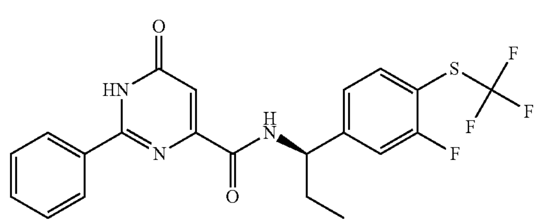 [SMILES: CC[C@@H](NC(=O)c1cc(=O)[nH]c(-c2ccccc2)n1)c1ccc(SC(F)(F)F)c(F)c1] | N-[(1R)-1-{3-fluoro-4-[(trifluoromethyl)sulfanyl]phenyl}propyl]-6-oxo-2-phenyl-1,6-dihydropyrimidine-4-carboxamide | Calc'd 452.1, found 452.1 |

TABLE 10-continued

| Example No. | Structure | IUPAC Name | Exact Mass [M + H]+ or [M + Na]+ |
|---|---|---|---|
| 386 | 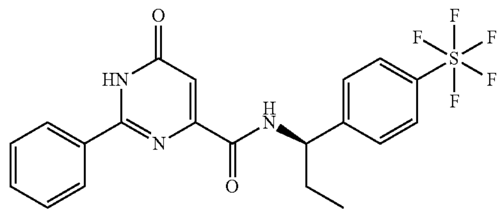 [SMILES: CC[C@@H](NC(=O)c1cc(=O)[nH]c(-c2ccccc2)n1)c1ccc(S(F)(F)(F)(F)F)cc1] | 6-oxo-N-{(1R)-1-[4-(pentafluoro-λ6-sulfanyl)phenyl]propyl}-2-phenyl-1,6-dihydropyrimidine-4-carboxamide | Calc'd 460.1, found 460.1 |
| 387 | 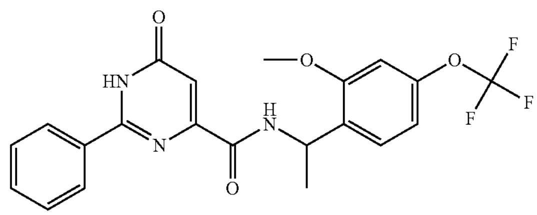 [SMILES: COc1cc(OC(F)(F)F)ccc1C(C)NC(=O)c1cc(=O)[nH]c(-c2ccccc2)n1] | N-{1-[2-methoxy-4-(trifluoromethoxy)phenyl]ethyl}-6-oxo-2-phenyl-1,6-dihydropyrimidine-4-carboxamide | Calc'd 434.1, found 434.1 |
| 388 | 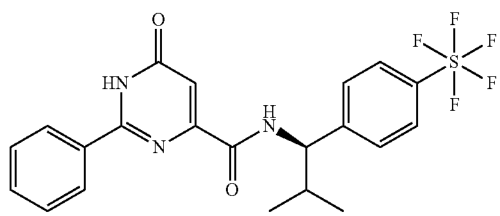 [SMILES: CC(C)[C@@H](NC(=O)c1cc(=O)[nH]c(-c2ccccc2)n1)c1ccc(S(F)(F)(F)(F)F)cc1] | N-{(1R)-2-methyl-1-[4-(pentafluoro-λ6-sulfanyl)phenyl]propyl}-6-oxo-2-phenyl-1,6-dihydropyrimidine-4-carboxamide | Calc'd 474.1, found 474.1 |
| 389 | 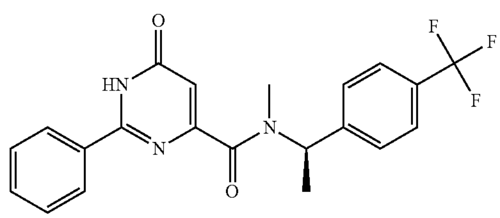 [SMILES: C[C@H](c1ccc(C(F)(F)F)cc1)N(C)C(=O)c1cc(=O)[nH]c(-c2ccccc2)n1] | N-methyl-6-oxo-2-phenyl-N-{(1R)-1-[4-(trifluoromethyl)phenyl]ethyl}-1,6-dihydropyrimidine-4-carboxamide | Calc'd 402.1, found 402.2 |
| 390 | 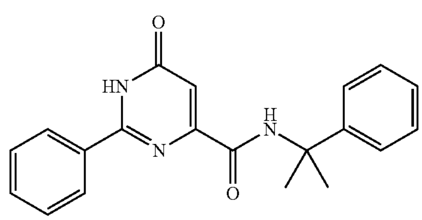 [SMILES: CC(C)(NC(=O)c1cc(=O)[nH]c(-c2ccccc2)n1)c1ccccc1] | N-(1-methyl-1-phenylethyl)-6-oxo-2-phenyl-1,6-dihydropyrimidine-4-carboxamide | Calc'd 334.2, found 334.1 |
| 391 | 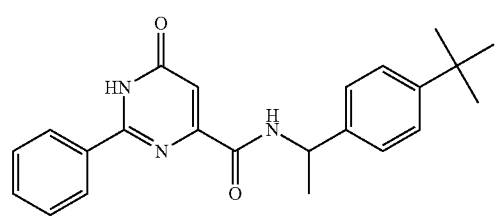 [SMILES: CC(NC(=O)c1cc(=O)[nH]c(-c2ccccc2)n1)c1ccc(C(C)(C)C)cc1] | N-[1-(4-tert-butylphenyl)ethyl]-6-oxo-2-phenyl-1,6-dihydropyrimidine-4-carboxamide | Calc'd 376.2, found 376.2 |
| 392 | 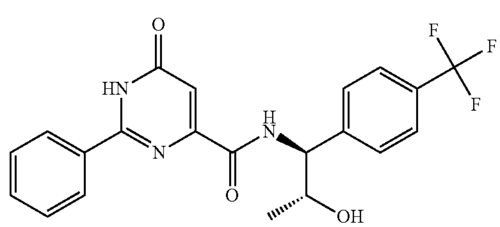 [SMILES: C[C@@H](O)[C@@H](NC(=O)c1cc(=O)[nH]c(-c2ccccc2)n1)c1ccc(C(F)(F)F)cc1] | N-{(1S,2R)-2-hydroxy-1-[4-(trifluoromethyl)phenyl]propyl}-6-oxo-2-phenyl-1,6-dihydropyrimidine-4-carboxamide | Calc'd 418.1, found 418.1 |

TABLE 10-continued

| Example No. | Structure | IUPAC Name | Exact Mass [M + H]+ or [M + Na]+ |
|---|---|---|---|
| 393 | 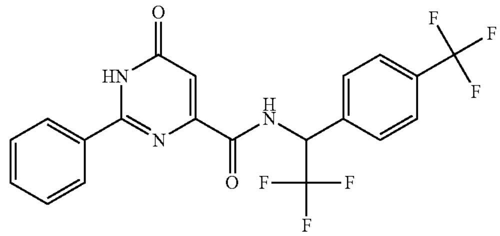 [SMILES: O=C(NC(c1ccc(C(F)(F)F)cc1)C(F)(F)F)c1cc(=O)[nH]c(-c2ccccc2)n1] | 6-oxo-2-phenyl-N-{2,2,2-trifluoro-1-[4-(trifluoromethyl)phenyl]ethyl}-1,6-dihydropyrimidine-4-carboxamide | Calc'd 442.1, found 442.1 |
| 394 | 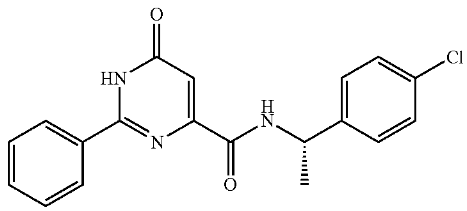 [SMILES: C[C@H](NC(=O)c1cc(=O)[nH]c(-c2ccccc2)n1)c1ccc(Cl)cc1] | N-[(1S)-1-(4-chlorophenyl)ethyl]-6-oxo-2-phenyl-1,6-dihydropyrimidine-4-carboxamide | Calc'd 354.1/356.1, found 354.1/356.1 |
| 395 | 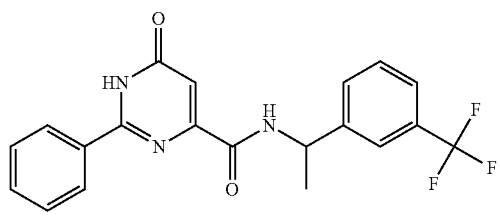 [SMILES: CC(NC(=O)c1cc(=O)[nH]c(-c2ccccc2)n1)c1cccc(C(F)(F)F)c1] | 6-oxo-2-phenyl-N-{1-[3-(trifluoromethyl)phenyl]ethyl}-1,6-dihydropyrimidine-4-carboxamide | Calc'd 388.1, found 388.2 |
| 396 | 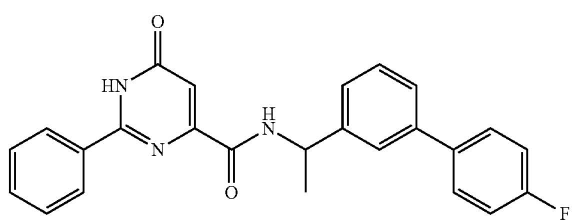 [SMILES: CC(NC(=O)c1cc(=O)[nH]c(-c2ccccc2)n1)c1cccc(-c2ccc(F)cc2)c1] | N-[1-(4'-fluorobiphenyl-3-yl)ethyl]-6-oxo-2-phenyl-1,6-dihydropyrimidine-4-carboxamide | Calc'd 414.2, found 414.2 |
| 397 | 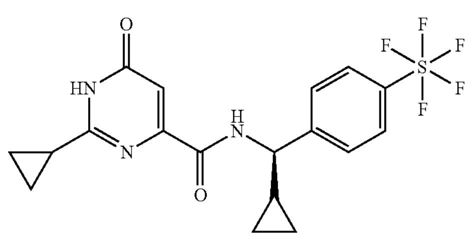 [SMILES: O=C(N[C@@H](c1ccc(S(F)(F)(F)(F)F)cc1)C1CC1)c1cc(=O)[nH]c(C2CC2)n1] | 2-cyclopropyl-N-{(R)-cyclopropyl[4-(pentafluoro-$\lambda^6$-sulfanyl)phenyl]methyl}-6-oxo-1,6-dihydropyrimidine-4-carboxamide | Calc'd 436.1, found 436.1 |
| 398 | 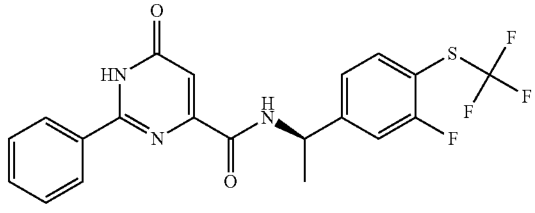 [SMILES: C[C@@H](NC(=O)c1cc(=O)[nH]c(-c2ccccc2)n1)c1ccc(SC(F)(F)F)c(F)c1] | N-[(1R)-1-{3-fluoro-4-[(trifluoromethyl)sulfanyl]phenyl}ethyl]-6-oxo-2-phenyl-1,6-dihydropyrimidine-4-carboxamide | Calc'd 438.1, found 438.1 |

TABLE 10-continued

| Example No. | Structure | IUPAC Name | Exact Mass [M + H]+ or [M + Na]+ |
|---|---|---|---|
| 399 | 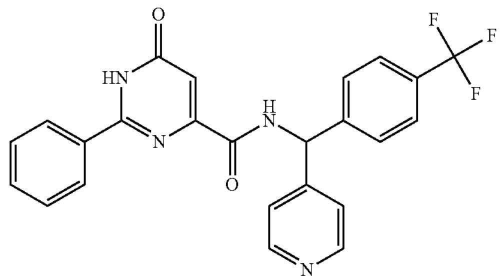 [SMILES: O=C(NC(c1ccncc1)c1ccc(C(F)(F)F)cc1)c1cc(=O)[nH]c(-c2ccccc2)n1] | 6-oxo-2-phenyl-N-{pyridin-4-yl[4-(trifluoromethyl)phenyl]methyl}-1,6-dihydropyrimidine-4-carboxamide | Calc'd 451.1, found 451.1 |
| 400 | 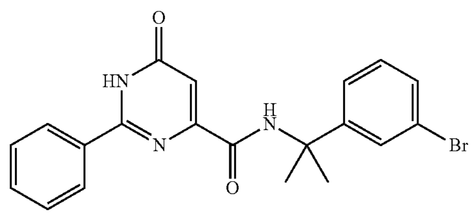 [SMILES: CC(C)(NC(=O)c1cc(=O)[nH]c(-c2ccccc2)n1)c1cccc(Br)c1] | N-[1-(3-bromophenyl)-1-methylethyl]-6-oxo-2-phenyl-1,6-dihydropyrimidine-4-carboxamide | Calc'd 412.1/ 414.1, found 412.0/ 414.0 |
| 401 | 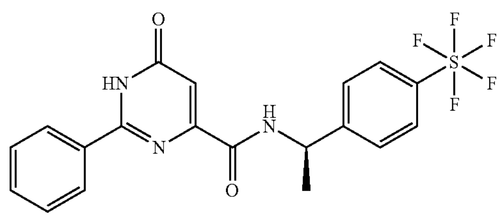 [SMILES: C[C@@H](NC(=O)c1cc(=O)[nH]c(-c2ccccc2)n1)c1ccc(S(F)(F)(F)(F)F)cc1] | 6-oxo-N-{(1R)-1-[4-(pentafluoro-$\lambda^6$-sulfanyl)phenyl]ethyl}-2-phenyl-1,6-dihydropyrimidine-4-carboxamide | Calc'd 446.1, found 446.1 |
| 402 | 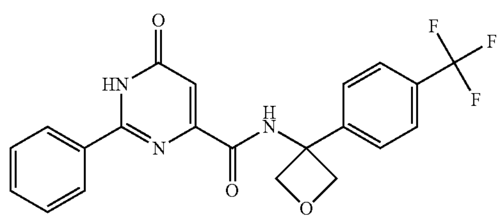 [SMILES: O=C(NC1(c2ccc(C(F)(F)F)cc2)COC1)c1cc(=O)[nH]c(-c2ccccc2)n1] | 6-oxo-2-phenyl-N-{3-[4-(trifluoromethyl)phenyl]oxetan-3-yl}-1,6-dihydropyrimidine-4-carboxamide | Calc'd 416.1, found 416.1 |
| 403 | 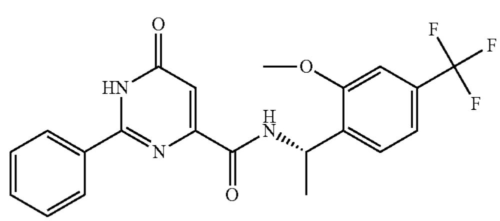 [SMILES: COc1cc(C(F)(F)F)ccc1[C@H](C)NC(=O)c1cc(=O)[nH]c(-c2ccccc2)n1] | N-{(1S)-1-[2-methoxy-4-(trifluoromethyl)phenyl]ethyl}-6-oxo-2-phenyl-1,6-dihydropyrimidine-4-carboxamide | Calc'd 418.1, found 418.1 |
| 404 | 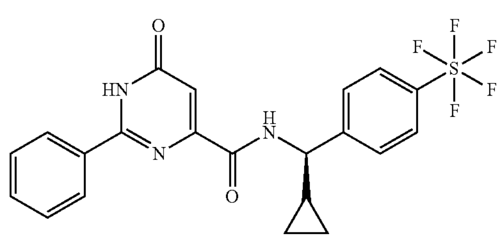 [SMILES: O=C(N[C@@H](c1ccc(S(F)(F)(F)(F)F)cc1)C1CC1)c1cc(=O)[nH]c(-c2ccccc2)n1] | N-{(R)-cyclopropyl[4-(pentafluoro-$\lambda^6$-sulfanyl)phenyl]methyl}-6-oxo-2-phenyl-1,6-dihydropyrimidine-4-carboxamide | Calc'd 472.1, found 472.1 |

TABLE 10-continued

| Example No. | Structure | IUPAC Name | Exact Mass [M + H]+ or [M + Na]+ |
|---|---|---|---|
| 405 | 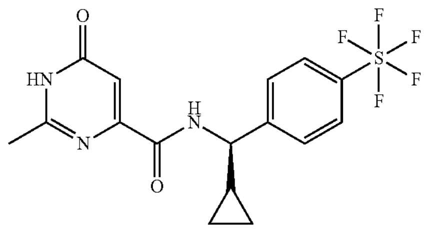 [SMILES: Cc1nc(C(=O)N[C@@H](c2ccc(S(F)(F)(F)(F)F)cc2)C2CC2)cc(=O)[nH]1] | N-{(R)-cyclopropyl[4-(pentafluoro-λ⁶-sulfanyl)phenyl]methyl}-2-methyl-6-oxo-1,6-dihydropyrimidine-4-carboxamide | Calc'd 410.1, found 410.1 |
| 406 | 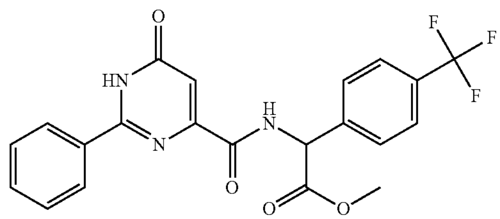 [SMILES: COC(=O)C(NC(=O)c1cc(=O)[nH]c(-c2ccccc2)n1)c1ccc(C(F)(F)F)cc1] | methyl {[(6-oxo-2-phenyl-1,6-dihydropyrimidin-4-yl)carbonyl]amino}[4-(trifluoromethyl)phenyl]acetate | Calc'd 432.1, found 432.1 |
| 407 | 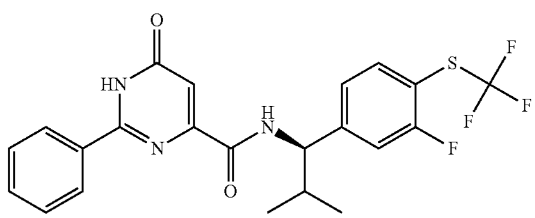 [SMILES: CC(C)[C@@H](NC(=O)c1cc(=O)[nH]c(-c2ccccc2)n1)c1ccc(SC(F)(F)F)c(F)c1] | N-[(1R)-1-{3-fluoro-4-[(trifluoromethyl)sulfanyl]phenyl}-2-methylpropyl]-6-oxo-2-phenyl-1,6-dihydropyrimidine-4-carboxamide | Calc'd 466.1, found 466.1 |
| 408 | 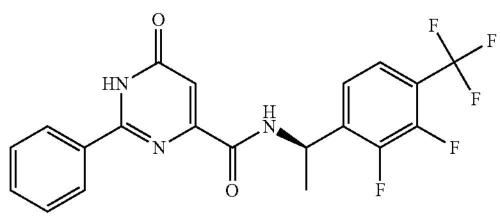 [SMILES: C[C@@H](NC(=O)c1cc(=O)[nH]c(-c2ccccc2)n1)c1ccc(C(F)(F)F)c(F)c1F] | N-{(1R)-1-[2,3-difluoro-4-(trifluoromethyl)phenyl]ethyl}-6-oxo-2-phenyl-1,6-dihydropyrimidine-4-carboxamide | Calc'd 424.1, found 424.1 |
| 409 | 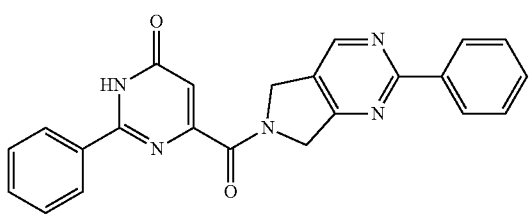 [SMILES: O=C(c1cc(=O)[nH]c(-c2ccccc2)n1)N1Cc2cnc(-c3ccccc3)nc2C1] | 2-phenyl-6-[(2-phenyl-5,7-dihydro-6H-pyrrolo[3,4-d]pyrimidin-6-yl)carbonyl]pyrimidin-4(3H)-one | Calc'd 396.1, found 396.2 |
| 410 | 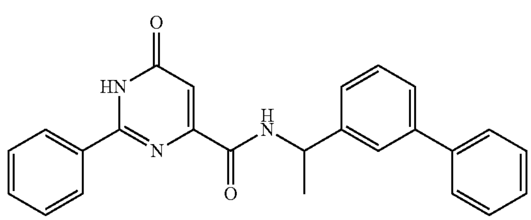 [SMILES: CC(NC(=O)c1cc(=O)[nH]c(-c2ccccc2)n1)c1cccc(-c2ccccc2)c1] | N-(1-biphenyl-3-ylethyl)-6-oxo-2-phenyl-1,6-dihydropyrimidine-4-carboxamide | Calc'd 396.2, found 396.2 |
| 411 | 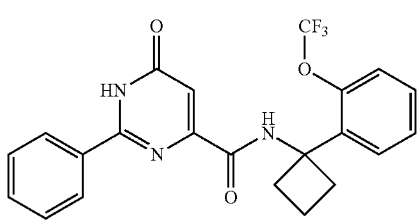 [SMILES: O=C(NC1(c2ccccc2OC(F)(F)F)CCC1)c1cc(=O)[nH]c(-c2ccccc2)n1] | 6-oxo-2-phenyl-N-{1-[2-(trifluoromethoxy)phenyl]cyclobutyl}-1,6-dihydropyrimidine-4-carboxamide | Calc'd 430.1, found 430.1 |

TABLE 10-continued

| Example No. | Structure | IUPAC Name | Exact Mass [M + H]+ or [M + Na]+ |
|---|---|---|---|
| 412 | 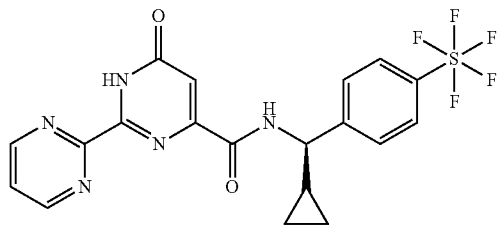 [SMILES: O=C(N[C@@H](c1ccc(S(F)(F)(F)(F)F)cc1)C1CC1)c1cc(=O)[nH]c(-c2ncccn2)n1] | N-{(R)-cyclopropyl[4-(pentafluoro-λ⁶-sulfanyl)phenyl]methyl}-6-oxo-1,6-dihydro-2,2'-bipyrimidine-4-carboxamide | Calc'd 474.1, found 474.1 |
| 413 | 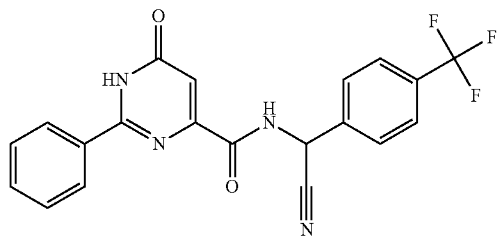 [SMILES: N#CC(NC(=O)c1cc(=O)[nH]c(-c2ccccc2)n1)c1ccc(C(F)(F)F)cc1] | N-{cyano[4-(trifluoromethyl)phenyl]methyl}-6-oxo-2-phenyl-1,6-dihydropyrimidine-4-carboxamide | Calc'd 399.1, found 399.1 |
| 414 | 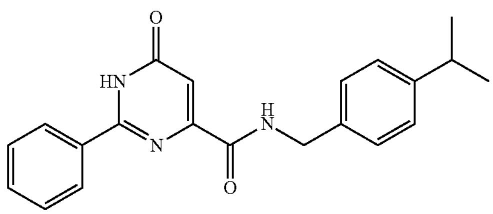 [SMILES: CC(C)c1ccc(CNC(=O)c2cc(=O)[nH]c(-c3ccccc3)n2)cc1] | N-[4-(1-methylethyl)benzyl]-6-oxo-2-phenyl-1,6-dihydropyrimidine-4-carboxamide | Calc'd 348.2, found 348.2 |
| 415 | 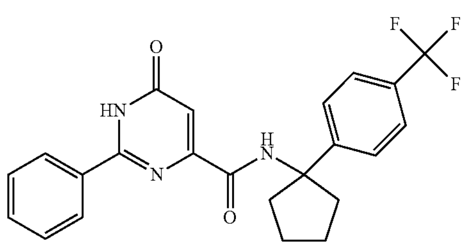 [SMILES: O=C(NC1(c2ccc(C(F)(F)F)cc2)CCCC1)c1cc(=O)[nH]c(-c2ccccc2)n1] | 6-oxo-2-phenyl-N-{1-[4-(trifluoromethyl)phenyl]cyclopentyl}-1,6-dihydropyrimidine-4-carboxamide | Calc'd 428.2, found 428.2 |
| 416 | 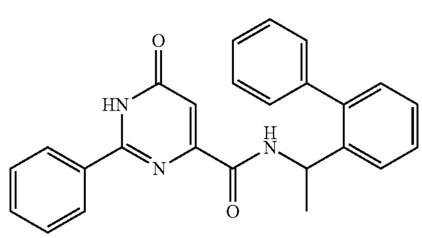 [SMILES: CC(NC(=O)c1cc(=O)[nH]c(-c2ccccc2)n1)c1ccccc1-c1ccccc1] | N-(1-biphenyl-2-ylethyl)-6-oxo-2-phenyl-1,6-dihydropyrimidine-4-carboxamide | Calc'd 396.2, found 396.2 |
| 417 | 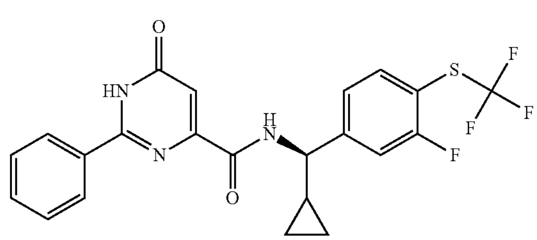 [SMILES: O=C(N[C@@H](c1ccc(SC(F)(F)F)c(F)c1)C1CC1)c1cc(=O)[nH]c(-c2ccccc2)n1] | N-[(R)-cyclopropyl{3-fluoro-4-[(trifluoromethyl)sulfanyl]phenyl}methyl]-6-oxo-2-phenyl-1,6-dihydropyrimidine-4-carboxamide | Calc'd 464.1, found 464.1 |

TABLE 10-continued

| Example No. | Structure | IUPAC Name | Exact Mass [M + H]+ or [M + Na]+ |
|---|---|---|---|
| 418 | 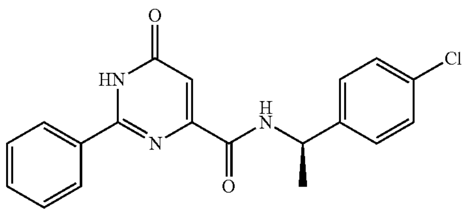 [SMILES: C[C@@H](NC(=O)c1cc(=O)[nH]c(-c2ccccc2)n1)c1ccc(Cl)cc1] | N-[(1R)-1-(4-chlorophenyl)ethyl]-6-oxo-2-phenyl-1,6-dihydropyrimidine-4-carboxamide | Calc'd 354.1, found 354.1 |
| 419 | 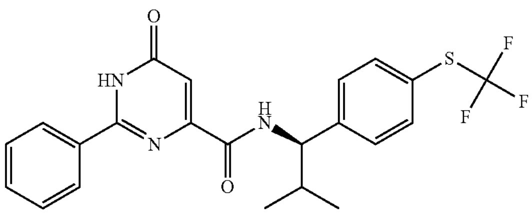 [SMILES: CC(C)[C@@H](NC(=O)c1cc(=O)[nH]c(-c2ccccc2)n1)c1ccc(SC(F)(F)F)cc1] | N-[(1R)-2-methyl-1-{4-[(trifluoromethyl)sulfanyl]phenyl}propyl]-6-oxo-2-phenyl-1,6-dihydropyrimidine-4-carboxamide | Calc'd 448.1, found 448.1 |
| 420 | 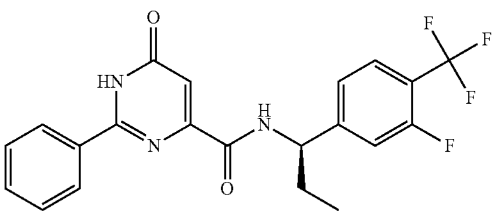 [SMILES: CC[C@@H](NC(=O)c1cc(=O)[nH]c(-c2ccccc2)n1)c1ccc(C(F)(F)F)c(F)c1] | N-{(1R)-1-[3-fluoro-4-(trifluoromethyl)phenyl]propyl}-6-oxo-2-phenyl-1,6-dihydropyrimidine-4-carboxamide | Calc'd 420.1, found 420.1 |
| 421 | 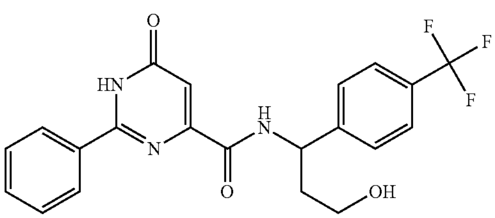 [SMILES: O=C(NC(CCO)c1ccc(C(F)(F)F)cc1)c1cc(=O)[nH]c(-c2ccccc2)n1] | N-{3-hydroxy-1-[4-(trifluoromethyl)phenyl]propyl}-6-oxo-2-phenyl-1,6-dihydropyrimidine-4-carboxamide | Calc'd 418.1, found 418.1 |
| 422 | 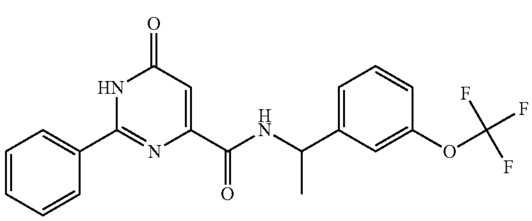 [SMILES: CC(NC(=O)c1cc(=O)[nH]c(-c2ccccc2)n1)c1cccc(OC(F)(F)F)c1] | 6-oxo-2-phenyl-N-{1-[3-(trifluoromethoxy)phenyl]ethyl}-1,6-dihydropyrimidine-4-carboxamide | Calc'd 404.1, found 404.1 |
| 423 | 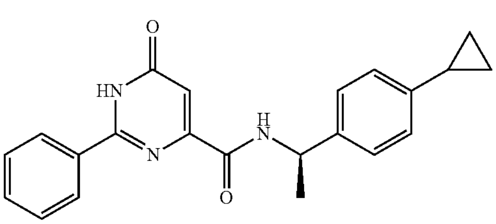 [SMILES: C[C@@H](NC(=O)c1cc(=O)[nH]c(-c2ccccc2)n1)c1ccc(C2CC2)cc1] | N-[(1R)-1-(4-cyclopropylphenyl)ethyl]-6-oxo-2-phenyl-1,6-dihydropyrimidine-4-carboxamide | Calc'd 360.2, found 360.3 |

Table 11 listed additional compounds of the invention prepared using the procedure shown in Scheme E, exemplified by Example 142.

TABLE 11

| Example Number | Structure | IUPAC Name | Exact Mass [M + H]+ |
|---|---|---|---|
| 424 | 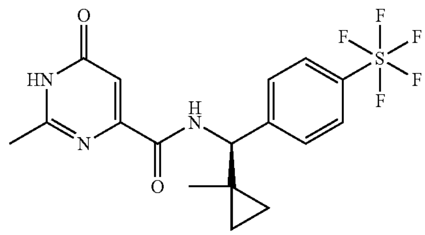 [SMILES: Cc1nc(C(=O)N[C@@H](c2ccc(S(F)(F)(F)(F)F)cc2)C2(C)CC2)cc(=O)[nH]1] | 2-methyl-N-{(R)-(1-methylcyclopropyl)[4-(pentafluoro-λ⁶-sulfanyl)phenyl]methyl}-6-oxo-1,6-dihydropyrimidine-4-carboxamide | Calc'd 424.1, found 424.1 |
| 425 | 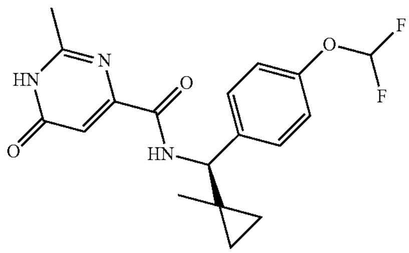 [SMILES: Cc1nc(C(=O)N[C@@H](c2ccc(OC(F)F)cc2)C2(C)CC2)cc(=O)[nH]1] | N-[(R)-[4-(difluoromethoxy)phenyl](1-methylcyclopropyl)methyl]-2-methyl-6-oxo-1,6-dihydropyrimidine-4-carboxamide | Calc'd 364.1, found 364.0 |
| 426 | 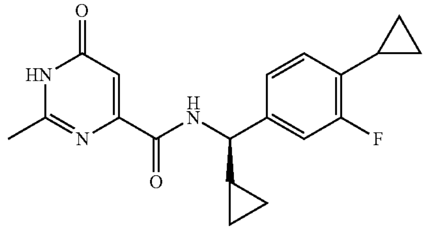 [SMILES: Cc1nc(C(=O)N[C@@H](c2ccc(C3CC3)c(F)c2)C2CC2)cc(=O)[nH]1] | N-[(R)-cyclopropyl(4-cyclopropyl-3-fluorophenyl)methyl]-2-methyl-6-oxo-1,6-dihydropyrimidine-4-carboxamide | Calc'd 342.2, found 342.3 |
| 427 | 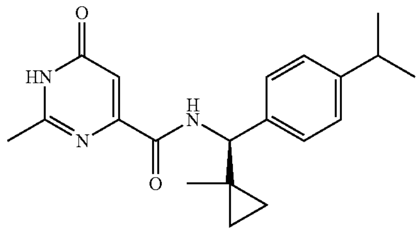 [SMILES: Cc1nc(C(=O)N[C@@H](c2ccc(C(C)C)cc2)C2(C)CC2)cc(=O)[nH]1] | 2-methyl-N-{(R)-(1-methylcyclopropyl)[4-(1-methylethyl)phenyl]methyl}-6-oxo-1,6-dihydropyrimidine-4-carboxamide | Calc'd 340.2, found 340.2 |
| 428 | 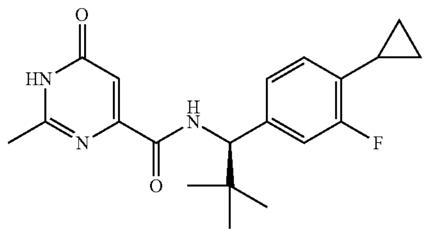 [SMILES: Cc1nc(C(=O)N[C@@H](c2ccc(C3CC3)c(F)c2)C(C)(C)C)cc(=O)[nH]1] | N-[(1R)-1-(4-cyclopropyl-3-fluorophenyl)-2,2-dimethylpropyl]-2-methyl-6-oxo-1,6-dihydropyrimidine-4-carboxamide | Calc'd 358.2, found 358.2 |
| 429 | 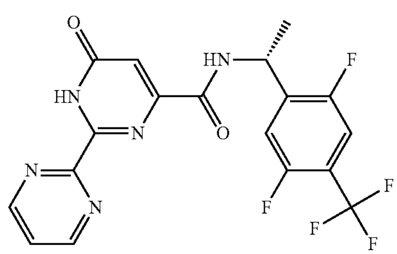 [SMILES: C[C@@H](NC(=O)c1cc(=O)[nH]c(-c2ncccn2)n1)c1cc(F)c(C(F)(F)F)cc1F] | N-{(1R)-1-[2,5-difluoro-4-(trifluoromethyl)phenyl]ethyl}-6-oxo-1,6-dihydro-2,2'-bipyrimidine-4-carboxamide | Calc'd 426.1, found 426.0 |

TABLE 11-continued

| Example Number | Structure | IUPAC Name | Exact Mass [M + H]+ |
|---|---|---|---|
| 430 | 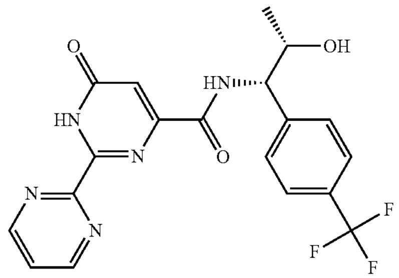 [SMILES: C[C@H](O)[C@@H](NC(=O)c1cc(=O)[nH]c(-c2ncccn2)n1)c1ccc(C(F)(F)F)cc1] | N-{(1S,2)S-2-hydroxy-1-[4-(trifluoromethyl)phenyl]propyl}-6-oxo-1,6-dihydro-2,2'-bipyrimidine-4-carboxamide | Calc'd 420.1, found 420.0 |
| 431 | 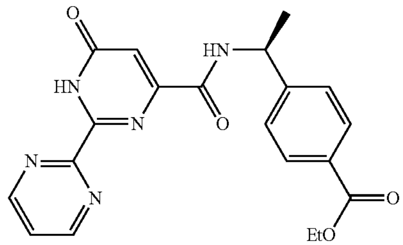 [SMILES: CCOC(=O)c1ccc([C@H](C)NC(=O)c2cc(=O)[nH]c(-c3ncccn3)n2)cc1] | ethyl 4-[(1S)-1-{[(6-oxo-1,6-dihydro-2,2'-bipyrimidin-4-yl)carbonyl]amino}ethyl]benzoate | Calc'd 394.2, found 394.1 |
| 432 | 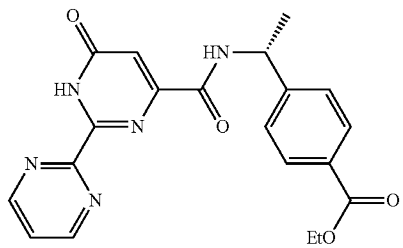 [SMILES: CCOC(=O)c1ccc([C@@H](C)NC(=O)c2cc(=O)[nH]c(-c3ncccn3)n2)cc1] | ethyl 4-[(1R)-1-{[(6-oxo-1,6-dihydro-2,2'-bipyrimidin-4-yl)carbonyl]amino}ethyl]benzoate | Calc'd 394.2, found 394.1 |
| 433 | 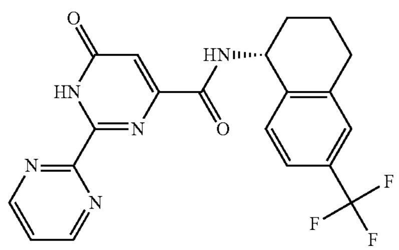 [SMILES: O=C(N[C@@H]1CCCc2cc(C(F)(F)F)ccc21)c1cc(=O)[nH]c(-c2ncccn2)n1] | 6-oxo-N-[(1R)-6-(trifluoromethyl)-1,2,3,4-tetrahydronaphthalen-1-yl]-1,6-dihydro-2,2'-bipyrimidine-4-carboxamide | Calc'd 416.1, found 416.1 |
| 434 | 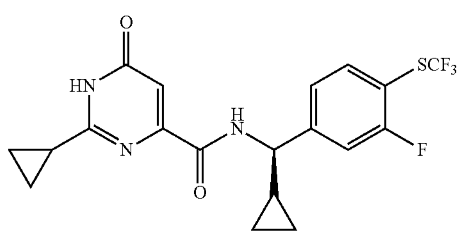 | 2-cyclopropyl-N-[(R)-cyclopropyl{3-fluoro-4-(trifluoromethyl)sulfanyl]phenyl}methyl]-6-oxo-1,6-dihydropyrimidine-4-carboxamide | Calc'd 428.1, found 428.1 |
| 435 | 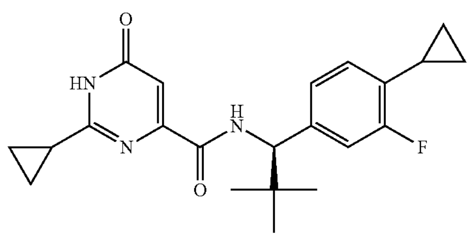 [SMILES: CC(C)(C)[C@@H](NC(=O)c1cc(=O)[nH]c(C2CC2)n1)c1ccc(C2CC2)c(F)c1] | 2-cyclopropyl-N-[(1R)-1-(4-cyclopropyl-3-fluorophenyl)-2,2-dimethylpropyl]-6-oxo-1,6-dihydropyrimidine-4-carboxamide | Calc'd 384.2, found 384.1 |

TABLE 11-continued

| Example Number | Structure | IUPAC Name | Exact Mass [M + H]+ |
|---|---|---|---|
| 436 | 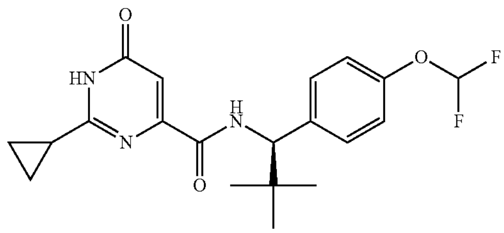 [SMILES: CC(C)(C)[C@@H](NC(=O)c1cc(=O)[nH]c(C2CC2)n1)c1ccc(OC(F)F)cc1] | 2-cyclopropyl-N-{(1R)-1-[4-(difluoromethoxy)phenyl]-2,2-dimethylpropyl}-6-oxo-1,6-dihydropyrimidine-4-carboxamide | Calc'd 392.2, found 392.1 |
| 437 | 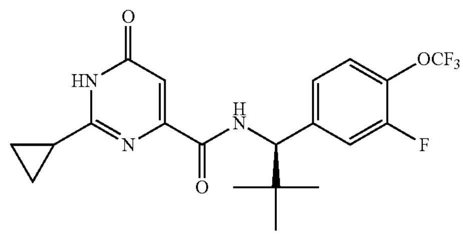 [SMILES: CC(C)(C)[C@@H](NC(=O)c1cc(=O)[nH]c(C2CC2)n1)c1ccc(OC(F)(F)F)c(F)c1] | 2-cyclopropyl-N-{(1R)-1-[3-fluoro-4-(trifluoromethoxy)phenyl]-2,2-dimethylpropyl}-6-oxo-1,6-dihydropyrimidine-4-carboxamide | Calc'd 428.2, found 428.1 |
| 438 | 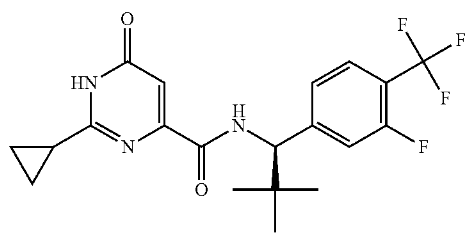 [SMILES: CC(C)(C)[C@@H](NC(=O)c1cc(=O)[nH]c(C2CC2)n1)c1ccc(C(F)(F)F)c(F)c1] | 2-cyclopropyl-N-{(1R)-1-[3-fluoro-4-(trifluoromethyl)phenyl]-2,2-dimethylpropyl}-6-oxo-1,6-dihydropyrimidine-4-carboxamide | Calc'd 412.2, found 412.1 |
| 439 | 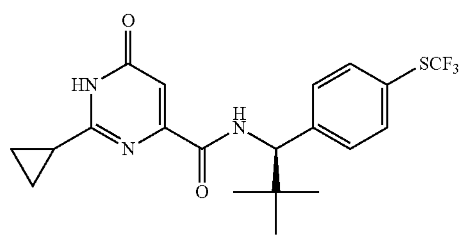 | 2-cyclopropyl-N-[(1R)-2,2-dimethyl-1-{4-[(trifluoromethyl)sulfanyl]phenyl}propyl]-6-oxo-1,6-dihydropyrimidine-4-carboxamide | Calc'd 426.1, found 426.1 |
| 440 | 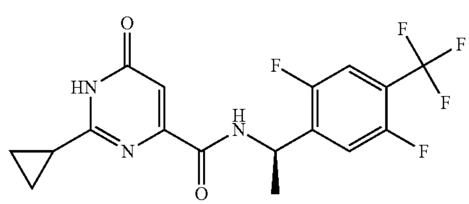 [SMILES: C[C@@H](NC(=O)c1cc(=O)[nH]c(C2CC2)n1)c1cc(F)c(C(F)(F)F)cc1F] | 2-cyclopropyl-N-{(1R)-1-[2,5-difluoro-4-(trifluoromethyl)phenyl]ethyl}-6-oxo-1,6-dihydropyrimidine-4-carboxamide | Calc'd 388.1, found 388.0 |
| 441 | 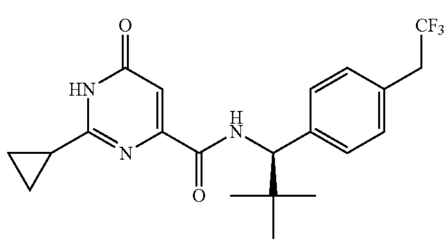 [SMILES: CC(C)(C)[C@@H](NC(=O)c1cc(=O)[nH]c(C2CC2)n1)c1ccc(CC(F)(F)F)cc1] | 2-cyclopropyl-N-{(1R)-2,2-dimethyl-1-[4-(2,2,2-trifluoroethyl)phenyl]propyl}-6-oxo-1,6-dihydropyrimidine-4-carboxamide | Calc'd 408.2, found 408.1 |

TABLE 11-continued

| Example Number | Structure | IUPAC Name | Exact Mass [M + H]+ |
|---|---|---|---|
| 442 | 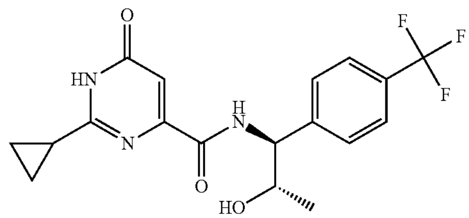 [SMILES: C[C@H](O)[C@@H](NC(=O)c1cc(=O)[nH]c(C2CC2)n1)c1ccc(C(F)(F)F)cc1] | 2-cyclopropyl-N-{(1S,2S)-2-hydroxy-1-[4-(trifluoromethyl)phenyl]propyl}-6-oxo-1,6-dihydropyrimidine-4-carboxamide | Calc'd 382.1, found 382.1 |
| 443 | 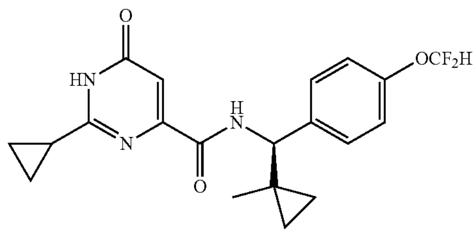 | 2-cyclopropyl-N-[(1R)-[4-(difluoromethoxy)phenyl](1-methylcyclopropyl)methyl]-6-oxo-1,6-dihydropyrimidine-4-carboxamide | Calc'd 390.2, found 390.1 |
| 444 | 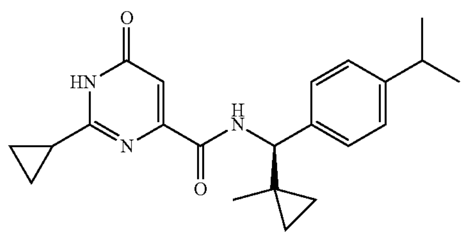 [SMILES: CC(C)c1ccc([C@H](NC(=O)c2cc(=O)[nH]c(C3CC3)n2)C2(C)CC2)cc1] | 2-cyclopropyl-N-{(R)-(1-methylcyclopropyl)[4-(1-methylethyl)phenyl]methyl}-6-oxo-1,6-dihydropyrimidine-4-carboxamide | Calc'd 366.2, found 366.1 |
| 445 | 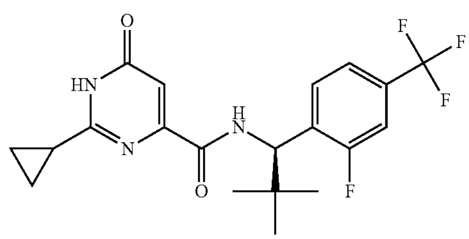 [SMILES: CC(C)(C)[C@@H](NC(=O)c1cc(=O)[nH]c(C2CC2)n1)c1ccc(C(F)(F)F)cc1F] | 2-cyclopropyl-N-{(1R)-1-[2-fluoro-4-(trifluoromethyl)phenyl]-2,2-dimethylpropyl}-6-oxo-1,6-dihydropyrimidine-4-carboxamide | Calc'd 412.2, found 412.1 |
| 446 | 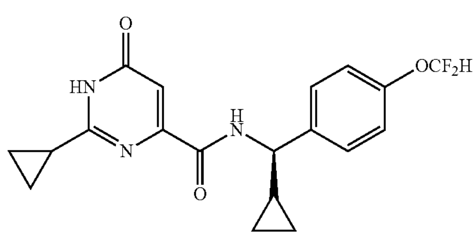 | 2-cyclopropyl-N-{(R)-cyclopropyl[4-(difluoromethoxy)phenyl]methyl}-6-oxo-1,6-dihydropyrimidine-4-carboxamide | Calc'd 376.1, found 376.1 |
| 447 | 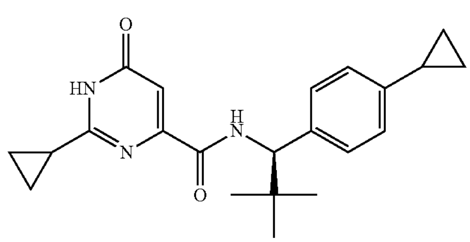 [SMILES: CC(C)(C)[C@@H](NC(=O)c1cc(=O)[nH]c(C2CC2)n1)c1ccc(C2CC2)cc1] | 2-cyclopropyl-N-[(1R)-1-(4-cyclopropylphenyl)-2,2-dimethylpropyl]-6-oxo-1,6-dihydropyrimidine-4-carboxamide | Calc'd 366.2, found 366.1 |

TABLE 11-continued

| Example Number | Structure | IUPAC Name | Exact Mass [M + H]+ |
|---|---|---|---|
| 448 | 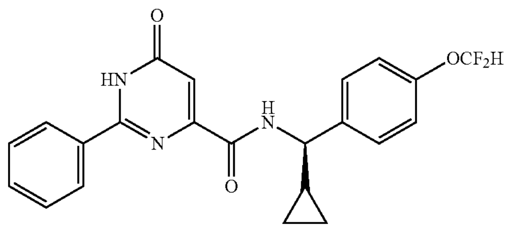 | N-{(R)-cyclopropyl[4-(difluoromethoxy)phenyl]methyl}-6-oxo-2-phenyl-1,6-dihydropyrimidine-4-carboxamide | Calc'd 412.1, found 412.1 |
| 449 | 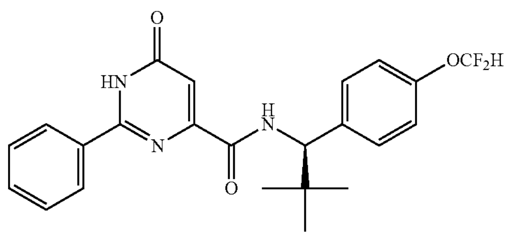 | N-{(1R)-1-[4-(difluoromethoxy)phenyl]-2,2-dimethylpropyl}-6-oxo-2-phenyl-1,6-dihydropyrimidine-4-carboxamide | Calc'd 428.2, found 428.2 |
| 450 | 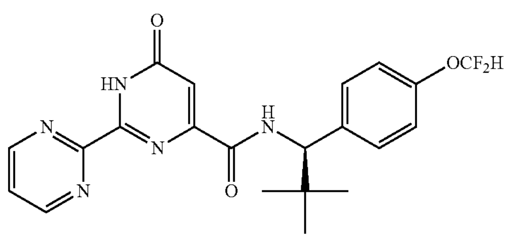 | N-{(1R)-1-[4-(difluoromethoxy)phenyl]-2,2-dimethylpropyl}-6-oxo-1,6-dihydro-2,2'-bipyrimidine-4-carboxamide | Calc'd 430.2, found 430.1 |
| 451 | 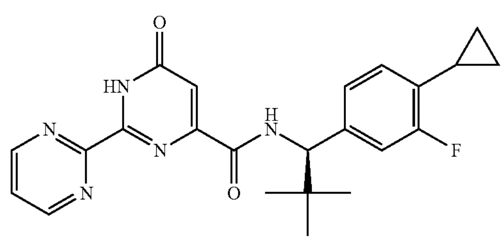 [SMILES: CC(C)(C)[C@@H](NC(=O)c1cc(=O)[nH]c(-c2ncccn2)n1)c1ccc(C2CC2)c(F)c1] | N-[(1R)-1-(4-cyclopropyl-3-fluorophenyl)-2,2-dimethylpropyl]-6-oxo-1,6-dihydro-2,2'-bipyrimidine-4-carboxamide | Calc'd 422.2, found 422.2 |
| 452 | 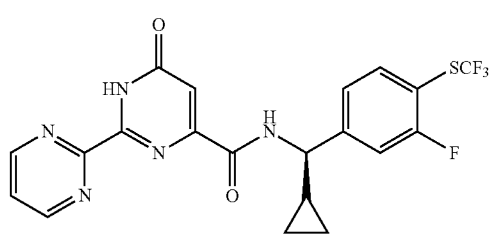 | N-[(R)-cyclopropyl{3-fluoro-4-[(trifluoromethyl)sulfanyl]phenyl}methyl]-6-oxo-1,6-dihydro-2,2'-bipyrimidine-4-carboxamide | Calc'd 466.1, found 466.0 |
| 453 | 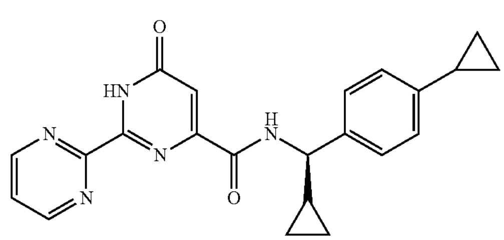 [SMILES: O=C(N[C@@H](c1ccc(C2CC2)cc1)C1CC1)c1cc(=O)[nH]c(-c2ncccn2)n1] | N-[(R)-cyclopropyl(4-cyclopropylphenyl)methyl]-6-oxo-1,6-dihydro-2,2'-bipyrimidine-4-carboxamide | Calc'd 388.2, found 388.1 |

TABLE 11-continued

| Example Number | Structure | IUPAC Name | Exact Mass [M + H]+ |
|---|---|---|---|
| 454 | 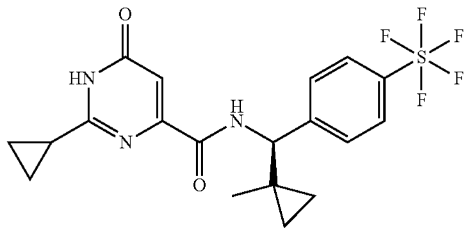 [SMILES: CC1([C@@H](NC(=O)c2cc(=O)[nH]c(C3CC3)n2)c2ccc(S(F)(F)(F)(F)F)cc2)CC1] | 2-cyclopropyl-N-{(R)-(1-methylcyclopropyl)[4-(pentafluoro-λ⁶-sulfanyl)phenyl]methyl}-6-oxo-1,6-dihydropyrimidine-4-carboxamide | Calc'd 450.1, found 450.1 |

Table 12 listed additional compounds of the invention prepared using the procedure shown in Scheme H, exemplified by Example 337.

TABLE 12

| Example Number | Structure | IUPAC Name | Exact Mass [M + H]+ |
|---|---|---|---|
| 455 | 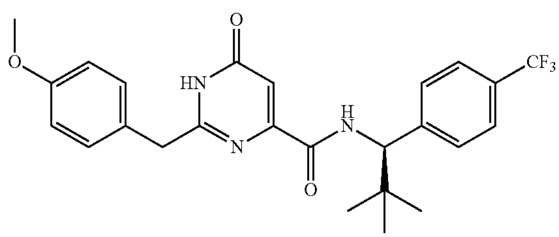 [SMILES: COc1ccc(Cc2nc(C(=O)N[C@@H](c3ccc(C(F)(F)F)cc3)C(C)(C)C)cc(=O)[nH]2)cc1] | N-{(1R)-2,2-dimethyl-1-[4-(trifluoromethyl)phenyl]propyl}-2-(4-methoxybenzyl)-6-oxo-1,6-dihydropyrimidine-4-carboxamide | 474.2 |
| 456 | 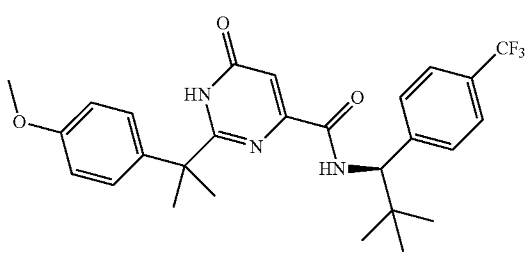 [SMILES: COc1ccc(C(C)(C)c2nc(C(=O)N[C@@H](c3ccc(C(F)(F)F)cc3)C(C)(C)C)cc(=O)[nH]2)cc1] | N-{(1R)-2,2-dimethyl-1-[4-(trifluoromethyl)phenyl]propyl}-2-[1-(4-methoxyphenyl)-1-methylethyl]-6-oxo-1,6-dihydropyrimidine-4-carboxamide | 502.4 |
| 457 | 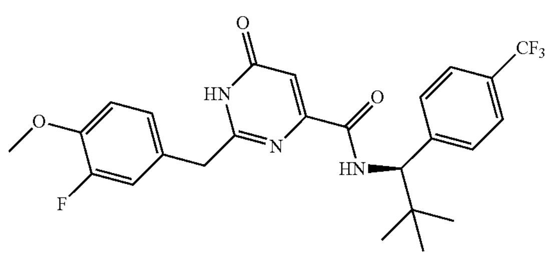 [SMILES: COc1ccc(Cc2nc(C(=O)N[C@@H](c3ccc(C(F)(F)F)cc3)C(C)(C)C)cc(=O)[nH]2)cc1F] | N-{(1R)-2,2-dimethyl-1-[4-(trifluoromethyl)phenyl]propyl}-2-(3-fluoro-4-methoxybenzyl)-6-oxo-1,6-dihydropyrimidine-4-carboxamide | 492.3 |
| 458 | 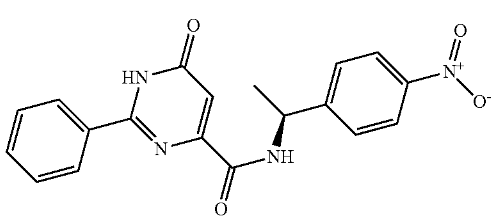 [SMILES: C[C@H](NC(=O)c1cc(=O)[nH]c(-c2ccccc2)n1)c1ccc([N+](=O)[O-])cc1] | N-[(1S)-1-(4-nitrophenyl)ethyl]-6-oxo-2-phenyl-1,6-dihydropyrimidine-4-carboxamide | 365.1 |

TABLE 12-continued

| Example Number | Structure | IUPAC Name | Exact Mass [M + H]+ |
|---|---|---|---|
| 459 | 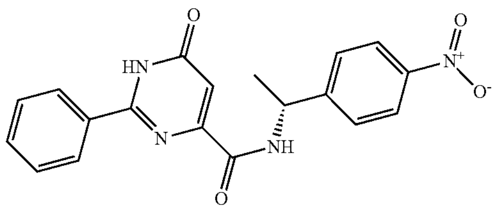 [SMILES: C[C@@H](NC(=O)c1cc(=O)[nH]c(-c2ccccc2)n1)c1ccc([N+](=O)[O-])cc1] | N-[(1R)-1-(4-nitrophenyl)ethyl]-6-oxo-2-phenyl-1,6-dihydropyrimidine-4-carboxamide | 365.1 |
| 460 | 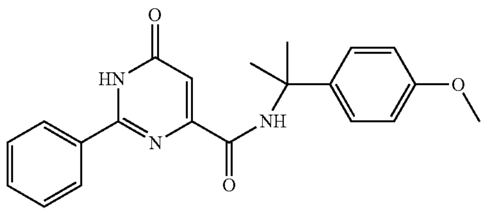 [SMILES: COc1ccc(C(C)(C)NC(=O)c2cc(=O)[nH]c(-c3ccccc3)n2)cc1] | N-[1-(4-methoxyphenyl)-1-methylethyl]-6-oxo-2-phenyl-1,6-dihydropyrimidine-4-carboxamide | 364.0 |
| 461 | 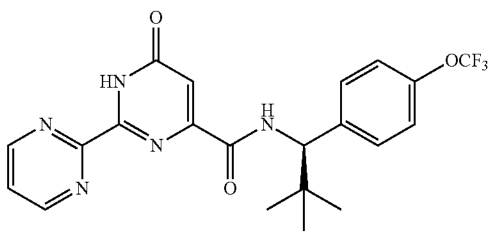 [SMILES: CC(C)(C)[C@@H](NC(=O)c1cc(=O)[nH]c(-c2ncccn2)n1)c1ccc(OC(F)(F)F)cc1] | N-{(1R)-2,2-dimethyl-1-[4-(trifluoromethoxy)phenyl]propyl}-6-oxo-1,6-dihydro-2,2'-bipyrimidine-4-carboxamide | 448.2 |
| 462 | 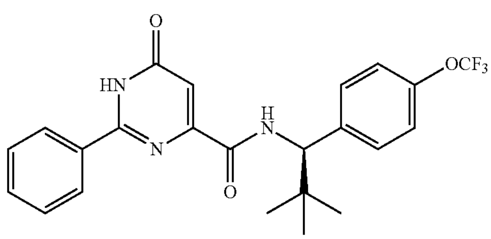 [SMILES: CC(C)(C)[C@@H](NC(=O)c1cc(=O)[nH]c(-c2ccccc2)n1)c1ccc(OC(F)(F)F)cc1] | N-{(1R)-2,2-dimethyl-1-[4-(trifluoromethoxy)phenyl]propyl}-6-oxo-2-phenyl-1,6-dihydropyrimidine-4-carboxamide | 446.2 |
| 463 | 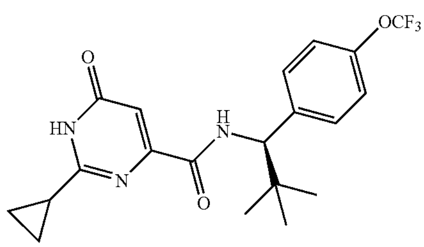 [SMILES: CC(C)(C)[C@@H](NC(=O)c1cc(=O)[nH]c(C2CC2)n1)c1ccc(OC(F)(F)F)cc1] | 2-cyclopropyl-N-{(1R)-2,2-dimethyl-1-[4-(trifluoromethoxy)phenyl]propyl}-6-oxo-1,6-dihydropyrimidine-4-carboxamide | 410.2 |
| 464 | 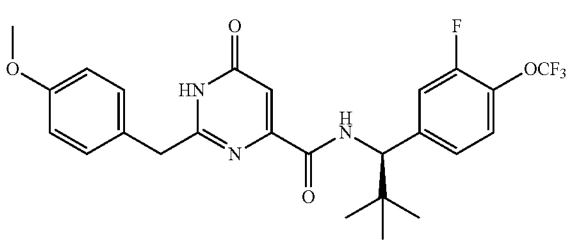 [SMILES: COc1ccc(Cc2nc(C(=O)N[C@@H](c3ccc(OC(F)(F)F)c(F)c3)C(C)(C)C)cc(=O)[nH]2)cc1] | N-{(1R)-1-[3-fluoro-4-(trifluoromethoxy)phenyl]-2,2-dimethylpropyl}-2-(4-methoxybenzyl)-6-oxo-1,6-dihydropyrimidine-4-carboxamide | 508.2 |

TABLE 12-continued

| Example Number | Structure | IUPAC Name | Exact Mass [M + H]+ |
|---|---|---|---|
| 465 | 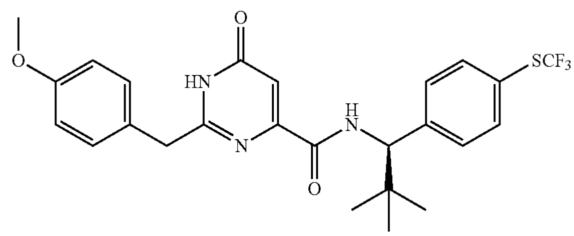 | N-[(1R)-2,2-dimethyl-1-{4-[(trifluoromethyl)sulfanyl]phenyl}propyl]-2-(4-methoxybenzyl)-6-oxo-1,6-dihydropyrimidine-4-carboxamide | 506.1 |
| 466 | 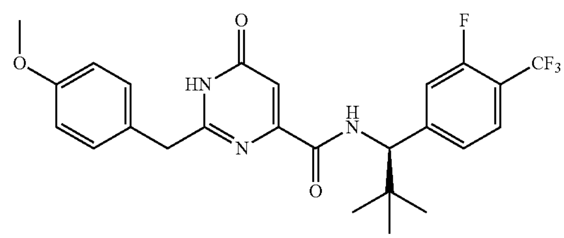 [SMILES: COc1ccc(Cc2nc(C(=O)N[C@@H](c3ccc(C(F)(F)F)c(F)c3)C(C)(C)C)cc(=O)[nH]2)cc1] | N-{(1R)-1-[3-fluoro-4-(trifluoromethyl)phenyl]-2,2-dimethylpropyl}-2-(4-methoxybenzyl)-6-oxo-1,6-dihydropyrimidine-4-carboxamide | 492.2 |
| 467 | 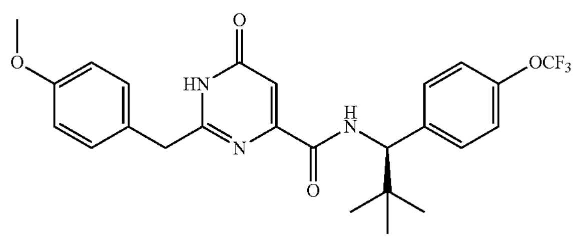 [SMILES: COc1ccc(Cc2nc(C(=O)N[C@@H](c3ccc(OC(F)(F)F)cc3)C(C)(C)C)cc(=O)[nH]2)cc1] | N-{(1R)-2,2-dimethyl-1-[4-(trifluoromethoxy)phenyl]propyl}-2-(4-methoxybenzyl)-6-oxo-1,6-dihydropyrimidine-4-carboxamide | 490.2 |
| 468 | 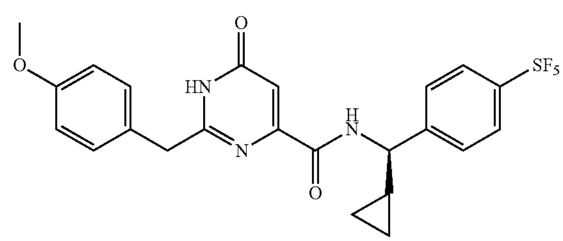 | N-{(R)-cyclopropyl[4-(pentafluoro-$\lambda^6$-sulfanyl)phenyl]methyl}-2-(4-methoxybenzyl)-6-oxo-1,6-dihydropyrimidine-4-carboxamide | 516.1 |
| 469 | 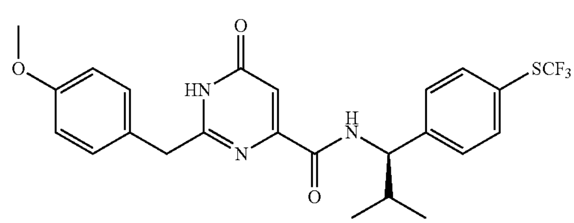 | 2-(4-methoxybenzyl)-N-[(1R)-2-methyl-1-{4-[(trifluoromethyl)sulfanyl]phenyl}propyl]-6-oxo-1,6-dihydropyrimidine-4-carboxamide | 492.2 |
| 470 | 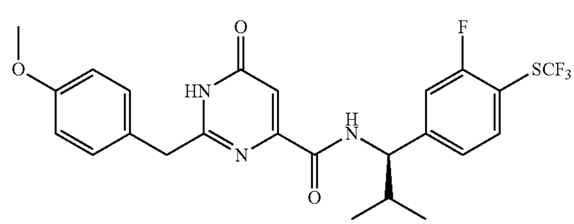 | N-[(1R)-1-{3-fluoro-4-[(trifluoromethyl)sulfanyl]phenyl}-2-methylpropyl]-2-(4-methoxybenzyl)-6-oxo-1,6-dihydropyrimidine-4-carboxamide | 510.1 |

TABLE 12-continued

| Example Number | Structure | IUPAC Name | Exact Mass [M + H]+ |
|---|---|---|---|
| 471 | 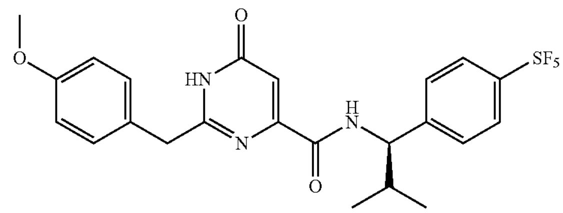 | 2-(4-methoxybenzyl)-N-[(1R)-2-methyl-1-[4-(pentafluoro-$\lambda^6$-sulfanyl)phenyl]propyl}-6-oxo-1,6-dihydropyrimidine-4-carboxamide | 518.1 |
| 472 | 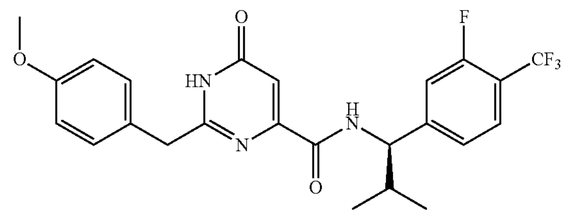 [SMILES: COc1ccc(Cc2nc(C(=O)N[C@@H](c3ccc(C(F)(F)F)c(F)c3)C(C)C)cc(=O)[nH]2)cc1] | N-{(1R)-1-[3-fluoro-4-(trifluoromethyl)phenyl]-2-methylpropyl}-2-(4-methoxybenzyl)-6-oxo-1,6-dihydropyrimidine-4-carboxamide | 478.2 |
| 473 | 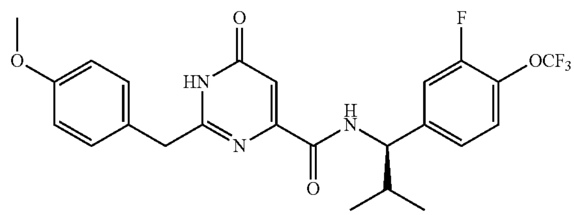 [SMILES: COc1ccc(Cc2nc(C(=O)N[C@@H](c3ccc(OC(F)(F)F)c(F)c3)C(C)C)cc(=O)[nH]2)cc1] | N-{(1R)-1-[3-fluoro-4-(trifluoromethoxy)phenyl]-2-methylpropyl}-2-(4-methoxybenzyl)-6-oxo-1,6-dihydropyrimidine-4-carboxamide | 494.2 |
| 474 | 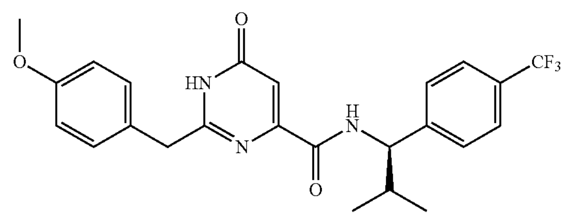 [SMILES: COc1ccc(Cc2nc(C(=O)N[C@@H](c3ccc(C(F)(F)F)cc3)C(C)C)cc(=O)[nH]2)cc1] | 2-(4-methoxybenzyl)-N-{(1R)-2-methyl-1-[4-(trifluoromethyl)phenyl]propyl}-6-oxo-1,6-dihydropyrimidine-4-carboxamide | 460.2 |
| 475 | 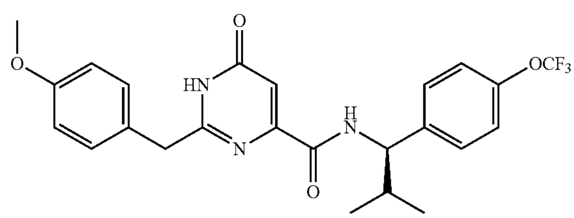 [SMILES: COc1ccc(Cc2nc(C(=O)N[C@@H](c3ccc(OC(F)(F)F)cc3)C(C)C)cc(=O)[nH]2)cc1] | 2-(4-methoxybenzyl)-N-{(1R)-2-methyl-1-[4-(trifluoromethoxy)phenyl]propyl}-6-oxo-1,6-dihydropyrimidine-4-carboxamide | 476.2 |
| 476 | 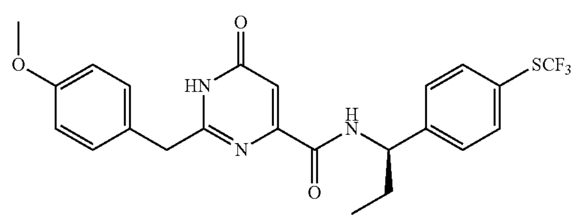 | 2-(4-methoxybenzyl)-6-oxo-N-[(1R)-1-{4-[(trifluoromethyl)sulfanyl]phenyl}propyl]-1,6-dihydropyrimidine-4-carboxamide | 478.1 |
| 477 | 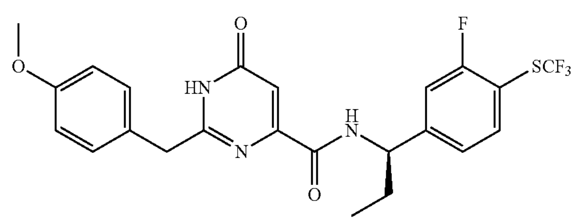 | N-[(1R)-1-{3-fluoro-4-[(trifluoromethyl)sulfanyl]phenyl}propyl]-2-(4-methoxybenzyl)-6-oxo-1,6-dihydropyrimidine-4-carboxamide | 496.1 |

TABLE 12-continued

| Example Number | IUPAC Name | Exact Mass [M + H]+ |
|---|---|---|
| 478 | N-{(R)-cyclopropyl[3-fluoro-4-(trifluoromethoxy)phenyl]methyl}-2-(4-methoxybenzyl)-6-oxo-1,6-dihydropyrimidine-4-carboxamide | 492.2 |
| 479 | N-[(R)-cyclopropyl{4-[(trifluoromethyl)sulfanyl]phenyl}methyl]-2-(4-methoxybenzyl)-6-oxo-1,6-dihydropyrimidine-4-carboxamide | 490.1 |
| 480 | N-{(R)-cyclopropyl[4-(trifluoromethoxy)phenyl]methyl}-2-(4-methoxybenzyl)-6-oxo-1,6-dihydropyrimidine-4-carboxamide | 474.2 |
| 481 | N-{(R)-cyclopropyl[4-(trifluoromethyl)phenyl]methyl}-2-(4-methoxybenzyl)-6-oxo-1,6-dihydropyrimidine-4-carboxamide | 458.2 |
| 482 | 2-(4-methoxybenzyl)-6-oxo-N-{(1R)-1-[4-(pentafluoro-$\lambda^6$-sulfanyl)phenyl]propyl}-1,6-dihydropyrimidine-4-carboxamide | 504.1 |
| 483 | N-{(1R)-1-[3-fluoro-4-(trifluoromethyl)phenyl]propyl}-2-(4-methoxybenzyl)-6-oxo-1,6-dihydropyrimidine-4-carboxamide | 464.2 |

TABLE 12-continued

| Example Number | Structure | IUPAC Name | Exact Mass [M + H]+ |
|---|---|---|---|
| 484 | 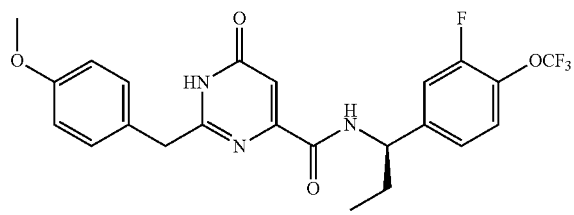 [SMILES: CC[C@@H](NC(=O)c1cc(=O)[nH]c(Cc2ccc(OC)cc2)n1)c1ccc(OC(F)(F)F)c(F)c1] | N-{(1R)-1-[3-fluoro-4-(trifluoromethoxy)phenyl]propyl}-2-(4-methoxybenzyl)-6-oxo-1,6-dihydropyrimidine-4-carboxamide | 480.2 |
| 485 | 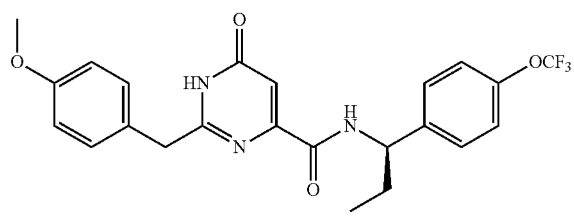 [SMILES: CC[C@@H](NC(=O)c1cc(=O)[nH]c(Cc2ccc(OC)cc2)n1)c1ccc(OC(F)(F)F)cc1] | 2-(4-methoxybenzyl)-6-oxo-N-{(1R)-1-[4-(trifluoromethoxy)phenyl]propyl}-1,6-dihydropyrimidine-4-carboxamide | 462.1 |
| 486 | 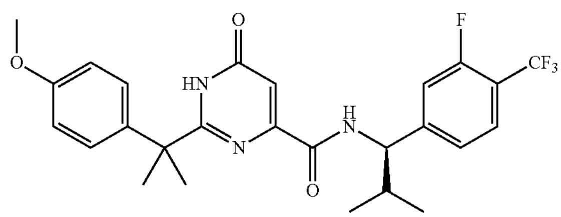 [SMILES: COc1ccc(C(C)(C)c2nc(C(=O)N[C@@H](c3ccc(C(F)(F)F)c(F)c3)C(C)C)cc(=O)[nH]2)cc1] | N-{(1R)-1-[3-fluoro-4-(trifluoromethyl)phenyl]-2-methylpropyl}-2-[1-(4-methoxyphenyl)-1-methylethyl]-6-oxo-1,6-dihydropyrimidine-4-carboxamide | 506.2 |
| 487 | 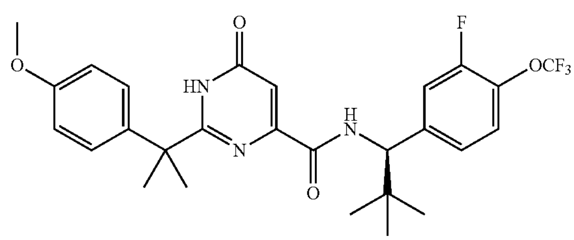 [SMILES: COc1ccc(C(C)(C)c2nc(C(=O)N[C@@H](c3ccc(OC(F)(F)F)c(F)c3)C(C)(C)C)cc(=O)[nH]2)cc1] | N-{(1R)-1-[3-fluoro-4-(trifluoromethoxy)phenyl]-2,2-dimethylpropyl}-2-[1-(4-methoxyphenyl)-1-methylethyl]-6-oxo-1,6-dihydropyrimidine-4-carboxamide | 536.2 |
| 488 | 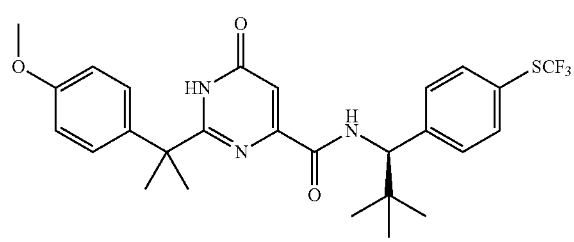 | N-[(1R)-2,2-dimethyl-1-{4-[(trifluoromethyl)sulfanyl]phenyl}propyl]-2-[1-(4-methoxyphenyl)-1-methylethyl]-6-oxo-1,6-dihydropyrimidine-4-carboxamide | 534.2 |
| 489 | 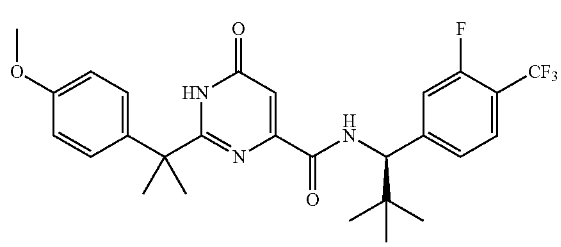 [SMILES: COc1ccc(C(C)(C)c2nc(C(=O)N[C@@H](c3ccc(C(F)(F)F)c(F)c3)C(C)(C)C)cc(=O)[nH]2)cc1] | N-{(1R)-1-[3-fluoro-4-(trifluoromethyl)phenyl]-2,2-dimethylpropyl}-2-[1-(4-methoxyphenyl)-1-methylethyl]-6-oxo-1,6-dihydropyrimidine-4-carboxamide | 520.2 |

TABLE 12-continued

| Example Number | Structure | IUPAC Name | Exact Mass [M + H]+ |
|---|---|---|---|
| 490 | 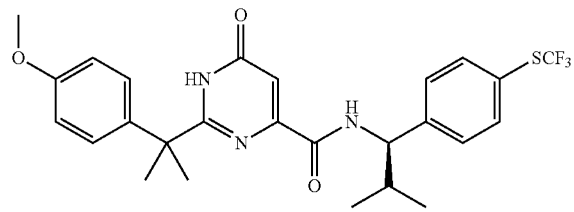 | 2-[1-(4-methoxyphenyl)-1-methylethyl]-N-[(1R)-2-methyl-1-{4-[(trifluoromethyl)sulfanyl]phenyl}propyl]-6-oxo-1,6-dihydropyrimidine-4-carboxamide | 520.2 |
| 491 | 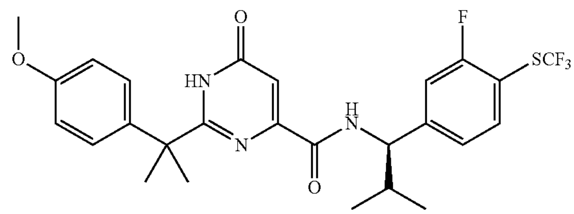 | N-[(1R)-1-{3-fluoro-4-[(trifluoromethyl)sulfanoyl]phenyl}-2-methylpropyl]-2-[1-(4-methoxyphenyl)-1-methylethyl]-6-oxo-1,6-dihydropyrimidine-4-carboxamide | 538.2 |
| 492 | 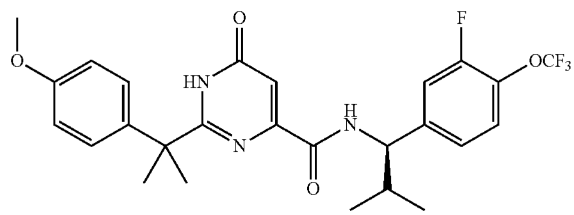 [SMILES: COc1ccc(C(C)(C)c2nc(C(=O)N[C@@H](c3ccc(OC(F)(F)F)c(F)c3)C(C)C)cc(=O)[nH]2)cc1] | N-{(1R)-1-[3-fluoro-4-(trifluoromethoxy)phenyl]-2-methylpropyl}-2-[1-(4-methoxyphenyl)-1-methylethyl]-6-oxo-1,6-dihydropyrimidine-4-carboxamide | 522.2 |
| 493 | 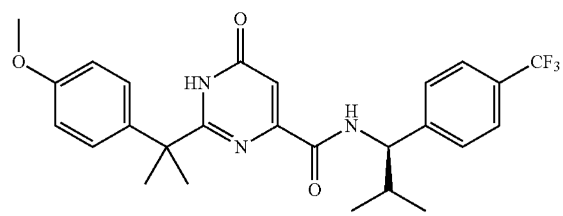 [SMILES: COc1ccc(C(C)(C)c2nc(C(=O)N[C@@H](c3ccc(C(F)(F)F)cc3)C(C)C)cc(=O)[nH]2)cc1] | 2-[1-(4-methoxyphenyl)-1-methylethyl]-N-{(1R)-2-methyl-1-[4-(trifluoromethyl)phenyl]propyl}-6-oxo-1,6-dihydropyrimidine-4-carboxamide | 488.2 |
| 494 | 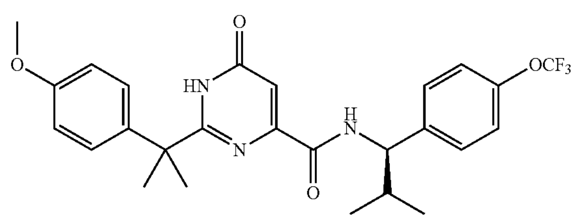 [SMILES: COc1ccc(C(C)(C)c2nc(C(=O)N[C@@H](c3ccc(OC(F)(F)F)cc3)C(C)C)cc(=O)[nH]2)cc1] | 2-[1-(4-methoxyphenyl)-1-methylethyl]-N-{(1R)-2-methyl-1-[4-(trifluoromethoxy)phenyl]propyl}-6-oxo-1,6-dihydropyrimidine-4-carboxamide | 504.2 |
| 495 | 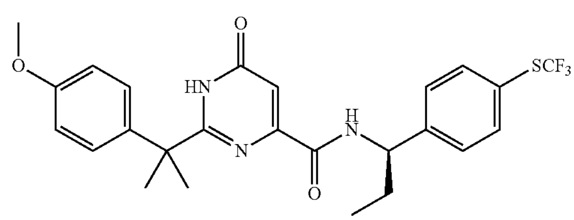 | 2-[1-(4-methoxyphenyl)-1-methylethyl]-6-oxo-N-[(1R)-1-{4-[(trifluoromethyl)sulfanyl]phenyl}propyl]-1,6-dihydropyrimidine-4-carboxamide | 506.2 |
| 496 | 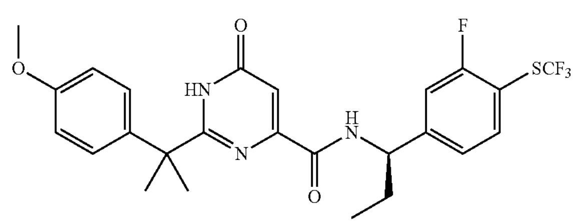 | N-[(1R)-1-{3-fluoro-4-[(trifluoromethyl)sulfanyl]phenyl}propyl]-2-[1-(4-methoxyphenyl)-1-methylethyl]-6-oxo-1,6-dihydropyrimidine-4-carboxamide | 524.1 |

TABLE 12-continued

| Example Number | Structure | IUPAC Name | Exact Mass [M + H]+ |
|---|---|---|---|
| 497 | 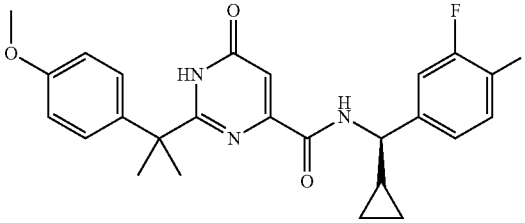 | N-[(R)-cyclopropyl{3-fluoro-4-[(trifluoromethyl)sulfanyl]phenyl}methyl]-2-[1-(4-methoxyphenyl)-1-methylethyl]-6-oxo-1,6-dihydropyrimidine-4-carboxamide | 536.1 |
| 498 | 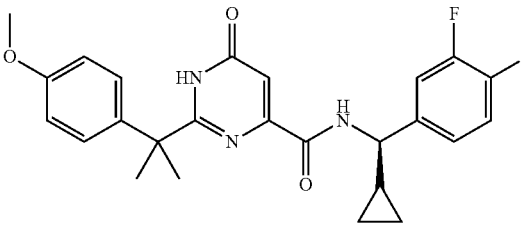 | N-{(R)-cyclopropyl[3-fluoro-4-(trifluoromethoxy)phenyl]methyl}-2-[1-(4-methoxyphenyl)-1-methylethyl]-6-oxo-1,6-dihydropyrimidine-4-carboxamide | 520.1 |
| 499 | 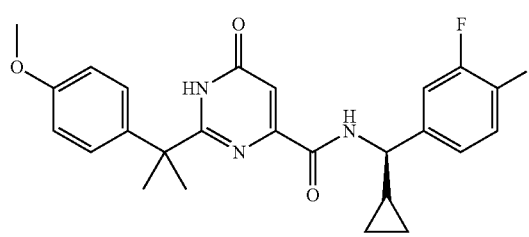 | N-{(R)-cyclopropyl[3-fluoro-4-(trifluoromethyl)phenyl]methyl}-2-[1-(4-methoxyphenyl)-1-methylethyl]-6-oxo-1,6-dihydropyrimidine-4-carboxamide | 504.2 |
| 500 | 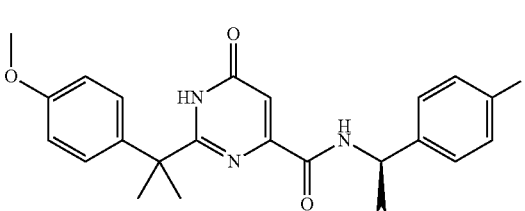 | N-[(R)-cyclopropyl{4-[(trifluoromethyl)sulfanyl]phenyl}methyl]-2-[1-(4-methoxyphenyl)-1-methylethyl]-6-oxo-1,6-dihydropyrimidine-4-carboxamide | 518.2 |
| 501 | 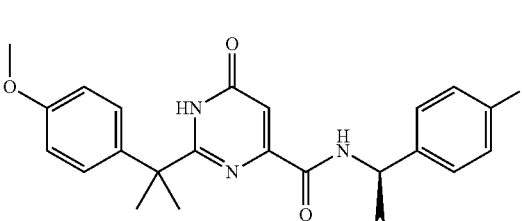 | N-{(R)-cyclopropyl[4-(trifluoromethoxy)phenyl]methyl}-2-[1-(4-methoxyphenyl)-1-methylethyl]-6-oxo-1,6-dihydropyrimidine-4-carboxamide | 502.2 |
| 502 | 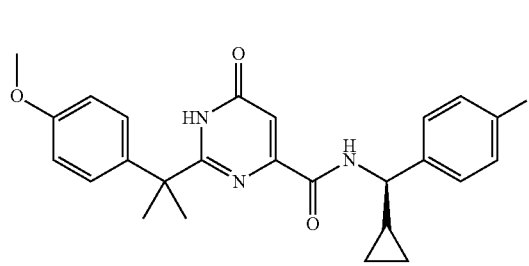 | N-{(R)-cyclopropyl[4-(trifluoromethyl)phenyl]methyl}-2-[1-(4-methoxyphenyl)-1-methylethyl]-6-oxo-1,6-dihydropyrimidine-4-carboxamide | 486.2 |

TABLE 12-continued

| Example Number | Structure | IUPAC Name | Exact Mass [M + H]+ |
|---|---|---|---|
| 503 | 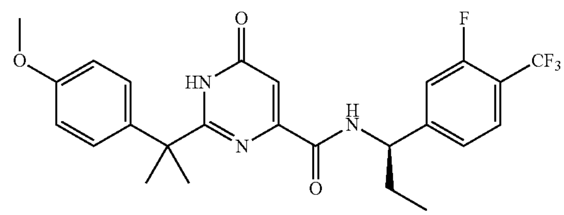 [SMILES: CC[C@@H](NC(=O)c1cc(=O)[nH]c(C(C)(C)c2ccc(OC)cc2)n1)c1ccc(C(F)(F)F)c(F)c1] | N-{(1R)-1-[3-fluoro-4-(trifluoromethyl)phenyl]propyl}-2-[1-(4-methoxyphenyl)-1-methylethyl]-6-oxo-1,6-dihydropyrimidine-4-carboxamide | 492.2 |
| 504 | 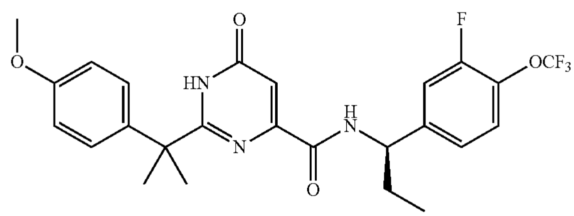 [SMILES: CC[C@@H](NC(=O)c1cc(=O)[nH]c(C(C)(C)c2ccc(OC)cc2)n1)c1ccc(OC(F)(F)F)c(F)c1] | N-{(1R)-1-[3-fluoro-4-(trifluoromethoxy)phenyl]propyl}-2-[1-(4-methoxyphenyl)-1-methylethyl]-6-oxo-1,6-dihydropyrimidine-4-carboxamide | 508.2 |
| 505 | 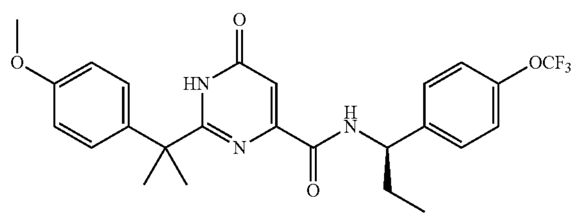 [SMILES: CC[C@@H](NC(=O)c1cc(=O)[nH]c(C(C)(C)c2ccc(OC)cc2)n1)c1ccc(OC(F)(F)F)cc1] | 2-[1-(4-methoxyphenyl)-1-methylethyl]-6-oxo-N-{(1R)-1-[4-(trifluoromethoxy)phenyl]propyl}-1,6-dihydropyrimidine-4-carboxamide | 490.2 |
| 506 | 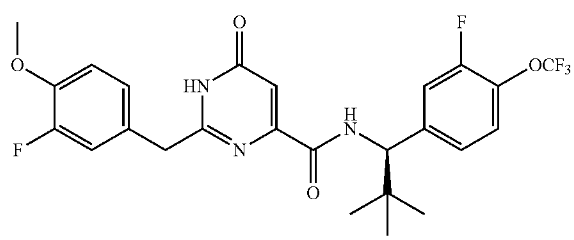 [SMILES: COc1ccc(Cc2nc(C(=O)N[C@@H](c3ccc(OC(F)(F)F)c(F)c3)C(C)(C)C)cc(=O)[nH]2)cc1F] | 2-(3-fluoro-4-methoxybenzyl)-N-{(1R)-1-[3-fluoro-4-(trifluoromethoxy)phenyl]-2,2-dimethylpropyl}-6-oxo-1,6-dihydropyrimidine-4-carboxamide | 526.2 |
| 507 | 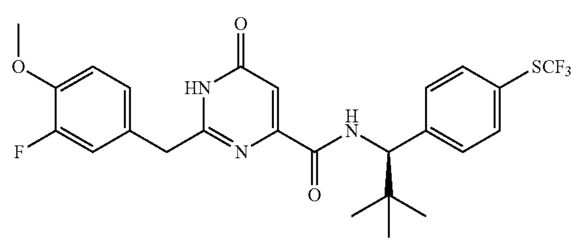 | N-[(1R)-2,2-dimethyl-1-{4-[(trifluoromethyl)sulfanyl]phenyl}propyl]-2-(3-fluoro-4-methoxybenzyl)-6-oxo-1,6-dihydropyrimidine-4-carboxamide | 524.1 |
| 508 | 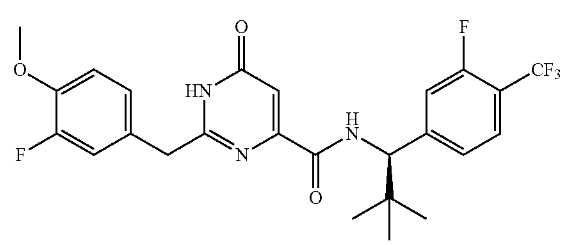 [SMILES: COc1ccc(Cc2nc(C(=O)N[C@@H](c3ccc(C(F)(F)F)c(F)c3)C(C)(C)C)cc(=O)[nH]2)cc1F] | 2-(3-fluoro-4-methoxybenzyl)-N-{(1R)-1-[3-fluoro-4-(trifluoromethyl)phenyl]-2,2-dimethylpropyl}-6-oxo-1,6-dihydropyrimidine-4-carboxamide | 510.2 |

TABLE 12-continued

| Example Number | Structure | IUPAC Name | Exact Mass [M + H]+ |
|---|---|---|---|
| 509 | 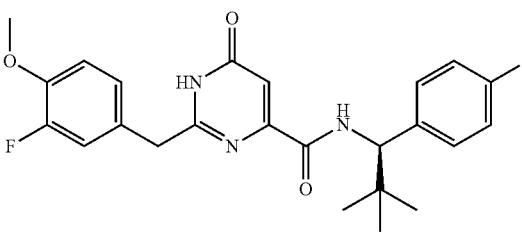 | N-{(1R)-2,2-dimethyl-1-[4-(trifluoromethoxy)phenyl]propyl}-2-(3-fluoro-4-methoxybenzyl)-6-oxo-1,6-dihydropyrimidine-4-carboxamide | 508.2 |
| 510 | 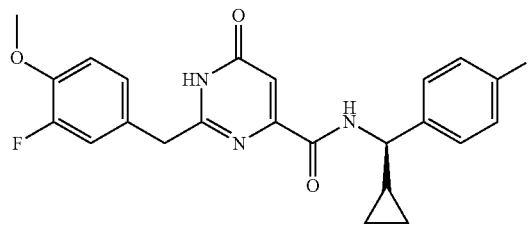 | N-{(R)-cyclopropyl[4-(pentafluoro-$\lambda^6$-sulfanyl)phenyl]methyl}-2-(3-fluoro-4-methoxybenzyl)-6-oxo-1,6-dihydropyrimidine-4-carboxamide | 534.1 |
| 511 | 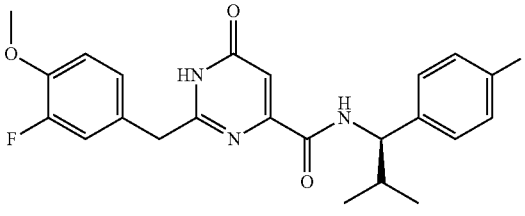 | 2-(3-fluoro-4-methoxybenzyl)-N-[(1R)-2-methyl-1-{4-[(trifluoromethyl)sulfanyl]phenyl}propyl]-6-oxo-1,6-dihydropyrimidine-4-carboxamide | 510.1 |
| 512 | 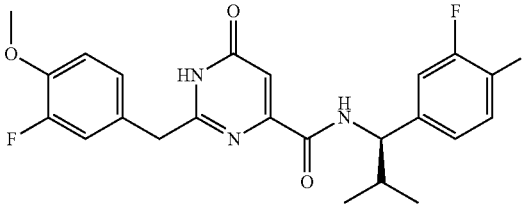 | 2-(3-fluoro-4-methoxybenzyl)-N-[(1R)-1-{3-fluoro-4-[(trifluoromethyl)sulfanyl]phenyl}-2-methylpropyl]-6-oxo-1,6-dihydropyrimidine-4-carboxamide | 528.1 |
| 513 | 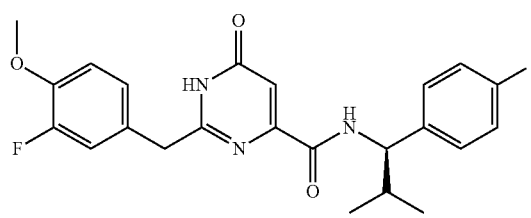 | 2-(3-fluoro-4-methoxybenzyl)-N-{(1R)-2-methyl-1-[4-(pentafluoro-$\lambda^6$-sulfanyl)phenyl]propyl}-6-oxo-1,6-dihydropyrimidine-4-carboxamide | 536.1 |
| 514 | 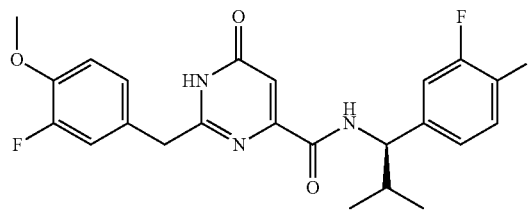 | 2-(3-fluoro-4-methoxybenzyl)-N-{(1R)-1-[3-fluoro-4-(trifluoromethyl)phenyl]-2-methylpropyl}-6-oxo-1,6-dihydropyrimidine-4-carboxamide | 496.2 |
| 515 | 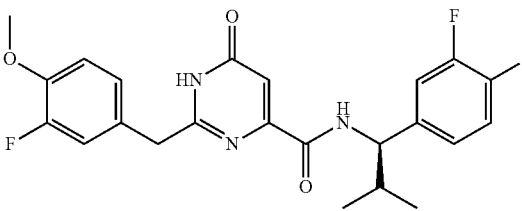 | 2-(3-fluoro-4-methoxybenzyl)-N-{(1R)-1-[3-fluoro-4-(trifluoromethoxy)phenyl]-2-methylpropyl}-6-oxo-1,6-dihydropyrimidine-4-carboxamide | 512.1 |

TABLE 12-continued

| Example Number | Structure | IUPAC Name | Exact Mass [M + H]+ |
|---|---|---|---|
| 516 | 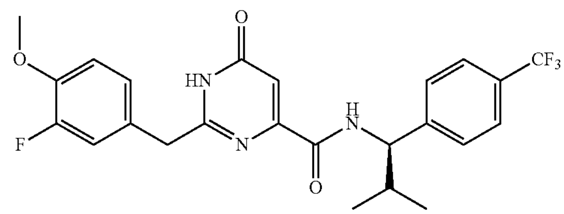 [SMILES: COc1ccc(Cc2nc(C(=O)N[C@@H](c3ccc(C(F)(F)F)cc3)C(C)C)cc(=O)[nH]2)cc1F] | 2-(3-fluoro-4-methoxybenzyl)-N-{(1R)-2-methyl-1-[4-(trifluoromethyl)phenyl]propyl}-6-oxo-1,6-dihydropyrimidine-4-carboxamide | 478.2 |
| 517 | 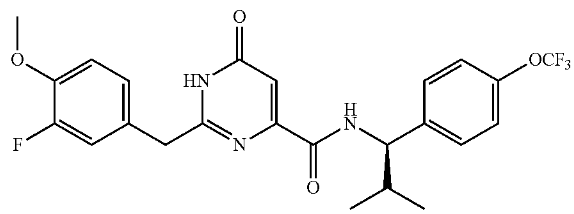 [SMILES: COc1ccc(Cc2nc(C(=O)N[C@@H](c3ccc(OC(F)(F)F)cc3)C(C)C)cc(=O)[nH]2)cc1F] | 2-(3-fluoro-4-methoxybenzyl)-N-{(1R)-2-methyl-1-[4-(trifluoromethoxy)phenyl]propyl}-6-oxo-1,6-dihydropyrimidine-4-carboxamide | 494.1 |
| 518 | 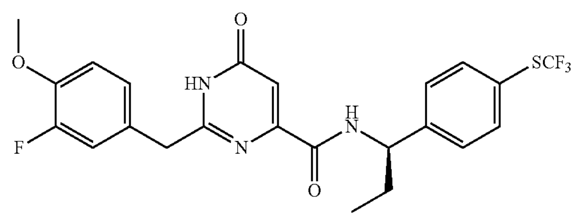 | 2-(3-fluoro-4-methoxybenzyl)-6-oxo-N-[(1R)-1-{4-[(trifluoromethyl)sulfanyl]phenyl}propyl]-1,6-dihydropyrimidine-4-carboxamide | 496.1 |
| 519 | 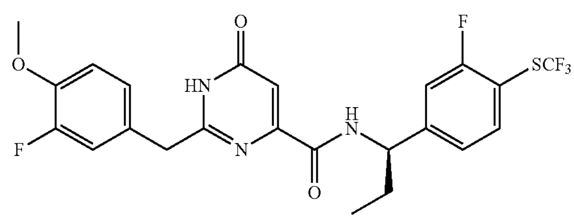 | 2-(3-fluoro-4-methoxybenzyl)-N-[(1R)-1-{3-fluoro-4-[(trifluoromethyl)sulfanyl]phenyl}propyl]-6-oxo-1,6-dihydropyrimidine-4-carboxamide | 514.1 |
| 520 | 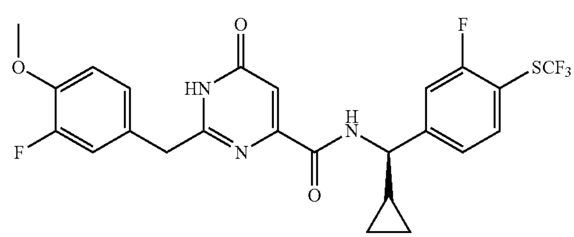 | N-[(R)-cyclopropyl{3-fluoro-4-[(trifluoromethyl)sulfanyl]phenyl}methyl]-2-(3-fluoro-4-methoxybenzyl)-6-oxo-1,6-dihydropyrimidine-4-carboxamide | 526.1 |
| 521 | 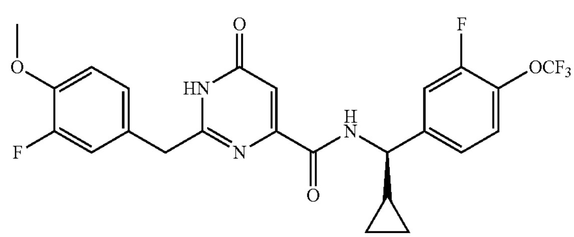 [SMILES: COc1ccc(Cc2nc(C(=O)N[C@@H](c3ccc(OC(F)(F)F)c(F)c3)C3CC3)cc(=O)[nH]2)cc1F] | N-{(R)-cyclopropyl[3-fluoro-4-(trifluoromethoxy)phenyl]methyl}-2-(3-fluoro-4-methoxybenzyl)-6-oxo-1,6-dihydropyrimidine-4-carboxamide | 510.1 |

TABLE 12-continued

| Example Number | Structure | IUPAC Name | Exact Mass [M + H]+ |
|---|---|---|---|
| 522 | 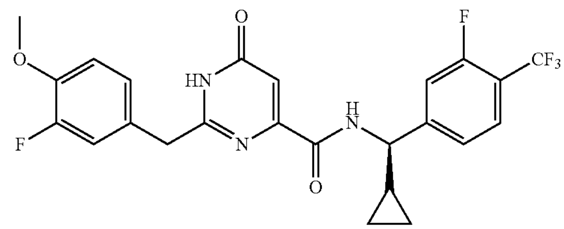 [SMILES: COc1ccc(Cc2nc(C(=O)N[C@@H](c3ccc(C(F)(F)F)c(F)c3)C3CC3)cc(=O)[nH]2)cc1F] | N-{(R)-cyclopropyl[3-fluoro-4-(trifluoromethyl)phenyl]methyl}-2-(3-fluoro-4-methoxybenzyl)-6-oxo-1,6-dihydropyrimidine-4-carboxamide | 494.1 |
| 523 | 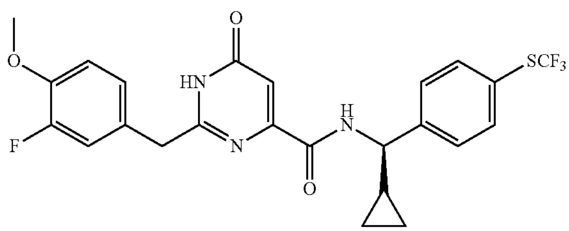 | N-[(R)-cyclopropyl{4-[(trifluoromethyl)sulfanyl]phenyl}methyl]-2-(3-fluoro-4-methoxybenzyl)-6-oxo-1,6-dihydropyrimidine-4-carboxamide | 508.1 |
| 524 | 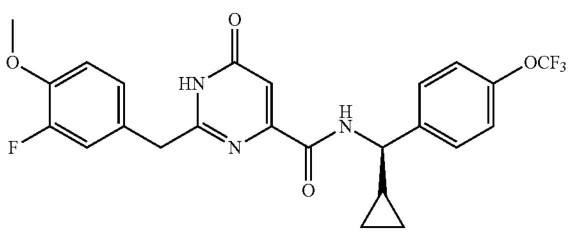 [SMILES: COc1ccc(Cc2nc(C(=O)N[C@@H](c3ccc(OC(F)(F)F)cc3)C3CC3)cc(=O)[nH]2)cc1F] | N-{(R)-cyclopropyl[4-(trifluoromethoxy)phenyl]methyl}-2-(3-fluoro-4-methoxybenzyl)-6-oxo-1,6-dihydropyrimidine-4-carboxamide | 492.1 |
| 525 | 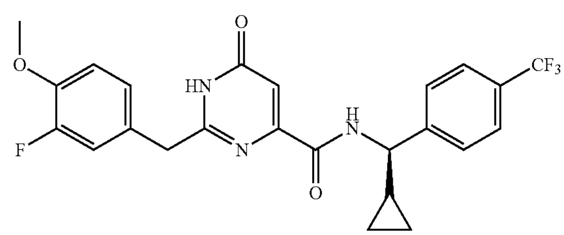 [SMILES: COc1ccc(Cc2nc(C(=O)N[C@@H](c3ccc(C(F)(F)F)cc3)C3CC3)cc(=O)[nH]2)cc1F] | N-{(R)-cyclopropyl[4-(trifluoromethyl)phenyl]methyl}-2-(3-fluoro-4-methoxybenzyl)-6-oxo-1,6-dihydropyrimidine-4-carboxamide | 476.1 |
| 526 | 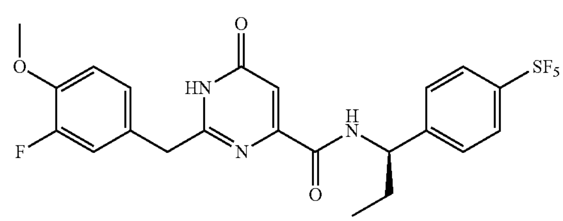 | 2-(3-fluoro-4-methoxybenzyl)-6-oxo-N-{(1R)-1-[4-(pentafluoro-$\lambda^6$-sulfanyl)phenyl]propyl}-1,6-dihydropyrimidine-4-carboxamide | 522.0 |
| 527 | 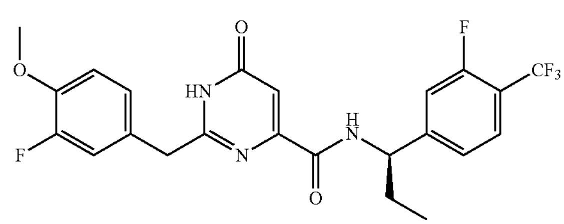 [SMILES: CC[C@@H](NC(=O)c1cc(=O)[nH]c(Cc2ccc(OC)c(F)c2)n1)c1ccc(C(F)(F)F)c(F)c1] | 2-(3-fluoro-4-methoxybenzyl)-N-{(1R)-1-[3-fluoro-4-(trifluoromethyl)phenyl]propyl}-6-oxo-1,6-dihydropyrimidine-4-carboxamide | 482.1 |

TABLE 12-continued

| Example Number | Structure | IUPAC Name | Exact Mass [M + H]+ |
|---|---|---|---|
| 528 | 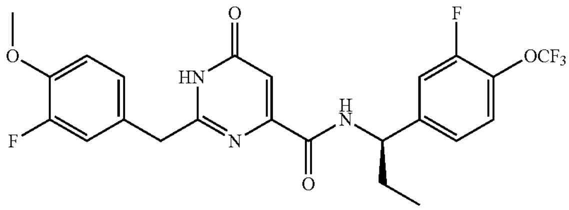 [SMILES: CC[C@@H](NC(=O)c1cc(=O)[nH]c(Cc2ccc(OC)c(F)c2)n1)c1ccc(OC(F)(F)F)c(F)c1] | 2-(3-fluoro-4-methoxybenzyl)-N-{(1R)-1-[3-fluoro-4-(trifluoromethoxy)phenyl]propyl}-6-oxo-1,6-dihydropyrimidine-4-carboxamide | 498.1 |
| 529 | 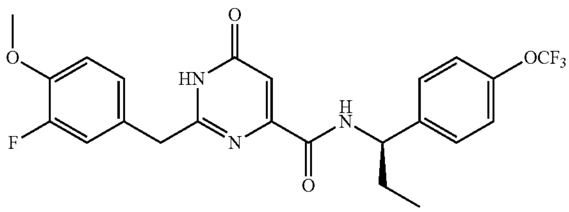 [SMILES: CC[C@@H](NC(=O)c1cc(=O)[nH]c(Cc2ccc(OC)c(F)c2)n1)c1ccc(OC(F)(F)F)cc1] | 2-(3-fluoro-4-methoxybenzyl)-6-oxo-N-{(1R)-1-[4-(trifluoromethoxy)phenyl]propyl}-1,6-dihydropyrimidine-4-carboxamide | 480.2 |
| 530 | 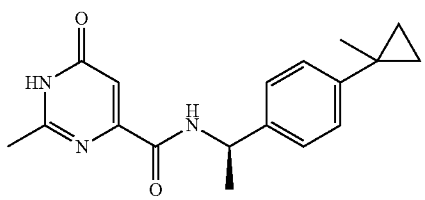 [SMILES: Cc1nc(C(=O)N[C@H](C)c2ccc(C3(C)CC3)cc2)cc(=O)[nH]1] | 2-methyl-N-{(1R)-1-[4-(1-methylcyclopropyl)phenyl]ethyl}-6-oxo-1,6-dihydropyrimidine-4-carboxamide | 312.2 |
| 531 | 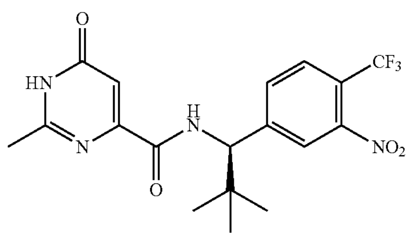 [SMILES: Cc1nc(C(=O)N[C@@H](c2ccc(C(F)(F)F)c([N+](=O)[O-])c2)C(C)(C)C)cc(=O)[nH]1] | N-{(1R)-2,2-dimethyl-1-[3-nitro-4-(trifluoromethyl)phenyl]propyl}-2-methyl-6-oxo-1,6-dihydropyrimidine-4-carboxamide | 413.0 |
| 532 | 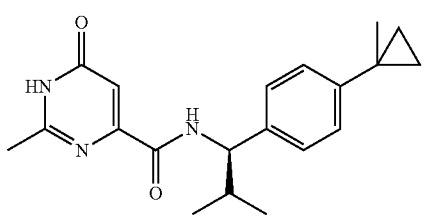 [SMILES: Cc1nc(C(=O)N[C@@H](c2ccc(C3(C)CC3)cc2)C(C)C)cc(=O)[nH]1] | 2-methyl-N-{(1R)-2-methyl-1-[4-(1-methylcyclopropyl)phenyl]propyl}-6-oxo-1,6-dihydropyrimidine-4-carboxamide | 340.1 |
| 533 | 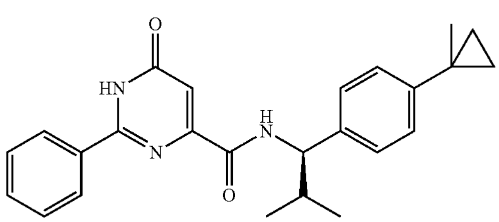 [SMILES: CC(C)[C@@H](NC(=O)c1cc(=O)[nH]c(-c2ccccc2)n1)c1ccc(C2(C)CC2)cc1] | N-{(1R)-2-methyl-1-[4-(1-methylcyclopropyl)phenyl]propyl}-6-oxo-2-phenyl-1,6-dihydropyrimidine-4-carboxamide | 402.2 |
| 534 | 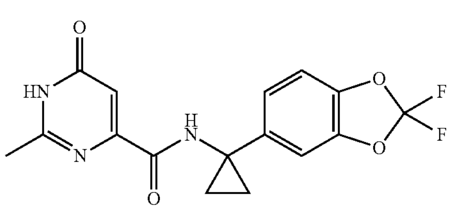 [SMILES: Cc1nc(C(=O)NC2(c3ccc4c(c3)OC(F)(F)O4)CC2)cc(=O)[nH]1] | N-[1-(2,2-difluoro-1,3-benzodioxol-5-yl)cyclopropyl]-2-methyl-6-oxo-1,6-dihydropyrimidine-4-carboxamide | 350.0 |

TABLE 12-continued

| Example Number | Structure | IUPAC Name | Exact Mass [M + H]+ |
|---|---|---|---|
| 535 | 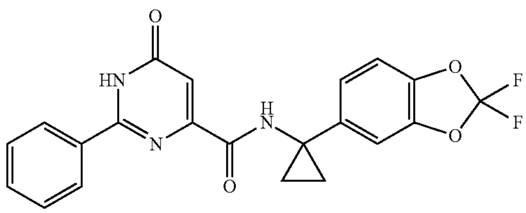 [SMILES: O=C(NC1(c2ccc3c(c2)OC(F)(F)O3)CC1)c1cc(=O)[nH]c(-c2ccccc2)n1] | N-[1-(2,2-difluoro-1,3-benzodioxol-5-yl)cyclopropyl]-6-oxo-2-phenyl-1,6-dihydropyrimidine-4-carboxamide | 411.8 |
| 536 | 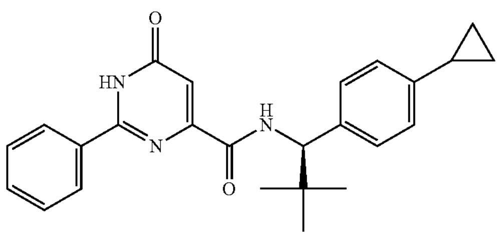 [SMILES: CC(C)(C)[C@@H](NC(=O)c1cc(=O)[nH]c(-c2ccccc2)n1)c1ccc(C2CC2)cc1] | N-[(1R)-1-(4-cyclopropylphenyl)-2,2-dimethylpropyl]-6-oxo-2-phenyl-1,6-dihydropyrimidine-4-carboxamide | Calc'd 402.2, found 402.2 |
| 537 | 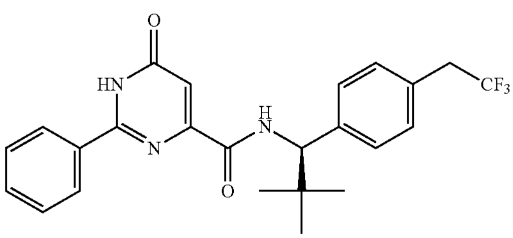 [SMILES: CC(C)(C)[C@@H](NC(=O)c1cc(=O)[nH]c(-c2ccccc2)n1)c1ccc(CC(F)(F)F)cc1] | N-{(1R)-2,2-dimethyl-1-[4-(2,2,2-trifluoroethyl)phenyl]propyl}-6-oxo-2-phenyl-1,6-dihydropyrimidine-4-carboxamide | Calc'd 444.2, found 444.1 |
| 538 | 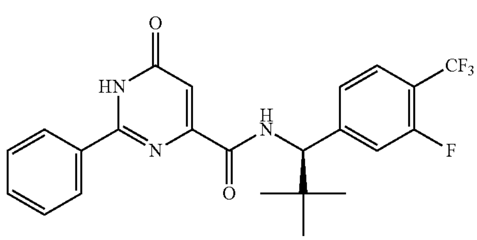 [SMILES: CC(C)(C)[C@@H](NC(=O)c1cc(=O)[nH]c(-c2ccccc2)n1)c1ccc(C(F)(F)F)c(F)c1] | N-{(1R)-1-[3-fluoro-4-(trifluoromethyl)phenyl]-2,2-dimethylpropyl}-6-oxo-2-phenyl-1,6-dihydropyrimidine-4-caboxamide | Calc'd 448.2, found 448.1 |
| 539 | 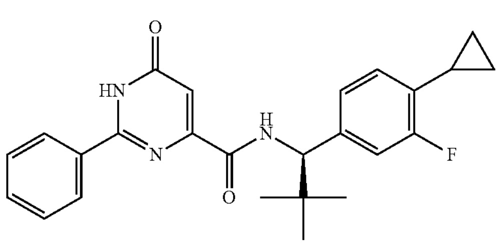 [SMILES: CC(C)(C)[C@@H](NC(=O)c1cc(=O)[nH]c(-c2ccccc2)n1)c1ccc(C2CC2)c(F)c1] | N-[(1R)-1-(4-cyclopropyl-3-fluorophenyl)-2,2-dimethylpropyl]-6-oxo-2-phenyl-1,6-dihydropyrimidine-4-carboxamide | Calc'd 420.2, found 420.2 |
| 540 | 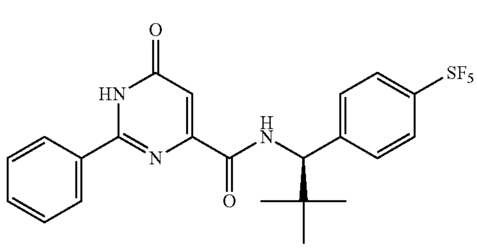 | N-{(1R)-2,2-dimethyl-1-[4-(pentafluoro-$\lambda^6$-sulfanyl)phenyl]propyl}-6-oxo-2-phenyl-1,6-dihydropyrimidine-4-carboxamide | Calc'd 488.1, found 488.1 |

TABLE 12-continued

| Example Number | Structure | IUPAC Name | Exact Mass [M + H]+ |
|---|---|---|---|
| 541 | 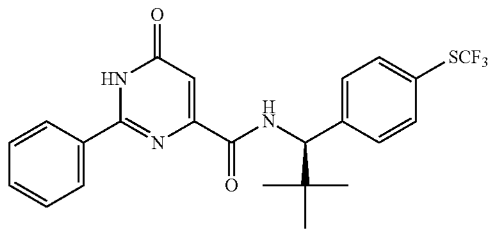 | N-[(1R)-2,2-dimethyl-1-{4-[(trifluoromethyl)sulfanyl]phenyl}propyl]-6-oxo-2-phenyl-1,6-dihydropyrimidine-4-carboxamide | Calc'd 462.1, found 462.1 |
| 542 | 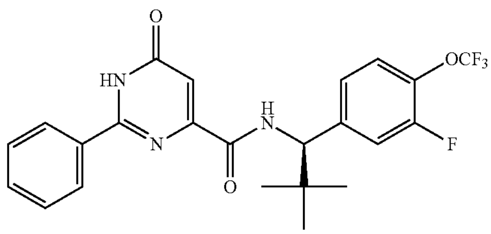 [SMILES: CC(C)(C)[C@@H](NC(=O)c1cc(=O)[nH]c(-c2ccccc2)n1)c1ccc(OC(F)(F)F)c(F)c1] | N-{(1R)-1-[3-fluoro-4-(trifluoromethoxy)phenyl]-2,2-dimethylpropyl}-6-oxo-2-phenyl-1,6-dihydropyrimidine-4-carboxamide | Calc'd 464.2, found 464.1 |
| 543 | 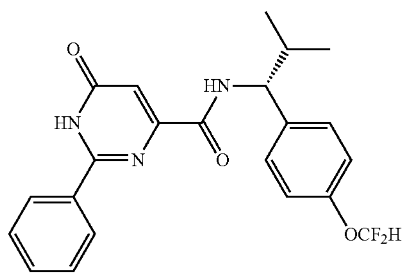 | N-{(1R)-1-[4-(difluoromethoxy)phenyl]-2-methylpropyl}-6-oxo-2-phenyl-1,6-dihydropyrimidine-4-carboxamide | Calc'd 414.2, found 414.2 |
| 544 | 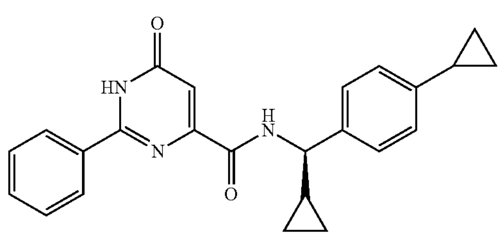 [SMILES: O=C(N[C@@H](c1ccc(C2CC2)cc1)C1CC1)c1cc(=O)[nH]c(-c2ccccc2)n1] | N-[(R)-cyclopropyl(4-cyclopropylphenyl)methyl]-6-oxo-2-phenyl-1,6-dihydropyrimidine-4-carboxamide | Calc'd 386.2, found 386.1 |
| 545 | 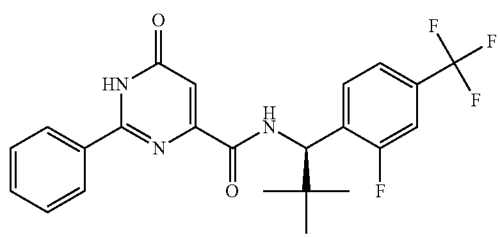 [SMILES: CC(C)(C)[C@@H](NC(=O)c1cc(=O)[nH]c(-c2ccccc2)n1)c1ccc(C(F)(F)F)cc1F] | N-{(1R)-1-[2-fluoro-4-(trifluoromethyl)phenyl]-2,2-dimethylpropyl}-6-oxo-2-phenyl-1,6-dihydropyrimidine-4-carboxamide | Calc'd 448.2, found 448.1 |
| 546 | 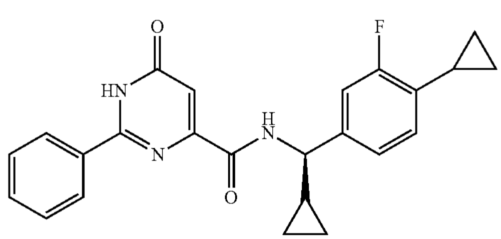 [SMILES: O=C(N[C@@H](c1ccc(C2CC2)c(F)c1)C1CC1)c1cc(=O)[nH]c(-c2ccccc2)n1] | N-[(R)-cyclopropyl(4-cyclopropyl-3-fluorophenyl)methyl]-6-oxo-2-phenyl-1,6-dihydropyrimidine-4-carboxamide | Calc'd 404.2, found 404.1 |

TABLE 12-continued

| Example Number | Structure | IUPAC Name | Exact Mass [M + H]+ |
|---|---|---|---|
| 547 | 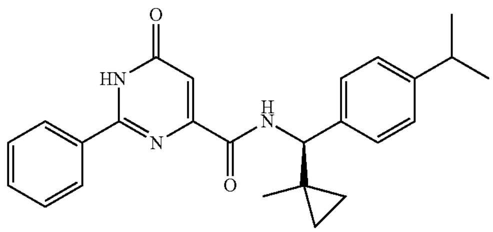 [SMILES: CC(C)c1ccc([C@H](NC(=O)c2cc(=O)[nH]c(-c3ccccc3)n2)C2(C)CC2)cc1] | N-{(R)-(1-methylcyclopropyl)[4-(1-methylethyl)phenyl]methyl}-6-oxo-2-phenyl-1,6-dihydropyrimidine-4-carboxamide | Calc'd 402.2, found 402.1 |
| 548 | 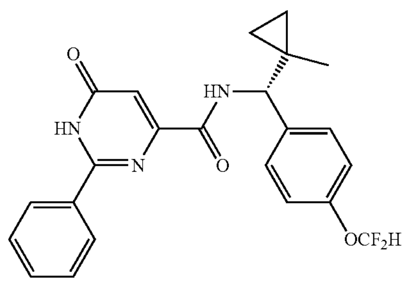 | N-[(R)-[4-(difluoromethoxy)phenyl](1-methylcyclopropyl)methyl]-6-oxo-2-phenyl-1,6-dihydropyrimidine-4-carboxamide | Calc'd 426.2, found 426.1 |
| 549 | 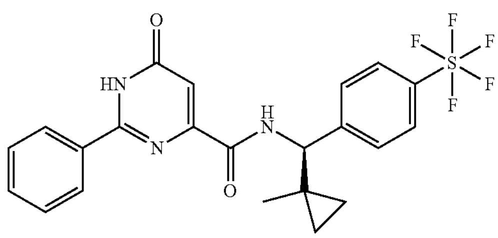 [SMILES: CC1([C@@H](NC(=O)c2cc(=O)[nH]c(-c3ccccc3)n2)c2ccc(S(F)(F)(F)(F)F)cc2)CC1] | N-{(R)-(1-methylcyclopropyl)[4-(pentafluoro-$\lambda^6$-sulfanyl)phenyl]methyl}-6-oxo-2-phenyl-1,6-dihydropyrimidine-4-carboxamide | Calc'd 486.1, found 486.1 |
| 550 | 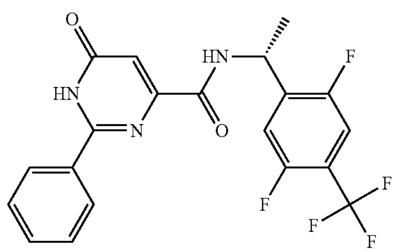 [SMILES: C[C@@H](NC(=O)c1cc(=O)[nH]c(-c2ccccc2)n1)c1cc(F)c(C(F)(F)F)cc1F] | N-{(1R)-1-[2,5-difluoro-4-(trifluoromethyl)phenyl]ethyl}-6-oxo-2-phenyl-1,6-dihydropyrimidine-4-carboxamide | Calc'd 424.1, found 424.0 |
| 551 | 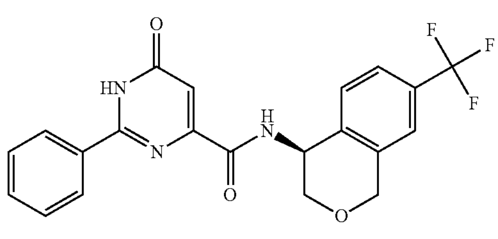 [SMILES: O=C(N[C@@H]1COCc2cc(C(F)(F)F)ccc21)c1cc(=O)[nH]c(-c2ccccc2)n1] | 6-oxo-2-phenyl-N-[(4S)-7-(trifluoromethyl)-3,4-dihydro-1H-isochromen-4-yl]-1,6-dihydropyrimidine-4-carboxamide | Calc'd 416.1, found 416.0 |
| 552 | 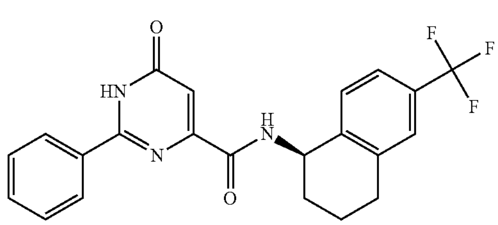 [SMILES: O=C(N[C@@H]1CCCc2cc(C(F)(F)F)ccc21)c1cc(=O)[nH]c(-c2ccccc2)n1] | 6-oxo-2-phenyl-N-[(1R)-6-(trifluoromethyl)-1,2,3,4-tetrahydronaphthalen-1-yl]-1,6-dihydropyrimidine-4-carboxamide | Calc'd 414.1, found 414.1 |

TABLE 12-continued

| Example Number | Structure | IUPAC Name | Exact Mass [M + H]+ |
|---|---|---|---|
| 553 | 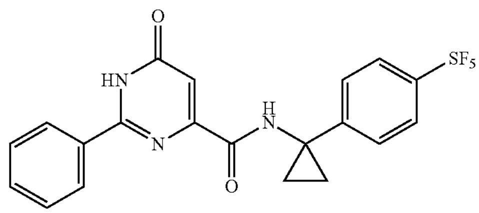 | 6-oxo-N-{1-[4-(pentafluoro-λ$^6$-sulfanyl)phenyl]cyclopropyl}-2-phenyl-1,6-dihydropyrimidine-4-carboxamide | Calc'd 458.1, found 458.0 |
| 554 | 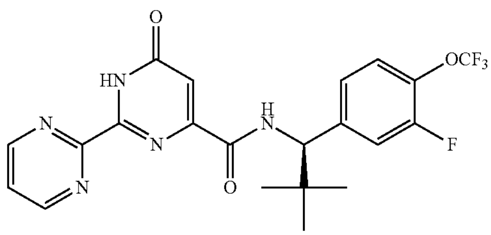 [SMILES: CC(C)(C)[C@@H](NC(=O)c1cc(=O)[nH]c(-c2ncccn2)n1)c1ccc(OC(F)(F)F)c(F)c1] | N-{(1R)-1-[3-fluoro-4-(trifluoromethoxy)phenyl]-2,2-dimethylpropyl}-6-oxo-1,6-dihydro-2,2'-bipyrimidine-4-carboxamide | Calc'd 466.2, found 466.1 |
| 555 | 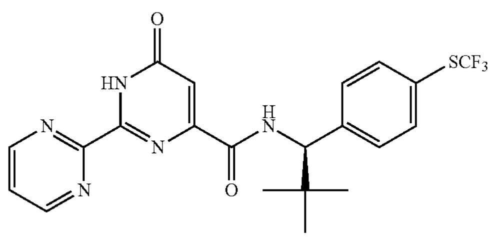 | N-[(1R)-2,2-dimethyl-1-{4-[(trifluoromethyl)sulfanyl]phenyl}propyl]-6-oxo-1,6-dihydro-2,2'-bipyrimidine-4-carboxamide | Calc'd 464.1, found 464.1 |
| 556 | 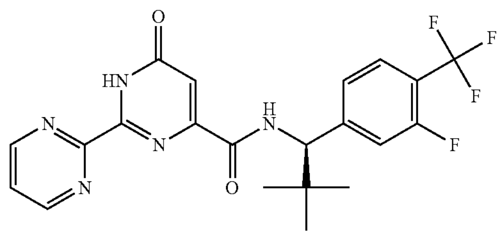 [SMILES: CC(C)(C)[C@@H](NC(=O)c1cc(=O)[nH]c(-c2ncccn2)n1)c1ccc(C(F)(F)F)c(F)c1] | N-{(1R)-1-[3-fluoro-4-(trifluoromethyl)phenyl]-2,2-dimethylpropyl}-6-oxo-1,6-dihydro-2,2'-bipyrimidine-4-carboxamide | Calc'd 450.2, found 450.1 |
| 557 | 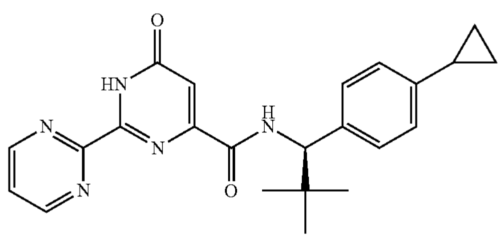 [SMILES: CC(C)(C)[C@@H](NC(=O)c1cc(=O)[nH]c(-c2ncccn2)n1)c1ccc(C2CC2)cc1] | N-[(1R)-1-(4-cyclopropylphenyl)-2,2-dimethylpropyl]-6-oxo-1,6-dihydro-2,2'-bipyrimidine-4-carboxamide | Calc'd 404.2, found 404.1 |
| 558 | 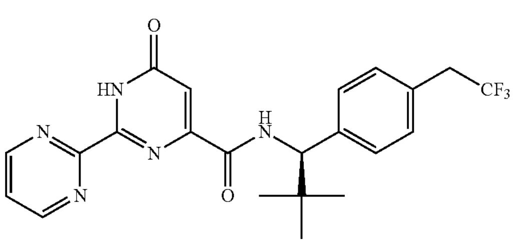 [SMILES: CC(C)(C)[C@@H](NC(=O)c1cc(=O)[nH]c(-c2ncccn2)n1)c1ccc(CC(F)(F)F)cc1] | N-[(1R)-2,2-dimethyl-1-[4-(2,2,2-trifluoroethyl)phenyl]propyl}-6-oxo-1,6-dihydro-2,2'-bipyrimidine-4-carboxamide | Calc'd 446.2, found 446.1 |

TABLE 12-continued

| Example Number | Structure | IUPAC Name | Exact Mass [M + H]+ |
|---|---|---|---|
| 559 | 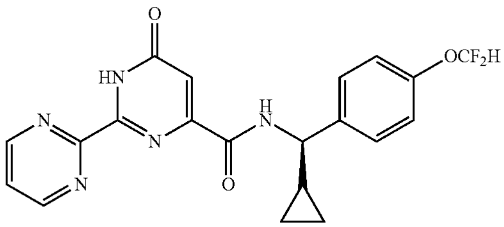 | N-{(R)-cyclopropyl[4-(difluoromethoxy)phenyl]methyl}-6-oxo-1,6-dihydro-2,2'-bipyrimidine-4-carboxamide | Calc'd 414.1, found 414.0 |
| 560 | 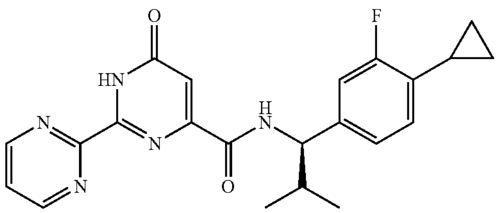 [SMILES: CC(C)[C@@H](NC(=O)c1cc(=O)[nH]c(-c2ncccn2)n1)c1ccc(C2CC2)c(F)c1] | N-[(1R)-1-(4-cyclopropyl-3-fluorophenyl)-2-methylpropyl]-6-oxo-1,6-dihydro-2,2'-bipyrimidine-4-carboxamide | Calc'd 408.2, found 408.1 |
| 561 | 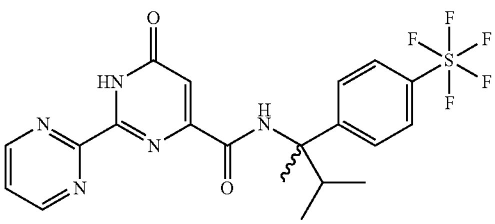 [SMILES: CC(C)C(C)(NC(=O)c1cc(=O)[nH]c(-c2ncccn2)n1)c1ccc(S(F)(F)(F)(F)F)cc1] | N-{1,2-dimethyl-1-[4-(pentafluoro-$\lambda^6$-sulfanyl)phenyl]propyl}-6-oxo-1,6-dihydro-2,2'-bipyrimidine-4-carboxamide | Calc'd 490.1, found 490.1 |
| 562 | 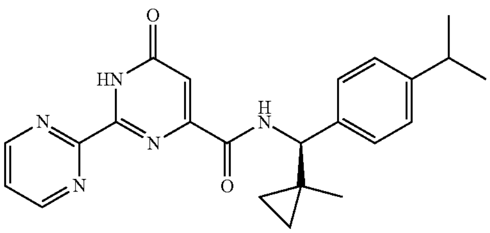 [SMILES: CC(C)c1ccc([C@H](NC(=O)c2cc(=O)[nH]c(-c3ncccn3)n2)C2(C)CC2)cc1] | N-{(R)-(1-methylcyclopropyl)[4-(1-methylethyl)phenyl]methyl}-6-oxo-1,6-dihydro-2,2'-bipyrimidine-4-carboxamide | Calc'd 404.2, found 404.2 |
| 563 | 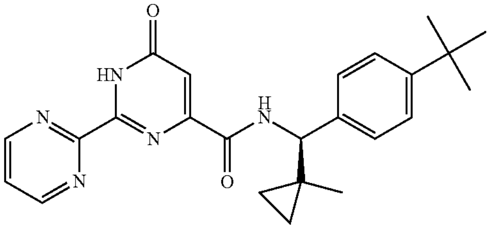 [SMILES: CC(C)(C)c1ccc([C@H](NC(=O)c2cc(=O)[nH]c(-c3ncccn3)n2)C2(C)CC2)cc1] | N-[(R)-(4-tert-butylphenyl)(1-methylcyclopropyl)methyl]-6-oxo-1,6-dihydro-2,2'-bipyrimidine-4-carboxamide | Calc'd 418.2, found 418.2 |
| 564 | 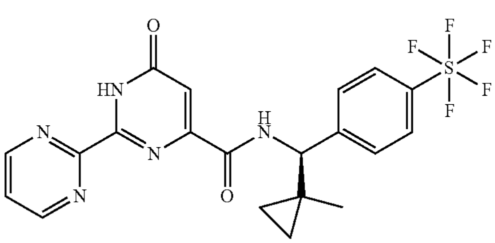 [SMILES: CC1([C@@H](NC(=O)c2cc(=O)[nH]c(-c3ncccn3)n2)c2ccc(S(F)(F)(F)(F)F)cc2)CC1] | N-{(R)-(1-methylcyclopropyl)[4-(pentafluoro-$\lambda^6$-sulfanyl)phenyl]methyl}-6-oxo-1,6-dihydro-2,2'-bipyrimidine-4-carboxamide | Calc'd 488.1, found 488.1 |

TABLE 12-continued

| Example Number | Structure | IUPAC Name | Exact Mass [M + H]+ |
|---|---|---|---|
| 565 | 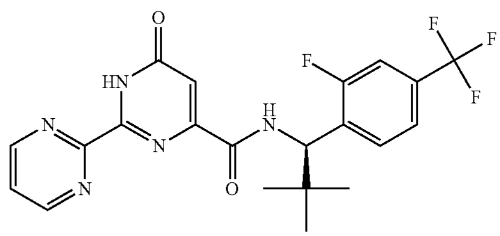 [SMILES: CC(C)(C)[C@@H](NC(=O)c1cc(=O)[nH]c(-c2ncccn2)n1)c1ccc(C(F)(F)F)cc1F] | N-{(1R)-1-[2-fluoro-4-(trifluoromethyl)phenyl]-2,2-dimethylpropyl}-6-oxo-1,6-dihydro-2,2'-bipyrimidine-4-carboxamide | Calc'd 450.2, found 450.2 |
| 566 | 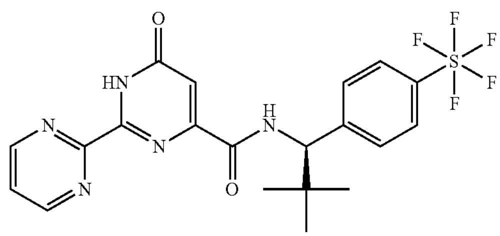 [SMILES: CC(C)(C)[C@@H](NC(=O)c1cc(=O)[nH]c(-c2ncccn2)n1)c1ccc(S(F)(F)(F)(F)F)cc1] | N-{(1R)-2,2-dimethyl-1-[4-(pentafluoro-$\lambda^6$-sulfanyl)phenyl]propyl}-6-oxo-1,6-dihydro-2,2'-bipyrimidine-4-carboxamide | Calc'd 490.1, found 490.1 |
| 567 | 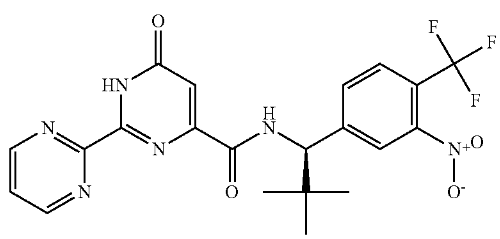 | N-{(1R)-2,2-dimethyl-1-[3-nitro-4-(trifluoromethyl)phenyl]propyl}-6-oxo-1,6-dihydro-2,2'-bipyrimidine-4-carboxamide | Calc'd 477.1, found 477.1 |
| 568 | 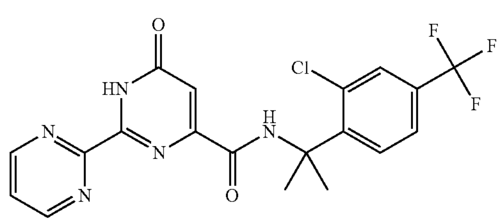 [SMILES: CC(C)(NC(=O)c1cc(=O)[nH]c(-c2ncccn2)n1)c1ccc(C(F)(F)F)cc1Cl] | N-{1-[2-chloro-4-(trifluoromethyl)phenyl]-1-methylethyl}-6-oxo-1,6-dihydro-2,2'-bipyrimidine-4-carboxamide | Calc'd 438.1, found 438.1 |
| 569 | 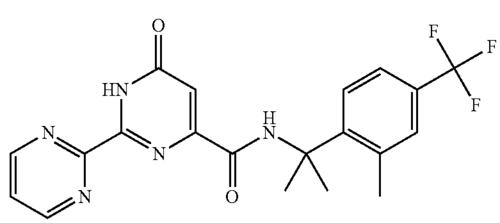 [SMILES: Cc1cc(C(F)(F)F)ccc1C(C)(C)NC(=O)c1cc(=O)[nH]c(-c2ncccn2)n1] | N-{1-methyl-1-[2-methyl-4-(trifluoromethyl)phenyl]ethyl}-6-oxo-1,6-dihydro-2,2'-bipyrimidine-4-carboxamide | Calc'd 418.1, found 418.1 |
| 570 | 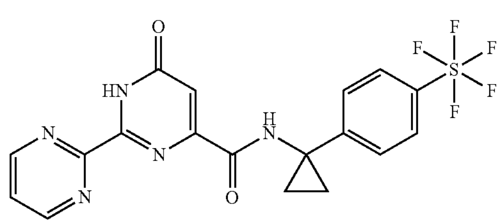 [SMILES: O=C(NC1(c2ccc(S(F)(F)(F)(F)F)cc2)CC1)c1cc(=O)[nH]c(-c2ncccn2)n1] | 6-oxo-N-{1-[4-(pentafluoro-$\lambda^6$-sulfanyl)phenyl]cyclopropyl}-1,6-dihydro-2,2'-bipyrimidine-4-carboxamide | Calc'd 460.1, found 460.0 |

TABLE 12-continued

| Example Number | Structure | IUPAC Name | Exact Mass [M + H]+ |
|---|---|---|---|
| 571 | 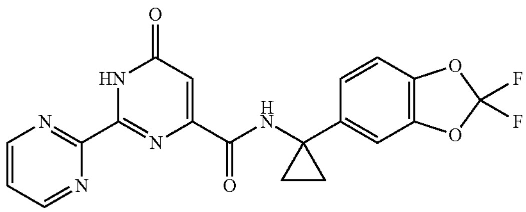 [SMILES: O=C(NC1(c2ccc3c(c2)OC(F)(F)O3)CC1)c1cc(=O)[nH]c(-c2ncccn2)n1] | N-[1-(2,2-difluoro-1,3-benzodioxol-5-yl)cyclopropyl]-6-oxo-1,6-dihydro-2,2'-bipyrimidine-4-carboxamide | Calc'd 414.1, found 414.0 |
| 572 | 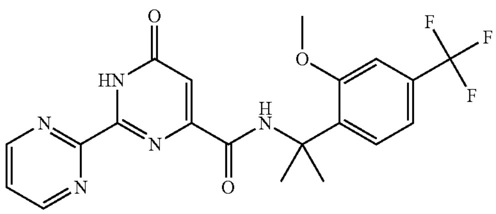 [SMILES: COc1cc(C(F)(F)F)ccc1C(C)(C)NC(=O)c1cc(=O)[nH]c(-c2ncccn2)n1] | N-{1-[2-methoxy-4-(trifluoromethyl)phenyl]-1-methylethyl}-6-oxo-1,6-dihydro-2,2'-bipyrimidine-4-carboxamide | Calc'd 434.1, found 434.1 |
| 573 | 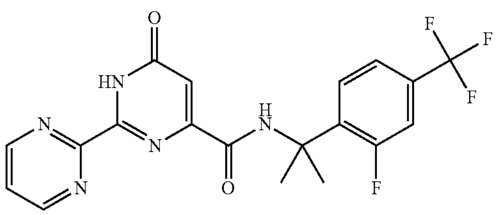 [SMILES: CC(C)(NC(=O)c1cc(=O)[nH]c(-c2ncccn2)n1)c1ccc(C(F)(F)F)cc1F] | N-{1-[2-fluoro-4-(trifluoromethyl)phenyl]-1-methylethyl}-6-oxo-1,6-dihydro-2,2'-bipyrimidine-4-carboxamide | Calc'd 422.1, found 422.1 |
| 574 | 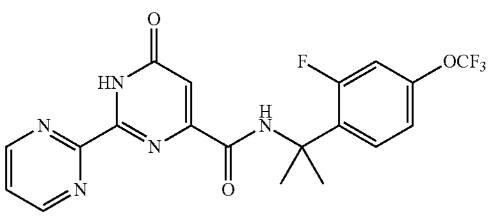 [SMILES: CC(C)(NC(=O)c1cc(=O)[nH]c(-c2ncccn2)n1)c1ccc(OC(F)(F)F)cc1F] | N-{1-[2-fluoro-4-(trifluoromethoxy)phenyl]-1-methylethyl}-6-oxo-1,6-dihydro-2,2'-bipyrimidine-4-carboxamide | Calc'd 438.1, found 438.1 |
| 575 | 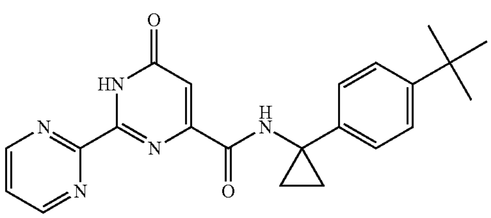 [SMILES: CC(C)(C)c1ccc(C2(NC(=O)c3cc(=O)[nH]c(-c4ncccn4)n3)CC2)cc1] | N-[1-(4-tert-butylphenyl)cyclopropyl]-6-oxo-1,6-dihydro-2,2'-bipyrimidine-4-carboxamide | Calc'd 390.2, found 390.1 |
| 576 | 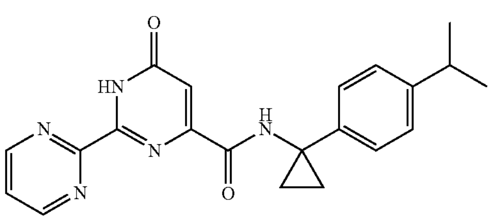 [SMILES: CC(C)c1ccc(C2(NC(=O)c3cc(=O)[nH]c(-c4ncccn4)n3)CC2)cc1] | N-{1-[4-(1-methylethyl)phenyl]cyclopropyl}-6-oxo-1,6-dihydro-2,2'-bipyrimidine-4-carboxamide | Calc'd 376.2, found 376.1 |
| 577 | 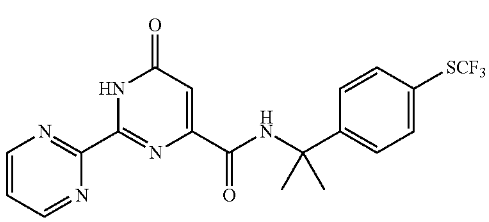 | N-(1-methyl-1-{4-[(trifluoromethyl)sulfanyl]phenyl}ethyl)-6-oxo-1,6-dihydro-2,2'-bipyrimidine-4-carboxamide | Calc'd 436.1, found 436.1 |

TABLE 12-continued

| Example Number | Structure | IUPAC Name | Exact Mass [M + H]+ |
|---|---|---|---|
| 578 | 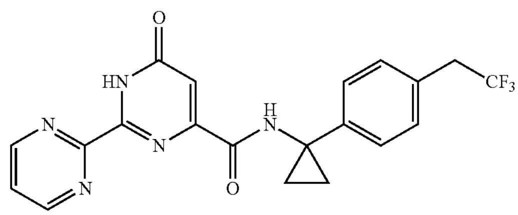 [SMILES: O=C(NC1(c2ccc(CC(F)(F)F)cc2)CC1)c1cc(=O)[nH]c(-c2ncccn2)n1] | 6-oxo-N-{1-[4-(2,2,2-trifluoroethyl)phenyl]cyclopropyl}-1,6-dihydro-2,2'-bipyrimidine-4-carboxamide | Calc'd 416.1, found 416.1 |
| 579 | 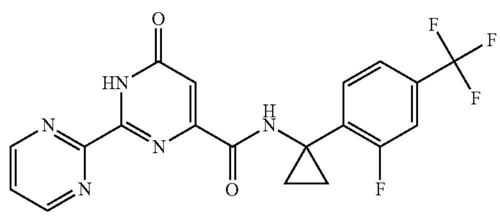 [SMILES: O=C(NC1(c2ccc(C(F)(F)F)cc2F)CC1)c1cc(=O)[nH]c(-c2ncccn2)n1] | N-{1-[2-fluoro-4-(trifluoromethyl)phenyl]cyclopropyl}-6-oxo-1,6-dihydro-2,2'-bipyrimidine-4-carboxamide | Calc'd 420.1, found 420.0 |
| 580 | 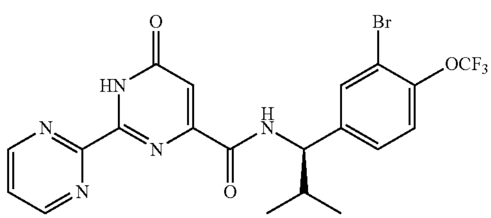 [SMILES: CC(C)[C@@H](NC(=O)c1cc(=O)[nH]c(-c2ncccn2)n1)c1ccc(OC(F)(F)F)c(Br)c1] | N-{(1R)-1-[3-bromo-4-(trifluoromethoxy)phenyl]-2-methylpropyl}-6-oxo-1,6-dihydro-2,2'-bipyrimidine-4-carboxamide | Calc'd 512.1, found 512.0 |
| 581 | 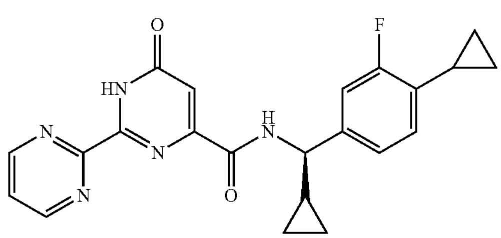 [SMILES: O=C(N[C@@H](c1ccc(C2CC2)c(F)c1)C1CC1)c1cc(=O)[nH]c(-c2ncccn2)n1] | N-[(R)-cyclopropyl(4-cyclopropyl-3-fluorophenyl)methyl]-6-oxo-1,6-dihydro-2,2'-bipyrimidine-4-carboxamide | Calc'd 406.2, found 406.3 |
| 582 | 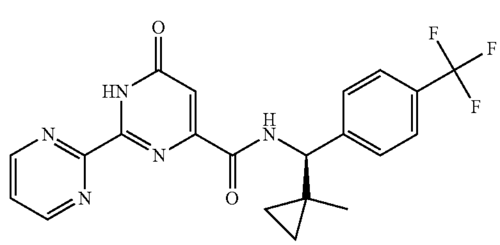 [SMILES: CC1([C@@H](NC(=O)c2cc(=O)[nH]c(-c3ncccn3)n2)c2ccc(C(F)(F)F)cc2)CC1] | N-{(R)-(1-methylcyclopropyl)[4-(trifluoromethyl)phenyl]methyl}-6-oxo-1,6-dihydro-2,2'-bipyrimidine-4-carboxamide | Calc'd 430.1, found 430.1 |
| 583 | 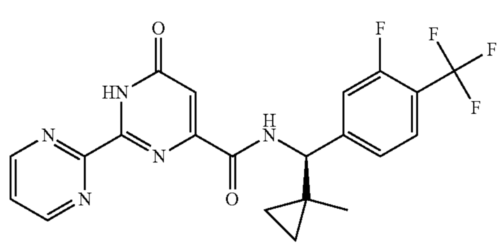 [SMILES: CC1([C@@H](NC(=O)c2cc(=O)[nH]c(-c3ncccn3)n2)c2ccc(C(F)(F)F)c(F)c2)CC1] | N-[(R)-[3-fluoro-4-(trifluoromethyl)phenyl](1-methylcyclopropyl)methyl]-6-oxo-1,6-dihydro-2,2'-bipyrimidine-4-carboxamide | Calc'd 448.1, found 448.1 |

TABLE 12-continued

| Example Number | Structure | IUPAC Name | Exact Mass [M + H]+ |
|---|---|---|---|
| 584 | 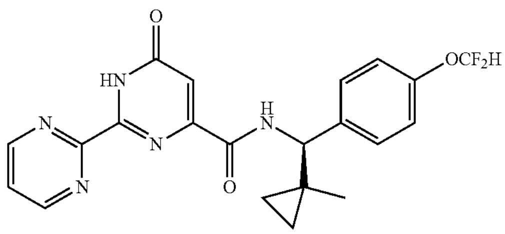 | N-[(R)-[4-(difluoromethoxy)phenyl](1-methylcyclopropyl)methyl]-6-oxo-1,6-dihydro-2,2'-bipyrimidine-4-carboxamide | Calc'd 428.2, found 428.2 |
| 585 | 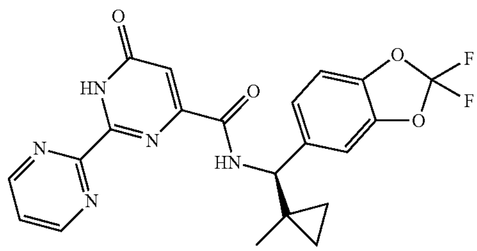 [SMILES: CC1([C@@H](NC(=O)c2cc(=O)[nH]c(-c3ncccn3)n2)c2ccc3c(c2)OC(F)(F)O3)CC1] | N-[(R)-(2,2-difluoro-1,3-benzodioxol-5-yl)(1-methylcyclopropyl)methyl]-6-oxo-1,6-dihydro-2,2'-bipyrimidine-4-carboxamide | Calc'd 442.1, found 442.2 |
| 586 | 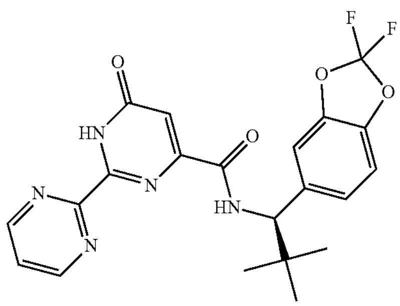 [SMILES: CC(C)(C)[C@@H](NC(=O)c1cc(=O)[nH]c(-c2ncccn2)n1)c1ccc2c(c1)OC(F)(F)O2] | N-[(1R)-1-(2,2-difluoro-1,3-benzodioxol-5-yl)-2,2-dimethylpropyl]-6-oxo-1,6-dihydro-2,2'-bipyrimidine-4-carboxamide | Calc'd 444.1, found 444.3 |
| 587 | 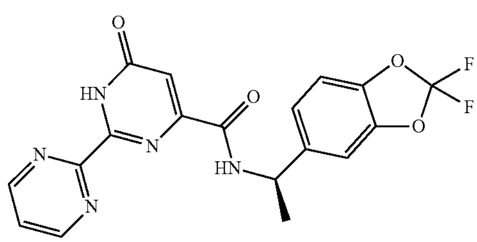 [SMILES: C[C@@H](NC(=O)c1cc(=O)[nH]c(-c2ncccn2)n1)c1ccc2c(c1)OC(F)(F)O2] | N-[(1R)-1-(2,2-difluoro-1,3-benzodioxol-5-yl)ethyl]-6-oxo-1,6-dihydro-2,2'-bipyrimidine-4-carboxamide | Calc'd 402.1, found 402.2 |
| 588 | 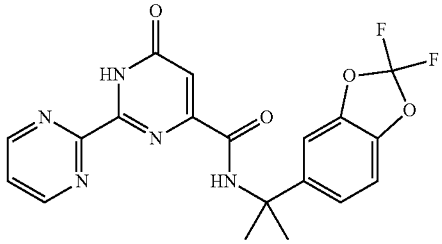 [SMILES: CC(C)(NC(=O)c1cc(=O)[nH]c(-c2ncccn2)n1)c1ccc2c(c1)OC(F)(F)O2] | N-[1-(2,2-difluoro-1,3-benzodioxol-5-yl)-1-methylethyl]-6-oxo-1,6-dihydro-2,2'-bipyrimidine-4-carboxamide | Calc'd 416.1, found 416.2 |
| 589 | 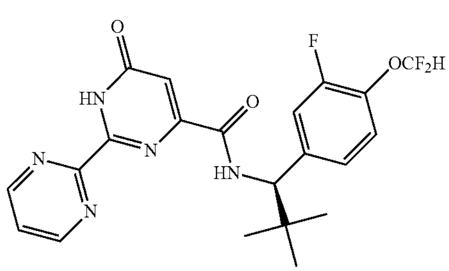 | N-{(1R)-1-[4-(difluoromethoxy)-3-fluorophenyl]-2,2-dimethylpropyl}-6-oxo-1,6-dihydro-2,2'-bipyrimidine-4-carboxamide | Calc'd 448.2, found 448.3 |

TABLE 12-continued

| Example Number | Structure | IUPAC Name | Exact Mass [M + H]+ |
|---|---|---|---|
| 590 | 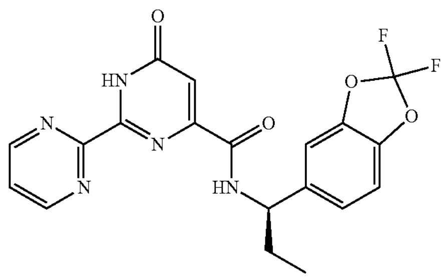 [SMILES: CC[C@@H](NC(=O)c1cc(=O)[nH]c(-c2ncccn2)n1)c1ccc2c(c1)OC(F)(F)O2] | N-[(1R)-1-(2,2-difluoro-1,3-benzodioxol-5-yl)propyl]-6-oxo-1,6-dihydro-2,2'-bipyrimidine-4-carboxamide | Calc'd 416.1, found 416.2 |
| 591 | 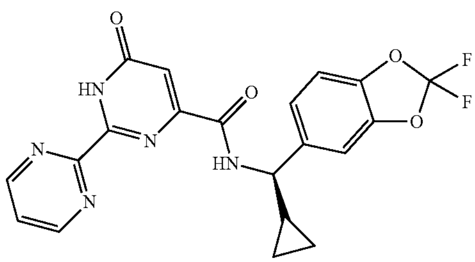 [SMILES: O=C(N[C@@H](c1ccc2c(c1)OC(F)(F)O2)C1CC1)c1cc(=O)[nH]c(-c2ncccn2)n1] | N-[(R)-cyclopropyl(2,2-difluoro-1,3-benzodioxol-5-yl)methyl]-6-oxo-1,6-dihydro-2,2'-bipyrimidine-4-carboxamide | Calc'd 428.1, found 428.2 |
| 592 | 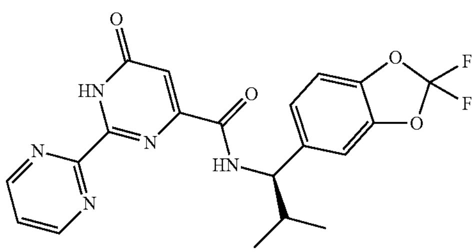 [SMILES: CC(C)[C@@H](NC(=O)c1cc(=O)[nH]c(-c2ncccn2)n1)c1ccc2c(c1)OC(F)(F)O2] | N-[(1R)-1-(2,2-difluoro-1,3-benzodioxol-5-yl)-2-methylpropyl]-6-oxo-1,6-dihydro-2,2'-bipyrimidine-4-carboxamide | Calc'd 430.1, found 430.2 |

Compounds in the Table 13 were prepared according to conditions shown in Scheme I, which were the same as in Scheme C except DMA was used as the solvent in Scheme I while DMF was used in Scheme C. The experimental details for Scheme C were exemplified in Example 35.

TABLE 13

| Example Number | Structure | IUPAC Name | Observed Exact Mass [M + H]+ |
|---|---|---|---|
| 593 | 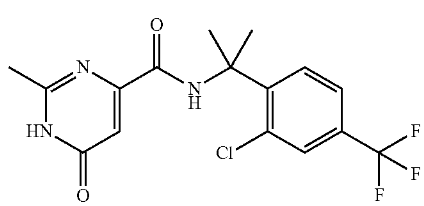 [SMILES: Cc1nc(C(=O)NC(C)(C)c2ccc(C(F)(F)F)cc2Cl)cc(=O)[nH]1] | N-{1-[2-chloro-4-(trifluoromethyl)phenyl]-1-methylethyl}-2-methyl-6-oxo-1,6-dihydropyrimidine-4-carboxamide | 373.9 |
| 594 | 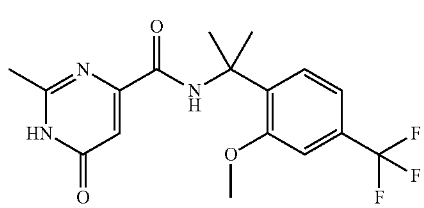 [SMILES: COc1cc(C(F)(F)F)ccc1C(C)(C)NC(=O)c1cc(=O)[nH]c(C)n1] | N-{1-[2-methoxy-4-(trifluoromethyl)phenyl]-1-methylethyl}-2-methyl-6-oxo-1,6-dihydropyrimidine-4-carboxamide | 369.9 |

TABLE 13-continued

| Example Number | Structure | IUPAC Name | Observed Exact Mass [M + H]+ |
|---|---|---|---|
| 595 | 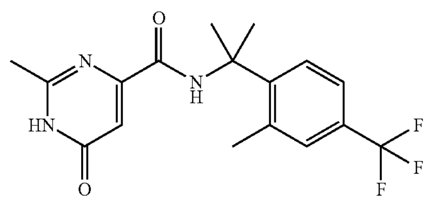 | 2-methyl-N-{1-methyl-1-[2-methyl-4-(trifluoromethyl)phenyl]ethyl}-6-oxo-1,6-dihydropyrimidine-4-carboxamide | 354.0 |
| 596 | 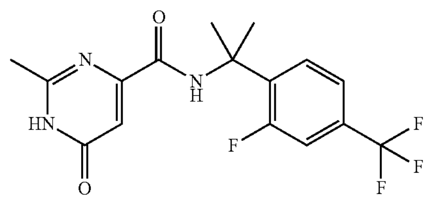 [SMILES: Cc1nc(C(=O)NC(C)(C)c2ccc(C(F)(F)F)cc2F)cc(=O)[nH]1] | N-{1-[2-fluoro-4-(trifluoromethyl)phenyl]-1-methylethyl}-2-methyl-6-oxo-1,6-dihydropyrimidine-4-carboxamide | 357.9 |
| 597 | 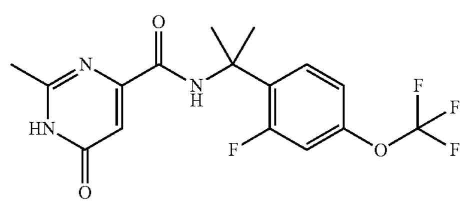 [SMILES: Cc1nc(C(=O)NC(C)(C)c2ccc(OC(F)(F)F)cc2F)cc(=O)[nH]1] | N-{1-[2-fluoro-4-(trifluoromethoxy)phenyl]-1-methylethyl}-2-methyl-6-oxo-1,6-dihydropyrimidine-4-carboxamide | 373.9 |
| 598 | 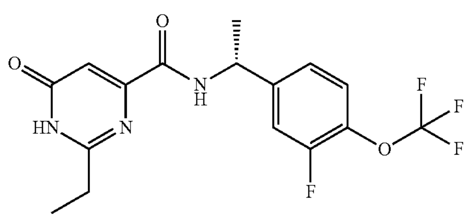 [SMILES: CCc1nc(C(=O)N[C@H](C)c2ccc(OC(F)(F)F)c(F)c2)cc(=O)[nH]1] | 2-ethyl-N-{(1R)-1-[3-fluoro-4-(trifluoromethoxy)phenyl]ethyl}-6-oxo-1,6-dihydropyrimidine-4-carboxamide | 373.9 |
| 599 | 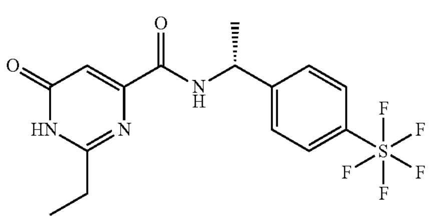 [SMILES: CCc1nc(C(=O)N[C@H](C)c2ccc(S(F)(F)(F)(F)F)cc2)cc(=O)[nH]1] | 2-ethyl-6-oxo-N-{(1R)-1-[4-(pentafluoro-$\lambda^6$-sulfanyl)phenyl]ethyl}-1,6-dihydropyrimidine-4-carboxamide | 397.9 |
| 600 | 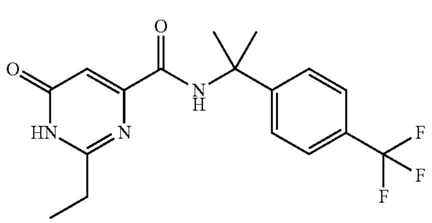 [SMILES: CCc1nc(C(=O)NC(C)(C)c2ccc(C(F)(F)F)cc2)cc(=O)[nH]1] | 2-ethyl-N-{1-methyl-1-[4-(trifluoromethyl)phenyl]ethyl}-6-oxo-1,6-dihydropyrimidine-4-carboxamide | 354.0 |
| 601 | 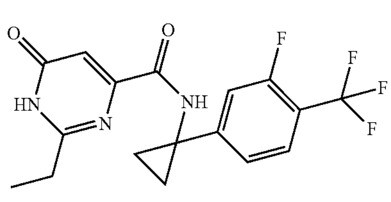 [SMILES: CCc1nc(C(=O)NC2(c3ccc(C(F)(F)F)c(F)c3)CC2)cc(=O)[nH]1] | 2-ethyl-N-{1-[3-fluoro-4-(trifluoromethyl)phenyl]cyclopropyl}-6-oxo-1,6-dihydropyrimidine-4-carboxamide | 370.0 |

TABLE 13-continued

| Example Number | Structure | IUPAC Name | Observed Exact Mass [M + H]+ |
|---|---|---|---|
| 602 | 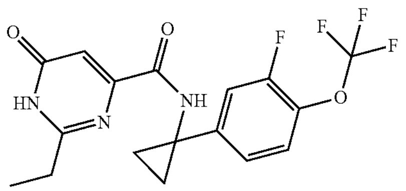 [SMILES: CCc1nc(C(=O)NC2(c3ccc(OC(F)(F)F)c(F)c3)CC2)cc(=O)[nH]1] | 2-ethyl-N-{1-[3-(fluoro-4-(trifluoromethoxy)phenyl]cyclopropyl}-6-oxo-1,6-dihydropyrimidine-4-carboxamide | 385.9 |
| 603 | 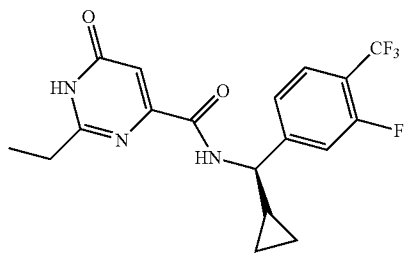 [SMILES: CCc1nc(C(=O)N[C@@H](c2ccc(C(F)(F)F)c(F)c2)C2CC2)cc(=O)[nH]1] | N-{(R)-cyclopropyl[3-fluoro-4-(trifluoromethyl)phenyl]methyl}-2-ethyl-6-oxo-1,6-dihydropyrimidine-4-carboxamide | 383.9 |
| 604 | 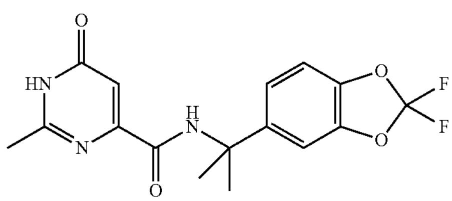 [SMILES: Cc1nc(C(=O)NC(C)(C)c2ccc3c(c2)OC(F)(F)O3)cc(=O)[nH]1] | N-[1-(2,2-difluoro-1,3-benzodioxol-5-yl)-1-methylethyl]-2-methyl-6-oxo-1,6-dihydropyrimidine-4-carboxamide | 352.0 |
| 605 | 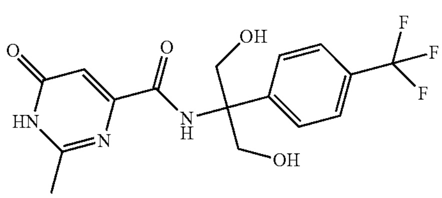 [SMILES: Cc1nc(C(=O)NC(CO)(CO)c2ccc(C(F)(F)F)cc2)cc(=O)[nH]1] | N-{2-hydroxy-1-(hydroxymethyl)-1-[4-(trifluoromethyl)phenyl]ethyl}-2-methyl-6-oxo-1,6-dihydropyrimidine-4-carboxamide | 372.0 |
| 606 | 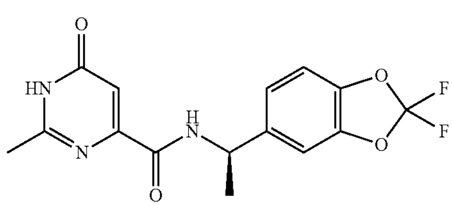 [SMILES: Cc1nc(C(=O)N[C@H](C)c2ccc3c(c2)OC(F)(F)O3)cc(=O)[nH]1] | N-[(1R)-1-(2,2-difluoro-1,3-benzodioxol-5-yl)ethyl]-2-methyl-6-oxo-1,6-dihydropyrimidine-4-carboxamide | 338.0 |
| 607 | 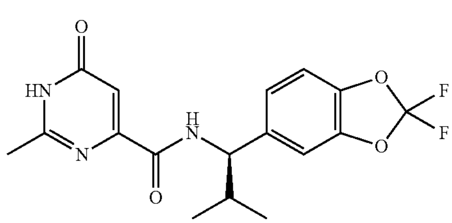 [SMILES: Cc1nc(C(=O)N[C@@H](c2ccc3c(c2)OC(F)(F)O3)C(C)C)cc(=O)[nH]1] | N-[(1R)-1-(2,2-difluoro-1,3-benzodioxol-5-yl)-2-methylpropyl]-2-methyl-6-oxo-1,6-dihydropyrimidine-4-carboxamide | 366.1 |
| 608 | 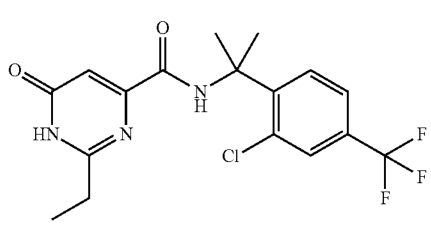 [SMILES: CCc1nc(C(=O)NC(C)(C)c2ccc(C(F)(F)F)cc2Cl)cc(=O)[nH]1] | N-{1-[2-chloro-4-(trifluoromethyl)phenyl]-1-methylethyl}-2-ethyl-6-oxo-1,6-dihydropyrimidine-4-carboxamide | 388.0 |

TABLE 13-continued

| Example Number | Structure | IUPAC Name | Observed Exact Mass [M + H]+ |
|---|---|---|---|
| 609 | 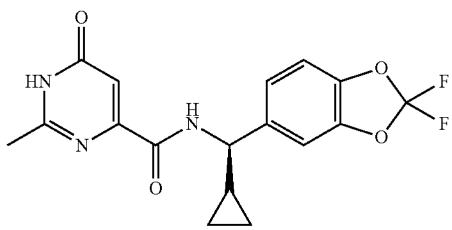 [SMILES: Cc1nc(C(=O)N[C@@H](c2ccc3c(c2)OC(F)(F)O3)C2CC2)cc(=O)[nH]1] | N-[(R)-cyclopropyl(2,2-difluoro-1,3-benzodioxol-5-yl)methyl]-2-methyl-6-oxo-1,6-dihydropyrimidine-4-carboxamide | 364.1 |
| 610 | 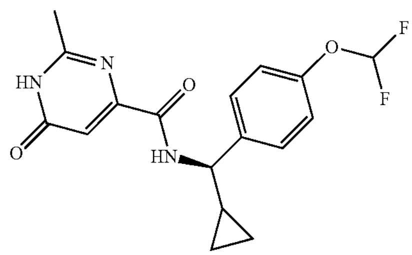 [SMILES: Cc1nc(C(=O)N[C@@H](c2ccc(OC(F)F)cc2)C2CC2)cc(=O)[nH]1] | N-{(R)-cyclopropyl[4-(difluoromethoxy)phenyl]methyl}-2-methyl-6-oxo-1,6-dihydropyrimidine-4-carboxamide | Calc'd 350.1, found 350.0 |
| 611 | 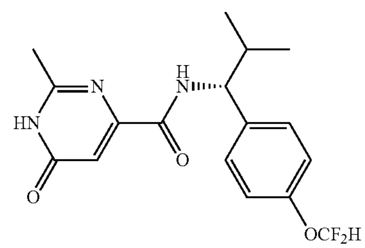 | N-{(1R)-1-[4-(difluoromethoxy)phenyl]-2-methylpropyl}-2-methyl-6-oxo-1,6-dihydropyrimidine-4-carboxamide | Calc'd 352.1, found 352.1 |
| 612 | 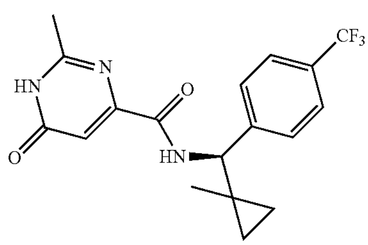 [SMILES: Cc1nc(C(=O)N[C@@H](c2ccc(C(F)(F)F)cc2)C2(C)CC2)cc(=O)[nH]1] | 2-methyl-N-{(R)-(1-methylcyclopropyl)[4-(trifluoromethyl)phenyl]methyl}-6-oxo-1,6-dihydropyrimidine-4-carboxamide | Calc'd 366.1, found 366.1 |
| 613 | 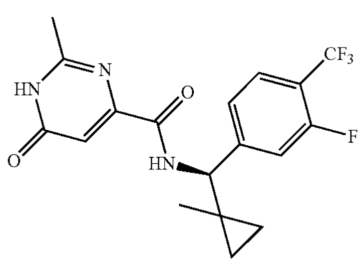 [SMILES: Cc1nc(C(=O)N[C@@H](c2ccc(C(F)(F)F)c(F)c2)C2(C)CC2)cc(=O)[nH]1] | N-[(R)-[3-fluoro-4-(trifluoromethyl)phenyl](1-methylcyclopropyl)methyl]-2-methyl-6-oxo-1,6-dihydropyrimidine-4-carboxamide | Calc'd 384.1, found 384.1 |
| 614 | 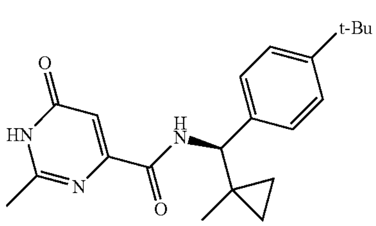 [SMILES: Cc1nc(C(=O)N[C@@H](c2ccc(C(C)(C)C)cc2)C2(C)CC2)cc(=O)[nH]1] | N-[(R)-(4-tert-butylphenyl)(1-methylcyclopropyl)methyl]-2-methyl-6-oxo-1,6-dihydropyrimidine-4-carboxamide | Calc'd 354.2, found 354.3 |

TABLE 13-continued

| Example Number | Structure | IUPAC Name | Observed Exact Mass [M + H]+ |
|---|---|---|---|
| 615 | 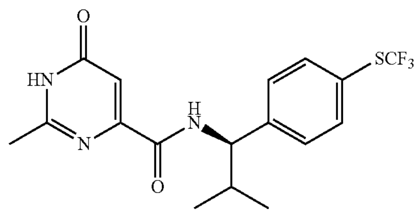 | 2-methyl-N-[(1S)-2-methyl-1-{4-[(trifluoromethyl)sulfanyl]phenyl}propyl]-6-oxo-1,6-dihydropyrimidine-4-carboxamide | Calc'd 386.1, found 386.2 |
| 616 | 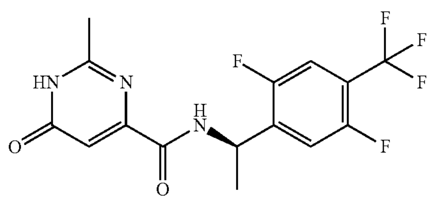 [SMILES: Cc1nc(C(=O)N[C@H](C)c2cc(F)c(C(F)(F)F)cc2F)cc(=O)[nH]1] | N-{1R)-1-[2,5-difluoro-4-(trifluoromethyl)phenyl]ethyl}-2-methyl-6-oxo-1,6-dihydropyrimidine-4-carboxamide | Calc'd 362.1, found 362.1 |
| 617 | 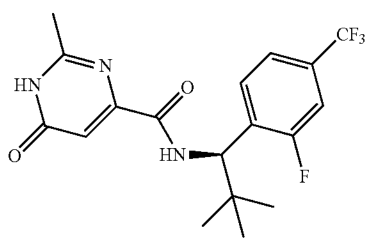 [SMILES: Cc1nc(C(=O)N[C@@H](c2ccc(C(F)(F)F)cc2F)C(C)(C)C)cc(=O)[nH]1] | N-{1R)-1-[2-fluoro-4-(trifluoromethyl)phenyl]-2,2-dimethylpropyl}-2-methyl-6-oxo-1,6-dihydropyrimidine-4-carboxamide | Calc'd 386.1, found 386.1 |
| 618 | 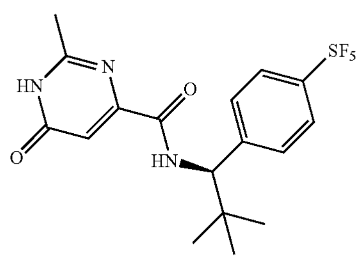 | N-{(1R)-2,2-dimethyl-1-[4-(pentafluoro-$\lambda^6$-sulfanyl)phenyl]propyl}-2-methyl-6-oxo-1,6-dihydropyrimidine-4-carboxamide | Calc'd 426.1, found 426.1 |
| 619 | 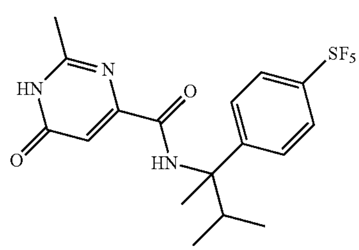 | N-{1,2-dimethyl-1-[4-(pentafluoro-$\lambda^6$-sulfanyl)phenyl]propyl}-2-methyl-6-oxo-1,6-dihydropyrimidine-4-carboxamide (racemic) | Calc'd 426.1, found 425.9 |
| 620 | 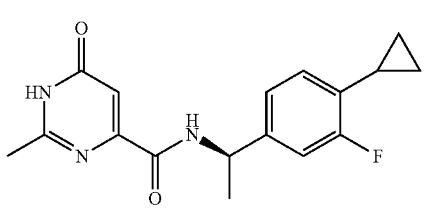 [SMILES: Cc1nc(C(=O)N[C@H](C)c2ccc(C3CC3)c(F)c2)cc(=O)[nH]1] | N-[(1R)-1-(4-cyclopropyl-3-fluorophenyl)ethyl]-2-methyl-6-oxo-1,6-dihydropyrimidine-4-carboxamide | Calc'd 316.1, found 316.1 |

TABLE 13-continued

| Example Number | Structure | IUPAC Name | Observed Exact Mass [M + H]+ |
|---|---|---|---|
| 621 | 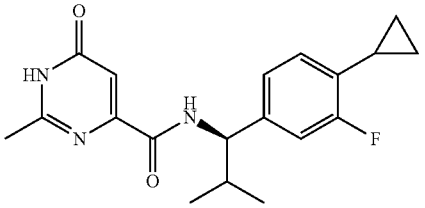 [SMILES: Cc1nc(C(=O)N[C@@H](c2ccc(C3CC3)c(F)c2)C(C)C)cc(=O)[nH]1] | N-[(1R)-1-(4-cyclopropyl-3-fluorophenyl)-2-methylpropyl]-2-methyl-6-oxo-1,6-dihydropyrimidine-4-carboxamide | Calc'd 344.2, found 344.1 |
| 622 | 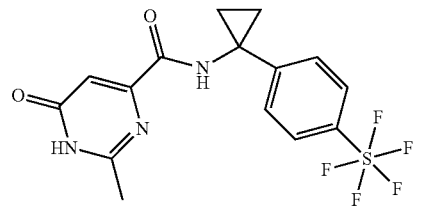 [SMILES: Cc1nc(C(=O)NC2(c3ccc(S(F)(F)(F)(F)F)cc3)CC2)cc(=O)[nH]1] | 2-methyl-6-oxo-N-{1-[4-(pentafluoro-$\lambda^6$-sulfanyl)phenyl]cyclopropyl}-1,6-dihydropyrimidine-4-carboxamide | Calc'd 396.1, found 395.9 |
| 623 | 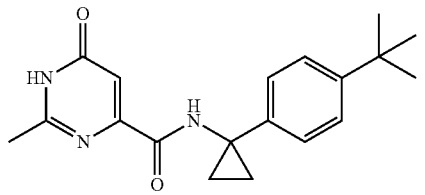 [SMILES: Cc1nc(C(=O)NC2(c3ccc(C(C)(C)C)cc3)CC2)cc(=O)[nH]1] | N-[1-(4-tert-butylphenyl)cyclopropyl]-2-methyl-6-oxo-1,6-dihydropyrimidine-4-carboxamide | Calc'd 326.2, found 326.1 |
| 624 | 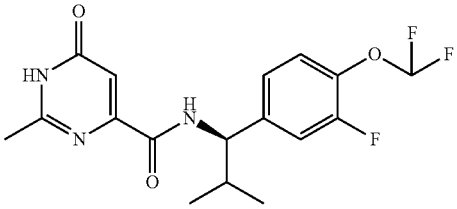 [SMILES: Cc1nc(C(=O)N[C@@H](c2ccc(OC(F)F)c(F)c2)C(C)C)cc(=O)[nH]1] | N-{(1R)-1-[4-(difluoromethoxy)-3-fluorophenyl]-2-methylpropyl}-2-methyl-6-oxo-1,6-dihydropyrimidine-4-carboxamide | Calc'd 370.1, found 370.1 |
| 625 | 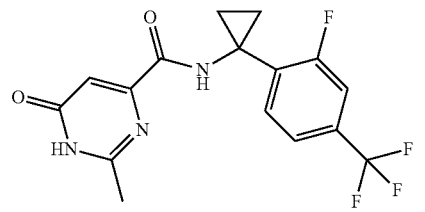 [SMILES: Cc1nc(C(=O)NC2(c3ccc(C(F)(F)F)cc3F)CC2)cc(=O)[nH]1] | N-{1-[2-fluoro-4-(trifluoromethyl)phenyl]cyclopropyl}-2-methyl-6-oxo-1,6-dihydropyrimidine-4-carboxamide | Calc'd 356.1, found 356.0 |
| 626 | 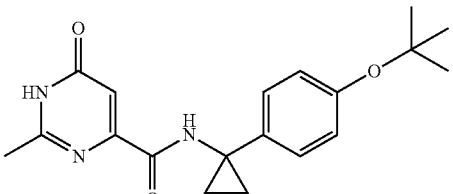 | N-[1-(4-tert-butoxyphenyl)cyclopropyl]-2-methyl-6-oxo-1,6-dihydropyrimidine-4-carboxamide | Calc'd 342.2, found 342.1 |
| 627 | 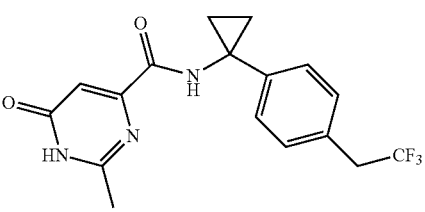 [SMILES: Cc1nc(C(=O)NC2(c3ccc(CC(F)(F)F)cc3)CC2)cc(=O)[nH]1] | 2-methyl-6-oxo-N-{1-[4-(2,2,2-trifluoroethyl)phenyl]cyclopropyl}-1,6-dihydropyrimidine-4-carboxamide | Calc'd 352.1, found 352.0 |

TABLE 13-continued

| Example Number | Structure | IUPAC Name | Observed Exact Mass [M + H]+ |
|---|---|---|---|
| 628 | 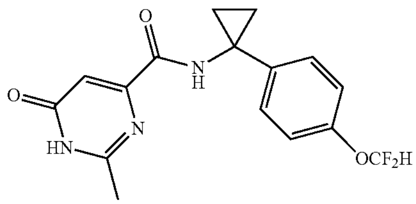 | N-{1-[4-(difluoromethoxy)phenyl]cyclopropyl}-2-methyl-6-oxo-1,6-dihydropyrimidine-4-carboxamide | Calc'd 336.1, found 336.1 |
| 629 | 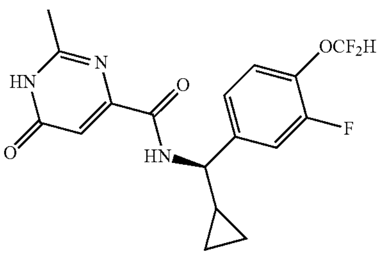 | N-{(R)-cyclopropyl[4-(difluoromethoxy)-3-fluorophenyl]methyl}-2-methyl-6-oxo-1,6-dihydropyrimidine-4-carboxamide | Calc'd 368.1, found 368.0 |
| 630 | 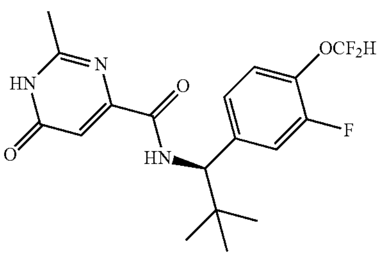 | N-{(1R)-1-[4-(difluoromethoxy)-3-fluorophenyl]-2,2-dimethylpropyl}-2-methyl-6-oxo-1,6-dihydropyrimidine-4-carboxamide | Calc'd 384.2, found 384.1 |
| 631 | 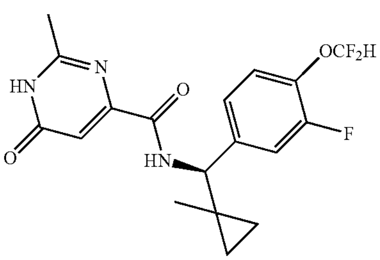 | N-[(R)-[4-(difluoromethoxy)-3-fluorophenyl](1-methylcyclopropyl)methyl]-2-methyl-6-oxo-1,6-dihydropyrimidine-4-carboxamide | Calc'd 382.1, found 382.0 |
| 632 | 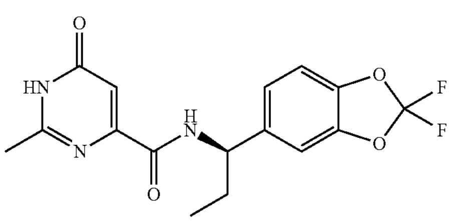 [SMILES: CC[C@@H](NC(=O)c1cc(=O)[nH]c(C)n1)c1ccc2c(c1)OC(F)(F)O2] | N-[(1R)-1-(2,2-difluoro-1,3-benzodioxol-5-yl)propyl]-2-methyl-6-oxo-1,6-dihydropyrimidine-4-carboxamide | Calc'd 352.1, found 352.0 |
| 633 | 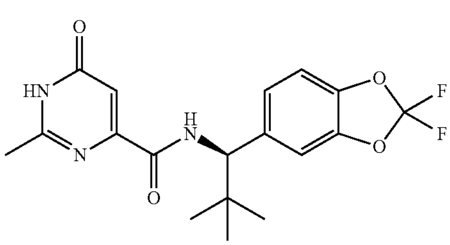 [SMILES: Cc1nc(C(=O)N[C@@H](c2ccc3c(c2)OC(F)(F)O3)C(C)(C)C)cc(=O)[nH]1] | N-[(1R)-1-(2,2-difluoro-1,3-benzodioxol-5-yl)-2,2-dimethylpropyl]-2-methyl-6-oxo-1,6-dihydropyrimidine-4-carboxamide | Calc'd 380.1, found 380.0 |

TABLE 13-continued

| Example Number | Structure | IUPAC Name | Observed Exact Mass [M + H]+ |
|---|---|---|---|
| 634 | 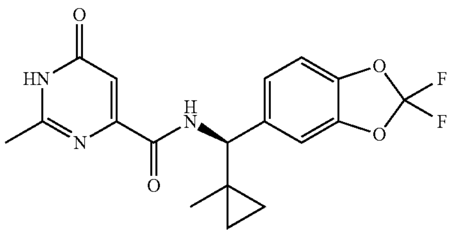 [SMILES: Cc1nc(C(=O)N[C@@H](c2ccc3c(c2)OC(F)(F)O3)C2(C)CC2)cc(=O)[nH]1] | N-[(R)-(2,2-difluoro-1,3-benzodioxol-5-yl)(1-methylcyclopropyl)methyl]-2-methyl-6-oxo-1,6-dihydropyrimide-4-carboxamide | Calc'd 378.1, found 378.0 |
| 635 | 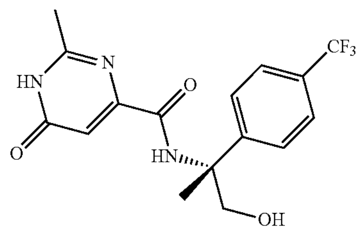 [SMILES: Cc1nc(C(=O)N[C@@](C)(CO)c2ccc(C(F)(F)F)cc2)cc(=O)[nH]1] | N-{(1R)-2-hydroxy-1-methyl-1-[4-(trifluoromethyl)phenyl]ethyl}-2-methyl-6-oxo-1,6-dihydropyrimidine-4-carboxamide | Calc'd 356.1, found 356.1 |
| 636 | 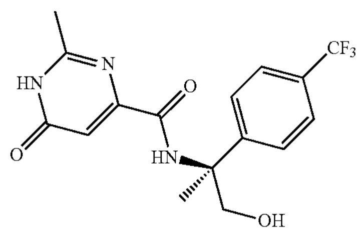 [SMILES: Cc1nc(C(=O)N[C@](C)(CO)c2ccc(C(F)(F)F)cc2)cc(=O)[nH]1] | N-{(1S)-2-hydroxy-1-methyl-1-[4-(trifluoromethyl)phenyl]ethyl}-2-methyl-6-oxo-1,6-dihydropyrimidine-4-carboxamide | Calc'd 356.1, found 356.0 |
| 637 | 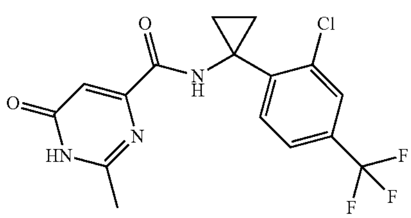 | N-{1-[2-chloro-4-(trifluoromethyl)phenyl]cyclopropyl}-2-methyl-6-oxo-1,6-dihydropyrimidine-4-carboxamide | Calc'd 372.1, found 372.0 |
| 638 | 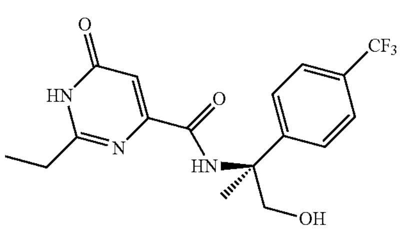 [SMILES: CCc1nc(C(=O)N[C@](C)(CO)c2ccc(C(F)(F)F)cc2)cc(=O)[nH]1] | 2-ethyl-N-{(1S)-2-hydroxy-1-methyl-1-[4-(trifluoromethyl)phenyl]ethyl}-6-oxo-1,6-dihydropyrimidine-4-carboxamide | Calc'd 370.1, found 370.0 |
| 639 | 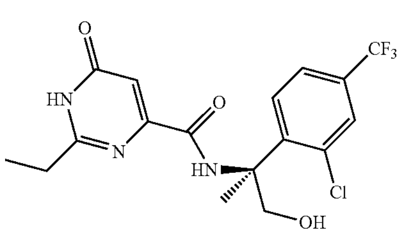 [SMILES: CCc1nc(C(=O)N[C@](C)(CO)c2ccc(C(F)(F)F)cc2Cl)cc(=O)[nH]1] | N-{(1S)-1-[2-chloro-4-(trifluoromethyl)phenyl]-2-hydroxy-1-methylethyl}-2-ethyl-6-oxo-1,6-dihydropyrimidine-4-carboxamide | Calc'd 404.1, found 403.8 |

TABLE 13-continued

| Example Number | Structure | IUPAC Name | Observed Exact Mass [M + H]+ |
|---|---|---|---|
| 640 | 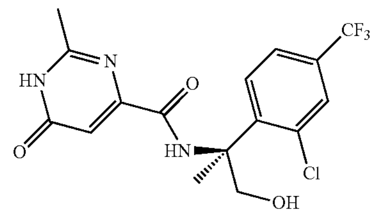 [SMILES: Cc1nc(C(=O)N[C@](C)(CO)c2ccc(C(F)(F)F)cc2Cl)cc(=O)[nH]1] | N-{(1S)-1-[2-chloro-4-(trifluoromethyl)phenyl]-2-hydroxy-1-methylethyl}-2-methyl-6-oxo-1,6-dihydropyrimidine-4-carboxamide | Calc'd 390.1, found 390.0 |
| 641 | 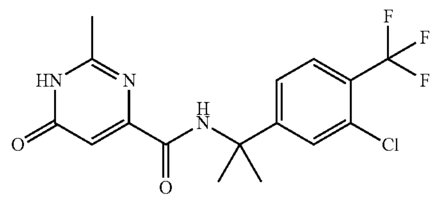 [SMILES: Cc1nc(C(=O)NC(C)(C)c2ccc(C(F)(F)F)c(Cl)c2)cc(=O)[nH]1] | N-{1-[3-chloro-4-(trifluoromethyl)phenyl]-1-methylethyl}-2-methyl-6-oxo-1,6-dihydropyrimidine-4-carboxamide | Calc'd 374.1, found 373.9 |
| 642 | 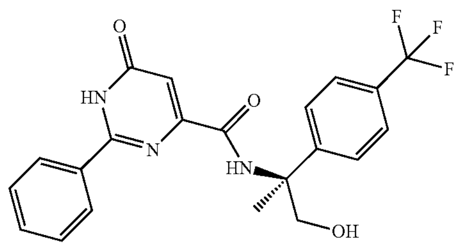 [SMILES: C[C@](CO)(NC(=O)c1cc(=O)[nH]c(-c2ccccc2)n1)c1ccc(C(F)(F)F)cc1] | N-{(1S)-2-hydroxy-1-methyl-1-[4-(trifluoromethyl)phenyl]ethyl}-6-oxo-2-phenyl-1,6-dihydropyrimidine-4-carboxamide | Calc'd 418.1, found 418.0 |
| 643 | 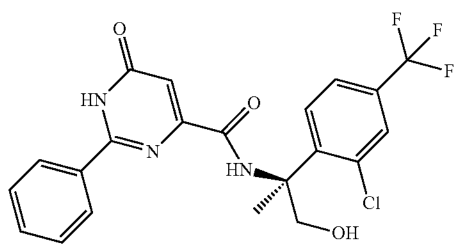 [SMILES: C[C@](CO)(NC(=O)c1cc(=O)[nH]c(-c2ccccc2)n1)c1ccc(C(F)(F)F)cc1Cl] | N-{(1S)-1-[2-chloro-4-(trifluoromethyl)phenyl]-2-hydroxy-1-methylethyl}-6-oxo-2-phenyl-1,6-dihydropyrimidine-4-carboxamide | Calc'd 452.1, found 452.0 |
| 644 | 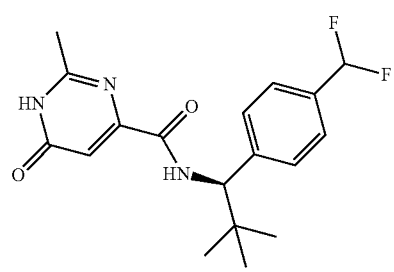 [SMILES: Cc1nc(C(=O)N[C@@H](c2ccc(C(F)F)cc2)C(C)(C)C)cc(=O)[nH]1] | N-{(1R)-1-[4-(difluoromethyl)phenyl]-2,2-dimethylpropyl}-2-methyl-6-oxo-1,6-dihydropyrimidine-4-carboxamide | Calc'd 350.2, found 350.1 |
| 645 | 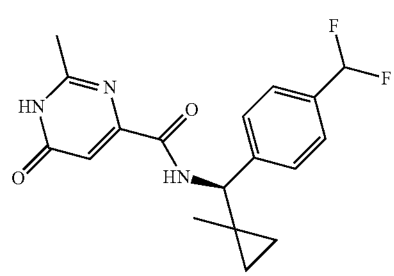 [SMILES: Cc1nc(C(=O)N[C@@H](c2ccc(C(F)F)cc2)C2(C)CC2)cc(=O)[nH]1] | N-[(R)-[4-(difluoromethyl)phenyl](1-methylcyclopropyl)methyl]-2-methyl-6-oxo-1,6-dihydropyrimidine-4-carboxamide | Calc'd 348.2, found 348.1 |

TABLE 13-continued

| Example Number | Structure | IUPAC Name | Observed Exact Mass [M + H]+ |
|---|---|---|---|
| 646 | 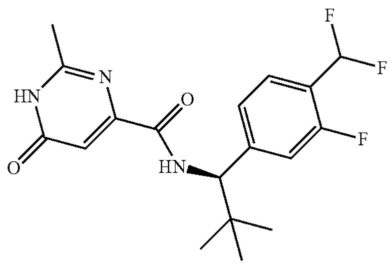 [SMILES: Cc1nc(C(=O)N[C@@H](c2ccc(C(F)F)c(F)c2)C(C)(C)C)cc(=O)[nH]1] | N-{(1R)-1-[4-(difluoromethyl)-3-fluorophenyl]-2,2-dimethylpropyl}-2-methyl-6-oxo-1,6-dihydropyrimidine-4-carboxamide | Calc'd 368.2, found 368.2 |
| 647 | 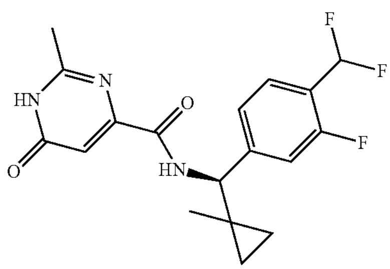 [SMILES: Cc1nc(C(=O)N[C@@H](c2ccc(C(F)F)c(F)c2)C2(C)CC2)cc(=O)[nH]1] | N-[(R)-[4-(difluoromethyl)-3-fluorophenyl](1-methylcyclopropyl)methyl]-2-methyl-6-oxo-1,6-dihydropyrimidine-4-carboxamide | Calc'd 366.1, found 366.1 |
| 648 | 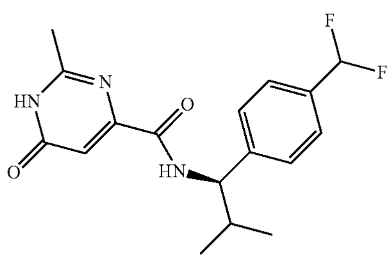 [SMILES: Cc1nc(C(=O)N[C@@H](c2ccc(C(F)F)cc2)C(C)C)cc(=O)[nH]1] | N-{(1R)-1-[4-(difluoromethyl)phenyl]-2-methylpropyl}-2-methyl-6-oxo-1,6-dihydropyrimidine-4-carboxamide | Calc'd 336.2, found 336.1 |
| 649 | 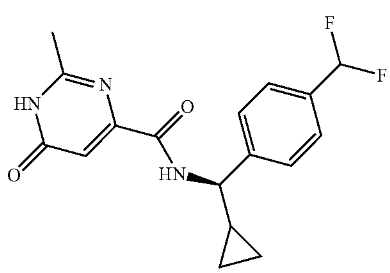 [SMILES: Cc1nc(C(=O)N[C@@H](c2ccc(C(F)F)cc2)C2CC2)cc(=O)[nH]1] | N-{(1R)-cyclopropyl[4-(difluoromethyl)phenyl]methyl}-2-methyl-6-oxo-1,6-dihydropyrimidine-4-carboxamide | Calc'd 334.1, found 334.1 |
| 650 | 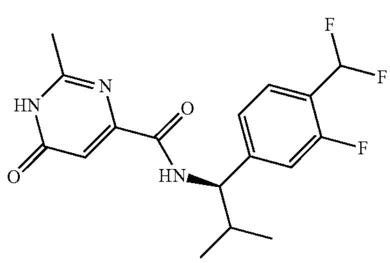 [SMILES: Cc1nc(C(=O)N[C@@H](c2ccc(C(F)F)c(F)c2)C(C)C)cc(=O)[nH]1] | N-{(1R)-1-[4-(difluoromethyl)-3-fluorophenyl]-2-methylpropyl}-2-methyl-6-oxo-1,6-dihydropyrimidine-4-carboxamide | Calc'd 354.1, found 354.1 |

TABLE 13-continued

| Example Number | Structure | IUPAC Name | Observed Exact Mass [M + H]+ |
| --- | --- | --- | --- |
| 651 | 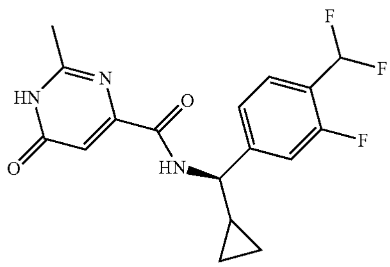 [SMILES: Cc1nc(C(=O)N[C@@H](c2ccc(C(F)F)c(F)c2)C2CC2)cc(=O)[nH]1] | N-{(R)-cyclopropyl[4-(difluoromethyl)-3-fluorophenyl]methyl}-2-methyl-6-oxo-1,6-dihydropyrimidine-4-carboxamide | Calc'd 352.1, found 351.9 |
| 652 | 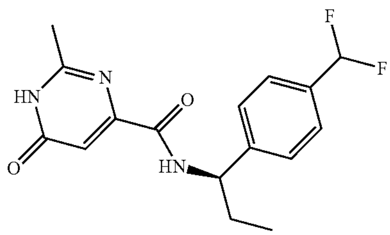 [SMILES: CC[C@@H](NC(=O)c1cc(=O)[nH]c(C)n1)c1ccc(C(F)F)cc1] | N-{(1R)-1-[4-(difluoromethyl)phenyl]propyl}-2-methyl-6-oxo-1,6-dihydropyrimidine-4-carboxamide | Calc'd 322.1, found 322.1 |
| 653 | 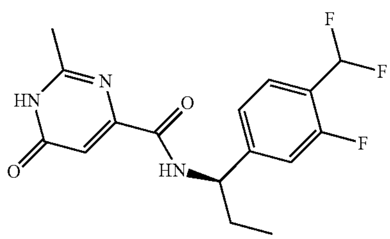 [SMILES: CC[C@@H](NC(=O)c1cc(=O)[nH]c(C)n1)c1ccc(C(F)F)c(F)c1] | N-{1R)-1-[4-(difluoromethyl)-3-fluorophenyl]propyl}-2-methyl-6-oxo-1,6-dihydropyrimidine-4-carboxamide | Calc'd 340.1, found 340.1 |
| 654 | 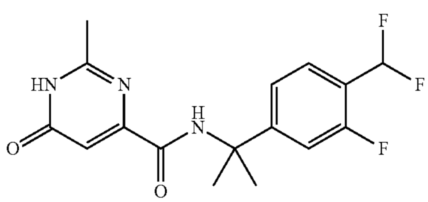 [SMILES: Cc1nc(C(=O)NC(C)(C)c2ccc(C(F)F)c(F)c2)cc(=O)[nH]1] | N-{1-[4-(difluoromethyl)-3-fluorophenyl]-1-methylethyl}-2-methyl-6-oxo-1,6-dihydropyrimidine-4-carboxamide | Calc'd 340.1, found 340.1 |
| 655 | 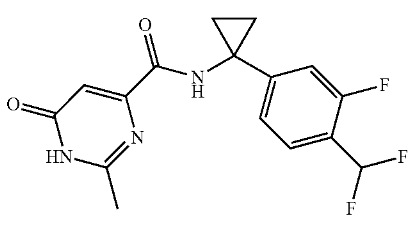 [SMILES: Cc1nc(C(=O)NC2(c3ccc(C(F)F)c(F)c3)CC2)cc(=O)[nH]1] | N-{1-[4-(difluoromethyl)-3-fluorophenyl]cyclopropyl}-2-methyl-6-oxo-1,6-dihydropyrimidine-4-carboxamide | Calc'd 338.1, found 338.1 |
| 656 | 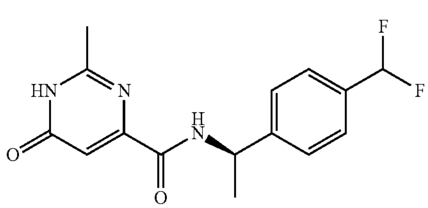 [SMILES: Cc1nc(C(=O)N[C@H](C)c2ccc(C(F)F)cc2)cc(=O)[nH]1] | N-{(1R)-1-[4-(difluoromethyl)phenyl]ethyl}-2-methyl-6-oxo-1,6-dihydropyrimidine-4-carboxamide | Calc'd 308.1, found 308.1 |

TABLE 13-continued

| Example Number | Structure | IUPAC Name | Observed Exact Mass [M + H]+ |
|---|---|---|---|
| 657 | 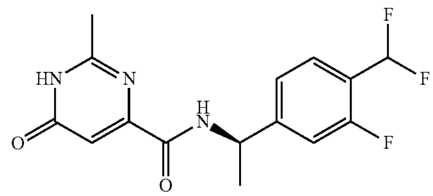 [SMILES: Cc1nc(C(=O)N[C@H](C)c2ccc(C(F)F)c(F)c2)cc(=O)[nH]1] | N-{(1R)-1-[4-(difluoromethyl)-3-fluorophenyl]ethyl}-2-methyl-6-oxo-1,6-dihydropyrimidine-4-carboxamide | Calc'd 326.1, found 326.1 |
| 658 | 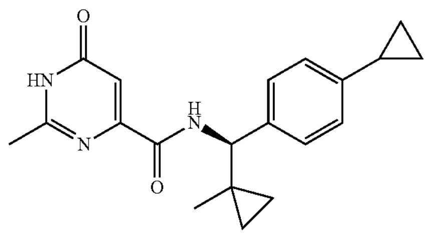 [SMILES: Cc1nc(C(=O)N[C@@H](c2ccc(C3CC3)cc2)C2(C)CC2)cc(=O)[nH]1] | N-[(R)-(4-cyclopropylphenyl)(1-methylcyclopropyl)methyl]-2-methyl-6-oxo-1,6-dihydropyrimidine-4-carboxamide | Calc'd 338.2, found 338.1 |
| 659 | 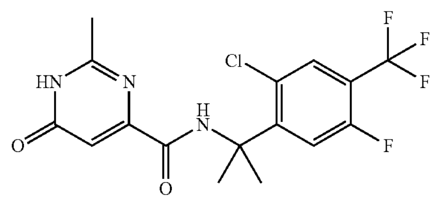 [SMILES: Cc1nc(C(=O)NC(C)(C)c2cc(F)c(C(F)(F)F)cc2Cl)cc(=O)[nH]1] | N-{1-[2-chloro-5-fluoro-4-(trifluoromethyl)phenyl]-1-methylethyl}-2-methyl-6-oxo-1,6-dihydropyrimidine-4-carboxamide | Calc'd 392.1, found 392.0 |
| 660 | 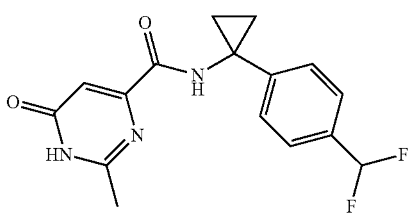 [SMILES: Cc1nc(C(=O)NC2(c3ccc(C(F)F)cc3)CC2)cc(=O)[nH]1] | N-{1-[4-(difluoromethyl)phenyl]cyclopropyl}-2-methyl-6-oxo-1,6-dihydropyrimidine-4-carboxamide | Calc'd 320.1, found 320.1 |
| 661 | 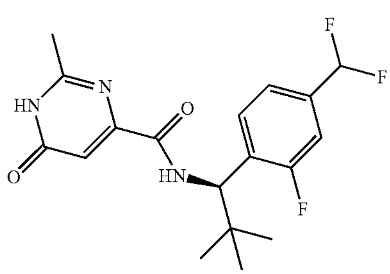 [SMILES: Cc1nc(C(=O)N[C@@H](c2ccc(C(F)F)cc2F)C(C)(C)C)cc(=O)[nH]1] | N-{(1R)-1-[4-(difluoromethyl)-2-fluorophenyl]-2,2-dimethylpropyl}-2-methyl-6-oxo-1,6-dihydropyrimidine-4-carboxamide | Calc'd 368.2, found 368.1 |

The compounds in Table 14 below were first prepared as racemates using conditions shown in Scheme I, which were the same as in Scheme C except DMA was used as the solvent in Scheme I while DMF was used in Scheme C. The experimental details for Scheme C were exemplified in Example 35. The resulting racemates were resolved on chiral columns specified in Table 14. The fast-eluting isomer of each racemate is always listed first in the Table. Examples 664 through 667 were prepared from racemic cyclopropylamines supplied by Ukrorgsyntez Ltd. (Riga, Latvia). The relative stereochemistries of these cyclopropylamines were not specified by the vendor. NMR studies of the amines and amide product showed the amines are mostly trans isomer. The racemic cyclopropylamine starting material for Examples 670 and 671 was obtained from ASW MedChem, Inc. (New Brunswick, N.J., USA) with unknown relative stereochemistry. NMR studies indicated that it is mostly cis isomer.

TABLE 14

| Example Number | Structure | IUPAC Name | Exact Mass [M + H]+ | Column |
|---|---|---|---|---|
| 662 | 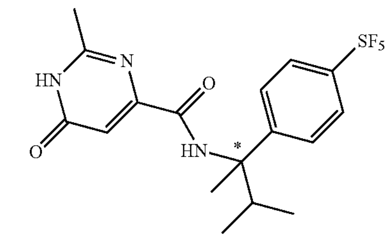 | (S)- or (R)-N-{1,2-dimethyl-1-[4-(pentafluoro-λ6-sulfanyl)phenyl]propyl}-2-methyl-6-oxo-1,6-dihydropyrimidine-4-carboxamide | Calc'd 426.1, found 425.9 | OD—H |
| 663 | 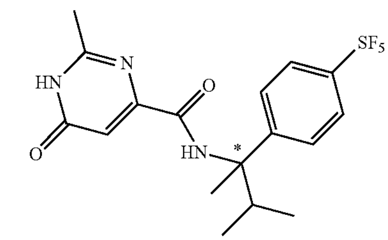 | (R)- or (S)-N-{1,2-dimethyl-1-[4-(pentafluoro-λ6-sulfanyl)phenyl]propyl}-2-methyl-6-oxo-1,6-dihydropyrimidine-4-carboxamide | Calc'd 426.1, found 425.9 | OD—H |
| 664 | 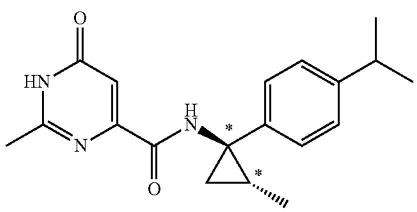 [SMILES: Cc1nc(C(=O)N[C@]2(c3ccc(C(C)C)cc3)C[C@H]2C)cc(=O)[nH]1] | 2-methyl-N-{2-methyl-1-[4-(1-methylethyl)phenyl]cyclopropyl}-6-oxo-1,6-dihydropyrimidine-4-carboxamide (trans, enantiomer A) | Calc'd 326.2, found 326.1 | OD—H |
| 665 | 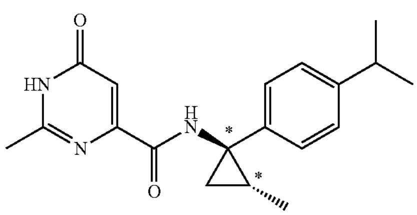 [SMILES: Cc1nc(C(=O)N[C@]2(c3ccc(C(C)C)cc3)C[C@H]2C)cc(=O)[nH]1] | 2-methyl-N-{2-methyl-1-[4-(1-methylethyl)phenyl]cyclopropyl}-6-oxo-1,6-dihydropyrimidine-4-carboxamide (trans, enantiomer B) | Calc'd 326.2, found 326.1 | OD—H |
| 666 | 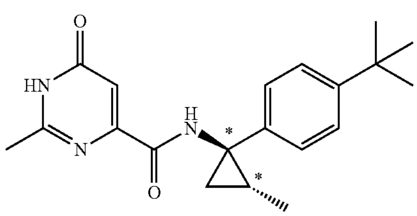 [SMILES: Cc1nc(C(=O)N[C@]2(c3ccc(C(C)(C)C)cc3)C[C@H]2C)cc(=O)[nH]1] | N-[1-(4-tert-butylphenyl)-2-methylcyclopropyl]-2-methyl-6-oxo-1,6-dihydropyrimidine-4-carboxamide (trans, enantiomer A) | Calc'd 340.2, found 340.1 | IC |
| 667 | 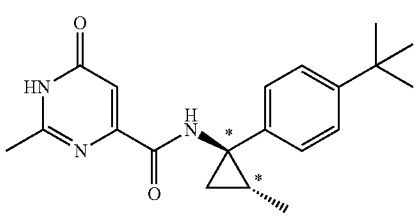 [SMILES: Cc1nc(C(=O)N[C@]2(c3ccc(C(C)(C)C)cc3)C[C@H]2C)cc(=O)[nH]1] | N-[1-(4-tert-butylphenyl)-2-methylcyclopropyl]-2-methyl-6-oxo-1,6-dihydropyrimidine-4-carboxamide (trans, enantiomer B) | Calc'd 340.2, found 340.1 | IC |
| 668 | 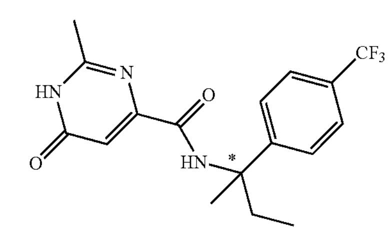 [SMILES: CCC(C)(NC(=O)c1cc(=O)[nH]c(C)n1)c1ccc(C(F)(F)F)cc1] | (S)- or (R)-2-methyl-N-{1-methyl-1-[4-(trifluoromethyl)phenyl]propyl}-6-oxo-1,6-dihydropyrimidine-4-carboxamide | Calc'd 354.1, found 354.1 | IC |

TABLE 14-continued

| Example Number | Structure | IUPAC Name | Exact Mass [M + H]+ | Column |
|---|---|---|---|---|
| 669 | 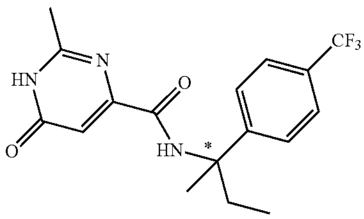 [SMILES: CCC(C)(NC(=O)c1cc(=O)[nH]c(C)n1)c1ccc(C(F)(F)F)cc1] | (R)- or (S)-2-methyl-N-{1-methyl-1-[4-(trifluoromethyl)phenyl]propyl}-6-oxo-1,6-dihydropyrimidine-4-carboxamide | Calc'd 354.1, found 354.1 | IC |
| 670 | 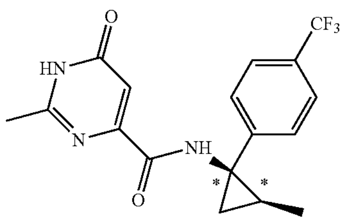 [SMILES: Cc1nc(C(=O)N[C@]2(c3ccc(C(F)(F)F)cc3)C[C@@H]2C)cc(=O)[nH]1] | 2-methyl-N-{2-methyl-1-[4-(trifluoromethyl)phenyl]cyclopropyl}-6-oxo-1,6-dihydropyrimidine-4-carboxamide (cis, enantiomer A) | Calc'd 352.1, found 352.1 | IC |
| 671 | 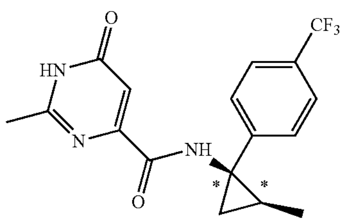 [SMILES: Cc1nc(C(=O)N[C@]2(c3ccc(C(F)(F)F)cc3)C[C@@H]2C)cc(=O)[nH]1] | 2-methyl-N-{2-methyl-1-[4-(trifluoromethyl)phenyl]cyclopropyl}-6-oxo-1,6-dihydropyrimidine-4-carboxamide (cis, enantiomer B) | Calc'd 352.1, found 352.1 | IC |

Examples 672 and 673

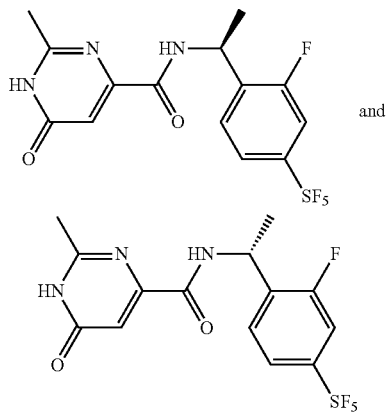

(R)—N-(1-(2-fluoro-4-(pentafluorothio)phenyl)ethyl)-2-methyl-6-oxo-1,6-dihydropyrimidine-4-carboxamide and (S)—N-(1-(2-fluoro-4-(pentafluorothio)phenyl)ethyl)-2-methyl-6-oxo-1,6-dihydropyrimidine-4-carboxamide Step 1. N-(1-(2-fluoro-4-(pentafluorothio)phenyl)ethyl)-2-methyl-6-oxo-1,6-dihydropyrimidine-4-carboxamide The title compound was prepared using procedures similar to those described in Scheme A using 2-methyl-6-oxo-1,6-dihydropyrimidine-4-carboxylic acid (51.1 mg, 0.3 mmol), 1-(2-fluoro-4-(pentafluorothio)phenyl) ethanamine hydrochloride from Preparatory Example 11 (50.0 mg, 0.2 mmol), HATU (82.0 mg, 0.2 mmol) and TEA (0.069 mL, 0.5 mmol) in NMP (1 mL) to afford the title compound as a solid. MS (+ESI) m/z=402.0.

Step 2. (R)- and (S)—N-(1-(2-fluoro-4-(pentafluorothio)phenyl)ethyl)-2-methyl-6-oxo-1,6-dihydropyrimidine-4-carboxamide N-(1-(2-fluoro-4-(pentafluorothio)phenyl)ethyl)-2-methyl-6-oxo-1,6-dihydropyrimidine-4-carboxamide (50.0 mg, 0.1 mmol) was separated on ChiralPak IA column with 10% EtOH in hexanes. The faster-eluting enantiomer of the title compound (Example 672) was obtained as a solid. MS (+ESI) m/z=402.0. $^1$H NMR (300 MHz, CDCl$_3$) δ: 13.16 (br, 1H), 8.28 (d, J=7.8 Hz, 1H), 7.54-7.42 (m, 3H), 7.13 (s, 1H), 5.45-5.36 (m, 1H), 2.56 (s, 3H), 1.64 (d, J=6.9 Hz, 3H). The slower-eluting enantiomer of the title compound (Example 673) was obtained as a solid. MS (+ESI) m/z=402.0. $^1$H NMR (300 MHz, CDCl$_3$) δ: 12.68 (br, 1H), 8.26 (d, J=7.8 Hz, 1H), 7.61-7.42 (m, 3H), 7.13 (s, 1H), 5.45-5.35 (m, 1H), 2.56 (s, 3H), 1.64 (d, J=6.9 Hz, 3H).

The following compounds in Table 15 were prepared using procedures similar to those described in Examples 672 and 673 using appropriate starting materials.

TABLE 15

| Example # | Structure | IUPAC Name | Exact Mass [M + H]+ |
|---|---|---|---|
| 674 | 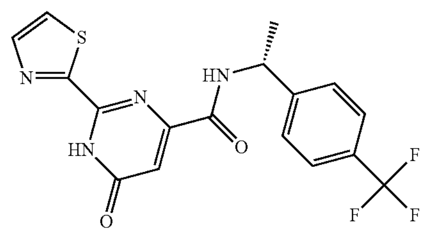 [SMILES: C[C@@H](NC(=O)c1cc(=O)[nH]c(-c2nccs2)n1)c1ccc(C(F)(F)F)cc1] | (R)-6-oxo-2-(thiazol-2-yl)-N-(1-(4-(trifluoromethyl)phenyl)ethyl)-1,6-dihydropyrimidine-4-carboxamide | Calc'd 395.1, Found 395.1 |
| 675 | 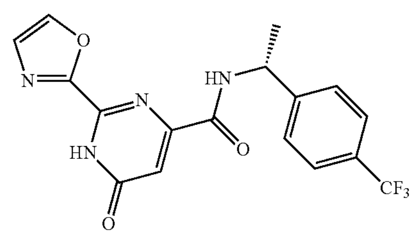 [SMILES: C[C@@H](NC(=O)c1cc(=O)[nH]c(-c2ncco2)n1)c1ccc(C(F)(F)F)cc1] | (R)-2-(oxazol-2-yl)-6-oxo-N-(1-(4-(trifluoromethyl)phenyl)ethyl)-1,6-dihydropyrimidine-4-carboxamide | Calc'd 379.1, found 379.0 |
| 676 | 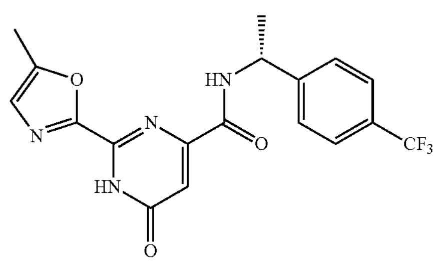 [SMILES: Cc1cnc(-c2nc(C(=O)N[C@H](C)c3ccc(C(F)(F)F)cc3)cc(=O)[nH]2)o1] | (R)-2-(5-methyloxazol-2-yl)-6-oxo-N-(1-(4-(trifluoromethyl)phenyl)ethyl)-1,6-dihydropyrimidine-4-carboxamide | Calc'd 393.1, found 393.1 |
| 677 | 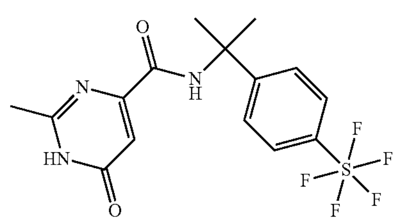 [SMILES: Cc1nc(C(=O)NC(C)(C)c2ccc(S(F)(F)(F)(F)F)cc2)cc(=O)[nH]1] | 2-methyl-N-{1-methyl-1-[4-(pentafluoro-$\lambda^6$-sulfanyl)phenyl]ethyl}-6-oxo-1,6-dihydropyrimidine-4-carboxamide | Calc'd 398.1, found 397.9 |
| 678 | 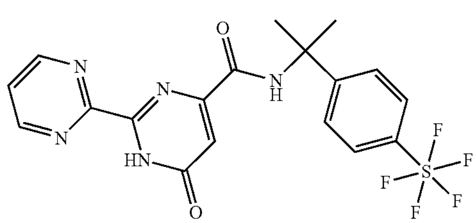 [SMILES: CC(C)(NC(=O)c1cc(=O)[nH]c(-c2ncccn2)n1)c1ccc(S(F)(F)(F)(F)F)cc1] | N-{1-methyl-1-[4-(pentafluoro-$\lambda^6$-sulfanyl)phenyl]ethyl}-6-oxo-1,6-dihydro-2,2'-bipyrimidine-4-carboxamide | Calc'd 462.1, found 462.1 |
| 679 | 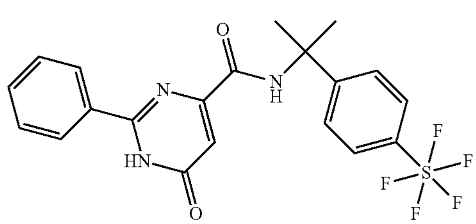 [SMILES: CC(C)(NC(=O)c1cc(=O)[nH]c(-c2ccccc2)n1)c1ccc(S(F)(F)(F)(F)F)cc1] | N-{1-methyl-1-[4-(pentafluoro-$\lambda^6$-sulfanyl)phenyl]ethyl}-6-oxo-2-phenyl-1,6-dihydropyrimidine-4-carboxamide | Calc'd 460.1, found 460.1 |

TABLE 15-continued

| Example # | Structure | IUPAC Name | Exact Mass [M + H]+ |
|---|---|---|---|
| 680 | 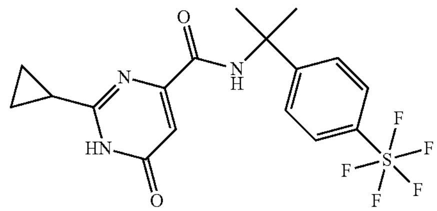 [SMILES: CC(C)(NC(=O)c1cc(=O)[nH]c(C2CC2)n1)c1ccc(S(F)(F)(F)(F)F)cc1] | 2-cyclopropyl-N-{1-methyl-1-[4-(pentafluoro-λ⁶-sulfanyl)phenyl]ethyl}-6-oxo-1,6-dihydropyrimidine-4-carboxamide | Calc'd 424.1, found 424.1 |
| 681 | 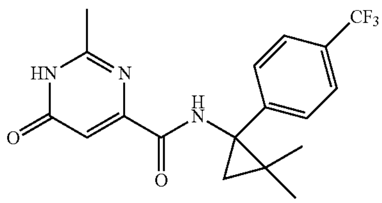 [SMILES: Cc1nc(C(=O)NC2(c3ccc(C(F)(F)F)cc3)CC2(C)C)cc(=O)[nH]1] | N-(2,2-dimethyl-1-(4-(trifluoromethyl)phenyl)cyclopropyl)-2-methyl-6-oxo-1,6-dihydropyrimidine-4-carboxamide | Calc'd 366.1, found 366.1 |

The following compounds in Table 16 were prepared using procedures similar to those described in Examples 672 and 673 using appropriate starting materials. Racemic products were separated using ChiralPak columns specified in the table. For those pairs of enantiomers, the fast-eluting isomer is always listed first in this table.

TABLE 16

| Example # | Structure | IUPAC Name | Exact Mass [M + H]+ | Chiral column |
|---|---|---|---|---|
| 682 | 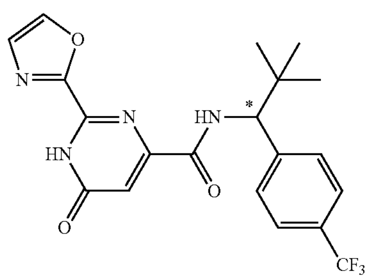 [SMILES: CC(C)(C)C(NC(=O)c1cc(=O)[nH]c(-c2ncco2)n1)c1ccc(C(F)(F)F)cc1] | (R)- or (S)-N-(2,2-dimethyl-1-(4-(trifluoromethyl)phenyl)propyl)-2-(oxazol-2-yl)-6-oxo-1,6-dihydropyrimidine-4-carboxamide | Calc'd 421.1, found 421.1 | AS—H |
| 683 | 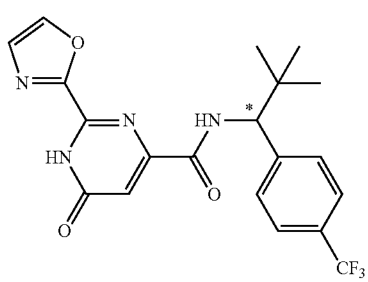 [SMILES: CC(C)(C)C(NC(=O)c1cc(=O)[nH]c(-c2ncco2)n1)c1ccc(C(F)(F)F)cc1] | (S)- or (R)-N-(2,2-dimethyl-1-(4-(trifluoromethyl)phenyl)propyl)-2-(oxazol-2-yl)-6-oxo-1,6-dihydropyrimidine-4-carboxamide | Calc'd 421.1, found 421.1 | AS—H |
| 684 | 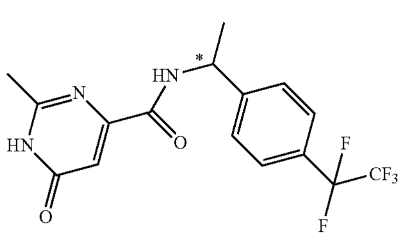 [SMILES: Cc1nc(C(=O)NC(C)c2ccc(C(F)(F)C(F)(F)F)cc2)cc(=O)[nH]1] | (S)- or (R)-2-methyl-6-oxo-N-(1-(4-(perfluoroethyl)phenyl)ethyl)-1,6-dihydropyrimidine-4-carboxamide | Calc'd 376.1, found 376.1 | IC |

TABLE 16-continued

| Example # | Structure | IUPAC Name | Exact Mass [M + H]+ | Chiral column |
|---|---|---|---|---|
| 685 | 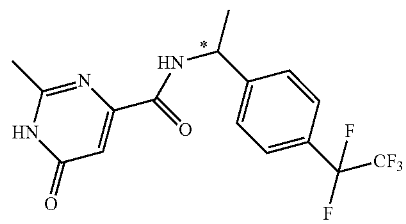 [SMILES: Cc1nc(C(=O)NC(C)c2ccc(C(F)(F)C(F)(F)F)cc2)cc(=O)[nH]1] | (R)- or (S)-methyl-6-oxo-N-(1-(4-(perfluoroethyl)phenyl)ethyl)-1,6-dihydropyrimidine-4-carboxamide | Calc'd 376.1, found 376.1 | IC |
| 686 | 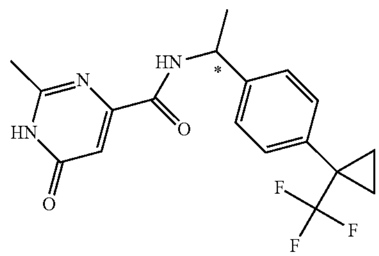 [SMILES: Cc1nc(C(=O)NC(C)c2ccc(C3(C(F)(F)F)CC3)cc2)cc(=O)[nH]1] | (S)- or (R)-2-methyl-6-oxo-N-(1-(4-(1-(trifluoromethyl)cyclopropyl)phenyl)-ethyl)-1,6-dihydropyrimidine-4-carboxamide | Calc'd 366.1, found 366.1, | IC |
| 687 | 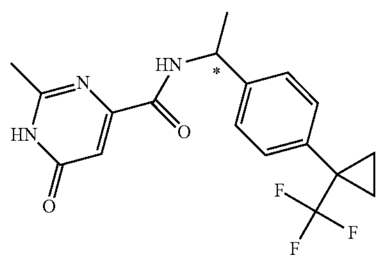 [SMILES: Cc1nc(C(=O)NC(C)c2ccc(C3(C(F)(F)F)CC3)cc2)cc(=O)[nH]1] | (R)- or (S)-2-methyl-6-oxo-N-(1-(4-(1-(trifluoromethyl)cyclopropyl)phenyl)-ethyl)-1,6-dihydropyrimidine-4-carboxamide | Calc'd 366.1, found 366.1, | IC |
| 688 | 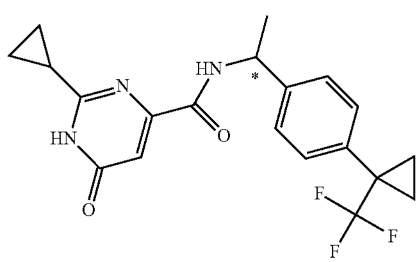 [SMILES: CC(NC(=O)c1cc(=O)[nH]c(C2CC2)n1)c1ccc(C2(C(F)(F)F)CC2)cc1] | (S)- or (R)-2-cyclopropyl-6-oxo-N-(1-(4-(1-(trifluoromethyl)cyclopropyl)phenyl)-ethyl)-1,6-dihydropyrimidine-4-carboxamide | Calc'd 392.1, found 392.1, | IC |
| 689 | 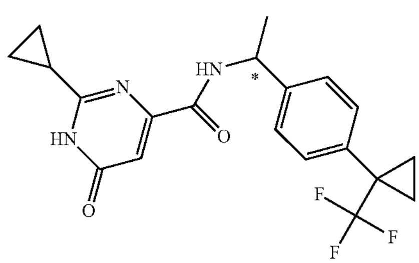 [SMILES: CC(NC(=O)c1cc(=O)[nH]c(C2CC2)n1)c1ccc(C2(C(F)(F)F)CC2)cc1] | (R)- or (S)-2-cyclopropyl-6-oxo-N-(1-(4-(1-(trifluoromethyl)cyclopropyl)phenyl)-ethyl)-1,6-dihydropyrimidine-4-carboxamide | Calc'd 392.1, found 392.1, | IC |
| 690 | 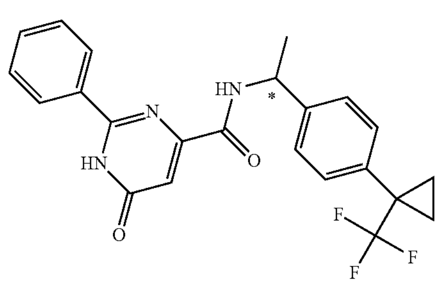 [SMILES: CC(NC(=O)c1cc(=O)[nH]c(-c2ccccc2)n1)c1ccc(C2(C(F)(F)F)CC2)cc1] | (S)- or (R)-6-oxo-2-phenyl-N-(1-(4-(1-(trifluoromethyl)cyclopropyl)phenyl)-ethyl)-1,6-dihydropyrimidine-4-carboxamide | Calc'd 428.2, found 428.1, | IC |

| Example # | Structure | IUPAC Name | Exact Mass [M + H]+ | Chiral column |
|---|---|---|---|---|
| 691 | 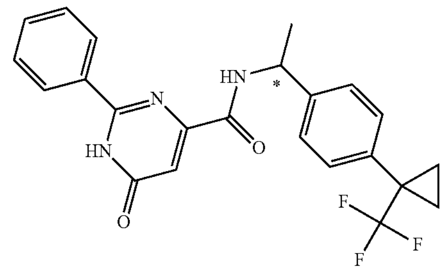 [SMILES: CC(NC(=O)c1cc(=O)[nH]c(-c2ccccc2)n1)c1ccc(C2(C(F)(F)F)CC2)cc1] | (R)- or (S)-6-oxo-2-phenyl-N-(1-(4-(1-(trifluoromethyl)cyclopropyl)phenyl)-ethyl)-1,6-dihydropyrimidine-4-carboxamide | Calc'd 428.2, found 428.1, | IC |
| 692 | 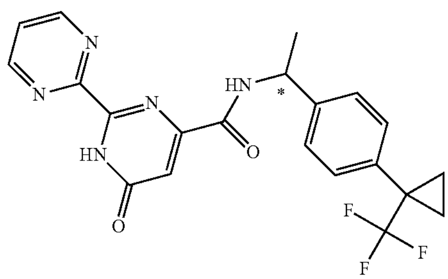 [SMILES: CC(NC(=O)c1cc(=O)[nH]c(-c2ncccn2)n1)c1ccc(C2(C(F)(F)F)CC2)cc1] | (S)- or (R)-6-oxo-2-(pyrimidin-2-yl)-N-(1-(4-(1-(trifluoromethyl)cyclopropyl)phenyl)-ethyl)-1,6-dihydropyrimidine-4-carboxamide | Calc'd 430.1, found 430.1, | IC |
| 693 | 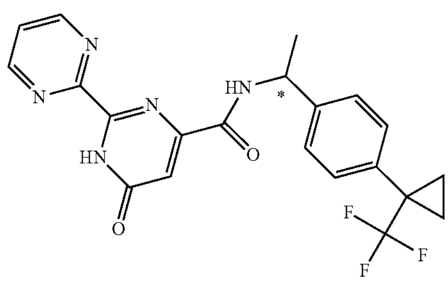 [SMILES: CC(NC(=O)c1cc(=O)[nH]c(-c2ncccn2)n1)c1ccc(C2(C(F)(F)F)CC2)cc1] | (R)- or (S)-6-oxo-2-(pyrimidin-2-yl)-N-(1-(4-(1-(trifluoromethyl)cyclopropyl)phenyl)-ethyl)-1,6-dihydropyrimidine-4-carboxamide | Calc'd 430.1, found 430.1, | IC |
| 694 | 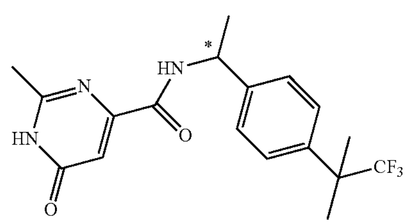 [SMILES: Cc1nc(C(=O)NC(C)c2ccc(C(C)(C)C(F)(F)F)cc2)cc(=O)[nH]1] | (S)- or (R)-2-methyl-6-oxo-N-(1-(4-(1,1,1-trifluoro-2-methylpropan-2-yl)phenyl)ethyl)-1,6-dihydropyrimidine-4-carboxamide | Calc'd 368.1, found 368.2 | IC |
| 695 | 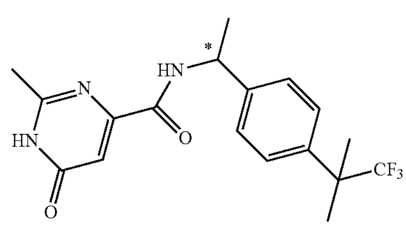 [SMILES: Cc1nc(C(=O)NC(C)c2ccc(C(C)(C)C(F)(F)F)cc2)cc(=O)[nH]1] | (R)- or (S)-2-methyl-6-oxo-N-(1-(4-(1,1,1-trifluoro-2-methylpropan-2-yl)phenyl)ethyl)-1,6-dihydropyrimidine-4-carboxamide | Calc'd 368.1, found 368.2 | IC |
| 696 | 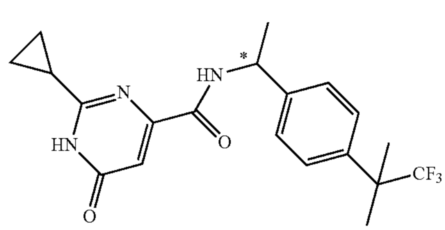 [SMILES: CC(NC(=O)c1cc(=O)[nH]c(C2CC2)n1)c1ccc(C(C)(C)C(F)(F)F)cc1] | (S)- or (R)-2-methyl-6-oxo-N-(1-(4-(1,1,1-trifluoro-2-methylpropan-2-yl)phenyl)ethyl)-1,6-dihydropyrimidine-4-carboxamide | Calc'd 394.2, found 394.2 | IC |

TABLE 16-continued

| Example # | Structure | IUPAC Name | Exact Mass [M + H]+ | Chiral column |
|---|---|---|---|---|
| 697 | 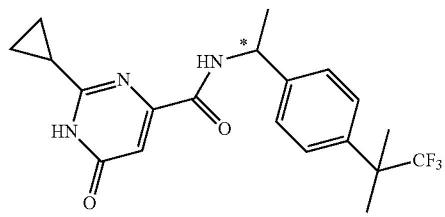 [SMILES: CC(NC(=O)c1cc(=O)[nH]c(C2CC2)n1)c1ccc(C(C)(C)C(F)(F)F)cc1] | (R)- or (S)-2-methyl-6-oxo-N-(1-(4-(1,1,1-trifluoro-2-methylpropan-2-yl)phenyl)ethyl)-1,6-dihydropyrimidine-4-carboxamide | Calc'd 394.2, found 394.2 | IC |
| 698 | 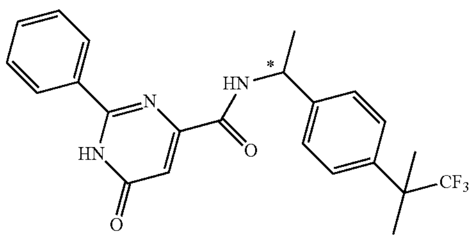 [SMILES: CC(NC(=O)c1cc(=O)[nH]c(-c2ccccc2)n1)c1ccc(C(C)(C)C(F)(F)F)cc1] | (S)- or (R)-6-oxo-2-phenyl-N-(1-(4-(1,1,1-trifluoro-2-methylpropan-2-yl)phenyl)ethyl)-1,6-dihydropyrimidine-4-carboxamide | Calc'd 430.2, found 430.2 | IC |
| 699 | 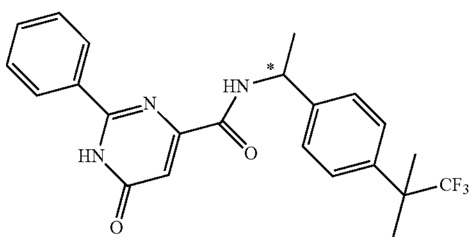 [SMILES: CC(NC(=O)c1cc(=O)[nH]c(-c2ccccc2)n1)c1ccc(C(C)(C)C(F)(F)F)cc1] | (R)- or (S)-6-oxo-2-phenyl-N-(1-(4-(1,1,1-trifluoro-2-methylpropan-2-yl)phenyl)ethyl)-1,6-dihydropyrimidine-4-carboxamide | Calc'd 430.2, found 430.2 | IC |
| 700 | 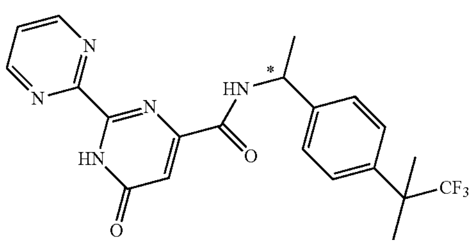 [SMILES: CC(NC(=O)c1cc(=O)[nH]c(-c2ncccn2)n1)c1ccc(C(C)(C)C(F)(F)F)cc1] | (S)- or (R)-6-oxo-N-(1-(4-(1,1,1-trifluoro-2-methylpropan-2-yl)phenyl)ethyl)-1,6-dihydro-[2,2'-bipyrimidine]-4-carboxamide | Calc'd 432.2, found 432.1 | IC |
| 701 | 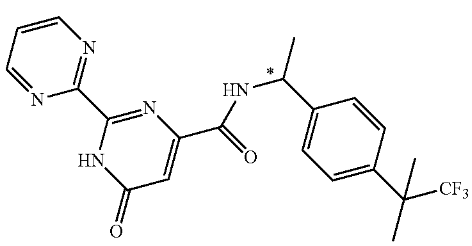 [SMILES: CC(NC(=O)c1cc(=O)[nH]c(-c2ncccn2)n1)c1ccc(C(C)(C)C(F)(F)F)cc1] | (R)- or (S)-6-oxo-N-(1-(4-(1,1,1-trifluoro-2-methylpropan-2-yl)phenyl)ethyl)-1,6-dihydro-[2,2'-bipyrimidine]-4-carboxamide | Calc'd 432.2, found 432.1 | IC |
| 702 | 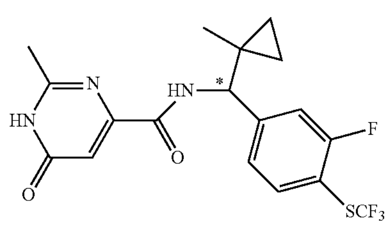 | (R)- or (S)-N-((3-fluoro-4-((trifluoromethyl)thio)phenyl)(1-methylcyclopropyl)methyl)-2-methyl-6-oxo-1,6-dihydropyrimidine-4-carboxamide | Calc'd 416.1, found 416.2 | IA |

TABLE 16-continued

| Example # | Structure | IUPAC Name | Exact Mass [M + H]+ | Chiral column |
|---|---|---|---|---|
| 703 | 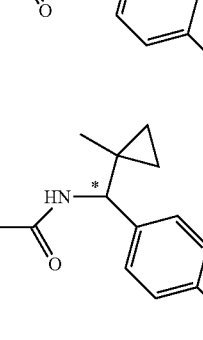 | (S)- or (R)-N-((3-fluoro-4-((trifluoromethyl)thio)phenyl)(1-methylcyclopropyl)methyl)-2-methyl-6-oxo-1,6-dihydropyrimidine-4-carboxamide | Calc'd 416.1, found 416.2 | IA |
| 704 | 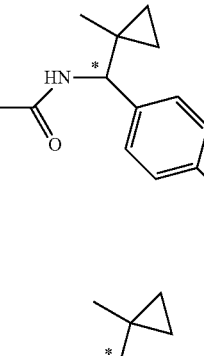 | (R)- or (S)-2-cyclopropyl-N-((3 fluoro-4-((trifluorormethyl)thio)phenyl)(1-methylcyclopropyl)methyl)-6-oxo-1,6-dihydropyrimidine-4-carboxamide | Calc'd 442.1, found 442.2 | IA |
| 705 | 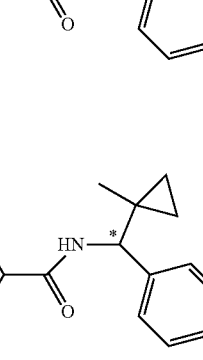 | (S)- or (R)-2-cyclopropyl-N-((3-fluoro-4-((trifluoromethyl)thio)phenyl)(1-methylcyclopropyl)methyl)-6-oxo-1,6-dihydropyrimidine-4-carboxamide | Calc'd 442.1, found 442.2 | IA |
| 706 | 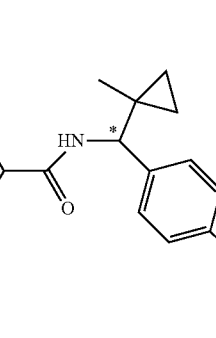 | (S)- or (R)-N-((3-fluoro-4-((trifluoromethyl)thio)phenyl)(1-methylcyclopropyl)methyl)-6-oxo-2-phenyl-1,6-dihydropyrimidine-4-carboxamide | Calc'd 478.1, found 478.1 | IC |
| 707 | 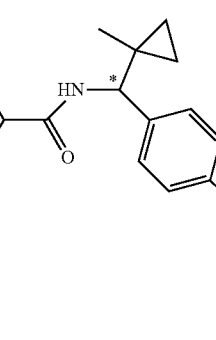 | (R)- or (S)-N-((3-fluoro-4-((trifluoromethyl)thio)phenyl)(1-methylcyclopropyl)methyl)-6-oxo-2-phenyl-1,6-dihydropyrimidine-4-carboxamide | Calc'd 478.1, found 478.1 | IC |
| 708 | 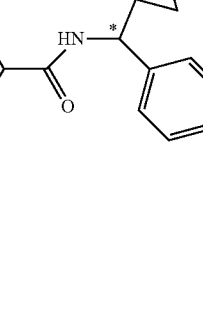 | (S)- or (R)-N-((3-fluoro-4-((trifluoromethyl)thio)phenyl)(1-methylcyclopropyl)methyl)-6-oxo-1,6-dihydro-[2,2'-bipyrimidine]-4-carboxamide | Calc'd 480.1, found 480.2 | IC |

TABLE 16-continued

| Example # | Structure | IUPAC Name | Exact Mass [M + H]+ | Chiral column |
|---|---|---|---|---|
| 709 | 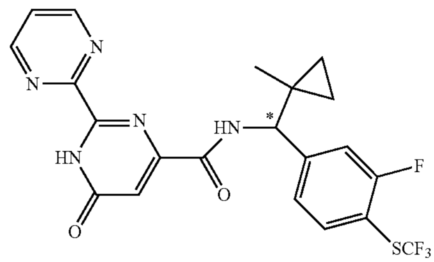 | (R)- or (S)-N-((3-fluoro-4-((trifluoromethyl)thio)phenyl)(1-methylcyclopropyl)methyl)-6-oxo-1,6-dihydro-[2,2'-bipyrimidine]-4-carboxamide | Calc'd 480.1, found 480.2 | IC |
| 710 | 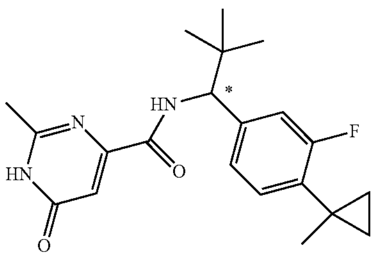 [SMILES: Cc1nc(C(=O)NC(c2ccc(C3(C)CC3)c(F)c2)C(C)(C)C)cc(=O)[nH]1] | (S)- or (R)-N-(1-(3-fluoro-4-(1-methylcyclopropyl)phenyl)-2,2-dimethylpropyl)-2-methyl-6-oxo-1,6-dihydropyrimidine-4-carboxamide | Calc'd 372.2, found 372.3 | IC |
| 711 | 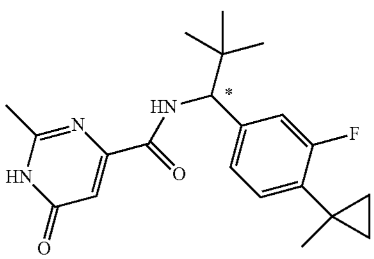 [SMILES: Cc1nc(C(=O)NC(c2ccc(C3(C)CC3)c(F)c2)C(C)(C)C)cc(=O)[nH]1] | (R)- or (S)-N-(1-(3-fluoro-4-(1-methylcyclopropyl)phenyl)-2,2-dimethylpropyl)-2-methyl-6-oxo-1,6-dihydropyrimidine-4-carboxamide | Calc'd 372.2, found 372.3 | IC |
| 712 | 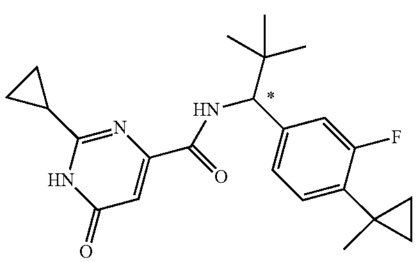 [SMILES: CC1(c2ccc(C(NC(=O)c3cc(=O)[nH]c(C4CC4)n3)C(C)(C)C)cc2F)CC1] | (S)- or (R)-2-cyclopropyl-N-(1-(3-fluoro-4-(1-methylcyclopropyl)phenyl)-2,2-dimethylpropyl)-6-oxo-1,6-dihydropyrimidine-4-carboxamide | Calc'd 398.2, found 398.3 | IC |
| 713 | 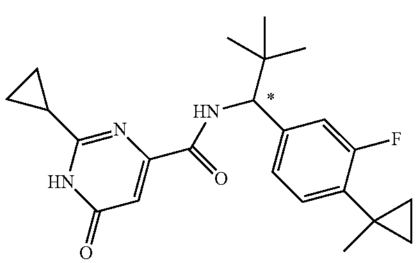 [SMILES: CC1(c2ccc(C(NC(=O)c3cc(=O)[nH]c(C4CC4)n3)C(C)(C)C)cc2F)CC1] | (R)- or (S)-2-cyclopropyl-N-(1-(3-fluoro-4-(1-methylcyclopropyl)phenyl)-2,2-dimethylpropyl)-6-oxo-1,6-dihydropyrimidine-4-carboxamide | Calc'd 398.2, found 398.3 | IC |
| 714 | 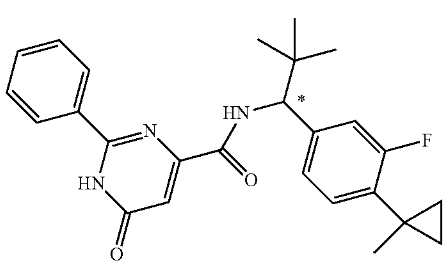 [SMILES: CC1(c2ccc(C(NC(=O)c3cc(=O)[nH]c(-c4ccccc4)n3)C(C)(C)C)cc2F)CC1] | (S)- or (R)-N-(1-(3-fluoro-4-(1-methylcyclopropyl)phenyl)-2,2-dimethylpropyl)-6-oxo-2-phenyl-1,6-dihydropyrimidine-4-carboxamide | Calc'd 434.2, found 434.4 | IC |

TABLE 16-continued

| Example # | Structure | IUPAC Name | Exact Mass [M + H]+ | Chiral column |
|---|---|---|---|---|
| 715 | 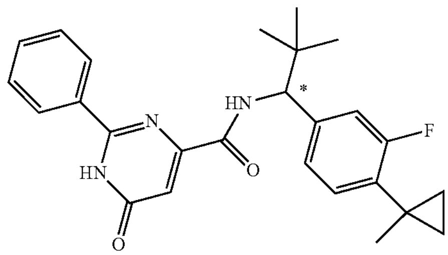 [SMILES: CC1(c2ccc(C(NC(=O)c3cc(=O)[nH]c(-c4ccccc4)n3)C(C)(C)C)cc2F)CC1] | (R)- or (S)-N-(1-(3-fluoro-4-(1-methylcyclopropyl)phenyl)-2,2-dimethylpropyl)-6-oxo-2-phenyl-1,6-dihydropyrimidine-4-carboxamide | Calc'd 434.2, found 434.3 | IC |
| 716 | 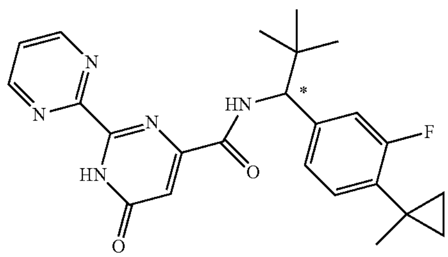 [SMILES: CC1(c2ccc(C(NC(=O)c3cc(=O)[nH]c(-c4ncccn4)n3)C(C)(C)C)cc2F)CC1] | (S)- or (R)-N-(1-(3-fluoro-4-(1-methylcyclopropyl)phenyl)-2,2-dimethylpropyl)-6-oxo-1,6-dihydro-[2,2'-bipyrimidine]-4-carboxamide | Calc'd 436.2, found 436.3 | IB |
| 717 | 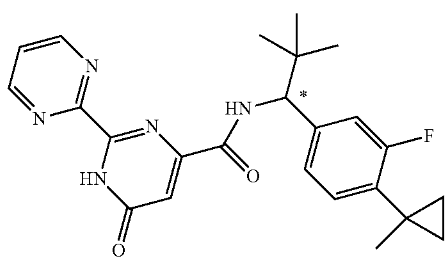 [SMILES: CC1(c2ccc(C(NC(=O)c3cc(=O)[nH]c(-c4ncccn4)n3)C(C)(C)C)cc2F)CC1] | (R)- or (S)-N-(1-(3-fluoro-4-(1-methylcyclopropyl)phenyl)-2,2-dimethylpropyl)-6-oxo-1,6-dihydro-[2,2'-bipyrimidine]-4-carboxamide | Calc'd 436.2 found 436.3 | IB |
| 718 | 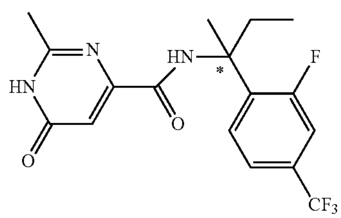 [SMILES: CCC(C)(NC(=O)c1cc(=O)[nH]c(C)n1)c1ccc(C(F)(F)F)cc1F] | (S)- or (R)-N-(2-(2-fluoro-4-(trifluoromethyl)phenyl)butan-2-yl)-2-methyl-6-oxo-1,6-dihydropyrimidine-4-carboxamide | Calc'd 372.1, found 372.1 | IC |
| 719 | 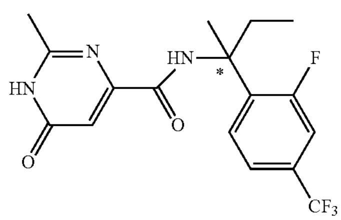 [SMILES: CCC(C)(NC(=O)c1cc(=O)[nH]c(C)n1)c1ccc(C(F)(F)F)cc1F] | (R)- or (S)-N-(2-(2-fluoro-4-(trifluoromethyl)phenyl)butan-2-yl)-2-methyl-6-oxo-1,6-dihydropyrimidine-4-carboxamide | Calc'd 372.1, found 372.1 | IC |
| 720 | 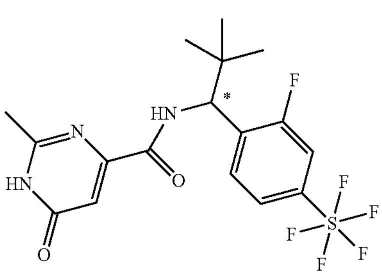 [SMILES: Cc1nc(C(=O)NC(c2ccc(S(F)(F)(F)(F)F)cc2F)C(C)(C)C)cc(=O)[nH]1] | (R)- or (S)-N-(1-(2-fluoro-4-(pentafluoro-$\lambda^6$-sulfanyl)phenyl)-2,2-dimethylpropyl)-2-methyl-6-oxo-1,6-dihydropyrimidine-4-carboxamide | Calc'd 444.1, found 444.2 | IA |

TABLE 16-continued

| Example # | Structure | IUPAC Name | Exact Mass [M + H]+ | Chiral column |
|---|---|---|---|---|
| 721 | 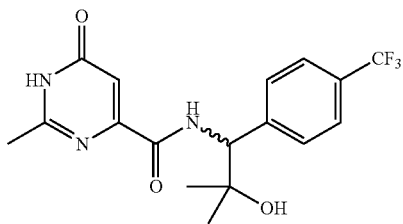 [SMILES: Cc1nc(C(=O)NC(c2ccc(C(F)(F)F)cc2)C(C)(C)O)cc(=O)[nH]1] | (S)- or (R)-N-(1-(2-fluoro-4-(pentafluoro-λ⁶-sulfanyl)phenyl)-2,2-dimethylpropyl)-2-methyl-6-oxo-1,6-dihydropyrimidine-4-carboxamide | Calc'd 444.1, found 444.2 | IA |

Example 722

N-{2-hydroxy-2-methyl-1-[4-(trifluoromethyl)phenyl]propyl}-2-methyl-6-oxo-1,6-dihydropyrimidine-4-carboxamide

Step 1. Methyl 2-(2-methyl-6-oxo-1,6-dihydropyrimidine-4-carboxamido)-2-(4-(trifluoromethyl)phenyl)-acetate To a stirring solution of 2-methyl-6-oxo-1,6-dihydropyrimidine-4-carboxylic acid (200 mg, 1.298 mmol) and methyl 2-amino-2-(4-(trifluoromethyl)phenyl)acetate (333 mg, 1.427 mmol) in $CH_2Cl_2$ (13 ml) was added TEA (543 pl, 3.89 mmol), followed by addition of 2,4,6-tripropyl-1,3,5,2,4,6-trioxatriphosphinane 2,4,6-trioxide (908 mg, 1.427 mmol). The reaction mixture was stirred at rt for 3 h and then concentrated and purified by column chromatography over silica gel eluting with 0 to 50% ethyl acetate/hexane to afford the tile compound. MS: 370.1 (M+H). The title compound was also prepared as Example 325 using a different coupling reagent.

Step 2. N-{2-hydroxy-2-methyl-1-[4-(trifluoromethyl)phenyl]propyl}-2-methyl-6-oxo-1,6-dihydro-pyri-midine-4-carboxamide To a stirring solution of methyl 2-(2-methyl-6-oxo-1,6-dihydropyrimidine-4-carboxamido)-2-(4-(trifluoromethyl) phenyl)acetate (32 mg, 0.087 mmol) in THF (867 μl) was charged with methylmagnesium bromide (144 μl, 0.433 mmol) at −78 C under an inert atmosphere. The reaction mixture was stirred at −78° C. for 2 h and then was acidified with aqueous ammonium chloride to pH 4 and extracted with ethyl acetate (3×). The combined organic phase was dried over anhydrous $Na_2SO_4$, filtered and concentrated to dryness under reduced pressure. The crude product was purified via reverse phase HPLC on a C18 column (14-54% $CH_3CN/H_2O$, 0.1% TFA) to afford the title compound. MS: 370.1 (M+H).

The Examples in Table 17 were prepared from the appropriate chiral aminoester using procedures described above for Example 722.

TABLE 17

| Example Number | Structure | IUPAC Name | Observed Exact Mass [M + H]+ |
|---|---|---|---|
| 723 | 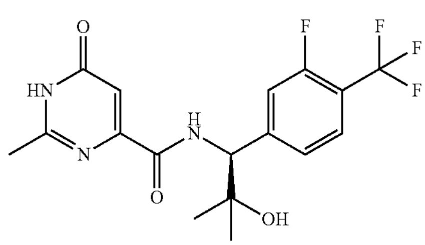 [SMILES: Cc1nc(C(=O)N[C@@H](c2ccc(C(F)(F)F)c(F)c2)C(C)(C)O)cc(=O)[nH]1] | N-{(1S)-1-[3-fluoro-4-(trifluoromethyl)phenyl]-2-hydroxy-2-methylpropyl}-2-methyl-6-oxo-1,6-dihydropyrimidine-4-carboxamide | 388.0 |

TABLE 17-continued

| Example Number | Structure | IUPAC Name | Observed Exact Mass [M + H]+ |
|---|---|---|---|
| 724 | ![structure] | N-{(1S)-2-hydroxy-2-methyl-1-[4-(trifluoromethoxy)phenyl]propyl}-2-methyl-6-oxo-1,6-dihydropyrimidine-4-carboxamide | 386.0 |

Examples 725 and 726

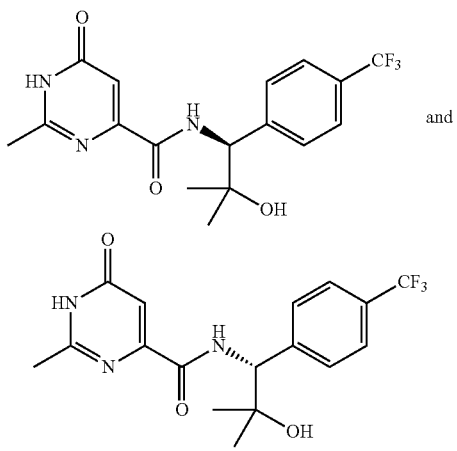

(R)— and (S)—N-{2-hydroxy-2-methyl-1-[4-(trifluoromethyl)phenyl]propyl}-2-methyl-6-oxo-1,6-dihydropyrimidine-4-carboxamide N-{2-hydroxy-2-methyl-1-[4-(trifluoromethyl)phenyl]propyl}-2-methyl-6-oxo-1,6-dihydropyrimidine-4-carboxamide (Example 722) was resolved on a ChiralPak IC column using 20% MeOH in $CO_2$ with 0.2% DEA to give individual enantiomers: the fast-eluting enantiomer (Example 725, MS: 370.1 (M+H)) and the slow-eluting enantiomer (Example 726 MS: 370.0 (M+H)).

Assay

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphate ester bond of a cyclic nucleotide.

In a typical experiment the PDE2 inhibitory activity of the compounds of the present invention was determined in accordance with the following experimental method. Rhesus PDE2A3 was amplified from rhesus macaque brain cDNA (Biochain Institute, Hayward, Calif.) using primers based on human PDE2A sequence (accession NM_002599.3) where the forward primer containing a Kozak consensus was 5'-gccaccatgggggcaggcatgtggc-3' and the reverse primer was 5'-tcactcagcatcaaggctgca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) according to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki-~0.2 nM) at 1 µM concentration for 100% inhibition. Bay 60-7550 was obtained from Axxora via Fisher Scientific (cat#ALX-270-421-M025/cat#NC9314773). Put another way, any compound with Ki of ~0.2 to about 2 nM could be used at 1 to 10 µM. 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product # R7506 from Molecular Devices) and the activator cGMP (1 uM final concentration), prepared in the assay buffer (10 mM Tris HCl, pH 7.2, 10 mM MgCl$_2$, 0.05% NaN$_3$ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation: Polarization (mP)=1000*(S/So−P/Po)/(S/So+P/Po).

Dose-inhibition profiles for each compound were characterized by fitting the mP data to a four-parameter equation given below. The apparent inhibition constant ($K_I$), the maximum inhibition at the low plateau relative to "100% Inhibition Control" (Imax: e.g. 1=> same as this control), the minimum inhibition at the high plateau relative to the "0% Inhibition Control" (Imin, e.g. 0=> same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\% \; mP - 100\% \; mP)(I\max - I\min)}{1 + \left[\frac{[Drug]}{\left(10^{-pK_I}\left(1 + \frac{[Substrate]}{K_M}\right)\right)}\right]^{nH}} +$$

$$100\% \; mP + (0\% \; mP - 100\% \; mP)(1 - I\max)$$

The median signal of the "0% inhibition controls" (0% mP) and the median signal of the "100% inhibition controls" (100% mP) are constants determined from the controls located in columns 1-2 and 23-24 of each assay plate. An apparent ($K_M$) for FAM-labeled cAMP of ~10 uM was used.

Selectivity for PDE2, as compared to other PDE families, was assessed using the IMAP® technology. Human PDE 10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), human PDE2A1 (Cat#60020), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM MgCl$_2$, 0.05% NaN$_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, human PDE2A1 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE2 inhibitory activity of a compound which may be used in accordance with the present invention may be determined by these assays.

The compounds of the following examples had activity in inhibiting the human PDE2 enzyme in the aforementioned assays with a Ki of less than about 50 µM. Many of compounds within the present invention had activity in inhibiting the human PDE2 enzyme in the aforementioned assays, with a Ki of less than about 1 µM, preferably less than or about 0.1 µM. Additional data is provided in the following Examples. Such a result is indicative of the intrinsic activity of the compounds in use as inhibitors of the PDE2 enzyme. In general, one of ordinary skill in the art would appreciate that a substance is considered to effectively inhibit PDE2 activity if it has a Ki of less than or about 1 µM, preferably less than or about 0.1 µM. The present invention also includes compounds within the generic scope of the invention which possess activity as inhibitors of other phosphodiesterase enzymes.

In the following tables representative data for the compounds of formula I as PDE2 inhibitors as determined by the foregoing assays and as conducted in laboratory (Lab) A or B are shown. The PDE2 Ki is a measure of the ability of the test compound to inhibit the action of the PDE2 enzyme.

TABLE 18

| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
|---|---|---|---|---|
| 1 | 21 | 28 | 16 | 36 |
| 2 | 38 | ND | 24 | ND |
| 3 | 0.54 | ND | 0.45 | ND |
| 4 | 0.56 | ND | 0.52 | ND |
| 5 | 1154 | ND | ND | ND |
| 6 | 55 | ND | 33 | ND |
| 7 | 2784 | ND | ND | ND |
| 8 | 410 | ND | 334 | ND |
| 9 | 21 | ND | 16 | ND |
| 10 | 9.9 | ND | 6.0 | ND |
| 11 | 21 | ND | 16 | ND |
| 12 | 102 | ND | ND | ND |
| 13 | 50 | 48 | 33 | 48 |
| 14 | 1857 | ND | ND | ND |
| 15 | 4.4 | ND | 3.5 | ND |
| 16 | 74 | ND | 67 | ND |
| 17 | 1156 | ND | 917 | ND |
| 18 | 472 | ND | 314 | ND |
| 19 | 96 | ND | 81 | ND |
| 20 | 25 | ND | 24 | ND |
| 21 | 46 | ND | 98 | ND |
| 22 | 13 | 14 | 8.6 | 14 |
| 23 | 3924 | ND | ND | ND |
| 24 | 3634 | ND | ND | ND |
| 25 | 1135 | ND | 663 | ND |
| 26 | 231 | ND | 104 | ND |
| 27 | 1161 | ND | ND | ND |
| 28 | 3492 | ND | ND | ND |
| 29 | 9.2 | ND | 4.9 | ND |
| 30 | 3.2 | ND | 2.2 | ND |
| 31 | 28 | ND | 15 | ND |
| 32 | 11 | ND | 5.1 | ND |
| 33 | 802 | ND | 656 | ND |
| 34 | 1421 | ND | ND | ND |
| 35 | 19 | ND | 15 | ND |
| 36 | 163 | ND | 116 | ND |
| 37 | 17 | 19 | 14 | 27 |
| 38 | 7.8 | ND | 5.6 | ND |
| 39 | 17 | ND | 8.8 | ND |
| 40 | 19 | ND | 9.3 | ND |
| 41 | 9.2 | ND | 5.2 | ND |
| 42 | 72 | ND | 31 | ND |
| 43 | 20 | 14 | 18 | 15 |
| 44 | 17 | 16 | 10 | 16 |
| 45 | 52 | ND | 35 | ND |
| 46 | 65 | ND | 72 | ND |
| 47 | 41 | ND | 32 | ND |
| 48 | 235 | ND | 127 | 80 |
| 49 | 79 | ND | 45 | ND |
| 50 | 8.0 | 11 | ND | 8.1 |
| 51 | 18 | 18 | ~6.1 | 20 |
| 52 | 5.1 | 6.0 | ND | 6.4 |
| 53 | 3.6 | ND | 2.8 | ND |
| 54 | 9.7 | ND | 5.5 | ND |
| 55 | 11 | ND | 7.8 | ND |
| 56 | 4590 | ND | ND | ND |
| 57 | ND | 5.8 | ND | 3.9 |
| 58 | ND | 2.5 | ND | 1.7 |
| 59 | ND | 6.4 | ND | 4.5 |
| 60 | ND | 4.8 | ND | 2.8 |
| 61 | ND | 10 | ND | 8.2 |
| 62 | ND | 9.8 | ND | 8.3 |
| 63 | ND | 1.9 | ND | 2.0 |
| 64 | ~39290 | ND | ND | ND |
| 65 | 38 | ND | 18 | ND |
| 66 | 11 | ND | 5.8 | ND |
| 67 | 16 | 19 | ~9.6 | 12 |
| 68 | 26 | ND | 17 | ND |
| 69 | 23 | ND | 18 | ND |
| 70 | 25 | 29 | ~14 | 29 |
| 71 | 1568 | ND | ND | ND |
| 72 | 333 | ND | ND | ND |
| 73 | 4.1 | 4.9 | ND | 5.3 |
| 74 | 5.0 | 4.8 | ND | 4.7 |
| 75 | 5.1 | ND | 3.0 | ND |

TABLE 18-continued

| | PDE2 Ki's | | | |
|---|---|---|---|---|
| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
| 76 | 17 | 18 | ND | 21 |
| 77 | 19 | 14 | ND | 21 |
| 78 | 1082 | ND | ND | ND |
| 79 | 22 | 25 | ND | 35 |
| 80 | 845 | ND | ND | ND |
| 81 | 23 | 17 | ND | 25 |
| 82 | 153 | ND | 82 | ND |
| 83 | 21 | 26 | ~5.4 | 27 |
| 84 | 117 | ND | 28 | ND |
| 85 | 60 | ND | 41 | ND |
| 86 | 237 | ND | 199 | ND |
| 87 | 1922 | ND | ND | ND |
| 88 | 2364 | ND | ND | ND |
| 89 | 6.4 | 9.3 | ND | 9.8 |
| 90 | 732 | ND | ND | ND |
| 91 | 34 | 28 | ~9.8 | 33 |
| 92 | 91 | ND | 21 | ND |
| 93 | 35 | ND | 9.6 | ND |
| 94 | 20 | ND | ND | ND |
| 95 | 7.4 | ND | 3.1 | ND |
| 96 | 1277 | ND | ND | ND |
| 97 | 1.5 | ND | ND | ND |
| 98 | 8.8 | 12 | ND | 15 |
| 99 | 58 | ND | 24 | ND |
| 100 | 2.6 | ND | ND | ND |
| 101 | 28 | 28 | ~8.9 | 33 |
| 102 | 5115 | ND | ND | ND |
| 103 | 5.5 | ND | 3.4 | ND |
| 104 | 524 | ND | ND | ND |
| 105 | 3470 | ND | ND | ND |
| 106 | 12 | ND | 5.6 | ND |
| 107 | 21 | ND | ND | ND |
| 108 | 25 | 33 | ~9.2 | 39 |
| 109 | 342 | ND | ND | ND |
| 110 | 12 | ND | 7.2 | ND |
| 111 | 3.6 | 3.9 | ND | 4.7 |
| 112 | 1111 | ND | ND | ND |
| 113 | 84 | ND | 16 | ND |
| 114 | 48 | ND | ~11 | ND |
| 115 | 73 | ND | 15 | ND |
| 116 | 70 | ND | 16 | ND |
| 117 | 80 | ND | ~13 | 42 |
| 118 | 76 | ND | 18 | ND |
| 119 | 74 | 53 | 17 | ND |
| 120 | 8.7 | ND | 4.2 | ND |
| 121 | 25 | 29 | ~6.2 | ND |
| 122 | 152 | ND | 38 | ND |
| 123 | 39 | 31 | ~8.2 | ND |
| 124 | 283 | ND | ND | ND |
| 125 | 176 | ND | 45 | ND |
| 126 | 48 | 61 | ~11 | 64 |
| 127 | 3.6 | 4.7 | 2.2 | 3.9 |
| 128 | 2.0 | ND | 1.2 | ND |
| 129 | 218 | ND | 184 | ND |
| 130 | 715 | ND | ND | ND |
| 131 | 170 | ND | 123 | ND |
| 132 | 34 | ND | 24 | ND |
| 133 | 21 | ND | 20 | ND |
| 134 | 54 | ND | 43 | 38 |
| 135 | 1647 | ND | 1138 | ND |
| 136 | 6.3 | ND | 2.2 | ND |
| 137 | 411 | ND | 231 | ND |
| 138 | 76 | ND | 69 | ND |
| 139 | 138 | ND | 144 | ND |
| 140 | 6.5 | ND | 5.1 | ND |
| 141 | 136 | ND | 110 | ND |
| 142 | 1.4 | ND | 1.5 | ND |
| 143 | 21 | ND | 11 | ND |
| 144 | 16 | ND | 6.0 | ND |
| 145 | 2.9 | ND | 2.3 | ND |
| 146 | 9.3 | ND | 7.1 | ND |
| 147 | 51 | ND | 35 | ND |
| 148 | 5.2 | ND | 2.6 | ND |
| 149 | 204 | ND | 117 | ND |
| 150 | 29 | ND | 15 | ND |

TABLE 18-continued

| | PDE2 Ki's | | | |
|---|---|---|---|---|
| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
| 151 | 3.3 | ND | 3.2 | ND |
| 152 | 16 | ND | 13 | ND |
| 153 | >1000, 41% inh. at 1 uM | ~1971 | ND | ND |
| 154 | 2.6 | ND | 1.5 | ND |
| 155 | 119 | ND | 143 | ND |
| 156 | >1000, 9% inh. at 1 uM | ND | ND | ND |
| 157 | 4.8 | ND | 3.1 | ND |
| 158 | 14 | ND | 9.0 | ND |
| 159 | 7.6 | ND | 4.9 | ND |
| 160 | 826 | ND | ND | ND |
| 161 | 88 | ND | 60 | ND |
| 162 | >1000, 45% inh. at 1 uM | 1003 | ND | ND |
| 163 | 61 | ND | 36 | ND |
| 164 | 9.0 | ND | 9.4 | ND |
| 165 | 16 | ND | 12 | ND |
| 166 | 3.3 | ND | 2.1 | ND |
| 167 | 2.3 | 3.5 | 1.9 | 2.3 |
| 168 | 467 | ND | ND | ND |
| 169 | 3417 | ND | ND | ND |
| 170 | 2340 | ND | ND | ND |
| 171 | 28 | ND | 32 | ND |
| 172 | 2.7 | ND | 1.9 | ND |
| 173 | 90 | ND | 76 | ND |
| 174 | 5.7 | ND | 4.5 | ND |
| 175 | 3.9 | ND | 3.9 | ND |
| 176 | 4.8 | ND | 3.9 | ND |
| 177 | 3.8 | ND | 3.1 | ND |
| 178 | 3.3 | ND | 2.4 | ND |
| 179 | 4.0 | ND | 2.2 | ND |
| 180 | 2053 | ND | ND | ND |
| 181 | 485 | ND | ND | ND |
| 182 | 141 | ND | 118 | ND |
| 183 | 6.4 | ND | 4.1 | ND |
| 184 | 20 | ND | 20 | ND |
| 185 | 13 | ND | 9.7 | ND |
| 186 | 60 | ND | 62 | ND |
| 187 | 4.5 | ND | 3.1 | ND |
| 188 | 1009 | ND | ND | ND |
| 189 | 10 | ND | 9.7 | ND |
| 190 | 6.4 | ND | 6.1 | ND |
| 191 | 3.4 | ND | 1.2 | ND |
| 192 | 151 | ND | 81 | ND |
| 193 | 3.9 | ND | 1.3 | ND |
| 194 | 72 | ND | 28 | ND |
| 195 | 33 | ND | 18 | ND |
| 196 | 915 | ND | ND | ND |
| 197 | 62 | ND | 29 | ND |
| 198 | 96 | ND | 59 | ND |
| 199 | 12 | ND | 7.0 | ND |
| 200 | 16 | ND | 9.2 | ND |
| 201 | 4.4 | ND | 2.8 | ND |
| 202 | 7.3 | ND | 3.0 | ND |
| 203 | 4319 | ND | ND | ND |
| 204 | 37 | ND | 20 | ND |
| 205 | 694 | ND | ND | ND |
| 206 | 24260 | ND | ND | ND |
| 207 | 5.8 | ND | 2.6 | ND |
| 208 | 291 | ND | ND | ND |
| 209 | 17390 | ND | ND | ND |
| 210 | 6.0 | ND | 3.0 | ND |
| 211 | 7.1 | ND | 2.5 | ND |
| 212 | 6.1 | ND | 2.6 | ND |
| 213 | 6.1 | ND | 3.3 | ND |
| 214 | 5.0 | ND | 2.4 | ND |
| 215 | 967 | ND | ND | ND |
| 216 | 247 | ND | ND | ND |
| 217 | 29 | ND | 14 | ND |
| 218 | 104 | ND | 56 | ND |
| 219 | 43 | ND | 31 | ND |
| 220 | 10690 | ND | ND | ND |
| 221 | 681 | ND | ND | ND |
| 222 | 89 | ND | 45 | ND |

TABLE 18-continued

| | PDE2 Ki's | | | |
|---|---|---|---|---|
| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
| 223 | 1018 | ND | ND | ND |
| 224 | 40 | ND | 20 | ND |
| 225 | 8.3 | ND | 4.6 | ND |
| 226 | 505 | ND | ND | ND |
| 227 | 12 | ND | 6.5 | ND |
| 228 | 1427 | ND | ND | ND |
| 229 | 864 | ND | ND | ND |
| 230 | 25 | ND | 11 | ND |
| 231 | 39 | ND | 23 | ND |
| 232 | 29 | ND | 17 | ND |
| 233 | 124 | ND | 78 | ND |
| 234 | 20 | ND | 18 | ND |
| 235 | 274 | ND | ND | ND |
| 236 | 4.3 | ND | 5.5 | ND |
| 237 | 61 | ND | 35 | ND |
| 238 | 683 | ND | ND | ND |
| 239 | 3074 | ND | ND | ND |
| 240 | 14 | ND | 8.8 | ND |
| 241 | 557 | ND | ND | ND |
| 242 | 5.0 | 10 | ND | 9.2 |
| 243 | 3.6 | 6.7 | ND | 5.8 |
| 244 | 0.99 | 2.4 | ND | 3.0 |
| 245 | 1.4 | 1.3 | ND | 1.3 |
| 246 | 3.1 | 5.4 | ND | 5.2 |
| 247 | 1.7 | 2.5 | ND | 2.7 |
| 248 | 2.0 | 3.4 | ND | 3.5 |
| 249 | 2.0 | 4.3 | ND | 4.1 |
| 250 | 5.3 | 5.4 | ND | 6.3 |
| 251 | 2.0 | 4.0 | ND | 3.6 |
| 252 | 8.7 | 14 | ~13 | 20 |
| 253 | 14 | ND | 17 | ND |
| 254 | 17 | 23 | ~13 | 22 |
| 255 | 3.7 | 4.7 | ND | 4.9 |
| 256 | 13 | 21 | ~12 | 20 |
| 257 | 2.6 | 4.0 | ND | 3.8 |
| 258 | 19 | 41 | ND | 39 |
| 259 | 124 | 209 | ND | 179 |
| 260 | 1.0 | 1.8 | ND | 1.8 |
| 261 | 18 | 37 | ND | 33 |
| 262 | 0.65 | 0.85 | ND | 0.79 |
| 263 | 1.5 | 1.9 | ND | 2.1 |
| 264 | 4.6 | 7.9 | ND | 7.7 |
| 265 | 1.2 | 1.6 | ND | 1.5 |
| 266 | 86 | ND | 65 | ND |
| 267 | 8061 | ND | ND | ND |
| 268 | 146 | ND | 83 | ND |
| 269 | 158 | ND | 118 | 96 |
| 270 | 225 | ND | 113 | ND |
| 271 | 2958 | ND | ND | ND |
| 272 | 42 | ND | 40 | 71 |
| 273 | 304 | ND | 278 | ND |
| 274 | 6.7 | ND | 6.7 | ND |
| 275 | 4.5 | ND | 3.0 | ND |
| 276 | 4.2 | ND | 3.8 | ND |
| 277 | 6.6 | ND | 5.6 | ND |
| 278 | 18 | ND | 12 | ND |
| 279 | 24 | ND | 16 | ND |
| 280 | 19 | ND | 16 | ND |
| 281 | 133 | ND | 82 | ND |
| 282 | 124 | ND | 61 | ND |
| 283 | 8.7 | ND | 6.0 | ND |
| 284 | 43 | ND | 36 | ND |
| 285 | 46 | ND | 46 | ND |
| 286 | 83 | ND | 60 | ND |
| 287 | 45 | ND | 28 | ND |
| 288 | 152 | ND | 123 | ND |
| 289 | 2321 | ND | ND | ND |
| 290 | 942 | ND | 540 | ND |
| 291 | 11 | ND | 10 | ND |
| 292 | 14 | ND | 12 | ND |
| 293 | 22 | ND | 20 | ND |
| 294 | 69 | ND | 46 | ND |
| 295 | 127 | ND | 77 | ND |
| 296 | 6.3 | ND | 3.1 | ND |
| 297 | 30 | ND | 16 | ND |

TABLE 18-continued

PDE2 Ki's

| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
|---|---|---|---|---|
| 298 | 18 | ND | 13 | ND |
| 299 | 14 | ND | 9.1 | ND |
| 300 | 88 | ND | 55 | ND |
| 301 | 53 | ND | 66 | ND |
| 302 | 51410 | ND | ND | ND |
| 303 | 208 | ND | 215 | ND |
| 304 | 91 | ND | 76 | ND |
| 305 | 26 | ND | 20 | ND |
| 306 | 2383 | ND | ND | ND |
| 307 | 17 | ND | 16 | ND |
| 308 | 2496 | ND | ND | ND |
| 309 | 63 | ND | 43 | ND |
| 310 | 5647 | ND | ND | ND |
| 311 | 9117 | ND | ND | ND |
| 312 | 71 | ND | 41 | 52 |
| 313 | 51 | ND | 54 | ND |
| 314 | 4743 | ND | ND | ND |
| 315 | 698 | ND | ND | ND |
| 316 | 13 | ND | 7.1 | ND |
| 317 | 1806 | ND | ND | ND |
| 318 | 73 | 189 | ND | ND |
| 319 | 1491 | ND | ND | ND |
| 320 | 1698 | ND | ND | ND |
| 321 | 911 | ND | ND | ND |
| 322 | 205 | ND | 171 | ND |
| 323 | 66 | ND | 50 | ND |
| 324 | 131 | ND | 138 | ND |
| 325 | 1097 | ND | 687 | ND |
| 326 | 70 | ND | 67 | ND |
| 327 | 4548 | ND | 8102 | ND |
| 328 | 33 | ND | 38 | ND |
| 329 | 1417 | ND | 565 | ND |
| 330 | 809 | ND | ND | ND |
| 331 | 304 | ND | ND | ND |
| 332 | 2900 | ND | 2268 | ND |
| 333 | 89 | ND | 80 | ND |
| 334 | 2829 | ND | 2366 | ND |
| 335 | 1317 | ND | 1221 | ND |
| 336 | 60 | ND | 59 | ND |
| 337 | 0.40 | 1.2 | ND | 1.1 |
| 338 | 29 | 71 | ND | 65 |
| 339 | ~417 | 653 | ND | ND |
| 340 | 49 | 109 | ND | 83 |
| 341 | ~11 | 24 | ND | 19 |
| 342 | ~605 | 963 | ND | ND |
| 343 | ~601 | 682 | ND | ND |
| 344 | ~449 | 681 | ND | ND |
| 345 | 8337 | ND | ND | ND |
| 346 | 2349 | ND | ND | ND |
| 347 | 45 | 74 | ND | 50 |
| 348 | ~877 | 1496 | ND | ND |
| 349 | ~525 | 713 | ND | ND |
| 350 | 21 | ND | ND | 39 |
| 351 | 124 | 217 | ND | 224 |
| 352 | 15 | 51 | ND | 54 |
| 353 | ~9.2 | 23 | ND | 21 |
| 354 | >1000, 42% inh. at 1 uM | 2796 | ND | ND |
| 355 | ND | ~29250 | ND | ND |
| 356 | 345 | 490 | ND | ND |
| 357 | ND | ~11300 | ND | ND |
| 358 | 11560 | ND | ND | ND |
| 359 | 62 | 173 | ND | 129 |
| 360 | 222 | 459 | ND | ~488 |
| 361 | ~78 | 99 | ND | 81 |
| 362 | ND | ~24660 | ND | ND |
| 363 | 245 | 356 | ND | 354 |
| 364 | ND | 3948 | ND | ND |
| 365 | 6850 | ND | ND | ND |
| 366 | 132 | 458 | ND | 386 |
| 367 | 74 | 314 | ND | 262 |
| 368 | ~880 | 1100 | ND | ND |
| 369 | ND | 8775 | ND | ND |
| 370 | 334 | 533 | ND | ND |
| 371 | 68 | 150 | ND | 117 |

TABLE 18-continued

| | PDE2 Ki's | | | |
|---|---|---|---|---|
| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
| 372 | ~149 | ND | ND | ~661 |
| 373 | 155 | 225 | ND | 183 |
| 374 | 24 | 36 | ND | 33 |
| 375 | 1000, 46% inh. at 1 uM | 2043 | ND | ND |
| 376 | ~672 | 891 | ND | ND |
| 377 | 28 | ND | ND | 58 |
| 378 | 26 | 41 | ND | 41 |
| 379 | 69 | ND | ND | 114 |
| 380 | ND | 353 | ND | ND |
| 381 | ND | ~20440 | ND | ND |
| 382 | ND | 3120 | ND | ND |
| 383 | ND | 4.2 | ND | 2.9 |
| 384 | ND | 319 | ND | ND |
| 385 | ND | 7.0 | ND | 4.4 |
| 386 | ND | 8.1 | ND | 6.5 |
| 387 | ND | 9.6 | ND | 8.1 |
| 388 | ND | 4.7 | ND | 3.9 |
| 389 | ND | 8980 | ND | ND |
| 390 | ND | 1704 | ND | ND |
| 391 | ND | 65 | ND | 40 |
| 392 | ND | 5.5 | ND | 3.3 |
| 393 | ND | 55 | ND | 49 |
| 394 | ND | 2216 | ND | ND |
| 395 | ND | 2053 | ND | ND |
| 396 | ND | ~20320 | ND | ND |
| 397 | ND | 8.2 | ND | 8.6 |
| 398 | ND | 2.9 | ND | 2.3 |
| 399 | ND | 407 | ND | ND |
| 400 | ND | 1069 | ND | ND |
| 401 | ND | 5.2 | ND | 5.8 |
| 402 | ND | 38 | ND | 29 |
| 403 | ND | 1907 | ND | ND |
| 404 | ND | 9.5 | ND | 6.5 |
| 405 | ND | 17 | ND | 15 |
| 406 | ND | 226 | ND | ND |
| 407 | ND | 4.5 | ND | 3.6 |
| 408 | ND | 17 | ND | 11 |
| 409 | ND | 3931 | ND | ND |
| 410 | ND | 1965 | ND | ND |
| 411 | ND | 1458 | ND | ND |
| 412 | ND | 9.9 | ND | 10 |
| 413 | ND | 105 | ND | 126 |
| 414 | ND | 136 | ND | ND |
| 415 | ND | 29 | ND | 30 |
| 416 | ND | 1767 | ND | ND |
| 417 | ND | 12 | ND | 9.8 |
| 418 | ND | 48 | ND | 41 |
| 419 | ND | 3.3 | ND | 2.9 |
| 420 | ND | 7.3 | ND | 5.9 |
| 421 | ND | 14 | ND | 9.4 |
| 422 | ND | 1839 | ND | ND |
| 423 | 3.0 | ND | ND | 5.6 |
| 424 | ND | 7.2 | ND | 9.2 |
| 425 | ND | 29 | ND | 30 |
| 426 | ND | 9.1 | ND | 9.5 |
| 427 | ND | 3.7 | ND | 3.7 |
| 428 | ND | 1.9 | ND | 1.8 |
| 429 | ND | 42 | ND | ND |
| 430 | ND | >2970 | ND | ND |
| 431 | ND | ~2894 | ND | ND |
| 432 | ND | >2970 | ND | ND |
| 433 | ND | ~1431 | ND | ND |
| 434 | ND | 6.7 | ND | 7.9 |
| 435 | ND | 1.1 | ND | 0.78 |
| 436 | ND | 3.5 | ND | 3.2 |
| 437 | ND | 1.2 | ND | 1.2 |
| 438 | ND | 1,5 | ND | 1.3 |
| 439 | ND | 1.0 | ND | 1,3 |
| 440 | ND | 51 | ND | 60 |
| 441 | ND | 3.8 | ND | 6.4 |
| 442 | ND | >2970 | ND | ND |
| 443 | ND | 8.0 | ND | 7.0 |
| 444 | ND | 2.0 | ND | 2.5 |
| 445 | ND | 2.1 | ND | 1.7 |

TABLE 18-continued

| | PDE2 Ki's | | | |
|---|---|---|---|---|
| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
| 446 | ND | 43 | ND | 42 |
| 447 | ND | 1.3 | ND | 1.4 |
| 448 | ND | 13 | ND | 12 |
| 449 | ND | 2.6 | ND | 1.8 |
| 450 | ND | 23 | ND | 21 |
| 451 | ND | 6.7 | ND | 4.8 |
| 452 | ND | 9.8 | ND | 9.3 |
| 453 | ND | 7.3 | ND | 7.6 |
| 454 | ND | 3.8 | ND | 4.0 |
| 455 | ND | 0.68 | ND | 0.60 |
| 456 | ND | 98 | ND | ND |
| 457 | ND | 0.68 | ND | 0.64 |
| 458 | ND | 8128 | ND | ND |
| 459 | ND | 224 | ND | ND |
| 460 | ND | 371 | ND | ND |
| 461 | ND | 7.5 | ND | 7.8 |
| 462 | ND | 1.4 | ND | 1.5 |
| 463 | ND | 1.2 | ND | 0.84 |
| 464 | ND | 0.60 | ND | 0.69 |
| 465 | ND | 0.62 | ND | 0.62 |
| 466 | ND | 0.85 | ND | 0.79 |
| 467 | ND | 0.62 | ND | 0.49 |
| 468 | ND | 2.8 | ND | 2.3 |
| 469 | ND | 0.96 | ND | 0.91 |
| 470 | ND | 1.2 | ND | 1.3 |
| 471 | ND | 1.5 | ND | 1.5 |
| 472 | ND | 1.6 | ND | 1.7 |
| 473 | ND | 1.1 | ND | 0.86 |
| 474 | ND | 1.4 | ND | 1.5 |
| 475 | ND | 1.3 | ND | 1.3 |
| 476 | ND | 1.4 | ND | 1.8 |
| 477 | ND | 1.5 | ND | 1.7 |
| 478 | ND | 2.1 | ND | 1.7 |
| 479 | ND | 1.9 | ND | 2.0 |
| 480 | ND | 1.9 | ND | 1.9 |
| 481 | ND | 1.9 | ND | 1.9 |
| 482 | ND | 3.3 | ND | 3.4 |
| 483 | ND | 3.0 | ND | 2.9 |
| 484 | ND | 1.3 | ND | 1.4 |
| 485 | ND | 1.9 | ND | 1.5 |
| 486 | ND | 60 | ND | 46 |
| 487 | ND | 61 | ND | 63 |
| 488 | ND | 116 | ND | ND |
| 489 | ND | 69 | ND | 61 |
| 490 | ND | 43 | ND | 31 |
| 491 | ND | 27 | ND | 27 |
| 492 | ND | 42 | ND | 29 |
| 493 | ND | 77 | ND | 62 |
| 494 | ND | 54 | ND | 46 |
| 495 | ND | 54 | ND | 45 |
| 496 | ND | 38 | ND | 40 |
| 497 | ND | 80 | ND | 60 |
| 498 | ND | 65 | ND | 49 |
| 499 | ND | 115 | ND | ND |
| 500 | ND | 79 | ND | 74 |
| 501 | ND | 77 | ND | 64 |
| 502 | ND | 115 | ND | 75 |
| 503 | ND | 111 | ND | ND |
| 504 | ND | 42 | ND | 30 |
| 505 | ND | 84 | ND | 56 |
| 506 | ND | 0.92 | ND | 0.80 |
| 507 | ND | 1.1 | ND | 1.0 |
| 508 | ND | 0.77 | ND | 0.80 |
| 509 | ND | 0.88 | ND | 0.99 |
| 510 | ND | 3.3 | ND | 2.8 |
| 511 | ND | 1.2 | ND | 1.4 |
| 512 | ND | 1.5 | ND | 1.6 |
| 513 | ND | 2.1 | ND | 1.9 |
| 514 | ND | 2.2 | ND | 1.8 |
| 515 | ND | 1.1 | ND | 1.0 |
| 516 | ND | 1.6 | ND | 1.5 |
| 517 | ND | 1.3 | ND | 1.7 |
| 518 | ND | 1.8 | ND | 1.7 |
| 519 | ND | 1.7 | ND | 2.0 |
| 520 | ND | 3.8 | ND | 3.6 |

TABLE 18-continued

| | PDE2 Ki's | | | |
|---|---|---|---|---|
| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
| 521 | ND | 2.3 | ND | 2.2 |
| 522 | ND | 2.9 | ND | 2.6 |
| 523 | ND | 2.8 | ND | 2.1 |
| 524 | ND | 2.1 | ND | 2.1 |
| 525 | ND | 2.3 | ND | 1.9 |
| 526 | ND | 4.1 | ND | 3.9 |
| 527 | ND | 3.1 | ND | 3.0 |
| 528 | ND | 1.2 | ND | 1.1 |
| 529 | ND | 2.2 | ND | 2.0 |
| 530 | ND | 47 | ND | 28 |
| 531 | ND | 32 | ND | ND |
| 532 | ND | ND | ND | 16 |
| 533 | ND | ND | ND | 8.0 |
| 534 | ND | ND | ND | 87 |
| 535 | ND | ND | ND | 24 |
| 536 | ND | ND | ND | 0.51 |
| 537 | ND | ND | ND | 2.4 |
| 538 | ND | ND | ND | 1.4 |
| 539 | ND | ND | ND | 1.2 |
| 540 | ND | ND | ND | 1.6 |
| 541 | ND | ND | ND | 1.3 |
| 542 | ND | ND | ND | 1.4 |
| 543 | ND | ND | ND | 5.2 |
| 544 | ND | ND | ND | 2.4 |
| 545 | ND | ND | ND | 1.2 |
| 546 | ND | ND | ND | 3.8 |
| 547 | ND | ND | ND | 1.8 |
| 548 | ND | ND | ND | 4.5 |
| 549 | ND | ND | ND | 4.5 |
| 550 | ND | ND | ND | 17 |
| 551 | ND | ND | ND | 157 |
| 552 | ND | ND | ND | 96 |
| 553 | ND | ND | ND | 10 |
| 554 | ND | ND | ND | 8.2 |
| 555 | ND | ND | ND | 4.5 |
| 556 | ND | ND | ND | 7.7 |
| 557 | ND | ND | ND | 8.9 |
| 558 | ND | ND | ND | 35 |
| 559 | ND | ND | ND | 128 |
| 560 | ND | ND | ND | 5.1 |
| 561 | ND | ND | ND | 202 |
| 562 | ND | ND | ND | 4.3 |
| 563 | ND | ND | ND | 27 |
| 564 | ND | ND | ND | 6.7 |
| 565 | ND | ND | ND | 7.0 |
| 566 | ND | ND | ND | 4.3 |
| 567 | ND | ND | ND | 49 |
| 568 | ND | ND | ND | 96 |
| 569 | ND | ND | ND | 139 |
| 570 | ND | ND | ND | 21 |
| 571 | ND | ND | ND | 71 |
| 572 | ND | ND | ND | 741 |
| 573 | ND | ND | ND | 88 |
| 574 | ND | ND | ND | 831 |
| 575 | ND | ND | ND | 65 |
| 576 | ND | ND | ND | 32 |
| 577 | ND | ND | ND | 287 |
| 578 | ND | ND | ND | 104 |
| 579 | ND | ND | ND | 37 |
| 580 | ND | ND | ND | 38 |
| 581 | ND | ND | ND | 13 |
| 582 | ND | ND | ND | 10 |
| 583 | ND | ND | ND | 8.0 |
| 584 | ND | ND | ND | 36 |
| 585 | ND | ND | ND | 39 |
| 586 | ND | ND | ND | 19 |
| 587 | ND | ND | ND | 71 |
| 588 | ND | ND | ND | 303 |
| 589 | ND | ND | ND | 22 |
| 590 | ND | ND | ND | 34 |
| 591 | ND | ND | ND | 30 |
| 592 | ND | ND | ND | 15 |
| 593 | ND | 11 | ND | 10 |
| 594 | ND | ND | ND | 120 |
| 595 | ND | ND | ND | 37 |

TABLE 18-continued

| | PDE2 Ki's | | | |
|---|---|---|---|---|
| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
| 596 | ND | 30 | ND | 22 |
| 597 | ND | ND | ND | 137 |
| 598 | ND | ND | ND | 3.7 |
| 599 | ND | ND | ND | 10 |
| 600 | ND | ND | ND | 21 |
| 601 | ND | 8.0 | ND | 8.2 |
| 602 | ND | 5.2 | ND | 4.2 |
| 603 | ND | ND | ND | 7.2 |
| 604 | ND | ND | ND | 108 |
| 605 | ND | ND | ND | 102 |
| 606 | ND | ND | ND | 237 |
| 607 | ND | ND | ND | 48 |
| 608 | ND | ND | ND | 3.2 |
| 609 | ND | ND | ND | 94 |
| 610 | ND | 68 | ND | 70 |
| 611 | ND | 44 | ND | 37 |
| 612 | ND | 11 | ND | 11 |
| 613 | ND | 13 | ND | 12 |
| 614 | ND | 20 | ND | 17 |
| 615 | ND | 441 | ND | ND |
| 616 | ND | 112 | ND | ND |
| 617 | ND | 4.2 | ND | 4.0 |
| 618 | ND | 2.0 | ND | 2.0 |
| 619 | ND | 62 | ND | 67 |
| 620 | ND | 15 | ND | 19 |
| 621 | ND | 5.1 | ND | 5.2 |
| 622 | ND | 32 | ND | 42 |
| 623 | ND | 29 | ND | 31 |
| 624 | ND | ND | ND | 17 |
| 625 | ND | ND | ND | 51 |
| 626 | ND | ND | ND | 58 |
| 627 | ND | ND | ND | 46 |
| 628 | ND | ND | ND | 87 |
| 629 | ND | ND | ND | 53 |
| 630 | ND | ND | ND | 5.1 |
| 631 | ND | ND | ND | 13 |
| 632 | ND | ND | ND | 106 |
| 633 | ND | ND | ND | 16 |
| 634 | ND | ND | ND | 29 |
| 635 | ND | ND | ND | 59 |
| 636 | ND | ND | ND | 19 |
| 637 | ND | ND | ND | 16 |
| 638 | ND | ND | ND | 12 |
| 639 | ND | ND | ND | 2.0 |
| 640 | ND | ND | ND | 4.4 |
| 641 | ND | ND | ND | 32 |
| 642 | ND | ND | ND | 4.8 |
| 643 | ND | ND | ND | 0.50 |
| 644 | ND | ND | ND | 7.3 |
| 645 | ND | ND | ND | 25 |
| 646 | ND | ND | ND | 15 |
| 647 | ND | ND | ND | 52 |
| 648 | ND | ND | ND | 34 |
| 649 | ND | ND | ND | 47 |
| 650 | ND | ND | ND | 33 |
| 651 | ND | ND | ND | 109 |
| 652 | ND | ND | ND | 138 |
| 653 | ND | ND | ND | 148 |
| 654 | ND | ND | ND | 72 |
| 655 | ND | ND | ND | 64 |
| 656 | ND | ND | ND | 111 |
| 657 | ND | ND | ND | 133 |
| 658 | ND | ND | ND | 3.8 |
| 659 | ND | ND | ND | 139 |
| 660 | ND | ND | ND | 54 |
| 661 | ND | ND | ND | 6.6 |
| 662 | ND | ~1219 | ND | ND |
| 663 | ND | 30 | ND | 34 |
| 664 | ND | ND | ND | ~1568 |
| 665 | ND | ND | ND | 4.954 |
| 666 | ND | ND | ND | 329 |
| 667 | ND | ND | ND | 10 |
| 668 | ND | ND | ND | 67 |
| 669 | ND | ND | ND | 15 |
| 670 | ND | ND | ND | 28 |

TABLE 18-continued

| | PDE2 Ki's | | | |
|---|---|---|---|---|
| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
| 671 | ND | ND | ND | 14 |
| 672 | ND | ND | ND | >2955 |
| 673 | ND | ND | ND | 32 |
| 674 | ND | 583 | ND | ND |
| 675 | ND | ND | ND | 234 |
| 676 | ND | ND | ND | 478 |
| 677 | ND | 129 | ND | ND |
| 678 | ND | 501 | ND | ND |
| 679 | ND | 90 | ND | ND |
| 680 | ND | 80 | ND | 87 |
| 681 | ND | ND | ND | 7.0 |
| 682 | ND | ND | ND | 48 |
| 683 | ND | ND | ND | >2955 |
| 684 | ND | ND | ND | >2955 |
| 685 | ND | ND | ND | 45 |
| 686 | ND | ND | ND | >2955 |
| 687 | ND | ND | ND | 108 |
| 688 | ND | ND | ND | >2955 |
| 689 | ND | ND | ND | 67 |
| 690 | ND | ND | ND | >2955 |
| 691 | ND | ND | ND | 39 |
| 692 | ND | ND | ND | >2955 |
| 693 | ND | ND | ND | 63 |
| 694 | ND | >2970 | ND | >1244 |
| 695 | ND | 473 | ND | ND |
| 696 | ND | ND | ND | >2955 |
| 697 | ND | ND | ND | 115 |
| 698 | ND | ND | ND | >2955 |
| 699 | ND | ND | ND | 103 |
| 700 | ND | ND | ND | >2955 |
| 701 | ND | ND | ND | 127 |
| 702 | ND | 8.7 | ND | 7.2 |
| 703 | ND | >2970 | ND | ND |
| 704 | ND | 4.7 | ND | 3.6 |
| 705 | ND | 1070 | ND | ND |
| 706 | ND | >2970 | ND | ND |
| 707 | ND | 8.3 | ND | 7.7 |
| 708 | ND | ~2118 | ND | ND |
| 709 | ND | 8.1 | ND | 7.4 |
| 710 | ND | >2970 | ND | ND |
| 711 | ND | 5.1 | ND | 3.7 |
| 712 | ND | ND | ND | 237 |
| 713 | ND | ND | ND | 1.5 |
| 714 | ND | ND | ND | ~1816 |
| 715 | ND | ND | ND | 3.8 |
| 716 | ND | ND | ND | >2955 |
| 717 | ND | 17 | ND | 14 |
| 718 | ND | ND | ND | 39 |
| 719 | ND | ND | ND | 7.7 |
| 720 | ND | ND | ND | 2.6 |
| 721 | ND | ND | ND | ~1217 |
| 722 | ND | 13 | ND | 17 |
| 723 | ND | ND | ND | 8.6 |
| 724 | ND | ND | ND | 3.1 |
| 725 | ND | >2970 | ND | >2955 |
| 726 | ND | 11 | ND | 7.3 |

(ND = Not determined)

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

The invention claimed is:

1. A compound represented by structural formula I

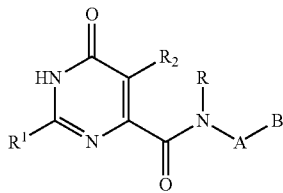

I or a pharmaceutically acceptable salt or hydrate thereof, wherein:

A is $CR^4R^5$, $C_{3-6}$cycloalkyl, or $C_{4-6}$heterocyclyl, said cycloalkyl and heterocyclyl unsubstituted or substituted with 1 to 3 groups of $R^a$;

B is selected from the group consisting of phenyl, naphthyl, $C_{3-6}$cycloalkyl, said phenyl, naphthyl, $C_{3-6}$cycloalkyl, unsubstituted or substituted with 1 to 3 groups of $R^a$;

R is hydrogen or $C_{1-6}$alkyl;

or R can combine with A and the nitrogen atom to which A is attached to form a five to six membered heterocycle, said heterocycle optionally substituted with one to three groups of $R^a$;

or R and B can combine with A and the nitrogen atom to which A is attached to form a five to ten membered heterocycle, said heterocycle optionally substituted with one to three groups of $R^a$;

$R^1$ is selected from the group consisting of H, $C_{1-6}$alkyl, $C_{1-6}$alkylSR, $C_{3-10}$cycloalkyl, $(CRR)_nC_{4-10}$heterocyclyl, and $(CRR)_nC_{6-10}$aryl, said alkyl, cycloalkyl, heterocyclyl and aryl optionally substituted with one to three groups of $R^a$;

$R^2$ is selected from the group consisting of hydrogen, $C_{1-6}$alkyl, $C_{3-10}$cycloallkyl, and $C_{1-4}$haloalkyl;

$R^4$ and $R^5$ are independently selected from H, $C_{1-6}$alkyl, $C_{3-10}$cycloalkyl, $C_{1-4}$hydroxyalkyl, and $C_{1-4}$haloalkyl, $(CH_2)_nSC_{1-6}$alkyl, $C(O)OR$, $C(O)N(R)_2$, $CN$, $(CH_2)_n$ $C_{5-10}$heterocyclyl, and $(CH_2)_nC_{6-10}$aryl, said alkyl, cycloalkyl, heterocyclyl and aryl optionally substituted with one to three groups of $R^a$, $R^a$ is selected from the group consisting of H, halo, CN, $C_{1-6}$alkyl, $(CH_2)_nOR$, $(O)_pC_{1-4}$haloalkyl, $C(O)OR$, $-O(CH_2)_nN(R)_2$, $(CHR)_nN(R)_2$, $NO_2$, $SCF_3$, $S(O)_s$ $CF_3$, $S(O)_sR$, $SF_5$, $C_{3-10}$cycloalkyl, $C_{5-10}$heterocyclyl, and $C_{6-10}$aryl, said alkyl, cycloalkyl, heterocyclyl and aryl optionally substituted with one to three groups of $R^b$;

$R^b$ is selected from the group consisting of H, halo, $C_{1-6}$alkyl, $(CH_2)_nOR$, and $(O)_pC_{1-4}$haloalkyl;

n represents 0, 1, 2, 3, or 4;

s represents 0, 1, or 2; and p represents 0 or 1, with the proviso that the compound of formula I is not:
N-(1-(4-methoxyphenyl)propyl)-2-methyl-6-oxo-1,6-dihydropyrimidine-4-carboxamide,
N-(4-fluoro-3-methoxybenzyl)-2-methyl-6-oxo-1,6-dihydropyrimidine-4-carboxamide,
N-((4-Methoxyphenyl)(phenyl)methyl)-2-methyl-6-oxo-1,6-dihydropyrimidine-4-carboxamide,
N-(2,2-dimethylchroman-4-yl)-6-oxo-2-phenyl-1,6-dihydropyrimidine-4-carboxamide,
N-(1-(2,3-dihydrobenzo[b][1,4]dioxin-6-yl)-2-phenylethyl)-2-methyl-6-oxo-1,6-dihydropyrimidine-4-carboxamide or
6-Oxo-N-((3-oxo-3,4-dihydro-2H-benzo[b][1,4]oxazin-6-yl)methyl)-1,6-dihydropyrimidine-4-carboxamide.

2. The compound according to claim 1 wherein A is $CR^4R^5$.

3. The compound according to claim 1 wherein A is $C_{3-6}$cycloalkyl.

4. The compound according to claim 2 wherein one of $R^4$ and $R^5$ is hydrogen or $CH_3$ and the other is selected from $C_{1-6}$alkyl, $C_{3-10}$cycloalkyl, $C_{1-4}$haloalkyl, $(CH_2)_nSC_{1-6}$ alkyl, $C(O)OR$, $C(O)N(R)_2$, $CN$, $(CH_2)_nC_{5-10}$heterocyclyl, and $(CH_2)_nC_{6-10}$aryl, said alkyl, cycloalkyl, heterocyclyl and aryl optionally substituted with one to three groups of $R^a$.

5. The compound according to claim 4 wherein one of $R^4$ and $R^5$ is hydrogen or $CH_3$ and the other is $CH_3$, $CH_2CH_3$, $C(CH_3)_2$, $CH_2OH$, $CH(CH_3)OH$, or $C(CH_3)_2OH$, $CN$, $C(O)OR$ $C(O)N(R)_2$, cyclopropyl, cyclobutyl, cyclopentyl, tetrazolyl, or phenyl, said tetrazolyl and phenyl optionally substituted with one to three groups of $R^a$.

6. The compound according to claim 5 wherein one of $R^4$ and $R^5$ is hydrogen and the other is $CH_3$, $CH_2CH_3$, $C(CH_3)_2$, $CH_2OH$, $CH(CH_3)OH$, $C(CH_3)_2OH$, cyclopropyl, cyclobutyl, or cyclopentyl.

7. The compound according to claim 3 wherein the cycloalkyl is cyclopropyl, cyclobutyl, or cyclopentyl.

8. The compound according to claim 1 wherein B is unsubstituted or substituted phenyl.

9. The compound according to claim 1 wherein B is unsubstituted or substituted naphthyl.

10. The compound according to claim 1 wherein $R^1$ is optionally substituted $C_{1-6}$alkyl.

11. The compound according to claim 1 wherein $R^1$ is optionally substituted $C_{3-10}$cycloalkyl.

12. The compound according to claim 1 wherein $R^1$ is optionally substituted $(CRR)_nC_{5-10}$heterocyclyl.

13. The compound according to claim 1 wherein $R^1$ is optionally substituted $(CRR)_nC_{6-10}$aryl.

14. The compound according to claim 1 of formula I represented by structural formula II:

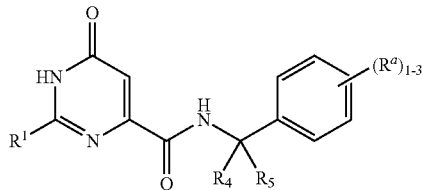

II and pharmaceutically acceptable salts and hydrates thereof.

15. The compound according to claim 1 wherein $R^1$ is selected from the group consisting of $CH_3$, or $CH_2OCH_3$, cyclopropyl, cyclobutyl, or optionally substituted phenyl, pyrimidinyl, or pyrazolyl, one of $R^4$ and $R^5$ is hydrogen or $CH_3$ and the other is $CH_3$, $CH_2CH_3$, $C(CH_3)_2$, $CH_2OH$, $CH(CH_3)OH$, or $C(CH_3)_2OH$, $CN$, $C(O)OR$ $C(O)N(R)_2$, cyclopropyl, cyclobutyl, cyclopentyl, tetrazolyl, or phenyl, said tetrazolyl and phenyl optionally substituted with one to three groups of $R^a$.

16. The compound according to claim 1 of formula 1 represented by structural formula III:

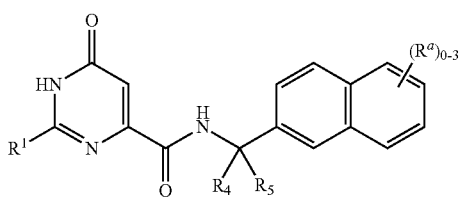

and pharmaceutically acceptable salts and hydrates thereof.

17. The compound of claim 1 wherein $R^1$ is selected from the group consisting of $CH_3$, or $CH_2OCH_3$, cyclopropyl, cyclobutyl, or optionally substituted phenyl, pyrimidinyl, or pyrazolyl and one of $R^4$ and $R^5$ is hydrogen or $CH_3$ and the other is $CH_3$, $CH_2CH_3$, $C(CH_3)_2$, $CH_2OH$, $CH(CH_3)OH$, or $C(CH_3)_2OH$, CN, C(O)OR C(O)N(R)_2$, cyclopropyl, cyclobutyl, cyclopentyl, tetrazolyl, or phenyl, said tetrazolyl and phenyl optionally substituted with one to three groups of $R^a$.

18. The compound of claim 1 wherein both R and $R^2$ are hydrogen, A is cyclopropyl, cyclobutyl, or cyclopentyl, B is optionally substituted phenyl, or naphthyl, $R^1$ is selected from the group consisting of $CH_3$, $CH_2OCH_3$, cyclopropyl, cyclobutyl, or optionally substituted phenyl, pyrimidinyl, or pyrazolyl and one of $R^4$ and $R^5$ is hydrogen and the other is $CH_3$, $CH_2CH_3$, $C(CH_3)_2$, $CH_2OH$, $CH(CH_3)OH$, or $C(CH_3)_2OH$, CN, C(O)OR C(O)N(R)_2$, cyclopropyl, cyclobutyl, cyclopentyl, tetrazolyl, or phenyl, said tetrazolyl and phenyl optionally substituted with one to three groups of $R^a$.

19. A compound which is:
2-methyl-6-oxo-N-{1-[4-(trifluoromethyl)phenyl]cyclopropyl}-1,6-dihydropyrimidine-4-carboxamide,
2-methyl-6-oxo-N-{1-[4-(trifluoromethyl)phenyl]cyclobutyl}-1,6-dihydropyrimidine-4-carboxamide,
2-(3,4-dimethoxybenzyl)-6-oxo-N-{1-[4-(trifluoromethyl)phenyl]cyclopropyl}-1,6-dihydropyrimidine-4-carboxamide,
2-(3,4-dimethoxybenzyl)-6-oxo-N-{(1R)-1-[4(trifluoromethyl)phenyl]ethyl}-1,6-dihydropyrimidine-4-carboxamide,
6-oxo-2-(pyridin-3-ylmethyl)-N-{(1R)-1-[4-(trifluoromethyl)phenyl]ethyl}-1,6-dihydropyrimidine-4-carboxamide,
2-[1-methyl-1-(1H-pyrazol-1-yl)ethyl]-6-oxo-N-{(1R)-1-[4-(trifluoromethyl)phenyl]ethyl}-1,6-dihydropyrimidine-4-carboxamide,
6-oxo-N-{(1R)-1-[4-(trifluoromethyl)phenyl]ethyl}-1,6-dihydropyrimidine-4-carboxamide,
2-methyl-6-oxo-N-{(1R)-1-[4-(trifluoromethoxy)phenyl]ethyl}-1,6-dihydropyrimidine-4-carboxamide,
2-cyclopropyl-6-oxo-N-{(1R)-1-[4-(trifluoromethoxy)phenyl]ethyl}-1,6-dihydropyrimidine-4-carboxamide,
2-cyclopropyl-6-oxo-N-{(1R)-1-[4-(trifluoromethyl)phenyl]ethyl}-1,6-dihydropyrimidine-4-carboxamide,
N-[1-(4-tert-butylphenyl)propyl]-2-methyl-6-oxo-1,6-dihydropyrimidine-4-carboxamide,
2-methyl-6-oxo-N-{(1R)-1-[4-(trifluoromethyl)phenyl]ethyl}-1,6-dihydropyrimidine-4-carboxamide,
N,2-dimethyl-6-oxo-N-(3,4,5-trimethoxybenzyl)-1,6-dihydropyrimidine-4-carboxamide,
2-cyclopropyl-6-oxo-N-[(1R)-1-{4-[(trifluoromethyl)sulfanyl]phenyl}ethyl]-1,6-dihydropyrimidine-4-carboxamide,
2-methyl-N-[(1R)-1-naphthalen-2-ylethyl]-6-oxo-1,6-dihydropyrimidine-4-carboxamide,
2-methyl-6-oxo-N-{1-[5-(trifluoromethyl)pyridin-2-yl]ethyl}1-1,6-dihydropyrimidine-4-carboxamide,
N-{1-[2-chloro-4-(trifluoromethyl)phenyl]ethyl}-2-methyl-6-oxo-1,6-dihydropyrimidine-4-carboxamide,
N-{(1R)-1-[2-fluoro-4-(trifluoromethyl)phenyl]ethyl}-2-methyl-6-oxo-1,6-dihydropyrimidine-4-carboxamide,
N-{(1R)-1-[3-fluoro-4-(trifluoromethyl)phenyl]ethyl}-2-methyl-6-oxo-1,6-dihydropyrimidine-4-carboxamide,
N-{(1R)-1-[2-fluoro-4-(trifluoromethoxy)phenyl]ethyl}-2-methyl-6-oxo-1,6-dihydropyrimidine-4-carboxamide,
N-{(1R)-1-[3-fluoro-4-(trifluoromethoxy)phenyl]ethyl}-2-methyl-6-oxo-1,6-dihydropyrimidine-4-carboxamide,
2-methyl-N-[2-methyl-4-(trifluoromethyl)benzyl]-6-oxo-1,6-dihy dropyrimidine-4-carboxamide,
N-[2-chloro-4-(trifluoromethyl)benzyl]-2-methyl-6-oxo-1,6-dihydropyrimidine-4-carboxamide,
2-methyl-N-{1-[2-methyl-4-(trifluoromethyl)phenyl]ethyl}-6-oxo-1,6-dihydropyrimidine-4-carboxamide,
N-{(1R)-1-[3,5-difluoro-4-(trifluoromethyl)phenyl]ethyl}-2-methyl-6-oxo-1,6-dihydropyrimidine-4-carboxamide,
N-{1-[3-methoxy-4-(trifluoromethyl)phenyl]ethyl}-2-methyl-6-oxo-1,6-dihydropyrimidine-4-carboxamide,
2-methyl-6-oxo-N-{(1R)-1-[4-(trifluoromethyl)naphthalen-1-yl]ethyl}1-1,6-dihydropyrimidine-4-carboxamide,
2-methyl-6-oxo-N-[(1R)-1-{4-[(trifluoromethyl)sulfanyl]phenyl}propyl]-1,6-dihydropyrimidine-4-carboxamide,
2-methyl-N-[(1R)-2-methyl-1-{4-[(trifluoromethyl)sulfanyl]phenyl}propyl]-6-oxo-1,6-dihydropyrimidine-4-carboxamide,
2-methyl-6-oxo-N-{(1R)-1-[4-(trifluoromethoxy)phenyl]propyl}-1,6-dihydropyrimidine-4-carboxamide,
2-methyl-N-{(1R)-2-methyl-1-[4-(trifluoromethoxy)phenyl]propyl}-6-oxo-1,6-dihydropyrimidine-4-carboxamide,
N-{cyano[4-(trifluoromethyl)phenyl]methyl}-2-methyl-6-oxo-1,6-dihydropyrimidine-4-carboxamide,
2-methyl-6-oxo-N-{phenyl[4-(trifluoromethyl)phenyl]methyl}-1,6-dihydropyrimidine-4-carboxamide,
2-methyl-6-oxo-N-(1-{4-[(trifluoromethyl)sulfanyl]phenyl}cyclopropyl)-1,6-dihydropyrimidine-4-carboxamide,
2-[(methylsulfanyl)methyl]-6-oxo-N-{(1R)-1-[4-(trifluoromethyl)phenyl]ethyl}-1,6-dihydropyrimidine-4-carboxamide,
2-methyl-6-oxo-N-{(1R)-1-[4-(pentafluoro-$\lambda^6$-sulfanyl)phenyl]ethyl}-1,6-dihydropyrimidine-4-carboxamide,
N-{(1R)-1-[3-fluoro-4-(trifluoromethoxy)phenyl]-2-methylpropyl}-2-methyl-6-oxo-1,6-dihydropyrimidine-4-carboxamide,
N-{(1R)-1-[3-fluoro-4-(trifluoromethoxy)phenyl]propyl}-2-methyl-6-oxo-1,6-dihydropyrimidine-4-carboxamide,
N-{(R)-cyclopropyl[3-fluoro-4-(trifluoromethoxy)phenyl]methyl}-2-methyl-6-oxo-1,6-dihydropyrimidine-4-carboxamide, N-[(R)-cyclopropyl{4-[(trifluoromethyl)sulfanyl]
phenyl}methyl]-2-methyl-6-oxo-1,6-dihydropyrimidine-4-carboxamide, N-[1-(4-cyclopropylphenyl)ethyl]-2-methyl-6-oxo-1,6-dihydropyrimidine-4-carboxamide, N-{1-[3-fluoro-4-(trifluoromethyl)phenyl]-1-methylethyl}-2-methyl-6-oxo-1,6-dihydropyrimidine-4-carboxamide, N-{1-[3-fluoro-4-(trifluoromethyl)phenyl]cyclopropyl}-2-methyl-6-oxo-1,6-dihydropyrimidine-4-carboxamide, 2-methyl-6-oxo-N-{(1R)-1-[4-(2,2,2-trifluoroethyl)phenyl]ethyl}-1,6-dihydropyrimidine-4-carboxamide, 2-methyl-N-{(1R)-1-[3-methyl-4-(trifluoromethyl)phenyl]ethyl}-6-oxo-1,6-dihydropyrimidine-4-carboxamide, N-{(1R)-1-[3-chloro-4-(trifluoromethyl)phenyl]ethyl}-2-methyl-6-oxo-1,6-dihydropyrimidine-4-carboxamide, N-{1-[3-fluoro-4-(trifluoromethoxy)phenyl]-1-methylethyl}-2-methyl-6-oxo-1,6-dihydropyrimidine-4-carboxamide, 2-methyl-6-oxo-N-(1-{4-[(trifluoromethyl)sulfanyl]phenyl}cyclobutyl)-1,6-dihydropyrimidine-4-carboxamide, N-[(R)-cyclopropyl(4-cyclopropylphenyl)methyl]-2-methyl-6-oxo-1,6-dihydropyrimidine-4-carboxamide, 2-methyl-6-oxo-N-{(1R)-1-[4-(pentafluoro-$\lambda^6$-sulfanyl)phenyl]propyl}-1,6-dihydropyrimidine-4-carboxamide, 2-methyl-N-{(1R)-2-methyl-1-[4-(pentafluoro-$\lambda^6$-sulfanyl)phenyl]propyl}-6-oxo-1,6-dihydropyrimidine-4-carboxamide, N-[(1R)-1-{3-fluoro-4-[(trifluoromethyl)sulfanyl]phenyl}-2-methylpropyl]-2-methyl-6-oxo-1,6-dihydropyrimidine-4-carboxamide, N-[(1R)-1-{3-fluoro-4-[(trifluoromethyl)sulfanyl]phenyl}propyl]-2-methyl-6-oxo-1,6-dihydropyrimidine-4-carboxamide, N-[(R)-cyclopropyl{3-fluoro-4-[(trifluoromethyl)sulfanyl]phenyl}methyl]-2-methyl-6-oxo-1,6-dihydropyrimidine-4-carboxamide, (S)-N-(1-(4-(difluoromethoxy)phenyl)ethyl)-2-methyl-6-oxo-1,6-dihydropyrimidine-4-carboxamide, (R)-N-(2,2-dimethyl-1-(4-(trifluoromethoxy)phenyl)propyl)-2-methyl-6-oxo-1,6-dihydropyrimidine-4-carboxamide, (R)-N-(2,2-dimethyl-1-(4-((trifluoromethyl)thio)phenyl)propyl)-2-methyl-6-oxo-1,6-dihydropyrimidine-4-carboxamide, (R)-N-(1-(3-fluoro-4-(trifluoromethyl)phenyl)-2,2-dimethylpropyl)-2-methyl-6-oxo-1,6-dihydropyrimidine-4-carboxamide, (R)-N-(1-(3-fluoro-4-(trifluoromethoxy)phenyl)-2,2-dimethylpropyl)-2-methyl-6-oxo-1,6-dihydropyrimidine-4-carboxamide, (R)-N-(2,2-dimethyl-1-(4-(2,2,2-trifluoroethyl)phenyl)propyl)-2-methyl-6-oxo-1,6-dihydropyrimidine-4-carboxamide, (R)-N-(1-(4-(difluoromethoxy)phenyl)-2,2-dimethylpropyl)-2-methyl-6-oxo-1,6-dihydropyrimidine-4-carboxamide, (R)-N-(1-(4-cyclopropylphenyl)-2,2-dimethylpropyl)-2-methyl-6-oxo-1,6-dihydropyrimidine-4-carboxamide, N-((1 S,2S)-2-hydroxy-1-(4-(trifluoromethyl)phenyl)propyl)-2-methyl-6-oxo-1,6-dihydropyrimidine-4-carboxamide, N-((1 S,2R)-2-hydroxy-1-(4-(trifluoromethyl)phenyl)propyl)-2-methyl-6-oxo-1,6-dihydropyrimidine-4-carboxamide, 2-methyl-6-oxo-N-[(1R)-1-{4-[(trifluoromethyl)sulfanyl]phenyl}ethyl]-1,6-dihydropyrimidine-4-carboxamide, N-{1-[3-fluoro-4-(trifluoromethoxy)phenyl]cyclopropyl}-2-methyl-6-oxo-1,6-dihydropyrimidine-4-carboxamide, N-{(R)-cyclopropyl[3-fluoro-4-(trifluoromethyl)phenyl]methyl}-2-methyl-6-oxo-1,6-dihydropyrimidine-4-carboxamide, N-{(R)-cyclopropyl[4-(trifluoromethyl)phenyl]methyl}-2-methyl-6-oxo-1,6-dihydropyrimidine-4-carboxamide, N-{(R)-cyclopropyl[4-(trifluoromethoxy)phenyl]methyl}-2-methyl-6-oxo-1,6-dihydropyrimidine-4-carboxamide, N-{1-[3-fluoro-4-(trifluoromethoxy)phenyl]-1-methylethyl}-6-oxo-1,6-dihydro-2,2'-bipyrimidine-4-carboxamide, 6-oxo-N-{1-[4-(trifluoromethyl)phenyl]cyclopentyl}-1,6-dihydro-2,2'-bipyrimidine-4-carboxamide, N-{(1R)-2-methyl-1-[4-(trifluoromethyl)phenyl]propyl}-6-oxo-1,6-dihydro-2,2'-bipyrimidine-4-carboxamide, N-{(1R)-1-[3-fluoro-4-(trifluoromethoxy)phenyl]-2-methylpropyl}-6-oxo-1,6-dihydro-2,2'-bipyrimidine-4-carboxamide, N-{(1R)-2-methyl-1-[4-(trifluoromethoxy)phenyl]propyl}-6-oxo-1,6-dihydro-2,2'-bipyrimidine-4-carboxamide, N-{1-[3-fluoro-4-(trifluoromethyl)phenyl]cyclopropyl}-6-oxo-1,6-dihydro-2,2'-bipyrimidine-4-carboxamide, 6-oxo-N-(1-{4-[(trifluoromethyl)sulfanyl]phenyl}cyclopropyl)-1,6-dihydro-2,2'-bipyrimidine-4-carboxamide, 6-oxo-N-{phenyl[4-(trifluoromethyl)phenyl]methyl}-1,6-dihydro-2,2'-bipyrimidine-4-carboxamide, N-[1-(4-ethylphenyl)ethyl]-6-oxo-1,6-dihydro-2,2'-bipyrimidine-4-carboxamide, 6-oxo-N-{(1R)-1-[3-(trifluoromethyl)phenyl]ethyl}-1,6-dihydro-2,2'-bipyrimidine-4-carboxamide, N-{1[-3-fluoro-4-(trifluoromethoxy)phenyl]cyclopropyl}-6-oxo-1,6-dihydro-2,2'-bipyrimidine-4-carboxamide, N-{1[-3-fluoro-4-(trifluoromethyl)phenyl]-1-methylethyl}-6-oxo-1,6-dihydro-2,2'-bipyrimidine-4-carboxamide, N-[1-(4-cyclopropylphenyl)ethyl]-6-oxo-1,6-dihydro-2,2'-bipyrimidine-4-carboxamide, N-[1-(6-methoxynaphthalen-2-yl)ethyl]-6-oxo-1,6-dihydro-2,2'-bipyrimidine-4-carboxamide, N-[1-(4-bromophenyl)ethyl]-6-oxo-1,6-dihydro-2,2'-bipyrimidine-4-carboxamide, N-[(1R)-1-(4-methoxyphenyl)ethyl]-6-oxo-1,6-dihydro-2,2'-bipyrimidine-4-carboxamide, N-{(4-methoxyphenyl)[4-(trifluoromethyl)phenyl]methyl}-6-oxo-1,6-dihydro-2,2'-bipyrimidine-4-carboxamide, N-[(1R)-1-(2,4-dimethoxyphenyl)ethyl]-6-oxo-1,6-dihydro-2,2'-bipyrimidine-4-carboxamide, N-{(1R)-1-[3-fluoro-4-(trifluoromethoxy)phenyl]propyl}-6-oxo-1,6-dihydro-2,2'-bipyrimidine-4-carboxamide, N-{1-[2-methyl-4-(trifluoromethyl)phenyl]ethyl}-6-oxo-1,6-dihydro-2,2'-bipyrimidine-4-carboxamide, N-{(R)-cyclopropyl[3-fluoro-4-(trifluoromethyl)phenyl]methyl}-6-oxo-1,6-dihydro-2,2'-bipyrimidine-4-carboxamide,
N-{(R)-cyclopropyl[4-(trifluoromethoxy)phenyl]methyl}-6-oxo-1,6-dihydro-2,2'-bipyrimidine-4-carboxamide,
N-{(R)-cyclopropyl[3-fluoro-4-(trifluoromethoxy)phenyl]methyl}-6-oxo-1,6-dihydro-2,2'-bipyrimidine-4-carboxamide,
N-{(R)-cyclopropyl[4-(trifluoromethyl)phenyl]methyl}-6-oxo-1,6-dihydro-2,2'-bipyrimidine-4-carboxamide,
N-[(R)-cyclopropyl{4-[(trifluoromethyl)sulfanyl]phenyl}methyl]-6-oxo-1,6-dihydro-2,2'-bipyrimidine-4-carboxamide,
N-{1-[2-chloro-4-(trifluoromethyl)phenyl]ethyl}-6-oxo-1,6-dihydro-2,2'-bipyrimidine-4-carboxamide,
N-[(1R)-2-methyl-1-{4-[(trifluoromethyl)sulfanyl]phenyl}propyl]-6-oxo-1,6-dihydro-2,2'-bipyrimidine-4-carboxamide,
N-{(1R)-1-[3-fluoro-4-(trifluoromethyl)phenyl]ethyl}-6-oxo-1,6-dihydro-2,2'-bipyrimidine-4-carboxamide,
N-{(1R)-1-[2-fluoro-4-(trifluoromethyl)phenyl]ethyl}-6-oxo-1,6-dihydro-2,2'-bipyrimidine-4-carboxamide,
6-oxo-N-[(1R)-1-{4-[(trifluoromethyl)sulfanyl]phenyl}propyl]-1,6-dihydro-2,2'-bipyrimidine-4-carboxamide,
N-{(1R)-1-[2-fluoro-4-(trifluoromethoxy)phenyl]ethyl}-6-oxo-1,6-dihydro-2,2'-bipyrimidine-4-carboxamide,
6-oxo-N-{(1R)-1-[4-(trifluoromethyl)naphthalen-1-yl]ethyl}-1,6-dihydro-2,2'-bipyrimidine-4-carboxamide,
N-{(1R)-1-[3-fluoro-4-(trifluoromethoxy)phenyl]ethyl}-6-oxo-1,6-dihydro-2,2'-bipyrimidine-4-carboxamide,
N-{1-[3-methoxy-4-(trifluoromethyl)phenyl]ethyl}-6-oxo-1,6-dihydro-2,2'-bipyrimidine-4-carboxamide,
6-oxo-N-{1-[5-(trifluoromethyl)pyrimidin-2-yl]ethyl}-1,6-dihydro-2,2'-bipyrimidine-4-carboxamide,
6-oxo-N-{(1R)-1-[4-(trifluoromethoxy)phenyl]propyl}-1,6-dihydro-2,2'-bipyrimidine-4-carboxamide,
6-oxo-N-{(1R)-1-[4-(2,2,2-trifluoroethyl)phenyl]ethyl}-1,6-dihydro-2,2'-bipyrimidine-4-carboxamide,
N-{(1R)-1-[3,5-difluoro-4-(trifluoromethyl)phenyl]ethyl}-6-oxo-1,6-dihydro-2,2'-bipyrimidine-4-carboxamide,
N-{(1R)-1-[2-methoxy-4-(trifluoromethyl)phenyl]ethyl}-6-oxo-1,6-dihydro-2,2'-bipyrimidine-4-carboxamide,
N-{(1R)-1-[3-chloro-4-(trifluoromethyl)phenyl]ethyl}-6-oxo-1,6-dihydro-2,2'-bipyrimidine-4-carboxamide,
6-oxo-N-{(1R)-1-[4-(pentafluoro-$\lambda^6$-sulfanyl)phenyl]ethyl}-1,6-dihydro-2,2'-bipyrimidine-4-carboxamide,
N-{2-hydroxy-1-[4-(trifluoromethyl)phenyl]ethyl}-2-(methoxymethyl)-6-oxo-1,6-dihydropyrimidine-4-carboxamide,
2-(methoxymethyl)-6-oxo-N-{(1R)-1-[4-(trifluoromethoxy)phenyl]ethyl}-1,6-dihydropyrimidine-4-carboxamide,
N-{(1R)-1-[3-fluoro-4-(trifluoromethoxy)phenyl]propyl}-2-(methoxymethyl)-6-oxo-1,6-dihydropyrimidine-4-carboxamide,
N-{(R)-cyclopropyl[3-fluoro-4-(trifluoromethyl)phenyl]methyl}-2-(methoxymethyl)-6-oxo-1,6-dihydropyrimidine-4-carboxamide,
N-{(R)-cyclopropyl[4-(trifluoromethoxy)phenyl]methyl}-2-(methoxymethyl)-6-oxo-1,6-dihydropyrimidine-4-carboxamide,
N-{(R)-cyclopropyl[3-fluoro-4-(trifluoromethoxy)phenyl]methyl}-2-(methoxymethyl)-6-oxo-1,6-dihydropyrimidine-4-carboxamide,
N-{(R)-cyclopropyl[4-(trifluoromethyl)phenyl]methyl}-2-(methoxymethyl)-6-oxo-1,6-dihydropyrimidine-4-carboxamide,
2-(methoxymethyl)-6-oxo-N-{(1R)-1-[4-(trifluoromethoxy)phenyl]propyl}-1,6-dihydropyrimidine-4-carboxamide,
2-(methoxymethyl)-N-[(1R)-2-methyl-1-{4-[(trifluoromethyl)sulfanyl]phenyl}propyl]-6-oxo-1,6-dihydropyrimidine-4-carboxamide,
2-(methoxymethyl)-6-oxo-N-[(1R)-1-{4-[(trifluoromethyl)sulfanyl]phenyl}propyl]-1,6-dihydropyrimidine-4-carboxamide,
2-(methoxymethyl)-N-{(1R)-1-[4-(1methylethyl)phenyl]ethyl}-6-oxo-1,6-dihydropyrimidine-4-carboxamide,
2-(methoxymethyl)-6-oxo-N-[(1R)-1-{4-[(trifluoromethyl)sulfanyl]phenyl}ethyl]-1,6-dihydropyrimidine-4-carboxamide,
2-(methoxymethyl)-N-{1-methyl-1-[4-(trifluoromethyl)phenyl]ethyl}-6-oxo-1,6-dihydropyrimidine-4-carboxamide,
N-{(1R)-1-[3-fluoro-4-(trifluoromethyl)phenyl]ethyl}-2-(methoxymethyl)-6-oxo-1,6-dihydropyrimidine-4-carboxamide,
N-{(1R)-1-[3-fluoro-4-(trifluoromethoxy)phenyl]ethyl}-2-(methoxymethyl)-6-oxo-1,6-dihydropyrimidine-4-carboxamide,
N-{(1R)-1-[3-fluoro-4-(trifluoromethoxy)phenyl]-2-methylpropyl}-6-oxo-2-phenyl-1,6-dihydropyrimidine-4-carboxamide,
2-cyclopropyl-N-{(1R)-1-[3-fluoro-4-(trifluoromethoxy)phenyl]-2-methylpropyl}-6-oxo -1,6-dihydropyrimidine-4-carboxamide,
N-(1-{3-fluoro-4-[(trifluoromethyl)sulfanyl]phenyl}cyclobutyl)-2-methyl-6-oxo-1,6-dihydropyrimidine-4-carboxamide,
N-{(4-fluorophenyl)[4-(trifluoromethyl)phenyl]methyl}-2-methyl-6-oxo-1,6-dihydropyrimidine-4-carboxamide,
2-methyl-N-{2-(methylsulfanyl)-1-[4-(trifluoromethyl)phenyl]ethyl}-6-oxo-1,6-dihydropyrimidine-4-carboxamide,
2-(4-fluorobenzyl)-6-oxo-N-{(1R)-1-[4-(trifluoromethyl)phenyl]ethyl}-1,6-dihydropyrimidine-4-carboxamide,
2-benzyl-6-oxo-N-{(1R)-1-[4-(trifluoromethyl)phenyl]ethyl}-1,6-dihydropyrimidine-4-carboxamide,
2-ethyl-6-oxo-N-{(1R)-1-[4-(trifluoromethyl)phenyl]ethyl}-1,6-dihydropyrimidine-4-carboxamide,
2-ethyl-6-oxo-N-{(1S)-1-[4-(trifluoromethyl)phenyl]ethyl}-1,6-dihydropyrimidine-4-carboxamide,
2-(4-methoxybenzyl)-6-oxo-N-{(1R)-1-[4-(trifluoromethyl)phenyl]ethyl}-1,6-dihydropyrimidine-4-carboxamide,
2(1-methylethyl)-6-oxo-N-{(1R)-1-[4-(trifluoromethyl)phenyl]ethyl}-1,6-dihydropyrimidine-4-carboxamide,
2-(3-fluorophenyl)-6-oxo-N-{(1R)-1-[4-(trifluoromethyl)phenyl]ethyl}-1,6-dihydropyrimidine-4-carboxamide,
2-(3,4-difluorophenyl)-6-oxo-N-{(1R)-1-[4-(trifluoromethyl)phenyl]ethyl}-1,6-dihydropyrimidine-4-carboxamide,
2-(3-methoxybenzyl)-6-oxo-N-{(1R)-1-[4-(trifluoromethyl)phenyl]ethyl}-1,6-dihydropyrimidine-4-carboxamide, 2-(2-methylphenyl)-6-oxo-N-{(1R)-1-[4-(trifluoromethyl)phenyl]ethyl}-1,6-dihydropyrimidine-4-carboxamide,
6-oxo-2-phenyl-N-[(1R)-1-{4-[(trifluoromethyl)sulfanyl]phenyl}ethyl]-1,6-dihydropyrimidine-4-carboxamide,
2-cyclopropyl-6-oxo-N-{1-[4-(trifluoromethyl)phenyl]cyclobutyl}-1,6-dihydropyrimidine-4-carboxamide,
N-[(1R)-1-biphenyl-4-ylethyl]-2-cyclopropyl-6-oxo-1,6-dihydropyrimidine-4-carboxamide,
N-{1-[3-fluoro-4-(trifluoromethyl)phenyl]cyclopropyl}-6-oxo-2-phenyl-1,6-dihydropyrimidine-4-carboxamide,
N-{(1R)-1-[4-(1-methylethyl)phenyl]ethyl}-6-oxo-2-phenyl-1,6-dihydropyrimidine-4-carboxamide,
N-{1-[2-chloro-4-(trifluoromethyl)phenyl]ethyl}-6-oxo-2-phenyl-1,6-dihydropyrimidine-4-carboxamide,
N-{(1R)-1-[3-fluoro-4-(trifluoromethyl)phenyl]ethyl}-6-oxo-2-phenyl-1,6-dihydropyrimidine-4-carboxamide,
6-oxo-2-phenyl-N-{1-[5-(trifluoromethyl)pyridin-2-yl]ethyl}-1,6-dihydropyrimidine-4-carboxamide,
N-{(1R)-1-[2-fluoro-4-(trifluoromethyl)phenyl]ethyl}-6-oxo-2-phenyl-1,6-dihydropyrimidine-4-carboxamide,
6-oxo-2-phenyl-N-[(1R)-1-{4-[(trifluoromethyl)sulfanyl]phenyl}propyl]-1,6-dihydropyrimidine-4-carboxamide,
N-{(1R)-1-[2-fluoro-4-(trifluoromethoxy)phenyl]ethyl}-6-oxo-2-phenyl-1,6-dihydropyrimidine-4-carboxamide,
6-oxo-2-phenyl-N-{(1R)-1-[4-(trifluoromethyl)naphthalen-1-yl]ethyl}-1,6-dihydropyrimidine-4-carboxamide,
N-{(1R)-1-[3-fluoro-4-(trifluoromethoxy)phenyl]ethyl}-6-oxo-2-phenyl-1,6-dihydropyrimidine-4-carboxamide,
N-{1-[3-methoxy-4-(trifluoromethyl)phenyl]ethyl}-6-oxo-2-phenyl-1,6-dihydropyrimidine-4-carboxamide,
N-[2,6-dichloro-4-(trifluoromethyl)benzyl]-6-oxo-2-phenyl-1,6-dihydropyrimidine-4-carboxamide,
N-{1-[3-fluoro-4-(trifluoromethoxy)phenyl]cyclopropyl}-6-oxo-2-phenyl-1,6-dihydropyrimidine-4-carboxamide,
N-{1-[3-fluoro-4-(trifluoromethyl)phenyl]-1-methylethyl}-6-oxo-2-phenyl-1,6-dihydropyrimidine-4-carboxamide,
6-oxo-2-phenyl-N-(1-{4-[(trifluoromethyl)sulfanyl]phenyl}cyclopropyl)-1,6-dihydropyrimidine-4-carboxamide,
methyl 4-(1-methyl-1-{[(6-oxo-2-phenyl-1,6-dihydropyrimidin-4-yl)carbonyl]amino}ethyl)benzoate,
N-{1-[3-fluoro-4-(trifluoromethoxy)phenyl]-1-methylethyl}-6-oxo-2-phenyl-1,6-dihydropyrimidine-4-carboxamide,
6-oxo-2-phenyl-N-{phenyl[4-(trifluoromethyl)phenyl]methyl}-1,6-dihydropyrimidine-4-carboxamide,
N-[1-(4-tert-butylphenyl)propyl]-6-oxo-2-phenyl-1,6-dihydropyrimidine-4-carboxamide,
N-[1-(4-cyclopropylphenyl)ethyl]-6-oxo-2-phenyl-1,6-dihydropyrimidine-4-carboxamide,
N-[1-(4-ethylphenyl)ethyl]-6-oxo-2-phenyl-1,6-dihydropyrimidine-4-carboxamide,
N-{(1R)-2-methyl-1-[4-(trifluoromethoxy)phenyl]propyl}-6-oxo-2-phenyl-1,6-dihydropyrimidine-4-carboxamide,
N-{(1R)-2-methyl-1-[4-(trifluoromethyl)phenyl]propyl}-6-oxo-2-phenyl-1,6-dihydropyrimidine-4-carboxamide,
6-oxo-2-phenyl-N-{(1R)-1-[3-(trifluoromethyl)phenyl]ethyl}-1,6-dihydropyrimidine-4-carboxamide,
6-oxo-2-phenyl-N-{1-[2-(trifluoromethyl)phenyl]ethyl}-1,6-dihydropyrimidine-4-carboxamide,
6-oxo-2-phenyl-N-{1-[5-(trifluoromethyl)pyrimidin-2-yl]ethyl}-1,6-dihydropyrimidine-4-carboxamide,
6-oxo-2-phenyl-N-(1-{4-[(trifluoromethyl)sulfanyl]phenyl}cyclobutyl)-1,6-dihydropyrimidine-4-carboxamide,
N-{(1R)-1-[3-fluoro-4-(trifluoromethoxy)phenyl]propyl}-6-oxo-2-phenyl-1,6-dihydropyrimidine-4-carboxamide,
N-{1-[2-methyl-4-(trifluoromethyl)phenyl]ethyl}-6-oxo-2-phenyl-1,6-dihydropyrimidine-4-carboxamide,
N-{(R)-cyclopropyl[3-fluoro-4-(trifluoromethyl)phenyl]methyl}-6-oxo-2-phenyl-1,6-dihydropyrimidine-4-carboxamide,
N-{(R)-cyclopropyl[4-(trifluoromethoxy)phenyl]methyl}-6-oxo-2-phenyl-1,6-dihydropyrimidine-4-carboxamide,
N-{(R)-cyclopropyl[3-fluoro-4-(trifluoromethoxy)phenyl]methyl}-6-oxo-2-phenyl-1,6-dihydropyrimidine-4-carboxamide,
N-{(R)-cyclopropyl[4-(trifluoromethyl)phenyl]methyl}-6-oxo-2-phenyl-1,6-dihydropyrimidine-4-carboxamide,
N-[(R)-cyclopropyl{4-[(trifluoromethyl)sulfanyl]phenyl}methyl]-6-oxo-2-phenyl-1,6-dihydropyrimidine-4-carboxamide,
6-oxo-2-phenyl-N-{(1R)-1-[4-(trifluoromethoxy)phenyl]propyl}-1,6-dihydropyrimidine-4-carboxamide,
N-[2-methyl-4-(trifluoromethyl)benzyl]-6-oxo-2-phenyl-1,6-dihydropyrimidine-4-carboxamide,
N-[2-chloro-4-(trifluoromethyl)benzyl]-6-oxo-2-phenyl-1,6-dihydropyrimidine-4-carboxamide,
N-(4-cyclopropylbenzyl)-6-oxo-2-phenyl-1,6-dihydropyrimidine-4-carboxamide,
6-oxo-2-phenyl-N-{(1R)-1-[4-(2,2,2-trifluoroethyl)phenyl]ethyl}-1,6-dihydropyrimidine-4-carboxamide,
N-{(1R)-1-[3,5-difluoro-4-(trifluoromethyl)phenyl]ethyl}-6-oxo-2-phenyl-1,6-dihydropyrimidine-4-carboxamide,
N-{2-hydroxy-1-[4-(trifluoromethyl)phenyl]ethyl}-6-oxo-2-phenyl-1,6-dihydropyrimidine-4-carboxamide,
N-(1-methyl-1-{4-[(trifluoromethyl)sulfanyl]phenyl}ethyl)-6-oxo-2-phenyl-1,6-dihydropyrimidine-4-carboxamide,
N-{1-[2-methoxy-4-(trifluoromethoxy)phenyl]ethyl}-6-oxo-2-phenyl-1,6-dihydropyrimidine-4-carboxamide,
N-{(1R)-1-[2-methoxy-4-(trifluoromethyl)phenyl]ethyl}-6-oxo-2-phenyl-1,6-dihydropyrimidine-4-carboxamide,
N-{(1R)-1-[3-methyl-4-(trifluoromethyl)phenyl]ethyl}-6-oxo-2-phenyl-1,6-dihydropyrimidine-4-carboxamide,
N-{(1R)-1-[3-chloro-4-(trifluoromethyl)phenyl]ethyl}-6-oxo-2-phenyl-1,6-dihydropyrimidine-4-carboxamide,
2-cyclopropyl-N-{(1R)-2-methyl-1-[4-(trifluoromethoxy)phenyl]propyl}-6-oxo-1,6-dihydropyrimidine-4-carboxamide,
2-cyclopropyl-N-[1-(6-methoxynaphthalen-2-yl)ethyl]-6-oxo-1,6-dihydropyrimidine-4-carboxamide,
2-cyclopropyl-N-{(1R)-2-methyl-1-[4-(trifluoromethyl)phenyl]propyl}-6-oxo-1,6-dihydropyrimidine-4-carboxamide,
2-cyclopropyl-N-[1-(4-ethylphenyl)ethyl]-6-oxo-1,6-dihydropyrimidine-4-carboxamide,
2-cyclopropyl-N-[1-(4-cyclopropylphenyl)ethyl]-6-oxo-1,6-dihydropyrimidine-4-carboxamide, 2-cyclopropyl-6-oxo-N-{phenyl[4-(trifluoromethyl)phenyl]methyl}-1,6-dihydropyrimidine-4-carboxamide, 2-cyclopropyl-6-oxo-N-{1-[4-(trifluoromethyl)phenyl]cyclopentyl}-1,6-dihydropyrimidine-4-carboxamide, 2-cyclopropyl-N-{1-[3-fluoro-4-(trifluoromethoxy)phenyl]-1-methylethyl}-6-oxo-1,6-dihydropyrimidine-4-carboxamide, 2-cyclopropyl-6-oxo-N-(1-{4-[(trifluoromethyl)sulfanyl]phenyl}cyclopropyl)-1,6-dihydropyrimidine-4-carboxamide, 2-cyclopropyl-N-{1-[3-fluoro-4-(trifluoromethyl)phenyl]-1-methylethyl}-6-oxo-1,6-dihydropyrimidine-4-carboxamide, 2-cyclopropyl-N-{1-[3-fluoro-4-(trifluoromethoxy)phenyl]cyclopropyl}-6-oxo-1,6-dihydropyrimidine-4-carboxamide, 2-cyclopropyl-N-{1-[3-fluoro-4-(trifluoromethyl)phenyl]cyclopropyl}-6-oxo-1,6-dihydropyrimidine-4-carboxamide, 2-cyclopropyl-6-oxo-N-{1-[5-(trifluoromethyl)pyrimidin-2-yl]ethyl}-1,6-dihydropyrimidine-4-carboxamide, 2-cyclopropyl-6-oxo-N-(1-{4-[(trifluoromethyl)sulfanyl]phenyl}cyclobutyl)-1,6-dihydropyrimidine-4-carboxamide, 2-cyclopropyl-N-{(4-methoxyphenyl)[4-(trifluoromethyl)phenyl]methyl}-6-oxo-1,6-dihydropyrimidine-4-carboxamide, 2-cyclopropyl-N-methyl-6-oxo-N-(3,4,5-trifluorobenzyl)-1,6-dihydropyrimidine-4-carboxamide, 2-cyclopropyl-N-{(1R)-1-[3-fluoro-4-(trifluoromethoxy)phenyl]propyl}-6-oxo-1,6-dihydropyrimidine-4-carboxamide, 2-cyclopropyl-N-{1-[2-methyl-4-(trifluoromethyl)phenyl]ethyl}-6-oxo-1,6-dihydropyrimidine-4-carboxamide, 2-cyclopropyl-N-methyl-6-oxo-N-{(1R)-1-[4-(trifluoromethyl)phenyl]ethyl}-1,6-dihydropyrimidine-4-carboxamide, 2-cyclopropyl-N-{(R)-cyclopropyl[3-fluoro-4-(trifluoromethyl)phenyl]methyl}-6-oxo-1,6-dihydropyrimidine-4-carboxamide, 2-cyclopropyl-N-{(R)-cyclopropyl[4-(trifluoromethoxy)phenyl]methyl}-6-oxo-1,6-dihydropyrimidine-4-carboxamide, 2-cyclopropyl-N-{(R)-cyclopropyl[3-fluoro-4-(trifluoromethoxy)phenyl]methyl}-6-oxo-1,6-dihydropyrimidine-4-carboxamide, 2-cyclopropyl-N-{(R)-cyclopropyl[4-(trifluoromethyl)phenyl]methyl}-6-oxo-1,6-dihydropyrimidine-4-carboxamide, 2-cyclopropyl-N-[(R)-cyclopropyl{4-[(trifluoromethyl)sulfanyl]phenyl}methyl]-6-oxo-1,6-dihydropyrimidine-4-carboxamide, methyl 4-(1-{[(2-cyclopropyl-6-oxo-1,6-dihydropyrimidin-4-yl)carbonyl]amino}-1-methylethyl)benzoate, 2-cyclopropyl-N-[(1R)-1-(4-methoxyphenyl)ethyl]-6-oxo-1,6-dihydropyrimidine-4-carboxamide, 2-cyclopropyl-6-oxo-N-{(1R)-1-[4-(2,2,2-trifluoroethyl)phenyl]ethyl}-1,6-dihydropyrimidine-4-carboxamide, 2-cyclopropyl-N-{(1R)-1-[3,5-difluoro-4-(trifluoromethyl)phenyl]ethyl}-6-oxo-1,6-dihydropyrimidine-4-carboxamide, 2-cyclopropyl-N-{(1R)-1-[2-methoxy-4-(trifluoromethyl)phenyl]ethyl}-6-oxo-1,6-dihydropyrimidine-4-carboxamide, 2-cyclopropyl-6-oxo-N-{1-[2-(trifluoromethyl)phenyl]ethyl}-1,6-dihydropyrimidine-4-carboxamide, 2-cyclopropyl-N-(4-cyclopropylbenzyl)-6-oxo-1,6-dihydropyrimidine-4-carboxamide, 2-cyclopropyl-N-(1-methyl-1-{4-[(trifluoromethyl)sulfanyl]phenyl}ethyl)-6-oxo-1,6-dihydropyrimidine-4-carboxamide, 2-cyclopropyl-N-{(1S)-1-[2-methoxy-4-(trifluoromethyl)phenyl]ethyl}-6-oxo-1,6-dihydropyrimidine-4-carboxamide, 2-cyclopropyl-N-[(1R)-1-naphthalen-2-ylethyl]-6-oxo-1,6-dihydropyrimidine-4-carboxamide, 2-cyclopropyl-6-oxo-N-{(1R)-1-[4-(trifluoromethoxy)phenyl]propyl}-1,6-dihydropyrimidine-4-carboxamide, 2-cyclopropyl-N-{1-[3-methoxy-4-(trifluoromethyl)phenyl]ethyl}-6-oxo-1,6-dihydropyrimidine-4-carboxamide, 2-cyclopropyl-6-oxo-N-{(1R)-1-[4-(pentafluoro-$\lambda^6$-sulfanyl)phenyl]ethyl}-1,6-dihydropyrimidine-4-carboxamide, 2-cyclopropyl-N-[2-methyl-4-(trifluoromethyl)benzyl]-6-oxo-1,6-dihydropyrimidine-4-carboxamide, N-[2-chloro-4-(trifluoromethyl)benzyl]-2-cyclopropyl-6-oxo-1,6-dihydropyrimidine-4-carboxamide, 2-cyclopropyl-N-{1-[2-methoxy-4-(trifluoromethoxy)phenyl]ethyl}-6-oxo-1,6-dihydropyrimidine-4-carboxamide, 2-cyclopropyl-N-{(1R)-1-[3-methyl-4-(trifluoromethyl)phenyl]ethyl}-6-oxo-1,6-dihydropyrimidine-4-carboxamide, N-{(1R)-1-[3-chloro-4-(trifluoromethyl)phenyl]ethyl}-2-cyclopropyl-6-oxo-1,6-dihydropyrimidine-4-carboxamide, N-{1-[2-chloro-4-(trifluoromethyl)phenyl]ethyl}-2-cyclopropyl-6-oxo-1,6-dihydropyrimidine-4-carboxamide, 2-cyclopropyl-N-{(1R)-1-[3-fluoro-4-(trifluoromethyl)phenyl]ethyl}-6-oxo-1,6-dihydropyrimidine-4-carboxamide, 2-cyclopropyl-6-oxo-N-{(1R)-1-[4-(trifluoromethyl)naphthalen-1-yl]ethyl}-1,6-dihydropyrimidine-4-carboxamide, 2-cyclopropyl-6-oxo-N-[(1R)-1-{4-[(trifluoromethyl)sulfanyl]phenyl}propyl]-1,6-dihydropyrimidine-4-carboxamide, 2-cyclopropyl-N-{(1R)-1-[2-fluoro-4-(trifluoromethyl)phenyl]ethyl}-6-oxo-1,6-dihydropyrimidine-4-carboxamide, 2-cyclopropyl-6-oxo-N-{1-[5-(trifluoromethyl)pyridin-2-yl]ethyl}-1,6-dihydropyrimidine-4-carboxamide, 2-cyclopropyl-N-[2,6-dichloro-4-(trifluoromethyl)benzyl]-6-oxo-1,6-dihydropyrimidine-4-carboxamide, N-{(1R)-1-[3-fluoro-4-(trifluoromethyl)phenyl]-2-methylpropyl}-2-methyl-6-oxo-1,6-dihydropyrimidine-4-carboxamide, N-(1-{3-fluoro-4-[(trifluoromethyl)sulfanyl]phenyl}-1-methylethyl)-6-oxo-1,6-dihydro-2,2'-bipyrimidine-4-carboxamide, 2-cyclopropyl-6-oxo-N-{(1R)-1-[4-(pentafluoro-$\lambda^6$-sulfanyl)phenyl]propyl}-1,6-dihydropyrimidine-4-carboxamide, 2-cyclopropyl-N-[(1R)-1-{3-fluoro-4-[(trifluoromethyl)sulfanyl]phenyl}ethyl]-6-oxo-1,6-dihydropyrimidine-4-carboxamide, 2-cyclopropyl-N-[(1R)-1-{3-fluoro-4-[(trifluoromethyl)sulfanyl]phenyl}-2-methylpropyl]-6-oxo-1,6-dihydropyrimidine-4-carboxamide, N-[(1R)-1-{3-fluoro-4-[(trifluoromethyl)sulfanyl]phenyl}-2-methylpropyl]-6-oxo-1,6-dihydro-2,2'-bipyrimidine-4-carboxamide, 2-cyclopropyl-N-[(1R)-1-{3-fluoro-4-[(trifluoromethyl)sulfanyl]phenyl}propyl]-6-oxo-1,6-dihydropyrimidine-4-carboxamide, 2-cyclopropyl-N-{(1R)-2-methyl-1-[4-(pentafluoro-$\lambda^6$-sulfanyl)phenyl]propyl}-6-oxo-1,6-dihydropyrimidine-4-carboxamide, N-{(1R)-1-[3-fluoro-4-(trifluoromethyl)phenyl]-2-methylpropyl}-6-oxo-1,6-dihydro-2,2'-bipyrimidine-4-carboxamide, N-{(1R)-2,2-dimethyl-1-[4-(trifluoromethyl)phenyl]propyl}-2-methyl-6-oxo-1,6-dihydropyrimidine-4-carboxamide, N-[(1R)-1-(4-cyclopropylphenyl)ethyl]-6-oxo-1,6-dihydro-2,2'-bipyrimidine-4-carboxamide, 2-cyclopropyl-N-{(1R)-1-[3-fluoro-4-(trifluoromethyl)phenyl]-2-methylpropyl}-6-oxo-1,6-dihydropyrimidine-4-carboxamide, 2-cyclopropyl-N-(1-{3-fluoro-4-[(trifluoromethyl)sulfanyl]phenyl}cyclopropyl)-6-oxo-1,6-dihydropyrimidine-4-carboxamide, N-(1-{3-fluoro-4-[(trifluoromethyl)sulfanyl]phenyl}cyclopropyl)-6-oxo-1,6-dihydro-2,2'-bipyrimidine-4-carboxamide, 2-cyclopropyl-N-{(1R)-1-[3-fluoro-4-(trifluoromethyl)phenyl]propyl}-6-oxo-1,6-dihydropyrimidine-4-carboxamide, N-{(1R)-2,2-dimethyl-1-[4-(trifluoromethyl)phenyl]propyl}-6-oxo-1,6-dihydro-2,2'-bipyrimidine-4-carboxamide, 2-cyclopropyl-N-[(1R)-1-(4-cyclopropylphenyl)ethyl]-6-oxo-1,6-dihydropyrimidine-4-carboxamide, 6-oxo-N-{(1R)-1-[4-(pentafluoro-$\lambda^6$-sulfanyl)phenyl]propyl}-1,6-dihydro-2,2'-bipyrimidine-4-carboxamide, N-[(1R)-1-(4-cyclopropylphenyl)ethyl]-2-methyl-6-oxo-1,6-dihydropyrimidine-4-carboxamide, N-(1-{3-fluoro-4-[(trifluoromethyl)sulfanyl]phenyl}-1-methylethyl)-2-methyl-6-oxo-1,6-dihydropyrimidine-4-carboxamide, N-[(1R)-1-{3-fluoro-4-[(trifluoromethyl)sulfanyl]phenyl}ethyl]-6-oxo-1,6-dihydro-2,2'-bipyrimidine-4-carboxamide, N-(1-{3-fluoro-4-[(trifluoromethyl)sulfanyl]phenyl}cyclopropyl)-2-methyl-6-oxo-1,6-dihydropyrimidine-4-carboxamide, 2-cyclopropyl-N-{(1R)-2,2-dimethyl-1-[4-(trifluoromethyl)phenyl]propyl}-6-oxo-1,6-dihydropyrimidine-4-carboxamide, N-[(1R)-1-{3-fluoro-4-[(trifluoromethyl)sulfanyl]phenyl}propyl]-6-oxo-1,6-dihydro-2,2'-bipyrimidine-4-carboxamide, N-{(1R)-1-[3-fluoro-4-(trifluoromethyl)phenyl]propyl}-6-oxo-1,6-dihydro-2,2'-bipyrimidine-4-carboxamide, N-{(1R)-2-methyl-1-[4-(pentafluoro-$\lambda^6$-sulfanyl)phenyl]propyl}-6-oxo-1,6-dihydro-2,2'-bipyrimidine-4-carboxamide, 2-cyclopropyl-N-(1-{3-fluoro-4-[(trifluoromethyl)sulfanyl]phenyl}-1-methylethyl)-6-oxo-1,6-dihydropyrimidine-4-carboxamide, N-[1-(4'-fluorobiphenyl-3-yl)ethyl]-2-methyl-6-oxo-1,6-dihydropyrimidine-4-carboxamide, N-[1-(4-ethylphenyl)ethyl]-2-methyl-6-oxo-1,6-dihydropyrimidine-4-carboxamide, 2-methyl-6-oxo-N-{1-[4-(trifluoromethoxy)phenyl]cyclobutyl}-1,6-dihydropyrimidine-4-carboxamide, 2-methyl-6-oxo-N-{1-[4-(trifluoromethyl)phenyl]cyclopentyl}-1,6-dihydropyrimidine-4-carboxamide, 2-methyl-6-oxo-N-{(1R)-1-[3-(trifluoromethyl)phenyl]ethyl}-1,6-dihydropyrimidine-4-carboxamide, 2-methyl-N-{1-methyl-1-[4-(trifluoromethyl)phenyl]ethyl}-6-oxo-1,6-dihydropyrimidine-4-carboxamide, 2-methyl-N-{1-methyl-1-[4-(trifluoromethoxy)phenyl]ethyl}-6-oxo-1,6-dihydropyrimidine-4-carboxamide, 6-oxo-2-phenyl-N-{(1R)-1-[4-(trifluoromethyl)phenyl]ethyl}-1,6-dihydropyrimidine-4-carboxamide, 6-oxo-2-phenyl-N-{(1R)-1-[4-(trifluoromethoxy)phenyl]ethyl}-1,6-dihydropyrimidine-4-carboxamide, 6-oxo-2-phenyl-N-{1-[4-(trifluoromethyl)phenyl]cyclopropyl}-1,6-dihydropyrimidine-4-carboxamide, 6-oxo-2-phenyl-N-{1-[4-(trifluoromethoxy)phenyl]cyclopropyl}-1,6-dihydropyrimidine-4-carboxamide, 6-oxo-2-phenyl-N-{1-[4-(trifluoromethyl)phenyl]cyclobutyl}-1,6-dihydropyrimidine-4-carboxamide, N-[(1R)-1-biphenyl-4-ylethyl]-6-oxo-2-phenyl-1,6-dihydropyrimidine-4-carboxamide, N-{1-methyl-1-[4-(trifluoromethyl)phenyl]ethyl}-6-oxo-2-phenyl-1,6-dihydropyrimidine-4-carboxamide, N-{1-methyl-1-[4-(trifluoromethoxy)phenyl]ethyl}-6-oxo-2-phenyl-1,6-dihydropyrimidine-4-carboxamide, 6-oxo-2-phenyl-N-{1[4-(trifluoromethoxy)phenyl]cyclobutyl}-1,6-dihydropyrimidine-4-carboxamide, 6-oxo-N-{(1R)-1-[4-(trifluoromethoxy)phenyl]ethyl}-1,6-dihydro-2,2'-bipyrimidine-4-carboxamide, 6-oxo-N-{1-[4-(trifluoromethyl)phenyl]cyclopropyl}-1,6-dihydro-2,2'-bipyrimidine-4-carboxamide, 6-oxo-N-{1-[4-(trifluoromethoxy)phenyl]cyclopropyl}1,6-dihydro-2,2'-bipyrimidine-4-carboxamide, 6-oxo-N-{1-[4-(trifluoromethyl)phenyl]cyclobutyl}1,6-dihydro-2,2'-bipyrimidine-4-carboxamide, N-[(1R)-1-biphenyl-4-ylethyl]-6-oxo-1,6-dihydro-2,2'-bipyrimidine-4-carboxamide, N-{1-methyl-1-[4-(trifluoromethyl)phenyl]ethyl}-6-oxo-1,6-dihydro-2,2'-bipyrimidine-4-carboxamide, N-{1-methyl-1-[4-(trifluoromethoxy)phenyl]ethyl}-6-oxo-1,6-dihydro-2,2'-bipyrimidine-4-carboxamide, 6-oxo-N-(1-(4-(trifluoromethoxy)phenyl)cyclobutyl)-1,6-dihydro-[2,2'-bipyrimidine]-4-carboxamide, 6-oxo-N-{(1R)-1-[4-(trifluoromethyl)phenyl]ethyl}-1,6-dihydro-2,2'-bipyrimidine-4-carboxamide, 2-cyclopropyl-6-oxo-N-{1-[4-(trifluoromethyl)phenyl]cyclopropyl}-1,6-dihydropyrimidine-4-carboxamide, 2-cyclopropyl-N-{1-methyl-1-[4-(trifluoromethyl)phenyl]ethyl}-6-oxo-1,6-dihydropyrimidine-4-carboxamide, 2-cyclopropyl-N-{2-hydroxy-1-[4-(trifluoromethyl)phenyl]ethyl}-6-oxo-1,6-dihydropyrimidine-4-carboxamide, 2-cyclopropyl-N-{1-methyl-1-[4-(trifluoromethoxy)phenyl]ethyl}-6-oxo-1,6-dihydropyrimidine-4-carboxamide, 2-cyclopropyl-N-{(1R)-1-[3-fluoro-4-(trifluoromethoxy)phenyl]ethyl}-6-oxo-1,6-dihydropyrimidine-4-carboxamide, 2-cyclopropyl-N-{(1R)-1-[2-fluoro-4-(trifluoromethoxy)phenyl]ethyl}-6-oxo-1,6-dihydropyrimidine-4-carboxamide, 2-cyclopropyl-N-{(1R)-1-[4-(1-methylethyl)phenyl]ethyl}-6-oxo-1,6-dihydropyrimidine-4-carboxamide, 2-cyclopropyl-6-oxo-N-{1-[4-(trifluoromethoxy)phenyl]cyclopropyl}-1,6-dihydropyrimidine-4-carboxamide,
2-cyclopropyl-6-oxo-N-{1-[4-(trifluoromethoxy)phenyl]cyclobutyl}-1,6-dihydropyrimidine-4-carboxamide,
(R)-2-methyl-N-(1-(naphthalen-1-yl)ethyl)-6-oxo-1,6-dihydropyrimidine-4-carboxamide,
2-methyl-N-[(1S)-1-naphthalen-1-ylethyl]-6-oxo-1,6-dihydropyrimidine-4-carboxamide,
N-(1-(1H-indo-6-yl)ethyl)-2-methyl-6-oxo-1,6-dihydropyrimidine-4-carboxamide,
(R)-N-(1-(4-(difluoromethoxy)phenyl)ethyl)-2-methyl-6-oxo-1,6-dihydropyrimidine-4-carboxamide,
(R)- and (S)-2-methyl-N-{1-[4-1-methylethyl)phenyl]ethyl}-6-oxo-1,6-dihydropyrimidine-4-carboxamide,
(R)- and (S)-N-(1-biphenyl-4-ylethyl)-2-methyl-6-oxo-1,6-dihydropyrimidine-4-carboxamide,
(R)- and (S)-N-[1-(4-tert-butylphenyl)ethyl]-2-methyl-6-oxo-1,6-dihydropyrimidine-4-carboxamide,
(R)- and (S)-N-{2-hydroxy-1-[4-(trifluoromethyl)phenyl]ethyl}-2-methyl-6-oxo-1,6-dihydropyrimidine-4-carboxamide,
(R)- and (S)-N-[1-(6-methoxynaphthalen-2-yl)ethyl]-2-methyl-6-oxo-1,6-dihydropyrimidine-4-carboxamide,
2-methyl-N-{(1S)-2-methyl-1-[4-(trifluoromethyl)phenyl]propyl}-6-oxo-1,6-dihydropyrimidine-4-carboxamide,
2-methyl-N-{(1R)-2-methyl-1-[4-(trifluoromethyl)phenyl]propyl}-6-oxo-1,6-dihydropyrimidine-4-carboxamide,
N-{(1R)-1-[4-(2-methoxypyridin-4-yl)phenyl]ethyl}-2-methyl-6-oxo-1,6-dihydropyrimidine-4-carboxamide,
2-methyl-6-oxo-N-{(1R)-1-[4'-(trifluoromethyl)biphenyl-4-yl]ethyl}-1,6-dihydropyrimidine-4-carboxamide,
2-methyl-N-{(1R)-1-[4-(2-methylpyridin-4-yl)phenyl]ethyl}-6-oxo-1,6-dihydropyrimidine-4-carboxamide,
2-methyl-6-oxo-N-[(1R)-1-(4-pyridin-3-ylphenyl)ethyl]-1,6-dihydropyrimidine-4-carboxamide,
2-methyl-6-oxo-N-[(1R)-1-{4-[6-(trifluoromethyl)pyridin-3-yl]phenyl}ethyl]-1,6-dihydropyrimidine-4-carboxamide,
N-[(1R)-1-(4'-fluorobiphenyl-4-yl)ethyl]-2-methyl-6-oxo-1,6-dihydropyrimidine-4-carboxamide,
N-[(1R)-1-(3'-fluorobiphenyl-4-yl)ethyl]-2-methyl-6-oxo-1,6-dihydropyrimidine-4-carboxamide,
N-[(1R)-1-(2'-fluorobiphenyl-4-yl)ethyl]-2-methyl-6-oxo-1,6-dihydropyrimidine-4-carboxamide,
methyl{[(2-methyl-6-oxo-1,6-dihydropyrimidin-4-yl)carbonyl]amino}[4-(trifluoromethyl)phenyl]acetate,
2-(2-methyl-6-oxo-1,6-dihydropyrimidine-4-carboxamido)-2-(4-(trifluoromethyl)phenyl)acetic acid
(R)- and (S)-2-(2-methyl-6-oxo-1,6-dihydropyrimidine-4-carboxamido)-2-(4-(trifluoromethyl)phenyl)acetic acid
N-{2-(dimethylamino)-2-oxo-1-[4-(trifluoromethyl)phenyl]ethyl}-2-methyl-6-oxo-1,6-dihydropyrimidine-4-carboxamide,
2-methyl-6-oxo-N-[(1R)-1-{4-[(trifluoromethyl)sulfinyl]phenyl}ethyl]-1,6-dihydropyrimidine-4-carboxamide,
2-methyl-6-oxo-N-[(1R)-1-{4-[(trifluoromethyl)sulfonyl]phenyl}ethyl]-1,6-dihydropyrimidine-4-carboxamide,
(R)-5-ethyl-6-oxo-N-(1-(4-(trifluoromethyl)phenyl)ethyl)-1,6-dihydropyrimidine-4-carboxamide,
(R)-2,5-diethyl-6-oxo-N-(1-(4-(trifluoromethyl)phenyl)ethyl)-1,6-dihydropyrimidine-4-carboxamide,
(R)-5-cyclobutyl-6-oxo-N-(1-(4-(trifluoromethyl)phenyl)ethyl)-1,6-dihydropyrimidine-4-carboxamide,
(R)-2,5-dicyclobutyl-6-oxo-N-(1-(4-(trifluoromethyl)phenyl)ethyl)-1,6-dihydropyrimidine-4-carboxamide,
2-methyl-6-oxo-N-{1H-tetrazol-5-yl[4-(trifluoromethyl)phenyl]methyl}-1,6-dihydropyrimidine-4-carboxamide,
N-{(1R)-2,2-dimethyl-1-[4-(trifluoromethyl)phenyl]propyl}-6-oxo-2-phenyl-1,6-dihydropyrimidine-4-carboxamide,
6-oxo-2-phenyl-N-(3,4,5-trimethoxybenzyl)-1,6-dihydropyrimidine-4-carboxamide,
N-[(1R)-1-(4-hydroxyphenyl)ethyl]-6-oxo-2-phenyl-1,6-dihydropyrimidine-4-carboxamide,
N-[1-(4-bromophenyl)-1-methylethyl]-6-oxo-2-phenyl-1,6-dihydropyrimidine-4-carboxamide,
N-{2-(methylsulfanyl)-1-[4-(trifluoromethyl)phenyl]ethyl}-6-oxo-2-phenyl-1,6-dihydropyrimidine-4-carboxamide,
6-oxo-2-phenyl-N-[(1R)-1-phenylethyl]-1,6-dihydropyrimidine-4-carboxamide,
N-[1-(4-fluorophenyl)ethyl]-6-oxo-2-phenyl-1,6-dihydropyrimidine-4-carboxamide,
N-[1-(3,4-difluorophenyl)-1-methylethyl]-6-oxo-2-phenyl-1,6-dihydropyrimidine-4-carboxamide,
N-methyl-6-oxo-2-phenyl-N-[4-(trifluoromethyl)benzyl]-1,6-dihydropyrimidine-4-carboxamide,
2-phenyl-6-({2-[4-(trifluoromethyl)phenyl]piperidin-1-yl}carbonyl)pyrimidin-4(3H)-one,
N-[(1R)-1-(4-methoxyphenyl)ethyl]-6-oxo-2-phenyl-1,6-dihydropyrimidine-4-carboxamide,
N-[1-(4-fluorophenyl)-1-methylethyl]-6-oxo-2-phenyl-1,6-dihydropyrimidine-4-carboxamide,
6-oxo-2-phenyl-N-{1-[4-(1H-pyrazol-1-yl)phenyl]ethyl}-1,6-dihydropyrimidine-4-carboxamide,
6-oxo-2-phenyl-N-[1-(3,4,5-trimethoxyphenyl)ethyl]-1,6-dihydropyrimidine-4-carboxamide,
N-(1-{3-fluoro-4-[(trifluoromethyl)sulfanyl]phenyl}cyclopropyl)-6-oxo-2-phenyl-1,6-dihydropyrimidine-4-carboxamide,
6-oxo-2-phenyl-N-{(1R)-3,3,3-trifluoro-1-[4-(trifluoromethyl)phenyl]propyl}-1,6-dihydropyrimidine-4-carboxamide,
N-[(1R)-1-naphthalen-1-ylethyl]-6-oxo-2-phenyl-1,6-dihydropyrimidine-4-carboxamide,
ethyl4-[(1R)-1-{[(6-oxo-2-phenyl-1,6-dihydropyrimidin-4-yl)carbonyl]amino}ethyl]benzoate,
6-oxo-2-phenyl-N-{1-[6-(trifluoromethyl)pyridin-3-yl]ethyl}-1,6-dihydropyrimidine-4-carboxamide,
N-[(1S)-1-(4-methoxyphenyl)ethyl]-6-oxo-2-phenyl-1,6-dihydropyrimidine-4-carboxamide,
6-oxo-2-phenyl-N-(1-pyridin-4-ylethyl)-1,6-dihydropyrimidine-4-carboxamide,
methyl4-[(1R)-1-{[(6-oxo-2-phenyl-1,6-dihydropyrimidin-4-yl)carbonyl]amino}ethyl]benzoate,
N-[1-(2,3-dihydro-1,4-benzodioxin-6-yl)ethyl]-6-oxo-2-phenyl-1,6-dihydropyrimidine-4-carboxamide,
N-(1-{3-fluoro-4-[(trifluoromethyl)sulfanyl]phenyl}-1-methylethyl)-6-oxo-2-phenyl-1,6-dihydropyrimidine-4-carboxamide,
N-[(1S)-1-naphthalen-1-ylethyl]-6-oxo-2-phenyl-1,6-dihydropyrimidine-4-carboxamide,
6-oxo-2-phenyl-N-{1-[4-(1H-1,2,4-triazol-1-yl)phenyl]ethyl}-1,6-dihydropyrimidine-4-carboxamide,
N-[(1S)-1-(4-methylphenyl)ethyl]-6-oxo-2-phenyl-1,6-dihydropyrimidine-4-carboxamide, N-[(1R)-1-{4-[(dimethylamino)methyl]phenyl}ethyl]-6-oxo-2-phenyl-1,6-dihydropyrimidine-4-carboxamide,
6-oxo-2-phenyl-N-{(1S)-3,3,3-trifluoro-1-[4-(trifluoromethyl)phenyl]propyl}-1,6-dihydropyrimidine-4-carboxamide,
N-{(4-fluorophenyl)[4-(trifluoromethyl)phenyl]methyl}-6-oxo-2-phenyl-1,6-dihydropyrimidine-4-carboxamide,
N-[1-(3-chlorophenyl)ethyl]-6-oxo-2-phenyl-1,6-dihydropyrimidine-4-carboxamide,
N-[1-(4-hydroxyphenyl)ethyl]-6-oxo-2-phenyl-1,6-dihydropyrimidine-4-carboxamide,
N-[1-(4-cyanophenyl)ethyl]-6-oxo-2-phenyl-1,6-dihydropyrimidine-4-carboxamide,
6-oxo-2-phenyl-N-[4-(trifluoromethyl)benzyl]-1,6-dihydropyrimidine-4-carboxamide,
N-(biphenyl-4-ylmethyl)-6-oxo-2-phenyl-1,6-dihydropyrimidine-4-carboxamide,
N-[1-(2-bromophenyl)-1-methylethyl]-6-oxo-2-phenyl-1,6-dihydropyrimidine-4-carboxamide,
N-{(1R)-1-[4-(dimethylamino)phenyl]ethyl}-6-oxo-2-phenyl-1,6-dihydropyrimidine-4-carboxamide,
N-[1-(1,3-benzodioxol-5-yl)ethyl]-6-oxo-2-phenyl-1,6-dihydropyrimidine-4-carboxamide,
6-oxo-N-[4-(pentafluoro-$\lambda^6$-sulfanyl)benzyl]-2-phenyl-1,6-dihydropyrimidine-4-carboxamide,
N-[1-(6-methoxynaphthalen-2-yl)ethyl]-6-oxo-2-phenyl-1,6-dihydropyrimidine-4-carboxamide,
N-[1-(2-methyl-2,3-dihydro-1-benzofuran-5-yl)ethyl]-6-oxo-2-phenyl-1,6-dihydropyrimidine-4-carboxamide,
6-oxo-2-phenyl-N-{1-[2-(trifluoromethoxy)phenyl]cyclopropyl}-1,6-dihydropyrimidine-4-carboxamide,
N-{(4-methoxyphenyl)[4-(trifluoromethyl)phenyl]methyl}-6-oxo-2-phenyl-1,6-dihydropyrimidine-4-carboxamide,
N-{1-[4-(methylsulfonyl)phenyl]ethyl}-6-oxo-2-phenyl-1,6-dihydropyrimidine-4-carboxamide,
N-{(1R)-1-[3-fluoro-4-(trifluoromethyl)phenyl]-2-methylpropyl}-6-oxo-2-phenyl-1,6-dihydropyrimidine-4-carboxamide,
6-oxo-2-phenyl-N-[1-(4-pyridin-4-ylphenyl)ethyl]-1,6-dihydropyrimidine-4-carboxamide,
N-[(1R)-1-{3-fluoro-4-[(trifluoromethyl)sulfanyl]phenyl}propyl]-6-oxo-2-phenyl-1,6-dihydropyrimidine-4-carboxamide,
6-oxo-N-{(1R)-1-[4-(pentafluoro-$\lambda^6$-sulfanyl)phenyl]propyl}-2-phenyl-1,6-dihydropyrimidine-4-carboxamide,
N-{1-[2-methoxy-4-(trifluoromethoxy)phenyl]ethyl}-6-oxo-2-phenyl-1,6-dihydropyrimidine-4-carboxamide,
N-{(1R)-2-methyl-1-[4-(pentafluoro-$\lambda^6$-sulfanyl)phenyl]propyl}-6-oxo-2-phenyl-1,6-dihydropyrimidine-4-carboxamide,
N-methyl-6-oxo-2-phenyl-N-{(1R)-1-[4-(trifluoromethyl)phenyl]ethyl}-1,6-dihydropyrimidine-4-carboxamide,
N-(1-methyl-1-phenylethyl)-6-oxo-2-phenyl-1,6-dihydropyrimidine-4-carboxamide,
N-[1-(4-tert-butylphenyl)ethyl]-6-oxo-2-phenyl-1,6-dihydropyrimidine-4-carboxamide,
N-{(1S,2R)-2-hydroxy-1-[4-(trifluoromethyl)phenyl]propyl}-6-oxo-2-phenyl-1,6-dihydropyrimidine-4-carboxamide,
6-oxo-2-phenyl-N-{2,2,2-trifluoro-1-[4-(trifluoromethyl)phenyl]ethyl}-1,6-dihydropyrimidine-4-carboxamide,
N-[(1S)-1-(4-chlorophenyl)ethyl]-6-oxo-2-phenyl-1,6-dihydropyrimidine-4-carboxamide,
6-oxo-2-phenyl-N-{1-[3-(trifluoromethyl)phenyl]ethyl}-1,6-dihydropyrimidine-4-carboxamide,
N-[1-(4'-fluorobiphenyl-3-yl)ethyl]-6-oxo-2-phenyl-1,6-dihydropyrimidine-4-carboxamide,
2-cyclopropyl-N-{(R)-cyclopropyl[4-(pentafluoro-$\lambda^6$-sulfanyl)phenyl]methyl}-6-oxo-1,6-dihydropyrimidine-4-carboxamide,
N-[(1R)-1-{3-fluoro-4-[(trifluoromethyl)sulfanyl]phenyl}ethyl]-6-oxo-2-phenyl-1,6-dihydropyrimidine-4-carboxamide,
6-oxo-2-phenyl-N-{pyridin-4-yl[4-(trifluoromethyl)phenyl]methyl}-1,6-dihydropyrimidine-4-carboxamide,
N-[1-(3-bromophenyl)-1-methylethyl]-6-oxo-2-phenyl-1,6-dihydropyrimidine-4-carboxamide,
6-oxo-N-{(1R)-1-[4-(pentafluoro-$\lambda^6$-sulfanyl)phenyl]ethyl}-2-phenyl-1,6-dihydropyrimidine-4-carboxamide,
6-oxo-2-phenyl-N-{3-[4-(trifluoromethyl)phenyl]oxetan-3-yl}-1,6-dihydropyrimidine-4-carboxamide,
N-{(1S)-1-[2-methoxy-4-(trifluoromethyl)phenyl]ethyl}-6-oxo-2-phenyl-1,6-dihydropyrimidine-4-carboxamide,
N-{(R)-cyclopropyl[4-(pentafluoro-$\lambda^6$-sulfanyl)phenyl]methyl}-6-oxo-2-phenyl-1,6-dihydropyrimidine-4-carboxamide,
N-{(R)-cyclopropyl[4-(pentafluoro-$\lambda^6$-sulfanyl)phenyl]methyl}-2-methyl-6-oxo-1,6-dihydropyrimidine-4-carboxamide,
methyl{[(6-oxo-2-phenyl-1,6-dihydropyrimidin-4-yl)carbonyl]amino}[4-(trifluoromethyl)phenyl]acetate,
N-[(1R)-1-{3-fluoro-4-[(trifluoromethyl)sulfanyl]phenyl}-2-methylpropyl]-6-oxo-2-phenyl-1,6-dihydropyrimidine-4-carboxamide,
N-{(1R)-1-[2,3-difluoro-4-(trifluoromethyl)phenyl]ethyl}-6-oxo-2-phenyl-1,6-dihydropyrimidine-4-carboxamide,
2-phenyl-6-[(2-phenyl-5,7-dihydro-6H-pyrrolo[3,4-d]pyrimidin-6-yl)carbonyl]pyrimidin-4(3H)-one,
N-(1-biphenyl-3-ylethyl)-6-oxo-2-phenyl-1,6-dihydropyrimidine-4-carboxamide,
6-oxo-2-phenyl-N-{1-[2-(trifluoromethoxy)phenyl]cyclobutyl}-1,6-dihydropyrimidine-4-carboxamide,
N-{(R)-cyclopropyl[4-(pentafluoro-$\lambda^6$-sulfanyl)phenyl]methyl}-6-oxo-1,6-dihydro-2,2'-bipyrimidine-4-carboxamide,
N-{cyano[4-(trifluoromethyl)phenyl]methyl}-6-oxo-2-phenyl-1,6-dihydropyrimidine-4-carboxamide,
N-[4-(1-methylethyl)benzyl]-6-oxo-2-phenyl-1,6-dihydropyrimidine-4-carboxamide,
6-oxo-2-phenyl-N-{1-[4-(trifluoromethyl)phenyl]cyclopentyl}-1,6-dihydropyrimidine-4-carboxamide,
N-(1-biphenyl-2-ylethyl)-6-oxo-2-phenyl-1,6-dihydropyrimidine-4-carboxamide,
N-[(R)-cyclopropyl{3-fluoro-4-[(trifluoromethyl)sulfanyl]phenyl}methyl]-6-oxo-2-phenyl-1,6-dihydropyrimidine-4-carboxamide,
N-[(1R)-1-(4-chlorophenyl)ethyl]-6-oxo-2-phenyl-1,6-dihydropyrimidine-4-carboxamide,
N-[(1R)-2-methyl-1-{4-[(trifluoromethyl)sulfanyl]phenyl}propyl]-6-oxo-2-phenyl-1,6-dihydropyrimidine-4-carboxamide,
N-{(1R)-1-[3-fluoro-4-(trifluoromethyl)phenyl]propyl}-6-oxo-2-phenyl-1,6-dihydropyrimidine-4-carboxamide,
N-{3-hydroxy-1-[4-(trifluoromethyl)phenyl]propyl}-6-oxo-2-phenyl-1,6-dihydropyrimidine-4-carboxamide, 6-oxo-2-phenyl-N-{1-[3-(trifluoromethoxy)phenyl]ethyl}-1,6-dihydropyrimidine-4-carboxamide,
N-[(1R)-1-(4-cyclopropylphenyl)ethyl]-6-oxo-2-phenyl-1,6-dihydropyrimidine-4-carboxamide,
2-methyl-N-{(R)-(1-methylcyclopropyl)[4-(pentafluoro-λ$^6$-sulfanyl)phenyl]methyl}-6-oxo-1,6-dihydropyrimidine-4-carboxamide,
N-[(R)-[4-(difluoromethoxy)phenyl](1-methylcyclopropyl)methyl]-2-methyl-6-oxo-1,6-dihydropyrimidine-4-carboxamide,
N-[(R)-cyclopropyl(4-cyclopropyl-3-fluorophenyl)methyl]-2-methyl-6-oxo-1,6-dihydropyrimidine-4-carboxamide,
2-methyl-N-{(R)-(1-methylcyclopropyl)[4-(1-methylethyl)phenyl]methyl}-6-oxo-1,6-dihydropyrimidine-4-carboxamide,
N-[(1R)-1-(4-cyclopropyl-3-fluorophenyl)-2,2-dimethylpropyl]-2-methyl-6-oxo-1,6-dihydropyrimidine-4-carboxamide,
N-{(1R)-1-[2,5-difluoro-4-(trifluoromethyl)phenyl]ethyl}-6-oxo-1,6-dihydro-2,2'-bipyrimidine-4-carboxamide,
N-{(1S,2S)-2-hydroxy-1-[4-(trifluoromethyl)phenyl]propyl}-6-oxo-1,6-dihydro-2,2'-bipyrimidine-4-carboxamide,
ethyl 4-[(1S)-1-{[(6-oxo-1,6-dihydro-2,2'-bipyrimidin-4-yl)carbonyl]amino}ethyl]benzoate,
ethyl 4-[(1R)-1-{[(6-oxo-1,6-dihydro-2,2'-bipyrimidin-4-yl)carbonyl]amino}ethyl]benzoate,
6-oxo-N-[(1R)-6-(trifluoromethyl)-1,2,3,4-tetrahydronaphthalen-1-yl]-1,6-dihydro-2,2'-bipyrimidine-4-carboxamide,
2-cyclopropyl-N-[(R)-cyclopropyl{3-fluoro-4-[(trifluoromethyl)sulfanyl]phenyl}methyl]-6-oxo-1,6-dihydropyrimidine-4-carboxamide,
2-cyclopropyl-N-[(1R)-1-(4-cyclopropyl-3-fluorophenyl)-2,2-dimethylpropyl]-6-oxo-1,6-dihydropyrimidine-4-carboxamide,
2-cyclopropyl-N-{(1R)-1-[4-(difluoromethoxy)phenyl]-2,2-dimethylpropyl}-6-oxo-1,6-dihydropyrimidine-4-carboxamide,
2-cyclopropyl-N-{(1R)-1-[3-fluoro-4-(trifluoromethoxy)phenyl]-2,2-dimethylpropyl}-6-oxo-1,6-dihydropyrimidine-4-carboxamide,
2-cyclopropyl-N-{(1R)-1-[3-fluoro-4-(trifluoromethyl)phenyl]-2,2-dimethylpropyl}-6-oxo-1,6-dihydropyrimidine-4-carboxamide,
2-cyclopropyl-N-[(1R)-2,2-dimethyl-1-{4-[(trifluoromethyl)sulfanyl]phenyl}propyl]-6-oxo-1,6-dihydropyrimidine-4-carboxamide,
2-cyclopropyl-N-{(1R)-1-[2,5-difluoro-4-(trifluoromethyl)phenyl]ethyl}-6-oxo-1,6-dihydropyrimidine-4-carboxamide,
2-cyclopropyl-N-{(1R)-2,2-dimethyl-1-[4-(2,2,2-trifluoroethyl)phenyl]propyl}-6-oxo-1,6-dihydropyrimidine-4-carboxamide,
2-cyclopropyl-N-{(1S,2S)-2-hydroxy-1-[4-(trifluoromethyl)phenyl]propyl}-6-oxo-1,6-dihydropyrimidine-4-carboxamide,
2-cyclopropyl-N-[(R)-[4-(difluoromethoxy)phenyl](1-methylcyclopropyl)methyl]-6-oxo-1,6-dihydropyrimidine-4-carboxamide,
2-cyclopropyl-N-{(R)-(1-methylcyclopropyl)[4-(1-methylethyl)phenyl]methyl}-6-oxo-1,6-dihydropyrimidine-4-carboxamide,
2-cyclopropyl-N-{(1R)-1-[2-fluoro-4-(trifluoromethyl)phenyl]-2,2-dimethylpropyl}-6-oxo-1,6-dihydropyrimidine-4-carboxamide,
2-cyclopropyl-N-{(R)-cyclopropyl[4-(difluoromethoxy)phenyl]methyl}-6-oxo-1,6-dihydropyrimidine-4-carboxamide,
2-cyclopropyl-N-[(1R)-1-(4-cyclopropylphenyl)-2,2-dimethylpropyl]-6-oxo-1,6-dihydropyrimidine-4-carboxamide,
N-{(R)-cyclopropyl[4-(difluoromethoxy)phenyl]methyl}-6-oxo-2-phenyl-1,6-dihydropyrimidine-4-carboxamide,
N-{(1R)-1-[4-(difluoromethoxy)phenyl]-2,2-dimethylpropyl}-6-oxo-2-phenyl-1,6-dihydropyrimidine-4-carboxamide,
N-{(1R)-1-[4-(difluoromethoxy)phenyl]-2,2-dimethylpropyl}-6-oxo-1,6-dihydro-2,2'-bipyrimidine-4-carboxamide,
N-[(1R)-1-(4-cyclopropyl-3-fluorophenyl)-2,2-dimethylpropyl]-6-oxo-1,6-dihydro-2,2'-bipyrimidine-4-carboxamide,
N-[(R)-cyclopropyl{3-fluoro-4-[(trifluoromethyl)sulfanyl]phenyl}methyl]-6-oxo-1,6-dihydro-2,2'-bipyrimidine-4-carboxamide,
N-[(R)-cyclopropyl(4-cyclopropylphenyl)methyl]-6-oxo-1,6-dihydro-2,2'-bipyrimidine-4-carboxamide,
2-cyclopropyl-N-{(R)-(1-methylcyclopropyl)[4-(pentafluoro-λ$^6$-sulfanyl)phenyl]methyl}-6-oxo-1,6-dihydropyrimidine-4-carboxamide,
N-{(1R)-2,2-dimethyl-1-[4-(trifluoromethyl)phenyl]propyl}-2-(4-methoxybenzyl)-6-oxo-1,6-dihydropyrimidine-4-carboxamide,
N-{(1R)-2,2-dimethyl-1-[4-(trifluoromethyl)phenyl]propyl}-2-[1-(4-methoxyphenyl)-1-methylethyl]-6-oxo-1,6-dihydropyrimidine-4-carboxamide,
N-{(1R)-2,2-dimethyl-1-[4-(trifluoromethyl)phenyl]propyl}-2-(3-fluoro-4-methoxybenzyl)-6-oxo-1,6-dihydropyrimidine-4-carboxamide,
N-[(1S)-1-(4-nitrophenyl)ethyl]-6-oxo-2-phenyl-1,6-dihydropyrimidine-4-carboxamide,
N-[(1R)-1-(4-nitrophenyl)ethyl]-6-oxo-2-phenyl-1,6-dihydropyrimidine-4-carboxamide,
N-[1-(4-methoxyphenyl)-1-methylethyl]-6-oxo-2-phenyl-1,6-dihydropyrimidine-4-carboxamide,
N-{(1R)-2,2-dimethyl-1-[4-(trifluoromethoxy)phenyl]propyl}-6-oxo-1,6-dihydro-2,2'-bipyrimidine-4-carboxamide,
N-{(1R)-2,2-dimethyl-1-[4-(trifluoromethoxy)phenyl]propyl}-6-oxo-2-phenyl-1,6-dihydropyrimidine-4-carboxamide,
2-cyclopropyl-N-{(1R)-2,2-dimethyl-1-[4-(trifluoromethoxy)phenyl]propyl}-6-oxo-1,6-dihydropyrimidine-4-carboxamide,
N-{(1R)-1-[3-fluoro-4-(trifluoromethoxy)phenyl]-2,2-dimethylpropyl}-2-(4-methoxybenzyl)-6-oxo-1,6-dihydropyrimidine-4-carboxamide,
N-[(1R)-2,2-dimethyl-1-{4-[(trifluoromethyl)sulfanyl]phenyl}propyl]-2-(4-methoxybenzyl)-6-oxo-1,6-dihydropyrimidine-4-carboxamide,
N-{(1R)-1-[3-fluoro-4-(trifluoromethyl)phenyl]-2,2-dimethylpropyl}-2-(4-methoxybenzyl)-6-oxo-1,6-dihydropyrimidine-4-carboxamide,
N-{(1R)-2,2-dimethyl-1-[4-(trifluoromethoxy)phenyl]propyl}-2-(4-methoxybenzyl)-6-oxo-1,6-dihydropyrimidine-4-carboxamide, N-{(R)-cyclopropyl[4-(pentafluoro-$\lambda^6$-sulfanyl)phenyl]methyl}-2-(4-methoxybenzyl)-6-oxo-1,6-dihydropyrimidine-4-carboxamide, 2-(4-methoxybenzyl)-N-[(1R)-2-methyl-1-{4-[(trifluoromethyl)sulfanyl]phenyl}propyl]-6-oxo-1,6-dihydropyrimidine-4-carboxamide, N-[(1R)-1-{3-fluoro-4-[(trifluoromethyl)sulfanyl]phenyl}-2-methylpropyl]-2-(4-methoxybenzyl)-6-oxo-1,6-dihydropyrimidine-4-carboxamide, 2-(4-methoxybenzyl)-N-{(1R)-2-methyl-1-[4-(pentafluoro-$\lambda^6$-sulfanyl)phenyl]propyl}-6-oxo-1,6-dihydropyrimidine-4-carboxamide, N-{(1R)-1-[3-fluoro-4-(trifluoromethyl)phenyl]-2-methylpropyl}-2-(4-methoxybenzyl)-6-oxo-1,6-dihydropyrimidine-4-carboxamide, N-{(1R)-1-[3-fluoro-4-(trifluoromethoxy)phenyl]-2-methylpropyl}-2-(4-methoxybenzyl)-6-oxo-1,6-dihydropyrimidine-4-carboxamide, 2-(4-methoxybenzyl)-N-{(1R)-2-methyl-1-[4-(trifluoromethyl)phenyl]propyl}-6-oxo-1,6-dihydropyrimidine-4-carboxamide, 2-(4-methoxybenzyl)-N-{(1R)-2-methyl-1-[4-(trifluoromethoxy)phenyl]propyl}-6-oxo-1,6-dihydropyrimidine-4-carboxamide, 2-(4-methoxybenzyl)-6-oxo-N-[(1R)-1-{4-[(trifluoromethyl)sulfanyl]phenyl}propyl]-1,6-dihydropyrimidine-4-carboxamide, N-[(1R)-1-{3-fluoro-4-[(trifluoromethyl)sulfanyl]phenyl}propyl]-2-(4-methoxybenzyl)-6-oxo-1,6-dihydropyrimidine-4-carboxamide, N-{(R)-cyclopropyl[3-fluoro-4-(trifluoromethoxy)phenyl]methyl}-2-(4-methoxybenzyl)-6-oxo-1,6-dihydropyrimidine-4-carboxamide, N-[(R)-cyclopropyl{4-[(trifluoromethyl)sulfanyl]phenyl}methyl]-2-(4-methoxybenzyl)-6-oxo-1,6-dihydropyrimidine-4-carboxamide, N-{(R)-cyclopropyl[4-(trifluoromethoxy)phenyl]methyl}-2-(4-methoxybenzyl)-6-oxo-1,6-dihydropyrimidine-4-carboxamide, N-{(R)-cyclopropyl[4-(trifluoromethyl)phenyl]methyl}-2-(4-methoxybenzyl)-6-oxo-1,6-dihydropyrimidine-4-carboxamide, 2-(4-methoxybenzyl)-6-oxo-N-{(1R)-1-[4-(pentafluoro-$\lambda^6$-sulfanyl)phenyl]propyl}-1,6-dihydropyrimidine-4-carboxamide, N-{(1R)-1-[3-fluoro-4-(trifluoromethyl)phenyl]propyl}-2-(4-methoxybenzyl)-6-oxo-1,6-dihydropyrimidine-4-carboxamide, N-{(1R)-1-[3-fluoro-4-(trifluoromethoxy)phenyl]propyl}-2-(4-methoxybenzyl)-6-oxo-1,6-dihydropyrimidine-4-carboxamide, 2-(4-methoxybenzyl)-6-oxo-N-{(1R)-1-[4-(trifluoromethoxy)phenyl]propyl}-1,6-dihydropyrimidine-4-carboxamide, N-{(1R)-1-[3-fluoro-4-(trifluoromethyl)phenyl]-2-methylpropyl}-2-[1-(4-methoxyphenyl)-1-methylethyl]-6-oxo-1,6-dihydropyrimidine-4-carboxamide, N-{(1R)-1-[3-fluoro-4-(trifluoromethoxy)phenyl]-2,2-dimethylpropyl}-2-[1-(4-methoxyphenyl)-1-methylethyl]-6-oxo-1,6-dihydropyrimidine-4-carboxamide, N-[(1R)-2,2-dimethyl-1-{4-[(trifluoromethyl)sulfanyl]phenyl}propyl]-2[1-(4-methoxyphenyl)-1-methylethyl]-6-oxo-1,6-dihydropyrimidine-4-carboxamide, N-{(1R)-1-[3-fluoro-4-(trifluoromethyl)phenyl]-2,2-dimethylpropyl}-2-[1-(4-methoxyphenyl)-1-methylethyl]-6-oxo-1,6-dihydropyrimidine-4-carboxamide, 2-[1-(4-methoxyphenyl)-1-methylethyl]-N-[(1R)-2-methyl-1-{4-[(trifluoromethyl)sulfanyl]phenyl}propyl]-6-oxo-1,6-dihydropyrimidine-4-carboxamide, N-[(1R)-1-{3-fluoro-4-[(trifluoromethyl)sulfanyl]phenyl}-2-methylpropyl]-2-[1-(4-methoxyphenyl)-1-methylethyl]-6-oxo-1,6-dihydropyrimidine-4-carboxamide, N-{(1R)-1-[3-fluoro-4-(trifluoromethoxy)phenyl]-2-methylpropyl}-2-[1-(4-methoxyphenyl)-1-methylethyl]-6-oxo-1,6-dihydropyrimidine-4-carboxamide, 2-[1-(4-methoxyphenyl)-1-methylethyl]-N-{(1R)-2-methyl-1-[4-(trifluoromethyl)phenyl]propyl}-6-oxo-1,6-dihydropyrimidine-4-carboxamide, 2-[1-(4-methoxyphenyl)-1-methylethyl]-N-{(1R)-2-methyl-1-[4-(trifluoromethoxy)phenyl]propyl}-6-oxo-1,6-dihydropyrimidine-4-carboxamide, 2-[1-(4-methoxyphenyl)-1-methylethyl]-6-oxo-N-[(1R)-1-{4-[(trifluoromethyl)sulfanyl]phenyl}propyl]-1,6-dihydropyrimidine-4-carboxamide, N-[(1R)-1-{3-fluoro-4-[(trifluoromethyl)sulfanyl]phenyl}propyl]-2-[1-(4-methoxyphenyl)-1-methylethyl]-6-oxo-1,6-dihydropyrimidine-4-carboxamide, N-[(R)-cyclopropyl{3-fluoro-4-[(trifluoromethyl)sulfanyl]phenyl}methyl]-2-[1-(4-methoxyphenyl)-1-methylethyl]-6-oxo-1,6-dihydropyrimidine-4-carboxamide, N-{(R)-cyclopropyl[3-fluoro-4-(trifluoromethoxy)phenyl]methyl}-2-[1-(4-methoxyphenyl)-1-methylethyl]-6-oxo-1,6-dihydropyrimidine-4-carboxamide, N-{(R)-cyclopropyl[3-fluoro-4-(trifluoromethyl)phenyl]methyl}-2-[1-(4-methoxyphenyl)-1-methylethyl]-6-oxo-1,6-dihydropyrimidine-4-carboxamide, N-[(R)-cyclopropyl{4-[(trifluoromethyl)sulfanyl]phenyl}methyl]-2-[1-(4-methoxyphenyl)-1-methylethyl]-6-oxo-1,6-dihydropyrimidine-4-carboxamide, N-{(R)-cyclopropyl[4-(trifluoromethoxy)phenyl]methyl}-2-[1-(4-methoxyphenyl)-1-methylethyl]-6-oxo-1,6-dihydropyrimidine-4-carboxamide, N-{(R)-cyclopropyl[4-(trifluoromethyl)phenyl]methyl}-2-[1-(4-methoxyphenyl)-1-methylethyl]-6-oxo-1,6-dihydropyrimidine-4-carboxamide, N-{(1R)-1-[3-fluoro-4-(trifluoromethyl)phenyl]propyl}-2-[1-(4-methoxyphenyl)-1-methylethyl]-6-oxo-1,6-dihydropyrimidine-4-carboxamide, N-{(1R)-1-[3-fluoro-4-(trifluoromethoxy)phenyl]propyl}-2-[1-(4-methoxyphenyl)-1-methylethyl]-6-oxo-1,6-dihydropyrimidine-4-carboxamide, 2-[1-(4-methoxyphenyl)-1-methylethyl]-6-oxo-N-{(1R)-1-[4-(trifluoromethoxy)phenyl]propyl}-1,6-dihydropyrimidine-4-carboxamide, 2-(3-fluoro-4-methoxybenzyl)-N-{(1R)-1-[3-fluoro-4-(trifluoromethoxy)phenyl]-2,2-dimethylpropyl}-6-oxo-1,6-dihydropyrimidine-4-carboxamide, N-[(1R)-2,2-dimethyl-1-{4-[(trifluoromethyl)sulfanyl]phenyl}propyl]-2-(3-fluoro-4-methoxybenzyl)-6-oxo-1,6-dihydropyrimidine-4-carboxamide, 2-(3-fluoro-4-methoxybenzyl)-N-{(1R)-1-[3-fluoro-4-(trifluoromethyl)phenyl]-2,2-dimethylpropyl}-6-oxo-1,6-dihydropyrimidine-4-carboxamide, N-{(1R)-2,2-dimethyl-1-[4-(trifluoromethoxy)phenyl]propyl}-2-(3-fluoro-4-methoxybenzyl)-6-oxo-1,6-dihydropyrimidine-4-carboxamide, N-{(R)-cyclopropyl[4-(pentafluoro-$\lambda^6$-sulfanyl)phenyl]methyl}-2-(3-fluoro-4-methoxybenzyl)-6-oxo-1,6-dihydropyrimidine-4-carboxamide, 2-(3-fluoro-4-methoxybenzyl)-N-[(1R)-2-methyl-1-{4-[(trifluoromethyl)sulfanyl]phenyl}propyl]-6-oxo-1,6-dihydropyrimidine-4-carboxamide, 2-(3-fluoro-4-methoxybenzyl)-N-[(1R)-1-{3-fluoro-4-[(trifluoromethyl)sulfanyl]phenyl}-2-methylpropyl]-6-oxo-1,6-dihydropyrimidine-4-carboxamide, 2-(3-fluoro-4-methoxybenzyl)-N-{(1R)-2-methyl-1-[4-(pentafluoro-$\lambda^6$-sulfanyl)phenyl]propyl}-6-oxo-1,6-dihydropyrimidine-4-carboxamide, 2-(3-fluoro-4-methoxybenzyl)-N-{(1R)-1-[3-fluoro-4-(trifluoromethyl)phenyl]-2-methylpropyl}-6-oxo-1,6-dihydropyrimidine-4-carboxamide, 2-(3-fluoro-4-methoxybenzyl)-N-{(1R)-1-[3-fluoro-4-(trifluoromethoxy)phenyl]-2-methylpropyl}-6-oxo-1,6-dihydropyrimidine-4-carboxamide, 2-(3-fluoro-4-methoxybenzyl)-N-{(1R)-2-methyl-1-[4-(trifluoromethyl)phenyl]propyl}-6-oxo-1,6-dihydropyrimidine-4-carboxamide, 2-(3-fluoro-4-methoxybenzyl)-N-{(1R)-2-methyl-1-[4-(trifluoromethoxy)phenyl]propyl}-6-oxo-1,6-dihydropyrimidine-4-carboxamide, 2-(3-fluoro-4-methoxybenzyl)-6-oxo-N-[(1R)-1-{4-[(trifluoromethyl)sulfanyl]phenyl}propyl]-1,6-dihydropyrimidine-4-carboxamide, 2-(3-fluoro-4-methoxybenzyl)-N-[(1R)-1-{3-fluoro-4-[(trifluoromethyl)sulfanyl]phenyl}propyl]-6-oxo-1,6-dihydropyrimidine-4-carboxamide, N-[(R)-cyclopropyl{3-fluoro-4-[(trifluoromethyl)sulfanyl]phenyl}methyl]-2-(3-fluoro-4-methoxybenzyl)-6-oxo-1,6-dihydropyrimidine-4-carboxamide, N-{(R)-cyclopropyl[3-fluoro-4-(trifluoromethoxy)phenyl]methyl}-2-(3-fluoro-4-methoxybenzyl)-6-oxo-1,6-dihydropyrimidine-4-carboxamide, N-{(R)-cyclopropyl[3-fluoro-4-(trifluoromethyl)phenyl]methyl}-2-(3-fluoro-4-methoxybenzyl)-6-oxo-1,6-dihydropyrimidine-4-carboxamide, N-[(R)-cyclopropyl{4-[(trifluoromethyl)sulfanyl]phenyl}methyl]-2-(3-fluoro-4-methoxybenzyl)-6-oxo-1,6-dihydropyrimidine-4-carboxamide, N-{(R)-cyclopropyl[4-(trifluoromethoxy)phenyl]methyl}-2-(3-fluoro-4-methoxybenzyl)-6-oxo-1,6-dihydropyrimidine-4-carboxamide, N-{(R)-cyclopropyl[4-(trifluoromethyl)phenyl]methyl}-2-(3-fluoro-4-methoxybenzyl)-6-oxo-1,6-dihydropyrimidine-4-carboxamide, 2-(3-fluoro-4-methoxybenzyl)-6-oxo-N-{(1R)-1-[4-(pentafluoro-$\lambda^6$-sulfanyl)phenyl]propyl}-1,6-dihydropyrimidine-4-carboxamide, 2-(3-fluoro-4-methoxybenzyl)-N-{(1R)-1-[3-fluoro-4-(trifluoromethyl)phenyl]propyl}-6-oxo-1,6-dihydropyrimidine-4-carboxamide, 2-(3-fluoro-4-methoxybenzyl)-N-{(1R)-1-[3-fluoro-4-(trifluoromethoxy)phenyl]propyl}-6-oxo-1,6-dihydropyrimidine-4-carboxamide, 2-(3-fluoro-4-methoxybenzyl)-6-oxo-N-{(1R)-1-[4-(trifluoromethoxy)phenyl]propyl}-1,6-dihydropyrimidine-4-carboxamide, 2-methyl-N-{(1R)-1-[4-(1-methylcyclopropyl)phenyl]ethyl}-6-oxo-1,6-dihydropyrimidine-4-carboxamide, N-{1R)-2,2-dimethyl-1-[3-nitro-4-(trifluoromethyl)phenyl]propyl}-2-methyl-6-oxo-1,6-dihydropyrimidine-4-carboxamide, 2-methyl-N-{(1R)-2-methyl-1-[4-(1-methylcyclopropyl)phenyl]propyl}-6-oxo-1,6-dihydropyrimidine-4-carboxamide, N-{(1R)-2-methyl-1-[4-(1-methylcyclopropyl)phenyl]propyl}-6-oxo-2-phenyl-1,6-dihydropyrimidine-4-carboxamide, N-[1-(2,2-difluoro-1,3-benzodioxoll-5-yl)cyclopropyl]-2-methyl-6-oxo-1,6-dihydropyrimidine-4-carboxamide, N-[1-(2,2-difluoro-1,3-benzodioxol-5-yl)cyclopropyl]-6-oxo-2-phenyl-1,6-dihydropyrimidine-4-carboxamide, N-[(1R)-1-(4-cyclopropylphenyl)-2,2-dimethylpropyl]-6-oxo-2-phenyl-1,6-dihydropyrimidine-4-carboxamide, N-{1R)-2,2-dimethyl-1-[4-(2,2,2-trifluoroethyl)phenyl]propyl}-6-oxo-2-phenyl-1,6-dihydropyrimidine-4-carboxamide, N-{(1R)-1-[3-fluoro-4-(trifluoromethyl)phenyl]-2,2-dimethylpropyl}-6-oxo-2-phenyl-1,6-dihydropyrimidine-4-carboxamide, N-[(1R)-1-(4-cyclopropyl-3-fluorophenyl)-2,2-dimethylpropyl]-6-oxo-2-phenyl-1,6-dihydropyrimidine-4-carboxamide, N-{(1R)-2,2-dimethyl-1-[4-(pentafluoro-$\lambda^6$-sulfanyl)phenyl]propyl}-6-oxo-2-phenyl-1,6-dihydropyrimidine-4-carboxamide, N-[(1R)-2,2-dimethyl-1-{4-[(trifluoromethyl)sulfanyl]phenyl}propyl]-6-oxo-2-phenyl-1,6-dihydropyrimidine-4-carboxamide, N-{(1R)-1-[3-fluoro-4-(trifluoromethoxy)phenyl]-2,2-dimethylpropyl}-6-oxo-2-phenyl-1,6-dihydropyrimidine-4-carboxamide, N-{(1R)-1-[4-(difluoromethoxy)phenyl]-2-methylpropyl}-6-oxo-2-phenyl-1,6-dihydropyrimidine-4-carboxamide, N-[(R)-cyclopropyl(4-cyclopropylphenyl)methyl]-6-oxo-2-phenyl-1,6-dihydropyrimidine-4-carboxamide, N-{(1R)-1-[2-fluoro-4-(trifluoromethyl)phenyl]-2,2-dimethylpropyl}-6-oxo-2-phenyl-1,6-dihydropyrimidine-4-carboxamide, N-[(R)-cyclopropyl(4-cyclopropyl-3-fluorophenyl)methyl]-6-oxo-2-phenyl-1,6-dihydropyrimidine-4-carboxamide, N-{(R)-(1-methylcyclopropyl)[4-(1-methylethyl)phenyl]methyl}-6-oxo-2-phenyl-1,6-dihydropyrimidine-4-carboxamide, N-[(R)-[4-(difluoromethoxy)phenyl](1-methylcyclopropyl)methyl]-6-oxo-2-phenyl-1,6-dihydropyrimidine-4-carboxamide, N-{(R)-(1-methylcyclopropyl)[4-(pentafluoro-$\lambda^6$-sulfanyl)phenyl]methyl}-6-oxo-2-phenyl-1,6-dihydropyrimidine-4-carboxamide, N-{(1R)-1-[2,5-difluoro-4-(trifluoromethyl)phenyl]ethyl}-6-oxo-2-phenyl-1,6-dihydropyrimidine-4-carboxamide, 6-oxo-2-phenyl-N-[(4S)-7-(trifluoromethyl)-3,4-dihydro-1H-isochromen-4-yl]-1,6-dihydropyrimidine-4-carboxamide, 6-oxo-2-phenyl-N-[(1R)-6-(trifluoromethyl)-1,2,3,4-tetrahydronaphthalen-1-yl]-1,6-dihydropyrimidine-4-carboxamide, 6-oxo-N-{1-[4-(pentafluoro-$\lambda^6$-sulfanyl)phenyl]cyclopropyl}-2-phenyl-1,6-dihydropyrimidine-4-carboxamide, N-{(1R)-1-[3-fluoro-4-(trifluoromethoxy)phenyl]-2,2-dimethylpropyl}-6-oxo-1,6-dihydro-2,2'-bipyrimidine-4-carboxamide, N-[(1R)-2,2-dimethyl-1-{4-[(trifluoromethyl)sulfanyl]phenyl}propyl]-6-oxo-1,6-dihydro-2,2'-bipyrimidine-4-carboxamide, N-{(1R)-1-[3-fluoro-4-(trifluoromethyl)phenyl]-2,2-dimethylpropyl}-6-oxo-1,6-dihydro-2,2'-bipyrimidine-4-carboxamide,
N-[(1R)-1-(4-cyclopropylphenyl)-2,2-dimethylpropyl]-6-oxo-1,6-dihydro-2,2'-bipyrimidine-4-carboxamide,
N-{(1R)-2,2-dimethyl-1-[4-(2,2,2-trifluoroethyl)phenyl]propyl}-6-oxo-1,6-dihydro-2,2'-bipyrimidine-4-carboxamide,
N-{(R)-cyclopropyl[4-(difluoromethoxy)phenyl]methyl}-6-oxo-1,6-dihydro-2,2'-bipyrimidine-4-carboxamide,
N-[(1R)-1-(4-cyclopropyl-3-fluorophenyl)-2-methylpropyl]-6-oxo-1,6-dihydro-2,2'-bipyrimidine-4-carboxamide,
N-{1,2-dimethyl-1-[4-(pentafluoro-$\lambda^6$-sulfanyl)phenyl]propyl}-6-oxo-1,6-dihydro-2,2'-bipyrimidine-4-carboxamide,
N-{(R)-(1-methylcyclopropyl)[4-(1-methylethyl)phenyl]methyl}-6-oxo-1,6-dihydro-2,2'-bipyrimidine-4-carboxamide,
N-[(R)-(4-tert-butylphenyl)(1-methylcyclopropyl)methyl]-6-oxo-1,6-dihydro-2,2'-bipyrimidine-4-carboxamide,
N-{(R)-(1-methylcyclopropyl)[4-(pentafluoro-$\lambda^6$-sulfanyl)phenyl]methyl}-6-oxo-1,6-dihydro-2,2'-bipyrimidine-4-carboxamide,
N-{(1R)-1-[2-fluoro-4-(trifluoromethyl)phenyl]-2,2-dimethylpropyl}-6-oxo-1,6-dihydro-2,2'-bipyrimidine-4-carboxamide,
N-{(1R)-2,2-dimethyl-1-[4-(pentafluoro-$\lambda^6$-sulfanyl)phenyl]propyl}-6-oxo-1,6-dihydro-2,2'-bipyrimidine-4-carboxamide,
N-{(1R)-2,2-dimethyl-1-[3-nitro-4-(trifluoromethyl)phenyl]propyl}-6-oxo-1,6-dihydro-2,2'-bipyrimidine-4-carboxamide,
N-{1-[2-chloro-4-(trifluoromethyl)phenyl]-1-methylethyl}-6-oxo-1,6-dihydro-2,2'-bipyrimidine-4-carboxamide,
N-{1-methyl-1-[2-methyl-4-(trifluoromethyl)phenyl]ethyl}-6-oxo-1,6-dihydro-2,2'-bipyrimidine-4-carboxamide,
6-oxo-N-{1-[4-(pentafluoro-$\lambda^6$-sulfanyl)phenyl]cyclopropyl}-1,6-dihydro-2,2'-bipyrimidine-4-carboxamide,
N-[1-(2,2-difluoro-1,3-benzodioxol-5-yl)cyclopropyl]-6-oxo-1,6-dihydro-2,2'-bipyrimidine-4-carboxamide,
N-{1-[2-methoxy-4-(trifluoromethyl)phenyl]-1-methylethyl}-6-oxo-1,6-dihydro-2,2'-bipyrimidine-4-carboxamide,
N-{1-[2-fluoro-4-(trifluoromethyl)phenyl]-1-methylethyl}-6-oxo-1,6-dihydro-2,2'-bipyrimidine-4-carboxamide,
N-{1-[2-fluoro-4-(trifluoromethoxy)phenyl]-1-methylethyl}-6-oxo-1,6-dihydro-2,2'-bipyrimidine-4-carboxamide,
N-[1-(4-tert-butylphenyl)cyclopropyl]-6-oxo-1,6-dihydro-2,2'-bipyrimidine-4-carboxamide,
N-{1-[4-(1-methylethyl)phenyl]cyclopropyl}-6-oxo-1,6-dihydro-2,2'-bipyrimidine-4-carboxamide,
N-(1-methyl-1-{4-[(trifluoromethyl)sulfanyl]phenyl}ethyl)-6-oxo-1,6-dihydro-2,2'-bipyrimidine-4-carboxamide,
6-oxo-N-{1-[4-(2,2,2-trifluoroethyl)phenyl]cyclopropyl}-1,6-dihydro-2,2'-bipyrimidine-4-carboxamide,
N-{1-[2-fluoro-4-(trifluoromethyl)phenyl]cyclopropyl}-6-oxo-1,6-dihydro-2,2'-bipyrimidine-4-carboxamide,
N-{(1R)-1-[3-bromo-4-(trifluoromethoxy)phenyl]-2-methylpropyl}-6-oxo-1,6-dihydro-2,2'-bipyrimidine-4-carboxamide,
N-[(R)-cyclopropyl(4-cyclopropyl-3-fluorophenyl)methyl]-6-oxo-1,6-dihydro-2,2'-bipyrimidine-4-carboxamide,
N-{(R)-(1-methylcyclopropyl)[4-(trifluoromethyl)phenyl]methyl}-6-oxo-1,6-dihydro-2,2'-bipyrimidine-4-carboxamide,
N-[(R)-[3-fluoro-4-(trifluoromethyl)phenyl](1-methylcyclopropyl)methyl]-6-oxo-1,6-dihydro-2,2'-bipyrimidine-4-carboxamide,
N-[(R)-[4-(difluoromethoxy)phenyl](1-methylcyclopropyl)methyl]-6-oxo-1,6-dihydro-2,2'-bipyrimidine-4-carboxamide,
N-[(R)-(2,2-difluoro-1,3-benzodioxol-5-yl)(1-methylcyclopropyl)methyl]-6-oxo-1,6-dihydro-2,2'-bipyrimidine-4-carboxamide,
N-[(1R)-1-(2,2-difluoro-1,3-benzodioxol-5-yl)-2,2-dimethylpropyl]-6-oxo-1,6-dihydro-2,2'-bipyrimidine-4-carboxamide,
N-[(1R)-1-(2,2-difluoro-1,3-benzodioxol-5-yl)ethyl]-6-oxo-1,6-dihydro-2,2'-bipyrimidine-4-carboxamide,
N-[1-(2,2-difluoro-1,3-benzodioxol-5-yl)-1-methylethyl]-6-oxo-1,6-dihydro-2,2'-bipyrimidine-4-carboxamide,
N-{(1R)-1-[4-(difluoromethoxy)-3-fluorophenyl]-2,2-dimethylpropyl}-6-oxo-1,6-dihydro-2,2'-bipyrimidine-4-carboxamide,
N-[(1R)-1-(2,2-difluoro-1,3-benzodioxol-5-yl)propyl]-6-oxo-1,6-dihydro-2,2'-bipyrimidine-4-carboxamide,
N-[(R)-cyclopropyl(2,2-difluoro-1,3-benzodioxol-5-yl)methyl]-6-oxo-1,6-dihydro-2,2'-bipyrimidine-4-carboxamide,
N-[(1R)-1-(2,2-difluoro-1,3-benzodioxol-5-yl)-2-methylpropyl]-6-oxo-1,6-dihydro-2,2'-bipyrimidine-4-carboxamide,
N-{1-[2-chloro-4-(trifluoromethyl)phenyl]-1-methylethyl}-2-methyl-6-oxo-1,6-dihydropyrimidine-4-carboxamide,
N-{1-[2-methoxy-4-(trifluoromethyl)phenyl]-1-methylethyl}-2-methyl-6-oxo-1,6-dihydropyrimidine-4-carboxamide,
2-methyl-N-{1-methyl-1-[2-methyl-4-(trifluoromethyl)phenyl]ethyl}-6-oxo-1,6-dihydropyrimidine-4-carboxamide,
N-{1-[2-fluoro-4-(trifluoromethyl)phenyl]-1-methylethyl}-2-methyl-6-oxo-1,6-dihydropyrimidine-4-carboxamide,
N-{1-[2-fluoro-4-(trifluoromethoxy)phenyl]-1-methylethyl}-2-methyl-6-oxo-1,6-dihydropyrimidine-4-carboxamide,
2-ethyl-N-{(1R)-1-[3-fluoro-4-(trifluoromethoxy)phenyl]ethyl}-6-oxo-1,6-dihydropyrimidine-4-carboxamide,
2-ethyl-6-oxo-N-{(1R)-1-[4-(pentafluoro-$\lambda^6$-sulfanyl)phenyl]ethyl}-1,6-dihydropyrimidine-4-carboxamide,
2-ethyl-N-{1-methyl-1-[4-(trifluoromethyl)phenyl]ethyl}-6-oxo-1,6-dihydropyrimidine-4-carboxamide,
2-ethyl-N-{1-[3-fluoro-4-(trifluoromethyl)phenyl]cyclopropyl}-6-oxo-1,6-dihydropyrimidine-4-carboxamide,
2-ethyl-N-{1-[3-fluoro-4-(trifluoromethoxy)phenyl]cyclopropyl}-6-oxo-1,6-dihydropyrimidine-4-carboxamide,
N-{(R)-cyclopropyl[3-fluoro-4-(trifluoromethyl)phenyl]methyl}-2-ethyl-6-oxo-1,6-dihydropyrimidine-4-carboxamide, N-[1-(2,2-difluoro-1,3-benzodioxol1-5-yl)-1-methylethyl]-2-methyl-6-oxo-1,6-dihydropyrimidine-4-carboxamide,
N-{2-hydroxy-1-(hydroxymethyl)-1-[4-(trifluoromethyl)phenyl]ethyl}-2-methyl-6-oxo-1,6-dihydropyrimidine-4-carboxamide,
N-[(1R)-1-(2,2-difluoro-1,3-benzodioxol-5-yl)ethyl]-2-methyl-6-oxo-1,6-dihydropyrimidine-4-carboxamide,
N-[(1R)-1-(2,2-difluoro-1,3-benzodioxol-5-yl)-2-methylpropyl]-2-methyl-6-oxo-1,6-dihydropyrimidine-4-carboxamide,
N-{1-[2-chloro-4-(trifluoromethyl)phenyl]-1-methylethyl}-2-ethyl-6-oxo-1,6-dihydropyrimidine-4-carboxamide,
N-[(R)-cyclopropyl(2,2-difluoro-1,3-benzodioxol-5-yl)methyl]-2-methyl-6-oxo-1,6-dihydropyrimidine-4-carboxamide,
N-{(R)-cyclopropyl[4-(difluoromethoxy)phenyl]methyl}-2-methyl-6-oxo-1,6-dihydropyrimidine-4-carboxamide,
N-{(1R)-1-[4-(difluoromethoxy)phenyl]-2-methylpropyl}-2-methyl-6-oxo-1,6-dihydropyrimidine-4-carboxamide,
2-methyl-N-{(R)-(1-methylcyclopropyl)[4-(trifluoromethyl)phenyl]methyl}-6-oxo-1,6-dihydropyrimidine-4-carboxamide,
N-[(R)[3-fluoro-4-(trifluoromethyl)phenyl](1-methylcyclopropyl)methyl]-2-methyl-6-oxo-1,6-dihydropyrimidine-4-carboxamide,
N-[(R)-(4-tert-butylphenyl)(1-methylcyclopropyl)methyl]-2-methyl-6-oxo-1,6-dihydropyrimidine-4-carboxamide,
2-methyl-N-[(1S)-2-methyl-1-{4-[(trifluoromethyl)sulfanyl]phenyl}propyl]-6-oxo-1,6-dihydropyrimidine-4-carboxamide,
N-{(1R)-1[2,5-difluoro-4-(trifluoromethyl)phenyl]ethyl}-2-methyl-6-oxo-1,6-dihydropyrimidine-4-carboxamide,
N-{(1R)-1-[2-fluoro-4-(trifluoromethyl)phenyl]-2,2-dimethylpropyl}-2-methyl-6-oxo-1,6-dihydropyrimidine-4-carboxamide,
N-{(1R)-2,2-dimethyl-1-[4-(pentafluoro-$\lambda^6$-sulfanyl)phenyl]propyl}-2-methyl-6-oxo-1,6-dihydropyrimidine-4-carboxamide,
N-{1,2-dimethyl-1-[4-(pentafluoro-$\lambda^6$-sulfanyl)phenyl]propyl}-2-methyl-6-oxo-1,6-dihydropyrimidine-4-carboxamide (racemic),
N-[(1R)-1-(4-cyclopropyl-3-fluorophenyl)ethyl]-2-methyl-6-oxo-1,6-dihydropyrimidine-4-carboxamide,
N-[(1R)-1-(4-cyclopropyl-3-fluorophenyl)-2-methylpropyl]-2-methyl-6-oxo-1,6-dihydropyrimidine-4-carboxamide,
2-methyl-6-oxo-N-{1-[4-(pentafluoro-$\lambda^6$-sulfanyl)phenyl]cyclopropyl}-1,6-dihydropyrimidine-4-carboxamide,
N-[1-(4-tert-butylphenyl)cyclopropyl]-2-methyl-6-oxo-1,6-dihydropyrimidine-4-carboxamide,
N-{(1R)-1-[4-(difluoromethoxy)-3-fluorophenyl]-2-methylpropyl}-2-methyl-6-oxo-1,6-dihydropyrimidine-4-carboxamide,
N-{1-[2-fluoro-4-(trifluoromethyl)phenyl]cyclopropyl}-2-methyl-6-oxo-1,6-dihydropyrimidine-4-carboxamide,
N-[1-(4-tert-butoxyphenyl)cyclopropyl]-2-methyl-6-oxo-1,6-dihydropyrimidine-4-carboxamide,
2-methyl-6-oxo-N-{1-[4-(2,2,2-trifluoroethyl)phenyl]cyclopropyl}-1,6-dihydropyrimidine-4-carboxamide,
N-{1-[4-(difluoromethoxy)phenyl]cyclopropyl}-2-methyl-6-oxo-1,6-dihydropyrimidine-4-carboxamide,
N-{(R)-cyclopropyl[4-(difluoromethoxy)-3-fluorophenyl]methyl}-2-methyl-6-oxo-1,6-dihydropyrimidine-4-carboxamide,
N-{(1R)-1-[4-(difluoromethoxy)-3-fluorophenyl]-2,2-dimethylpropyl}-2-methyl-6-oxo-1,6-dihydropyrimidine-4-carboxamide,
N-[(R)-[4-(difluoromethoxy)-3-fluorophenyl](1-methylcyclopropyl)methyl]-2-methyl-6-oxo-1,6-dihydropyrimidine-4-carboxamide,
N-[(1R)-1-(2,2-difluoro-1,3-benzodioxol-5-yl)propyl]-2-methyl-6-oxo-1,6-dihydropyrimidine-4-carboxamide,
N-[(1R)-1-(2,2-difluoro-1,3-benzodioxol-5-yl)-2,2-dimethylpropyl]-2-methyl-6-oxo-1,6-dihydropyrimidine-4-carboxamide,
N-[(R)-(2,2-difluoro-1,3-benzodioxol-5-yl)(1-methylcyclopropyl)methyl]-2-methyl-6-oxo-1,6-dihydropyrimidine-4-carboxamide,
N-{(1R)-2-hydroxy-1-methyl-1-[4-(trifluoromethyl)phenyl]ethyl}-2-methyl-6-oxo-1,6-dihydropyrimidine-4-carboxamide,
N-{(1S)-2-hydroxy-1-methyl-1-[4-(trifluoromethyl)phenyl]ethyl}-2-methyl-6-oxo-1,6-dihydropyrimidine-4-carboxamide,
N-{1-[2-chloro-4-(trifluoromethyl)phenyl]cyclopropyl}-2-methyl-6-oxo-1,6-dihydropyrimidine-4-carboxamide,
2-ethyl-N-{(1S)-2-hydroxy-1-methyl-1-[4-(trifluoromethyl)phenyl]ethyl}-6-oxo-1,6-dihydropyrimidine-4-carboxamide,
N-{(1S)-1-[2-chloro-4-(trifluoromethyl)phenyl]-2-hydroxy-1-methylethyl}-2-ethyl-6-oxo-1,6-dihydropyrimidine-4-carboxamide,
N-{(1S)-1-[2-chloro-4-(trifluoromethyl)phenyl]-2-hydroxy-1-methylethyl}-2-methyl-6-oxo-1,6-dihydropyrimidine-4-carboxamide,
N-{1-[3-chloro-4-(trifluoromethyl)phenyl]-1-methylethyl}-2-methyl-6-oxo-1,6-dihydropyrimidine-4-carboxamide,
N-{(1S)-2-hydroxy-1-methyl-1-[4-(trifluoromethyl)phenyl]ethyl}-6-oxo-2-phenyl-1,6-dihydropyrimidine-4-carboxamide,
N-{(1S)-1-[2-chloro-4-(trifluoromethyl)phenyl]-2-hydroxy-1-methylethyl}-6-oxo-2-phenyl-1,6-dihydropyrimidine-4-carboxamide,
N-{(1R)-1-[4-(difluoromethyl)phenyl]-2,2-dimethylpropyl}-2-methyl-6-oxo-1,6-dihydropyrimidine-4-carboxamide,
N-[(R)-[4-(difluoromethyl)phenyl](1-methylcyclopropyl)methyl]-2-methyl-6-oxo-1,6-dihydropyrimidine-4-carboxamide,
N-{(1R)-1-[4-(difluoromethyl)-3-fluorophenyl]-2,2-dimethylpropyl}-2-methyl-6-oxo-1,6-dihydropyrimidine-4-carboxamide,
N-[(R)-[4-(difluoromethyl)-3-fluorophenyl](1-methylcyclopropyl)methyl]-2-methyl-6-oxo-1,6-dihydropyrimidine-4-carboxamide,
N-{(1R)-1-[4-(difluoromethyl)phenyl]-2-methylpropyl}-2-methyl-6-oxo-1,6-dihydropyrimidine-4-carboxamide,
N-{(R)-cyclopropyl[4-(difluoromethyl)phenyl]methyl}-2-methyl-6-oxo-1,6-dihydropyrimidine-4-carboxamide,
N-{(1R)-1-[4-(difluoromethyl)-3-fluorophenyl]-2-methylpropyl}-2-methyl-6-oxo-1,6-dihydropyrimidine-4-carboxamide, N-{(R)-cyclopropyl[4-(difluoromethyl)-3-fluorophenyl]methyl}-2-methyl-6-oxo-1,6-dihydropyrimidine-4-carboxamide,
N-{(1R)-1-[4-(difluoromethyl)phenyl]propyl}-2-methyl-6-oxo-1,6-dihydropyrimidine-4-carboxamide,
N-{(1R)-1-[4-(difluoromethyl)-3-fluorophenyl]propyl}-2-methyl-6-oxo-1,6-dihydropyrimidine-4-carboxamide,
N-{1-[4-(difluoromethyl)-3-fluorophenyl]-1-methylethyl}-2-methyl-6-oxo-1,6-dihydropyrimidine-4-carboxamide,
N-{1-[4-(difluoromethyl)-3-fluorophenyl]cyclopropyl}-2-methyl-6-oxo-1,6-dihydropyrimidine-4-carboxamide,
N-{(1R)-1-[4-(difluoromethyl)phenyl]ethyl}-2-methyl-6-oxo-1,6-dihydropyrimidine-4-carboxamide,
N-{(1R)-1-[4-(difluoromethyl)-3-fluorophenyl]ethyl}-2-methyl-6-oxo-1,6-dihydropyrimidine-4-carboxamide,
N-[(R)-(4-cyclopropylphenyl)(1-methylcyclopropyl)methyl]-2-methyl-6-oxo-1,6-dihydropyrimidine-4-carboxamide,
N-{1-[2-chloro-5-fluoro-4-(trifluoromethyl)phenyl]-1-methylethyl}-2-methyl-6-oxo-1,6-dihydropyrimidine-4-carboxamide,
N-{1-[4-(difluoromethyl)phenyl]cyclopropyl}-2-methyl-6-oxo-1,6-dihydropyrimidine-4-carboxamide,
N-{(1R)-1-[4-(difluoromethyl)-2-fluorophenyl]-2,2-dimethylpropyl}-2-methyl-6-oxo-1,6-dihydropyrimidine-4-carboxamide,
(S)- and (R)-N-{1,2-dimethyl-1-[4-(pentafluoro-$\lambda^6$-sulfanyl)phenyl]propyl}-2-methyl-6-oxo-1,6-dihydropyrimidine-4-carboxamide,
2-methyl-N-{2-methyl-1-[4-(1-methylethyl)phenyl]cyclopropyl}-6-oxo-1,6-dihydropyrimidine-4-carboxamide (trans, enantiomer A),
2-methyl-N-{2-methyl-1-[4-(1-methylethyl)phenyl]cyclopropyl}-6-oxo-1,6-dihydropyrimidine-4-carboxamide (trans, enantiomer B),
N-[1-(4-tert-butylphenyl)-2-methylcyclopropyl]-2-methyl-6-oxo-1,6-dihydropyrimidine-4-carboxamide (trans, enantiomer A),
N-[1-(4-tert-butylphenyl)-2-methylcyclopropyl]-2-methyl-6-oxo-1,6-dihydropyrimidine-4-carboxamide (trans, enantiomer B),
(R)- and (S)-2-methyl-N-{1-methyl-1-[4-(trifluoromethyl)phenyl]propyl}-6-oxo-1,6-dihydropyrimidine-4-carboxamide,
2-methyl-N-{2-methyl-1-[4-(trifluoromethyl)phenyl]cyclopropyl}-6-oxo-1,6-dihydropyrimidine-4-carboxamide (cis, enantiomer A),
2-methyl-N-{2-methyl-1-[4-(trifluoromethyl)phenyl]cyclopropyl}-6-oxo-1,6-dihydropyrimidine-4-carboxamide (cis, enantiomer B),
(R)-N-(1-(2-fluoro-4-(pentafluorothio)phenyl)ethyl)-2-methyl-6-oxo-1,6-dihydropyrimidine-4-carboxamide,
(S)-N-(1-(2-fluoro-4-(pentafluorothio)phenyl)ethyl)-2-methyl-6-oxo-1,6-dihydropyrimidine-4-carboxamide,
(R)-6-oxo-2-(thiazol-2-yl)-N-(1-(4-(trifluoromethyl)phenyl)ethyl)-1,6-dihydropyrimidine-4-carboxamide,
(R)-2-(oxazol-2-yl)-6-oxo-N-(1-(4-(trifluoromethyl)phenyl)ethyl)-1,6-dihydropyrimidine-4-carboxamide,
(R)-2-(5-methyloxazol-2-yl)-6-oxo-N-(1-(4-(trifluoromethyl)phenyl)ethyl)-1,6-dihydropyrimidine-4-carboxamide,
2-methyl-N-{1-methyl-1-[4-(pentafluoro-$\lambda^6$-sulfanyl)phenyl]ethyl}-6-oxo-1,6-dihydropyrimidine-4-carboxamide,
N-{1-methyl-1-[4-(pentafluoro-$\lambda^6$-sulfanyl)phenyl]ethyl}-6-oxo-1,6-dihydro-2,2'-bipyrimidine-4-carboxamide,
N-{1-methyl-1-[4-(pentafluoro-$\lambda^6$-sulfanyl)phenyl]ethyl}-6-oxo-2-phenyl-1,6-dihydropyrimidine-4-carboxamide,
2-cyclopropyl-N-{1-methyl-1-[4-(pentafluoro-$\lambda^6$-sulfanyl)phenyl]ethyl}-6-oxo-1,6-dihydropyrimidine-4-carboxamide,
N-(2,2-dimethyl-1-(4-(trifluoromethyl)phenyl)cyclopropyl)-2-methyl-6-oxo-1,6-dihydropyrimidine-4-carboxamide,
(R)- and (S)-N-(2,2-dimethyl-1-(4-(trifluoromethyl)phenyl)propyl)-2-(oxazol-2-yl)-6-oxo-1,6-dihydropyrimidine-4-carboxamide,
(R)- and (S)-methyl-6-oxo-N-(1-(4-(perfluoroethyl)phenyl)ethyl)-1,6-dihydropyrimidine-4-carboxamide,
(R)- and (S)-2-methyl-6-oxo-N-(1-(4-(1-(trifluoromethyl)cyclopropyl)phenyl)-ethyl)-1,6-dihydropyrimidine-4-carboxamide,
(S)- or-(R)-2-cyclopropyl-6-oxo-N-(1-(4-(1-(trifluoromethyl)cyclopropyl)phenyl)-ethyl)-1,6-dihydropyrimidine-4-carboxamide,
(R)- or-(S)-2-cyclopropyl-6-oxo-N-(1-(4-(1-(trifluoromethyl)cyclopropyl)phenyl)-ethyl)-1,6-dihydropyrimidine-4-carboxamide,
(S)- or-(R)-6-oxo-2-phenyl-N-(1-(4-(1-(trifluoromethyl)cyclopropyl)phenyl)-ethyl)-1,6-dihydropyrimidine-4-carboxamide,
(R)- or-(S)-6-oxo-2-phenyl-N-(1-(4-(1-(trifluoromethyl)cyclopropyl)phenyl)-ethyl)-1,6-dihydropyrimidine-4-carboxamide,
(S)- or-(R)-6-oxo-2-(pyrimidin-2-yl)-N-(1-(4-(1-(trifluoromethyl)cyclopropyl)phenyl)-ethyl)-1,6-dihydropyrimidine-4-carboxamide,
(R)- or-(S)-6-oxo-2-(pyrimidin-2-yl)-N-(1-(4-(1-(trifluoromethyl)cyclopropyl)phenyl)-ethyl)-1,6-dihydropyrimidine-4-carboxamide,
(R)- and (S)-2-methyl-6-oxo-N-(1-(4-(1,1,1-trifluoro-2-methylpropan-2-yl)phenyl)ethyl)-1,6-dihydropyrimidine-4-carboxamide,
(R)- and (S)-2-methyl-6-oxo-N-(1-(4-(1,1,1-trifluoro-2-methylpropan-2-yl)phenyl)ethyl)-1,6-dihydropyrimidine-4-carboxamide,
(R)- and (S)-6-oxo-2-phenyl-N-(1-(4-(1,1,1-trifluoro-2-methylpropan-2-yl)phenyl)ethyl)-1,6-dihydropyrimidine-4-carboxamide,
(R)- and (S)-6-oxo-N-(1-(4-(1,1,1-trifluoro-2-methylpropan-2-yl)phenyl)ethyl)-1,6-dihydro-[2,2'-bipyrimidine]-4-carboxamide,
(R)- and (S)-N-((3-fluoro-4-((trifluoromethyl)thio)phenyl)(1-methylcyclopropyl)methyl)-2-methyl-6-oxo-1,6-dihydropyrimidine-4-carboxamide,
(R)- and (S)-2-cyclopropyl-N-((3-fluoro-4-((trifluoromethyl)thio)phenyl)(1-methylcyclopropyl)methyl)-6-oxo-1,6-dihydropyrimidine-4-carboxamide,
(R)- and (S)-N-((3-fluoro-4-((trifluoromethyl)thio)phenyl)(1-methylcyclopropyl)methyl)-6-oxo-2-phenyl-1,6-dihydropyrimidine-4-carboxamide,
(R)- and (S)-N-((3-fluoro-4-((trifluoromethyl)thio)phenyl)(1-methylcyclopropyl)methyl)-6-oxo-1,6-dihydro-[2,2'-bipyrimidine]-4-carboxamide,
(R)- and (S)-N-(1-(3-fluoro-4-(1-methylcyclopropyl)phenyl)-2,2-dimethylpropyl)-2-methyl-6-oxo-1,6-dihydropyrimidine-4-carboxamide, (R)- and (S)-2-cyclopropyl-N-(1-(3-fluoro-4-(1-methylcyclopropyl)phenyl)-2,2-dimethylpropyl)-6-oxo-1,6-dihydropyrimidine-4-carboxamide, (R)- and (S)-N-(1-(3-fluoro-4-(1-methylcyclopropyl)phenyl)-2,2-dimethylpropyl)-6-oxo-2-phenyl-1,6-dihydropyrimidine-4-carboxamide, (R)- and (S)-N-(1-(3-fluoro-4-(1-methylcyclopropyl)phenyl)-2,2-dimethylpropyl)-6-oxo-1,6-dihydro-[2,2'-bipyrimidine]-4-carboxamide, (R)- and (S)-N-(2-(2-fluoro-4-(trifluoromethyl)phenyl)butan-2-yl)-2-methyl-6-oxo-1,6-dihydropyrimidine-4-carboxamide, (R)- and (S)-N-(1-(2-fluoro-4-(pentafluoro-$\lambda^6$-sulfanyl)phenyl)-2,2-dimethylpropyl)-2-methyl-6-oxo-1,6-dihydropyrimidine-4-carboxamide, N-{2-hydroxy-2-methyl-1-[4-(trifluoromethyl)phenyl]propyl}-2-methyl-6-oxo-1,6-dihydropyrimidine-4-carboxamide, N-{(1S)-1-[3-fluoro-4-(trifluoromethyl)phenyl]-2-hydroxy-2-methylpropyl}-2-methyl-6-oxo-1,6-dihydropyrimidine-4-carboxamide, N-{(1S)-2-hydroxy-2-methyl-1-[4-(trifluoromethoxy)phenyl]propyl}-2-methyl-6-oxo-1,6-dihydropyrimidine-4-carboxamide, (R)-N-{2-hydroxy-2-methyl-1-[4-(trifluoromethyl)phenyl]propyl}-2-methyl-6-oxo-1,6-dihydropyrimidine-4-carboxamide, (S)-N-{2-hydroxy-2-methyl-1-[4-(trifluoromethyl)phenyl]propyl}-2-methyl-6-oxo-1,6-dihydropyrimidine-4-carboxamide, or a pharmaceutically acceptable salt or hydrate thereof.

20. A pharmaceutical composition which comprises a pharmaceutically acceptable carrier and a compound of claim 1 or a pharmaceutically acceptable salt thereof.

21. A compound of claim 1 or a pharmaceutically acceptable salt thereof for use in medicine.

\* \* \* \* \*